(12) United States Patent
Chivukula et al.

(10) Patent No.: US 12,351,834 B2
(45) Date of Patent: Jul. 8, 2025

(54) COMPOSITIONS AND METHODS FOR THE TREATMENT OF ORNITHINE TRANSCARBAMYLASE DEFICIENCY

(71) Applicant: Arcturus Therapeutics, Inc., San Diego, CA (US)

(72) Inventors: Padmanabh Chivukula, San Diego, CA (US); Priya Prakash Karmali, San Diego, CA (US); Kiyoshi Tachikawa, San Diego, CA (US); Suezanne E. Parker, Ramona, CA (US); Marciano Rodriguez Sablad, San Diego, CA (US); Pattraranee Limphong, San Diego, CA (US); Yanjie Bao, San Diego, CA (US); Jerel Boyd Lee Vega, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 940 days.

(21) Appl. No.: 17/191,247

(22) Filed: Mar. 3, 2021

(65) Prior Publication Data

US 2021/0284974 A1 Sep. 16, 2021

Related U.S. Application Data

(60) Provisional application No. 62/984,764, filed on Mar. 3, 2020.

(51) Int. Cl.
| | |
|---|---|
| *C07H 21/02* | (2006.01) |
| *A61K 9/1272* | (2025.01) |
| *A61K 31/221* | (2006.01) |
| *A61K 48/00* | (2006.01) |
| *C07H 21/04* | (2006.01) |
| *C12N 9/10* | (2006.01) |
| *A61K 9/1271* | (2025.01) |
| *A61K 39/00* | (2006.01) |

(52) U.S. Cl.
CPC .......... *C12N 9/1018* (2013.01); *A61K 9/1272* (2013.01); *A61K 31/221* (2013.01); *A61K 48/00* (2013.01); *A61K 48/0033* (2013.01); *A61K 9/1271* (2013.01); *A61K 2039/51* (2013.01); *C12Y 201/03003* (2013.01)

(58) Field of Classification Search
CPC .................... C12N 15/67; C12Y 201/03003
See application file for complete search history.

(56) References Cited

U.S. PATENT DOCUMENTS

| 8,058,069 | B2 | 11/2011 | Yaworski et al. |
|---|---|---|---|
| 8,093,367 | B2 | 1/2012 | Kore et al. |
| 8,158,601 | B2 | 4/2012 | Chen et al. |
| 8,278,036 | B2 | 10/2012 | Kariko et al. |
| 8,304,529 | B2 | 11/2012 | Kore et al. |
| 8,492,359 | B2 | 7/2013 | Yaworski et al. |
| 8,691,966 | B2 | 4/2014 | Kariko et al. |
| 8,748,089 | B2 | 6/2014 | Kariko et al. |
| 8,822,668 | B2 | 9/2014 | Yaworski et al. |
| 9,006,191 | B2 | 4/2015 | Maclachlan et al. |
| 9,006,417 | B2 | 4/2015 | Yaworski et al. |
| 9,364,435 | B2 | 6/2016 | Yaworski et al. |
| 9,404,127 | B2 | 8/2016 | Yaworski et al. |
| 9,428,535 | B2 | 8/2016 | De Fougerolles et al. |
| 9,518,272 | B2 | 12/2016 | Yaworski et al. |
| 9,572,874 | B2 | 2/2017 | Fotin-mleczek et al. |
| 9,750,824 | B2 | 9/2017 | Kariko et al. |
| 9,751,925 | B2 | 9/2017 | Hoge et al. |
| 9,890,365 | B2 | 2/2018 | Wang et al. |
| 9,896,413 | B2 | 2/2018 | Payne et al. |
| 10,072,057 | B2 | 9/2018 | Hoge et al. |
| 10,143,758 | B2 | 12/2018 | Guild et al. |
| 10,167,454 | B2 | 1/2019 | Wang et al. |
| 10,188,748 | B2 | 1/2019 | Von Der Mülbe et al. |
| 10,201,620 | B2 | 2/2019 | Meis et al. |
| 10,232,055 | B2 | 3/2019 | Kariko et al. |
| 10,238,754 | B2 | 3/2019 | Guild et al. |
| 10,487,105 | B2 | 11/2019 | Chivukula et al. |
| 10,501,512 | B2 | 12/2019 | De Fougerolles et al. |
| 10,526,284 | B2 | 1/2020 | Payne et al. |
| 10,568,972 | B2 | 2/2020 | Von Der Mülbe et al. |
| 11,685,906 | B2 | 6/2023 | Perez-Garcia et al. |
| 11,859,215 | B2 * | 1/2024 | Zhuo ............. C12Y 201/03003 |
| 2005/0147993 | A1 | 7/2005 | Khan |
| 2007/0196334 | A1 | 8/2007 | Khan |
| 2011/0256175 | A1 | 10/2011 | Hope et al. |

(Continued)

FOREIGN PATENT DOCUMENTS

| SG | 11201903460 | 5/2019 |
|---|---|---|
| WO | 9207065 A1 | 4/1992 |

(Continued)

OTHER PUBLICATIONS

Database Geneseq-Human ornithine transcarbamylase protein, SEQ ID 5, Feb. 8, 2018.
Database USPTO Proteins, Sequence 2 from U.S. Pat. No. 10,626,382, Aug. 12, 2020.
European Search Report from corresponding European Application No. 19893199.0, mailed on Jul. 29, 2022, 2 Pages.
Federation of Experimental Biologists Society Letter, 1978, 96:1-11.
Remington's Pharmaceutical Sciences, Mack Publishing Company, 17th edition, 1985, 4 pages.
Altschul et al. (1990) "Basic Local Alignment Search Tool", Journal of Molecular Biology, 215(3):403-410.

(Continued)

*Primary Examiner* — Amy Rose Hudson
(74) *Attorney, Agent, or Firm* — Mintz, Levin, Cohn, Ferris, Glovsky and Popeo, P.C.

(57) ABSTRACT

The present disclosure describes compositions and methods for treating ornithine transcarbamylase (OTC) deficiency. The compositions include a lipid formulation and messenger RNA (mRNA) encoding an OTC enzyme. The lipid formulations can comprise an ionizable cationic lipid in a lipid nanoparticle encapsulating the mRNA.

37 Claims, 26 Drawing Sheets

Specification includes a Sequence Listing.

(56) References Cited

U.S. PATENT DOCUMENTS

| | | |
|---|---|---|
| 2012/0027803 A1 | 2/2012 | Manoharan et al. |
| 2012/0128760 A1 | 5/2012 | Manoharan et al. |
| 2014/0090108 A1 | 3/2014 | Garabagi et al. |
| 2015/0064235 A1 | 3/2015 | Bancel et al. |
| 2015/0104476 A1 | 4/2015 | Von Der Mülbe et al. |
| 2016/0089451 A1 | 3/2016 | Armstrong |
| 2016/0136301 A1 | 5/2016 | Von Der Mülbe et al. |
| 2016/0161403 A1 | 6/2016 | Sugimoto |
| 2016/0354493 A1 | 12/2016 | Roy et al. |
| 2017/0056528 A1 | 3/2017 | De Fougerolles et al. |
| 2017/0130216 A1 | 5/2017 | Armstrong |
| 2017/0252461 A1 | 9/2017 | Chakraborty et al. |
| 2017/0362627 A1 | 12/2017 | Reynders et al. |
| 2018/0135030 A1 | 5/2018 | Wang et al. |
| 2018/0169268 A1 | 6/2018 | Payne et al. |
| 2018/0222863 A1 | 8/2018 | Payne et al. |
| 2018/0273576 A1 | 9/2018 | Hogrefe et al. |
| 2018/0327471 A1 | 11/2018 | Limphong et al. |
| 2018/0353618 A1 | 12/2018 | Burkhardt et al. |
| 2019/0002906 A1 | 1/2019 | Limphong et al. |
| 2019/0192688 A1 | 6/2019 | Askew et al. |
| 2019/0307897 A1 | 10/2019 | Angel et al. |
| 2020/0181584 A1 | 6/2020 | Perez-garcia et al. |
| 2020/0297634 A1 | 9/2020 | Karmali et al. |
| 2024/0002815 A1 | 1/2024 | Perez-Garcia et al. |

FOREIGN PATENT DOCUMENTS

| | | |
|---|---|---|
| WO | 9315187 A1 | 8/1993 |
| WO | 2009086558 A1 | 7/2009 |
| WO | 2009127060 A1 | 10/2009 |
| WO | 2010048536 A2 | 4/2010 |
| WO | 2010054406 A1 | 5/2010 |
| WO | 2010088537 A2 | 8/2010 |
| WO | 2010129709 A1 | 11/2010 |
| WO | 2011068810 A1 | 6/2011 |
| WO | 2011153493 A2 | 12/2011 |
| WO | 2014170896 A2 | 10/2014 |
| WO | 2015017519 A1 | 2/2015 |
| WO | 2015051169 A2 | 4/2015 |
| WO | 2015061491 A1 | 4/2015 |
| WO | 2015074085 A1 | 5/2015 |
| WO | 2015138348 A1 | 9/2015 |
| WO | 2015138357 A2 | 9/2015 |
| WO | 2016070166 A2 | 5/2016 |
| WO | 2016081029 A1 | 5/2016 |
| WO | 2016118697 A1 | 7/2016 |
| WO | 2017023817 A1 | 2/2017 |
| WO | 2017117530 A1 | 7/2017 |
| WO | 2017218524 A1 | 12/2017 |
| WO | 2018078053 A1 | 5/2018 |
| WO | 2018089846 A1 | 5/2018 |
| WO | 2018118102 A1 | 6/2018 |
| WO | 2018119163 A1 | 6/2018 |
| WO | 2018127382 A1 | 7/2018 |
| WO | 2018222890 A1 | 12/2018 |
| WO | 2018222926 A1 | 12/2018 |
| WO | 2020118115 A1 | 6/2020 |

OTHER PUBLICATIONS

Berge et al. (Jan. 1977) "Pharmaceutical Salts", Journal of Pharmaceutical Sciences, 66(1):1-19.

Bochicchio et al. (2014) "Liposomes as siRNA Delivery Vectors", Current Drug Metabolism, 15(9):882-892.

Both et al. (Mar. 1, 1975) "Methylation-Dependent Translation of Viral Messenger RNAs In Vitro", Proceedings of the National Academy of Sciences, 72(3):1189-1193.

Bouloy et al. (Jul. 1, 1980) "Both the 7-Methyl and the 2'-O-Methyl Groups in the Cap of mRNA Strongly Influence Its Ability to Act as Primer for Influenza Virus RNA Transcription", Proceedings of the National Academy of Sciences, 77(7):3952-3956.

Burgin et al. (1996) "Chemically Modified Hammerhead Ribozymes with Improved Catalytic Rates", Biochemistry, 35(45):14090-14097.

Carillo et al. (Oct. 1988) "The Multiple Sequence Alignment Problem in Biology", SIAM Journal on Applied Mathematics, 48(5):1073-1082.

Cunningham et al. (2011) "Induction And Prevention of Severe Hyperammonemia in the Spfash Mouse Model of Ornithine Transcarbamylase Deficiency Using Shrna and Raav-mediated Gene Delivery", Molecular Therapy, 854-859.

Dabkowska et al. (Mar. 7, 2012) "The Effect of Neutral Helper Lipids on the Structure of Cationic Lipid Monolayers", Journal of the Royal Society Interface, 9(68):548-561.

Dam et al. (Mar. 6, 1998) "Garlic (*Allium sativum*) Lectins Bind to High Mannose Oligosaccharide Chains", Journal of Biological Chemistry, 273(10):5528-5535.

Devereux et al. (Jan. 11, 1984) "A Comprehensive Set of Sequence Analysis Programs for the VAX", Nucleic Acids Research, 12(1 Pt 1):387-395.

Furuichi et al. (1977) "5'-Terminal Structure and mRNA Stability", Nature, 266:235-239.

Gingras et al. (1999) "eIF4 Initiation Factors: Effectors of mRNA Recruitment to Ribosomes and Regulators of Translation", Annual Review of Biochemistry, 68:913-963.

Gordon Neil (May 2003) "Ornithine Transcarbamylase Deficiency: a Urea Cycle Defect", European Journal of Paediatric Neurology, 7(3):115-121.

Gustafsson et al. (Jul. 2004) "Codon Bias And Heterologous Protein Expression", Trends in Biotechnology, 22(7):346-353.

Hata et al. (1986) "Isolation and Characterization of the Human Ornithine Transcarbamylase Gene: Structure of the 5'-End Region", Journal of Biochemistry, 100:717-725.

Horwich et al. (Jun. 8, 1984) "Structure And Expression of a Complementary DNA For the Nuclear Coded Precursor of Human Mitochondrial Ornithine Transcarbamylase", Science, 224(4653):1068-1074.

Horwich (Feb. 14, 1986) "Targeting of Pre-Ornithine Transcarbamylase to Mitochondria: Definition of Critical Regions And Residues in the Leader Peptide", Cell, 44(3):451-459.

Huang et al. (Aug. 2011) "In Vivo Delivery of RNAi with Lipid-Based Nanoparticles", Annual Review of Biomedical Engineering, 13:507-530.

Ishikawa et al. (Sep. 27, 2009) "Preparation of Eukaryotic mRNA having Differently Methylated Adenosine at the 5'-Terminus and the Effect of the Methyl Group in Translation", Nucleic Acids Symposium, 53(1):129-130.

Jemielity et al. (2003) "Novel "Anti-Reverse" Cap Analogs with Superior Translational Properties", RNA, 9(9):1108-1122.

Jokerst et al. (Jun. 2011) "Nanoparticle PEGylation for Imaging and Therapy", Nanomedicine (Lond), 6(4):715-728.

Kawabata et al. (1995) "The Fate of Plasmid DNA After Intravenous Injection in Mice: Involvement of Scavenger Receptors in Its Hepatic Uptake", Pharmaceutical Research, 12:825-830.

Kozak Marilyn (1988) "Leader Length And Secondary Structure Modulate mRNA Function Under Conditions of Stress.", Molecular and Cellular Biology, 8:2737-2744.

Kozak Marilyn (Oct. 25, 1991) "Structural Features In Eukaryotic mRNAs that Modulate the Initiation of Translation", Journal of Biological Chemistry, 266(30):19867-19870.

Kratz Marilyn (Nov. 1990) "Downstream Secondary Structure Facilitates Recognition of Initiator Codons by Eukaryotic Ribosomes", Proceedings of the National Academy of Sciences of the United States of America, 87:8301-8305.

Kratz Marilyn (Feb. 1989) "The Scanning Model For Translation: An Update", Journal of Cell Biology, 108(2):229-241.

Lasic Dand (Jul. 1, 1998) "Novel Applications of Liposomes", Trends in Biotechnology, 16(7):307-321.

Li et al. (Aug. 3, 2010) "Stealth Nanoparticles: High Density but Sheddable PEG is a Key for Tumor Targeting", Journal of Controlled Release, 145(3):178-181.

Lichter-Koneki et al. (2016) "Ornithine Transcarbamylase Deficiency, GeneReviews® [Internet]", University of Washington, Seattle.

Limbach et al. (Jun. 25) "Summary: the Modified Nucleosides of RNA", Nucleic Acids Research, 1994, 22(12):2183-2196.

(56) References Cited

OTHER PUBLICATIONS

Lin et al. (2014) "Lipid-Based Nanoparticles in the Systemic Delivery of siRNA", Nanomedicine, 9(1):105-120.

Lindgren et al. (Nov. 9, 1984) "Human Ornithine Transcarbamylase Locus Mapped to Band Xp21.1 Near the Duchenne Muscular Dystrophy Locus", Science, 226(4675)698-700.

Love et al. (2010) "Lipid-Like Materials for Low-Dose, In Vivo Gene Silencing", Proceedings of the National Academy of Sciences, 107(5):1864-1869.

Muthukrishnan et al. (1975) "5'-Terminal 7-Methylguanosine in Eukaryotic mRNA is Required for Translation", Nature, 255:33-37.

Myers et al. (1988) "Optimal Alignments in Linear Space", Computer Applications in the Biosciences, 4(1):11-17.

Patil et al. (Jan. 2014) "Novel Methods for Liposome Preparation", Chemistry and Physics of Lipids, 177:8-18.

Prieve et al. (2018) "Targeted mRNA therapy for Ornithine Transcarbamylase Deficiency", Molecular Therapy, 801-813.

Rhoads R.E. (Oct. 22, 1999) "Signal Transduction Pathways That Regulate Eukaryotic Protein Synthesis", Journal of Biological Chemistry, 274(43):30337-30340.

Rodriguez-Gascon et al. (2014) "Development Of Nucleic Acid Vaccines: Use Of Self-Amplifying RNA In Lipid Nanoparticles", International Journal of Nanomedicine, 9:1833-1843.

Sablad et al. (2019) "mRNA Therapy for Ornithine Transcarbamlyse Deficiency", Poster Presented at 41st Annual Meeting for the Society for Inherited Metabolic Disorders, 1 page.

Shatkin Aaronj. (Dec. 1976) "Capping of Eucaryotic mRNAs", Cell, 9(4 PT 2):645-653.

Shatkin A.J. (Feb. 1985) "mRNA Cap Binding Proteins: Essential Factors for Initiating Translation", 40(2):223-224.

Sonenberg Nahum (1988) "Cap-Binding Proteins of Eukaryotic Messenger RNA: Functions in Initiation and Control of Translation", Progress in Nucleic Acid Research and Molecular Biology, 35:173-207.

Taverniti et al. (Jan. 9, 2015) "Elimination of Cap Structures Generated by mRNA Decay Involves the New Scavenger mRNA Decapping Enzyme Aph1/FHIT Together with DcpS", Nucleic Acids Research, 43(1):482-492.

Villalobos et al. (2006)"Gene Designer: A Synthetic Biology Tool For Constructing Artificial DNA Segments", BMC Bioinformatics, 7:285.

International Search Report and Written Opinion issued in International Application No. PCT/US2021/020634, mailed on May 27, 2021, 11 pages.

Kwok et al. (2015) "A Stable RNA G-Quadruplex within the 5'-UTR of *Arabidopsis thaliana* ATR mRNA Inhibits Translation", Biochemical Journal, 467(1):91-102.

Extended European Search Report issued in European Application No. 21763861.8, mailed on Mar. 18, 2024, 10 pages.

\* cited by examiner

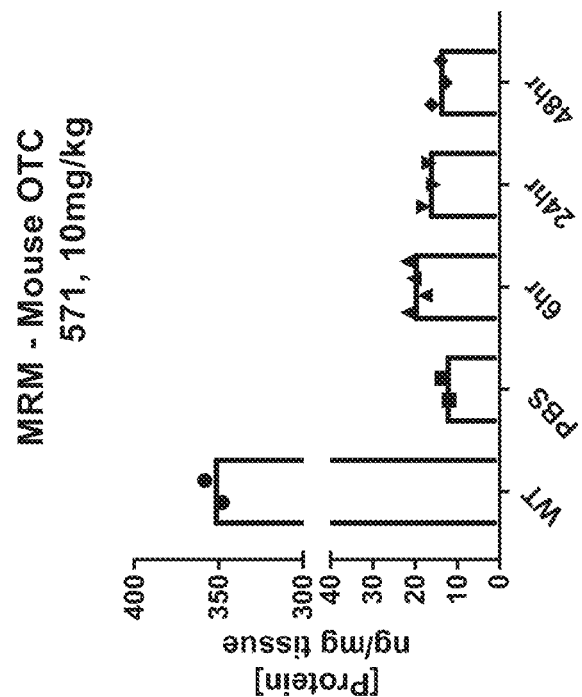
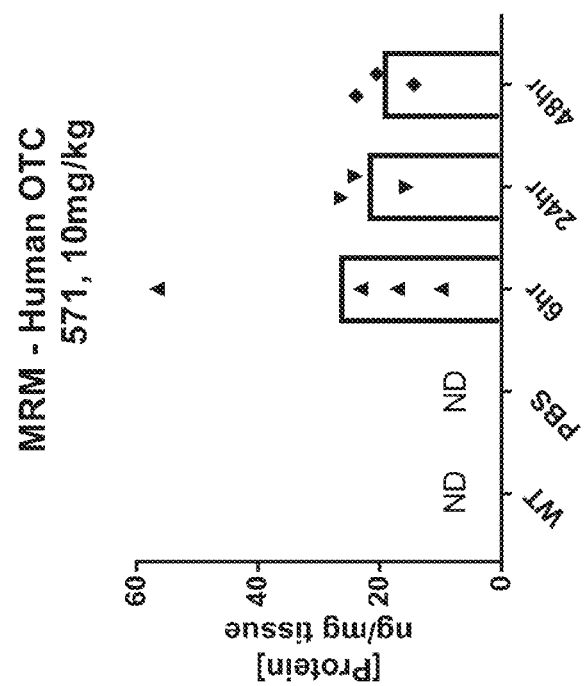
FIG. 9A
FIG. 9B

SEQUENCE LISTING

<160> NUMBER OF SEQ ID NOS: 258

<210> SEQ ID NO 1
<211> LENGTH: 1065
<212> TYPE: RNA
<213> ORGANISM: Artificial sequence
<220> FEATURE:
<223> OTHER INFORMATION: Synthetic polynucleotide

<400> SEQUENCE: 1

| | | | | | |
|---|---|---|---|---|---|
| augcuguuua | aucugaggau | ccuguuaaac | aaugcagcuu | uuagaaaugg | ucacaacuuc     60 |
| augguucgaa | auuuucggug | uggacaacca | cuacaaaaua | aagugcagcu | gaagggccgu    120 |
| gaccuucuca | cucuaaaaaa | cuuuaccgga | gaagaaauua | aauauaugcu | auggcuauca    180 |
| gcagaucuga | aauuuaggau | aaaacagaaa | ggagaguauu | ugccuuuauu | gcaagggaag    240 |
| uccuuaggca | ugauuuuuga | gaaagaagu  | acucgaacaa | gauugucuac | agaaacaggc    300 |
| uuugcacuuc | ugggaggaca | uccuuguuuu | cuuaccacac | aagauauuca | uuugggugug    360 |
| aaugaaaguc | ucacggacac | ggcccgugua | uugucuagca | uggcagaugc | aguauuggcu    420 |
| cgaguguaua | aacaaucaga | uuuggacacc | cuggcuaaag | aagcauccau | cccaauuauc    480 |
| aaugggcugu | cagauuugua | ccauccuauc | cagauccugg | cugauuaccu | cacgcuccag    540 |
| gaacacuaua | gcucucugaa | aggucuuacc | cucagcugga | ucggggaugg | gaacaauauc    600 |
| cugcacucca | ucaugaugag | cgcagcgaaa | uucggaaugc | accuucaggc | agcuacucca    660 |
| aaggguuaug | agccggaugc | uaguguaacc | aaguuggcag | agcaguaugc | caaagagaau    720 |
| gguaccaagc | uguugcugac | aaaugauccca | uuggaagcag | cgcauggagg | caauguauua    780 |
| auuacagaca | cuuggauaag | caugggacaa | gaagaggaga | agaaaaagcg | gcuccaggcu    840 |
| uuccaagguu | accagguuac | aaugaagacu | gcuaaaguug | cugccucuga | cuggacauuu    900 |
| uuacacugcu | ugcccagaaa | gccagaagaa | guggaugaug | aagucuuuua | uucuccucga    960 |
| ucacuagugu | ucccagaggc | agaaaacaga | aaguggacaa | ucauggcugu | cauggugucc   1020 |
| cugcugacag | auuacucacc | ucagcuccag | aagccuaaau | uuuga |                     1065 |

<210> SEQ ID NO 2
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 2

| | | | | | |
|---|---|---|---|---|---|
| atgctgttta | atctgaggat | cctgttaaac | aatgcagctt | ttagaaatgg | tcacaacttc     60 |
| atggttcgaa | attttcggtg | tggacaacca | ctacaaaata | aagtgcagct | gaagggccgt    120 |
| gaccttctca | ctctaaaaaa | ctttaccgga | gaagaaatta | aatatatgct | atggctatca    180 |
| gcagatctga | aatttaggat | aaaacagaaa | ggagagtatt | tgcctttatt | gcaagggaag    240 |

-continued

```
tccttaggca tgatttttga gaaaagaagt actcgaacaa gattgtctac agaaacaggc      300
tttgcacttc tgggaggaca tccttgtttt cttaccacac aagatattca tttgggtgtg      360
aatgaaagtc tcacggacac ggcccgtgta ttgtctagca tggcagatgc agtattggct      420
cgagtgtata aacaatcaga tttggacacc ctggctaaag aagcatccat cccaattatc      480
aatgggctgt cagatttgta ccatcctatc cagatcctgg ctgattacct cacgctccag      540
gaacactata gctctctgaa aggtcttacc ctcagctgga tcggggatgg gaacaatatc      600
ctgcactcca tcatgatgag cgcagcgaaa ttcggaatgc accttcaggc agctactcca      660
aagggttatg agccggatgc tagtgtaacc aagttggcag agcagtatgc caaagagaat      720
ggtaccaagc tgttgctgac aaatgatcca ttggaagcag cgcatggagg caatgtatta      780
attacagaca cttggataag catgggacaa gaagaggaga agaaaaagcg gctccaggct      840
ttccaaggtt accaggttac aatgaagact gctaaagttg ctgcctctga ctggacattt      900
ttacactgct tgcccagaaa gccagaagaa gtggatgatg aagtcttta ttctcctcga      960 tcactagtgt tcccagaggc agaaaacaga aagtggacaa tcatggctgt catggtgtcc     1020
ctgctgacag attactcacc tcagctccag aagcctaaat tttga                     1065
```

<210> SEQ ID NO 3
<211> LENGTH: 355
<212> TYPE: PRT
<213> ORGANISM: Artificial sequence
<220> FEATURE:
<223> OTHER INFORMATION: Synthetic polypeptide

<400> SEQUENCE: 3

```
Ala Met Leu Phe Asn Leu Arg Ile Leu Leu Asn Asn Ala Ala Phe Arg
1               5                   10                  15

Asn Gly His Asn Phe Met Val Arg Asn Phe Arg Cys Gly Gln Pro Leu
            20                  25                  30

Gln Asn Lys Val Gln Leu Lys Gly Arg Asp Leu Leu Thr Leu Lys Asn
        35                  40                  45

Phe Thr Gly Glu Glu Ile Lys Tyr Met Leu Trp Leu Ser Ala Asp Leu
    50                  55                  60

Lys Phe Arg Ile Lys Gln Lys Gly Glu Tyr Leu Pro Leu Leu Gln Gly
65                  70                  75                  80

Lys Ser Leu Gly Met Ile Phe Glu Lys Arg Ser Thr Arg Thr Arg Leu
                85                  90                  95

Ser Thr Glu Thr Gly Phe Ala Leu Leu Gly Gly His Pro Cys Phe Leu
            100                 105                 110

Thr Thr Gln Asp Ile His Leu Gly Val Asn Glu Ser Leu Thr Asp Thr
        115                 120                 125

Ala Arg Val Leu Ser Ser Met Ala Asp Ala Val Leu Ala Arg Val Tyr
    130                 135                 140

Lys Gln Ser Asp Leu Asp Thr Leu Ala Lys Glu Ala Ser Ile Pro Ile
145                 150                 155                 160

Ile Asn Gly Leu Ser Asp Leu Tyr His Pro Ile Gln Ile Leu Ala Asp
                165                 170                 175

Tyr Leu Thr Leu Gln Glu His Tyr Ser Ser Leu Lys Gly Leu Thr Leu
            180                 185                 190

Ser Trp Ile Gly Asp Gly Asn Asn Ile Leu His Ser Ile Met Met Ser
        195                 200                 205
```

```
Ala Ala Lys Phe Gly Met His Leu Gln Ala Ala Thr Pro Lys Gly Tyr
        210                 215                 220

Glu Pro Asp Ala Ser Val Thr Lys Leu Ala Glu Gln Tyr Ala Lys Glu
225                 230                 235                 240

Asn Gly Thr Lys Leu Leu Leu Thr Asn Asp Pro Leu Glu Ala Ala His
                245                 250                 255

Gly Gly Asn Val Leu Ile Thr Asp Thr Trp Ile Ser Met Gly Gln Glu
                260                 265                 270

Glu Glu Lys Lys Lys Arg Leu Gln Ala Phe Gln Gly Tyr Gln Val Thr
            275                 280                 285

Met Lys Thr Ala Lys Val Ala Ala Ser Asp Trp Thr Phe Leu His Cys
        290                 295                 300

Leu Pro Arg Lys Pro Glu Glu Val Asp Asp Glu Val Phe Tyr Ser Pro
305                 310                 315                 320

Arg Ser Leu Val Phe Pro Glu Ala Glu Asn Arg Lys Trp Thr Ile Met
                325                 330                 335

Ala Val Met Val Ser Leu Leu Thr Asp Tyr Ser Pro Gln Leu Gln Lys
                340                 345                 350

Pro Lys Phe
        355

<210> SEQ ID NO 4
<211> LENGTH: 355
<212> TYPE: PRT
<213> ORGANISM: Artificial sequence
<220> FEATURE:
<223> OTHER INFORMATION: Synthetic polypeptide

<400> SEQUENCE: 4

Met Leu Val Phe Asn Leu Arg Ile Leu Leu Asn Asn Ala Ala Phe Arg
1               5                   10                  15

Asn Gly His Asn Phe Met Val Arg Asn Phe Arg Cys Gly Gln Pro Leu
                20                  25                  30

Gln Asn Arg Val Gln Leu Lys Gly Arg Asp Leu Leu Thr Leu Lys Asn
            35                  40                  45

Phe Thr Gly Glu Glu Ile Arg Tyr Met Leu Trp Leu Ser Ala Asp Leu
        50                  55                  60

Lys Phe Arg Ile Lys Gln Lys Gly Glu Tyr Leu Pro Leu Leu Gln Gly
65                  70                  75                  80

Lys Ser Leu Gly Met Ile Phe Glu Lys Arg Ser Thr Arg Thr Arg Leu
                85                  90                  95

Ser Thr Glu Thr Gly Phe Ala Leu Leu Gly Gly His Pro Cys Phe Leu
                100                 105                 110

Thr Thr Gln Asp Ile His Leu Gly Val Asn Glu Ser Leu Thr Asp Thr
            115                 120                 125

Ala Arg Val Leu Ser Ser Met Ala Asp Ala Val Leu Ala Arg Val Tyr
        130                 135                 140

Lys Gln Ser Asp Leu Asp Thr Leu Ala Lys Glu Ala Ser Ile Pro Ile
145                 150                 155                 160

Ile Asn Gly Leu Ser Asp Leu Tyr His Pro Ile Gln Ile Leu Ala Asp
                165                 170                 175

Tyr Leu Thr Leu Gln Glu His Tyr Ser Ser Leu Lys Gly Leu Thr Leu
                180                 185                 190

Ser Trp Ile Gly Asp Gly Asn Asn Ile Leu His Ser Ile Met Met Ser
            195                 200                 205
```

```
Ala Ala Lys Phe Gly Met His Leu Gln Ala Ala Thr Pro Lys Gly Tyr
    210                 215                 220

Glu Pro Asp Ala Ser Val Thr Lys Leu Ala Glu Gln Tyr Ala Lys Glu
225                 230                 235                 240

Asn Gly Thr Lys Leu Leu Leu Thr Asn Asp Pro Leu Glu Ala Ala His
            245                 250                 255

Gly Gly Asn Val Leu Ile Thr Asp Thr Trp Ile Ser Met Gly Gln Glu
            260                 265                 270

Glu Glu Lys Lys Lys Arg Leu Gln Ala Phe Gln Gly Tyr Gln Val Thr
        275                 280                 285

Met Lys Thr Ala Lys Val Ala Ala Ser Asp Trp Thr Phe Leu His Cys
    290                 295                 300

Leu Pro Arg Lys Pro Glu Glu Val Asp Asp Glu Val Phe Tyr Ser Pro
305                 310                 315                 320

Arg Ser Leu Val Phe Pro Glu Ala Glu Asn Arg Lys Trp Thr Ile Met
            325                 330                 335

Ala Val Met Val Ser Leu Leu Thr Asp Tyr Ser Pro Gln Leu Gln Lys
            340                 345                 350

Pro Lys Phe
    355

<210> SEQ ID NO 5
<211> LENGTH: 129
<212> TYPE: DNA
<213> ORGANISM: Artificial sequence
<220> FEATURE:
<223> OTHER INFORMATION: Synthetic polynucleotide

<400> SEQUENCE: 5
tcaacacaac atatacaaaa caaacgaatc tcaagcaatc aagcattcta cttctattgc      60
agcaatttaa atcatttctt ttaaagcaaa agcaattttc tgaaaatttt caccatttac     120
gaacgatag                                                              129

<210> SEQ ID NO 6
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 6
attattacat caaaacaaaa agccgcca                                          28

<210> SEQ ID NO 7
<211> LENGTH: 245
<212> TYPE: DNA
<213> ORGANISM: Artificial sequence
<220> FEATURE:
<223> OTHER INFORMATION: Synthetic polynucleotide

<400> SEQUENCE: 7
cttaaggggg cgctgcctac ggaggtggca gccatctcct tctcggcatc aagcttacca      60
tggtgcccca ggccctgctc ttggtcccgc tgctggtgtt ccccctctgc ttcggcaagt     120
tccccatcta caccatcccc gacaagctgg ggccgtggag ccccatcgac atccaccacc     180
tgtcctgccc caacaacctc gtggtcgagg acgagggctg caccaacctg agcgggttct     240
cctac                                                                  245
```

<210> SEQ ID NO 8
<211> LENGTH: 177
<212> TYPE: DNA
<213> ORGANISM: Artificial sequence
<220> FEATURE:
<223> OTHER INFORMATION: Synthetic polynucleotide

<400> SEQUENCE: 8
tgagtgtcgt acagcctcca ggccccccc tcccgggaga gccatagtgg tctgcggaac      60
cggtgagtac accggaattg ccgggaagac tgggtccttt cttggataaa cccactctat    120
gcccggccat ttgggcgtgc ccccgcaaga ctgctagccg agtagtgttg ggttgcg       177

<210> SEQ ID NO 9
<211> LENGTH: 89
<212> TYPE: DNA
<213> ORGANISM: Artificial sequence
<220> FEATURE:
<223> OTHER INFORMATION: Synthetic polynucleotide

<400> SEQUENCE: 9
aattattggt taaagaagta tattagtgct aatttccctc cgtttgtcct agcttttctc     60
ttctgtcaac cccacacgcc tttggcaca                                      89

<210> SEQ ID NO 10
<211> LENGTH: 569
<212> TYPE: DNA
<213> ORGANISM: Artificial sequence
<220> FEATURE:
<223> OTHER INFORMATION: Synthetic polynucleotide

<400> SEQUENCE: 10
ctccctcccc cccccctaac gttactggcc gaagccgctt ggaataaggc cggtgtgcgt     60
ttgtctatat gttatttttcc accatattgc cgtcttttgg caatgtgagg gcccggaaac   120
ctggccctgt cttcttgacg agcattccta ggggtctttc ccctctcgcc aaaggaatgc   180
aaggtctgtt gaatgtcgtg aaggaagcag ttcctctgga agcttcttga agacaaacaa   240
cgtctgtagc gacccttttgc aggcagcgga accccccacc tggcgacagg tgcctctgcg   300
gccaaaagcc acgtgtataa gatacacctg caaaggcggc acaaccccag tgccacgttg    360
tgagttggat agttgtggaa agagtcaaat ggctctcctc aagcgtattc aacaaggggc   420
tgaaggatgc ccagaaggta ccccattgta tgggatctga tctggggcct cggtgcacat    480
gctttacgtg tgtttagtcg aggttaaaaa acgtctaggc ccccgaacc acggggacgt    540 ggttttcctt tgaaaaacac gatgataat                                     569

<210> SEQ ID NO 11
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 11
gtcagctttc aaactctttg tttcttgttt gttgattgag aata                     44

<210> SEQ ID NO 12
<211> LENGTH: 54
<212> TYPE: DNA
<213> ORGANISM: Artificial sequence
<220> FEATURE:
<223> OTHER INFORMATION: Synthetic polynucleotide

<400> SEQUENCE: 12
ctctcgcctg agaaaaaaaa tccacgaacc aatttctcag caaccagcag cacg    54

<210> SEQ ID NO 13
<211> LENGTH: 52
<212> TYPE: DNA
<213> ORGANISM: Artificial sequence
<220> FEATURE:
<223> OTHER INFORMATION: Synthetic polynucleotide

<400> SEQUENCE: 13
acctgtgagg gttcgaagga agtagcagtg tttttgttc ctagaggaag ag    52

<210> SEQ ID NO 14
<211> LENGTH: 71
<212> TYPE: DNA
<213> ORGANISM: Artificial sequence
<220> FEATURE:
<223> OTHER INFORMATION: Synthetic polynucleotide

<400> SEQUENCE: 14
acacagaaac attcgcaaaa acaaaatccc agtatcaaaa ttcttctctt tttttcatat    60
ttcgcaaaga c    71

<210> SEQ ID NO 15
<211> LENGTH: 52
<212> TYPE: DNA
<213> ORGANISM: Artificial sequence
<220> FEATURE:
<223> OTHER INFORMATION: Synthetic polynucleotide

<400> SEQUENCE: 15
cagaaaaatt tgctacattg tttcacaaac ttcaaatatt attcatttat tt    52

<210> SEQ ID NO 16
<211> LENGTH: 158
<212> TYPE: DNA
<213> ORGANISM: Artificial sequence
<220> FEATURE:
<223> OTHER INFORMATION: Synthetic polynucleotide

<400> SEQUENCE: 16
ctagtgactg actaggatct ggttaccact aaaccagcct caagaacacc cgaatggagt    60
ctctaagcta cataatacca acttacactt acaaaatgtt gtcccccaaa atgtagccat    120
tcgtatctgc tcctaataaa aagaaagttt cttcacat    158

<210> SEQ ID NO 17
<211> LENGTH: 166
<212> TYPE: DNA
<213> ORGANISM: Artificial sequence
<220> FEATURE:
<223> OTHER INFORMATION: Synthetic polynucleotide

<400> SEQUENCE: 17
tgcaaggctg gccggaagcc cttgcctgaa agcaagattt cagcctggaa gagggcaaag    60
tggacgggag tggacaggag tggatgcgat aagatgtggt ttgaagctga tgggtgccag    120
ccctgcattg ctgagtcaat caataaagag ctttctttg acccat    166

<210> SEQ ID NO 18
<211> LENGTH: 143
<212> TYPE: DNA

```
<213> ORGANISM: Artificial sequence
<220> FEATURE:
<223> OTHER INFORMATION: Synthetic polynucleotide

<400> SEQUENCE: 18
acgccgaagc ctgcagccat gcgacccac  gccaccccgt gcctcctgcc tccgcgcagc    60
ctgcagcggg agaccctgtc cccgccccag ccgtcctcct ggggtggacc ctagtttaat   120
aaagattcac caagtttcac gca                                           143

<210> SEQ ID NO 19
<211> LENGTH: 220
<212> TYPE: DNA
<213> ORGANISM: Artificial sequence
<220> FEATURE:
<223> OTHER INFORMATION: Synthetic polynucleotide

<400> SEQUENCE: 19
tagagcggca aaccctagct acactccata gctagtttct tttttttttg tttttttttt    60
tttttttttt tttttttttt tttttttttc ctttctttc  cttcttttt  tcctcttttc   120 ttggtggctc catcttagcc ctagtcacgg ctagctgtga aggtccgtg  agccgcatga   180 ctgcagagag tgccgtaact ggtctctctg cagatcatgt                         220

<210> SEQ ID NO 20
<211> LENGTH: 170
<212> TYPE: DNA
<213> ORGANISM: Artificial sequence
<220> FEATURE:
<223> OTHER INFORMATION: Synthetic polynucleotide

<400> SEQUENCE: 20
acacatcaca accacaacct tctcaggcta ccctgagaaa aaaagacatg aagactcagg    60
actcatcttt tctgttggtg taaaatcaac accctaagga acacaaattt ctttaaacat   120
ttgacttctt gtctctgtgc tgcaattaat aaaaaatgga aagaatctac               170

<210> SEQ ID NO 21
<211> LENGTH: 110
<212> TYPE: DNA
<213> ORGANISM: Artificial sequence
<220> FEATURE:
<223> OTHER INFORMATION: Synthetic polynucleotide

<400> SEQUENCE: 21
gctggagcct cggtagccgt tcctcctgcc cgctgggcct cccaacgggc cctcctcccc    60
tccttgcacc ggcccttcct ggtctttgaa taaagtctga gtgggcagca               110

<210> SEQ ID NO 22
<211> LENGTH: 123
<212> TYPE: DNA
<213> ORGANISM: Artificial sequence
<220> FEATURE:
<223> OTHER INFORMATION: Synthetic polynucleotide

<400> SEQUENCE: 22
tagtgcagtc actggcacaa cgcgttgccc ggtaagccaa tcgggtatac acggtcgtca    60
tactgcagac agggttcttc tactttgcaa gatagtctag agtagtaaaa taaatagtat   120
aag                                                                 123

<210> SEQ ID NO 23
<211> LENGTH: 6
```

```
<212> TYPE: DNA
<213> ORGANISM: Artificial sequence
<220> FEATURE:
<223> OTHER INFORMATION: Synthetic polynucleotide

<400> SEQUENCE: 23 gccacc                                                                      6

<210> SEQ ID NO 24
<211> LENGTH: 4
<212> TYPE: DNA
<213> ORGANISM: Artificial sequence
<220> FEATURE:
<223> OTHER INFORMATION: Synthetic polynucleotide

<400> SEQUENCE: 24 gcca                                                                        4

<210> SEQ ID NO 25
<211> LENGTH: 9
<212> TYPE: RNA
<213> ORGANISM: Artificial sequence
<220> FEATURE:
<223> OTHER INFORMATION: Synthetic polynucleotide

<400> SEQUENCE: 25 auaagugaa                                                                   9

<210> SEQ ID NO 26
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 26
ucaacacaac auauacaaaa caaacgaauc ucaagcaauc aagcauucua cuucuauugc           60
agcaauuuaa aucauuucuu uuaaagcaaa agcaauuuuc ugaaaauuuu caccauuuac          120
gaacgauagc caccaugcug uuuaaucuga ggauccuguu aaacaaugca gcuuuuagaa          180
auggucacaa cuucaugguu cgaaauuuuc gguguggaca accacuacaa aauaaagugc          240
agcugaaggg ccgugaccuu cucacucuaa aaacuuuac cggagaagaa auuaaauaua           300
ugcuauggcu aucagcagau cugaaauuua ggauaaaaca gaaggagag uauuugccuu           360 uauugcaagg gaaguccuua ggcaugauuu uugagaaaag aaguacucga caagauugu           420 cuacagaaac aggcuuugca cuucggagg acauccuug uuuucuuacc acacaagaua            480
uucauuuggg ugugaaugaa agcucacgg acacggcccg uguauugucu agcauggcag           540
augcaguauu ggcucgagug uauaaacaau cagauuugga cacccuggcu aaagaagcau          600
ccaucccaau uaucaauggg cugucagauu guaccaucc uauccagauc cuggcugauu           660
accucacgcu ccaggaacac uauagcucuc ugaaaggucu acccucagc uggaucgggg           720 augggaacaa uauccugcac uccaucauga ugagcgcagc gaaauucgga augcaccuuc          780
aggcagcuac uccaaagggu uaugagccgg augcuagugu aaccaaguug gcagagcagu          840
augccaaaga gaauggguacc aagcuguugc ugacaaauga uccauggaa gcagcgcaug          900 gaggcaaugu auuaauuaca gacacuugga uaagcauggg acaagaagag gagaagaaaa          960
agcggcucca ggcuuccaa gguuaccagg uuacaaugaa gacugcuaaa guugcugccu          1020
cugacuggac auuuuuacac ugcuugccca gaaagccaga agaaguggau gaugaagucu         1080
```

| | |
|---|---|
| uuuauucucc ucgaucacua uguucccag aggcagaaaa cagaaagugg acaaucaugg | 1140 |
| cugucauggu gucccugcug acagauuacu caccucagcu ccagaagccu aaauuuugac | 1200 |
| ucgagcuagu gacugacuag gaucugguua ccacuaaacc agccucaaga cacccgaau | 1260 |
| ggagucucua agcuacauaa uaccaacuua cacuuacaaa auguugcccc ccaaaaugua | 1320 |
| gccauucgua ucugcuccua auaaaaagaa aguuucuuca cauucuag | 1368 |

<210> SEQ ID NO 27
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 27

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuc uuuaaucugc gcaucuuacu gaacaacgcc gcauccggaa | 180 |
| acggucacaa cuucauggug cgcaauuucc gcuguggcca gccgcuucaa aacaaggucc | 240 |
| agcugaaggg acgggaucug cugacacuga agaacuuacc cggagaagag aucaaguaca | 300 |
| ugcuguggcu cagcgcagac uugaaguucc ggaucaagca gaagggagaa uacuugcccc | 360 |
| ugcugcaagg aaagucgcug ggaaugauuu uugagaagcg gucaacucgc accagacucu | 420 |
| ccaccgaaac ugguuucgca cugcuuggcg ggcacccuug cuuccugacg acucaggaca | 480 |
| uccaccucgg cgugaacgaa ucgcuaaccg auaccgccag agugcuuucu uccaauggccg | 540 |
| acgcggugcu ggccaggguga uacaagcagu ccgaccucga uaccuuggca aaggaggcuu | 600 |
| ccauccccau caucacggc cugagcgacc uguaccaccc aauccaaauc cuggcugacu | 660 |
| accugacccu gcaagagcac uacagcagcc ugaagggucu gacccuguca uggauuggcg | 720 |
| auggaaacaa uauucugcac uccaucauga uguccgccgc gaaguucgga augcaucugc | 780 |
| aagccgccac uccaaaagga uacgaaccgg augcguccgu gaccaaguug gcggaacagu | 840 |
| acgcgaagga gaacggaacc aagcuucugc ugacuaacga cccccucgag gcugcgcaug | 900 |
| ggggcaacgu gcugauuacc gacaccugga ucuccauggg gcaggaggaa gagaagaaga | 960 |
| agagacugca ggcauuccag ggguaccagg ucaccaugaa aaccgcaaaa guggcagcuu | 1020 |
| cggacuggac uuuccugcau ugccugccga ggaagccgga ggaagucgac gacgaagugu | 1080 |
| ucuacucgcc ucggucccug guguucccg aggccgaaaa ccggaagugg accaucaugg | 1140 |
| ccgugauggu guccuugcug acugacuaua gcccgcagcu gcagaagccu aaguucuagc | 1200 |
| ucgagcuagu gacugacuag gaucugguua ccacuaaacc agccucaaga cacccgaau | 1260 |
| ggagucucua agcuacauaa uaccaacuua cacuuacaaa auguugcccc ccaaaaugua | 1320 |
| gccauucgua ucugcuccua auaaaaagaa aguuucuuca cauucuag | 1368 |

<210> SEQ ID NO 28
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 28

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |

| | |
|---|---|
| gaacgauagc caccaugcug uuuaaccuac guauuuugcu caacaaugca gccuuuagaa | 180 |
| acggacauaa cuuuaugguu cgaaacuuuc gcugcgggca gccacugcag aacaaggucc | 240 |
| agcugaaagg gagagauuug cucacgcuga agaacuuuac uggcgaagaa aucaaguaua | 300 |
| ugcugugguu guccgcggac cucaaguuuc ggauuaagca gaaaggggag uaucugccac | 360 |
| ugcugcaagg aaagagccuc ggcaugaucu ucgagaagcg gagcacucgg accaggcuga | 420 |
| guaccgaaac uggcuucgca uuguugggug gacauccaug uuuucugaca acgcaggaca | 480 |
| uucaucuggg cgugaacgag agucugacgg acacagcucg cguucugucc ucuauggcug | 540 |
| augcggucuu ggcccggguc uauaagcagu ccgauuugga caccuggcu aaggaagcua | 600 |
| gcauaccgau uaucaauggg cuguccgacc uguaucaccc uauucaaauc cuggccgacu | 660 |
| accucacacu gcaagaacac uauagcucau ugaagggacu gacccugagc uggauagggg | 720 |
| acggaaacaa cauccuacau agcauuauga uguccgcugc caaguuuggc augcaucuuc | 780 |
| aagccgccac gccaaagggu uaugagcccg acgcgucagu gacaaagcug gccgagcagu | 840 |
| acgcuaagga gaauggguacc aaauuacugc ugacuaauga uccacuggag gcugcacaug | 900 |
| gcggcaaugu acugaucacc gacacauggau ucucgauggg ccaggaggaa gaaaagaaga | 960 |
| agaggcuuca ggccuuccaa ggcuaccagg ucaccaugaa aacagcuaag guugcagcau | 1020 |
| cugauuggac cuuucugcac ugucugccaa ggaagcccga gaggugguac gaugaaguau | 1080 |
| ucuauagccc acggaguuug guguucccug aggcugaaaa uaggaagugg acaauuaugg | 1140 |
| ccguaauggu gucccuguua accgacuacu cuccgcaacu gcagaaaccu aaguuuuagc | 1200 |
| ucgagcuagu gacugacuag gaucugguua ccacuaaacc agcccaaga acacccgaau | 1260 |
| ggagucucua agcuacauaa uaccaacuua cacuuacaaa auguugucc ccaaaaugua | 1320 |
| gccauucgua ucugcuccua auaaaaagaa aguuucuuca cauucuag | 1368 |

<210> SEQ ID NO 29
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 29

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug uuuaacuuaa ggauccugcu gaacaacgcc gcuuuucgua | 180 |
| acggucauaa cuuuauggu cggaacuuua gaugugggcca gccgcugcag aacaagguuc | 240 |
| agcugaaggg gagggaucug cugaccuuga gaacuuuac cggcgaagag aucaaguaca | 300 |
| uguuguggcu gagcgccgau cugaaguuua ggauuaagca gaaggggag uauuugccac | 360 |
| ugcugcaagg aaaauccuug gggaugaucu ucgagaagcg cuccacuaga acccggcuaa | 420 |
| gcacagaaac cggcuucgca cuucggggug gacauccccug uuuucugacg acgcaggaua | 480 |
| uacaccuggg cgugaaugag agucugacgg acacagcuag ggguugagc agcauggccg | 540 |
| augcaguacu ggcccgcguu uauaagcaga gcgacuggga cacacuggcc aaggaagcgu | 600 |
| caauuccgau uaucaauggg cugucagacc uguaucaucc cauucaaauc uuggcugacu | 660 |
| aucugacccu gcaagaacau uacagcuccc ugaagggccu cacguugucc uggauuggcg | 720 |
| acggaaacaa cauucugcau ucgauucauga ugagcgcugc uaaguuuggc augcaccucc | 780 |

| | |
|---|---|
| aagccgcuac accuaaggga uaugagccug augccagcgu aaccaagcug gccgaacagu | 840 |
| acgcgaagga gaauggcacg aaacugcugu ugacaaauga cccacuggag gcagcucacg | 900 |
| guggcaacgu gcugaucacc gacacgugga uaucuauggg acaggaagaa gagaagaaga | 960 |
| agcggcugca ggcauccaa ggguaucagg ucaccaugaa acggccaag guugcugcau | 1020 |
| ccgacuggac auuucugcau ugcuugcccc gcaaaccaga agaaguagac gacgaagucu | 1080 |
| uuuauucccc acggucgcug uguucccog aggcggagaa ucgaaagugg acgauuaugg | 1140 |
| ccgugauggu gucccugcug acugauuacu cuccccaacu gcaaaagccu aaguuuuagc | 1200 |
| ucgagcuagu gacugacuag gaucgguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 30
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 30

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaccuga ggauccuccu gaacaacgcc gccuuucgca | 180 |
| auggucacaa cuuuauggu cggaacuuca gaugcggcca gccgcugcag aacaaggucc | 240 |
| agcugaaggg acgggaucug cugacucuga agaacuucac cggagaagag aucaaguaca | 300 |
| ugcugugcu gucggccgac cugaaguuca ggaucaagca gaaggagaa uaccucccgc | 360 |
| ugcugcaagg aaagucccug ggcaugauuu ucgagaagcg cucgaccaga acucgguugu | 420 |
| ccaccgaaac cggguuugcg cugcgggcg gacauccuug cuuccugacg acucaggaua | 480 |
| uucaccuggg agugaacgag ucgcugaccg acaccgccag agugcugagc ucgauggccg | 540 |
| acgccguguu ggcacgcgug uacaagcagu ccgaucugga uacccuggcc aaagaagcuu | 600 |
| ccauccocgau cauuaacggg cugagcgacc ucuaccaccc cauucaaauc cuggccgacu | 660 |
| accugacucu gcaagaacac uacagcucgc ugaaggggu gacucugucc uggaucggcg | 720 |
| acggaaacaa cauccugcac uccaucauga ugucggccgc aaaguucggc augcauuugc | 780 |
| aagccgccac cccaaagggc uacgaaccag acgcgagcgu caccaagcug gccgaacagu | 840 |
| acgcgaagga aaaugguacu aagcugcugc ugaccaacga cccauuggaa gcugcccaug | 900 |
| guggaaacgu gcugaucacc gacaccugga ucucgauggg ccaggaagag gagaagaaga | 960 |
| agcggcugca ggcguuccag ggguaucagg ucaccaugaa acagccaaa guggcagcgu | 1020 |
| cagacuggac cuuccuccac ugucugccuc gcaagccaga ggagguggac gacgaggugu | 1080 |
| ucuacuccccc ucggucccuc uguuucccug aggcugagaa ccggaagugg accauuaugg | 1140 |
| ccgugauggu gucacuccug acugauuacu ccccgcaacu gcagaagccc aaguucuagc | 1200 |
| ucgagcuagu gacugacuag gaucgguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 31
<211> LENGTH: 1368

```
<212> TYPE: RNA
<213> ORGANISM: Artificial sequence
<220> FEATURE:
<223> OTHER INFORMATION: Synthetic polynucleotide

<400> SEQUENCE: 31
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccaugcug uuuaaccuga ggauccuauu gaacaaugcu gcuuuucgua     180
auggccauaa cuuuaugguu cggaacuuua gaugcgggca gccacugcag aacaaggucc     240
aguugaaagg ccgcgaucug uugacauuga agaacuuuac cggcgaagag auuaaguaua     300
ugcuguggcu gucugcugac cucaaguuuc gaaucaagca gaagggcgaa uaucuccccc     360
ugcugcaagg aaagucucuc ggcaugaucu uugagaagcg gaguacccga acacggcuga     420
gcaccgaaac gggcuucgca cugcuggggg gccaucccug uuuucugaca acgcaggaca     480
uccacuuggg gguuaacgaa ucauugacug auaccgcccg cguacuguca uccauggccg     540
acgcugugcu ggcuagggug uacaagcagu cagaucugga uacacuggcc aaggaagcua     600
gcauaccaau caucaaugga cugagugacc uuuaucaccc gauucaaaua cuagccgauu     660
aucugacccu gcaagagcau uacuccucgc ugaaaggccu cacgcugucc uggaucggcg     720
acggcaacaa cauucugcau aguauuauga ugucugcugc caaauucggc augcaucugc     780
aagcugcuac gccgaagggu uaugaacccg acgcgucagu uacgaagcuc gcugagcagu     840
augcaaagga gaauggcaca aagcuguugc uuaccaacga uccccuggaa gcugcucaug     900
gcggcaaugu gcugauuacu gacaccugga uuucaauggg ccaggaggag gagaagaaga     960
agagguuaca ggcuuuucaa gguuaccaag ucacgaugaa aaccgcuaag gucgcagcca    1020
gcgacuggac auccugcac ugucugccaa gaaagccgga agaaguggac gacgaggugu    1080
ucuauucccc gcggucuuug uguuuccgg aggccgaaaa caggaaaugg accauuaugg    1140
ccgugauggu aucguugcug acggacuaca gcccucaguu gcaaaagccc aaguucuagc    1200
ucgagcuagu gacugacuag gaucgguua ccacuaaacc agccucaaga cacccgaau    1260 ggagucucua agcuacauaa uaccaacuua cacuuacaaa auguugucc ccaaaaugua    1320 gccauucgua ucugcuccua auaaaaagaa aguuucuuca cauucuag                1368

<210> SEQ ID NO 32
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 32
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccaugcuc uuuaaccucc gcauccuccu caacaacgcc gccuuccgga     180
augggcauaa cuucaugguc cggaacuuca gaugcggcca gccccugcaa aacaaggucc     240
aguugaaggg acgggaccuc cuuacgcuga agaacuuuac cggagaagag auuaaguaca     300
ugcugugguu gucgcugac cucaaguucc gcauuaagca gaagggagaa uaucugccgc     360
ugcugcaagg aaagagccug ggcaugaucu ucgaaagcg cuccacuaga acccggcugu     420
cgacugagac uggauucgcc uugcucgguu gacacccgug cuuccugacg acccaggaca     480
```

| | |
|---|---|
| uccaccuggg agugaacgag ucacuuacgg auaccgcgag ggugcuguccucaauggccg | 540 |
| acgcagugcu cgcgcgcgug uacaagcagu cagaucugga uacccuggcc aaggaagcca | 600 |
| gcauucccau caucaacgga cugagcgacc uuuaccaccc aauccagauc cucgccgacu | 660 |
| acuuaacccu gcaagagcac uacagcuccc ugaagggacu gacucuguccuggaucgggg | 720 |
| auggaaacaa cauccugcac uccaucauga ugucugccgc uaaguuuggg augcaucugc | 780 |
| aagccgcaac cccuaaggga uacgagcccg acgccucggu gaccaaacuu gcggaacagu | 840 |
| acgccaagga aaacgguacc aagcugcugc ugaccaacga cccucuggaa gcggcccacg | 900 |
| gaggaaaugu gcugauuacc gacaccugga uuucgauggg ccaggaggag agaagaaga | 960 |
| agagacugca ggcguuccag ggauaucagg ucaccaugaa aaccgccaag gucgccgcca | 1020 |
| gcgacuggac cuuccugcac ugucucccuc ggaaaccgga agaaguggau gacgaggugu | 1080 |
| ucuacucccc gcgcucgcug guguucccgg aggcugaaaa caggaagugg acaaucaugg | 1140 |
| ccgugauggu gucccuguug accgacuacu ccccacaacu gcagaagccc aaguucuagc | 1200 |
| ucgagcuagu gacugacuag gaucugguua ccacuaaacc agcccaaga acacccgaau | 1260 |
| ggagucucua agcuacauaa uaccaacuua cacuuacaaa auguugucccccaaaaugua | 1320 |
| gccauucgua ucugcuccua auaaaaagaa aguuucuuca cauucuag | 1368 |

<210> SEQ ID NO 33
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 33

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucugc gcauccuccu gaacaacgcc gccuuccgca | 180 |
| auggacacaa cuuuauggucuu cgcaacuucc gcuguggggca gccgcugcag aacaaggucc | 240 |
| agcucaaggg gagagaucuc cugacccuga agaacuucac uggagaggag aucaaguaca | 300 |
| ugcuguggcu guccgccgac cugaaauuuc ggauuaagca gaagggcgaa uaccucccac | 360 |
| ugcugcaagg aaagucuuug ggcaugaucu ucgaaaagag aagcacccgg acccgguuga | 420 |
| gcaccgaaac ugggguucgcg cuccucggug gacacccgug cuuccugacc acccaagaua | 480 |
| uucaucuggg ugucaacgaa agccugaccg acaccgccag ggugcuguca uccauggcug | 540 |
| acgcagugcu cgcccggguu gtacaagcagu cagaccugga caccccucgcc aaggaagcuu | 600 |
| cgaucccuau caucaacgga cuuuccgacc uguaccaccc cauccaaauu cuggccgacu | 660 |
| accugacucu gcaagaacac uauagcucgc ugaaggacu uacucuguccuggaucgggg | 720 |
| acggcaacaa cauucuccau uccaucauga ugucccgcugc caaguucgga augcaccuuc | 780 |
| aagcagcgac ucccaaggga uacgaaccug augccuccgu gacuaagcug gcagagcagu | 840 |
| acgccaagga aacggguaca aagcugcugc ucacgaacga ccccccuggag gcggcccacg | 900 |
| gcggaaacgu gcugauuacc gauaccggga ucucaauggg ccaggaagag agaagaaga | 960 |
| agcggcucca ggcguuucaa ggcuaccagg ucaccaugaa aaccgcgaag gucgccgccu | 1020 |
| ccgacuggac uuucuugcac ugccgccgc ggaagcccga ggaaguggau gacgaagugu | 1080 |
| ucuacucgcc gagaucguug guguucccug aggccgaaaa caggaagugg accaucaugg | 1140 |
| ccgugauggu gucccugcug acugauuaca gcccacagcu gcagaagccu aaguucuagc | 1200 |

| | |
|---|---|
| ucgagcuagu gacugacuag gaucugguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 34
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 34

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucucc gcauccuccu uaacaacgcc gcguuuagaa | 180 |
| acggccacaa cuucaugguc cggaacuuca gauguggcca gccgcuucaa aacaaggucc | 240 |
| agcugaaggg ccgggaucuu cugacccuga agaacuuuac uggcgaagag aucaaguaca | 300 |
| ugcucuggcu cuccgcggac uugaaguccc gcauuaagca gaaggggggaa uaccuuccgc | 360 |
| ugcuucaagg aaagagccuc ggcaugaucu uugagaagcg cucaaccagg acccgccuuu | 420 |
| cuacugaaac uggguucgcg cugcucggug gccaccccug cuuccugacg acccaggaca | 480 |
| uccaccucgg agugaacgaa ucccucaccg auaccgcccg ggguguaucg agcauggcag | 540 |
| augccgugcu ggccaggguc uacaaacagu ccgaucugga cacucuggcc aaggaggcgu | 600 |
| caauuccuau uaucaacggc cuuagugacc ucuaccaucc gauucagauc cuggccgauu | 660 |
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagcccuga agaaguggac gacgaggugu | 1080 |
| ucuacucgcc acggagccuc guguucccccg aggccgagaa uagaaagugg accaucaugg | 1140 |
| ccgugauggu gucacugcuc accgacuaca gcccgcagcu ucagaagccc aaguucuagc | 1200 |
| ucgagcuagu gacugacuag gaucugguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 35
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 35

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaccuga gaauccuccu gaacaacgcc gccuuccgca | 180 |

| | |
|---|---|
| augguauaa cuucaugguc cgcaacuuuc gcugcggaca gccucuccaa aacaaggucc | 240 |
| agcucaaggg gcgcgaccuc cucacacuga agaacuucac uggagaagaa aucaaguaca | 300 |
| ugcuguggcu gagcgccgau cugaaguucc ggaucaagca gaagggagag uaccuuccuc | 360 |
| ugcugcaagg gaaguccuug ggaaugauuu ucgagaagcg guccacccgg accaggcuga | 420 |
| gcacugaaac uggcuucgcc cugcugggag gccacccuug uuuccugacc acucaggaca | 480 |
| uccaccuggg cgugaacgag ucccugaccg auacugccag agugcuguuc uccauggccg | 540 |
| acgccgugcu cgcccgggug uacaagcagu cagaccucga uacgcuggcc aaggaagccu | 600 |
| ccauucccau uaucaauggu cugucggacc ucuaccaucc aauccaaauc ucgccgacu | 660 |
| accugacucu gcaagaacac uacagcucac ucaagggccu cacccucucc uggaucggcg | 720 |
| acggaaacaa cauccuucac ucgauuauga ugucggccgc gaaguucggg augcaccucc | 780 |
| aagcugccac uccaaaaggc uacgagccgg augccucagu gacuaaguug gcggaacagu | 840 |
| augcgaagga gaacgguacc aagcccucugc ugacuaacga cccgcuggag gccgcccacg | 900 |
| ggggaaacgu gcucaucacc gauacuugga uuuccauggg acaggaggaa gagaagaaga | 960 |
| agcgguugca ggcauuucag ggcuaccagu ucaccaugaa aacugccaaa gucgccgcca | 1020 |
| gcgacuggac cuuccugcac ugccugcccc gcaagccuga agaaguggac gacgagugu | 1080 |
| ucuacucucc ccgguccue cguuucccug aggccgaaaa caggaagugg accaucaugg | 1140 |
| cugugauggu gucccuccug accgacuaca gcccucagcu ccaaaaaccc aaguuuuagc | 1200 |
| ucgagcuagu gacugacuag gaucgguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 36
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 36

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaccuga gaauccucuu gaacaaugcu gcuuuucgga | 180 |
| auggccacaa cuuuaugguu cggaacuucc guugcggcca gccuuuacaa aacaaggucc | 240 |
| agcugaaggg ccgggauuug cucacacuga agaacuuuac uggggaggag auuaaguaua | 300 |
| ugcuguggcu guccgcugac cugaaguuua ggaucaagca gaagggcgaa uaucugccgc | 360 |
| ugcugcaagg gaaaagucug ggcaugauuu uugaaaagcg cucuacccgg accagacugu | 420 |
| cuacggaaac aggcuuugcc cugcugggcg ccaccccug uuuucugaca acgcaggaca | 480 |
| uccaucuggg cgugaacgaa ucacugaccg auacugcucg gguacucagu ucuauggcug | 540 |
| acgcagugcu ggcuagggug uacaagcaga gcgacuugga cacacuggcu aaggaggcca | 600 |
| gcauccccau uaucaauggc cugucugauu uguaccaucc cauucaaauc cuggcugauu | 660 |
| aucugacacu acaagagcau uacucaaguc ugaagggguu gacucucucc uggaucggcg | 720 |
| acggcaacaa cauuuacau uccauuauga ugagugcugc uaaguuuggc augcauuugc | 780 |
| aagcugcuac cccaaagggc uaugaaccug acgcuagcgu aaccaaguug gccgaacagu | 840 |
| augcuaaaga gaauggcacc aagcugcucc ugacgaauga cccccuggaa gcugcucaug | 900 |

```
gcggaaacgu acuuauaacu gauacaugga uuagcauggg ccaggaagag gagaagaaga    960
agagacugca ggccuuccaa ggcuaucagg ucaccaugaa aacugccaag guugcagcua   1020
gcgacuggac cuuccugcac uguuugccga ggaaacccga ggagguggac gaugaagucu   1080
uuuauucucc ccgcuccuug uguuucccg aggcugaaaa ucgaagugg acgauaaugg     1140 cagugauggu gucccuacug accgacuauu uccacaacu gcagaagccu aaauucuagc    1200
ucgagcuagu gacugacuag gaucggguua ccacuaaacc agccucaaga acacccgaau   1260
ggagucucua agcuacauaa uaccaacuua cacuuacaaa auguugucccc ccaaaaugua  1320 gccauucgua ucugcuccua auaaaaagaa aguuucuuca cauucuag                1368
```

<210> SEQ ID NO 37
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 37

```
ucaacacaac auauacaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcuu uucaaucuga ggaccugcu gaacaacgcu gcuuuucgca    180
acggucauaa cuuuauggu ucgcaauuuc guuguggcca gccgcugcag aacaagguuc    240
agcugaaggg cagagaucug cugacucuga agaacuucac uggggaagaa aucaaguaua   300
uguuauggcu guccgcggau cugaaauuuc gaaucaagca gaagggcgaa uaucuucccc   360
ugcugcaagg gaaauccuug ggcaugauuu ugagaagag gagcacuagg acuagauugu    420
caacagaaac aggcuuugcu uuguugggcg gacaucccug cuuucugacg acacaggaua   480
uccaccucgg cguaaacgag ucccucaccg acacugcuag gguacugagc agcauggccg   540
acgcugugcu agcccggguu uacaagcagu cagaccugga cacccuugcc aaggaagcuu   600
cuauuccaau uaucaacggc cugagugacc uguaucaccc uauucaauaa ucgccgacu    660 auuugacgcu ucaagaacau uacagcagcc ucaagggcuu aaccugagu uggauaggcg    720 acggcaacaa uauccugcau uccauuauga ugucugccgc uaaguuuggc augcaucuac    780
aagccgcaac acccaagggc uaugaacccg acgcuagcgu gaccaagcug gccgagcagu   840
augcuaagga aaauggcaca aagcuccuuc uuaccaacga ucccuggag gcugcucacg    900 gcggcaacgu gcugauuacc gauacaugga uuagcauggg ccaggaggag gagaaaaaga   960
agcggcucca ggcuuuucaa ggcuaucagg ucaccaugaa aacugcaaag gucgcugccu   1020
ccgacuggac uuuccugcau ugucuacccc gcaagccuga ggaaguggac gaugaggugu   1080
ucuacucccc acggagucug guguucccgg aagcagagaa ucggaagugg accaucaugg   1140
cugucauggu gucgcucuug acugacuauu uccccaacu gcaaaaaccc aaguuuuagc    1200
ucgagcuagu gacugacuag gaucggguua ccacuaaacc agccucaaga acacccgaau   1260
ggagucucua agcuacauaa uaccaacuua cacuuacaaa auguugucccc ccaaaaugua  1320 gccauucgua ucugcuccua auaaaaagaa aguuucuuca cauucuag                1368
```

<210> SEQ ID NO 38
<211> LENGTH: 1368
<212> TYPE: RNA
<213> ORGANISM: Artificial sequence
<220> FEATURE:

<223> OTHER INFORMATION: Synthetic polynucleotide

<400> SEQUENCE: 38

| | | | | | |
|---|---|---|---|---|---|
| ucaacacaac | auauacaaaa | caaacgaauc | ucaagcaauc | aagcauucua | cuucuauugc | 60 |
| agcaauuuaa | aucauuucuu | uuaaagcaaa | agcaauuuuc | ugaaaauuuu | caccauuuac | 120 |
| gaacgauagc | caccauguua | uucaaccuuc | guauccugcu | aaacaaugcu | gcuuuucgca | 180 |
| auggccauaa | cuuuaugguu | cgcaacuuua | gaugcggcca | gccgcugcag | aacaagguuc | 240 |
| agcugaaggg | ccgggacuug | cugacgcuga | aaaacuuuac | cggggaagag | auuaaguaua | 300 |
| ugcuguggcu | aagcgcugau | cugaaguuua | ggaucaagca | gaagggcgaa | uaucugccac | 360 |
| ugcugcaagg | gaagagucuu | ggcaugauuu | uugaaaagcg | gucuaccaga | acccggcugu | 420 |
| cgaccgagac | agguuuugcu | cugcuggggg | gccaucccug | uuuucugaca | acucaggaca | 480 |
| uucaccuggg | cgugaaugag | ucccugaccg | auacugcuag | gguguugagu | agcauggccg | 540 |
| acgcuguacu | cgcucgagug | uauaagcagu | cugaucugga | cacucuggcu | aaggaagcuu | 600 |
| ccauuccuau | uaucaacggc | uugagcgacc | uguaccaccc | cauucaaauc | ucgcugauu | 660 |
| acuugacuuu | gcaagaacau | uacagcagcu | ugaagggcuu | aacacugagc | uggauaggcg | 720 |
| acggaaacaa | caucuugcau | uccauaauga | ugucgccgc | uaaguucggg | augcaccucc | 780 |
| aagcagccac | acccaagggc | uaugaaccgg | augcuuccgu | gacaaaacug | gcugagcagu | 840 |
| augcuaagga | gaauggcacg | aaacugcugc | ucaccaacga | cccauggaa | gcugcacaug | 900 |
| guggcaacgu | acugaucacu | gacacuugga | ucucaauggg | ccaggaggaa | gagaagaaga | 960 |
| aaaggcugca | ggcauuucag | ggauaccaag | ucacuaugaa | aacugccaag | gucgcugccu | 1020 |
| ccgacuggac | auuccugcau | ugucugccac | ggaagccuga | ggaagucgau | gacgaagugu | 1080 |
| ucuauagccc | acgaagcuug | guguuucccg | aggcugagaa | uaggaagugg | accauuaugg | 1140 |
| cuguuauggu | gucccugcuc | accgacuauu | ccccucaacu | gcaaaacccc | aaguuuuagc | 1200 |
| ucgagcuagu | gacugacuag | gaucggguua | ccacuaaacc | agccucaaga | acacccgaau | 1260 |
| ggagucucua | agcuacauaa | uaccaacuua | cacuuacaaa | auguugcccc | ccaaaaugua | 1320 |
| gccauucgua | ucugcuccua | auaaaaagaa | aguuucuuca | cauucag | | 1368 |

<210> SEQ ID NO 39
<211> LENGTH: 1365
<212> TYPE: RNA
<213> ORGANISM: Artificial sequence
<220> FEATURE:
<223> OTHER INFORMATION: Synthetic polynucleotide

<400> SEQUENCE: 39

| | | | | | |
|---|---|---|---|---|---|
| ucaacacaac | auauacaaaa | caaacgaauc | ucaagcaauc | aagcauucua | cuucuauugc | 60 |
| agcaauuuaa | aucauuucuu | uuaaagcaaa | agcaauuuuc | ugaaaauuuu | caccauuuac | 120 |
| gaacgauagc | caugcuuuuu | aaucuccgca | uccuccuuaa | caacgccgcg | uuuagaaacg | 180 |
| gccacaacuu | cauggaccgg | aacuucagau | guggccagcc | gcuucaaaac | aagguccagc | 240 |
| ugaagggccg | ggaucuucug | acccugaaga | acuuuacugg | cgaagagauc | aaguacaugc | 300 |
| ucuggcucuc | cgcggacuug | aaguccgca | uuaagcagaa | ggggaauac | cuuccgcugc | 360 |
| uucaaggaaa | gagccucggc | augaucuuug | agaagcgcuc | aaccaggacc | cgccuuucua | 420 |
| cugaaacugg | guucgcgcug | cucggugcc | accccugcuu | ccugacgacc | caggacaucc | 480 |
| accucgagu | gaacgaauccc | cucaccgaua | ccgcccgggu | guuaucgagc | auggcagaug | 540 |
| ccgugcuggc | cagggucuac | aaacaguccg | aucuggacac | ucuggccaag | gaggcgucaa | 600 |

```
uucccaucau caacggccug agcgaccugu accacccaau ccaaauccug gcugacuacc    660
ugacccugca agagcacuac agcagccuga agggucugac ccugucaugg auuggcgaug    720
gaaacaauau ucugcacucc aucaugaugu ccgccgcgaa guucggaaug caucugcaag    780
ccgccacgcc aaaaggauac gaaccggaug cguccgugac gaaguggcg gaacaguacg     840 cgaaggagaa cggaaccaag cuucugcuga cuaacgaccc ccucgaggcu gcgcauggggg   900 gcaacgugcu gauuaccgac accuggaucu ccaugggcca ggaggaagag aagaagaaga    960
gacugcaggc auuccagggg uaccagguca ccaugaaaac cgcaaaagug gcagcuucgg   1020
acuggacuuu ccugcauugc cugccgagga agcggagga agucgacgac gaaguguucu   1080
acucgccucg gucccuggug uuccccgagg ccgaaaaccg gaaguggacc aucauggccg   1140
ugauggugac cuugcugacu gacuauagcc cgcagcugca gaagccuaag uucuagcucg   1200
agcuagugac ugacuaggau cugguuacca cuaaaccagc cucaagaaca cccgaaugga   1260
gucucuaagc uacauaauac caacuuacac uuacaaaaug uugucccca aaauguagcc    1320 auucguaucu gcuccuaaua aaaagaaagu uucuucacau ucuag                   1365
```

<210> SEQ ID NO 40
<211> LENGTH: 1365
<212> TYPE: RNA
<213> ORGANISM: Artificial sequence
<220> FEATURE:
<223> OTHER INFORMATION: Synthetic polynucleotide

<400> SEQUENCE: 40

```
ucaacacaac auauacaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caugcuuuuc aaccugagaa uccucuugaa caaugcugcu uuucggaaug    180
gccacaacuu uauggguucgg aacuuccguu gcggccagcc uuuacaaaac aagguccagc   240
ugaagggccg ggauuugcuc acacugaaga acuuuacugg agaagagauc aaguacaugc    300
uguggcuguc ggccgaccug aaguucagga ucaagcagaa gggagaauac cuuccgcugc    360
uucaaggaaa gagccucggc augaucuuug agaagcgcuc aaccaggacc cgccuuucua    420
cugaaacugg guucgcgcug cucgguggcc accccugcuu ccugacgacc caggacaucc    480
accucggagu gaacgaaucc cucaccgaua ccgcccgggu guuaucgagc auggcagaug    540
ccgugcuggc caggguguac aaacaguccg aucucgauac cuuggcaaag gaggcuucca    600
uucccaucau caacggccug agcgaccugu accacccaau ccaaauccug gcugacuacc    660
ugacccugca agagcacuac agcagccuga agggucugac ccugucaugg auuggcgaug    720
gaaacaauau ucugcacucc aucaugaugu ccgccgcgaa guucggaaug caucugcaag    780
ccgccacucc aaaaggauac gaaccggaug cguccgugac caaguuggcg gaacaguacg    840
cgaaggagaa cggaaccaag cuucugcuga cuaacgaccc ccucgaggcu gcgcauggggg   900 gcaacgugcu gauuaccgac accuggaucu ccaugggcca ggaggaagag aagaagaaga    960
gacugcaggc auuccagggg uaccagguca ccaugaaaac cgcaaaagug gcagcuucgg   1020
acuggacuuu ccugcauugc cugccgagga agcggagga agucgacgac gaaguguucu   1080
acucgccucg gucccuggug uuccccgagg ccgaaaaccg gaaguggacc aucauggccg   1140
ugauggugac cuugcugacu gacuauagcc cgcagcugca gaagccuaag uucuagcucg   1200
agcuagugac ugacuaggau cugguuacca cuaaaccagc cucaagaaca cccgaaugga   1260
```

| | |
|---|---|
| gucucuaagc uacauaauac caacuuacac uuacaaaaug uugcccccca aaauguagcc | 1320 |
| auucguaucu gcuccuaaua aaaagaaagu uucuucacau ucuag | 1365 |

<210> SEQ ID NO 41
<211> LENGTH: 1365
<212> TYPE: RNA
<213> ORGANISM: Artificial sequence
<220> FEATURE:
<223> OTHER INFORMATION: Synthetic polynucleotide

<400> SEQUENCE: 41

| | |
|---|---|
| ucaacacaac auauacaaaa caaacgaauc ucaagcaauc aagcauucua cuucuauugc | 60 |
| agcauuuaa aucauuucuu uuaaagcaaa agcaauuuuc ugaaaauuuu caccauuuac | 120 |
| gaacgauagc caugcuuuuc aaccugagaa uccucuugaa caaugcugcu uuucggaaug | 180 |
| gccacaacuu uaugguucgg aacuccguu gcggccagcc uuuacaaaac aagguccagc | 240 |
| ugaagggccg ggauuugcuc acacuaaaga acuuuacugg agaagagauc aaguacaugc | 300 |
| uauggcuguc ggccgaccug aaguuccgua ucaagcagaa gggagaauac cuuccgcugc | 360 |
| uucaaggaaa gagccucggc augaucuuug agaagcgcuc aaccaggacc cgccuuucua | 420 |
| cugaaacugg guucgcgcug cucgguggcc accccugcuu ccugacgacc caggacaucc | 480 |
| accucggagu gaacgaaucc cucaccgaua ccgcccgggu guuaucgagc auggcagaug | 540 |
| ccgugcugga caggguguac aaacaguccg aucucgauac cuuggcaaag gaggcuucca | 600 |
| uucccaucau caacggccug agcgaccugu accacccaau ccaaauccug gcugacuacc | 660 |
| ugacccugca agagcacuac agcagccuga agggucugac ccugucaugg auuggcgaug | 720 |
| gaaacaauau ucugcacucc aucaugaugu ccgccgcgaa guucggaaug caucugcaag | 780 |
| ccgccacucc aaaaggauac gaaccggaug cauccgugac caaguuggcg gaacaguacg | 840 |
| cgaaggagaa cggaaccaag cuccugcuga cuaacgaccc gcucgaggcu gcgcaugggg | 900 |
| guaacgugcu gauuacggac accuggaucu ccauggggca ggaggaagag aagaagaaga | 960 |
| gacugcaggc auuccagggg uaccaagguca ccaugaaaac cgcaaaagug gcagcuucgg | 1020 |
| acuggacuuu ccugcauugc cugccgagga agccggagga agucgacgac gaaguguucu | 1080 |
| acucgccucg gucccuggug uuccccgagg ccgaaaaccg gaaguggacc aucauggccg | 1140 |
| ugauggugcuc cuugcugacu gacuauagcc cgcagcugca gaagccuaag uucuagcucg | 1200 |
| agcuagugac ugacuaggau cugguuacca cuaaaccagc cucaagaaca cccgaaugga | 1260 |
| gucucuaagc uacauaauac caacuuacac uuacaaaaug uugcccccca aaauguagcc | 1320 |
| auucguaucu gcuccuaaua aaaagaaagu uucuucacau ucuag | 1365 |

<210> SEQ ID NO 42
<211> LENGTH: 1365
<212> TYPE: RNA
<213> ORGANISM: Artificial sequence
<220> FEATURE:
<223> OTHER INFORMATION: Synthetic polynucleotide

<400> SEQUENCE: 42

| | |
|---|---|
| ucaacacaac auauacaaaa caaacgaauc ucaagcaauc aagcauucua cuucuauugc | 60 |
| agcauuuaa aucauuucuu uuaaagcaaa agcaauuuuc ugaaaauuuu caccauuuac | 120 |
| gaacgauagc caugcuuuuc aaccugagaa uccucuugaa caaugcugcu uuucggaaug | 180 |
| gccacaacuu uaugguucgg aacuccguu gcggccagcc uuuacaaaac aagguccagc | 240 |
| ugaagggccg ggauuugcuc acacuaaaga acuuuacugg agaagagauc aaguacaugc | 300 |

```
uauggcuguc ggccgaccug aaguuccgua ucaagcagaa gggagaauac cuuccgcugc    360
uucaaggaaa gagccucggc augaucuuug agaagcgcuc aaccaggacc cgccuuucua    420
cugaaacugg guucgcgcug cucgguggcc accccugcuu ccugacgacc caggacaucc    480
accucggagu gaacgaaucc cucaccgaua ccgcccgggu guuaucgagc auggcagaug    540 ccgucuggc cagggguguac aaacagcccg aucucgauac cuuggcaaag gaggcuucca    600
uucccaucau caacggccug agcgaccugu accacccaau ccaaauccug gcugacuacc    660
ugacccugca agagcacuac agcagccuga agggucugac ccugucaugg auuggcgaug    720
gaaacaauau ucugcacucc aucaugaugu ccgccgcgaa guucgaaaug caucugcaag    780
ccgccacucc aaaaggauac gaaccggaug cguccgugac caaguuggcg aacaguacg    840 cgaaggagaa cggaaccaag cuucugcuga cuaacgaccc ccucgaggcu gcgcauggg    900 gcaacgugcu gauuaccgac accuggaucu ccaugggca ggaggaagag aagaagaaga    960
gacugcaggc auccagggg uaccagguca ccaugaaaac cgcaaaagug gcagcuucgg   1020
acuggacuuu ccugcauugc cugccgagga agccggagga agucgacgac gaaguguucu   1080
acucgccucg gucccuggug uucccgagg ccgaaaaccg gaaguggacc aucauggccg   1140 ugauggguc cuugcugacu gacuauagcc cgcagcugca gaagccuaag uucuagcucg   1200 agcuaguga ugacuaggau cugguuacca cuaaaccagc cucaagaaca cccgaaugga   1260
gucucuaagc uacauaauac caacuuacac uuacaaaaug uugccccca aauguagcc   1320 auucguaucu gcuccuaaua aaagaaagu uucuucacau ucuag                    1365
```

<210> SEQ ID NO 43
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 43

```
ucaacacaac auauacaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcug uucaaccugc gaauccugcu gaacaacgcc gcuuuucgga    180
acgggcacaa cuuuauggug aggaacuuuc gcugcggaca gccccuccag aauaaggucc    240
agcugaaggg cagggaccug cugacccuga aaauuucac aggggaggaa caucaaguaua    300 ugcuguggcu gucagcugau cugaaguucc ggaucaagca gaagggcgaa uaucugccuc    360
ugcuccaggg caaaagccug gggaugaucu ucgaaaagcg caguacucgg accagacugu    420
caaccgagac uggauucgcu cugcugggag gacacccuug uuuucugacc acucaggaca    480
uucaccuggg agugaacgag ucccugaccg acacugcucg cguccugagc ucuauggccg    540
acgcugugcu ggcucgaguc uacaaacagu ccgaccugga uacccuggcc aaggaagcuu    600
cuaucccaau uauuaacggc cugucagacc uguaucaccc cauccagauu cuggccgauu    660
accugacccu ccaggagcac uauucuaguc ugaaagggcu gacacugagu uggauuggg    720 acggaaacaa uauccugcac ucuauuauga gucagccgc caaguuugga augcaccucc    780
aggcugcaac cccaaaaggc uacgaacccg augccucagu gacaaagcug gcgaacagu    840 acgccaaaga gaacggcacu aagcugcugc ugaccaacga cccucuggag gccgcucacg    900
gaggcaacgu gcugaucacc gauaccugga uuaguaugg acaggaggaa gagaagaaga    960
```

| agcggcucca ggccuuccag ggcuaccagg ugacaaugaa aaccgcuaag gucgcagcca | 1020 |
| gcgauuggac cuuucugcac ugccugccca gaaagcccga agagguggac gacgaggucu | 1080 |
| ucuacucucc cagaagccug uguuucccg aagcugagaa uaggaagugg acaauuaugg | 1140 |
| cagugauggu cagccugcug acugauuauu caccucagcu ccagaaacca aaguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu ccccaaaau | 1320 |
| guagccauuc guaucugcuc cuaauaaaaa gaaaguuucu ucacauucua g | 1371 |

<210> SEQ ID NO 44
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 44

| ucaacacaac auaucaaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug uucaaccugc gcauccugcu gaacaacgcc gccuccgca | 180 |
| acggccacaa cuucaugguc gcaacuuccg cugcggcca gccccugcag aacaaggugc | 240 |
| agcugaaggg ccgcgaccug cugacccuga gaacuucac cggcgaggag aucaaguaca | 300 |
| ugcuguggcu gagcgccgac cugaaguucc gcaucaagca aagggcgag uaccugcccc | 360 |
| ugcugcaggg caagagccug ggcaugaucu ucgagaagcg cagcacccgc acccgccuga | 420 |
| gcaccgagac aggccuggcc cugcugggcg ccaccccug cuccugacc acccaggaca | 480 |
| uccaccuggg cgugaacgag agccugaccg acaccgcccg cgugcugagc agcauggccg | 540 |
| acgccgugcu ggccccgcgug acaagcaga gcgaccugga cacccuggcc aaggaggcca | 600 |
| gcauccccau caucaacggc cugagcgacc uguaccaccc cauccagauc cuggccgacu | 660 |
| accugacccu gcaggagcac uacagcagcc ugaagggccu gacccugagc uggaucggcg | 720 |
| acggcaacaa cauccugcac agcaucauga ugagcgccgc caaguucggc augcaccugc | 780 |
| aggccgccac ccccaagggc uacgagcccg acgccagcgu gaccaagcug gccgagcagu | 840 |
| acgccaagga gaacggcacc aagcugcugc ugaccaacga ccccugaag gccgccacg | 900 |
| gcggcaacgu gcugaucacc gacaccugga ucagcauggg ccaggaggag gagaagaaga | 960 |
| agcgccugca ggccuuccag ggcuaccagg ugaccaugaa gaccgccaag guggccgcca | 1020 |
| gcgacuggac cuuccugcac ugccugcccc gcaagcccga ggagguggac gacgagguga | 1080 |
| ucuacagccc ccgcagccug uguuccccg aggccgagaa ccgcaagugg accaucaugg | 1140 |
| ccgugauggu gagccugcug accgacuaca gccccagcu gcagaagccc aaguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu ccccaaaau | 1320 |
| guagccauuc guaucugcuc cuaauaaaaa gaaaguuucu ucacauucua g | 1371 |

<210> SEQ ID NO 45
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 45

```
ucaacacaac auaucaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcug uucaaccugc gaauccugcu gaacaacgcc gcuuuucgga   180
acgggcacaa cuuuaugguc aggaacuuuc gcugcggaca gccccuccag aauaaggucc   240
agcugaaggg cagggaccug cugacccuga aaaauuucac aggggaggaa aucaaguaua   300
ugcuguggcu gucagcugau cugaaguucc ggaucaagca aagggcgaa uaucugccuc    360
ugcuccaggg caaaagccug gggaugaucu ucgaaaagcg caguacucgg accagacugu   420
caaccgagac uggauucgcu cugcgggag acacccuug uuuucugacc acucaggaca    480
uucaccuggg agugaacgag ucccugaccg acacugcucg cguccugagc ucuauggccg   540
acgcugugcu agcucgaguc uacaaacagu ccgaccugga uacccuggcc aaggaagcuu   600
cuaucccaau uauuaacggc cugucagacc uguaucaccc cauccagauu cuggccgauu   660
accugacccu ccaggagcac uauucuaguc ugaaagggcu gacacugagu uggauugggg   720
acggaaacaa uauccugcac ucuauuauga gucagccgc caaguuugga augcaccucc    780
aggcugcaac cccaaaaggc uacgaacccg augccucagu acaaagcug gcugaacagu    840
acgccaaaga gaacggcacu aagcugcugc ugaccaacga cccucuggag ccgcucacg    900
gaggcaacgu gcugaucacc gauaccugga uuaguauggg acaggaggaa gagaagaaga   960
agcggcucca ggccuuccag ggcuaccagg ugacaaugaa aaccgcuaag gucgcagcca  1020
gcgauuggac cuuucugcac ugccugccca gaaagcccga gaggugac gacgagucu    1080
ucuacucucc cagaagccug uguuucccg aagcugagaa uaggaagugg acaauuaugg   1140
cagugauggu cagccugcug acugauuauu caccucagcu ccagaaacca aaguucugau   1200
aacucgagcu agugacugac uaggaucugg uuaccacaa accagcccuca gaacacccg    1260
aauggagucu cuaagcuaca uaauaccaac uuacacuuac aaaauguugu cccccaaaau   1320
guagccauuc guaucugcuc cuaauaaaaa gaaaguuucu ucacauucua g            1371
```

<210> SEQ ID NO 46
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 46

```
ucaacacaac auaucaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcug uucaaccugc gaauccugcu gaacaaugcc gcuuuucgga   180
acgggcacaa uuucaugguc aggaacuuuc gcugcggaca gccccuccag aacaaggucc   240
agcugaaggg cagggaccug cugacccuga aaaauuucac aggggaggaa aucaaguaca   300
ugcuguggcu gucagccgau cugaaguucc ggaucaagca aagggcgaa uaucugccuc    360
ugcuccaggg caaaagccug gggaugaucu ucgaaaagcg caguacucgg accagacugu   420
caacagagac uggauucgca cugcgggag acacccaug uuuucugacc acacaggaca    480
uucaucuggg agugaacgag ucccugaccg acacagcacg cguccugagc uccauggcug   540
augcagugcu ggcucgaguc uacaaacagu cugaccugga uacccuggcc aaggaagcuu   600
```

| | |
|---|---|
| cuaucccaau cauuaauggc cugagugacc uguaucaccc cauccagauu cuggccgauu | 660 |
| accugacccu ccaggagcau uauucuaguc ugaaagggcu gacacugagc uggauugggg | 720 |
| acggaaacaa uauccugcac uccauuauga ugagcgccgc caaguuugga augcaccucc | 780 |
| aggcugcaac cccaaaaggc uacgaacccg augccuccgu gacaaagcug gcagaacagu | 840 |
| augccaaaga gaacggcacu aagcugcugc ugaccaauga cccucuggag gccgcucacg | 900 |
| gaggcaacgu gcugaucacu gauaccugga uuaguauggg acaggaggaa gagaagaaga | 960 |
| agcggcucca ggccuuccag ggcuaccagg ugacaaugaa aacugcuaag gucgcagcca | 1020 |
| gcgacuggac cuuucugcau ugccugccca gaaagccuga gagguggac gaugaggucu | 1080 |
| ucuacucacc cagaagccug uguuuccug aagcugagaa uaggaagugg acaaucaugg | 1140 |
| cagugauggu cagccugcug acugauuauu ccccucagcu ccagaaacca aguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu ccccaaaau | 1320 |
| guagccauuc guaucugcuc cuauaaaaaa gaaaguuucu ucacauucua g | 1371 |

<210> SEQ ID NO 47
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 47

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaccuuc gcauucuccu caacaacgcc gcguuuagaa | 180 |
| acggacacaa cuucaugguc cgcaacuccc gcugcggaca gccgcugcag aacaaggucc | 240 |
| agcucaaggg ucgggaucuc cugacgcuga agaacuuuac cggcgaagag auuaaguaca | 300 |
| ugcuguggcu guccgccgac cuuaaguucc ggaucaagca gaagggcgaa uaccuucccc | 360 |
| ugcugcaagg aaagucccug ggcaugaucu ucgagaagcg caguaccaga accagacucu | 420 |
| ccacugaaac cggguucgcg cugcuuggcg gccacccgug uuccucacu acgcaagaca | 480 |
| uccaucuugg cgugaacgag ucccuuaccg acaccgccag ggugcuguca agcauggccg | 540 |
| acgccguccu ugcgcgcgug uacaagcagu cagaccuuga uacucuggcc aaggaagccu | 600 |
| ccaucccuau uaucaacggc cuauccgacc uuuaccaccc gauccagauc ucgcugacu | 660 |
| accugacccu gcaagaacac uacagcagcc ucaagggacu gacucuguuc uggaucggcg | 720 |
| acgggaacaa cauccugcac ucaaucauga ugagcgcagc caaguucggc augcaucucc | 780 |
| aagccgcuac acccaagggu uaugaaccgg acgccucugu gaccaaguug gcagaacagu | 840 |
| acgccaagga gaacggguacu aagcuccuuu uaaccaacga cccccucgaa gcagcccaug | 900 |
| gcgggaaugu gcucauuacc gauaccugga uucgaugggg ccaggaggag gagaagaaga | 960 |
| agcggcugca ggcguuccag ggcuaccagg ucaccaugaa aacugccaaa guggccgccu | 1020 |
| cggauuggac cuuucuccac ugccugccuc ggaagccuga ggagguggac gacgaagugu | 1080 |
| ucuacucccc acggucccuc guguccccg aggccgaaaa uaggaagugg accaucaugg | 1140 |
| ccgugauggu gucccucuug accgauuaca gcccgcagcu ucagaagccu aaauucuagc | 1200 |
| ucgagcuagu gacugacuag gaucugguua ccacuaaacc agccucaaga cacccgaau | 1260 |

| | |
|---|---|
| ggagucucua agcuacauaa uaccaacuua cacuuacaaa auguugcccc ccaaaaugua | 1320 |
| gccauucgua ucugcuccua auaaaaagaa aguuucuuca cauucuag | 1368 |

<210> SEQ ID NO 48
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 48

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucuuc gcauccuguu gaacaacgcc gccuuccgca | 180 |
| auggucacaa cuucaugguc cggaacuuca gauguggaca gccucuccaa aacaaggucc | 240 |
| agcugaaggg aagggaccuc uuaacccuca aaaacuuuac uggagaggag aucaaguaca | 300 |
| ugcuguggcu uagcgccgac cuuaaguucc ggaucaagca aagggagag uaccucccgc | 360 |
| ugcugcaagg aaagagucuu ggaaugaucu ucgagaagcg guccaccaga acucgccucu | 420 |
| ccacugaaac cggauucgca cuccugggug acacccgug cuuucugacc acccaagaca | 480 |
| uccaccucgg agugaacgag agccucacgg acaccgcgag agucuguca uccauggccg | 540 |
| acgccgugcu ugcacgguc uacaagcagu ccgaucugga cacucuugcc aaggaagccu | 600 |
| ccauuccuau cauuaacggu cugucggauc uguaccaccc gauucagauc cuugcggacu | 660 |
| accucacacu ucaagaacac uauucaagcc uaaagggucu gacccugucc uggaucggag | 720 |
| auggaaacaa cauucuccau uccaucauga ugagcgcugc caaguucgga augcaucucc | 780 |
| aagcagcgac uccuaagggu uacgagccgg acgccucagu gacuaagcug gccgagcagu | 840 |
| acgccaagga gaacgguacc aaacuguugc uuacuaacga cccgcuugaa gcggcccaug | 900 |
| gaggaaacgu gcugauuacc gacaccugga uuucgauggg acaggaagag gagaagaaga | 960 |
| agcggcucca ggcguuccag ggauaccagg ucaccaugaa acggccaaa guggccgcua | 1020 |
| gcgauuggac cuuucugcac ugccucccgc gcaagccuga agaagguggac gacgaagugu | 1080 |
| ucuacucccc ucgcucucuu guguucccgg aagccgaaaa caggaagugg accaucaugg | 1140 |
| ccgugauggu gucccuccug accgauuaca gcccgcagcu gcagaagccu aaguucuagc | 1200 |
| ucgagcuagu gacugacuag gaucugguua ccacuaaacc agccucaaga cacccgaaau | 1260 |
| ggagucucua agcuacauaa uaccaacuua cacuuacaaa auguugcccc ccaaaaugua | 1320 |
| gccauucgua ucugcuccua auaaaaagaa aguuucuuca cauucuag | 1368 |

<210> SEQ ID NO 49
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 49

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucucc gcauccuccu caacaacgcc gcguuuagaa | 180 |
| acggccacaa cuucaugguc cggaacuuca gauguggcca gccgcuucag aacaaggucc | 240 |

| | |
|---|---|
| agcucaaggg ccgggaucuuu cugacccuga agaacuuuac uggcgaagaa aucaaguaca | 300 |
| ugcucuggcu cuccgccgac uugaaguucc gcauuaagca gaaggggaa uaccuuccgc | 360 |
| ugcugcaagg aaagucgcuc ggcaugaucu uugagaagcg cucaacccgc accaggcugu | 420 |
| ccacugaaac cggguucgcg cugcuuggug gccaccccug cuccugacc acccaagaca | 480 |
| uucaccucgg agugaacgaa ucgcucacug auacugcccg ggugcugucg ucgauggccg | 540 |
| augcagugcu ggccaggggug uacaaacagu ccgaucugga cacucuggcc aaggaggcgu | 600 |
| ccaucccuau uaucaacggc cuuuccgacc ucuaccaccc gauucagauc cuugccgauu | 660 |
| accucacccu gcaagaacac uacucgucac ugaagggucu gaccuugucc uggaucggcg | 720 |
| acggcaacaa cauccuccau uccauuauga ugucgccgc caaauucggc augcaucuuc | 780 |
| aagccgcaac cccuaagggu uacgagccgg acgcuuccgu gaccaagcuc gccgagcagu | 840 |
| acgcuaagga gaacggaacc aagcuucgc ugacuaacga cccccuagag gcagcccacg | 900 |
| ggggcaacgu gcuuauuacu gacaccugga ucuccauggg acaggaagaa gagaagaaga | 960 |
| agcgguuaca ggcguuccag ggcuaucagg ucaccaugaa aaccgccaag gucgcugccu | 1020 |
| cggacuggac cuuccugcau ugccugccuc gcaagcccga agaguggac gacgagugu | 1080 |
| ucuacucgcc acgucccuu uguucccug aggccgagaa uagaaagugg accauuaugg | 1140 |
| ccgugauggu ucccuucuc accgacuacu cgccgcaacu gcagaaaccc aaguucuagc | 1200 |
| ucgagcuagu gacugacuag gaucugguua ccacuaaacc agccucaaga cacccgaau | 1260 |
| ggagucucua agcuacauaa uaccaacuua cacuuacaaa auguugcccc ccaaaaugua | 1320 |
| gccauucgua ucugcuccua auaaaaagaa aguuucuuca cauucuag | 1368 |

<210> SEQ ID NO 50
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 50

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucuuc gcauccuccu caacaacgcc gccuuccgga | 180 |
| acggucacaa cuucauggu cggaacuucc gcugcggcca gccgcuccaa acaaagugc | 240 |
| agcuuaaggg ccgcgaucuc cugacccuga agaacuucac cggagaggaa aucaaguaca | 300 |
| ugcugugggcu cucggcggac cugaaguuua ggauuaagca gaaggggag uaucugccgc | 360 |
| ugcuccaagg gaagucccuu ggcaugaucu ucgaaaagag guccacccgg acucggcuca | 420 |
| gcaccgaaac agguuuugca cuucgggggg gccacccgug cuuccugacg acccaggaca | 480 |
| uccaucuggg ugucaacgag aguuugaccg acacugccag agugcuguca uccauggcgg | 540 |
| acgcggugcu cgcgagagug uacaagcagu ccgaucuuga cacccuggca aaagaggcuu | 600 |
| caaucccgau cauuaacgga cucucggauc uguaccaccc uauccaaauc uuggccgacu | 660 |
| accugacccu gcaagaacac uacagcuccc ugaagggccu gacucuuuc uggauuggcg | 720 |
| auggaaacaa cauucuccau ucuauuauga ugucgccgc caaguucggc augcaccuuc | 780 |
| aagccgccac cccgaagggc uacgaaccug acgccuccgu gacuaagcua gccgaacagu | 840 |
| acgcuaagga gaacggcacu aagcuucgcc uuaccaacga uccgcuggag gcggcccaug | 900 |
| gcggaaaugu gcuuaucacc gacaccugga uuagcauggg gcaggaagaa gagaagaaga | 960 |

| | | |
|---|---|---|
| aacggcucca ggcauuccag ggcuaccagg ucaccaugaa aacugccaag gucgccgcua | 1020 | |
| gcgacuggac cuuccuccac ugucugccuc gcaagccuga agaaguggac gacgaggugu | 1080 | |
| ucuaccccc gcgcucccuc guguuuccug aggccgagaa cagaaagugg accaucaugg | 1140 | |
| ccgugauggu ucauuacuu acggacuaca gcccgcagcu gcagaagccg aaguucuagc | 1200 | |
| ucgagcuagu gacugacuag gaucggguua ccacuaaacc agccucaaga acacccgaau | 1260 | |
| ggagucucua agcacauaa uaccaacuua cacuuacaaa auguugcccc ccaaaaugua | 1320 | |
| gccauucgua ucugcuccua auaaaaagaa aguuucuuca cauucuag | 1368 | |

<210> SEQ ID NO 51
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 51

| | | |
|---|---|---|
| ucaacacaac auauacaaaa caaacgaauc ucaagcaauc aagcauucua cuucuauugc | 60 | |
| agcaauuuaa aucauuucuu uuaaagcaaa agcaauuuuc ugaaaauuuu caccauuuac | 120 | |
| gaacgauagc caccaugcuu uuuaacuuga gaauccuucu gaacaacgcc gcuuuccgca | 180 | |
| acgucauaa cuucuggguc cggaacuuca gauguggcca gccccuccaa aacaaagugc | 240 | |
| agcugaaggg ccgggaccuu cuuacgcuga agaauuucac cggcgaagaa aucaaguaca | 300 | |
| ugcucuggcu guccgccgau cuuaaguucc gcauuaagca gaaggggaa uaccucccgc | 360 | |
| ugcugcaagg gaagucgcug ggcaugauuu uugagaagcg gucaacucgc acccgccugu | 420 | |
| ccacugaaac uggaucgca cugcucggug gccaucccug cuuccugacc acccaagaca | 480 | |
| uccaccucgg cgugaacgag ucccugacug acaccgcccg ggucuuaucc ucgauggccg | 540 | |
| augcugugcu ugcgagggug uacaagcagu ccgaccucga cacacucgcg aaggaggccu | 600 | |
| ccaucccau caucaacggc cugucgacc uuuaccaccc aauucagauc ucgccgauu | 660 | |
| accugacccu gcaagagcac uacucgucgc ucaaggggcu uacccucucg uggauuggcg | 720 | |
| acggcaacaa cauccuucac uccaucauga ugucggcagc gaaguucggc augcaucugc | 780 | |
| aagccgccac gccuaagggu uaugaaccgg augccucagu gaccaagcuc gccgaacagu | 840 | |
| acgcgaaaga gaauggaacc aagcauuuc ugaccaacga cccccuggag gccgcucacg | 900 | |
| gcggcaacgu ccucauuacc gauacuugga uucgaugggg acaggaagag gaaaagaaga | 960 | |
| agagacugca ggcguuccag ggauaccagg ucaccaugaa aacugccaaa guggcagccu | 1020 | |
| ccgacuggac cuuccuucac ugccugccga ggaagccuga agagguggac gacgaggugu | 1080 | |
| ucuaccccc gcgcucccuug guguuuccug aggccgaaaa ccggaagugg acuaucaugg | 1140 | |
| ccgugauggu ucccuccuc accgacuacu cgccgcaacu gcagaagccu aaguucuagc | 1200 | |
| ucgagcuagu gacugacuag gaucggguua ccacuaaacc agccucaaga acacccgaau | 1260 | |
| ggagucucua agcacauaa uaccaacuua cacuuacaaa auguugcccc ccaaaaugua | 1320 | |
| gccauucgua ucugcuccua auaaaaagaa aguuucuuca cauucuag | 1368 | |

<210> SEQ ID NO 52
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 52

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccauguua uucaaccuua gaauucuccu uaacaacgcc gccuuccgga   180
augggcauaa cuuuauggug cgcaauuucc gcuguggaca gccucugcaa aacaaggucc   240
agcucaaggg ccgggaucug cugacucuca agaacuucac uggggaagaa ucaaguaca   300
ugcucuggcu gagcgccgac cucaaguucc gcaucaagca gaagggagag uaccucccgc   360
ugcuccaagg gaaguccug gcaugaaucu ucgagaagag auccacccgc accagacuuu    420
ccacugagac uggcuucgcc uugcugggag gccacccaug cuuccugacg acccaggaca   480
uucaccuugg cgugaacgag ucccugacug acaccgcaag ggguguuguc ucgauggccg   540
acgccgugcu ugcccggug uacaagcaga gcgaucuuga cacccuggcu aaggaagcuu    600
ccauucccau caucaacggu cugagcgacc uguaccaccc gauucagauc cuggcggacu   660
accuaacccu gcaagagcac auaagcuccc ugaagggccu cacacuuuca uggaucggcg   720
acggcaacaa cauccugcac ucuauuauga ugagcgcugc caaauucggc augcaccucc   780
aagccgccac gccuaaaggc uacgagcccg acgccucggu gaccaagcuu gcggagcagu   840
acgcgaagga aaacggcacc aagcugcuuc ucaccaacga uccucuggaa gcggcccaug   900
guggcaacgu gcucauuacc gacacuugga ucuccauggg acaggaggag gaaaagaaga   960
agcggcucca ggcguuucag gguuaccagg ucaccaugaa aaccgccaag gucgcagccu  1020
ccgacuggac cuuccuucau ugccuuccgc gcaagcccga agaaguggac gaugaagugu  1080
uuuacucacc ucggucacuc gguguuccgg aagcagagaa caggaaaugg accauuaugg  1140
ccgugauggu gucccugcuc accgauuaca guccgcaacu gcagaagccc aaguucuagc  1200
ucgagcuagu gacugacuag gaucugguua ccacuaaaacc agccucaaga acacccgaau  1260
ggagucucua agcuacauaa uaccaacuua cacuuacaaa auuguguccc ccaaaaugua  1320
gccauucgua ucugcuccua auaaaagaa aguuucuuca cauucuag                1368
```

<210> SEQ ID NO 53
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 53

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcuu uucaaucucc gcauccuccu uaacaacgcc gcguuuagaa   180
acggccacaa cuucugguc cggaacuuca gauguggcca gccgcuucaa aacaaggucc   240
agcugaaggg ccgggaucuu cugacccuga gaacuuuac uggcgaagag aucaaguaca   300
ugcucuggcu cuccgcggac uugaaguucc gcauuaagca aaggggggaa uaccuuccgc   360
ugcuucaagg aaagagccuc ggcaugaucu uugagaagcg cucaaccagg acccgccuuu   420
cuacugaaac uggguucgcg cugcucggug gccacccccug cuuccugacg acccaggaca   480
uccaccucgg agugaacgaa ucccucaccg auaccgcccg gguguuaucg agcauggcag   540
augccgugcu ggccaggguug uacaaacagu ccgaucgga cacucuggcc aaggaggcgu   600
caauuccuau uaucaacggc cuuagugacc ucuaccaucc gauucaaauc cuggccgauu   660
```

| | |
|---|---|
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccuaagggu uacgaacccg acgcuuccgu gacuaagcuc gccgagcagu | 840 |
| acgcuaagga gaacggaacc aagcugcugc ugacuaacga cccgcuagaa gcagccacg | 900 |
| ggggcaacgu gcuuauuacu gacaccugga ucuccauggg ccaggaggaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagccuga agaaguggac gacgaggugu | 1080 |
| ucuacucgcc acggagccuc guguuccccg aggccgagaa uagaaagugg accaucaugg | 1140 |
| ccgugauggu gucacuucuc accgacuaca gcccgcagcu ucagaagccc aaguucuagc | 1200 |
| ucgagcuagu gacugacuag gaucugguua ccacuaaacc agccucaaga cacccgaau | 1260 |
| ggagucucua agcuacauaa uaccaacuua cacuuacaaa auguguccc ccaaaaugua | 1320 |
| gccauucgua ucugcuccua auaaaaagaa aguuucuuca cauucuag | 1368 |

<210> SEQ ID NO 54
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 54

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucucc gcauccuccu uaacaacgcc gcguuuagaa | 180 |
| acggccacaa cuucuggguc cggaacuuca gaugugggca gccgcuucaa aacaaggucc | 240 |
| agcuuaaggg ccgggaucuc cucacccuua aaaacuuuac cggcgaagag aucaaguaca | 300 |
| ugcucuggcu cuccgcggac cuuaaguucc gcauuaagca gaaggggggaa uaccuuccgc | 360 |
| ugcuucaagg aaagagccuc ggcaugaucu uugagaagcg cucaaccagg accaggcuuu | 420 |
| cuacugaaac ugggguucgcg cuucucggcg gucaucccug cuuccucacg acccaagaca | 480 |
| uccaccucgg agugaacgaa uccucacggg auacugcccg cgugcuuucg agcauggcag | 540 |
| acgccgugcu cgcccggggug uacaaacagu ccgaucucga cacucucgcc aaggaggcgu | 600 |
| caauuccuau uaucaacggu cuuagugacc uuuaccaccc gauccagauc ucgccgauu | 660 |
| accucacacu ccaagaacac uacagcuccc uuaaggggucu uacccucucc uggaucggcg | 720 |
| acggcaacaa cauucuccac uccaucauga uguccgccgc aaaguucggc augcaucuuc | 780 |
| aagccgccac cccgaagggc uacgagccug augcuuccgu gacuaagcuc gccgagcagu | 840 |
| acgcuaagga gaacggaacc aagcuucuuc ucacuaacga cccacucgaa gcagcccaug | 900 |
| ggggcaacgu gcuuaucacu gacaccugga ucuccauggg ccaggaagaa gagaagaaga | 960 |
| agcggcucca ggcguuccag ggauaucagg ucaccaugaa aaccgccaag gucgcugccu | 1020 |
| ccgacuggac cuuucuccac ugccucccuc gcaaaccuga agaaguggac gacgaggugu | 1080 |
| ucuacucgcc ccggagccuc guguuccccg aggccgagaa uagaaaguggg accauuaugg | 1140 |
| ccgugauggu gucacuccuc accgacuaca gcccgcagcu ucagaagccc aaguucuagc | 1200 |
| ucgagcuagu gacugacuag gaucugguua ccacuaaacc agccucaaga cacccgaau | 1260 |

-continued

| | |
|---|---|
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 55
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 55

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaucucc gcauccuccu uaacaacgcc gcguuuagaa | 180 |
| acggacauaa cuucaugguc cggaacuuca gauggacagc cgcuucaa aacaaggucc | 240 |
| agcugaaggg ucgggaucuu cugacccuga gaacuuuac cggagaagag aucaaguaca | 300 |
| ugcucuggcu cuccgcggac uugaaguucc gcauuaagca gaagggagaa uaccucccgc | 360 |
| ugcuucaagg aaagagccuc ggaaugauuu uugagaagcg cucaaccagg acccgccuuu | 420 |
| cuacugaaac uggauucgcg cugcugggug gacaccccug cuuccugacg acccaggaca | 480 |
| uccaccucgg agugaacgaa ucccucacug auaccgcccg gguguuaucg agcauggcag | 540 |
| augccgugcu ggccaggugu acaaacagu ccgaucugga cacucuggcc aaggaggcgu | 600 |
| caauuccuau caucaacgga cuuagugacc ucuaccaucc gauucaaauc cuggccgacu | 660 |
| accucacccu gcaagaacac uacagcuccc ugaagggucu gacauugucc uggaucggag | 720 |
| auggaaacaa cauucuccac uccaucauga uguccgccgc aaaauucgga augcaucuuc | 780 |
| aagccgccac gccuaagggu uacgaacccg acgcuuccgu gacuaagcuc gccgagcagu | 840 |
| acgcuaagga gaacgguacc aagcuucucc ugaccaacga cccacuagaa gcagcccacg | 900 |
| guggaaacgu gcuuauuacu gacacuugga ucuccauggg acaggaggaa gagaaaaaga | 960 |
| agcggcugca ggcguuccag ggauaucagg ucaccaugaa aaccgccaag gucgcugccu | 1020 |
| ccgacuggac cuuccugcac ugccugcccuc gcaagccuga agaaguggac gacgaggugu | 1080 |
| ucuacucgcc gcggagccuc uguucccccg aggccgagaa uagaaagugg accaucaugg | 1140 |
| ccgugauggu gucacugcuc accgacuaca gcccgcagcu ucagaagccc aaguucuagc | 1200 |
| ucgagcuagu gacugacuag gaucgguua ccacuaaacc agccucaaga acacccgaau | 1260 |
| ggagucucua agcuacauaa uaccaacuua cacuuacaaa auguuguccc ccaaaaugua | 1320 |
| gccauucgua ucugcuccua auaaaaagaa aguuucuuca cauucuag | 1368 |

<210> SEQ ID NO 56
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 56

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu uucaaccucc gcauucuccu caacaacgcu gccuuccgga | 180 |
| auggacauaa cuucaugguc cggaacuuca gaugcggaca gccgcuucag aacaaggucc | 240 |

```
agcuuaaggg gagagaucuc cuuacccuca aaaacuucac uggcgaagaa aucaaguaca      300
ugcucuggcu uagugcggau ucaaguucc gcaucaagca gaaggagaa uaccucccgc       360 uccuucaagg aaagagccuc ggcaugauuu ugagaagag guccaccaga acucgccuuu      420
caaccgagac uggguucgcc cugcuuggcg gucacccug cuuccucacu acccaagaca      480
uccaccucgg cgugaacgag agccuuaccg acaccgcccg cgugcucucc ucaauggccg     540
acgcugugcu cgcccgggug uacaagcagu ccgaccuuga uacucucgcc aaggaggccu     600
ccaucccaau uaucaacggg cucucugauc ucuaccaccc uaccaaauc ucgcggacu       660 accucacccu ccaagagcac uauagcucg ucaagggccu caccuuucc uggauuggcg      720 acggcaacaa cauucuucac ucgaucauga ugaccgccgc caaguucggc augcaucuc     780 aagccgcgac ccccaagggc uacgagccug acgcauccgu gaccaagcuc gccgagcagu    840
acgcgaagga aaauggcacc aagcuucuuc ucaccaacga cccccuugag gccgucaug     900 gcggcaacgu gcucaucacu gacacuggga ucagcaugg ccaggaggag gaaaagaaga    960
agcgccuuca ggcauccag gguuaccagg ucaccaugaa aaccgccaaa guggccgccu    1020
ccgacuggac cuuucuuac ugucucccgc ggaagccuga agaaguggau gacgaagugu     1080
uuuacucccc ucggucacuc guguuccgg aagcagaaaa caggaagugg accauuaugg    1140
cggucauggu ucccuccuc accgacuaca gcccgcagcu ucagaaaccc aaguucuagc     1200
ucgagcuagu gacugacuag gaucggguua ccacuaaaacc agccucaaga acacccgaau   1260
ggagucucua agcuacauaa uaccaacuua cacuuacaaa auguugcccc ccaaaauguga  1320 gccauucgua ucugcuccua auaaaaagaa aguuucuuca cauucuag                1368
```

<210> SEQ ID NO 57
<211> LENGTH: 1368
<212> TYPE: RNA
<213> ORGANISM: Artificial sequence
<220> FEATURE:
<223> OTHER INFORMATION: Synthetic polynucleotide
<400> SEQUENCE: 57

```
ucaacacaac auauacaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcuu uucaaucucc gcauccuccu uaacaacgca gcguuuagaa    180
acggucacaa cuucaugguc cggaacuucc gcuguggaca gccgcuucaa aacaaggucc    240
agcugaaggg ucgggaccuu cugacccuga agaacuuuac uggagaagag aucaaguaca   300
ugcuuuggcu guccgcggac uugaaguucc gcauuaagca gaagggagaa uaccuuccgc    360
ugcuccaagg aaagagccug ggaaugaucu uugagaagcg cucaaccagg acccgccuuu    420
cuacugaaac uggauucgcg cugcugggug ucacccuug cuuccugacg acccaggaca    480
uucaccucgg agugaacgag ucccucacug uauccgccag agugguaucg agcauggcag   540
augccgugcu ggcuagggug uacaaacagu ccgaucugga cacccuggcc aaggaggcau    600
caauuccuau uaucaacgga cuuagugacc ucuaccaucc gauucaaauc cuggccgauu    660
accucacccu gcaagaacac uacagcuccc ugaagggucu gacauugucc uggaucggag   720
auggaaacaa cauucuccau uccaucauga ugaccgcggc caaguucgga augcaucuc    780 aagccgccac gccgaaagga uacgagccgg acgcuuccgu gacuaagcuc gccgagcagu    840
acgcuaagga gaacggaacc aagcuucgc ugacuaacga cccgcuagaa gccgccacg    900 guggaaacgu gcuuauuacu gacaccugga ucuccaugg acaggaagaa gagaaaaaga   960
```

| | | |
|---|---|---|
| agcggcugca ggcguuccag ggauaucagg ucaccaugaa aaccgccaag gucgccgccu | 1020 | |
| ccgacuggac cuuccuucac ugccugccuc ggaagccuga agaaguggac gacgaggugu | 1080 | |
| ucuacucgcc gcggagccuc uguucccug aggccgagaa uagaaagugg accaucaugg | 1140 | |
| ccgugauggu gucacuccuc accgacuaca gcccgcagcu ucagaagccu aaguucuagc | 1200 | |
| ucgagcuagu gacugacuag gaucugguua ccacuaaacc agccucaaga acacccgaau | 1260 | |
| ggagucucua agcuacauaa uaccaacuua cacuuacaaa auguugcccc ccaaaaugua | 1320 | |
| gccauucgua ucugcuccua auaaaaagaa aguuucuuca cauucuag | 1368 | |

<210> SEQ ID NO 58
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 58

| | | |
|---|---|---|
| ucaacacaac auauacaaaa caaacgaauc ucaagcaauc aagcauucua cuucuauugc | 60 | |
| agcaauuuaa aucauuucuu uuaaagcaaa agcaauuuuc ugaaaauuuu caccauuuac | 120 | |
| gaacgauagc caccaugcuu uucaaucucc gcauucccu caacaacgca gccuuuagaa | 180 | |
| acggccacaa cuucuggguc cggaacuuca gaugugggca gccgcuucag aacaaggucc | 240 | |
| agcucaaggg ccgggaccuc cucacccuca aaaacuuuac cggcgaagag aucaaguaca | 300 | |
| ugcucuggcu uucggccgac cuuaagucc gcaucaagca gaaggggggaa uaccuuccgc | 360 | |
| ugcuucaagg aaaguccccuc ggcaugaucu uugaaaagcg cucgaccagg acccgccuuu | 420 | |
| ccacugaaac cgggucgcg cuucucggug gccaccccug cuuccucacc acccaagaca | 480 | |
| uucaccucgg agugaacgaa ucccuuaccg auaccgcaag agugcuuucg ucgauggccg | 540 | |
| augccgugcu ugcgcgggug uacaagcagu cagaucucga cacucucgcc aaggaggcgu | 600 | |
| ccauuccuau uaucaacggc cuuuccgacc uuuaccaccc gauucagauc ucgccgauu | 660 | |
| accucacccu gcaagagcac uacucgucac ucaagggucu uacccucucc uggaucggcg | 720 | |
| acggaaacaa cauccuccau ucgaucauga uguccgccgc caaauucggc augcaccucc | 780 | |
| aagccgcgac cccgaagggu uacgagcccg acgcuuccgu gaccaagcuc gccgaacagu | 840 | |
| acgcuaagga aaacggcacc aagcccuccu ucacuaacga cccucucgaa gcagcccaug | 900 | |
| ggggcaacgu gcucauuacu gacacuugga ucucgauggg ccaggaagag gagaaaaaga | 960 | |
| agcggcuuca ggcguuccag ggauaucagg ucaccaugaa aaccgccaag gucgcugccu | 1020 | |
| cggacuggac cuuccuucac ugccuuccgc gcaagccuga agagguggac gaugaggugu | 1080 | |
| ucuacucccc acggucccuu guguucccg aggccgagaa uaggaagugg accaucaugg | 1140 | |
| ccgugauggu gucgcuccuc acugacuacu ccccgcaacu ucagaagccu aaguucuagc | 1200 | |
| ucgagcuagu gacugacuag gaucugguua ccacuaaacc agccucaaga acacccgaau | 1260 | |
| ggagucucua agcuacauaa uaccaacuua cacuuacaaa auguugcccc ccaaaaugua | 1320 | |
| gccauucgua ucugcuccua auaaaaagaa aguuucuuca cauucuag | 1368 | |

<210> SEQ ID NO 59
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 59

```
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccaugcug uuuaaucuga gaauacuucu aaacaacgcc gccuuccgga     180
auggccauaa cuuuaugguu cggaauuucc gcugcggcca gccgcugcag aacaaggucc     240
agcugaaggg aagagacuug cugacccuca gaacuucac cggagaagaa aucaaguaua      300
ugcuguggcu guccgccgac cugaaauucc gcaucaagca aagggcgaa uaucugccgc      360
uguugcaagg gaaguccug gggaugaucu ucgagaagag guccaccaga acacggcuuu      420
caaccgaaac cggguuugca cugcugggug acaccccug uuuucugacc acucaagaua      480
uccaccuggg cgugaacgag ucccuuaccg acacugcuag ggguugucc agcauggccg      540
augccguccu ggcucgcgug uacaagcagu ccgaccugga uacccuggca aaggaagcgu     600
ccauucccau uaucaacggg cuguccgacc uguaccaucc gauucaaauc cuggcggacu     660
accugacucu gcaagagcau acagcagcu ugaaggggcu uacucucucg uggaucggcg     720
acgggaacaa cauccugcac uccaucauga uguccgccgc caaguucggg augcauuugc     780
aagcugcgac cccgaaaggu uacgagcccg augcuagcgu aacuaagcuu gccgaacagu     840
acgccaaaga gaauggguaca aaacugcuuc ugacuaacga cccgcuggaa gcagcccacg     900
gcgggaacgu gcugauaacc gacaccugga uuucaauggg gcaggaggaa gagaagaaga     960
agcgacugca ggcguuccaa ggcuaucagg uuaccaugaa aaccgccaaa guggcagcca    1020
gcgauuggac uuuccugcac ugucgccgc ggaagcccga ggaaguugau gacgaaguau     1080
ucuacucacc ccggagccuc guguccccg aggccgaaaa ccggaagugg acuauuaugg     1140
ccgugauggu gucgcuguug accgacuaca gcccgcaacu gcagaagccg aaguuuuagc    1200
ucgagcuagu gacugacuag gaucugguua ccacuaaacc agccucaaga acacccgaau    1260
ggagucucua agcuacauaa uaccaacuua cacuuacaaa auguuguccc ccaaaaugua    1320
gccauucgua ucugcuccua auaaaaagaa aguuucuuca cauucuag                1368
```

<210> SEQ ID NO 60
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 60

```
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccaugcuu uucaaccuga ggauccuuuu gaacaacgcc gccuuucgca     180
acggccacaa cuuuaugguc cgcaauuucc gcugcgggca gccgcugcag aacaaggucc     240
agcugaaggg ccgggaucug cugacccuga gaacuucac cggggaggaa aucaaguaca      300
ugcuuuggcu cuccgccgau cugaaguuca gaaucaagca aagggagag uaccucccgu      360
ugcugcaagg aaagucacuc ggaaugauuu ucgaaaagag aagcacuagg acccgccucu     420
caacugaaac cggguucgcg cugcucgggg ccauccgug uuuccugacu acccaagaca     480
uccaccuggg agugaacgag ucgcugaccg acaccgcacg cgugcuguca uccauggcgg     540
acgcagugcu gcccggggug uacaagcagu cggaccugga cacucuugcc aaggaggcau     600
caaucccau cauuaacgga cuguccgauc ucuaccaccc gauucagauc cuggcugacu     660
```

| | |
|---|---:|
| accuaacccu gcaagagcac uacucaagcc ugaaggggcu gacccugucg uggaucgggg | 720 |
| acggcaacaa cauucugcac uccaucauga ugucggcggc uaaguucggg augcauuugc | 780 |
| aagcggcaac uccgaagggu uaugaacccg acgccuccgu gaccaagcug gccgaacagu | 840 |
| acgcaagga aaacggaacc aaguugcugc ugacuaauga uccccuggag gcggcccacg | 900 |
| ggggaacgu gcugauaacc gauaccugga ucuccauggg gcaggaagaa gagaagaaaa | 960 |
| agcggcugca ggcauuccag ggauaccagg ucaccaugaa aaccgcaaaa guggcagcca | 1020 |
| gcgacuggac uuuccuccau ugccugccgc gaaagccgga ggaggucgau gacgaggugu | 1080 |
| ucuacuccc gcggucgcug uguuccggg aggcggaaaa ccggaagugg accauuaugg | 1140 |
| ccgugauggu gucacuccug acugacuaca gcccgcaacu gcagaagccg aaguucuagc | 1200 |
| ucgagcuagu gacugacuag gaucgguua ccacuaaaacc agccucaaga cacccgaauu | 1260 |
| ggagucucua agcuacauaa uaccaacuua cacuuacaaa auguugucc ccaaaaugua | 1320 |
| gccauucgua ucugcuccua auaaaaagaa aguuucuuca cauucuag | 1368 |

<210> SEQ ID NO 61
<211> LENGTH: 1496
<212> TYPE: RNA
<213> ORGANISM: Artificial sequence
<220> FEATURE:
<223> OTHER INFORMATION: Synthetic polynucleotide

<400> SEQUENCE: 61

| | |
|---|---:|
| cuuaagggg cgcugccuac ggagguggca gccaucuccu ucucggcauc aagcuuacca | 60 |
| uggugcccca ggcccugcuc uugguccgc ugcugguguu cccccucugc uucggcaagu | 120 |
| ucccaucua caccauccc gacaagcugg ggccguggag ccccaucgac auccaccacc | 180 |
| uguccugccc caacaaccuc guggcgagg acgagggcug caccaaccug agcggguucu | 240 |
| ccuacaugcu uuucaaucuc cgcauccucc uuaacaacgc cgcguuuaga aacggccaca | 300 |
| acuucauggu ccggaacuuc agaugguggcc agccgcuuca aaacaagguc cagcugaagg | 360 |
| gccgggaucu ucugacccug aagaacuuua cuggcgaaga gaucaaguac augcucuggc | 420 |
| ucuccgcgga cuugaaguuc cgcauuaagc agaagggga auaccuuccg cugcuucaag | 480 |
| gaaagagccu cggcaugauc uuugagaagc gcucaaccag gacccgccuu ucuacugaaa | 540 |
| cugguucgc gcugcucggu ggccacccu gcuccugac gacccaggac auccaccucg | 600 |
| gagugaacga aucccucacc gauaccgccc ggguguuauc gagcauggca gaugccgugc | 660 |
| uggccagggu guacaaacag uccgaucugg acacucuggc caaggaggcg ucaauuccua | 720 |
| uuaucaacgg ccuuagugac cucuaccauc cgauucagau ccuggccgau uacucucaccc | 780 |
| ugcaagaaca cuacagcucc cugaaggguc ugacauuguc cuggaucggc gacggcaaca | 840 |
| acauucucca uuccaucaug auguccgccg caaaauucgg caugcaucuu caagccgcca | 900 |
| cgccgaaggg uuacgagccc gacgcuuccg ugacuaagcu cgccgagcag uacgcuaagg | 960 |
| agaacggaac caagcuucug cugacuaacg acccacuaga agcagcccac ggggcaacg | 1020 |
| ugcuuauuac ugacaccugg auccaaugg ccaggaagaa agagaaaaag aagcggcugc | 1080 |
| aggcguucca gggauaucag gucaccauga aaaccgccaa ggucgcugcc uccgacugga | 1140 |
| ccuuccugca cugccugccu cgcaagccug aagaaguggga cgacgaggug uucuacucgc | 1200 |
| cacggagccu cguguccccc gaggccgaga auagaaagug gaccaucaug gccgugaugg | 1260 |
| ugucacugcu caccgacuac agcccgcagc uucagaagcc caaguucuag auaagugaau | 1320 |

| | |
|---|---|
| gcaaggcugg ccggaagccc uugccugaaa gcaagauuuc agccuggaag agggcaaagu | 1380 |
| ggacgggagu ggacaggagu ggaugcgaua agaugugguu ugaagcugau ggugccagc | 1440 |
| ccugcauugc ugagucaauc aauaaagagc uuucuuuuga cccauucuag aucuag | 1496 |

<210> SEQ ID NO 62
<211> LENGTH: 1235
<212> TYPE: RNA
<213> ORGANISM: Artificial sequence
<220> FEATURE:
<223> OTHER INFORMATION: Synthetic polynucleotide

<400> SEQUENCE: 62

| | |
|---|---|
| auuauuacau caaaacaaaa agccgccaau gcuguucaac cugcgcaucc ugcugaacaa | 60 |
| cgccgccuuc cgcaacggcc acaacuucau ggugcgcaac uuccgcugcg gccagcccu | 120 |
| gcagaacaag gugcagcuga agggccgcga ccugcugacc cugaagaacu ucaccggcga | 180 |
| ggagaucaag uacaugcugu ggcugagcgc cgaccugaag uuccgcauca agcagaaggg | 240 |
| cgaguaccug cccucugcugc agggcaagag ccugggcaug aucuucgaga agcgcagcac | 300 |
| ccgcacccgc cugagcaccg agacaggccu ggcccugcug gcggccacc ccugcuuccu | 360 |
| gaccaccccag gacauccacc ugggcgugaa cgagagccuu accgacaccg cccgcgugcu | 420 |
| gagcagcaug gccgacgccg ugcuggcccg cguguacaag cagagcgacc uggacacccu | 480 |
| ggccaaggag gccagcaucc ccaucaucaa cggccugagc gaccuguacc accccaucca | 540 |
| gauccuggcc gacuaccuga cccugcagga gcacuacagc agccugaagg gccugacccu | 600 |
| gagcuggauc ggcgacggca acaacauccu gcacagcauc augaugagcg ccgccaaguu | 660 |
| cggcaugcac cugcaggccg ccacccccaa gggcuacgag cccgacgcca gcgugaccaa | 720 |
| gcuggccgag caguacgcca aggagaacgg caccaagcug cugcugacca cgaccccccu | 780 |
| ggaggccgcc cacggcggca acgugcugau caccgacacc uggaucagca ugggccagga | 840 |
| ggaggagaag aagaagcgcc ugcaggccuu ccagggcuac caggugacca ugaagaccgc | 900 |
| caaggugggcc gccagcgacu ggaccuuccu gcacugccug ccccgcaagc ccgaggaggu | 960 |
| ggacgacgag guguucuaca gcccccgcag ccugguguuc cccgaggccg agaaccgcaa | 1020 |
| guggaccauc auggccgugu aggugagccu gcugaccgac uacagccccc agcugcagaa | 1080 |
| gcccaaguuc ugaacgccga agccugcagc caugcgaccc cacgccaccc cgugccuccu | 1140 |
| gccuccgcgc agccugcagc gggagacccu gucccgccc cagccgucco ccuggggugg | 1200 |
| acccuaguuu aauaaagauu caccaaguuu cacgc | 1235 |

<210> SEQ ID NO 63
<211> LENGTH: 1495
<212> TYPE: RNA
<213> ORGANISM: Artificial sequence
<220> FEATURE:
<223> OTHER INFORMATION: Synthetic polynucleotide

<400> SEQUENCE: 63

| | |
|---|---|
| cuuaagggg cgcugccuac ggagguggca gccaucuccu ucucggcauc aagcuuacca | 60 |
| uggugcccca ggcccugcuc uuggcccgc ugcugguguu cccccucugc uucggcaagu | 120 |
| ucccccaucua caccaucccc gacaagcugg ggccguggag ccccaucgac auccaccacc | 180 |
| uguccugccc caacaaccuc guggucgagg acgagggcug caccaaccug agcgguucu | 240 |
| ccuacaugcu guucaaccug cgcauccugc ugaacaacgc cgccuccgc aacgccaca | 300 |
| acuucauggu gcgcaacuuc cgcugcggcc agccccugca gaacaaggug cagcugaagg | 360 |

| | |
|---|---|
| gccgcgaccu gcugacccug aagaacuuca ccggcgagga gaucaaguac augcugggc | 420 |
| ugagcgccga ccugaaguuc cgcaucaagc agaagggcga guaccugccc cugcugcagg | 480 |
| gcaagagccu gggcaugauc uucgagaagc gcagcacccg cacccgccug agcaccgaga | 540 |
| caggccuggc ccugcugggc ggccacccu gcuuccugac cacccaggac auccaccugg | 600 |
| gcgugaacga gagccugacc gacaccgccc gcgugcugag cagcauggcc gacgccgugc | 660 |
| uggcccgcgu guacaagcag agcgaccugg acacccuggc caaggaggcc agcauccca | 720 |
| ucaucaacgg ccugagcgac cuguaccacc ccauccagau ccuggccgac uaccugaccc | 780 |
| ugcaggagca cuacagcagc cugaagggcc ugcccugag cuggaucggc gacggcaaca | 840 |
| acauccugca cagcaucaug augagcgccg ccaaguucgg caugcaccug caggccgcca | 900 |
| cccccaaggg cuacgagccc gacgccagcg ugaccaagcu ggccgagcag uacgccaagg | 960 |
| agaacggcac caagcugcug cugaccaacg accccccuga ggccgcccac ggcggcaacg | 1020 |
| ugcugaucac cgacaccugg aucagcaugg ccaggagga ggagaagaag aagcgccugc | 1080 |
| aggccuucca gggcuaccag gugaccauga agaccgccaa gguggccgcc agcgacugga | 1140 |
| ccuuccugca cugccugccc cgcaagcccg aggaggugga cgacgaggug uucuacagcc | 1200 |
| cccgcagccu gguguccccc gaggccgaga accgcaagug gaccaucaug gccgugaugg | 1260 |
| ugagccugcu gaccgacuac agcccccagc ugcagaagcc caaguucuga auaagugaug | 1320 |
| caaggcuggc cggaagcccu ugccugaaag caagauuuca gccuggaaga gggcaaagug | 1380 |
| gacgggagug gacaggagug gaugcgauaa gaugugguuu gaagcugaug ggugccagcc | 1440 |
| cugcauugcu gagucaauca auaaagagcu uucuuuugac ccauucuaga ucuag | 1495 |

<210> SEQ ID NO 64
<211> LENGTH: 1235
<212> TYPE: RNA
<213> ORGANISM: Artificial sequence
<220> FEATURE:
<223> OTHER INFORMATION: Synthetic polynucleotide

<400> SEQUENCE: 64

| | |
|---|---|
| auuauuacau caaaacaaaa agccgccaau gcuuucaau cuccgcaucc uccuuaacaa | 60 |
| cgccgcguuu agaaacggcc acaacuucau gguccggaac uucagaugug gccagccgcu | 120 |
| ucaaaacaag guccagcuga aggggccggga ucuucgaccc cugaagaacu uuacuggcga | 180 |
| agagaucaag uacaugcucu ggcucuccgc ggacuugaag uuccgcauua agcagaaggg | 240 |
| ggaauaccuu ccgcugcuuc aaggaaagag ccucggcaug aucuuugaga agcgucaaac | 300 |
| caggacccgc cuuucuacug aaacugggu ucgcgcugcuc gguggccacc ccugcuuccu | 360 |
| gacgacccag gacauccacc ucggagugaa cgaaucccuc accgauaccg cccggguguu | 420 |
| aucgagcaug gcagaugccg ugcuggccag ggugacaaa caguccgauc uggacacucu | 480 |
| ggccaaggag cgucaauuc cuauuaucaa cggccuuagu gaccucuacc auccgauuca | 540 |
| gauccuggcc gauuaccuca cccugcaaga acacuacagc ucccugaagg gucugacauu | 600 |
| guccuggauc ggcgacggca acaacauucu ccauccauc augaugccg ccgcaaaauu | 660 |
| cggcaugcau cuucaagccg ccacgccgaa gguuacgag cccgacgcuu ccgugacuaa | 720 |
| gcucgccgag caguacgcua aggagaacgg aaccaagcuu cugcugacua acgacccacu | 780 |
| agaagcagcc cacgggggca acgucuuau uacugacacc uggaucucca ugggccagga | 840 |
| agaagagaaa aagaagcggc ugcaggcguu ccagggauau caggucacca ugaaaaccgc | 900 |

| | |
|---|---|
| caaggucgcu gccuccgacu ggaccuuccu gcacugccug ccucgcaagc cugaagaagu | 960 |
| ggacgacgag uguucuacuc cgccacggag ccucguguuc cccgaggccg agaauagaaa | 1020 |
| guggaccauc auggccguga uggugucacu gcucaccgac uacagcccgc agcuucagaa | 1080 |
| gcccaaguuc uagacgccga agccugcagc caugcgaccc cacgccaccc cgugccuccu | 1140 |
| gccuccgcgc agccugcagc gggagacccu gucccgccc cagccguccu ccuggggugg | 1200 |
| acccuaguuu aauaaagauu caccaaguuu cacgc | 1235 |

```
<210> SEQ ID NO 65
<211> LENGTH: 1495
<212> TYPE: RNA
<213> ORGANISM: Artificial sequence
<220> FEATURE:
<223> OTHER INFORMATION: Synthetic polynucleotide

<400> SEQUENCE: 65
```

| | |
|---|---|
| cuuaaggggg cgcugccuac ggagguggca gccaucuccu ucucggcauc aagcuuacca | 60 |
| uggugcccca ggcccugcuc uuggucccgc ugcuggugua cccccucugc uucggcaagu | 120 |
| uccccaucua caccauccc gacaagcugg ggccguggag ccccaucgac auccaccacc | 180 |
| uguccugccc caacaaccuc guggucgagg acgagggcug caccaaccug agcggguucu | 240 |
| ccuacaugcu uuucaaccug agaauccucu ugaacaaugc ugcuuuucgg aauggccaca | 300 |
| acuuuauggu ucggaacuuc cguugcggcc agccuuuaca aaacaagguc cagcugaagg | 360 |
| gccgggauuu gcucacacua aagaacuuua cuggagaaga gaucaaguac augcuauggc | 420 |
| ugucggccga ccugaaguuc cguaucaagc agaagggaga auaccuuccg cugcuucaag | 480 |
| gaaagagccu cggcaugauc uuugagaagc gcucaaccag gacccgccuu ucuacugaaa | 540 |
| cugguucgc gcugcucggu ggccacccu gcuuccugac gacccaggac auccaccucg | 600 |
| gagugaacga aucccucacc gauaccgccc ggguguuauc gagcauggca gaugccgugc | 660 |
| uggccagggu guacaaacag uccgaucucg uaccuuggc aaaggaggcu uccauuccca | 720 |
| ucaucaacgg ccugagcgac cuguaccacc caauccaaau ccuggcugac uaccugaccc | 780 |
| ugcaagagca cuacagcagc cugaaggguc ugcccugguc auggauuggc gauggaaaca | 840 |
| auauucugca cuccaucaug auguccgccg cgaaguucgg aaugcaucug caagccgcca | 900 |
| cuccaaaagg auacgaaccg gaugcauccug ugaccaaguu ggcggaacag uacgcgaagg | 960 |
| agaacggaac caagcuccug cugacuaacg acccgcucga ggcugcgcau gggggguaacg | 1020 |
| ugcugauuac ggacaccugg aucuccaugg ggcaggagga agagaagaag aagagacugc | 1080 |
| aggcauucca gggguaccag gucaccauga aaaccgcaaa aguggcagcu ucggacugga | 1140 |
| cuuccugca uugccugccg aggaagccgg aggaagucga cgacgaagug uucuacccgc | 1200 |
| cucgguccu gguguucccc gaggccgaaa accggaagug gaccaucaug gccgugaugg | 1260 |
| uguccuugcu gacugacuau agcccgcagc ugcagaagcc uaaguucuag auaaguguag | 1320 |
| caaggcuggc cggaagcccu ugccugaaag caagauuuca gccuggaaga gggcaaagug | 1380 |
| gacgggagug gacaggagug gaugcgauaa gaugugguuu gaagcugaug ggugccagcc | 1440 |
| cugcauugcu gagucaauca auaaagagcu uucuuuugac ccauucuaga ucuag | 1495 |

```
<210> SEQ ID NO 66
<211> LENGTH: 1475
<212> TYPE: RNA
<213> ORGANISM: Artificial sequence
<220> FEATURE:
<223> OTHER INFORMATION: Synthetic polynucleotide
```

<400> SEQUENCE: 66

```
ugagugucgu acagccucca ggcccccccc ucccgggaga gccauagugg ucugcggaac      60
cggugaguac accggaauug ccgggaagac ugggguccuuu cuuggauaaa cccacucuau     120
gcccggccau uugggcgugc ccccgcaaga cugcuagccg aguaguguug gguucgaug      180
cguucaacc ugcgcauccu gcugaacaac gccgccuucc gcaacggcca caacuucaug     240
gugcgcaacu uccgcugcgg ccagccccug cagaacaagg ugcagcugaa gggccgcgac     300
cugcugaccc ugaagaacuu caccggcgag gagaucaagu acaugcugug gcugagcgcc     360
gaccugaagu uccgcaucaa gcagaagggc gaguaccugc cccugcugca gggcaagagc     420
cugggcauga ucuucgagaa gcgcagcacc cgcacccgcc ugagcaccga acaggccug     480
gcccugcugg gcggccaccc cugcuuccug accacccagg acauccaccu gggcgugaac     540
gagagccuga ccgacaccgc ccgcgugcug agcagcaugg ccgacgccgu gcuggcccgc     600
guguacaagc agagcgaccu ggacacccug gccaaggagg ccagcauccc caucaucaac     660
ggccugagcg accuguacca ccccauccag auccuggccg acuaccugac ccugcaggag     720
cacuacagca gccugaaggg ccugacccug agcuggaucg cgacggcaa caacauccug     780
cacagcauca ugaugagcgc cgccaaguuc ggcaugcacc ugcaggccgc cacccccaag     840
ggcuacgagc ccgacgccag cgugaccaag cuggccgagc aguacgccaa ggagaacggc     900
accaagcugc ugcugaccaa cgaccccccug gaggccgccc acggcggcaa cgugcugauc     960
accgacaccu ggaucagcau gggccaggag gaggagaaga agagcgccu gcaggccuuc    1020
cagggcuacc aggugaccau gaagaccgcc aagguggccg ccagcgacug gaccuuccug    1080
cacugccugc cccgcaagcc cgaggaggug gacgacgagg uguucuacag cccccgcagc    1140
cugguguucc ccgaggccga gaaccgcaag uggaccauca uggccgugau ggugagccug    1200
cugaccgacu acagccccca gcugcagaag cccaaguucu gaauaaguga uagagcggca    1260
aacccuagcu acacuccaua gcaguuucu uuuuuuuug uuuuuuuuuu uuuuuuuuuu    1320
uuuuuuuuuu uuuuuuuuuc cuuucuuuuc cuucuuuuuu uccucuuuuc uugguggcuc    1380
caucuuagcc cuagucacgg cuagcuguga aagguccgug agccgcauga cugcagagag    1440
ugccguaacu ggccucucug cagaucaugu ucuag                              1475
```

<210> SEQ ID NO 67
<211> LENGTH: 1202
<212> TYPE: RNA
<213> ORGANISM: Artificial sequence
<220> FEATURE:
<223> OTHER INFORMATION: Synthetic polynucleotide

<400> SEQUENCE: 67

```
auuauuacau caaaacaaaa agccgccaau gcuuuucaau cuccgcaucc uccuuaacaa      60
cgccgcguuu agaaacggcc acaacuucau ggguccggaac uucagaugug ccagccgcu    120
ucaaaacaag guccagcuga agggccggga ucuucugacc cugaagaacu uuacuggcga    180
agagaucaag uacaugcucu ggcucuccgc ggacuugaag uuccgcauua agcagaaggg    240
ggaauaccuu ccgcugcuuc aaggaaagag ccucggcaug aucuuugaga gcgcucaac    300
caggacccgc cuucuacug aaacugggu ucgcgcugcuc gguggccacc ccugcuuccu    360
gacgacccag gacauccacc ucggagugaa cgaaucccuc accgauaccg cccgggugu    420
aucgagcaug gcagaugccg ugcuggccag ggguacaaa caguccgauc uggacacucu    480
```

| | |
|---|---:|
| ggccaaggag gcgucaauuc cuauuaucaa cggccuuagu gaccucuacc auccgauuca | 540 |
| gauccuggcc gauuaccuca cccugcaaga acacuacagc ucccugaagg gucugacauu | 600 |
| guccuggauc ggcgacggca acaacauucu ccauuccauc augaugccg ccgcaaaauu | 660 |
| cggcaugcau cuucaagccg ccacgccgaa ggguuacgag cccgacgcuu ccgugacuaa | 720 |
| gcucgccgag caguacgcua aggagaacgg aaccaagcuu cugcugacua acgacccacu | 780 |
| agaagcagcc cacgggggca acgugcuuau uacugacacc uggaucucca ugggccagga | 840 |
| agaagagaaa aagaagcggc ugcaggcguu ccagggauau caggucacca ugaaaaccgc | 900 |
| caaggucgcu gccuccgacu ggaccuuccu gcacugccug ccucgcaagc cugaagaagu | 960 |
| ggacgacgag guguucuacu cgccacggag ccucguguuc cccgaggccg agaauagaaa | 1020 |
| guggaccauc auggccguga uggugucacu gcucaccgac uacagcccgc agcuucagaa | 1080 |
| gcccaaguuc uaggcuggag ccucgguagc cguuccuccu gcccgcuggg ccucccaacg | 1140 |
| ggccccuccuc cccuccuugc accggcccuu ccuggucuuu gaauaaaguc ugagugggca | 1200 |
| gc | 1202 |

<210> SEQ ID NO 68
<211> LENGTH: 1202
<212> TYPE: RNA
<213> ORGANISM: Artificial sequence
<220> FEATURE:
<223> OTHER INFORMATION: Synthetic polynucleotide

<400> SEQUENCE: 68

| | |
|---|---:|
| auuauuacau caaacaaaaa agccgccaau gcuguucaac cugcgcaucc ugcugaacaa | 60 |
| cgccgccuuc cgcaacggcc acaacuucau ggugcgcaac uuccgcugcg gccagccccu | 120 |
| gcagaacaag gugcagcuga aggggccgcga ccugcugacc cugaagaacu ucaccggcga | 180 |
| ggagaucaag uacaugcugu ggcugagcgc cgaccugaag uuccgcauca agcagaaggg | 240 |
| cgaguaccug cccugcgc agggcaagag ccugggcaug aucuucgaga agcgcagcac | 300 |
| ccgcacccgc cugagcaccg agacaggccu ggcccugcug ggcggccacc ccugcuuccu | 360 |
| gaccacccag gacauccacc ugggcgugaa cgagagccug accgacaccg cccgcgugcu | 420 |
| gagcagcaug gccgacgccg ugcuggcccg cguguacaag cagagcgacc uggacacccu | 480 |
| ggccaaggag gccagcaucc ccaucaucaa cggccgagc gaccuguacc accccaucca | 540 |
| gauccuggcc gacuaccuga cccugcagga gcacuacagc agccugaagg gccugacccu | 600 |
| gagcuggauc ggcgacggca acaacauccu gcacagcauc augaugagcg ccgccaaguu | 660 |
| cggcaugcac cugcaggccg ccacccccaa gggcuacgag cccgacgcca gcgugaccaa | 720 |
| gcuggccgag caguacgcca aggagaacgg caccaagcug cugcugacca acgacccccu | 780 |
| ggaggccgcc cacggcggca acgugcugau caccgacacc uggaucagca ugggccagga | 840 |
| ggaggagaaa aagaagcgcc ugcaggccuu ccagggcuac caggugacca ugaagaccgc | 900 |
| caaggugggcc gccagcgacu ggaccuuccu gcacugccug ccccgcaagc ccgaggaggu | 960 |
| ggacgacgag guguucuaca gcccccgcag ccugguguuc cccgaggccg agaaccgcaa | 1020 |
| guggaccauc auggccguga uggugagccu gcugaccgac uacagccccc agcugcagaa | 1080 |
| gcccaaguuc ugagcuggag ccucgguagc cguuccuccu gcccgcuggg ccucccaacg | 1140 |
| ggccccuccuc cccuccuugc accggcccuu ccuggucuuu gaauaaaguc ugagugggca | 1200 |
| gc | 1202 |

<210> SEQ ID NO 69
<211> LENGTH: 1202
<212> TYPE: RNA
<213> ORGANISM: Artificial sequence
<220> FEATURE:
<223> OTHER INFORMATION: Synthetic polynucleotide

<400> SEQUENCE: 69

| | | | | | |
|---|---|---|---|---|---|
| auuauuacau | caaaacaaaa | agccgccaau | gcuuucaac | cugagaaucc | ucuugaacaa | 60 |
| ugcugcuuuu | cggaauggcc | acaacuuuau | gguucggaac | uuccguugcg | gccagccuuu | 120 |
| acaaaacaag | guccagcuga | agggccggga | uuugcucaca | cuaaagaacu | uuacuggaga | 180 |
| agagaucaag | uacaugcuau | ggcugucggc | cgaccugaaa | uuccguauca | agcagaaggg | 240 |
| agaauaccuu | ccgcugcuuc | aaggaaagag | ccucggcaug | aucuuugaga | agcgcucaac | 300 |
| caggacccgc | cuuucuacug | aaacugggu | cgcgcugcuc | gguggccacc | ccugcuuccu | 360 |
| gacgacccag | gacauccacc | ucggagugaa | cgaaucccuc | accgauaccg | cccggguguu | 420 |
| aucgagcaug | gcagaugccg | ugcuggccag | ggguacaaa | caguccgauc | ucgauaccuu | 480 |
| ggcaaaggag | gcuuccauuc | ccaucaucaa | cggccugagc | gaccuguacc | acccaauca | 540 |
| aauccuggcu | gacuaccuga | cccugcaaga | gcacuacagc | agccgaagg | gucugacccu | 600 |
| gucauggauu | ggcgauggaa | acaauauucu | gcacuccauc | augaugucg | ccgcgaaguu | 660 |
| cggaaugcau | cugcaagccg | ccacuccaaa | aggauacgaa | ccggaugcau | ccgugaccaa | 720 |
| guuggcggaa | caguacgcga | aggagaacgg | aaccaagcuc | cugcugacua | cgacccgcu | 780 |
| cgaggcugcg | caugggggua | acgugcugau | uacggacacc | uggaucucca | uggggcagga | 840 |
| ggaagagaag | aagaagagac | ugcaggcauu | ccagggguac | caggucacca | ugaaaaccgc | 900 |
| aaaaguggca | gcuucggacu | ggacuuuccu | gcauugccug | ccgaggaagc | cggaggaagu | 960 |
| cgacgacgaa | guguucuacu | cgccucgguc | ccuggguuc | cccgaggccg | aaaaccggaa | 1020 |
| guggaccauc | auggccguga | uggugccuu | gcugacugac | auagcccgc | agcugcagaa | 1080 |
| gccuaaguuc | uaggcuggag | ccucggu agc | cguuccuccu | gcccgcuggg | ccucccaacg | 1140 |
| ggccccuccuc | cccuccuugc | accggcccuu | ccuggucuuu | gaauaaaguc | ugagugggca | 1200 |
| gc | | | | | | 1202 |

<210> SEQ ID NO 70
<211> LENGTH: 1334
<212> TYPE: RNA
<213> ORGANISM: Artificial sequence
<220> FEATURE:
<223> OTHER INFORMATION: Synthetic polynucleotide

<400> SEQUENCE: 70

| | | | | | |
|---|---|---|---|---|---|
| aauuauuggu | uaaagaagua | uauuagugcu | aauuucccuc | cguuugccu | agcuuuucuc | 60 |
| uucugucaac | cccacacgcc | uuuggcacaa | ugcuuuucaa | ucuccgcauc | cuccuuaaca | 120 |
| acgccgcguu | uagaaacggc | cacaacuuca | uggucccggaa | cuucagaugu | ggccagccgc | 180 |
| uucaaaacaa | gguccagcug | aagggccggg | aucuucgac | ccugaagaac | uuuacuggcg | 240 |
| aagagaucaa | guacaugcuc | uggcucuccg | cggacuugaa | guuccgcauu | aagcagaagg | 300 |
| gggaauaccu | uccgcugcuu | caaggaaaga | gccucggcau | gaucuuugag | aagcgcucaa | 360 |
| ccaggacccg | ccuuucuacu | gaaacugggu | cgcgcugcu | cgguggccac | cccugcuucc | 420 |
| ugacgaccca | ggacauccac | cucggagguga | acgaaucccu | caccgauacc | gcccggguguu | 480 |
| uaucgagcau | ggcagaugcc | gugcugggcca | ggguacaa | acaguccgau | cuggacacuc | 540 |

| | | |
|---|---|---|
| uggccaagga ggcgucaauu ccuauuauca acggccuuag ugaccucuac cauccgauuc | 600 |
| agauccuggc cgauuaccuc acccugcaag aacacuacag cucccugaag ggucugacau | 660 |
| uguccuggau cggcgacggc aacaacauuc uccauuccau caugaugucc gccgcaaaau | 720 |
| ucggcaugca ucuucaagcc gccacgccga agggsuuacga gcccgacgcu uccgugacua | 780 |
| agcucgccga gcaguacgcu aaggagaacg gaaccaagcu ucugcugacu aacgacccac | 840 |
| uagaagcagc ccacggggggc aacgugcuua uuacugacac cuggaucucc augggccagg | 900 |
| aagaagagaa aaagaagcgg cugcaggcgu uccagggaua ucaggucacc augaaaaccg | 960 |
| ccaaggucgc ugccuccgac uggaccuucc ugcacugccu gccucgcaag ccugaagaag | 1020 |
| uggacgacga ggguguucuac ucgccacgga gccucgyguu ccccgaggcc gagaauagaa | 1080 |
| aguggaccau cauggccgug auggugucac ugcucaccga cuacagcccg cagcuucaga | 1140 |
| agcccaaguu cuagcucgag acacaucaca accacaaccu ucucaggcua cccugagaaa | 1200 |
| aaaagacaug aagacucagg acucaucuuu ucguuggug uaaaaucaac acccuaagga | 1260 |
| acacaaauuu cuuuaaacau uugacuucuu gucucugugc ugcaauuaau aaaaaaugga | 1320 |
| aagaaucuau cuag | 1334 |

<210> SEQ ID NO 71
<211> LENGTH: 1334
<212> TYPE: RNA
<213> ORGANISM: Artificial sequence
<220> FEATURE:
<223> OTHER INFORMATION: Synthetic polynucleotide

<400> SEQUENCE: 71

| | | |
|---|---|---|
| aauuauuggu uaagaaguga uauuagugcu aauuucccuc cguuugaccu agcuuuucuc | 60 |
| uucugucaac cccacacgcc uuuggcacaa ugcuguucaa ccugcgcauc cugcugaaca | 120 |
| acgccgccuu ccgcaacggc acaacuuuca uggugcgcaa cuuccgcugc ggccagcccc | 180 |
| ugcagaacaa ggugcagcug aagggccgcg accugcugac ccugaagaac uucaccggcg | 240 |
| aggagaucaa guacaugcug uggcugagcg ccgaccugaa guuccgcauc aagcagaagg | 300 |
| gcgaguaccu gccccugcug cagggcaaga gccugggcau gaucuucgag aagcgcagca | 360 |
| cccgcacccg ccugagcacc gagacaggcc uggcccugcu gggcggccac cccugcuucc | 420 |
| ugaccaccca ggacauccac cugggcguga acgagagccu gaccgacacc gcccgcgugc | 480 |
| ugagcagcau ggccgacgcc gugcuggccc gcguguacaa gcagagcgac cuggacaccc | 540 |
| uggccaagga ggccagcauc cccaucauca acggccugag cgaccuguac caccccaucc | 600 |
| agauccuggc cgacuaccug acccugcagg agcacuacag cagccugaag ggccugaccc | 660 |
| ugagcuggau cggcgacggc aacaacaucc ugcacagcau caugaugagc gccgccaagu | 720 |
| ucggcaugca ccugcaggcc gccacccccca agggcuacga gcccgacgcc agcgugacca | 780 |
| agcuggccga gcaguacgcc aaggagaacg gcaccaagcu gcugcugacc aacgacccca | 840 |
| uggaggccgc ccacggcggc aacgugcuga ucaccgacac cuggaucagc augggccagg | 900 |
| aggaggagaa gaagaagcgc cugcaggccu ccagggcua ccaggugacc augaagaccg | 960 |
| ccaagguggc cgccagcgac uggaccuucc ugcacugccu gccccgcaag cccgaggagg | 1020 |
| uggacgacga ggguguucuac agcccccgca gccuggugu ccccgaggcc gagaaccgca | 1080 |
| aguggaccau cauggccgug auggugagcc ugcugaccga cuacagcccc cagcugcaga | 1140 |
| agcccaaguu cugacucgag acacaucaca accacaaccu ucucaggcua cccugagaaa | 1200 |
| aaaagacaug aagacucagg acucaucuuu ucguuggug uaaaaucaac acccuaagga | 1260 |

| | |
|---|---|
| acacaaauuu cuuuaaacau uugacuucuu gucucugugc ugcaauuaau aaaaaaugga | 1320 |
| aagaaucuau cuag | 1334 |

<210> SEQ ID NO 72
<211> LENGTH: 1334
<212> TYPE: RNA
<213> ORGANISM: Artificial sequence
<220> FEATURE:
<223> OTHER INFORMATION: Synthetic polynucleotide

<400> SEQUENCE: 72

| | |
|---|---|
| aauuauggu uaaagaagua uauuagugcu aauuucccuc cguuugcccu agcuuuucuc | 60 |
| uucugucaac cccacacgcc uuuggcacaa ugcuuucaa ccugagaauc cucuugaaca | 120 |
| augcugcuuu ucggaaugc cacaacuuua ugguucggaa cuuccguugc ggccagccuu | 180 |
| uacaaaacaa gguccagcug aagggccggg auuugcucac acuaaagaac uuuacuggag | 240 |
| aagagaucaa guacaugcua uggcugucgg ccgaccugaa guuccguauc aagcagaagg | 300 |
| gagaauaccu uccgcugcuu caaggaaaga gccucggcau gaucuuugag aagcgcucaa | 360 |
| ccaggacccg ccuuucuacu gaaacugggu ucgcgcugcu cgguggccac cccugcuucc | 420 |
| ugacgaccca ggacauccac cucggaguga acgaauccu caccgauacc gcccggguu | 480 |
| uaucgagcau ggcagaugcc gugcuggcca ggguguacaa acaguccgau ucgauaccu | 540 |
| uggcaaagga ggcuuccauu cccaucauca acggccugag cgaccuguac cacccaaucc | 600 |
| aaauccuggc ugacuaccug acccugcaag agcacuacag cagccugaag ggucugaccc | 660 |
| ugucauggau uggcgaugga aacaauauuc ugcacuccau caugaugucc gccgcgaagu | 720 |
| ucggaaugca ucugcaagcc gccacuccaa aaggauacga accggaugca uccgugacca | 780 |
| aguuggcgga acaguacgcg aaggagaacg gaaccaagcu ccugcugacu aacgacccgc | 840 |
| ucgaggcugc gcauggggu aacgugcuga uuacgacac cuggauccc augggggcagg | 900 |
| aggaagagaa gaagaagaga cugcaggcau uccaggggua ccaggucacc augaaaaccg | 960 |
| caaaagugc agcuucggac uggacuuucu gcauugccu gccgaggaag ccggaggaag | 1020 |
| ucgacgacga aguguucuac ucgccucggu ccccuggugu ucccgaggcc gaaaaccgga | 1080 |
| aguggaccau cauggccgug auggugucca ugcugacuga cuauagcccg cagcugcaga | 1140 |
| agccuaaguu cuagcucgag acacaucaca accacaaccu ucucaggcua cccugagaaa | 1200 |
| aaaagacaug aagacucagg acucaucuuu ucuguuggug uaaaaucaac acccuaagga | 1260 |
| acacaaauuu cuuuaaacau uugacuucuu gucucugugc ugcaauuaau aaaaaaugga | 1320 |
| aagaaucuau cuag | 1334 |

<210> SEQ ID NO 73
<211> LENGTH: 1222
<212> TYPE: RNA
<213> ORGANISM: Artificial sequence
<220> FEATURE:
<223> OTHER INFORMATION: Synthetic polynucleotide

<400> SEQUENCE: 73

| | |
|---|---|
| auuauuacau caaaacaaaa agccgccacc augcuguuca accugcgcau ccugcugaac | 60 |
| aacgccgccu uccgcaacgg ccacaacuuc augguggcgca acuuccgcug cggccagccc | 120 |
| cugcagaaca aggugcagcu gaagggccgc gaccugcuga cccugaagaa cuucaccggc | 180 |
| gaggagauca aguacaugcu guggcugagc gccgaccuga aguccgcau caagcagaag | 240 |

```
ggcgaguacc ugcccugcu gcagggcaag agccugggca ugaucuucga gaagcgcagc      300
acccgcaccc gccugagcac cgagacaggc uucgcccugc ugggcggcca cccugcuuc      360 cugaccaccc aggacaucca ccugggcgug aacgagagcc ugaccgacac cgcccgcgug     420
cugagcagca uggccgacgc cgucuggcc cgcguguaca agcagagcga ccuggacacc      480
cuggccaagg aggccagcau ccccaucauc aacggccuga gcgaccugua ccaccccauc     540
cagauccugg ccgacuaccu gacccugcag gagcacuaca gcagccugaa gggccugacc     600
cugagcugga ucggcgacgg caacaacauc cugcacagca ucaugaugag cgccgccaag    660
uucggcaugc accugcaggc cgccaccccc aagggcuacg agcccgacgc cagcgugacc     720
aagcuggccg agcaguacgc caaggagaac ggcaccaagc ugcugcugac caacgacccc    780
cuggaggccg cccacggcgg caacgugcug aucaccgaca ccuggaucag cauggccag    840 gaggaggaga agaagaagcg ccugcaggcc uuccagggcu accaggugac caugaagacc    900
gccaaggugg ccgccagcga cuggaccuuc cugcacugcc ugccccgcaa gcccgaggag   960
guggacgacg agguguucua cagccccgc agccuggugu ccccgaggc cgagaaccgc     1020 aaguggacca ucauggccgu gauggugagc cugcugaccg acuacagccc ccagcugcag    1080
aagcccaagu ucgaggucu cuaguaauga gcuggagccc cgguagccgu uccuccugcc    1140
cgcugggccu cccaacgggc ccuccucccc uccuugcacc ggcccuuccu ggucuuugaa   1200
uaaagucuga gugggcaucu ag                                             1222
```

<210> SEQ ID NO 74
<211> LENGTH: 1334
<212> TYPE: RNA
<213> ORGANISM: Artificial sequence
<220> FEATURE:
<223> OTHER INFORMATION: Synthetic polynucleotide

<400> SEQUENCE: 74

```
aauuauuggu uaaagaagua uauuagugcu aauuucccuc cguuuguccu agcuuuucuc     60
uucugucaac cccacacgcc uuuggcacaa ugcuguucaa ccugcgcauc cugcugaaca    120
acgccgccuu ccgcaacggc cacaacuuca uggugcgcaa cuuccgcugc ggccagcccc   180
ugcagaacaa ggugcagcug aagggccgcg accugcugac ccugaagaac uucaccggcg   240
aggagaucaa guacaugcug uggcugacgc ccgaccugaa guuccgcauc aagcagaagg    300
gcgaguaccu gccccugcug cagggcaaga gccugggcau gaucuucgag aagcgcagca   360
cccgcacccg ccugagcacc gagacaggcu ucgcccugcu gggcggccac cccugcuucc   420
ugaccaccca ggacauccac cugggcguga acgagagccu gaccgacacc gcccgcguc    480 ugagcagcau ggccgacgcc gucuggccc gcguguacaa gcagagcgac cuggacaccc    540
uggccaagga ggccagcauc cccaucauca acggccugag cgaccuguac caccccaucc   600
agauccuggc cgacuaccug acccugcagg agcacuacag cagccugaag gccugaccc    660 ugagcuggau cggcgacggc aacaacaucc ugcacagcau caugaugagc gccgccaagu   720
ucggcaugca ccugcaggcc gccaccccca agggcuacga gcccgacgcc agcgugacca   780
agcuggccga gcaguacgcc aaggagaacg gcaccaagcu gcugcugacc aacgaccccc   840
uggaggccgc ccacggcggc aacgugcuga ucaccgacac cuggaucagc augggccagg   900
aggaggagaa gaagaagcgc cugcaggccu ccagggcua ccaggugacc augaagaccg    960 ccaaggudggg cgccagcgac uggaccuucc ugcacugccu gccccgcaag cccgaggagg  1020
uggacgacga gguguucuac agccccgca gccuggguguu ccccgaggcc gagaaccgca   1080
```

| | |
|---|---|
| aguggaccau cauggccgug auggugagcc ugcugaccga cuacagcccc cagcugcaga | 1140 |
| agcccaaguu cugacucgag acacaucaca accacaaccu ucucaggcua cccugagaaa | 1200 |
| aaaagacaug aagacucagg acucaucuuu ucguuggug uaaaaucaac acccuaagga | 1260 |
| acacaaauuu cuuuaaacau uugacuucuu gucucugugc ugcaauuaau aaaaaugga | 1320 |
| aagaaucuau cuag | 1334 |

<210> SEQ ID NO 75
<211> LENGTH: 1235
<212> TYPE: RNA
<213> ORGANISM: Artificial sequence
<220> FEATURE:
<223> OTHER INFORMATION: Synthetic polynucleotide

<400> SEQUENCE: 75

| | |
|---|---|
| auuauuacau caaaacaaaa agccgccaau gcuguucaac cugcgcaucc ugcugaacaa | 60 |
| cgccgccuuc cgcaacggcc acaacuucau ggugcgcaac uuccgcugcg ccagccccu | 120 |
| gcagaacaag gugcagcuga agggccgcga ccugcugacc cugaagaacu ucaccggcga | 180 |
| ggagaucaag uacaugcugu ggcugagcgc cgaccgaag uuccgcauca agcagaaggg | 240 |
| cgaguaccug ccccugcugc agggcaagag ccugggcaug aucuucgaga agcgcagcac | 300 |
| ccgcacccgc cugagcaccg agacaggcuu cgcccugcug gcggccacc ccugcuuccu | 360 |
| gaccacccag gacauccacc ugggcgugaa cgagagccug accgacaccg cccgcgugcu | 420 |
| gagcagcaug gccgacgccg ugcuggcccg cguguacaag cagagcgacc uggacacccu | 480 |
| ggccaaggag gccagcaucc ccaucaucaa cggccugagc gaccuguacc accccaucca | 540 |
| gauccuggcc gacuaccuga cccugcagga gcacuacagc agccgaagg gccugacccu | 600 |
| gagcuggauc ggcgacggca acaacauccu gcacagcauc augaugagcg ccgccaaguu | 660 |
| cggcaugcac cugcaggccg ccaccccaa gggcuacgag cccgacgcca gcgugaccaa | 720 |
| gcuggccgag caguacgcca aggagaacgg caccaagcug cugcugacca acgacccccu | 780 |
| ggaggccgcc cacggcggca acgugcugau caccgacacc uggaucagca ugggccagga | 840 |
| ggaggagaag aagaagcgcc ugcaggccuu ccagggcuac caggugacca ugaagaccgc | 900 |
| caagguggcc gccagcgacu ggaccuuccu gcacugccug ccccgcaagc ccgaggaggu | 960 |
| ggacgacgag guguucuaca gccccgcag ccugguguuc cccgaggccg agaaccgcaa | 1020 |
| guggaccauc auggccguga uggugagccu gcugaccgac uacagccccc agcugcagaa | 1080 |
| gcccaaguuc ugaacgccga agccugcagc caugcgaccc cacgccaccc cgugccuccu | 1140 |
| gccuccgcgc agccugcagc gggagacccu guccccgccc agccguccu ccuggggugg | 1200 |
| acccuaguuu aauaaagauu caccaaguuu cacgc | 1235 |

<210> SEQ ID NO 76
<211> LENGTH: 1496
<212> TYPE: RNA
<213> ORGANISM: Artificial sequence
<220> FEATURE:
<223> OTHER INFORMATION: Synthetic polynucleotide

<400> SEQUENCE: 76

| | |
|---|---|
| cuuaaggggg cgcugccuac ggagguggca gccaucuccu ucucggcauc aagcuuacca | 60 |
| uggugcccca ggcccugcuc uuggcccgc ugcggguguu cccccucugc uucggcaagu | 120 |
| uccccaucua caccauccc gacaagcugg ggccguggag ccccaucgac auccaccacc | 180 |

-continued

| | |
|---|---|
| uguccugccc caacaaccuc guggucgagg acgagggcug caccaaccug agcggguucu | 240 |
| ccuacaugcu guucaaccug cgcauccugc ugaacaacgc cgccuuccgc aacggccaca | 300 |
| acuucauggu gcgcaacuuc cgcugcggcc agccccugca gaacaaggug cagcugaagg | 360 |
| ccgcgaccu gcugacccug aagaacuuca ccggcgagga gaucaaguac augcugggc | 420 |
| ugagcgccga ccugaaguuc cgcaucaagc agaagggcga guaccugccc cugcugcagg | 480 |
| gcaagagccu gggcaugauc uucgagaagc gcagcacccg cacccgccug agcaccgaga | 540 |
| caggcuucgc ccugcugggc ggccaccccu gcuuccugac acccaggac auccaccugg | 600 |
| gcgugaacga gagccugacc gacaccgccc gcgugcugag cagcauggcc gacgccgugc | 660 |
| uggcccgcgu guacaagcag agcgaccugg acacccuggc caaggaggcc agcauccca | 720 |
| ucaucaacgg ccugagcgac cuguaccacc ccauccagau ccuggccgac uaccugaccc | 780 |
| ugcaggagca cuacagcagc cugaagggcc ugacccugag cuggaucggc gacggcaaca | 840 |
| acauccugca cagcaucaug augagcgccc ccaaguucgg caugcaccug caggccgcca | 900 |
| cccccaaggg cuacgagccc gacgccgcg ugaccaagcu ggccgagcag uacgccaagg | 960 |
| agaacggcac caagcugcug cugaccaacg accccccugga ggccgccac ggcggcaacg | 1020 |
| ugcugaucac cgacaccugg aucagcaugg ccaggagga ggagaagaag aagcgccugc | 1080 |
| aggccuucca gggcuaccag gugaccauga agaccgccaa gguggccgcc agcgacugga | 1140 |
| ccuuccugca cugccugccc cgcaagcccg aggagguga cgacgaggug uucuacagcc | 1200 |
| cccgcagccu gguguucccc gaggccgaga accgcaagug gaccaucaug gccgugaugg | 1260 |
| ugagccugcu gaccgacuac agcccccagc ugcagaagcc caaguucuga auaagugaau | 1320 |
| gcaaggcugg ccggaagccc uugccugaaa gcaagauuuc agccuggaag agggcaaagu | 1380 |
| ggacgggagu ggacaggagu ggaugcgaua agaugugguu ugaagcugau ggugccagc | 1440 |
| ccugcauugc ugagucaauc aauaaagagc uuucuuuuga cccauucuag aucuag | 1496 |

<210> SEQ ID NO 77
<211> LENGTH: 1380
<212> TYPE: RNA
<213> ORGANISM: Artificial sequence
<220> FEATURE:
<223> OTHER INFORMATION: Synthetic polynucleotide

<400> SEQUENCE: 77

| | |
|---|---|
| ucaacacaac auaucaaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccauggc gucuucaacc ugcggauccu gcugaacaac gccgccuucc | 180 |
| ggaacggcca caacuucaug gucogcaacu ucagaugcgg ccagcccug cagaacaagg | 240 |
| ugcagcugaa gggccgggac cugcugaccc ugaagaacuu caccggcgaa gagaucaagu | 300 |
| acaugcugug gcugagcgcc gaccugaagu uccggaucaa gcagaagggc gaguaccugc | 360 |
| cccugcugca aggcaagagc cugggcauga ucuucgagaa gcggagcacc cggacccggc | 420 |
| ugagcaccga caggcuuuu gccugcugg gaggccaccc cugcuuucug accacccagg | 480 |
| acauccaccu gggcgugaac gagagccuga ccgacaccgc cagagugcug agcagcaugg | 540 |
| ccgacgccgu gcuggcccgg guguacaagc agagcgaccu ggacacccug gccaaagagg | 600 |
| ccagcauccc caucaucaac ggccugagcg accuguacca ccccauccag auccuggccg | 660 |
| acuaccugac ccugcaggaa cacuacagcu cccugaaggg ccugacccug agcuggaucg | 720 |
| gcgacggcaa caacauccug cacagcauca ugaugagcgc cgccaaguuc ggcaugcauc | 780 |

```
ugcaggccgc caccccccaag ggcuacgagc cugaugccag cgugaccaag cuggccgagc    840
aguacgccaa agagaacggc accaagcugc ugcugaccaa cgaccccug gaagccgccc     900 acggcggcaa cgucugauc accgacaccu ggaucagcau gggccaggaa gaggaaaaga    960
agaagcggcu gcaggccuuc cagggcuacc aggucacaau gaagaccgcc aaggugccg    1020 ccagcgacug gaccuuccug cacugccugc cccggaagcc cgaagaggug gacgacgagg   1080
uguucuacag cccccggucc cuggguguucc ccgaggccga gaaccggaag uggaccauua    1140
uggccgugau ggugucccug cugaccgacu acuccccccca gcugcagaag cccaaguucu   1200
agauaaguga acucgagcua gugacugacu aggaucuggu uaccacuaaa ccagccucaa   1260
gaacacccga auggagucuc uaagcuacau aauaccaacu uacacuuaca aaauguuguc    1320
ccccaaaaug uagccauucg uaucugcucc uaauaaaaag aaaguuucuu cacauucuag    1380
```

<210> SEQ ID NO 78
<211> LENGTH: 1380
<212> TYPE: RNA
<213> ORGANISM: Artificial sequence
<220> FEATURE:
<223> OTHER INFORMATION: Synthetic polynucleotide

<400> SEQUENCE: 78

```
ucaacacaac auaucaaaa caaacgaauc ucaagcaauc aagcauucua cuucuauugc      60
agcaauuuaa aucauuucuu uuaaagcaaa agcaauuuuc ugaaaauuuu caccauuuac    120
gaacgauagc caccaugggc gucuucaacc ugcggauccu gcugaacaac gccgccuucc    180
ggaacggcca caacuucaug guccgcaacu ucagaugcgg ccagccccug cagaacaggg    240
ugcagcugaa gggccgggac cugcugaccc ugaagaacuu caccggcgaa gagaucaggu    300
acaugcugug gcugagcgcc gaccugaagu uccggaucaa gcagaagggc gaguaccugc    360
cccugcugca aggcaagagc cugggcauga ucuucgagaa gcggagcacc cggacccggc    420
ugagcaccga gacaggcuuu gcccugcugg gaggccaccc cugcuuucug accacccagg    480
acauccaccu gggcgugaac gagagccuga ccgacaccgc cagagugcug agcagcaugg    540
ccgacgccgu gcuggcccgg guguacaagc agagcgaccu ggacacccug gccaaagagg    600 ccagcaucccc caucaucaac ggccugagcg accuguacca ccccauccag auccuggccg    660
acuaccugac ccugcaggaa cacuacagcu cccugaaggg ccugaccccug agcuggaucg    720 gcgacggcaa caacauccug cacagcauca ugaugagcgc cgccaaguuc ggcaugcauc    780
ugcaggccgc caccccccaag ggcuacgagc cugaugccag cgugaccaag cuggccgagc    840
aguacgccaa agagaacggc accaagcugc ugcugaccaa cgaccccug gaagccgccc     900 acggcggcaa cgucugauc accgacaccu ggaucagcau gggccaggaa gaggaaaaga    960
agaagcggcu gcaggccuuc cagggcuacc aggucacaau gaagaccgcc aaggugccg    1020 ccagcgacug gaccuuccug cacugccugc cccggaagcc cgaagaggug gacgacgagg   1080
uguucuacag cccccggucc cuggguguucc ccgaggccga gaaccggaag uggaccauua    1140
uggccgugau ggugucccug cugaccgacu acuccccccca gcugcagaag cccaaguucu   1200
agauaaguga acucgagcua gugacugacu aggaucuggu uaccacuaaa ccagccucaa   1260
gaacacccga auggagucuc uaagcuacau aauaccaacu uacacuuaca aaauguuguc    1320
ccccaaaaug uagccauucg uaucugcucc uaauaaaaag aaaguuucuu cacauucuag    1380
```

<210> SEQ ID NO 79

<211> LENGTH: 1380
<212> TYPE: RNA
<213> ORGANISM: Artificial sequence
<220> FEATURE:
<223> OTHER INFORMATION: Synthetic polynucleotide

<400> SEQUENCE: 79

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug gucuucaacc ugcggauccu gcugaacaac gccgccuucc | 180 |
| ggaacggcca caacuucaug guccgcaacu ucagaugcgg ccagcccug cagaacaggg | 240 |
| ugcagcugaa gggccgggac cugcugaccc ugaagaacuu caccggcgaa gagaucaggu | 300 |
| acaugcugug gcugagcgcc gaccugaagu uccggaucaa gcagaagggc gaguaccugc | 360 |
| cccugcugca aggcaagagc cugggcauga ucuucgagaa gcggagcacc cggacccggc | 420 |
| ugagcaccga gacaggcuuu gcccugcugg gaggccaccc cugcuuucug accacccagg | 480 |
| acauccaccu gggcgugaac gagagccuga ccgacaccgc cagagugcug agcagcaugg | 540 |
| ccgacgccgu gcuggcccgg guguacaagc agagcgaccu ggacacccug gccaaagagg | 600 |
| ccagcauccc caucaucaac ggccugagcg accuguacca ccccauccag auccuggccg | 660 |
| acuaccugac ccugcaggaa cacuacagcu cccugaaggg ccugacccug agcuggaucg | 720 |
| gcgacggcaa caacauccug cacagcauca ugaugagcgc cgccaaguuc ggcaugcauc | 780 |
| ugcaggccgc cacccccaag ggcuacgagc ugaugccag cgugaccaag cuggccgagc | 840 |
| aguacgccaa agagaacggc accaagcugc ugcugaccaa cgaccccug gaagccgccc | 900 |
| acggcggcaa cgucugauc accgacaccu ggaucagcau gggccaggaa gaggaaaaga | 960 |
| agaagcggcu gcaggccuuc cagggcuacc aggucacaau gaagaccgcc aagguggccg | 1020 |
| ccagcgacug gaccuuccug cacugccugc cccggaagcc cgaagaggug gacgacgagg | 1080 |
| uguucuacag ccccccgguc cugguguucc cgaggccga gaaccggaag uggaccauua | 1140 |
| uggccgugau ggugucccug cugaccgacu acuccccca gcugcagaag cccaaguucu | 1200 |
| agauaaguga cucgagcua gugacugacu aggaucuggu uaccacuaaa ccagccucaa | 1260 |
| gaacacccga auggagucuc uaagcuacau aauaccaacu uacacuuaca aaauguuguc | 1320 |
| ccccaaaaug uagccauucg uaucugcucc uaauaaaag aaaguuucuu cacauucuag | 1380 |

<210> SEQ ID NO 80
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 80

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug uucaaccuga ggauccugcu gaacaacgca gcuuucagga | 180 |
| acggccacaa cuucauggug aggaacuucc ggugcggcca gcccugcag aacaaggugc | 240 |
| agcugaaggg cagggaccug cugacccuga gaacuuacc ggagaggag aucaaguaca | 300 |
| ugcuguggcu gagcgcagac cugaaguuca ggaucaagca gaaggagag uaccugcccc | 360 |
| ugcugcaggg gaaguccug ggcaugaucu ucgagaagag gaguaccagg accaggcuga | 420 |
| gcaccgaaac cggcuucgcc cugcugggag gacacccug cuuccugacc acccaggaca | 480 |

| | | |
|---|---|---|
| uccaccuggg cgugaacgag agucugaccg acaccgccag ggugcugucu agcauggccg | 540 |
| acgccgugcu ggccagggug uacaagcagu cagaccugga cacccuggcu aaggaggcca | 600 |
| gcauccccau caucaacggc cugagcgacc uguaccaccc cauccagauc cuggcugacu | 660 |
| accugacccu gcaggagcac uacagcucuc ugaagggccu gacccugagc uggaucggcg | 720 |
| acgggaacaa cauccugcac agcaucauga ugagcgccgc caaguucggc augcaccugc | 780 |
| aggccgcuac ccccaagggu uacgagcccg acgccagcgu gaccaagcug gcagagcagu | 840 |
| acgccaagga gaacggcacc aagcugcugc ugaccaacga ccccuggag gccgccacg | 900 |
| gaggcaacgu gcugaucacc gacaccugga ucagcauggg acaggaggag agaagaaga | 960 |
| agcggcugca ggcuuuccag gguuaccagg ugaccaugaa gaccgccaag gugcugcca | 1020 |
| gcgacuggac cuuccugcac ugccugccca ggaagcccga ggagguggac gacgaggugu | 1080 |
| ucuacucucc caggagccug guguuccccg aggccgagaa caggaagugg accaucaugg | 1140 |
| cugugauggu gucccugcug accgacuaca gcccccagcu gcagaagccc aaguucgaa | 1200 |
| uaagugaacu cgagcuagug acugacuagg aucgguuac cacuaaacca gccucaagaa | 1260 |
| cacccgaaug gagucucuaa gcuacauaau accaacuuac acuuacaaaa uguugucccc | 1320 |
| caaaauguag ccauucguau cugcuccuaa uaaaagaaa guuucuucac auucuag | 1377 |

<210> SEQ ID NO 81
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 81

| | | |
|---|---|---|
| ucaacacaac auaucaaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug uucaaccuga ggauccugcu gaacaacgca gcuuucagga | 180 |
| acggccacaa cuucaugguu aggaacuucg ggucggcca gccccugcag aacaaggugc | 240 |
| agcugaaggg cagggaccug cugacccuga gaacuuacac cggagaggag aucaaguaca | 300 |
| ugcuguggcu gagcgcagac cugaaguuca ggaucaagca gaagggagag uaccugcccc | 360 |
| ugcugcaggg gaaguccug gcaugaucu ucgagaagag gaguaccagg accaggcuga | 420 |
| gcaccgaaac cggcuucgcc cugcugggag acacccccug cuuccugacg acccaggaca | 480 |
| uccaccucga agugaacgaa ucccucaccg auaccgcccg ggugauauca agcauggcag | 540 |
| augccgugcu ggccagggug uacaaacagu ccgaucugga cacucuggcu aaggaggcca | 600 |
| gcauccccau caucaacggc cugagcgacc uguaccaccc cauccagauc cuggcugacu | 660 |
| accugacccu gcaggagcac uacagcucuc ugaagggccu gacccugagc uggaucggcg | 720 |
| acgggaacaa cauccugcac uccaucauga ugucgccgc gaaguucgga augcaucugc | 780 |
| aagccgccac gccaaaagga uacgaaccgg augcgcccgu gacaaaguug gcggaacagu | 840 |
| acgcuaagga gaacggaacc aagcugcugc ugaccaacga ccccuggag gccgccacg | 900 |
| gaggcaacgu gcugaucacc gacaccugga ucagcauggg acaggaggag agaagaaga | 960 |
| agcggcugca ggcuuuccag gguuaccagg ugaccaugaa gaccgccaag gugcugcca | 1020 |
| gcgacuggac cuuccugcac ugccugccca ggaagcccga ggagguggac gacgaggugu | 1080 |
| ucuacucucc caggagccug guguuccccg aggccgagaa caggaagugg accaucaugg | 1140 |

| | |
|---|---|
| cugugauggu gucccugcug accgacuaca gcccccagcu gcagaagccc aaguucugaa | 1200 |
| uaagugaacu cgagcuagug acugacuagg aucgguuac cacuaaacca gccucaagaa | 1260 |
| cacccgaaug gagucucuaa gcuacauaau accaacuuac acuuacaaaa uguugucccc | 1320 |
| caaaauguag ccauucguau cugcuccuaa uaaaagaaa guuucuucac auucuag | 1377 |

<210> SEQ ID NO 82
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 82

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug uucaaccugc gcauccugcu gaacaacgcc gccuuccgca | 180 |
| acggccacaa cuucauggug cgcaacuucc gcugcggcca gccccugcag aacaaggugc | 240 |
| agcugaaggg ccgcgaccug cugacccuga gaacuucac cggcgaggag aucaaguaca | 300 |
| ugcugugggcu gagcgccgac cugaaguucc gcaucaagca aagggcgag uaccugcccc | 360 |
| ugcugcaggg caagagccug ggcaugaucu cgagaagcg cagcacccgc acccgccuga | 420 |
| gcaccgagac aggcuucgcc cugcugggcg ccaccccug cuccugacc acccaggaca | 480 |
| uccaccuggg cgugaacgag agccugaccg acaccgcccg cgugcugagc agcaugggccg | 540 |
| acgccgugcu ggcccgcgug uacaagcaga gcgaccugga cacccuggcc aaggaggcca | 600 |
| gcauccccau caucaacggc cugagcgacc uguaccaccc cauccagauc cuggccgacu | 660 |
| accugacccu gcaggagcac uacagcagcc ugaagggccu gacccugagc uggaucggcg | 720 |
| acggcaacaa cauccugcac agcaucauga ugagcgccgc caaguucggc augcaccugc | 780 |
| aggccgccac ccccaagggc uacgagcccc acgccagcgu gaccaagcug gccgagcagu | 840 |
| acgccaagga gaacggcacc aagcugcugc ugaccaacga cccccuggag gccgccacg | 900 |
| gcggcaacgu gcugaucacc gacaccugga ucagcauggg ccaggaggag gagaagaaga | 960 |
| agcgccugca ggccuuccag ggcuaccagg ugaccaugaa gaccgccaag guggccgcca | 1020 |
| gcgacuggac cuuccugcac ugccugcccc gcaagcccga ggagguggac gacgaggugu | 1080 |
| ucuacagccc ccgcagccug guguuccccg aggccgagaa ccgcaagugg accaucaugg | 1140 |
| ccgugauggu gagccugcug accgacuaca gcccccagcu gcagaagccc aaguucugaa | 1200 |
| uaagugaacu cgagcuagug acugacuagg aucgguuac cacuaaacca gccucaagaa | 1260 |
| cacccgaaug gagucucuaa gcuacauaau accaacuuac acuuacaaaa uguugucccc | 1320 |
| caaaauguag ccauucguau cugcuccuaa uaaaagaaa guuucuucac auucuag | 1377 |

<210> SEQ ID NO 83
<211> LENGTH: 1359
<212> TYPE: RNA
<213> ORGANISM: Artificial sequence
<220> FEATURE:
<223> OTHER INFORMATION: Synthetic polynucleotide

<400> SEQUENCE: 83

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caugcuguuc aaccugcgca uccugcugaa caacgccgcc uuccgcaacg | 180 |

```
gccacaacuu cauggugcgc aacuuccgcu gcggccagcc ccugcagaac aaggugcagc    240
ugaagggccg cgaccugcug acccugaaga acuucaccgg cgaggagauc aaguacaugc    300
uguggcugag cgccgaccug aaguuccgcu caagcagaa gggcgaguac cugcccugc     360 ugcagggcaa gagccugggc augaucuucg agaagcgcag cacccgcacc cgccugagca    420
ccgagacagg cuucgcccug cugggcggcc accccugcuu ccugaccacc caggacaucc    480
accugggcgu gaacgagagc cugaccgaca ccgcccgcgu gcugagcagc augggccgacg    540 ccgugcuggc ccgcguguac aagcagagcg accuggacac ccuggccaag gaggccagca    600
uccccaucau caacggccug agcgaccugu accaccccau ccagauccug ccgacuacc    660 ugacccugca ggagcacuac agcagccuga agggccugac ccugagcugg aucggcgacg    720
gcaacaacau ccugcacagc aucaugauga gcgccgccaa guucggcaug caccugcagg    780
ccgccacccc caagggcuac gagcccgacg ccagcgugac caagcuggcc gagcaguacg    840
ccaaggagaa cggcaccaag cugcugcuga ccaacgaccc ccuggaggcc gcccacggcg    900
gcaacgugcu gaucaccgac accuggauca gcaugggcca ggaggaggag aagaagaagc    960
gccugcaggc cuuccagggc uaccaggug ccaugaagac cgccaaggug gccgccagcg   1020
acuggaccuu ccugcacugc cugccccgca gcccgagga gguggacgac gaggugucu   1080 acagccccg cagccugg uucccgagg ccgagaaccg caaguggacc aucauggccg    1140
ugauggugag ccugcugacc gacuacagcc cccagcugca gaagcccaag uucugacuag   1200
ugacugacua ggaucuggu accacuaaac cagccucaag aacacccgaa uggagucucu   1260
aagcuacaua auaccaacuu acacuuacaa aauguugucc cccaaaaugu agccauucgu   1320
aucugcuccu aauaaaaga aaguuucuuc acauucuag                          1359
```

<210> SEQ ID NO 84  
<211> LENGTH: 1371  
<212> TYPE: RNA  
<213> ORGANISM: Artificial sequence  
<220> FEATURE:  
<223> OTHER INFORMATION: Synthetic polynucleotide

<400> SEQUENCE: 84

```
ucaacacaac auaucaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcuu uucaacuuga gaauccugcu gaacaacgcc gccuuucgca    180
acggucacaa uuuuauggu agaaacuuca gaugcggaca gccccuccaa aacaaggucc    240
agcugaaggg ccgcgaucuc cucacccuga gaacuucac gggggaggag aucaaguaca    300 ugcugugggcu cuccgcugac cugaaguuca ggaucaagca gaagggagaa uaucugccgc    360
ugcugcaagg gaagucccug gggaugauuu ucgagaagcg gagcacccgg acucggcucu    420
ccacugaaac ugguucgcc cuucggggcg gucaccccug cuuccugacc acucaagaca    480
uucaccucgg agugaacgag uccuugacug acaccgcccg ggugcugucg agcauggcag    540
acgccgugcu agcccgcgug uacaagcagu cagaccucga uaccuggcc aaggaggcuu    600 cgauccccau caucaacggg uuguccgacc uguaccaccc cauucagauu cucgccgacu    660
accucacccu gcaagagcau acagcucccc ugaaggggcu uacccugucc uggauuggcg    720
acggaaacaa cauccugcac uccauuauga gucggcggc caaguucggc augcaccucc    780
aagccgcgac cccuaagggu uacgaaccag acgcgucagu gacuaagcug gccgaacagu    840
```

```
acgcaaagga aaauggcacg aagcugcucc ugaccaacga uccguuggaa gccgcccaug    900
gcggaaaugu gcucaucacc gacaccugga ucucgauggg acaggaggaa gagaagaaga    960
agcggcugca ggcguuccag ggcuaccagg ucaccaugaa aacugccaag guggccgcca   1020
gcgacuggac cuuccugcac ugccuuccgc gcaagccuga ggagguggac gaugaagugu   1080
ucuacucucc acggucccug uguucccccg aggcggagaa ccgcaaaugg accaucaugg   1140
cugugauggu cagccugcug accgauuaca gcccucaguu gcaaaagccg aaguuuugau   1200
aacucgagcu agugacugac uaggaucugg uuaccacuaa accagccuca agaacacccg   1260
aauggagucu cuaagcuaca uaauaccaac uuacacuuac aaaauguugu cccccaaaau   1320
guagccauuc guaucugcuc cuaauaaaaa gaaaguuucu cacauucua g             1371
```

<210> SEQ ID NO 85
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 85

```
ucaacacaac auaucaaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcug uucaaccucc gcauccuccu caacaacgcc gcauucagaa    180
acgggcacaa cuucaugguc agaaacuucc gcugcgggca accccuacaa acaaggucc     240 agcucaaggg gcgggaccuc cugacccuga gaaacuucac cggcgaagag aucaaguaca    300
ugcuguggcu cuccgccgac cugaaguucc gcaucaagca aagggagag uaccucccgc     360 ugcugcaagg gaagucgcug gggaugaucu ucgagaagcg gucaaccaga acccggcugu    420
caaccgaaac cgdguucgca cugcuggggg acacccgug cuuccugacc acccaagaca    480
uccaccuggg agugaacgaa ucgcugaccg acaccgcccg cgucugagc ucaauggcgg    540 acgccgugcu ggcccgcgug uacaagcagu ccgaccugga cacccuggcc aaggaagcgu    600
ccaucccgau caucaacgga cuguccgacc uguaccaccc gauccagauc cuggcagacu    660
accugacccu gcaagaacac uacagcuccc ugaagggccu gacccuguca uggaucgggg    720 acggaacaa cauccugcac uccauaauga ugucagccgc caaguucgga augcaccucc    780
aagccgcaac cccgaagggc uacgaaccgg acgcaucagu gaccaaacug gccgagcagu    840 acgcaagga aaacggcacc aagcccugc ugaccaacga cccgcuggag gccgcacacg    900
gggggaacgu gcugaucacc gacaccugga ucuccauggg acaggaggag gaaaagaaga    960
agcggcugca ggcguuccag ggguaccagg ucaccaugaa aaccgcgaag ucgcggcau    1020 cagacuggac cuuccugcac ugccugcccc ggaagccgga gagguggac gacgaggugu   1080 ucuacucgcc gcgcucgcug uguucccccg aggcggagaa caggaagugg accaucaugg   1140
cggugauggu cagccuccug accgacuacu cgccgcagcu gcagaagccg aaguucugau   1200
aacucgagcu agugacugac uaggaucugg uuaccacuaa accagccuca agaacacccg   1260
aauggagucu cuaagcuaca uaauaccaac uuacacuuac aaaauguugu cccccaaaau   1320
guagccauuc guaucugcuc cuaauaaaaa gaaaguuucu cacauucua g             1371
```

<210> SEQ ID NO 86
<211> LENGTH: 1771
<212> TYPE: RNA
<213> ORGANISM: Artificial sequence

```
<220> FEATURE:
<223> OTHER INFORMATION: Synthetic polynucleotide

<400> SEQUENCE: 86
cucccucccc ccccccuaac guuacuggcc gaagccgcuu ggaauaaggc cggugugcgu      60
uugucuauau guuauuuucc accauauugc cgucuuuugg caaugugagg gcccggaaac     120
cuggcccugu cuucuugacg agcauuccua ggggucuuuc cccucucgcc aaaggaaugc     180
aaggucuguu gaaugucgug aaggaagcag uuccucugga agcuucuuga agacaaacaa     240
cgucuguagc gacccuuugc aggcagcgga accccccacc uggcgacagg ugccucugcg     300
gccaaaagcc acguguauaa gauacaccug caaaggcggc acaacccccag ugccacguug     360
ugaguuggau aguguggaa agagucaaau ggcucuccuc aagcguauuc aacaaggggc     420
ugaaggaugc ccagaaggua ccccauugua ugggaucuga ucuggggccu cggugcacau     480
gcuuuacgug uguuuagucg agguuaaaaa acgucuaggc ccccgaacc acggggacgu     540
gguuuuccuu ugaaaaacac gaugauaaua ugcuuuucaa ucuccgcauc uccuuaaca     600
acgccgcguu uagaaacggc cacaacuuca uggguccggaa cuucagaugu ggccagccgc     660
uucaaaacaa gguccagcug aagggccggg aucuucugac ccugaagaac uuuacuggcg     720
aagagaucaa guacaugcuc uggcucuccg cggacuugaa guuccgcauu aagcagaagg     780
gggaauaccu uccgcugcuu caaggaaaga gccucggcau gaucuuugag aagcgcucaa     840
ccaggacccg ccuuucuacu gaaacugggu ucgcgcugcu cgguggccac cccugcuucc     900
ugacgaccca ggacauccac cucggaguga acgaauccccu caccgauacc gcccgggugu     960
uaucgagcau ggcagaugcc gugcuggcca ggguguacaa acagucccgau cuggacacuc    1020
uggccaagga ggcgucaauu ccuauuauca acggccuuag ugaccucuac cauccgauuc    1080
agauccuggc cgauuaccuc acccugcaag aacacuacag cucccugaag ggucugacau    1140
uguccuggau cggcgacggc aacaacauuc uccauccau caugaugucc gccgcaaaau    1200
ucggcaugca ucuucaagcc gccacgccga aggguuacga gccgacgcu uccgugacua    1260
agcucgccga gcaguacgcu aaggagaacg gaaccaagcu ucugcugacu aacgacccac    1320
uagaagcagc ccacggggggc aacgugcuua uuacugacac cuggaucucc augggccagg    1380
aagaagagaa aaagaagcgg cugcaggcgu ccagggaua ucaggucacc augaaaaccg    1440
ccaaggucgc ugccuccgac uggaccuucc ugcacugccu gccucgcaag ccugaagaag    1500
uggacgacga ggguguucuac ucgccacgga gccucguguu ccccgaggcc gagaauagaa    1560
aguggaccau cauggccgug auggugcac ugcucaccga cuacagcccg cagcuucaga    1620
agcccaaguu cugaauaagu agauagugca gucacuggca caacgcguug cccgguaagc    1680
caaucgggua uacacggucg ucauacgca gacagggguuc uucuacuuug caagauaguc    1740
uagaguagua aaauaaauag uauaagucua g                                   1771

<210> SEQ ID NO 87
<211> LENGTH: 1771
<212> TYPE: RNA
<213> ORGANISM: Artificial sequence
<220> FEATURE:
<223> OTHER INFORMATION: Synthetic polynucleotide

<400> SEQUENCE: 87
cucccucccc ccccccuaac guuacuggcc gaagccgcuu ggaauaaggc cggugugcgu      60
uugucuauau guuauuuucc accauauugc cgucuuuugg caaugugagg gcccggaaac     120
```

| | |
|---|---:|
| cuggcccugu cuucuugacg agcauuccua ggguucuuuc cccucucgcc aaaggaaugc | 180 |
| aaggucuguu gaaugucgug aaggaagcag uuccucugga agcuucuuga agacaaacaa | 240 |
| cgucuguagc gacccuuugc aggcagcgga acccccacc uggcgacagg ugccucugcg | 300 |
| gccaaaagcc acguguauaa gauacaccug caaaggcggc acaacccag ugccacguug | 360 |
| ugaguuggau aguguggaa agagucaaau ggcucuccuc aagcguauuc aacaaggggc | 420 |
| ugaaggaugc ccagaaggua ccccauugua ugggaucuga ucuggggccu cggugcacau | 480 |
| gcuuuacgug uguuuagucg agguuaaaaa acgucuaggc cccccgaacc acggggacgu | 540 |
| gguuuuccuu ugaaaaacac gaugauaaua ugcuuuucaa ccugagaauc ucuugaaca | 600 |
| augcugcuuu ucggaauggc cacaacuuua ugguucggaa cuuccguugc ggccagccuu | 660 |
| uacaaaacaa ggccagcug aagggccggg auuugcucac acuaaagaac uuuacuggag | 720 |
| aagagaucaa guacaugcua uggcugucgg ccgaccugaa guuccguauc aagcagaagg | 780 |
| gagaauaccu uccgcugcuu caaggaaaga gccucggcau gaucuuugag aagcgcucaa | 840 |
| ccaggacccg ccuucuacu gaaacugggu ucgcgcugcu cgguggccac cccugcuucc | 900 |
| ugacgaccca ggacauccac cucggagauga acgaaucccu caccgauacc gcccggugu | 960 |
| uaucgagcau ggcagaugcc gugcuggcca ggguguacaa acaguccgau cucgauaccu | 1020 |
| uggcaaagga ggcuuccauu cccaucauca acggccugag cgaccuguac cacccaaucc | 1080 |
| aaauccuggc ugacuaccug acccugcaag agcacuacag cagccugaag ggucugaccc | 1140 |
| ugucauggau uggcgaugga acaauauuc ugcacuccau caugaugucc gccgcgaagu | 1200 |
| ucggaaugca ucugcaagcc gccacuccaa aaggauacga accggaugca uccgugacca | 1260 |
| aguuggcgga acaguacgcg aaggagaacg gaaccaagcu ccugcugacu aacgacccgc | 1320 |
| ucgaggcugc gcauggggu aacgugcuga uuacggacac cuggaucucc augggggcagg | 1380 |
| aggaagagaa gaagaagaga cugcaggcau uccaggggua ccaggucacc augaaaaccg | 1440 |
| caaaagugcc agcuucggac uggacuuucc ugcauugccu gccgaggaag ccggaggaag | 1500 |
| ucgacgacga aguguucuac ucgccucggu cccuggguguu ccccgaggcc gaaaaccgga | 1560 |
| aguggaccau caugggccgug augguguccu ugcugacuga cuauagcccg cagcugcaga | 1620 |
| agccuaaguu cugaauaagu agauagugca gucacuggca caacgcguug cccgguaagc | 1680 |
| caaucgggua uacacggucg ucauacgca gacagggguuc uucuacuuug caagauaguc | 1740 |
| uagaguagua aaauaaauag uauaagucua g | 1771 |

<210> SEQ ID NO 88
<211> LENGTH: 1771
<212> TYPE: RNA
<213> ORGANISM: Artificial sequence
<220> FEATURE:
<223> OTHER INFORMATION: Synthetic polynucleotide

<400> SEQUENCE: 88

| | |
|---|---:|
| cucccucccc ccccccuaac guuacuggcc gaagccgcuu ggaauaaggc cggugugcgu | 60 |
| uugucuauau guuauuuucc accauauugc cgucuuuugg caaugugagg gcccggaaac | 120 |
| cuggcccugu cuucuugacg agcauuccua ggguucuuuc cccucucgcc aaaggaaugc | 180 |
| aaggucuguu gaaugucgug aaggaagcag uuccucugga agcuucuuga agacaaacaa | 240 |
| cgucuguagc gacccuuugc aggcagcgga acccccacc uggcgacagg ugccucugcg | 300 |
| gccaaaagcc acguguauaa gauacaccug caaaggcggc acaacccag ugccacguug | 360 |
| ugaguuggau aguguggaa agagucaaau ggcucuccuc aagcguauuc aacaaggggc | 420 |

```
ugaaggaugc ccagaaggua ccccauugua ugggaucuga ucuggggccu cggugcacau      480
gcuuuacgug uguuuagucg agguuaaaaa acgucuaggc cccccgaacc acggggacgu      540
gguuuuccuu ugaaaaacac gaugauaaua ugcuguucaa ccugcgcauc cugcugaaca      600
acgccgccuu ccgcaacggc cacaacuuca uggugcgcaa cuuccgcugc ggccagcccc      660
ugcagaacaa ggugcagcug aagggccgcg accugcugac ccugaagaac uucaccggcg      720
aggagaucaa guacaugcug ggcugagcg ccgaccugaa guuccgcauc aagcagaagg      780
gcgaguaccu gccccugcug cagggcaaga gccugggcau gaucuucgag aagcgcagca      840
cccgcacccg ccugagcacc gagacaggcc uggcccugcu gggcggccac cccugcuucc      900
ugaccaccca ggacauccac cugggcguga acgagagccu gaccgacacc gcccgcgugc      960
ugagcagcau ggccgacgcc gugcuggccc gcguguacaa gcagagcgac cuggacaccc     1020
uggccaagga ggccagcauc cccaucauca acggccugag cgaccuguac caccccaucc     1080
agauccuggc cgacuaccug acccugcagg agcacuacag cagccugaag ggccugaccc     1140
ugagcuggau cggcgacggc aacaacaucc ugcacagcau caugaugagc gccgccaagu     1200
ucggcaugca ccugcaggcc gccaccccca agggcuacga gcccgacgcc agcgugacca     1260
agcuggccga gcaguacgcc aaggagaacg gcaccaagcu gcugcugacc aacgaccccc     1320
uggaggccgc ccacgcggc aacgugcuga ucaccgacac cuggaucagc augggccagg     1380
aggaggagaa gaagaagcgc cugcaggccu ccagggcua ccaggugacc augaagaccg     1440 ccaaggugc cgccagcgac uggaccuucc ugcacgccu gccccgcaag cccgaggagg     1500
uggacgacga ggguucuac agcccccgca gccuggguu ccccgaggcc gagaaccgca     1560
aguggaccau cauggccgug auggugagcc ugcugaccga cuacagcccc cagcugcaga     1620
agcccaaguu cugaauaagu agauagugca gucacuggca caacgcguug cccgguaagc     1680
caaucgggua uacacggucg ucauacgcua gacagguuc uucuacuuug caagauaguc     1740
uagaguagua aauaaauag uauaagucua g                                    1771

<210> SEQ ID NO 89
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 89
ucaacacaac auaucaaaa caaacgaauc ucaagcaauc aagcauucua cuucuauugc        60
agcaauuuaa aucauuucuu uuaaagcaaa agcaauuuuc ugaaaauuuu caccauuuac       120
gaacgauagc caccaugcuu uucaaucccc gcauccuccu uaacaacgcc gcguuuagaa       180
acggccacaa cuucaugguc cggaacuuca gauguggcca gccgcuucaa aacaaggucc       240
agcugaaggg ccgggaucuu cugacccuga gaacuuuac uggcgaagag aucaaguaca       300
ugcucuggcu cuccgcggac uugaaguucc gcauuaagca gaaggggaa uaccuuccgc       360 ugcuucaagg aaaagccuc ggcaugaucu uugagaagcg cucaaccagg acccgccuuu       420
cuacugaaac ugguucgcg cugcucggug gccacccccug cuuccugacg acccaggaca       480
uccaccucgg agugaacgaa ucccucaccg auaccgcccg ggguuuaucg agcauggcag       540
augccgugcu ggccagggug uacaaacagu ccgaucugga cacucuggcc aaggaggcgu       600
caauuccuau uaucaacggc cuuagugacc ucuaccaucc gauucagauc cuggccgauu       660
```

| | |
|---|---|
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagccuga agaaguggac gacgaggugu | 1080 |
| ucuacgcc acggagccuc uguucccg aggccgagaa uagaaaguggg accaucaugg | 1140 |
| ccgugauggu gucacugcuc accgacuaca gcccgcagcu ucagaagccc aaguucuagc | 1200 |
| ucgagcuagu gacugacuag gaucggguua ccacuaaacc agccucaaga acacccgaau | 1260 |
| ggagucucua agcuacauaa uaccaacuua cacuuacaaa auguugucc ccaaaaugua | 1320 |
| gccauucgua ucugcuccua auaaaaagaa aguuucuuca cauucuag | 1368 |

<210> SEQ ID NO 90
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 90

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcuu ucaaucucc gcauccuccu uaacaacgcc gcguuuagaa | 180 |
| acggccacaa cuucugguc cggaacuuca gauguggcca gccgcuucaa aacaaggucc | 240 |
| agcugaaggg ccgggaucuu cugacccuga agaacuuuac uggcgaagag aucaaguaca | 300 |
| ugcucuggcu cuccgcggac uugaaguccc gcauuaagca gaaggggggaa uaccuuccgc | 360 |
| ugcuucaagg aaagagccuc ggcaugaucu uugagaagcg cucaaccagg acccgccuuu | 420 |
| cuacugaaac ugggguucgcg cugcucggug gccaccccug cuuccugacg acccaggaca | 480 |
| uccaccucgg agugaacgaa ucccucaccg auaccgcccg ggguguaucg agcauggcag | 540 |
| augccgugcu ggccagggug uacaaacagu ccgaucugga cacucuggcc aaggaggcgu | 600 |
| caauuccuau uaucaacggc cuuagugacc ucuaccaucc gauucagauc cuggccgauu | 660 |
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagccuga agaaguggac gacgaggugu | 1080 |
| ucuacgcc acggagccuc uguucccg aggccgagaa uagaaaguggg accaucaugg | 1140 |
| ccgugauggu gucacugcuc accgacuaca gcccgcagcu ucagaagccc aaguucuagc | 1200 |
| ucgagcuagu gacugacuag gaucggguua ccacuaaacc agccucaaga acacccgaau | 1260 |
| ggagucucua agcuacauaa uaccaacuua cacuuacaaa auguugucc ccaaaaugua | 1320 |
| gccauucgua ucugcuccua auaaaaagaa aguuucuuca cauucuag | 1368 |

<210> SEQ ID NO 91
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 91

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcuu uucaaucucc gcauccuccu uaacaacgcc gcguuuagaa   180
acggccacaa cuucaugguc cggaacuuca gauguggcca gccgcuucaa aacaaggucc   240
agcugaaggg ccgggaucuu cugacccuga agaacuuuac uggcgaagag aucaaguaca   300
ugcucuggcu cuccgcggac uugaaguucc gcauuaagca gaaggggggaa uaccuuccgc   360
ugcuucaagg aaagagccuc ggcaugaucu uugagaagcg cucaaccagg acccgccuuu   420
cuacugaaac uggguucgcg cugcucggug gccaccccug cuuccugacg acccaggaca   480
uccaccucgg agugaacgaa ucccucaccg auaccgcccg ggguguaucg agcauggcag   540
augccgugcu ggccagggug uacaaacagu ccgaucugga cacucuggcc aaggaggcgu   600
caauuccuau uaucaacggc cuuagugacc ucuaccaucc gauucagauc cuggccgauu   660
accucacccu gcaagaacac uacagcuccc ugaagggucu gacauugucc uggaucggcg   720
acggcaacaa cauucuccau uccaucauga ugccgccgc aaaauucggc augcaucuuc   780
aagccgccac gccgaagggu uacgagcccg acgcuuccgu gacuaagcuc gccgagcagu   840
acgcuaagga gaacggaacc aagcuucugc ugacuaacga cccacuagaa gcagcccacg   900
ggggcaacgu gcuuauuacu gacaccugga ucuccauggg ccaggaagaa gagaaaaaga   960
agcggcugca ggcguuccag ggauaucagg ucaccaugaa aaccgccaag gucgcugccu  1020
ccgacuggac cuuccugcac ugccugccuc gcaagccuga agaaguggac gacgaggugu  1080
ucuacucgcc acggagccuc guguuccccg aggccgagaa uagaaagugg accaucaugg  1140
ccgugauggu gucacugcuc accgacuaca gcccgcagcu ucagaagccc aaguucuagc  1200
ucgagcuagu gacugacuag gaucugguua ccacuaaaacc agccucaaga cacccgaau  1260
ggagucucua agcuacauaa uaccaacuua cacuuacaaa auguugucc ccaaaaugua  1320
gccauucgua ucugcuccua auaaaagaa aguuucuuca cauucuag                1368
```

<210> SEQ ID NO 92
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 92

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcuu uucaaucucc gcauccuccu uaacaacgcc gcguuuagaa   180
acggccacaa cuucaugguc cggaacuuca gauguggcca gccgcuucaa aacaaggucc   240
agcugaaggg ccgggaucuu cugacccuga agaacuuuac uggcgaagag aucaaguaca   300
ugcucuggcu cuccgcggac uugaaguucc gcauuaagca gaaggggggaa uaccuuccgc   360
```

```
ugcuucaagg aaagagccuc ggcaugaucu uugagaagcg cucaaccagg acccgccuuu    420
cuacugaaac uggguucgcg cugcucggug gccacccug cuuccugacg acccaggaca     480
uccaccucgg agugaacgaa ucccucaccg auaccgcccg ggaguuaucg agcauggcag    540
augccgugcu ggccagggug uacaaacagu ccgaucugga cacucuggcc aaggaggcgu    600
caauuccuau uaucaacggc cuuagugacc ucuaccaucc gauucagauc cuggccgauu    660
accucacccu gcaagaacac uacagcuccc ugaagggucu gacauugucc uggaucggcg    720
acggcaacaa cauucuccau uccaucauga uguccgccgc aaaauucggc augcaucuuc    780
aagccgccac gccgaagggu uacgagcccg acgcuuccgu gacuaagcuc gccgagcagu    840
acgcuaagga gaacggaacc aagcuucugc ugacuaacga cccacuagaa gcagcccacg    900
ggggcaacgu gcuuauuacu gacaccugga ucuccauggg ccaggaagaa gagaaaaaga    960
agcggcugca ggcguuccag ggauaucagg ucaccaugaa aaccgccaag gucgcugccu   1020
ccgacuggac cuuccugcac ugccugccuc gcaagcccuga agaaguggac gacgaggugu   1080
ucuacucgcc acggagccuc uguuuccccg aggccgagaa uagaaagugg accaucaugg   1140
ccgugauggu gucacugcuc accgacuaca gcccgcagcu ucagaagccc aaguucuagc   1200
ucgagcuagu gacugacuag gaucugguua ccacuaaaacc agccucaaga acacccgaau   1260
ggagucucua agcuacauaa uaccaacuua cacuuacaaa auguugucc ccaaaaugua    1320 gccauucgua ucugcuccua auaaaaagaa aguuucuuca cauucuag                1368

<210> SEQ ID NO 93
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 93
ucaacacaac auaucaaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcuu uucaaucucc gcauccuccu uaacaacgcc gcguuuagaa    180
acggccacaa cuucauggu cggaacuuca gaugugggcca gccgcuucaa aacaaggucc    240
agcugaaggg ccgggaucuu cugacccuga gaacuuuac uggcgaagag aucaaguaca    300
ugcucuggcu cuccgcggac uugaaguucc gcauuaagca gaaggggggaa uaccuuccgc    360 ugcuucaagg aaagagccuc ggcaugaucu uugagaagcg cucaaccagg acccgccuuu    420
cuacugaaac ugggucgcg cugcucggug gccacccug cuuccugacg acccaggaca      480
uccaccucgg agugaacgaa ucccucaccg auaccgcccg ggaguuaucg agcauggcag    540
augccgugcu ggccagggug uacaaacagu ccgaucugga cacucuggcc aaggaggcgu    600
caauuccuau uaucaacggc cuuagugacc ucuaccaucc gauucagauc cuggccgauu    660
accucacccu gcaagaacac uacagcuccc ugaagggucu gacauugucc uggaucggcg    720
acggcaacaa cauucuccau uccaucauga uguccgccgc aaaauucggc augcaucuuc    780
aagccgccac gccgaagggu uacgagcccg acgcuuccgu gacuaagcuc gccgagcagu    840
acgcuaagga gaacggaacc aagcuucugc ugacuaacga cccacuagaa gcagcccacg    900
ggggcaacgu gcuuauuacu gacaccugga ucuccauggg ccaggaagaa gagaaaaaga    960
agcggcugca ggcguuccag ggauaucagg ucaccaugaa aaccgccaag gucgcugccu   1020
ccgacuggac cuuccugcac ugccugccuc gcaagcccuga agaaguggac gacgaggugu   1080
```

```
ucuacucgcc acggagccuc guguuccccg aggccgagaa uagaaagugg accaucaugg   1140
ccgugauggu gucacugcuc accgacuaca gcccgcagcu ucagaagccc aaguucuagc   1200
ucgagcuagu gacugacuag gaucugguua ccacuaaacc agccucaaga acacccgaau   1260
ggagucucua agcuacauaa uaccaacuua cacuuacaaa auguugucccc ccaaaaugua   1320 gccauucgua ucugcuccua auaaaaagaa aguuucuuca cauucuag             1368
```

```
<210> SEQ ID NO 94
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 94
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccauggug uucaaccucc gcauccuccu caacaacgcc gcauucagaa   180
acgggcacaa cuucaugguc agaaacuucc gcugcgggca accccuacaa aacaaggucc   240
agcucaaggg gcgggaccuc cugacccuga gaaacuucac cggcgaagag aucaaguaca   300 ugcugguggcu cuccgccgac cugaaguucc gcaucaagca gaagggagag uaccucccgc   360
ugcugcaagg gaagucgcug gggaugaucu ucgagaagcg gucaaccaga acccggcugu   420
caaccgaaac cggguucgca cugcgggggg acacccgug cuuccugacc acccaagaca   480
uccaccuggg agugaacgaa ucgcugaccg acaccgcccg cgugcugagc ucaauggcgg   540
acgccgugcu ggcccgcgug uacaagcagu ccgaccugga cacccuggcc aaggaagcgu   600 ccauccgau caucaacgga cugucccgacc uguaccaccc gaccagauc cuggcagacu   660 accugacccu gcaagaacac uacagcuccc ugaagggccu gacccuguca uggaucgggg   720
acgggaacaa cauccugcac uccauaauga ugucagccgc caaguucgga augcaccucc   780
aagccgcaac cccgaagggc uacgaaccgg acgcaucagu gaccaaacug gccgagcagu   840
acgccaagga aaacggcacc aagcuccugc ugaccaacga cccgcuggag gccgcacacg   900
gggggaacgu gcugaucacc gacaccugga ucuccauggg acaggaggag gaaaagaaga   960
agcggcugca ggcguuccag ggguaccagg ucaccaugaa aaccgcgaag gucgcggcau   1020
cagacuggac cuuccugcac ugccugcccc ggaagccgga agagguggac gacgaggugu   1080
ucuacucgcc gcgcucgcug guguuccccg aggcggagaa caggaagugg accaucaugg   1140
cggugauggu cagccuccug accgacuacu cgccgcagcu gcagaagccg aaguucugau   1200
aacucgagcu agugacugac uaggaucugg uuaccacuaa accagccuca agaacacccg   1260
aauggagucu cuaagcuaca uaauaccaac uuacacuuca aaaauguugu ccccaaaau   1320 guagccauuc guaucugcuc cuaauaaaaa gaaaguuucu ucacauucua g           1371
```

```
<210> SEQ ID NO 95
<211> LENGTH: 1371
<212> TYPE: RNA
<213> ORGANISM: Artificial sequence
<220> FEATURE:
<223> OTHER INFORMATION: Synthetic polynucleotide
```

<400> SEQUENCE: 95

```
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccauggug uucaaccucc gcauccuccu caacaacgcc gcauucagaa     180
acgggcacaa cuucaugguc agaaacuucc gcugcgggca accccuacaa aaccgggucc     240
agcucaaggg gcgggaccuc cugacccuga agaacuucac cggcgaagag aucaaguaca     300
ugcuguggcu cuccgccgac cugaaguucc gcaucaagca gaagggagag uaccucccgc     360
ugcugcaagg gaagucgcug gggaugaucu cgagaagcg gucaaccaga acccggcugu     420
caaccgaaac cggguucgca cugcuggggg acacccgug cuuccugacc acccaagaca     480
uccaccuggg agugaacgaa ucgcugaccg acaccgcccg cgucugagc ucaauggcgg      540
acgccgugcu ggcccgcgug uacaagcagu ccgaccugga cacccuggcc aaggaagcgu     600
ccaucccgau caucaacgga cuguccgacc uguaccaccc gauccagauc cuggcagacu     660
accugacccu gcaagaacac uacagcuccc ugaagggccu gacccuguca uggaucgggg     720
acgggaacaa cauccugcac uccauaauga ugucagccgc caaguucgga augcaccucc     780
aagccgcaac cccgaagggc uacgaaccgg acgcaucagu gaccaaacug gccgagcagu     840
acgccaagga aaacggcacc aagcuccugc ugaccaacga cccgcuggag gccgcacacg     900
gggggaacgu gcugaucacc gacaccugga ucuccauggg acaggaggag gaaaagaaga     960
agcggcugca ggcguuccag ggguaccagg ucaccaugaa aaccgcgaag gucgcggcau    1020
cagacuggac cuuccugcac ugccugcccc ggaagccgga agagguggac gacgaggugu    1080
ucuacucgcc gcgcucgcug guguuccccg aggcggagaa caggaagugg accaucaugg    1140
cggugauggu cagccuccug accgacuacu cgccgcagcu gcagaagccg aaguucugau    1200
aacucgagcu agugacugac uaggaucugg uuaccacuaa accagccuca agaacacccg    1260
aauggagucu cuaagcuaca uaauaccaac uuacacuuac aaaauguugu cccccaaaau    1320
guagccauuc guaucugcuc cuaauaaaaa gaaaguuucu ucacauucua g             1371
```

<210> SEQ ID NO 96
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 96

```
ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccauggug uucaaccucc gcauccuccu caacaacgcc gcauucagaa     180
acgggcacaa cuucaugguc agaaacuucc gcugcgggca accccuacaa aaccgggucc     240
agcucaaggg gcgggaccuc cugacccuga agaacuucac cggcgaagag aucggguaca     300
ugcuguggcu cuccgccgac cugaaguucc gcaucaagca gaagggagag uaccucccgc     360
ugcugcaagg gaagucgcug gggaugaucu cgagaagcg gucaaccaga acccggcugu     420
caaccgaaac cggguucgca cugcuggggg acacccgug cuuccugacc acccaagaca     480
uccaccuggg agugaacgaa ucgcugaccg acaccgcccg cgucugagc ucaauggcgg      540
acgccgugcu ggcccgcgug uacaagcagu ccgaccugga cacccuggcc aaggaagcgu     600
```

| | |
|---|---|
| ccaucccgau caucaacgga cuguccgacc uguaccaccc gauccagauc cuggcagacu | 660 |
| accugacccu gcaagaacac uacagcuccc ugaagggccu gacccuguca uggaucgggg | 720 |
| acgggaacaa cauccugcac uccauaauga gucagccgc caaguucgga augcaccucc | 780 |
| aagccgcaac cccgaagggc uacgaaccgg acgcaucagu gaccaaacug gccgagcagu | 840 |
| acgccaagga aaacggcacc aagcuccugc ugaccaacga cccgcuggag gccgcacacg | 900 |
| gggggaacgu gcugaucacc gacaccugga ucuccauggg acaggaggag gaaaagaaga | 960 |
| agcggcugca ggcguuccag ggguaccagg ucaccaugaa aaccgcgaag gucgcggcau | 1020 |
| cagacuggac cuuccugcac ugccugcccc ggaagccgga agagguggac gacgaggugu | 1080 |
| ucuacucgcc gcgcucgcug guguucccg aggcggagaa caggaagugg accaucaugg | 1140 |
| cggugauggu cagccuccug accgacuacu cgccgcagcu gcagaagccg aaguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu cccccaaaau | 1320 |
| guagccauuc guaucugcuc cuauaaaaa gaaaguuucu cacauucua g | 1371 |

<210> SEQ ID NO 97
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 97

| | |
|---|---|
| ucaacacaac auauacaaaa caaacgaauc ucaagcaauc aagcauucua cuucuauugc | 60 |
| agcauuuaa aucauuucuu uuaaagcaaa agcaauuuuc ugaaaauuuu caccauuuac | 120 |
| gaacgauagc caccaugcug gucaaccucc gcauccuccu caacaacgcc gcauucagaa | 180 |
| acgggcacaa cuucauggu agaaacuucc gcugcgggca accccuacaa aacaaggucc | 240 |
| agcucaaggg gcgggaccuc cugacccuga agaacuucac cggcgaagag aucaaguaca | 300 |
| ugcuguggcu cuccgccgac cugaaguucc gcaucaagca gaagggagag uaccucccgc | 360 |
| ugcugcaagg gaagucgcug gggaugaucu ucgagaagcg gucaaccaga acccggcugu | 420 |
| caaccgaaac cggguucgca cugcuggggg gacacccgug cuuccugacc acccaagaca | 480 |
| uccaccuggg agugaacgaa ucgcugaccg acaccgcccg cgugcugagc ucaauggcgg | 540 |
| acgccgugcu ggcccgcgug uacaagcagu ccgaccugga cacccuggcc aaggaagcgu | 600 |
| ccaucccgau caucaacgga cuguccgacc uguaccaccc gauccagauc cuggcagacu | 660 |
| accugacccu gcaagaacac uacagcuccc ugaagggccu gacccuguca uggaucgggg | 720 |
| acgggaacaa cauccugcac uccauaauga gucagccgc caaguucgga augcaccucc | 780 |
| aagccgcaac cccgaagggc uacgaaccgg acgcaucagu gaccaaacug gccgagcagu | 840 |
| acgccaagga aaacggcacc aagcuccugc ugaccaacga cccgcuggag gccgcacacg | 900 |
| gggggaacgu gcugaucacc gacaccugga ucuccauggg acaggaggag gaaaagaaga | 960 |
| agcggcugca ggcguuccag ggguaccagg ucaccaugaa aaccgcgaag gucgcggcau | 1020 |
| cagacuggac cuuccugcac ugccugcccc ggaagccgga agagguggac gacgaggugu | 1080 |
| ucuacucgcc gcgcucgcug guguucccg aggcggagaa caggaagugg accaucaugg | 1140 |
| cggugauggu cagccuccug accgacuacu cgccgcagcu gcagaagccg aaguucugau | 1200 |
| aacucgagcu agugacugac uaggaucugg uuaccacuaa accagccuca agaacacccg | 1260 |

|  |  |  |  |  |  |
|---|---|---|---|---|---|
| aauggagucu | cuaagcuaca | uaauaccaac | uuacacuuac | aaaauguugu | cccccaaaau | 1320 |
| guagccauuc | guaucugcuc | cuaauaaaaa | gaaaguuucu | ucacauucua | g | 1371 |

<210> SEQ ID NO 98
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 98

|  |  |  |  |  |  |
|---|---|---|---|---|---|
| ucaacacaac | auauacaaaa | caaacgaauc | ucaagcaauc | aagcauucua | cuucuauugc | 60 |
| agcaauuuaa | aucauuucuu | uuaaagcaaa | agcaauuuuc | ugaaaauuuu | caccauuuac | 120 |
| gaacgauagc | caccaugcug | gucaaccucc | gcauccuccu | caacaacgcc | gcauucagaa | 180 |
| acgggcacaa | cuucaugguc | agaaacuucc | gcugcgggca | accccuacaa | aaccggaucc | 240 |
| agcucaaggg | gcgggaccuc | cugacccuga | agaacuucac | cggcgaagag | aucaaguaca | 300 |
| ugcuguggcu | cuccgccgac | cugaaguucc | gcaucaagca | gaagggagag | uaccucccgc | 360 |
| ugcugcaagg | gaagucgcug | gggaugaucu | ucgagaagcg | gucaaccaga | acccggcugu | 420 |
| caaccgaaac | cgggauucgca | cugcuggggg | gacacccgug | cuuccugacc | acccaagaca | 480 |
| uccaccuggg | agugaacgaa | ucgcugaccg | acaccgcccg | cgugcugagc | ucaauggcgg | 540 |
| acgccgugcu | ggcccgcgug | uacaagcagu | ccgaccugga | cacccuggcc | aaggaagcgu | 600 |
| ccauccccgau | caucaacgga | cuguccgacc | uguaccaccc | gauccagauc | cuggcagacu | 660 |
| accugacccu | gcaagaacac | uacagcuccc | ugaagggccu | gacccuguca | uggaucgggg | 720 |
| acggaacaa | cauccugcac | uccauaauga | ugucagccgc | caaguucgga | augcaccucc | 780 |
| aagccgcaac | cccgaagggc | uacgaaccgg | acgcaucagu | gaccaaacug | gccgagcagu | 840 |
| acgccaagga | aaacggcacc | aagcuccugc | ugaccaacga | cccgcuggag | gccgcacacg | 900 |
| gggggaacgu | gcugaucacc | gacaccugga | ucuccauggg | acaggaggag | gaaaagaaga | 960 |
| agcggcugca | ggcguuccag | ggguaccagg | ucaccaugaa | aaccgcgaag | gucgcggcau | 1020 |
| cagacuggac | cuuccugcac | ugccugcccc | ggaagccgga | agagguggac | gacgaggugu | 1080 |
| ucuacucgcc | gcgcucgcug | uguuccccg | aggcggagaa | caggaagugg | accaucaugg | 1140 |
| cggugauggu | cagccuccug | accgacuacu | cgccgcagcu | gcagaagccg | aaguucugau | 1200 |
| aacucgagcu | agugacugac | uaggaucugg | uuaccacuaa | accagccuca | agaacacccg | 1260 |
| aauggagucu | cuaagcuaca | uaauaccaac | uuacacuuac | aaaauguugu | cccccaaaau | 1320 |
| guagccauuc | guaucugcuc | cuaauaaaaa | gaaaguuucu | ucacauucua | g | 1371 |

<210> SEQ ID NO 99
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 99

|  |  |  |  |  |  |
|---|---|---|---|---|---|
| ucaacacaac | auauacaaaa | caaacgaauc | ucaagcaauc | aagcauucua | cuucuauugc | 60 |
| agcaauuuaa | aucauuucuu | uuaaagcaaa | agcaauuuuc | ugaaaauuuu | caccauuuac | 120 |
| gaacgauagc | caccaugcug | gucaaccucc | gcauccuccu | caacaacgcc | gcauucagaa | 180 |
| acgggcacaa | cuucaugguc | agaaacuucc | gcugcgggca | accccuacaa | aaccggaucc | 240 |

```
agcucaaggg gcgggaccuc cugacccuga agaacuucac cggcgaagag auccgguaca    300
ugcuguggcu cuccgccgac cugaaguucc gcaucaagca gaaggagag uaccucccgc     360 ugcugcaagg gaagucgcug gggaugaucu ucgagaagcg gucaaccaga acccggcugu   420
caaccgaaac cggguucgca cugcugggg gacacccgug cuuccugacc acccaagaca    480
uccaccuggg agugaacgaa ucgcugaccg acaccgcccg cgugcugagc ucaauggcgg    540
acgccgugcu ggcccgcgug uacaagcagu ccgaccugga cacccuggcc aaggaagcgu    600
ccaucccgau caucaacgga cugucccgacc uguaccaccc gauccagauc cuggcagacu  660
accugacccu gcaagaacac uacagcuccc ugaagggccu gacccuguca uggaucgggg    720
acgggaacaa cauccugcac uccauaauga gucagccgc caaguucgga augcaccucc    780
aagccgcaac cccgaagggc uacgaaccgg acgcaucagu gaccaaacug gccgagcagu    840
acgccaagga aaacggcacc aagcccugc ugaccaacga cccgcuggag gccgcacacg     900 ggggaacgu gcugaucacc gacaccugga ucuccauggg acaggaggag gaaaagaaga    960
agcggcugca ggcguuccag ggguaccagg ucaccaugaa aaccgcgaag gucgcggcau   1020
cagacuggac cuuccugcac ugccugcccc ggaagccgga agagguggac gacgaggugu   1080
ucuacucgcc gcgcucgcug guguucccg aggcggagaa caggaagugg accaucaugg   1140
cggugauggu cagccuccug accgacuacu cgccgcagcu gcagaagccg aaguucugau  1200
aacucgagcu agugacugac uaggaucugg uuaccacuaa accagccuca gaacacccg   1260 aauggagucu cuaagcuaca uaauaccaac uuacacuuac aaaauguugu cccccaaaau  1320
guagccauuc guaucugcuc cuaauaaaaa gaaaguuucu ucacauucua g            1371

<210> SEQ ID NO 100
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 100
ucaacacaac auaucaaaaa caaacgaauc ucaagcaauc aagcauucua cuucuauugc     60
agcaauuuaa aucauuucuu uuaaagcaaa agcaauuuuc ugaaaauuuu caccauuuac   120
gaacgauagc caccaugcug gucaaccugc gcaccugcu gaacaacgcc gccuuccgca   180
acggccacaa cuucaugguug cgcaacuucc gcugcggcca gccccugcag aacaaggugc   240
agcugaaggg ccgcgaccug cugacccuga agaacuucac cggcgaggag aucaaguaca   300
ugcuguggcu gagcgccgac cugaaguucc gcaucaagca gaagggcgag uaccugcccc   360
ugcugcaggg caagagccug ggcaugaucu ucgagaagcg cagcacccgc acccgccuga   420
gcaccgagac aggcuucgcc cugcugggcg ccacccccug cuuccugacc acccaggaca   480
uccaccuggg cguaacgag agccugaccg acaccgcccg cgugcugagc agcauggccg   540
acgccgugcu ggcccgcgug uacaagcaga gcgaccugga cacccuggcc aaggaggcca   600
gcauccccau caucaacggc cugagcgacc uguaccaccc caucagauc cuggccgacu    660 accugacccu gcaggagcac uacagcagcc ugaagggccu gacccugagc uggaucggcg    720
acggcaacaa cauccugcac agcaucauga gcgccgcc caaguucggc augcaccugc     780
aggccgccac ccccaagggc uacgagcccg acgccagcgu gaccaagcug gccgagcagu    840
acgccaagga gaacggcacc aagcucugc ugaccaacga ccccuggag gccgccacacg     900 gcggcaacgu gcugaucacc gaccugga ucagcauggg ccaggaggag gagaagaaga    960
```

| | |
|---|---|
| agcgccugca ggccuuccag ggcuaccagg ugaccaugaa gaccgccaag guggccgcca | 1020 |
| gcgacuggac cuuccugcac ugccugcccc gcaagcccga ggagguggac gacgaggugu | 1080 |
| ucuacagccc ccgcagccug guguuccccg aggccgagaa ccgcaagugg accaucaugg | 1140 |
| ccgugauggu gagccugcug accgacuaca gcccccagcu gcagaagccc aaguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu cccccaaaau | 1320 |
| guagccauuc guaucugcuc cuaauaaaaa gaaaguuucu ucacauucua g | 1371 |

<210> SEQ ID NO 101
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 101

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc caccaugcug gucaaccugc gcauccugcu gaacaacgcc gccuuccgca | 180 |
| acggccacaa cuucauggug cgcaaccucc gcugcggcca gcccugcag aaccggugc | 240 |
| agcugaaggg ccgcgaccug cugacccuga gaacuucac cggcgaggag aucaaguaca | 300 |
| ugcuguggcu gagcgccgac cugaaguucc gcaucaagca gaagggcgag uaccugcccc | 360 |
| ugcugcaggg caagagccug ggcaugaucu ucgagaagcg cagcacccgc acccgccuga | 420 |
| gcaccgagac aggcuucgcc cugcggggcg gccacccug cuuccugacc acccaggaca | 480 |
| uccaccuggg cgugaacgag agccugaccg acaccgcccg cgugcugagc agcauggccg | 540 |
| acgccgugcu ggcccgcgug uacaagcaga gcgaccugga cacccuggcc aaggaggcca | 600 |
| gcauccccau caucaacggc cugagcgacc uguaccaccc caucagauc cuggccgacu | 660 |
| accugacccu gcaggagcac uacagcagcc ugagggccu gacccugagc uggaucggcg | 720 |
| acggcaacaa cauccugcac agcaucauga ugagcgccgc caaguucggc augcaccugc | 780 |
| aggccgccac ccccaagggc uacgagcccg acgccagcgu gaccaagcug gccgagcagu | 840 |
| acgccaagga gaacggcacc aagcugcugc ugaccaacga ccccuggag ccgccacg | 900 |
| gcggcaacgu gcugaucacc gacaccugga ucagcauggg ccaggaggag gagaagaaga | 960 |
| agcgccugca ggccuuccag ggcuaccagg ugaccaugaa gaccgccaag guggccgcca | 1020 |
| gcgacuggac cuuccugcac ugccugcccc gcaagcccga ggagguggac gacgaggugu | 1080 |
| ucuacagccc ccgcagccug guguuccccg aggccgagaa ccgcaagugg accaucaugg | 1140 |
| ccgugauggu gagccugcug accgacuaca gcccccagcu gcagaagccc aaguucugau | 1200 |
| aacucgagcu agugacugac uaggaucugg uuaccacuaa accagccuca agaacacccg | 1260 |
| aauggagucu cuaagcuaca uaauaccaac uuacacuuac aaaauguugu cccccaaaau | 1320 |
| guagccauuc guaucugcuc cuaauaaaaa gaaaguuucu ucacauucua g | 1371 |

<210> SEQ ID NO 102
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 102

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcuu gucaaucucc gcauccuccu uaacaacgcc gcguuuagaa   180
acggccacaa cuucaugguc cggaacuuca gauguggcca gccgcuucaa aacaaggucc   240
agcugaaggg ccgggaucuu cugacccuga agaacuuuac uggcgaagag aucaaguaca   300
ugcucuggcu cuccgcggac uugaaguucc gcauuaagca gaaggggggaa uaccuuccgc   360
ugcuucaagg aaagagccuc ggcaugaucu uugagaagcg cucaaccagg acccgccuuu   420
cuacugaaac uggguucgcg cugcucggug gccaccccug cuuccugacg acccaggaca   480
uccaccucgg agugaacgaa ucccucaccg auaccgcccg ggguguuaucg agcauggcag   540
augccgugcu ggccagggug uacaaacagu ccgaucugga cacucuggcc aaggaggcgu   600
caauuccuau uaucaacggc cuuagugacc ucuaccaucc gauucagauc cuggccgauu   660
accucacccu gcaagaacac uacagcuccc ugaagggucu gacauugucc uggaucggcg   720
acggcaacaa cauucuccau uccaucauga uguccgccgc aaaauucggc augcaucuuc   780
aagccgccac gccgaagggu uacgagcccg acgcuuccgu gacuaagcuc gccgagcagu   840
acgcuaagga gaacggaacc aagcuucugc ugacuaacga cccacuagaa gcagcccacg   900
ggggcaacgu gcuuauuacu gacaccugga ucuccauggg ccaggaagaa gagaaaaaga   960
agcggcugca ggcguuccag ggauaucagg ucaccaugaa aaccgccaag gucgcugccu  1020
ccgacuggac cuuccugcac ugccugccuc gcaagccuga agaaguggac gacgagugu   1080
ucuacucgcc acggagccuc guguccccg aggccgagaa uagaaagugg accaucaugg  1140
ccgugauggu gucacugcuc accgacuaca gcccgcagcu ucagaagccc aaguucuagc  1200
ucgagcuagu gacugacuag gaucugguua ccacuaaacc agccucaaga acacccgaau  1260
ggagucucua agcuacauaa uaccaacuua cacuuacaaa auguugucc ccaaaaugua  1320
gccauucgua ucugcuccua auaaaaagaa aguuucuuca cauucuag           1368
```

<210> SEQ ID NO 103
<211> LENGTH: 1368
<212> TYPE: RNA
<213> ORGANISM: Artificial sequence
<220> FEATURE:
<223> OTHER INFORMATION: Synthetic polynucleotide

<400> SEQUENCE: 103

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc caccaugcuu gucaaucucc gcauccuccu uaacaacgcc gcguuuagaa   180
acggccacaa cuucaugguc cggaacuuca gauguggcca gccgcuucaa accgggucc    240
agcugaaggg ccgggaucuu cugacccuga agaacuuuac uggcgaagag aucaaguaca   300
ugcucuggcu cuccgcggac uugaaguucc gcauuaagca gaaggggggaa uaccuuccgc   360
ugcuucaagg aaagagccuc ggcaugaucu uugagaagcg cucaaccagg acccgccuuu   420
cuacugaaac uggguucgcg cugcucggug gccaccccug cuuccugacg acccaggaca   480
uccaccucgg agugaacgaa ucccucaccg auaccgcccg ggguguuaucg agcauggcag   540
augccgugcu ggccagggug uacaaacagu ccgaucugga cacucuggcc aaggaggcgu   600
caauuccuau uaucaacggc cuuagugacc ucuaccaucc gauucagauc cuggccgauu   660
```

```
accucacccu gcaagaacac uacagcuccc ugaagggucu gacauugucc uggaucggcg    720
acggcaacaa cauucuccau uccaucauga uguccgccgc aaaauucggc augcaucuuc    780
aagccgccac gccgaagggu uacgagcccg acgcuuccgu gacuaagcuc gccgagcagu    840
acgcuaagga gaacggaacc aagcuucugc ugacuaacga cccacuagaa gcagcccacg    900
ggggcaacgu gcuuauuacu gacaccugga ucuccauggg ccaggaagaa gagaaaaaga    960
agcggcugca ggcguuccag ggauaucagg ucaccaugaa aaccgccaag gucgcugccu   1020
ccgacuggac cuuccugcac ugccugccuc gcaagccuga agaaguggac gacgaggugu   1080
ucuacucgcc acgagccuc uguuccccg aggccgagaa uagaaagugg accaucaugg     1140
ccgugauggu gucacugcuc accgacuaca gcccgcagcu ucagaagccc aaguucuagc   1200
ucgagcuagu gacugacuag gaucgguua ccacuaaacc agccucaaga cacccgaau     1260 ggagucucua agcuacauaa uaccaacuua cacuuacaaa auguguccc ccaaaaugua    1320 gccauucgua ucugcuccua auaaaaagaa aguuucuuca cauucuag               1368
```

<210> SEQ ID NO 104
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 104

```
ucaacacaac auauacaaaa caaacgaauc ucaagcaauc aagcauucua cuucuauugc      60 agcauuuaa aucauuucuu uuaaagcaaa agcaauuuuc ugaaaauuuu caccauuuac      120
gaacgauagc caccauggc cuugucaauc uccgcauccu ccuuaacaac gccgcguuua     180
gaaacggcca caacuucaug guccggaacu ucagaugugg ccagccgcuu caaaacaagg    240
uccagcugaa gggccgggau cuucugaccc ugaagaacuu uacuggcgaa gagaucaagu    300
acaugcucug gcucuccgcg gacuugaagu uccgcauuaa gcagaagggg gaauaccuuc    360
cgcugcuuca aggaaagagc cucggcauga ucuuugagaa gcgcucaacc aggacccgcc    420
uuucuacuga aacuggguuc gcgcugcucg guggccaccc cugcuuccug acgacccagg    480
acauccaccu cggagugaac gaaucccuca ccgauaccgc ccggguguua ucgagcaugg    540
cagaugccgu gcuggccagg guguacaaac agccgaucu ggacacucug gccaaggagg    600
cgucaauucc uauuaucaac ggccuuagug acccuacca uccgauucag auccuggccg    660
auuaccucac ccugcaagaa cacuacagcu cccugaaggg ucugacauug ccuggaucg    720 gcgacggcaa caacauucuc cauuccauca ugaugccgc cgcaaaauuc ggcaugcauc     780
uucaagccgc cacgccgaag gguuacgagc ccgacgcuuc cgugacuaag cucgccgagc   840
aguacgcuaa ggagaacgga accaagcuuc ugcugacuaa cgacccacua gaagcagccc   900 acggggcaa cgugcuuauu acugacaccu ggaucuccau gggccaggaa gagagaaaa    960 agaagcggcu gcaggcguuc caggauauc aggucaccau gaaaaccgcc aaggucgcug    1020
ccuccgacug gaccuuccug cacugccugc cucgcaagcc ugaagaagug gacgacgagg   1080
uguucuacuc gccacggagc cucguguucc cgaggccga gaauagaaag uggaccauca    1140
uggccgugau ggugucacug cucaccgacu acagcccgca gcuucagaag cccaaguucu   1200
agcucgagcu agugacugac uaggaucugg uuaccacuaa accagccuca gaacacccg    1260
```

```
aauggagucu cuaagcuaca uaauaccaac uuacacuuac aaaauguugu cccccaaaau    1320
guagccauuc guaucugcuc cuaauaaaaa gaaaguuucu ucacauucua g             1371
```

<210> SEQ ID NO 105
<211> LENGTH: 1371
<212> TYPE: RNA
<213> ORGANISM: Artificial sequence
<220> FEATURE:
<223> OTHER INFORMATION: Synthetic polynucleotide

<400> SEQUENCE: 105

```
ucaacacaac auaucaaaa caaacgaauc ucaagcaauc aagcauucua cuucuauugc      60
agcaauuuaa aucauuucuu uuaaagcaaa agcaauuuuc ugaaaauuuu caccauuuac    120
gaacgauagc caccauggc cuugucaauc uccgcauccu ccuuaacaac gccgcguuua    180
gaaacggcca caacuucaug guccggaacu ucagaugugg ccagccgcuu caaaaccggg    240
uccagcugaa gggccgggau cuucugaccc ugaagaacuu acuggcgaa gagaucaagu    300 acaugcucug gcucuccgcg gacuugaagu ccgcauuaa gcagaagggg gaauaccuuc    360
cgcugcuuca aggaaagagc cucggcauga ucuuugagaa gcgcucaacc aggacccgcc    420
uuucuacuga aacuggguuc gcgcugcucg guggccaccc cugcuuccug acgacccagg    480
acauccaccu cggagugaac gaaucccuca ccgauaccgc ccggguguua ucgagcaugg    540
cagaugccgu gcuggccagg guguacaaac aguccgaucu ggacacucug gccaaggagg    600
cgucaauucc uauuaucaac ggccuuagug accucuacca uccgauucag auccuggccg    660
auuaccucac ccugcaagaa cacuacagcu cccugaaggg ucugacauug uccuggaucg    720
gcgacggcaa caacauucuc cauuccauca ugauguccgc cgcaaaauuc ggcaugcauc    780
uucaagccgc cacgccgaag gguuacgagc ccgacgcuuc cgugacuaag cucgccgagc    840
aguacgcuaa ggagaacgga accaagcuuc ugcugacuaa cgacccacua gaagcagccc    900 acggggggcaa cgugcuuauu acugacaccu ggaucuccau gggccaggaa gaagagaaaa    960
agaagcggcu gcaggcguuc cagggauauc aggucaccau gaaaaccgcc aaggucgcug   1020
ccuccgacug gaccuuccug cacugccugc ucgcaagcc ugaagaagug gacgacgagg   1080
uguucuacuc gccacggagc cucguguucc ccgaggccga gaauagaaag uggaccauca   1140
uggccgugau ggugucacug cucaccgacu acagcccgca gcuucagaag cccaaguucu   1200
agcucgagcu agugacugac uaggaucugg uuaccacuaa accagccuca agaacacccg   1260
aauggagucu cuaagcuaca uaauaccaac uuacacuuac aaaauguugu cccccaaaau   1320
guagccauuc guaucugcuc cuaauaaaaa gaaaguuucu ucacauucua g            1371
```

<210> SEQ ID NO 106
<211> LENGTH: 1374
<212> TYPE: RNA
<213> ORGANISM: Artificial sequence
<220> FEATURE:
<223> OTHER INFORMATION: Synthetic polynucleotide

<400> SEQUENCE: 106

```
ucaacacaac auaucaaaa caaacgaauc ucaagcaauc aagcauucua cuucuauugc      60
agcaauuuaa aucauuucuu uuaaagcaaa agcaauuuuc ugaaaauuuu caccauuuac    120
gaacgauagc caccauggc ggacuuguca aucccgcau ccuccuuaac aacgccgcgu    180
uuagaaacgg ccacaacuuc auggguccgga acuucagaug uggccagccg cuucaaaaca    240
```

| | |
|---|---|
| agguccagcu gaagggccgg gaucuucuga cccugaagaa cuuuacuggc gaagagauca | 300 |
| aguacaugcu cuggcucucc gcggacuuga aguuccgcau uaagcagaag ggggaauacc | 360 |
| uuccgcugcu ucaaggaaag agccucggca ugaucuuuga gaagcgcuca accaggaccc | 420 |
| gccuuucuac ugaaacuggg uucgcgcugc ucgguggcca ccccugcuuc cugacgaccc | 480 |
| aggacaucca ccucggagug aacgaauccc ucaccgauac cgcccgggug uuaucgagca | 540 |
| uggcagaugc cgugcuggcc aggguguaca aacaguccga ucuggacacu cuggccaagg | 600 |
| aggcgucaau uccuauuauc aacggccuua gugaccucua ccauccgauu cagauccugg | 660 |
| ccgauuaccu cacccugcaa gaacacuaca gcucccugaa gggucugaca uugccuggga | 720 |
| ucggcgacgg caacaacauu cuccauucca ucaugauguc cgccgcaaaa ucggcaugc | 780 |
| aucuucaagc cgccacgccg aagggguuacg agcccgacgc uuccgugacu aagcucgccg | 840 |
| agcaguacgc uaaggagaac ggaaccaagc uucugcugac uaacgaccca cuagaagcag | 900 |
| cccacggggg caacgugcuu auuacugaca ccuggaucuc caugggccag gaagaagaga | 960 |
| aaaagaagcg gcugcaggcg uuccagggau caggucac caugaaaacc gccaaggucg | 1020 |
| cugccuccga cuggaccuuc cugcacugcc ugccucgcaa gccugaagaa guggacgacg | 1080 |
| agguguucua cucgccacgg agccucgugu cccccgaggc cgagaauaga aaguggacca | 1140 |
| ucauggccgu gaugguguca cugcucaccg acuacagccc gcagcuucag aagcccaagu | 1200 |
| ucuagcucga gcuagugacu gacuaggauc ugguuaccau aaaccagcc ucaagaacac | 1260 |
| ccgaauggag ucucuaagcu acauaauacc aacuuacacu uacaaaaugu gucccccaa | 1320 |
| aauguagcca uucguaucug cuccuaauaa aaagaaaguu cuucacauu cuag | 1374 |

<210> SEQ ID NO 107
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 107

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc cauggcccuu uucaaucucc gcauccuccu uaacaacgcc gcguuuagaa | 180 |
| acggccacaa cuucaugguc cggaacuuca gauguggcca gccgcuucaa ggcaaggucc | 240 |
| agcugaaggg ccgggaucuu cugacccuga agaacuuuac uggcgaagag aucaaguaca | 300 |
| ugcucuggcu cuccgcggac uugaaguucc gcauuaagca gaagggggaa uaccuuccgc | 360 |
| ugcuucaagg aaagagccuc ggcaugaucu uugagaagcg cucaaccagg acccgccuuu | 420 |
| cuacugaaac ugguucgcg cugcucggug gccacccug cuccugacg acccaggaca | 480 |
| uccaccucgg agugaacgaa ucccucaccg auaccgcccg ggguguuaucg agcauggcag | 540 |
| augccgugcu ggcaggggug uacaaacagu ccgaucugga cacucuggcc aaggaggcgu | 600 |
| caauuccuau uaucaacggc cuuagugacc ucuaccaucc gauucagauc cuggccgauu | 660 |
| accucacccu gcaagaacac uacagcccc ugaaggggucu gacauugccc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |

```
agcggcugca ggcguuccag ggauaucagg ucaccaugaa aaccgccaag gucgcugccu   1020
ccgacuggac cuuccugcac ugccugccuc gcaagccuga agaaguggac gacgaggugu   1080
ucuacucgcc acggagccuc guguuccccg aggccgagaa uagaaagugg accaucaugg   1140
ccgugauggu gucacugcuc accgacuaca gcccgcagcu ucagaagccc aaguucuaga   1200
uaagugaacu cgagcuagug acugacuagg aucgguuac cacuaaacca gccucaagaa    1260
cacccgaaug gagucucuaa gcacauaau ccaacuuac acuucaaaa uguugucccc     1320 caaaauguag ccauucguau cugcuccuaa uaaaagaaa guuucuucac auucuag       1377
```

<210> SEQ ID NO 108
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 108

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc cauggcccuu uucaaucucc gcauccuccu uaacaacgcc gcguuuagaa   180
acggccacaa cuucaugguc cggaacuuca gaugaggcca gccgcuucaa ggccgggucc   240
agcugaaggg ccgggaucuu cugacccuga agaacuuuac uggcgaagag aucaaguaca   300
ugcucuggcu cuccgcggac uugaaguucc gcauuaagca gaaggggggaa uaccuuccgc   360 ugcuucaagg aaagagccuc ggcaugaucu uugagaagcg cucaaccagg acccgccuuu   420
cuacugaaac uggguucgcg cugcucggug gccaccccug cuuccugacg acccaggaca   480
uccaccucgg agugaacgaa ucccucaccg auaccgcccg ggguguaucg agcauggcag   540
augccgugcu ggccagggug uacaaacagu ccgaucugga cacucuggcc aaggaggcgu   600
caauuccuau uaucaacggc cuuagugacc ucuaccaucc gauucagauc cuggccgauu   660
accucacccu gcaagaacac uacagcuccc ugaagggucu gacauugucc uggaucggcg   720
acggcaacaa cauucuccau uccaucauga ugucgccgc aaaauucggc augcaucuuc    780
aagccgccac gccgaagggu uacgagcccg acgcuuccgu gacuaagcuc gccgagcagu   840
acgcuaagga gaacgaaccg aagcuucugc ugacuaacga cccacuagaa gcagcccacg   900
ggggcaacgu gcuuauuacu gacaccugga ucuccauggg ccaggaagaa gagaaaaaga   960
agcggcugca ggcguuccag ggauaucagg ucaccaugaa aaccgccaag gucgcugccu   1020
ccgacuggac cuuccugcac ugccugccuc gcaagccuga agaaguggac gacgaggugu   1080
ucuacucgcc acggagccuc guguuccccg aggccgagaa uagaaagugg accaucaugg   1140
ccgugauggu gucacugcuc accgacuaca gcccgcagcu ucagaagccc aaguucuaga   1200
uaagugaacu cgagcuagug acugacuagg aucgguuac cacuaaacca gccucaagaa    1260
cacccgaaug gagucucuaa gcacauaau ccaacuuac acuacaaaa uguugucccc     1320 caaaauguag ccauucguau cugcuccuaa uaaaagaaa guuucuucac auucuag       1377
```

<210> SEQ ID NO 109
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 109

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc cauggcccuu uucaaucucc gcauccuccu uaacaacgcc gcguuuagaa   180
acggccacaa cuucaugguc cggaacuuca gauguggcca gccgcuucaa ggccgggucc   240
agcugaaggg ccgggaucuu cugacccuga agaacuuuac uggcgaagag aucagguaca   300
ugcucuggcu cuccgcggac uugaaguucc gcauuaagca gaaggggaaa uaccuuccgc   360
ugcuucaagg aaagagccuc ggcaugaucu uugagaagcg cucaaccagg acccgccuuu   420
cuacugaaac uggguucgcg cugcucggug gccaccccug cuuccgacg  acccaggaca   480
uccaccucgg agugaacgaa ucccucaccg auaccgcccg ggguguuaucg agcauggcag   540
augccgugcu ggccaggggu uacaaacagu ccgaucugga cacucuggcc aaggaggcgu   600
caauuccuau uaucaacggc cuuagugacc ucuaccaucc gauucagauc cuggccgauu   660
accucacccu gcaagaacac uacagcuccc ugaagggucu gacauguucc uggaucggcg   720
acggcaacaa cauucuccau uccaucauga uguccgccgc aaaauucggc augcaucuuc   780
aagccgccac gccgaagggu uacgagcccg acgcuuccgu gacuaagcuc gccgagcagu   840
acgcuaagga gaacggaacc aagcuucugc ugacuaacga cccacuagaa gcagcccacg   900
ggggcaacgu gcuuauuacu gacaccugga ucuccauggg ccaggaagaa gagaaaaaga   960
agcggcugca ggcguuccag ggauaucagg ucaccaugaa aaccgccaag gucgcugccu  1020
ccgacuggac cuuccugcac ugccugccuc gcaagccuga agaguggac gacgaggugu  1080
ucuacucgcc acggagccuc guguccccg aggccgagaa uagaaagugg accaucaugg  1140
ccgugauggu gucacugcuc accgacuaca gcccgcagcu ucagaagccc aaguucuaga  1200
uaagugaacu cgagcuagug acugacuagg aucugguuac cacuaaacca gccucaagaa  1260
cacccgaaug gagucucuaa gcuacauaau accaacuuac acuuacaaaa uguuguccc  1320
caaaauguag ccauucgua ucugcuccua uaaaaagaaa guuucuucac auucuag    1377
```

<210> SEQ ID NO 110
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 110

```
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc cauggcccuu gucaaucucc gcauccuccu uaacaacgcc gcguuuagaa   180
acggccacaa cuucaugguc cggaacuuca gauguggcca gccgcuucaa ggcagggucc   240
agcugaaggg ccgggaucuu cugacccuga agaacuuuac uggcgaagag aucaaguaca   300
ugcucuggcu cuccgcggac uugaaguucc gcauuaagca gaaggggaaa uaccuuccgc   360
ugcuucaagg aaagagccuc ggcaugaucu uugagaagcg cucaaccagg acccgccuuu   420
cuacugaaac uggguucgcg cugcucggug gccaccccug cuuccugacg acccaggaca   480
uccaccucgg agugaacgaa ucccucaccg auaccgcccg ggguguuaucg agcauggcag   540
augccgugcu ggccaggggu uacaaacagu ccgaucugga cacucuggcc aaggaggcgu   600
caauuccuau uaucaacggc cuuagugacc ucuaccaucc gauucagauc cuggccgauu   660
```

| | |
|---|---|
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagccuga agaaguggac gacgaggugu | 1080 |
| ucuacucgcc acggagccuc guguuccccg aggccgagaa uagaaagugg accaucaugg | 1140 |
| ccgugauggu gucacugcuc accgacuaca gcccgcagcu ucagaagccc aaguucuaag | 1200 |
| ugaauagacu cgagcuagug acugacuagg aucggguuac cacuaaacca gccucaagaa | 1260 |
| cacccgaaug gagucucuaa gcuacauaau accaacuuac acuuacaaaa uguugucccc | 1320 |
| caaaauguag ccauucguau cugcuccuaa uaaaaagaaa guuucuucac auucuag | 1377 |

<210> SEQ ID NO 111
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 111

| | |
|---|---|
| ucaacacaac auauacaaaa caaacgaauc ucaagcaauc aagcauucua cuucuauugc | 60 |
| agcaauuuaa aucauuucuu uuaaagcaaa agcaauuuuc ugaaaauuuu caccauuuac | 120 |
| gaacgauagc cauggcccuu uucaaucucc gcauccuccu uaacaacgcc gcguuuagaa | 180 |
| acggccacaa cuucaugguc cggaacuuca gaugugggcca gccgcuucaa gucaaggucc | 240 |
| agcugaaggg ccgggaucuu cugacccuga gaacuuuac uggcgaagag aucaaguaca | 300 |
| ugcucuggcu cuccgcggac uugaaguucc gcauuaagca gaaggggggaa uaccuuccgc | 360 |
| ugcuucaagg aaagagccuc ggcaugaucu uugagaagcg cucaaccagg acccgccuuu | 420 |
| cuacugaaac uggguucgcg cugcucggug gccacccug cuuccugacg acccaggaca | 480 |
| uccaccucgg agugaacgaa ucccucaccg auaccgcccg ggguguaucg agcaauggcag | 540 |
| augccgugcu ggccaggguu acaaacagu ccgaucugga cacucuggcc aaggaggcgu | 600 |
| caauuccuau uaucaacggc cuuagugacc ucuaccaucc gauucagauc cuggccgauu | 660 |
| accucacccu gcaagaacac uacagcuccc ugaagggucu gacauugucc uggaucggcg | 720 |
| acggcaacaa cauucuccau uccaucauga uguccgccgc aaaauucggc augcaucuuc | 780 |
| aagccgccac gccgaagggu uacgagcccg acgcuuccgu gacuaagcuc gccgagcagu | 840 |
| acgcuaagga gaacggaacc aagcuucugc ugacuaacga cccacuagaa gcagcccacg | 900 |
| ggggcaacgu gcuuauuacu gacaccugga ucuccauggg ccaggaagaa gagaaaaaga | 960 |
| agcggcugca ggcguuccag ggauaucagg ucaccaugaa aaccgccaag gucgcugccu | 1020 |
| ccgacuggac cuuccugcac ugccugccuc gcaagccuga agaaguggac gacgaggugu | 1080 |
| ucuacucgcc acggagccuc guguuccccg aggccgagaa uagaaagugg accaucaugg | 1140 |
| ccgugauggu gucacugcuc accgacuaca gcccgcagcu ucagaagccc aaguucuaga | 1200 |
| uaagugaacu cgagcuagug acugacuagg aucggguuac cacuaaacca gccucaagaa | 1260 |

```
cacccgaaug gagucucuaa gcuacauaau accaacuuac acuuacaaaa uguuguccc    1320 caaaauguag ccauucguau cugcuccuaa uaaaagaaa guuucuucac auucuag      1377

<210> SEQ ID NO 112
<211> LENGTH: 1377
<212> TYPE: RNA
<213> ORGANISM: Artificial sequence
<220> FEATURE:
<223> OTHER INFORMATION: Synthetic polynucleotide

<400> SEQUENCE: 112
ucaacacaac auauacaaaa caaacgaauc ucaagcaauc aagcauucua cuucuauugc    60
agcaauuuaa aucauuucuu uuaaagcaaa agcaauuuuc ugaaaauuuu caccauuuac   120
gaacgauagc cauggcccuu uucaaucucc gcauccuccu uaacaacgcc gcguuuagaa   180
acggccacaa cuucaugguc cggaacuuca gauguggcca gccgcuucaa gucagggucc   240
agcugaaggg ccgggaucuu cugacccuga agaacuuuac uggcgaagag aucaaguaca   300
ugcucuggcu cuccgcggac uugaaguucc gcauuaagca gaaggggaa uaccuuccgc    360 ugcuucaagg aaagagccuc ggcaugaucu uugagaagcg cucaaccagg acccgccuuu   420
cuacugaaac ugggucgcg cugcucggug gccaccccug cuuccugacg acccaggaca    480
uccaccucgg agugaacgaa ucccucaccg auaccgcccg ggguguaucg agcauggcag   540
augccgugcu ggccagggug uacaaacagu ccgaucugga cacucuggcc aaggaggcgu   600
caauuccuau uaucaacggc cuuagugacc ucuaccaucc gauucagauc cuggccgauu   660
accucacccu gcaagaacac uacagcuccc ugaagggucu gacauugucc uggaucggcg   720
acggcaacaa cauucuccau uccaucauga ugccgccgc aaaauucggc augcaucuuc    780
aagccgccac gccgaagggu uacgagcccg acgcuuccgu gacuaagcuc gccgagcagu   840
acgcuaagga gaacgaaacc aagcuucugc ugacuaacga cccacuagaa gcagcccacg   900
ggggcaacgu gcuuauuacu gacaccugga ucuccauggg ccaggaagaa gagaaaaaga   960
agcggcugca ggcguuccag ggauaucagg ucaccaugaa aaccgccaag gucgcugccu  1020
ccgacuggac cuuccugcac ugccugccuc gcaagccuga agaaguggac gacgagguu    1080 ucuacucgcc acggagccuc uguuuccccg aggccgagaa uagaaagugg accaucaugg  1140
ccgugauggu gucacugcuc accgacuaca gcccgcagcu ucagaagccc aaguucuaga  1200
uaagugaacu cgagcuagug acugacuagg aucgguuac cacuaaacca gccucaagaa   1260
cacccgaaug gagucucuaa gcuacauaau accaacuuac acuuacaaaa uguuguccc   1320 caaaauguag ccauucguau cugcuccuaa uaaaagaaa guuucuucac auucuag     1377

<210> SEQ ID NO 113
<211> LENGTH: 1282
<212> TYPE: RNA
<213> ORGANISM: Artificial sequence
<220> FEATURE:
<223> OTHER INFORMATION: Synthetic polynucleotide

<400> SEQUENCE: 113
ggcagaaaaa uuugcuacau uguuucacaa acuucaaaua uuauucauuu auuuagaucu    60
auuauuacau caaaacaaaa agccgccacc augcuguuca accugcgcau ccugcugaac   120
aacgccgccu uccgcaacgg ccacaacuuc auggugcgca acuuccgcug cggccagccc   180
cugcagaaca aggugcagcu gaagggccgc gaccugcuga cccugaagaa cuucaccggc   240
```

| | |
|---|---|
| gaggagauca aguacaugcu guggcugagc gccgaccuga aguuccgcau caagcagaag | 300 |
| ggcgaguacc ugcccctgcu gcagggcaag agccugggca ugaucuucga gaagcgcagc | 360 |
| acccgcaccc gccugagcac cgagacaggc uucgcccugc ugggcggcca ccccugcuuc | 420 |
| cugaccaccc aggacaucca ccugggcgug aacgagagcc ugaccgacac cgcccgcgug | 480 |
| cugagcagca uggccgacgc cgugcuggcc cgcguguaca agcagagcga ccuggacacc | 540 |
| cuggccaagg aggccagcau ccccaucauc aacggccuga cgaccugua ccaccccauc | 600 |
| cagauccugg ccgacuaccu gacccugcag gagcacuaca gcagccugaa gggccugacc | 660 |
| cugagcugga ucggcgacgg caacaacauc cugcacagca ucaugaugag cgccgccaag | 720 |
| uucggcaugc accugcaggc cgccaccccc aagggcuacg agcccgacgc cagcgugacc | 780 |
| aagcuggccg agcaguacgc caaggagaac ggcaccaagc ugcugcugac caacgacccc | 840 |
| cuggaggccc cccacggcgg caacgugcug aucaccgaca ccuggaucag cauggggccag | 900 |
| gaggaggaga agaagaagcg ccugcaggcc uuccagggcu accaggugac caugaagacc | 960 |
| gccaaggugg ccgccagcga cuggaccuuc cugcacugcc ugccccgcaa gcccgaggag | 1020 |
| guggacgacg aggugucua cagccccgc agccuggugu ccccgaggc cgagaaccgc | 1080 |
| aaguggacca ucauggccgu gauggugagc cugcugaccg acuacagccc ccagcugcag | 1140 |
| aagcccaagu ucugaggucu cuaguaauga gcuggagccu cgguagccgu uccuccugcc | 1200 |
| cgcugggccu cccaacgggc ccuccucccc uccuugcacc ggcccuuccu ggucuuugaa | 1260 |
| uaaagucuga gugggcaucu ag | 1282 |

<210> SEQ ID NO 114
<211> LENGTH: 1285
<212> TYPE: RNA
<213> ORGANISM: Artificial sequence
<220> FEATURE:
<223> OTHER INFORMATION: Synthetic polynucleotide

<400> SEQUENCE: 114

| | |
|---|---|
| ggcagaaaaa uuugcuacau uguuucacaa acuucaaaua uuauucauuu auuuagaucu | 60 |
| auuauuacau caaaacaaaa agccgccacc augggaguau caaccugcg cauccugcug | 120 |
| aacaacgccg ccuuccgcaa cggccacaac uucauggugc gcaacuuccg cugcggccag | 180 |
| cccccugcaga acaaggugca gcugaagggc cgcgaccugc ugacccugaa gaacuucacc | 240 |
| ggcgaggaga ucaaguacau gcuguggcug agcgccgacc ugaaguuccg caucaagcag | 300 |
| aagggcgagu accugccccu gcugcagggc aagagccugg gcaugaucuu cgagaagcgc | 360 |
| agcacccgca cccgccugag caccgagaca ggcuucgccc ugcugggcgg ccaccccugc | 420 |
| uuccugacca cccaggacau ccaccugggc gugaacgaga gccugaccga caccgcccgc | 480 |
| gugcugagca gcauggccga cgccgugcug gcccgcgugu acaagcagag cgaccuggac | 540 |
| acccuggcca aggaggccag cauccccauc aucaacggcc ugagcgaccu guaccacccc | 600 |
| auccagaucc uggccgacua ccugacccug caggagcacu acagcagccu gaagggccug | 660 |
| acccugagcu ggaucggcga cggcaacaac aucccugcaca gcaucaugau gagcgccgcc | 720 |
| aaguucggca ugcaccugca ggccgccacc cccaagggcu acgagcccga cgccagcgug | 780 |
| accaagcugg ccgagcagua cgccaaggag aacggcacca agcugcugcu gaccaacgac | 840 |
| ccccuggagg ccccccacgg cggcaacgug cugaucaccg acaccuggau cagcaugggc | 900 |
| caggaggagg agaagaagaa gcgccugcag gccuuccagg gcuaccaggu gaccaugaag | 960 |
| accgccaagg uggccgccag cgacuggacc uuccugcacu gccugccccg caagcccgag | 1020 |

| gagguggacg acgaggguguu cuacagcccc cgcagccugg uguucccga ggccgagaac | 1080 |
| cgcaagugga ccaucauggc cgugaugguig agccugcuga ccgacacag ccccagcug | 1140 |
| cagaagccca aguucugagg ucucuaguaa ugagcuggag ccucgguagc cguuccuccu | 1200 |
| gcccgcuggg ccucccaacg ggccuccuc cccuccuugc accggcccuu ccuggucuuu | 1260 |
| gaauaaaguc ugagugggca ucuag | 1285 |

```
<210> SEQ ID NO 115
<211> LENGTH: 1285
<212> TYPE: RNA
<213> ORGANISM: Artificial sequence
<220> FEATURE:
<223> OTHER INFORMATION: Synthetic polynucleotide

<400> SEQUENCE: 115
```

| ggcagaaaaa uuugcuacau uguuucacaa acuucaaaua uuauucauuu auuuagaucu | 60 |
| auuauuacau caaaacaaaa agccgccacc augggaguau caaccugcg cauccugcug | 120 |
| aacaacgccg ccuuccgcaa cggccacaac uucaugguigc gcaacuuccg cugcggccag | 180 |
| ccccugcaga accgggugca gcugaagggc cgcgaccugc ugacccugaa gaacuucacc | 240 |
| ggcgaggaga uccgguacau gcuguiggcug agcgccgacc ugaaguuccg caucaagcag | 300 |
| aagggcgagu accugccccu gcugcagggc aagagccugg gcaugaucuu cgagaagcgc | 360 |
| agcacccgca cccgccugag caccgagaca ggcuucgccc ugcugggcgg ccaccccugc | 420 |
| uuccugacca cccaggacau ccaccugggc gugaacgaga gccugaccga caccgcccgc | 480 |
| gugcugagca gcauggccga cgccgugcug gcccgcgugu acaagcagag cgaccuggac | 540 |
| acccuggcca aggaggccag cauccccauc aucaacggcc ugagcgaccu guaccacccc | 600 |
| auccagaucc uggccgacua ccugacccug caggagcacu acagcagccu gaagggccug | 660 |
| acccugagcu ggaucggcga cggcaacaac auccugcaca gcaucaugau gagcgccgcc | 720 |
| aaguucggca ugcaccugca ggccgccacc cccaagggcu acgagcccga cgccagcgug | 780 |
| accaagcugg ccgagcagua cgccaaggag aacggcacca gcugcugcu gaccaacgac | 840 |
| ccccuggagg ccgccacgg cggcaacgug cugaucaccg acaccuggau cagcaugggc | 900 |
| caggaggagg agaagaagaa cgccugcag gccuuccagg gcuaccaggu gaccaugaag | 960 |
| accgccaagg uggccgccag cgacuggacc uuccugcacu gccugcccg caagcccgag | 1020 |
| gagguggacg acgaggugui cuacagcccc cgcagccugg uguucccga ggccgagaac | 1080 |
| cgcaagugga ccaucauggc cgugaugguig agccugcuga ccgacacag ccccagcug | 1140 |
| cagaagccca aguucugagg ucucuaguaa ugagcuggag ccucgguagc cguuccuccu | 1200 |
| gcccgcuggg ccucccaacg ggccuccuc cccuccuugc accggcccuu ccuggucuuu | 1260 |
| gaauaaaguc ugagugggca ucuag | 1285 |

```
<210> SEQ ID NO 116
<211> LENGTH: 1285
<212> TYPE: RNA
<213> ORGANISM: Artificial sequence
<220> FEATURE:
<223> OTHER INFORMATION: Synthetic polynucleotide

<400> SEQUENCE: 116
```

| ggcagaaaaa uuugcuacau uguuucacaa acuucaaaua uuauucauuu auuuagaucu | 60 |
| auuauuacau caaaacaaaa agccgccacc augcugguau caaccugcg cauccugcug | 120 |

| | |
|---|---|
| aacaacgccg ccuuccgcaa cggccacaac uucauggugc gcaacuuccg cugcggccag | 180 |
| ccccugcaga accggguugca gcugaagggc gcgaccugc ugacccugaa gaacuucacc | 240 |
| ggcgaggaga uccgguacau gcuguggcug agcgccgacc ugaaguuccg caucaagcag | 300 |
| aagggcgagu accugccccu gcugcagggc aagagccugg gcaugaucuu cgagaagcgc | 360 |
| agcacccgca cccgccugag caccgagaca ggcuucgccc ugcugggcgg ccaccccugc | 420 |
| uuccugacca cccaggacau ccaccugggc gugaacgaga gccugaccga caccgcccgc | 480 |
| gugcugagca gcauggccga cgccgugcug gcccgcgugu acaagcagag cgaccuggac | 540 |
| acccuggcca aggaggccag caucccauc aucaacggcc ugagcgaccu guaccacccc | 600 |
| auccagaucc uggccgacua ccugacccug caggagcacu acagcagccu gaagggccug | 660 |
| acccugagcu ggaucggcga cggcaacaac auccugcaca gcaucaugau gagcgccgcc | 720 |
| aaguucggca ugcaccugca ggccgccacc cccaagggcu acgagcccga cgccagcgug | 780 |
| accaagcugg ccgagcagua cgccaaggag aacggcacca agcugcugcu gaccaacgac | 840 |
| ccccuggagg ccgccacgg cggcaacgug cugaucaccg acaccuggau cagcaugggc | 900 |
| caggaggagg agaagaagaa gcgccugcag gccuuccagg gcuaccaggu gaccaugaag | 960 |
| accgccaagg uggccgccag cgacuggacc uuccugcacu gccugccccg caagcccgag | 1020 |
| gagguggacg acgaggucuu cuacagcccc cgcagccugg uguuccccga ggccgagaac | 1080 |
| cgcaagugga ccaucauggc cgugauggug agccugcuga ccgacuacag ccccccagcug | 1140 |
| cagaagccca aguucugagg ucucuaguaa ugagcuggag ccucgguagc cguuccuccu | 1200 |
| gccccgcuggg ccucccaacg ggccucucuc cccuccuugc accggcccuu ccugucuuu | 1260 |
| gaauaaaguc ugaguggcca ucuag | 1285 |

<210> SEQ ID NO 117
<211> LENGTH: 1225
<212> TYPE: RNA
<213> ORGANISM: Artificial sequence
<220> FEATURE:
<223> OTHER INFORMATION: Synthetic polynucleotide

<400> SEQUENCE: 117

| | |
|---|---|
| auuauuacau caaaacaaaa agccgccacc augggaguau ucaaccugcg caccugcug | 60 |
| aacaacgccg ccuuccgcaa cggccacaac uucauggugc gcaacuuccg cugcggccag | 120 |
| ccccugcaga acaaggugca gcugaagggc gcgaccugc ugacccugaa gaacuucacc | 180 |
| ggcgaggaga ucaaguacau gcuguggcug agcgccgacc ugaaguuccg caucaagcag | 240 |
| aagggcgagu accugccccu gcugcagggc aagagccugg gcaugaucuu cgagaagcgc | 300 |
| agcacccgca cccgccugag caccgagaca ggcuucgccc ugcugggcgg ccaccccugc | 360 |
| uuccugacca cccaggacau ccaccugggc gugaacgaga gccugaccga caccgcccgc | 420 |
| gugcugagca gcauggccga cgccgugcug gcccgcgugu acaagcagag cgaccuggac | 480 |
| acccuggcca aggaggccag caucccauc aucaacggcc ugagcgaccu guaccacccc | 540 |
| auccagaucc uggccgacua ccugacccug caggagcacu acagcagccu gaagggccug | 600 |
| acccugagcu ggaucggcga cggcaacaac auccugcaca gcaucaugau gagcgccgcc | 660 |
| aaguucggca ugcaccugca ggccgccacc cccaagggcu acgagcccga cgccagcgug | 720 |
| accaagcugg ccgagcagua cgccaaggag aacggcacca agcugcugcu gaccaacgac | 780 |
| ccccuggagg ccgccacgg cggcaacgug cugaucaccg acaccuggau cagcaugggc | 840 |
| caggaggagg agaagaagaa gcgccugcag gccuuccagg gcuaccaggu gaccaugaag | 900 |

```
accgccaagg uggccgccag cgacuggacc uuccugcacu gccugccccg caagcccgag     960
gagguggacg acgaggucuu cuacagcccc cgcagccugu guucccga ggccgagaac     1020 cgcaagugga ccaucauggc cgugauggug agccugcuga ccgacuacag cccccagcug    1080
cagaagccca aguucugagg ucucuaguaa ugagcuggag ccucgguagc cguuccuccu    1140
gcccgcuggg ccucccaacg ggccuccuc cccuccuugc accggcccuu ccuggucuuu     1200
gaauaaaguc ugagugggca ucuag                                          1225

<210> SEQ ID NO 118
<211> LENGTH: 1225
<212> TYPE: RNA
<213> ORGANISM: Artificial sequence
<220> FEATURE:
<223> OTHER INFORMATION: Synthetic polynucleotide

<400> SEQUENCE: 118
auuauuacau caaaacaaaa agccgccacc augggaguau caaccugcg cauccugcug      60 aacaacgccg ccuuccgcaa cggccacaac uucaugguc gcaacuuccg cugcggccag     120
ccccugcaga accggugca gcugaagggc cgcgaccugc ugacccugaa gaacuucacc     180
ggcgaggaga uccgguacau gcugugcug agcgccgacc ugaaguuccg caucaagcag    240
aagggcgagu accugccccu gcugcagggc aagagccugg gcaugaucuu cgagaagcgc   300
agcacccgca cccgccugag caccgagaca ggcuucgccc ugcugggcgg ccaccccugc  360
uuccugacca cccaggacau ccaccugggc gugaacgaga gccugaccga caccgcccgc   420
gugcugagca gcauggccga cgccgugcug gcccgcgugu acaagcagag cgaccuggac    480
acccuggcca aggaggccag cauccccauc aucaacggcc ugagcgaccu guaccacccc   540
auccagaucc uggccgacua ccugacccug caggagcacu acagcagccu gaagggccug    600
acccugagcu ggaucggcga cggcaacaac auccugcaca gcaucaugau gagcgccgcc   660
aaguucggca ugcaccugca ggccgccacc cccaagggcu acgagcccga cgccagcgug   720
accaagcugg ccgagcagua cgccaaggag aacggcacca agcugcugcu gaccaacgac    780
ccccuggagg ccgccacggc cggcaacgug cugaucaccg acaccuggau cagcauggc     840 caggaggagg agaagaagaa cgccugcag gccuuccagg cuaccaggu gaccaugaag    900 accgccaagg uggccgccag cgacuggacc uuccugcacu gccugccccg caagcccgag    960
gagguggacg acgaggucuu cuacagcccc cgcagccugu guucccga ggccgagaac    1020 cgcaagugga ccaucauggc cgugauggug agccugcuga ccgacuacag cccccagcug   1080
cagaagccca aguucugagg ucucuaguaa ugagcuggag ccucgguagc cguuccuccu    1140
gcccgcuggg ccucccaacg ggccuccuc cccuccuugc accggcccuu ccuggucuuu     1200
gaauaaaguc ugagugggca ucuag                                          1225

<210> SEQ ID NO 119
<211> LENGTH: 1228
<212> TYPE: RNA
<213> ORGANISM: Artificial sequence
<220> FEATURE:
<223> OTHER INFORMATION: Synthetic polynucleotide

<400> SEQUENCE: 119
auuauuacau caaaacaaaa agccgccacc augcugguau caaccugcg cauccugcug      60 aacaacgccg ccuuccgcaa cggccacaac uucaugguc gcaacuuccg cugcggccag     120
```

| ccccugcaga | accggguguca | gcugaagggc | cgcgaccugc | ugacccugaa | gaacuucacc | 180 |
| ggcgaggaga | uccgguacau | gcuguggcug | agcgccgacc | ugaaguuccg | caucaagcag | 240 |
| aagggcgagu | accugccccu | gcugcagggc | aagagccugg | gcaugaucuu | cgagaagcgc | 300 |
| agcacccgca | cccgccugag | caccgagaca | ggcuucgccc | ugcugggcgg | ccaccccugc | 360 |
| uuccugacca | cccaggacau | ccaccugggc | gugaacgaga | gccugaccga | caccgcccgc | 420 |
| gugcugagca | gcauggccga | cgccgugcug | gcccgcgugu | acaagcagag | cgaccuggac | 480 |
| acccuggcca | aggaggccag | caucccccauc | aucaacggcc | ugagcgaccu | guaccacccc | 540 |
| auccagaucc | uggccgacua | ccugacccug | caggagcacu | acagcagccu | gaagggccug | 600 |
| acccugagcu | ggaucggcga | cggcaacaac | auccugcaca | gcaucaugau | gagcgccgcc | 660 |
| aaguucggca | ugcaccugca | ggccgccacc | cccaagggcu | acgagcccga | cgccagcgug | 720 |
| accaagcugg | ccgagcagua | cgccaaggag | aacggcacca | gcugcugcu | gaccaacgac | 780 |
| ccccuggagg | ccgccacgg | cggcaacgug | cugaucaccg | acaccuggau | cagcaugggc | 840 |
| caggaggagg | agaagaagaa | cgccugcag | gccuuccagg | gcuaccaggu | gaccaugaag | 900 |
| accgccaagg | uggccgccag | cgacuggacc | uucccugcacu | gccugccccg | caagcccgag | 960 |
| gaggugacg | acgaggguguu | cuacagcccc | cgcagccugg | uguucccccga | ggccgagaac | 1020 |
| cgcaagugga | ccaucauggc | cgugauggug | agccugcuga | ccgacuacag | ccccccagcug | 1080 |
| cagaagccca | aguucugagg | ucucuaguaa | ugagcuggag | ccucgguagc | cguuccuccu | 1140 |
| gcccgcuggg | ccucccaacg | ggccuccuc | cccuccuugc | accggcccuu | ccuggucuuu | 1200 |
| gaauaaaguc | ugaguggggca | gcaucuag | | | | 1228 |

<210> SEQ ID NO 120
<211> LENGTH: 1376
<212> TYPE: RNA
<213> ORGANISM: Artificial sequence
<220> FEATURE:
<223> OTHER INFORMATION: Synthetic polynucleotide

<400> SEQUENCE: 120

| ucaacacaac | auaucaaaaa | caaacgaauc | ucaagcaauc | aagcauucua | cuucuauugc | 60 |
| agcaauuuaa | aucauuucuu | uuaaagcaaa | agcaauuuuc | ugaaaauuuu | caccauuuac | 120 |
| gaacgauagc | caccauguug | uucaacuuga | ggaucuuguu | gaacaacgcc | gccuucagga | 180 |
| acggacacaa | cuucaugguuu | aggaacuuca | ggugcggaca | gcccuugcag | aacaaaguac | 240 |
| aguugaaagg | aagggacuug | uugacauuga | aaacuucac | aggagaagaa | aucaaauaca | 300 |
| uguguggguu | gucggccgac | uugaaauuca | ggaucaaaca | gaaaggagaa | uacuugcccu | 360 |
| uguugcaggaa | aaaaucguug | ggaaugaucu | ucgaaaaaag | gucgacaagg | acaagguugu | 420 |
| cgacagaaac | aggauucgcc | uuguugggag | gacaccccug | cuucuugaca | acacaggaca | 480 |
| uccacuuggg | aguaaacgaa | ucguugacag | acacagccag | gguauugucg | ucgauggccg | 540 |
| acgccguauu | ggccagggua | uacaaacagu | cggacuugga | cacaugggcc | aaagaagccu | 600 |
| cgaucccccau | caucaacgga | uugucggacu | guaccacccc | cauccagauc | uuggccgacu | 660 |
| acuugacauu | gcaggaacac | uacucgucgu | ugaaaggauu | gacauugucg | uggaucggag | 720 |
| acggaaacaa | caucuugcac | ucgaucauga | ugucggccgc | caaauucgga | augcacuugc | 780 |
| aggccgccac | acccaaagga | uacgaacccg | acgccucggu | aacaaaauug | gccgaacagu | 840 |
| acgccaaaga | aaacgaaaca | aaauuguugu | ugacaaacga | ccccuuggaa | gccgccacg | 900 |
| gaggaaacgu | auugaucaca | gacacaugga | ucucgauggg | acaggaagaa | gaaaaaaaaa | 960 |

```
aaaggauugca ggccuuccag ggauaccagg uaacaaugaa acagccaaa guagccgccu   1020 cggacuggac auucuugcac ugcuugccca ggaaacccga agaaguagac gacgaaguau   1080
ucuacucgcc caggucguug guauucccg aagccgaaaa caggaaaugg acaaucaugg   1140
ccguaauggu aucguuguug acagacuacu cgccccaguu gcagaaaccc aaauucugaa   1200
uagugaacuc gagcuaguga cugacuagga ucugguuacc acuaaaccag ccucaagaac   1260
acccgaaugg agucucuaag cuacauaaua ccaacuuaca cuuacaaaau guugucccc   1320 aaaauguagc cauucguauc ugcuccuaau aaaaagaaag uucuuccaca uucuag       1376
```

<210> SEQ ID NO 121  
<211> LENGTH: 1222  
<212> TYPE: RNA  
<213> ORGANISM: Artificial sequence  
<220> FEATURE:  
<223> OTHER INFORMATION: Synthetic polynucleotide

<400> SEQUENCE: 121

```
auuauuacau caaaacaaaa agccgccacc augcuguuca accugcgcau ccugcugaac     60
aacgccgccu uccgcaacgg ccacaacuuc auggugcgca acuccgcug cggccagccc    120 cugcagggca aggugcagcu gaagggccgc gaccugcuga cccugaagaa cuucaccggc    180
gaggagauca aguacaugcu guggcugagc gccgaccuga aguccgcau caagcagaag    240 ggcgaguacc ugcccugcu gcagggcaag agccugggca ugaucuucga aagcgcagc    300 acccgcaccc gccugagcac cgagacaggc uucgcccugc ugggcggcca ccccugcuuc    360
cugaccaccc aggacaucca ccugggcgug aacgagagcc ugaccgacac cgcccgcgug    420
cugagcagca uggccgacgc cgugcuggcc gcguguaca agcagagcga ccuggacacc    480
cuggccaagg aggccagcau ccccaucauc aacggccuga gcgaccugua ccaccccauc    540
cagauccugg ccgacuaccu gacccugcag gagcacuaca gcagccugaa gggccugacc    600
cugagcugga ucggcgacgg caacaacauc cugcacagca ucaugaugag cgccgccaag    660
uucggcaugc accugcaggc cgccaccccc aagggcuacg agcccgacgc cagcgugacc    720
aagcuggccg agcaguacgc caaggagaac ggcaccaagc ugcugcugac caacgacccc    780
cuggaggccg cccacggcgg caacgugcug aucaccgaca ccuggaucag caugggccag    840
gaggaggaga agaagaagcg ccugcaggcc uuccagggcu accaggugac caugaagacc    900 gccaagguqq ccgccagcga cuggaccuuc cugcacugcc ugcccgcaa gcccgaggag    960 guggacgacg aggugcuucua cagccccgc agccuggugu uccccgaggc cgagaaccgc   1020
aaguggacca ucauggccgu gaugugagc cugcugaccg acuacagccc ccagcugcag   1080
aagcccaagu ucugaggucu cuaguaauga gcuggagccu cgguaggcgu uccuccugcc   1140
cgcuggcccu cccaacgggc ccuccucccc uccuugcacc ggcccuuccu ggucuuugaa   1200
uaaagucuga gugggcaucu ag                                             1222
```

<210> SEQ ID NO 122  
<211> LENGTH: 1222  
<212> TYPE: RNA  
<213> ORGANISM: Artificial sequence  
<220> FEATURE:  
<223> OTHER INFORMATION: Synthetic polynucleotide

<400> SEQUENCE: 122

```
auuauuacau caaaacaaaa agccgccacc augcuguuca accugcgcau ccugcugaac      60
aacgccgccu uccgcaacgg ccacaacuuc augugcgca acuccgcug cggccagccc      120
cugcagggcc gggugcagcu gaagggccgc gaccugcuga cccugaagaa cuucaccggc      180
gaggagauca aguacaugcu guggcugagc gccgaccuga aguccgcau caagcagaag      240
ggcgaguacc ugcccugcu gcagggcaag agccugggca ugaucuucga aagcgcagc      300
acccgcaccc gccugagcac cgagacaggc uucgcccugc ugggcggcca ccccugcuuc      360
cugaccaccc aggacaucca ccugggcgug aacgagagcc ugaccgacac cgcccgcgug      420
cugagcagca uggccgacgc cgugcuggcc cgcguguaca agcagagcga ccuggacacc      480
cuggccaagg aggccagcau ccccaucauc aacggccuga cgaccugua ccaccccauc      540
cagauccugg ccgacuaccu gacccugcag gagcacuaca gcagccugaa gggccugacc      600
cugagcugga ucggcgacgg caacaacauc cugcacagca ucaugaugag cgccgccaag      660
uucggcaugc accugcaggc cgccacccccc aagggcuacg agcccgacgc cagcgugacc      720
aagcuggccg agcaguacgc caaggagaac ggcaccaagc ugcugcugac caacgacccc      780
cuggaggccg cccacggcgg caacgugcug aucaccgaca ccuggaucag caugggccag      840
gaggaggaga agaagaagcg ccugcaggcc uuccagggcu accaggugac caugaagacc      900
gccaaggugg ccgccagcga cuggaccuuc cugcacugcc ugccccgcaa gcccgaggag      960
guggacgacg agguguucua cagccccgc agccuggugu ccccgaggc cgagaaccgc      1020
aaguggacca ucauggccgu gauggugagc cugcugaccg acuacagccc ccagcugcag      1080
aagcccaagu ucuagggucu cuaguaauga gcuggagccu cgguagccgu uccuccugcc      1140
cgcugggccu cccaacgggc ccuccucccc uccuugcacc ggcccuuccu gguucuuugaa      1200
uaaagucuga gugggcaucu ag                                                1222
```

<210> SEQ ID NO 123
<211> LENGTH: 1222
<212> TYPE: RNA
<213> ORGANISM: Artificial sequence
<220> FEATURE:
<223> OTHER INFORMATION: Synthetic polynucleotide

<400> SEQUENCE: 123

```
auuauuacau caaaacaaaa agccgccacc augcuguuca accugcgcau ccugcugaac      60
aacgccgccu uccgcaacgg ccacaacuuc augugcgca acuccgcug cggccagccc      120
cugcagggcc gggugcagcu gaagggccgc gaccugcuga cccugaagaa cuucaccggc      180
gaggagaucc ggugacaugcu guggcugagc gccgaccuga aguccgcau caagcagaag      240
ggcgaguacc ugcccugcu gcagggcaag agccgggca ugaucuucga aagcgcagc      300
acccgcaccc gccugagcac cgagacaggc uucgcccugc ugggcggcca ccccugcuuc      360
cugaccaccc aggacaucca ccugggcgug aacgagagcc ugaccgacac cgcccgcgug      420
cugagcagca uggccgacgc cgugcuggcc cgcguguaca agcagagcga ccuggacacc      480
cuggccaagg aggccagcau ccccaucauc aacggccuga cgaccugua ccaccccauc      540
cagauccugg ccgacuaccu gacccugcag gagcacuaca gcagccugaa gggccugacc      600
cugagcugga ucggcgacgg caacaacauc cugcacagca ucaugaugag cgccgccaag      660
uucggcaugc accugcaggc cgccacccccc aagggcuacg agcccgacgc cagcgugacc      720
```

| | |
|---|---|
| aagcuggccg agcaguacgc caaggagaac ggcaccaagc ugcugcugac caacgacccc | 780 |
| cuggaggccg cccacggcgg caacgugcug aucaccgaca ccuggaucag caugggccag | 840 |
| gaggaggaga agaagaagcg ccugcaggcc uuccagggcu accaggugac caugaagacc | 900 |
| gccaaggugg ccgccagcga cuggaccuuc cugcacugcc ugcccgcaa gcccgaggag | 960 |
| guggacgacg aggguucua cagcccccgc agccuggugu uccccgaggc cgagaaccgc | 1020 |
| aaguggacca ucauggccgu gauggugagc cugcugaccg acuacagccc ccagcugcag | 1080 |
| aagcccaagu ucugaggucu cuaguaauga gcuggagccu cgguagccgu uccuccugcc | 1140 |
| cgcugggccu cccaacgggc ccuccucccc uccuugcacc ggcccuuccu ggucuuugaa | 1200 |
| uaaagucuga gugggcaucu ag | 1222 |

<210> SEQ ID NO 124
<211> LENGTH: 1282
<212> TYPE: RNA
<213> ORGANISM: Artificial sequence
<220> FEATURE:
<223> OTHER INFORMATION: Synthetic polynucleotide

<400> SEQUENCE: 124

| | |
|---|---|
| ggcagaaaaa uuugcuacau uguuucacaa acuucaaaua uuauucauuu auuuagaucu | 60 |
| auuauuacau caaaacaaaa agccgccacc augcuguuca accugcgcau ccugcugaac | 120 |
| aacgccgccu uccgcaacgg ccacaacuuc auggugcgca acuuccgcug cggccagccc | 180 |
| cugcagggca aggugcagcu gaagggccgc gaccugcuga cccugaagaa cuucaccggc | 240 |
| gaggagauca aguacaugcu guggcugagc gccgaccuga aguuccgcau caagcagaag | 300 |
| ggcgaguacc ugccccugcu gcagggcaag agccugggca ugaucuucga aagcgcagc | 360 |
| acccgcaccc gccugagcac cgagacaggc uucgcccugc ugggcggcca ccccugcuuc | 420 |
| cugaccaccc aggacaucca ccugggcgug aacgagagcc ugaccgacac cgcccgcgug | 480 |
| cugagcagca uggccgacgc cgugcuggcc cgcguguaca agcagagcga ccuggacacc | 540 |
| cuggccaagg aggccagcau ccccaucauc aacggccuga gcgaccugua ccaccccauc | 600 |
| cagauccugg ccgacuaccu gacccugcag gagcacuaca gcagccugaa gggccugacc | 660 |
| cugagcugga ucggcgacgg caacaacauc cugcacagca ucaugaugag cgccgccaag | 720 |
| uucggcaugc accugcaggc cgccaccccc aagggcuacg agcccgacgc cagcgugacc | 780 |
| aagcuggccg agcaguacgc caaggagaac ggcaccaagc ugcugcugac caacgacccc | 840 |
| cuggaggccg cccacggcgg caacgugcug aucaccgaca ccuggaucag caugggccag | 900 |
| gaggaggaga agaagaagcg ccugcaggcc uuccagggcu accaggugac caugaagacc | 960 |
| gccaaggugg ccgccagcga cuggaccuuc cugcacugcc ugcccgcaa gcccgaggag | 1020 |
| guggacgacg aggguucua cagcccccgc agccuggugu uccccgaggc cgagaaccgc | 1080 |
| aaguggacca ucauggccgu gauggugagc cugcugaccg acuacagccc ccagcugcag | 1140 |
| aagcccaagu ucugaggucu cuaguaauga gcuggagccu cgguagccgu uccuccugcc | 1200 |
| cgcugggccu cccaacgggc ccuccucccc uccuugcacc ggcccuuccu ggucuuugaa | 1260 |
| uaaagucuga gugggcaucu ag | 1282 |

<210> SEQ ID NO 125
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 125
cacaaagagu aaagaagaac a                                              21

<210> SEQ ID NO 126
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 126
aacacuaaaa guagaagaaa a                                              21

<210> SEQ ID NO 127
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 127
cucagaaaga uaagaucagc c                                              21

<210> SEQ ID NO 128
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 128
atgctgttta atctgaggat cctgttaaac aatgcagctt ttagaaatgg tcacaacttc    60
atggttcgaa attttcggtg tggacaacca ctacaaaata aagtgcagct gaagggccgt   120
gaccttctca ctctaaaaaa ctttaccgga gaagaaatta aatatatgct atggctatca   180
gcagatctga aatttaggat aaaacagaaa ggagagtatt tgcctttatt gcaagggaag   240
tccttaggca tgattttttga gaaaagaagt actcgaacaa gattgtctac agaaacaggc   300
tttgcacttc tgggaggaca tccttgtttt cttaccacac aagatattca tttgggtgtg   360
aatgaaagtc tcacggacac ggcccgtgta ttgtctagca tggcagatgc agtattggct   420
cgagtgtata acaatcaga tttggacacc ctggctaaag aagcatccat cccaattatc    480
aatgggctgt cagatttgta ccatcctatc cagatcctgg ctgattacct cacgctccag   540
gaacactata gctctctgaa aggtcttacc ctcagctgga tcggggatgg gaacaatatc   600
ctgcactcca tcatgatgag cgcagcgaaa ttcggaatgc accttcaggc agctactcca   660
aagggttatg agccggatgc tagtgtaacc aagttggcag agcagtatgc caaagagaat   720
ggtaccaagc tgttgctgac aaatgatcca ttggaagcag cgcatggagg caatgtatta   780
attacagaca cttggataag catgggacaa gaagaggaga gaaaaaagcg gctccaggct   840
ttccaaggtt accaggttac aatgaagact gctaaagttg ctgcctctga ctggacattt   900
ttacactgct tgcccagaaa gccagaagaa gtggatgatg aagtcttttta ttctcctcga   960 tcactagtgt tcccagaggc agaaaacaga agtggacaa tcatggctgt catggtgtcc   1020
ctgctgacag attactcacc tcagctccag aagcctaaat tttga                  1065

<210> SEQ ID NO 129
<211> LENGTH: 1065
<212> TYPE: DNA

<213> ORGANISM: Artificial sequence
<220> FEATURE:
<223> OTHER INFORMATION: Synthetic polynucleotide

<400> SEQUENCE: 129

| | |
|---|---|
| atgctcttta atctgcgcat cttactgaac aacgccgcat tccggaacgg tcacaacttc | 60 |
| atggtccgca atttccgctg tggccagccg cttcaaaaca aggtccagct gaagggacgg | 120 |
| gatctgctga cactgaagaa cttcaccgga gaagagatca agtacatgct gtggctcagc | 180 |
| gcagacttga agttccggat caagcagaag ggagaatact tgcccctgct gcaaggaaag | 240 |
| tcgctgggaa tgattttga agcggtca actcgcacca gactctccac cgaaactggt | 300 |
| ttcgcactgc ttggcgggca cccttgcttc ctgacgactc aggacatcca cctcggcgtg | 360 |
| aacgaatcgc taaccgatac cgccagagtg cttcttcca tggccgacgc ggtgctggcc | 420 |
| agggtgtaca agcagtccga cctcgatacc ttggcaaagg aggcttccat tcccatcatc | 480 |
| aacggcctga cgacctgta ccacccaatc caaatcctgg ctgactacct gaccctgcaa | 540 |
| gagcactaca gcagcctgaa gggtctgacc ctgtcatgga ttggcgatgg aaacaatatt | 600 |
| ctgcactcca tcatgatgtc cgccgcgaag ttcggaatgc atctgcaagc cgccactcca | 660 |
| aaaggatacg aaccggatgc gtccgtgacc aagttggcgg aacagtacgc gaaggagaac | 720 |
| ggaaccaagc ttctgctgac taacgacccc ctcgaggctg cgcatggggg caacgtgctg | 780 |
| attaccgaca cctggatctc catggggcag gaggaagaga agaagaagag actgcaggca | 840 |
| ttccaggggt accaggtcac catgaaaacc gcaaaagtgg cagcttcgga ctggactttc | 900 |
| ctgcattgcc tgccgaggaa gccggaggaa gtcgacgacg aagtgttcta ctcgcctcgg | 960 |
| tccctggtgt tccccgaggc cgaaaaacgg aagtggacca tcatggccgt gatggtgtcc | 1020 |
| ttgctgactg actatagccc gcagctgcag aagcctaagt ctag | 1065 |

<210> SEQ ID NO 130
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 130

| | |
|---|---|
| atgctgttta acctacgtat tttgctcaac aatgcagcct ttagaaacgg acataacttt | 60 |
| atggttcgaa actttcgctg cgggcagcca ctgcagaaca aggtccagct gaaagggaga | 120 |
| gatttgctca cgctgaagaa ctttactggc gaagaaatca agtatatgct gtggttgtcc | 180 |
| gcggacctca gtttcggat taagcagaaa ggggagtatc tgccactgct gcaaggaaag | 240 |
| agcctcggca tgatcttcga gaagcggagc actcggacca ggctgagtac cgaaactggc | 300 |
| ttcgcattgt tgggtggaca tccatgtttt ctgacaacgc aggacattca tctgggcgtg | 360 |
| aacgagagtc tgacggacac agctcgcgtt ctgtcctcta tggctgatgc ggtgttggcc | 420 |
| cgggtctata agcagtccga tttggacacc ttggctaagg aagctagcat accgattatc | 480 |
| aatgggctgt ccgacctgta tcaccctatt caaatcctgg ccgactacct cacactgcaa | 540 |
| gaacactata gctcattgaa gggactgacc ctgagctgga tagggacgg aaacaacatc | 600 |
| ctacatagca ttatgatgtc cgctgccaag tttggcatgc atcttcaagc cgccacgcca | 660 |
| aagggttatg agcccgacgc gtcagtgaca aagctggccg agcagtacgc taaggagaat | 720 |
| ggtaccaaat tactgctgac taatgatcca ctggaggctg cacatggcgg caatgtactg | 780 |
| atcaccgaca catggatctc gatgggccag gaggaagaaa agaagaagag gcttcaggcc | 840 |

```
ttccaaggct accaggtcac catgaaaaca gctaaggttg cagcatctga ttggacctttt    900 ctgcactgtc tgccaaggaa gcccgaagag gtggacgatg aagtattcta tagcccacgg    960
agtttggtgt tccctgaggc tgaaaatagg aagtggacaa ttatggccgt aatggtgtcc   1020
ctgttaaccg actactctcc gcaactgcag aaacctaagt tttag                    1065
```

<210> SEQ ID NO 131
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 131

```
atgctgttta acttaaggat cctgctgaac aacgccgctt tcgtaacgg tcataacttt     60 atggtccgga actttagatg tggccagccg ctgcagaaca aggttcagct gaaggggagg   120
gatctgctga ccttgaagaa ctttaccggc gaagagatca agtacatgtt gtggctgagc   180
gccgatctga agtttaggat taagcagaag ggggagtatt tgccactgct gcaaggaaaa   240
tccttgggga tgatcttcga gaagcgctcc actagaaccc ggctaagcac agaaaccggc   300
ttcgcacttc tgggtggaca tccctgtttt ctgacgacgc aggatataca cctgggcgtg   360
aatgagagtc tgacggacac agctagggtg ttgagcagca tggccgatgc agtactggcc   420 cgcgttta agcagagcga cttggacaca ctggccaagg aagcgtcaat tccgattatc      480
aatgggctgt cagacctgta tcatcccatt caaatcttgg ctgactatct gaccctgcaa    540
gaacattaca gctccctgaa gggcctcacg ttgtcctgga ttggcgacgg aaacaacatt    600
ctgcattcga tcatgatgag cgctgctaag tttggcatgc acctccaagc cgctacacct    660
aagggatatg agcctgatgc cagcgtaacc aagctggccg aacagtacgc gaaggagaat    720
ggcacgaaac tgctgttgac aaatgaccca ctggaggcag ctcacggtgg caacgtgctg    780
atcaccgaca cgtggatatc tatgggacag gaagaagaga agaaagaagcg gctgcaggca    840 ttccaagggt atcaggtcac catgaaaacg gccaaggttg ctgcatccga ctggacatttt  900 ctgcattgct tgcccccgcaa accagaagaa gtagacgacg aagtcttta ttccccacgg    960 tcgctggtgt tccccgaggc ggagaatcga agtggacga ttatggccgt gatggtgtcc   1020
ctgctgactg attactctcc ccaactgcaa agcctaagt tttag                    1065
```

<210> SEQ ID NO 132
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 132

```
atgcttttca acctgaggat cctcctgaac aacgccgcct tcgcaatggg tcacaacttt     60
atggtccgga acttcagatg cggccagccg ctgcagaaca aggtccagct gaagggacgg   120
gatctgctga ctctgaagaa cttcaccgga gaagagatca agtacatgct gtggctgtcg   180
gccgacctga agttcaggat caagcagaag ggagaatacc tcccgctgct gcaaggaaag   240
tccctgggca tgattttcga gaagcgctcg accagaactc ggttgtccac cgaaaccggg    300
tttgcgctgc tgggcggaca tccttgcttc ctgacgactc aggatattca cctgggagtg    360
aacgagtcgc tgaccgacac cgccagagtg ctgagctcga tggccgacgc cgtgttggca    420
```

```
cgcgtgtaca agcagtccga tctggatacc ctggccaaag aagcttccat cccgatcatt    480
aacgggctga gcgacctcta ccaccccatt caaatcctgg ccgactacct gactctgcaa    540
gaacactaca gctcgctgaa gggggttgact ctgtcctgga tcggcgacgg aaacaacatc    600
```
```
gaacactaca gctcgctgaa ggggttgact ctgtcctgga tcggcgacgg aaacaacatc    600
ctgcactcca tcatgatgtc ggccgcaaag ttcggcatgc atttgcaagc cgccacccca    660
aagggctacg aaccagacgc gagcgtcacc aagctggccg aacagtacgc gaaggaaaat    720
ggtactaagc tgctgctgac caacgaccca ttggaagctg cccatggtgg aaacgtgctg    780
atcaccgaca cctggatctc gatgggccag gaagaggaga agaagaagcg gctgcaggcg    840
ttccaggggt atcaggtcac catgaaaaca gccaaagtgg cagcgtcaga ctggaccttc    900
ctccactgtc tgcctcgcaa gccagaggag gtggacgacg aggtgttcta ctcccctcgg    960
tccctcgtgt tccctgaggc tgagaaccgg aagtggacca ttatggccgt gatggtgtca    1020
ctcctgactg attactcccc gcaactgcag aagcccaagt ctag                    1065

<210> SEQ ID NO 133
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 133
atgctgttta acctgaggat cctattgaac aatgctgctt ttcgtaatgg ccataacttt    60
atggttcgga actttagatg cgggcagcca ctgcagaaca aggtccagtt gaaaggccgc    120
gatctgttga cattgaagaa ctttaccggc gaagagatta agtatatgct gtggctgtct    180
gctgacctca gtttcgaat caagcagaag ggcgaatatc tccccctgct gcaaggaaag    240
tctctcggca tgatctttga aagcggagt acccgaacac ggctgagcac cgaaacgggc    300
ttcgcactgc tggggggcca tccctgtttt ctgacaacgc aggacatcca cttgggggtt    360
aacgaatcat tgactgatac cgcccgcgta ctgtcatcca tggccgacgc tgtgctggct    420
agggtgtaca agcagtcaga tctggataca ctggccaagg aagctagcat accaatcatc    480
aatggactga gtgacctta tcacccgatt caaatactag ccgattatct gaccctgcaa    540
gagcattact cctcgctgaa aggcctcacg ctgtcctgga tcggcgacgg caacaacatt    600
ctgcatagta ttatgatgtc tgctgccaaa ttcggcatgc atctgcaagc tgctacgccg    660
aagggttatg aacccgacgc gtcagttacg aagctcgctg agcagtatgc aaaggagaat    720
ggcacaaagc tgttgcttac caacgatccc tggaagctg ctcatggcgg caatgtgctg    780
attactgaca cctggatttc aatgggccag gaggaggaga agaagaagag gttacaggct    840
tttcaaggtt accaagtcac gatgaaaacc gctaaggtcg cagccagcga ctggacattc    900
ctgcactgtc tgccaagaaa gccggaagaa gtggacgacg aggtgttcta ttccccgcgg    960
tctttggtgt ttccggaggc cgaaaacagg aaatggacca ttatggccgt gatggtatcg    1020
ttgctgacgg actacagccc tcagttgcaa aagcccaagt ctag                   1065

<210> SEQ ID NO 134
<211> LENGTH: 1065
<212> TYPE: DNA
<213> ORGANISM: Artificial sequence
<220> FEATURE:
<223> OTHER INFORMATION: Synthetic polynucleotide
```

<400> SEQUENCE: 134

```
atgctcttta acctccgcat cctcctcaac aacgccgcct tccggaatgg gcataacttc      60
atggtccgga acttcagatg cggccagccc ctgcaaaaca aggtccagtt gaagggacgg     120
gacctcctta cgctgaagaa ctttaccgga gaagagatta agtacatgct gtggttgtcc     180
gctgacctca agttccgcat taagcagaag ggagaatatc tgccgctgct gcaaggaaag     240
agcctgggca tgatcttcga aaagcgctcc actagaaccc ggctgtcgac tgagactgga     300
ttcgccttgc tcggtggaca cccgtgcttc ctgacgaccc aggacatcca cctgggagtg     360
aacgagtcac ttacggatac cgcgagggtg ctgtcctcaa tggccgacgc agtgctcgcg     420
cgcgtgtaca agcagtcaga tctggatacc ctggccaagg aagccagcat tcccatcatc     480
aacggactga cgaccttta ccacccaatc cagatcctcg ccgactactt aaccctgcaa     540
gagcactaca gctccctgaa gggactgact ctgtcctgga tcgggatgg aaacaacatc      600
ctgcactcca tcatgatgtc tgccgctaag tttgggatgc atctgcaagc cgcaaccccct    660
aagggatacg agcccgacgc ctcggtgacc aaacttgcgg aacagtacgc caaggaaaac     720
ggtaccaagc tgctgctgac caacgaccct ctggaagcgg cccacggagg aaatgtgctg     780
attaccgaca cctggatttc gatgggccag gaggaggaga agaagaagag actgcaggcg     840
ttccagggat atcaggtcac catgaaaacc gccaaggtcg ccgccagcga ctggaccttc     900
ctgcactgtc tccctcggaa accggaagaa gtggatgacg aggtgttcta ctccccgcgc     960
tcgctggtgt tcccggaggc tgaaaacagg aagtggacaa tcatggccgt gatggtgtcc    1020
ctgttgaccg actactcccc acaactgcag aagcccaagt tctag                    1065
```

<210> SEQ ID NO 135
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 135

```
atgcttttca atctgcgcat cctcctgaac aacgccgcct tccgcaatgg acacaacttt      60
atggtccgca acttccgctg tgggcagccg ctgcagaaca aggtccagct caaggggaga     120
gatctcctga ccctgaagaa cttcactgga gaggagatca agtacatgct gtggctgtcc     180
gccgacctga atttccgat taagcagaag ggcgaatacc tcccactgct gcaaggaaag     240
tctttgggca tgatcttcga aaagagaagc acccggaccc ggttgagcac cgaaactggg     300
ttcgcgctcc tcggtggaca cccgtgcttc ctgaccaccc aagatattca tctgggtgtc     360
aacgaaagcc tgaccgacac cgccaggtg ctgtcatcca tggctgacgc agtgctcgcc      420
cgggtgtaca agcagtcaga cctggacacc ctcgccaagg aagcttcgat ccctatcatc     480
aacggacttt ccgacctgta ccaccccatc caaattctgg ccgactacct gactctgcaa     540
gaacactata gctcgctgaa aggacttact ctgtcctgga tcgggacgg caacaacatt      600
ctccattcca tcatgatgtc cgctgccaag ttcggaatgc accttcaagc agcgactccc     660
aagggatacg aacctgatgc ctccgtgact aagctggcag agcagtacgc caaggagaac     720
ggtacaaagc tgctgctcac gaacgacccc ctggaggcgg cccacggcgg aaacgtgctg     780
attaccgata cctggatctc aatgggccag gaagaggaga agaagaagcg gctccaggcg     840
tttcaaggct accaggtcac catgaaaacc gcgaaggtcg ccgcctccga ctggactttc     900
```

| | |
|---|---|
| ttgcactgcc tgccgcggaa gcccgaggaa gtggatgacg aagtgttcta ctcgccgaga | 960 |
| tcgttggtgt tccctgaggc cgaaaacagg aagtggacca tcatggccgt gatggtgtcc | 1020 |
| ctgctgactg attacagccc acagctgcag aagcctaagt tctag | 1065 |

<210> SEQ ID NO 136
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 136

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct gaagggccgg | 120 |
| gatcttctga ccctgaagaa ctttactggc gaagagatca agtacatgct ctggctctcc | 180 |
| gcggacttga agttccgcat taagcagaag ggggaatacc ttccgctgct tcaaggaaag | 240 |
| agcctcggca tgatctttga agcgctca accaggaccc gcctttctac tgaaactggg | 300 |
| ttcgcgctgc tcggtggcca cccctgcttc ctgacgaccc aggacatcca cctcggagtg | 360 |
| aacgaatccc tcaccgatac cgcccgggtg ttatcgagca tggcagatgc cgtgctggcc | 420 |
| agggtgtaca acagtccga tctggacact ctggccaagg aggcgtcaat tcctattatc | 480 |
| aacggcctta gtgacctcta ccatccgatt cagatcctgg ccgattacct caccctgcaa | 540 |
| gaacactaca gctccctgaa gggtctgaca ttgtcctgga tcggcgacgg caacaacatt | 600 |
| ctccattcca tcatgatgtc cgccgcaaaa ttcggcatgc atcttcaagc cgccacgccg | 660 |
| aagggttacg agcccgacgc ttccgtgact aagctcgccg agcagtacgc taaggagaac | 720 |
| ggaaccaagc ttctgctgac taacgaccca ctagaagcag cccacggggg caacgtgctt | 780 |
| attactgaca cctggatctc catgggccag gaagaagaga aaaagaagcg gctgcaggcg | 840 |
| ttccagggat atcaggtcac catgaaaacc gccaaggtcg ctgcctccga ctggaccttc | 900 |
| ctgcactgcc tgcctcgcaa gcctgaagaa gtggacgacg aggtgttcta ctcgccacgg | 960 |
| agcctcgtgt tccccgaggc cgagaataga agtggacca tcatggccgt gatggtgtca | 1020 |
| ctgctcaccg actacagccc gcagcttcag aagcccaagt tctag | 1065 |

<210> SEQ ID NO 137
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 137

| | |
|---|---|
| atgcttttca acctgagaat cctcctgaac aacgccgcct tccgcaatgg tcataacttc | 60 |
| atggtccgca actttcgctg cggacagcct ctccaaaaca aggtccagct caaggggcgc | 120 |
| gacctcctca cactgaagaa cttcactgga gaagaaatca agtacatgct gtggctgagc | 180 |
| gccgatctga agttccggat caagcagaag ggagagtacc ttcctctgct gcaagggaag | 240 |
| tccttgggaa tgatttttcga gaagcggtcc acccggacca ggctgagcac tgaaactggc | 300 |
| ttcgccctgc tgggaggcca ccccttgtttc ctgaccactc aggacatcca cctgggcgtg | 360 |
| aacgagtccc tgaccgatac tgccagagtg ctgtcctcca tggccgacgc cgtgctcgcc | 420 |
| cgggtgtaca agcagtcaga cctcgatacg ctggccaagg aagcctccat tcccattatc | 480 |
| aatggtctgt cggacctcta ccatccaatc caaatcctcg ccgactacct gactctgcaa | 540 |

```
gaacactaca gctcactcaa gggcctcacc ctctcctgga tcggcgacgg aaacaacatc    600
cttcactcga ttatgatgtc ggccgcgaag ttcgggatgc acctccaagc tgccactcca    660
aaaggctacg agccggatgc ctcagtgact aagttggcgg aacagtatgc gaaggagaac    720
ggtaccaagc tcctgctgac taacgacccg ctggaggccg cccacggggg aaacgtgctc    780
atcaccgata cttggatttc catgggacag gaggaagaga agaagaagcg gttgcaggca    840
tttcagggct accaggtcac catgaaaact gccaaagtcg ccgccagcga ctggaccttc    900
ctgcactgcc tgccccgcaa gcctgaagaa gtggacgacg aggtgttcta ctctccccgg    960
tccctcgtgt tccctgaggc cgaaaacagg aagtggacca tcatggctgt gatggtgtcc   1020
ctcctgaccg actacagccc tcagctccaa aacccaagt tttag                   1065

<210> SEQ ID NO 138
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 138
atgcttttca acctgagaat cctcttgaac aatgctgctt ttcggaatgg ccacaacttt     60
atggttcgga acttccgttg cggccagcct ttacaaaaca aggtccagct gaagggccgg    120
gatttgctca cactgaagaa ctttactggg gaggagatta agtatatgct gtggctgtcc    180
gctgacctga gtttaggat caagcagaag ggcgaatatc tgccgctgct gcaagggaaa    240
agtctgggca tgattttga aaagcgctct acccggacca gactgtctac ggaaacaggc    300
tttgccctgc tgggcggcca ccctgttttt ctgacaacgc aggacatcca tctgggcgtg    360
aacgaatcac tgaccgatac tgctcgggta ctcagttcta tggctgacgc agtgctggct    420
agggtgtaca gcagagcga cttggacaca ctggctaagg aggccagcat ccccattatc    480
aatggcctgt ctgatttgta ccatcccatt caaatcctgg ctgattatct gacactacaa    540
gagcattact caagtctgaa ggggttgact ctctcctgga tcggcgacgg caacaacatt    600
ttacattcca ttatgatgag tgctgctaag tttggcatga atttgcaagc tgctacccca    660
aagggctatg aacctgacgc tagcgtaacc aagttggccg aacagtatgc taaagagaat    720
ggcaccaagc tgctcctgac gaatgacccc ctggaagctg ctcatggcgg aaacgtactt    780
ataactgata catggattag catgggccag gaagaggaga agaagaagag actgcaggcc    840
ttccaaggct atcaggtcac catgaaaact gccaaggttg cagctagcga ctggaccttc    900
ctgcactgtt tgccgaggaa acccgaggag gtggacgatg aagtctttta ttctccccgc    960
tccttggtgt ttcccgaggc tgaaaatcga agtggacga taatggcagt gatggtgtcc   1020
ctactgaccg actattctcc acaactgcag aagcctaaat tctag                  1065

<210> SEQ ID NO 139
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 139
atgcttttca atctgaggat cctgctgaac aacgctgctt ttcgcaacgg tcataacttt     60
atggttcgca attttcgttg tggccagccg ctgcagaaca aggttcagct gaagggcaga    120
```

| | |
|---|---|
| gatctgctga ctctgaagaa cttcactggg aagaaatca agtatatgtt atggctgtcc | 180 |
| gcggatctga aatttcgaat caagcagaag ggcgaatatc ttcccctgct gcaagggaaa | 240 |
| tccttgggca tgattttga agaggagc actaggacta gattgtcaac agaaacaggc | 300 |
| tttgctttgt tgggcggaca tccctgcttt ctgacgacac aggatatcca cctcggcgta | 360 |
| aacgagtccc tcaccgacac tgctagggta ctgagcagca tggccgacgc tgtgctagcc | 420 |
| cgggtttaca agcagtcaga cctggacacc cttgccaagg aagcttctat tccaattatc | 480 |
| aacggcctga gtgacctgta tcaccctatt caaatactcg ccgactattt gacgcttcaa | 540 |
| gaacattaca gcagcctcaa gggcttaacc ttgagttgga taggcgacgg caacaatatc | 600 |
| ctgcattcca ttatgatgtc tgccgctaag tttggcatgc atctacaagc cgcaacaccc | 660 |
| aagggctatg aacccgacgc tagcgtgacc aagctggccg agcagtatgc taaggaaaat | 720 |
| ggcacaaagc tccttcttac caacgatccc ctggaggctg ctcacggcgg caacgtgctg | 780 |
| attaccgata catggattag catgggccag gaggaggaga aaagaagcg gctccaggct | 840 |
| tttcaaggct atcaggtcac catgaaaact gcaaaggtcg ctgcctccga ctggactttc | 900 |
| ctgcattgtc taccccgcaa gcctgaggaa gtggacgatg aggtgttcta ctccccacgg | 960 |
| agtctggtgt tcccggaagc agagaatcgg aagtggacca tcatggctgt catggtgtcg | 1020 |
| ctcttgactg actattctcc ccaactgcaa aaacccaagt tttag | 1065 |

<210> SEQ ID NO 140
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 140

| | |
|---|---|
| atgctttca atctgaggat cctgctgaac aacgctgctt ttcgcaacgg tcataacttt | 60 |
| atggttcgca attttcgttg tggccagccg ctgcagaaca aggttcagct gaagggcaga | 120 |
| gatctgctga ctctgaagaa cttcactggg aagaaatca agtatatgtt atggctgtcc | 180 |
| gcggatctga aatttcgaat caagcagaag ggcgaatatc ttcccctgct gcaagggaaa | 240 |
| tccttgggca tgattttga agaggagc actaggacta gattgtcaac agaaacaggc | 300 |
| tttgctttgt tgggcggaca tccctgcttt ctgacgacac aggatatcca cctcggcgta | 360 |
| aacgagtccc tcaccgacac tgctagggta ctgagcagca tggccgacgc tgtgctagcc | 420 |
| cgggtttaca agcagtcaga cctggacacc cttgccaagg aagcttctat tccaattatc | 480 |
| aacggcctga gtgacctgta tcaccctatt caaatactcg ccgactattt gacgcttcaa | 540 |
| gaacattaca gcagcctcaa gggcttaacc ttgagttgga taggcgacgg caacaatatc | 600 |
| ctgcattcca ttatgatgtc tgccgctaag tttggcatgc atctacaagc cgcaacaccc | 660 |
| aagggctatg aacccgacgc tagcgtgacc aagctggccg agcagtatgc taaggaaaat | 720 |
| ggcacaaagc tccttcttac caacgatccc ctggaggctg ctcacggcgg caacgtgctg | 780 |
| attaccgata catggattag catgggccag gaggaggaga aaagaagcg gctccaggct | 840 |
| tttcaaggct atcaggtcac catgaaaact gcaaaggtcg ctgcctccga ctggactttc | 900 |
| ctgcattgtc taccccgcaa gcctgaggaa gtggacgatg aggtgttcta ctccccacgg | 960 |
| agtctggtgt tcccggaagc agagaatcgg aagtggacca tcatggctgt catggtgtcg | 1020 |
| ctcttgactg actattctcc ccaactgcaa aaacccaagt tttag | 1065 |

<210> SEQ ID NO 141
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 141

```
atgcttttta atctccgcat cctccttaac aacgccgcgt ttagaaacgg ccacaacttc      60
atggtccgga acttcagatg tggccagccg cttcaaaaca aggtccagct gaagggccgg     120
gatcttctga ccctgaagaa ctttactggc aagagatca agtacatgct ctggctctcc     180
gcggacttga agttccgcat taagcagaag ggggaatacc ttccgctgct tcaaggaaag     240
agcctcggca tgatctttga agcgctcca accaggaccc gcctttctac tgaaactggg     300
ttcgcgctgc tcggtggcca ccctgcttc ctgacgaccc aggacatcca cctcggagtg     360
aacgaatccc tcaccgatac cgcccgggtg ttatcgagca tggcagatgc cgtgctggcc     420
agggtgtaca acagtccga tctggacact ctggccaagg aggcgtcaat tcccatcatc     480
aacggcctga gcgacctgta ccacccaatc caaatcctgg ctgactacct gaccctgcaa     540
gagcactaca gcagcctgaa gggtctgacc ctgtcatgga ttggcgatgg aaacaatatt     600
ctgcactcca tcatgatgtc cgccgcgaag ttcggaatgc atctgcaagc cgccacgcca     660
aaaggatacg aaccggatgc gtccgtgacg aagttggcgg aacagtacgc gaaggagaac     720
ggaaccaagc ttctgctgac taacgacccc ctcgaggctg cgcatggggg caacgtgctg     780
attaccgaca cctggatctc catggggcag gaggaagaga agaagaagag actgcaggca     840
ttccaggggt accaggtcac catgaaaacc gcaaaagtgg cagcttcgga ctggactttc     900
ctgcattgcc tgccgaggaa gccggaggaa gtcgacgacg aagtgttcta ctcgcctcgg     960
tccctggtgt tcccgaggc cgaaaaccgg aagtggacca tcatggccgt gatggtgtcc    1020
ttgctgactg actatagccc gcagctgcag aagcctaagt tctag                   1065
```

<210> SEQ ID NO 142
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 142

```
atgctttca acctgagaat cctcttgaac aatgctgctt ttcggaatgg ccacaacttt      60
atggttcgga acttccgttg cggccagcct ttacaaaaca aggtccagct gaagggccgg     120
gatttgctca cactgaagaa ctttactgga aagagatca agtacatgct gtggctgtcg     180
gccgacctga agttcaggat caagcagaag ggagaatacc ttccgctgct tcaaggaaag     240
agcctcggca tgatctttga agcgctcca accaggaccc gcctttctac tgaaactggg     300
ttcgcgctgc tcggtggcca ccctgcttc ctgacgaccc aggacatcca cctcggagtg     360
aacgaatccc tcaccgatac cgcccgggtg ttatcgagca tggcagatgc cgtgctggcc     420
agggtgtaca acagtccga tctcgatacc ttggcaaagg aggcttccat tcccatcatc     480
aacggcctga gcgacctgta ccacccaatc caaatcctgg ctgactacct gaccctgcaa     540
gagcactaca gcagcctgaa gggtctgacc ctgtcatgga ttggcgatgg aaacaatatt     600
ctgcactcca tcatgatgtc cgccgcgaag ttcggaatgc atctgcaagc cgccactcca     660
aaaggatacg aaccggatgc gtccgtgacc aagttggcgg aacagtacgc gaaggagaac     720
```

| | |
|---|---|
| ggaaccaagc ttctgctgac taacgacccc ctcgaggctg cgcatggggg caacgtgctg | 780 |
| attaccgaca cctggatctc catggggcag gaggaagaga agaagaagag actgcaggca | 840 |
| ttccaggggt accaggtcac catgaaaacc gcaaaagtgg cagcttcgga ctggactttc | 900 |
| ctgcattgcc tgccgaggaa gccggaggaa gtcgacgacg aagtgttcta ctcgcctcgg | 960 |
| tccctggtgt tccccgaggc cgaaaaccgg aagtggacca tcatggccgt gatggtgtcc | 1020 |
| ttgctgactg actatagccc gcagctgcag aagcctaagt tctag | 1065 |

<210> SEQ ID NO 143
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 143

| | |
|---|---|
| atgcttttca acctgagaat cctcttgaac aatgctgctt ttcggaatgg ccacaacttt | 60 |
| atggttcgga acttccgttg cggccagcct ttacaaaaca aggtccagct gaagggccgg | 120 |
| gatttgctca cactaaagaa ctttactgga gaagagatca agtacatgct atggctgtcg | 180 |
| gccgacctga agttccgtat caagcagaag ggagaatacc ttccgctgct tcaaggaaag | 240 |
| agcctcggca tgatctttga gaagcgctca accaggaccc gcctttctac tgaaactggg | 300 |
| ttcgcgctgc tcggtggcca ccctgcttc ctgacgaccc aggacatcca cctcggagtg | 360 |
| aacgaatccc tcaccgatac cgcccgggtg ttatcgagca tggcagatgc cgtgctggcc | 420 |
| agggtgtaca acagtccga tctcgatacc ttggcaaagg aggcttccat tcccatcatc | 480 |
| aacggcctga gcgacctgta ccacccaatc caaatcctgg ctgactacct gaccctgcaa | 540 |
| gagcactaca gcagctgaa gggtctgacc ctgtcatgga ttggcgatgg aaacaatatt | 600 |
| ctgcactcca tcatgatgtc cgccgcgaag ttcggaatgc atctgcaagc cgccactcca | 660 |
| aaaggatacg aaccggatgc atccgtgacc aagttggcgg aacagtacgc gaaggagaac | 720 |
| ggaaccaagc tcctgctgac taacgacccg ctcgaggctg cgcatggggg taacgtgctg | 780 |
| attacggaca cctggatctc catggggcag gaggaagaga agaagaagag actgcaggca | 840 |
| ttccaggggt accaggtcac catgaaaacc gcaaaagtgg cagcttcgga ctggactttc | 900 |
| ctgcattgcc tgccgaggaa gccggaggaa gtcgacgacg aagtgttcta ctcgcctcgg | 960 |
| tccctggtgt tccccgaggc cgaaaaccgg aagtggacca tcatggccgt gatggtgtcc | 1020 |
| ttgctgactg actatagccc gcagctgcag aagcctaagt tctag | 1065 |

<210> SEQ ID NO 144
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 144

| | |
|---|---|
| atgcttttca acctgagaat cctcttgaac aatgctgctt ttcggaatgg ccacaacttt | 60 |
| atggttcgga acttccgttg cggccagcct ttacaaaaca aggtccagct gaagggccgg | 120 |
| gatttgctca cactaaagaa ctttactgga gaagagatca agtacatgct atggctgtcg | 180 |
| gccgacctga agttccgtat caagcagaag ggagaatacc ttccgctgct tcaaggaaag | 240 |
| agcctcggca tgatctttga gaagcgctca accaggaccc gcctttctac tgaaactggg | 300 |
| ttcgcgctgc tcggtggcca ccctgcttc ctgacgaccc aggacatcca cctcggagtg | 360 |

```
aacgaatccc tcaccgatac cgcccgggtg ttatcgagca tggcagatgc cgtgctggcc      420
agggtgtaca acagtccga tctcgatacc ttggcaaagg aggcttccat tcccatcatc      480
aacggcctga gcgacctgta ccacccaatc caaatcctgg ctgactacct gaccctgcaa      540
gagcactaca gcagcctgaa gggtctgacc ctgtcatgga ttggcgatgg aaacaatatt      600
ctgcactcca tcatgatgtc cgccgcgaag ttcggaatgc atctgcaagc cgccactcca      660
aaaggatacg aaccggatgc gtccgtgacc aagttggcgg aacagtacgc gaaggagaac      720
ggaaccaagc ttctgctgac taacgacccc tcgaggctg cgcatggggg caacgtgctg       780
attaccgaca cctggatctc catggggcag gaggaagaga agaagaagag actgcaggca      840
ttccaggggt accaggtcac catgaaaacc gcaaagtgg cagcttcgga ctggactttc       900
ctgcattgcc tgccgaggaa gccggaggaa gtcgacgacg aagtgttcta ctcgcctcgg      960
tccctggtgt tccccgaggc cgaaaaccgg aagtggacca tcatggccgt gatggtgtcc     1020
ttgctgactg actatagccc gcagctgcag aagcctaagt tctag                      1065

<210> SEQ ID NO 145
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 145
atgctgttca acctgcgaat cctgctgaac aacgccgctt tcggaacgg gcacaacttt        60 atggtgagga actttcgctg cggacagccc ctccagaata aggtccagct gaagggcagg      120
gacctgctga ccctgaaaaa tttcacaggg gaggaaatca gtatatgct gtggctgtca       180 gctgatctga gttccggat caagcagaag ggcgaatatc tgcctctgct ccagggcaaa      240
agcctgggga tgatcttcga aaagcgcagt actcggacca gactgtcaac cgagactgga      300
ttcgctctgc tgggaggaca ccctttgtttt ctgaccactc aggacattca cctgggagtg    360
aacgagtccc tgaccgacac tgctcgcgtc ctgagctcta tggccgacgc tgtgctggct     420
cgagtctaca acagtccga cctggatacc ctggccaagg aagcttctat cccaattatt      480
aacggcctgt cagacctgta tcaccccatc cagattctgg ccgattacct gaccctccag     540
gagcactatt ctagtctgaa agggctgaca ctgagttgga ttggggacgg aaacaatatc     600
ctgcactcta ttatgatgtc agccgccaag tttggaatgc acctccaggc tgcaaccccca    660 aaaggctacg aacccgatgc ctcagtgaca aagctggctg aacagtacgc caagagaaac    720
ggcactaagc tgctgctgac caacgaccct ctggaggccg ctcacggagg caacgtgctg     780
atcaccgata cctggattag tatgggacag gaggaagaga agaagaagcg gctccaggcc    840
ttccagggct accaggtgac aatgaaaacc gctaaggtcg cagccagcga ttggaccttt    900
ctgcactgcc tgcccagaaa gcccgaagag gtggacgacg aggtcttcta ctctcccaga    960
agcctggtgt ttcccgaagc tgagaatagg aagtggacaa ttatggcagt gatggtcagc   1020
ctgctgactg attattcacc tcagctccag aaaccaaagt tctga                      1065

<210> SEQ ID NO 146
<211> LENGTH: 1065
<212> TYPE: DNA
<213> ORGANISM: Artificial sequence
<220> FEATURE:
<223> OTHER INFORMATION: Synthetic polynucleotide
```

<400> SEQUENCE: 146

```
atgctgttca acctgcgcat cctgctgaac aacgccgcct tccgcaacgg ccacaacttc      60
atggtgcgca acttccgctg cggccagccc ctgcagaaca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga gaagcgcagc acccgcaccc gcctgagcac cgagacaggc     300
ctggccctgc tgggcggcca ccctgcttc ctgaccaccc aggacatcca cctgggcgtg      360
aacgagagcc tgaccgacac cgcccgcgtg ctgagcagca tggccgacgc cgtgctggcc     420
cgcgtgtaca agcagagcga cctggacacc ctggccaagg aggccagcat ccccatcatc     480
aacggcctga cgacctgta ccaccccatc cagatcctgg ccgactacct gaccctgcag      540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
atcaccgaca cctggatcag catgggccag gaggaggaga agaagaagcg cctgcaggcc     840
ttccagggct accaggtgac catgaagacc gccaaggtgg ccgccagcga ctggaccttc     900
ctgcactgcc tgccccgcaa gcccgaggag gtggacgacg aggtgttcta cagccccgc      960
agcctggtgt cccccgaggc cgagaaccgc aagtggacca tcatggccgt gatggtgagc    1020
ctgctgaccg actacagccc ccagctgcag aagcccaagt tctga                    1065
```

<210> SEQ ID NO 147
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 147

```
atgctgttca acctgcgaat cctgctgaac aacgccgcct tcggaacgg gcacaacttt       60
atggtgagga actttcgctg cggacagccc ctccagaata aggtccagct gaagggcagg     120
gacctgctga ccctgaaaaa tttcacaggg gaggaaatca agtatatgct gtggctgtca     180
gctgatctga agttccggat caagcagaag ggcgaatatc tgcctctgct ccagggcaaa     240
agcctgggga tgatcttcga aaagcgcagt actcggacca gactgtcaac cgagactgga     300
ttcgctctgc tgggaggaca cccttgtttt ctgaccactc aggacattca cctgggagtg     360
aacgagtccc tgaccgacac tgctcgcgtc ctgagctcta tggccgacgc tgtgctagct     420
cgagtctaca acagtccga cctggatacc ctggccaagg aagcttctat cccaattatt      480
aacggcctgt cagacctgta tcaccccatc cagattctgg ccgattacct gaccctccag     540
gagcactatt ctagtctgaa agggctgaca ctgagttgga ttggggacgg aaacaatatc     600
ctgcactcta ttatgatgtc agccgccaag tttggaatgc acctccaggc tgcaaccccca    660
aaaggctacg aacccgatgc ctcagtgaca aagctggctg aacagtacgc caaagagaac     720
ggcactaagc tgctgctgac caacgaccct ctggaggccg ctcacggagg caacgtgctg     780
atcaccgata cctggattag tatgggacag gaggaagaga agaagaagcg gctccaggcc     840
ttccagggct accaggtgac aatgaaaacc gctaaggtcg cagccagcga ttggaccttt     900
ctgcactgcc tgcccagaaa gcccgaagag gtggacgacg aggtcttcta ctctcccaga     960
```

```
agcctggtgt ttcccgaagc tgagaatagg aagtggacaa ttatggcagt gatggtcagc    1020
ctgctgactg attattcacc tcagctccag aaaccaaagt tctga                    1065

<210> SEQ ID NO 148
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 148
atgctgttca acctgcgaat cctgctgaac aatgccgctt tcggaacgg gcacaatttc      60 atggtgagga actttcgctg cggacagccc ctccagaaca aggtccagct gaagggcagg    120
gacctgctga ccctgaaaaa tttcacaggg gaggaaatca agtacatgct gtggctgtca    180
gccgatctga agttccggat caagcagaag ggcgaatatc tgcctctgct ccagggcaaa    240
agcctgggga tgatcttcga aaagcgcagt actcggacca gactgtcaac agagactgga    300
ttcgcactgc tgggaggaca cccatgtttt ctgaccacac aggacattca tctgggagtg    360
aacgagtccc tgaccgacac agcacgcgtc ctgagctcca tggctgatgc agtgctggct    420
cgagtctaca acagtctga cctggatacc ctggccaagg aagcttctat cccaatcatt    480
aatggcctga gtgacctgta tcaccccatc cagattctgg ccgattacct gaccctccag    540
gagcattatt ctagtctgaa agggctgaca ctgagctgga ttggggacgg aaacaatatc    600
ctgcactcca ttatgatgag cgccgccaag tttggaatgc acctccaggc tgcaaccccca   660 aaaggctacg aacccgatgc ctccgtgaca aagctggcag aacagtatgc caaagagaac    720
ggcactaagc tgctgctgac caatgaccct ctggaggccg ctcacggagg caacgtgctg    780
atcactgata cctggattag tatgggacag gaggaagaga agaagaagcg gctccaggcc    840
ttccagggct accaggtgac aatgaaaact gctaaggtcg cagccagcga ctggaccttt    900
ctgcattgcc tgcccagaaa gcctgaagag gtggacgatg aggtcttcta ctcacccaga    960
agcctggtgt ttcctgaagc tgagaatagg aagtggacaa tcatggcagt gatggtcagc    1020
ctgctgactg attattcccc tcagctccag aaaccaaagt tctga                    1065

<210> SEQ ID NO 149
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 149
atgcttttca accttcgcat tctcctcaac aacgccgcgt ttagaaacgg acacaacttc     60
atggtccgca acttccgctg cggacagccg ctgcagaaca aggtccagct caagggtcgg    120
gatctcctga cgctgaagaa ctttaccggc gaagagatta gtacatgct gtggctgtcc    180 gccgacctta agttccggat caagcagaag ggcgaatacc ttcccctgct gcaaggaaag    240
tccctgggca tgatcttcga gaagcgcagt accagaacca gactctccac tgaaaccggg    300
ttcgcgctgc ttggcggcca cccgtgtttc ctcactacgc aagacatcca tcttggcgtg    360
aacgagtccc ttaccgacac cgccagggtg ctgtcaagca tggccgacgc cgtccttgcg    420
cgcgtgtaca gcagtcaga ccttgatact ctggccaagg aagcctccat ccctattatc    480
aacggcctat ccgaccttta ccaccccgatc cagatcctcg ctgactacct gaccctgcaa    540
```

```
gaacactaca gcagcctcaa gggactgact ctgtcctgga tcggcgacgg gaacaacatc    600
ctgcactcaa tcatgatgag cgcagccaag ttcggcatgc atctccaagc cgctacaccc    660
aagggttatg aaccggacgc ctctgtgacc aagttggcag aacagtacgc caaggagaac    720
ggtactaagc tccttttaac caacgacccc ctcgaagcag cccatggcgg gaatgtgctc    780
attaccgata cctggatttc gatgggccag gaggaggaga agaagaagcg gctgcaggcg    840
ttccagggct accaggtcac catgaaaact gccaaagtgg ccgcctcgga ttggaccttt    900
ctccactgcc tgcctcggaa gcctgaggag gtggacgacg aagtgttcta ctccccacgg    960
tccctcgtgt tccccgaggc cgaaaatagg aagtggacca tcatggccgt gatggtgtcc    1020
ctcttgaccg attacagccc gcagcttcag aagcctaaat tctag                   1065

<210> SEQ ID NO 150
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 150
atgcttttca atcttcgcat cctgttgaac aacgccgcct tccgcaatgg tcacaacttc     60
atggtccgga acttcagatg tggacagcct ctccaaaaca aggtccagct gaagggaagg    120
gacctcttaa ccctcaaaaa ctttactgga gaggagatca agtacatgct gtggcttagc    180
gccgacctta agttccggat caagcagaag ggagagtacc tcccgctgct gcaaggaaag    240
agtcttggaa tgatcttcga gaagcggtcc accagaactc gcctctccac tgaaaccgga    300
ttcgcactcc tgggtggaca cccgtgcttt ctgaccaccc aagacatcca cctcggagtg    360
aacgagagcc tcacggacac cgcgagagtg ctgtcatcca tggccgacgc cgtgcttgca    420
cgggtctaca gcagtccga tctggacact cttgccaagg aagcctccat tcctatcatt    480
aacggtctgt cggatctgta ccacccgatt cagatccttg cggactacct cacacttcaa    540
gaacactatt caagcctaaa gggtctgacc ctgtcctgga tcggagatgg aaacaacatt    600
ctccattcca tcatgatgag cgctgccaag ttcggaatgc atctccaagc agcgactcct    660
aagggttacg agccggacgc ctcagtgact aagctggccg agcagtacgc caaggagaac    720
ggtaccaaac tgttgcttac taacgacccg cttgaagcgg cccatggagg aaacgtgctg    780
attaccgaca cctggatttc gatgggacag gaagaggaga agaagaagcg gctccaggcg    840
ttccagggat accaggtcac catgaaaacg gccaaagtgg ccgctagcga ttggaccttt    900
ctgcactgcc tcccgcgcaa gcctgaagaa gtggacgacg aagtgttcta ctcccctcgc    960
tctcttgtgt tcccggaagc cgaaaacagg aagtggacca tcatggccgt gatggtgtcc    1020
ctcctgaccg attacagccc gcagctgcag aagcctaagt tctag                   1065

<210> SEQ ID NO 151
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 151
atgcttttca atctccgcat cctcctcaac aacgccgcgt ttagaaacgg ccacaacttc     60
atggtccgga acttcagatg tggccagccg cttcagaaca aggtccagct caagggccgg    120
gatcttctga ccctgaagaa ctttactggc gaagaaatca agtacatgct ctggctctcc    180
```

```
gccgacttga agttccgcat taagcagaag ggggaatacc ttccgctgct gcaaggaaag      240
tcgctcggca tgatctttga gaagcgctca acccgcacca ggctgtccac tgaaaccggg      300
ttcgcgctgc ttggtggcca ccctgcttc ctgaccaccc aagacattca cctcggagtg       360
aacgaatcgc tcactgatac tgcccggtg ctgtcgtcga tggccgatgc agtgctggcc       420
agggtgtaca acagtccga tctggacact ctggccaagg aggcgtccat ccctattatc       480
aacggccttt ccgacctcta ccacccgatt cagatccttg ccgattacct caccctgcaa      540
gaacactact cgtcactgaa gggtctgacc ttgtcctgga tcggcgacgg caacaacatc      600
ctccattcca ttatgatgtc cgccgccaaa ttcggcatgc atcttcaagc cgcaacccct      660
aagggttacg agccggacgc ttccgtgacc aagctcgccg agcagtacgc taaggagaac      720
ggaaccaagc ttctgctgac taacgacccc ctagaggcag cccacggggg caacgtgctt      780
attactgaca cctggatctc catgggacag gaagaagaga agaagaagcg gttacaggcg      840
ttccagggct atcaggtcac catgaaaacc gccaaggtcg ctgcctcgga ctggaccttc      900
ctgcattgcc tgcctcgcaa gcccgaagaa gtggacgacg aggtgttcta ctcgccacgg      960
tcccttgtgt tccctgaggc cgagaataga aagtggacca ttatggccgt gatggtgtcc     1020
cttctcaccg actactcgcc gcaactgcag aaacccaagt tctag                     1065

<210> SEQ ID NO 152
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 152 atgctttca atcttcgcat cctcctcaac aacgccgcct tccggaacgg tcacaacttc        60
atggtccgga acttccgctg cggccagccg ctccaaaaca aagtgcagct taagggccgc      120
gatctcctga ccctgaagaa cttcaccgga gaggaaatca agtacatgct gtggctctcg      180
gcggacctga gtttaggat taagcagaag ggggagtatc tgccgctgct ccaagggaag       240
tcccttggca tgatcttcga aaagaggtcc acccggactc ggctcagcac cgaaacaggt      300
tttgcacttc tggggggcca cccgtgcttc ctgacgaccc aggacatcca tctgggtgtc      360
aacgagagtt tgaccgacac tgccagagtg ctgtcatcca tggcggacgc ggtgctcgcg      420
agagtgtaca agcagtccga tcttgacacc ctggcaaaag aggcttcaat cccgatcatt      480
aacggactct cggatctgta ccaccctatc caaatcttgg ccgactacct gaccctgcaa      540
gaacactaca gctccctgaa gggcctgact ctttcctgga ttggcgatgg aaacaacatt      600
ctccattcta ttatgatgtc cgccgccaag ttcggcatgc accttcaagc cgccaccccg      660
aagggctacg aacctgacgc ctccgtgact aagctagccg aacagtacgc taaggagaac      720
ggcactaagc ttctccttac caacgatccg ctggaggcgg cccatggcgg aaatgtgctt      780
atcaccgaca cctggattag catggggcag gaagaagaga agaagaaacg gctccaggca      840
ttccagggct accaggtcac catgaaaact gccaaggtcg ccgctagcga ctggaccttc      900
ctccactgtc tgcctcgcaa gcctgaagaa gtggacgacg aggtgttcta ctccccgcgc      960
tccctcgtgt ttcctgaggc cgagaacaga aagtggacca tcatggccgt gatggtgtca     1020
ttacttacgg actacagccc gcagctgcag aagccgaagt tctag                     1065

<210> SEQ ID NO 153
```

```
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 153
atgcttttta acttgagaat ccttctgaac aacgccgctt ccgcaacgg tcataacttc      60
atggtccgga acttcagatg tggccagccc ctccaaaaca aagtgcagct gaagggccgg     120
gaccttctta cgctgaagaa tttcaccggc gaagaaatca agtacatgct ctggctgtcc     180
gccgatctta agtccgcat taagcagaag ggggaatacc tcccgctgct gcaagggaag      240
tcgctgggca tgattttga aagcggtca actcgcaccc gcctgtccac tgaaactgga       300
ttcgcactgc tcggtggcca tccctgcttc ctgaccaccc aagacatcca cctcggcgtg     360
aacgagtccc tgactgacac cgcccgggtc ttatcctcga tggccgatgc tgtgcttgcg     420
agggtgtaca agcagtccga cctcgacaca ctcgcgaagg aggcctccat ccccatcatc    480
aacggcctgt ccgaccttta ccacccaatt cagatcctcg ccgattacct gaccctgcaa    540
gagcactact cgtcgctcaa ggggcttacc ctctcgtgga ttggcgacgg caacaacatc    600
cttcactcca tcatgatgtc ggcagcgaag ttcggcatgc atctgcaagc cgccacgcct    660
aagggttatg aaccggatgc ctcagtgacc aagctcgccg aacagtacgc gaaagagaat    720
ggaaccaagc tacttctgac caacgacccc ctggaggccg ctcacggcgg caacgtcctc    780
attaccgata cttggatttc gatgggacag gaagaggaaa agaagaagag actgcaggcg    840
ttccagggat accaggtcac catgaaaact gccaaagtgg cagcctccga ctggaccttc    900
cttcactgcc tgccgaggaa gcctgaagag gtggacgacg aggtgttcta ctccccgcgc    960
tccttggtgt ttcctgaggc cgaaaaccgg aagtggacta tcatggccgt gatggtgtcc   1020
ctcctcaccg actactcgcc gcaactgcag aagcctaagt tctag                   1065

<210> SEQ ID NO 154
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 154
atgttattca accttagaat tctccttaac aacgccgcct tccggaatgg gcataacttt      60
atggtccgca atttccgctg tggacagcct ctgcaaaaca aggtccagct caagggccgg     120
gatctgctga ctctccaagaa cttcactggg gaagaaatca agtacatgct ctggctgagc    180
gccgacctca gtccgcat caagcagaag ggagagtacc tcccgctgct ccaagggaag       240
tccctgggca tgatcttcga aagagatcc accccgcacca gactttccac tgagactggc     300
ttcgccttgc tgggaggcca cccatgcttc ctgacgaccc aggacattca ccttggcgtg    360
aacgagtccc tgactgacac cgcaagggtg ttgtcctcga tggccgacgc cgtgcttgcc    420
cgggtgtaca agcagagcga tcttgacacc ctggctaagg aagcttccat tcccatcatc    480
aacggtctga cgaccgtgta ccacccgatt cagatcctgg cggactacct aaccctgcaa    540
gagcactata gctccctgaa gggcctcaca ctttcatgga tcggcgacgg caacaacatc    600
ctgcactcta ttatgatgag cgctgccaaa ttcggcatgc acctccaagc cgccacgcct    660
aaaggctacg agcccgacgc ctcggtgacc aagcttgcgg agcagtacgc gaaggaaaac    720
ggcaccaagc tgcttctcac caacgatcct ctggaagcgg cccatggtgg caacgtgctc    780
```

| | |
|---|---|
| attaccgaca cttggatctc catgggacag gaggaggaaa agaagaagcg gctccaggcg | 840 |
| tttcagggtt accaggtcac catgaaaacc gccaaggtcg cagcctccga ctggaccttc | 900 |
| cttcattgcc ttccgcgcaa gcccgaagaa gtggacgatg aagtgtttta ctcacctcgg | 960 |
| tcactcgtgt tcccggaagc agagaacagg aaatggacca ttatggccgt gatggtgtcc | 1020 |
| ctgctcaccg attacagtcc gcaactgcag aagcccaagt tctag | 1065 |

<210> SEQ ID NO 155
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 155

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct gaagggccgg | 120 |
| gatcttctga ccctgaagaa ctttactggc gaagagatca agtacatgct ctggctctcc | 180 |
| gcggacttga agttccgcat taagcagaag ggggaatacc ttccgctgct tcaaggaaag | 240 |
| agcctcggca tgatctttga gaagcgctca accaggaccc gcctttctac tgaaactggg | 300 |
| ttcgcgctgc tcggtggcca ccctgcttc ctgacgaccc aggacatcca cctcggagtg | 360 |
| aacgaatccc tcaccgatac cgcccgggtg ttatcgagca tggcagatgc cgtgctggcc | 420 |
| agggtgtaca acagtccga tctggacact ctggccaagg aggcgtcaat tcctattatc | 480 |
| aacggcctta gtgacctcta ccatccgatt caaatcctgg ccgattacct caccctgcaa | 540 |
| gaacactaca gctccctgaa gggtctgaca ttgtcctgga tcggcgacgg caacaacatt | 600 |
| ctccattcca tcatgatgtc cgccgcaaaa ttcggcatgc atcttcaagc cgccacgcct | 660 |
| aagggttacg aacccgacgc ttccgtgact aagctcgccg agcagtacgc taaggagaac | 720 |
| ggaaccaagc tgctgctgac taacgacccg ctagaagcag cccacggggg caacgtgctt | 780 |
| attactgaca cctggatctc catgggccag gaggaagaga aaagaagcg gctgcaggcg | 840 |
| ttccagggat atcaggtcac catgaaaacc gccaaggtcg ctgcctccga ctggaccttc | 900 |
| ctgcactgcc tgcctcgcaa gcctgaagaa gtggacgacg aggtgttcta ctcgccacgg | 960 |
| agcctcgtgt tccccgaggc cgagaataga agtggacca tcatggccgt gatggtgtca | 1020 |
| cttctcaccg actacagccc gcagcttcag aagcccaagt tctag | 1065 |

<210> SEQ ID NO 156
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 156

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct taagggccgg | 120 |
| gatctcctca cccttaaaaa cttcaccggc gaagagatca agtacatgct ctggctctcc | 180 |
| gcggacctta agttccgcat taagcagaag ggggaatacc ttccgctgct tcaaggaaag | 240 |
| agcctcggca tgatctttga gaagcgctca accaggacca ggctttctac tgaaactggg | 300 |
| ttcgcgcttc tcggcggtca tccctgcttc ctcacgaccc aagacatcca cctcggagtg | 360 |

```
aacgaatccc tcacggatac tgcccgcgtg ctttcgagca tggcagacgc cgtgctcgcc      420
cgggtgtaca acagtccga tctcgacact ctcgccaagg aggcgtcaat tcctattatc      480
aacggtctta gtgaccttta ccacccgatc cagatcctcg ccgattacct cacactccaa      540
gaacactaca gctcccttaa gggtcttacc ctctcctgga tcggcgacgg caacaacatt      600
ctccactcca tcatgatgtc cgccgcaaag ttcggcatgc atcttcaagc cgccaccccg      660
aagggctacg agcctgatgc ttccgtgact aagctcgccg agcagtacgc taaggagaac      720
ggaaccaagc ttcttctcac taacgaccca ctcgaagcag cccatggggg caacgtgctt      780
atcactgaca cctggatctc catgggccag gaagaagaga agaagaagcg gctccaggcg      840
ttccagggat atcaggtcac catgaaaacc gccaaggtcg ctgcctccga ctggaccttt      900
ctccactgcc tccctcgcaa acctgaagaa gtggacgacg aggtgttcta ctcgccccgg      960
agcctcgtgt tccccgaggc cgagaataga agtggacca ttatggccgt gatggtgtca     1020
ctcctcaccg actacagccc gcagcttcag aagcccaagt tctag                    1065
```

<210> SEQ ID NO 157
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 157

```
atgcttttca atctccgcat cctccttaac aacgccgcgt ttagaaacgg acataacttc       60
atggtccgga acttcagatg tggacagccg cttcaaaaca aggtccagct gaagggtcgg      120
gatcttctga ccctgaagaa cttaccgga gaagagatca agtacatgct ctggctctcc      180
gcggacttga agttccgcat taagcagaag ggagaatacc tcccgctgct tcaaggaaag      240
agcctcggaa tgatttttga gaagcgctca accaggaccc gcctttctac tgaaactgga      300
ttcgcgctgc tgggtggaca ccctgcttc ctgacgaccc aggacatcca cctcggagtg      360
aacgaatccc tcactgatac cgcccgggtg ttatcgagca tggcagatgc cgtgctggcc      420
agggtgtaca acagtccga tctggacact ctggccaagg aggcgtcaat tcctatcatc      480
aacggactta gtgacctcta ccatccgatt caaatcctgg ccgactacct caccctgcaa      540
gaacactaca gctcccttaa gggtctgaca ttgtcctgga tcggagatgg aaacaacatt      600
ctccactcca tcatgatgtc cgccgcaaaa ttcggaatgc atcttcaagc cgccacgcct      660
aagggttacg aacccgacgc ttccgtgact aagctcgccg agcagtacgc taaggagaac      720
ggtaccaagc ttctcctgac caacgaccca ctagaagcag cccacggtgg aaacgtgctt      780
attactgaca cttggatctc catgggacag gaggaagaga aaagaagcg gctgcaggcg      840 ttccagggat atcaggtcac catgaaaacc gccaaggtcg ctgcctccga ctggaccttc      900
ctgcactgcc tgcctcgcaa gcctgaagaa gtggacgacg aggtgttcta ctcgccgcgg      960
agcctcgtgt tccccgaggc cgagaataga agtggacca tcatggccgt gatggtgtca     1020
ctgctcaccg actacagccc gcagcttcag aagcccaagt tctag                    1065
```

<210> SEQ ID NO 158
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 158

```
atgcttttca acctccgcat tctcctcaac aacgctgcct tccggaatgg acataacttc      60
atggtccgga acttcagatg cggacagccg cttcagaaca aggtccagct taagggaga     120
gatctcctta ccctcaaaaa cttcactggc gaagaaatca agtacatgct ctggcttagt    180
gcggatctca agttccgcat caagcagaag ggagaatacc tcccgctcct tcaaggaaag    240
agcctcggca tgattttga gaagaggtcc accagaactc gcctttcaac cgagactggg     300
ttcgccctgc ttggcggtca ccctgcttc ctcactaccc aagacatcca cctcggcgtg     360
aacgagagcc ttaccgacac cgcccgcgtg ctctcctcaa tggccgacgc tgtgctcgcc    420
cgggtgtaca agcagtccga ccttgatact ctcgccaagg aggcctccat cccaattatc    480
aacgggctct ctgatctcta ccaccctatc caaatcctcg cggactacct caccctccaa    540
gagcactata gctcgctcaa gggcctcacc ctttcctgga ttggcgacgg caacaacatt    600
cttcactcga tcatgatgtc cgccgccaag ttcggcatgc atctccaagc cgcgaccccc    660
aagggctacg agcctgacgc atccgtgacc aagctcgccg agcagtacgc gaaggaaaat    720
ggcaccaagc ttcttctcac caacgacccc cttgaggccg ctcatggcgg caacgtgctc    780
atcactgaca cttggatcag catgggccag gaggaggaaa agaagaagcg ccttcaggca    840
ttccaggggtt accaggtcac catgaaaaac gccaaagtgg ccgcctccga ctggaccttt    900
cttcactgtc tcccgcggaa gcctgaagaa gtggatgacg aagtgtttta ctcccctcgg    960
tcactcgtgt tcccggaagc agaaaacagg aagtggacca ttatggcggt catggtgtcc   1020
ctcctcaccg actacagccc gcagcttcag aaacccaagt tctag                   1065
```

<210> SEQ ID NO 159
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 159

```
atgcttttca atctccgcat cctccttaac aacgcagcgt ttagaaacgg tcacaacttc      60
atggtccgga acttccgctg tggacagccg cttcaaaaca aggtccagct gaagggtcgg    120
gaccttctga ccctgaagaa ctttactgga gaagagatca agtacatgct ttggctgtcc    180
gcggacttga agttccgcat taagcagaag ggagaatacc ttccgctgct ccaaggaaag    240
agcctgggaa tgatctttga gaagcgctca accaggaccc gcctttctac tgaaactgga    300
ttcgcgctgc tggtggtca cccttgcttc ctgacgaccc aggacattca cctcggagtg    360
aacgagtccc tcactgatac cgccagagtg ttatcgagca tggcagatgc cgtgctggct    420
agggtgtaca acagtccga tctggacacc ctggccaagg aggcatcaat tcctattatc    480
aacggactta gtgacctcta ccatccgatt caaatcctgg ccgattacct caccctgcaa    540
gaacactaca gctccctgaa gggtctgaca ttgtcctgga tcggagatgg aaacaacatt    600
ctccattcca tcatgatgtc cgcggccaag ttcggaatgc atctccaagc cgccacgccg    660
aaaggatacg agccggacgc ttccgtgact aagctcgccg agcagtacgc taaggagaac    720
ggaaccaagc ttctgctgac taacgacccg ctagaagccg cccacggtgg aaacgtgctt    780
attactgaca cctggatctc catgggacag gaagaagaga aaaagaagcg gctgcaggcg    840
ttccagggat atcaggtcac catgaaaacc gccaaggtcg ccgcctccga ctggaccttc    900
```

| | |
|---|---|
| cttcactgcc tgcctcggaa gcctgaagaa gtggacgacg aggtgttcta ctcgccgcgg | 960 |
| agcctcgtgt tccctgaggc cgagaataga aagtggacca tcatggccgt gatggtgtca | 1020 |
| ctcctcaccg actacagccc gcagcttcag aagcctaagt tctag | 1065 |

```
<210> SEQ ID NO 160
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 160
```

| | |
|---|---|
| atgcttttca atctccgcat tctcctcaac aacgcagcct ttagaaacgg ccacaacttc | 60 |
| atggtccgga acttcagatg tggccagccg cttcagaaca aggtccagct caagggccgg | 120 |
| gacctcctca ccctcaaaaa ctttaccggc gaagagatca agtacatgct ctggctttcg | 180 |
| gccgaccttc agttccgcat caagcagaag ggggaatacc ttccgctgct tcaaggaaag | 240 |
| tccctcggca tgatctttga aaagcgctcg accaggaccc gcctttccac tgaaaccggg | 300 |
| ttcgcgcttc tcggtggcca cccctgcttc ctcaccaccc aagacattca cctcggagtg | 360 |
| aacgaatccc ttaccgatac cgcaagagtg cttcgtcga tggccgatgc cgtgcttgcg | 420 |
| cgggtgtaca agcagtcaga tctcgacact ctcgccaagg aggcgtccat tcctattatc | 480 |
| aacggccttt ccgaccttta ccacccgatt cagatcctcg ccgattacct caccctgcaa | 540 |
| gagcactact cgtcactcaa gggtcttacc ctctcctgga tcggcgacgg aaacaacatc | 600 |
| ctccattcga tcatgatgtc cgccgccaaa ttcggcatgc acctccaagc cgcgacccca | 660 |
| aagggttacg agcccgacgc ttccgtgacc aagctcgccg aacagtacgc taaggaaaac | 720 |
| ggcaccaagc tcctcctcac taacgaccct ctcgaagcag cccatggggg caacgtgctc | 780 |
| attactgaca cttggatctc gatgggccag gaagaggaga aaagaagcg gcttcaggcg | 840 |
| ttccagggat atcaggtcac catgaaaacc gccaaggtcg ctgcctcgga ctggaccttc | 900 |
| cttcactgcc ttccgcgcaa gcctgaagag gtggacgatg aggtgttcta ctccccacgg | 960 |
| tcccttgtgt tccccgaggc cgagaatagg aagtggacca tcatggccgt gatggtgtcg | 1020 |
| ctcctcactg actactcccc gcaacttcag aagcctaagt tctag | 1065 |

```
<210> SEQ ID NO 161
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 161
```

| | |
|---|---|
| atgctgttta atctgagaat acttctaaac aacgccgcct tccggaatgg ccataacttt | 60 |
| atggttcgga atttccgctg cggccagccg ctgcagaaca aggtccagct gaagggaaga | 120 |
| gacttgctga ccctcaagaa cttcaccgga gaagaaatca agtatatgct gtggctgtcc | 180 |
| gccgacctga aattccgcat caagcagaag ggcgaatatc tgccgctgtt gcaagggaag | 240 |
| tccctgggga tgatcttcga agaggtcc accagaacac ggctttcaac cgaaaccggg | 300 |
| tttgcactgc tgggtggaca cccctgtttt ctgaccactc aagatatcca cctgggcgtg | 360 |
| aacgagtccc ttaccgacac tgctagggtg ttgtccagca tggccgatgc cgtcctggct | 420 |
| cgcgtgtaca agcagtccga cctggatacc ctggcaaagg aagcgtccat tcccattatc | 480 |
| aacgggctgt ccgacctgta ccatccgatt caaatcctgg cggactacct gactctgcaa | 540 |

```
gagcattaca gcagcttgaa ggggcttact ctctcgtgga tcggcgacgg gaacaacatc      600
ctgcactcca tcatgatgtc cgccgccaag ttcgggatgc atttgcaagc tgcgaccccg      660
aaaggttacg agcccgatgc tagcgtaact aagcttgccg aacagtacgc caaagagaat      720
ggtacaaaac tgcttctgac taacgacccg ctggaagcag cccacggcgg gaacgtgctg      780
ataaccgaca cctggatttc aatggggcag gaggaagaga agaagaagcg actgcaggcg      840
ttccaaggct atcaggttac catgaaaacc gccaaagtgg cagccagcga ttggactttc      900
ctgcactgtc tgccgcggaa gcccgaggaa gttgatgacg aagtattcta ctcaccccgg      960
agcctcgtgt tccccgaggc cgaaaaccgg aagtggacta ttatggccgt gatggtgtcg     1020
ctgttgaccg actacagccc gcaactgcag aagccgaagt tttag                     1065

<210> SEQ ID NO 162
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 162
atgcttttca acctgaggat cctttttgaac aacgccgcct tcgcaacgg ccacaacttt       60 atggtccgca atttccgctg cgggcagccg ctgcagaaca aggtccagct gaagggccgg      120
gatctgctga ccctgaagaa cttcaccggg gaggaaatca agtacatgct ttggctctcc      180
gccgatctga agttcagaat caagcagaag ggagagtacc tcccgttgct gcaaggaaag      240
tcactcggaa tgattttcga aagagaagc actaggaccc gcctctcaac tgaaaccggg      300
ttcgcgctgc tcgggggcca tccgtgtttc ctgactaccc aagacatcca cctgggagtg      360
aacgagtcgc tgaccgacac cgcacgcgtg ctgtcatcca tggcggacgc agtgcttgcc      420
cgggtgtaca agcagtcgga cctggacact cttgccaagg aggcatcaat ccccatcatt      480
aacggactgt ccgatctcta ccacccgatt cagatcctgg ctgactacct aaccctgcaa      540
gagcactact caagcctgaa ggggctgacc ctgtcgtgga tcggggacgg caacaacatt      600
ctgcactcca tcatgatgtc ggcggctaag ttcgggatgc atttgcaagc ggcaactccg      660
aagggttatg aacccgacgc ctccgtgacc aagctggccg aacagtacgc caaggaaaac      720
ggaaccaagt tgctgctgac taatgatccc ctggaggcgg cccacggggg gaacgtgctg      780
ataaccgata cctggatctc catggggcag gaagaagaga agaaaaagcg gctgcaggca      840
ttccagggat accaggtcac catgaaaacc gcaaaagtgg cagccagcga ctggactttc      900
ctccattgcc tgccgcgaaa gccggaggag gtcgatgacg aggtgttcta ctccccgcgg      960
tcgctggtgt tccggaggc ggaaaaccgg aagtggacca ttatggccgt gatggtgtca     1020
ctcctgactg actacagccc gcaactgcag aagccgaagt tctag                     1065

<210> SEQ ID NO 163
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 163
atgcttttca atctccgcat cctccttaac aacgccgcgt ttagaaacgg ccacaacttc       60
atggtccgga acttcagatg tggccagccg cttcaaaaca aggtccagct gaagggccgg      120
```

```
gatcttctga ccctgaagaa ctttactggc aagagatca agtacatgct ctggctctcc    180
gcggacttga agttccgcat taagcagaag ggggaatacc ttccgctgct tcaaggaaag    240
agcctcggca tgatctttga agcgctcca accaggaccc gcctttctac tgaaactggg    300
ttcgcgctgc tcggtggcca ccctgcttc ctgacgaccc aggacatcca cctcggagtg    360
aacgaatccc tcaccgatac cgcccgggtg ttatcgagca tggcagatgc cgtgctggcc    420
agggtgtaca acagtccga tctggacact ctggccaagg aggcgtcaat tcctattatc    480
aacggcctta gtgacctcta ccatccgatt cagatcctgg ccgattacct cacctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga agtggacca tcatggccgt gatggtgtca   1020
ctgctcaccg actacagccc gcagcttcag aagcccaagt tctagataag tgaa          1074
```

<210> SEQ ID NO 164
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 164

```
atgctgttca acctgcgcat cctgctgaac aacgccgcct tccgcaacgg ccacaacttc     60
atggtgcgca acttccgctg cggccagccc ctgcagaaca aggtgcagct gaagggccgc    120
gacctgctga ccctgaagaa cttcaccggc gaggagatca agtacatgct gtggctgagc    180
gccgacctga agttccgcat caagcagaag ggcgagtacc tgccctgct gcagggcaag    240
agcctgggca tgatcttcga agcgcagc accgcaccc gcctgagcac cgagacaggc    300
ctggccctgc tggcggcca ccctgcttc ctgaccaccc aggacatcca cctgggcgtg    360
aacgagagcc tgaccgacac cgcccgcgtg ctgagcagca tggccgacgc cgtgctggcc    420
cgcgtgtaca gcagagcga cctggacacc ctggccaagg aggccagcat ccccatcatc    480
aacggcctga gcgacctgta ccacccatc cagatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccg cccacggcgg caacgtgctg    780
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagccccgc    960
agcctggtgt tccccgaggc cgagaaccgc aagtggacca tcatggccgt gatggtgagc   1020
ctgctgaccg actacagccc ccagctgcag aagcccaagt tctgaataag tga           1073
```

<210> SEQ ID NO 165
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 165

| | | | | | |
|---|---|---|---|---|---|
| atgctgttca | acctgcgcat | cctgctgaac | aacgccgcct | tccgcaacgg | ccacaacttc | 60 |
| atggtgcgca | acttccgctg | cggccagccc | ctgcagaaca | aggtgcagct | gaagggccgc | 120 |
| gacctgctga | ccctgaagaa | cttcaccggc | gaggagatca | agtacatgct | gtggctgagc | 180 |
| gccgacctga | agttccgcat | caagcagaag | ggcgagtacc | tgcccctgct | gcagggcaag | 240 |
| agcctgggca | tgatcttcga | gaagcgcagc | acccgcaccc | gcctgagcac | cgagacaggc | 300 |
| ctggccctgc | tgggcggcca | ccctgcttc | ctgaccaccc | aggacatcca | cctgggcgtg | 360 |
| aacgagagcc | tgaccgacac | cgcccgcgtg | ctgagcagca | tggccgacgc | cgtgctggcc | 420 |
| cgcgtgtaca | agcagagcga | cctggacacc | ctggccaagg | aggccagcat | ccccatcatc | 480 |
| aacggcctga | gcgacctgta | ccaccccatc | cagatcctgg | ccgactacct | gaccctgcag | 540 |
| gagcactaca | gcagcctgaa | gggcctgacc | ctgagctgga | tcggcgacgg | caacaacatc | 600 |
| ctgcacagca | tcatgatgag | cgccgccaag | ttcggcatgc | acctgcaggc | cgccaccccc | 660 |
| aagggctacg | agcccgacgc | cagcgtgacc | aagctggccg | agcagtacgc | caaggagaac | 720 |
| ggcaccaagc | tgctgctgac | caacgacccc | ctggaggccg | cccacggcgg | caacgtgctg | 780 |
| atcaccgaca | cctggatcag | catgggccag | gaggaggaga | gaagaagcg | cctgcaggcc | 840 |
| ttccagggct | accaggtgac | catgaagacc | gccaaggtgg | ccgccagcga | ctggaccttc | 900 |
| ctgcactgcc | tgccccgcaa | gcccgaggag | gtggacgacg | aggtgttcta | cagccccgc | 960 |
| agcctggtgt | tccccgaggc | cgagaaccgc | aagtggacca | tcatggccgt | gatggtgagc | 1020 |
| ctgctgaccg | actacagccc | ccagctgcag | aagcccaagt | tctgaataag | tga | 1073 |

<210> SEQ ID NO 166
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 166

| | | | | | |
|---|---|---|---|---|---|
| atgcttttca | atctccgcat | cctccttaac | aacgccgcgt | ttagaaacgg | ccacaacttc | 60 |
| atggtccgga | acttcagatg | tggccagccg | cttcaaaaca | aggtccagct | gaagggccgg | 120 |
| gatcttctga | ccctgaagaa | ctttactggc | gaagagatca | agtacatgct | ctggctctcc | 180 |
| gcggacttga | agttccgcat | taagcagaag | ggggaatacc | ttccgctgct | tcaaggaaag | 240 |
| agcctcggca | tgatctttga | gaagcgctca | accaggaccc | gcctttctac | tgaaactggg | 300 |
| ttcgcgctgc | tcggtggcca | ccctgcttc | ctgacgaccc | aggacatcca | cctcggagtg | 360 |
| aacgaatccc | tcaccgatac | cgcccgggtg | ttatcgagca | tggcagatgc | cgtgctggcc | 420 |
| agggtgtaca | aacagtccga | tctggacact | ctggccaagg | aggcgtcaat | tcctattatc | 480 |
| aacggcctta | gtgacctcta | ccatcccgatt | cagatcctgg | ccgattacct | caccctgcaa | 540 |
| gaacactaca | gctccctgaa | gggtctgaca | ttgtcctgga | tcggcgacgg | caacaacatt | 600 |
| ctccattcca | tcatgatgtc | cgccgcaaaa | ttcggcatgc | atcttcaagc | cgccacgccg | 660 |
| aagggttacg | agcccgacgc | ttccgtgact | aagctcgccg | agcagtacgc | taaggagaac | 720 |

```
ggaaccaagc ttctgctgac taacgaccca ctagaagcag cccacggggg caacgtgctt      780
attactgaca cctggatctc catgggccag gaagaagaga aaaagaagcg gctgcaggcg      840
ttccagggat atcaggtcac catgaaaacc gccaaggtcg ctgcctccga ctggaccttc      900
ctgcactgcc tgcctcgcaa gcctgaagaa gtggacgacg aggtgttcta ctcgccacgg      960
agcctcgtgt tccccgaggc cgagaataga aagtggacca tcatggccgt gatggtgtca     1020
ctgctcaccg actacagccc gcagcttcag aagcccaagt tctagataag tgaa           1074
```

<210> SEQ ID NO 167
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 167

```
atgcttttca acctgagaat cctcttgaac aatgctgctt ttcggaatgg ccacaacttt       60
atggttcgga acttccgttg cggccagcct ttacaaaaca aggtccagct gaagggccgg      120
gatttgctca cactaaagaa ctttactgga gaagagatca agtacatgct atggctgtcg      180
gccgacctga agttccgtat caagcagaag ggagaatacc ttccgctgct caaggaaag      240 agcctcggca tgatctttga gaagcgctca accaggaccc gcctttctac tgaaactggg      300
ttcgcgctgc tcggtggcca cccctgcttc ctgacgaccc aggacatcca cctcggagtg      360
aacgaatccc tcaccgatac cgcccgggtg ttatcgagca tggcagatgc cgtgctggcc      420
agggtgtaca acagtccga tctcgatacc ttggcaaagg aggcttccat tcccatcatc      480
aacggcctga gcgacctgta ccacccaatc caaatcctgg ctgactacct gaccctgcaa      540
gagcactaca gcagctgaa gggtctgacc ctgtcatgga ttggcgatgg aaacaatatt      600
ctgcactcca tcatgatgtc cgccgcgaag ttcggaatgc atctgcaagc cgccactcca      660
aaaggatacg aaccggatgc atccgtgacc aagttggcgg aacagtacgc gaaggagaac      720
ggaaccaagc tcctgctgac taacgacccg ctcgaggctg cgcatggggg taacgtgctg      780
attacggaca cctggatctc catggggcag gaggaagaga agaagaagag actgcaggca      840
ttccaggggt accaggtcac catgaaaacc gcaaaagtgg cagcttcgga ctggactttc      900
ctgcattgcc tgccgaggaa gccggaggaa gtcgacgacg aagtgttcta ctcgcctcgg      960
tccctggtgt tccccgaggc cgaaaaccgg aagtggacca tcatggccgt gatggtgtcc     1020
ttgctgactg actatagccc gcagctgcag aagcctaagt tctagataag tga            1073
```

<210> SEQ ID NO 168
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 168

```
atgctgttca acctgcgcat cctgctgaac aacgccgcct tccgcaacgg ccacaacttc       60
atggtgcgca acttccgctg cggccagccc ctgcagaaca aggtgcagct gaagggccgc      120
gacctgctga ccctgaagaa cttcaccggc gaggagatca gtacatgct gtggctgagc      180 gccgacctga agttccgcat caagcagaag ggcgagtacc tgcccctgct gcagggcaag      240
agcctgggca tgatcttcga gaagcgcagc acccgcaccc gcctgagcac cgagacaggc      300
ctggccctgc tgggcggcca cccctgcttc ctgaccaccc aggacatcca cctgggcgtg      360
```

```
aacgagagcc tgaccgacac cgcccgcgtg ctgagcagca tggccgacgc cgtgctggcc    420
cgcgtgtaca agcagagcga cctggacacc ctggccaagg aggccagcat ccccatcatc    480
aacggcctga gcgacctgta ccaccccatc cagatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccg ccacggcgg caacgtgctg    780 atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgcccgcaa gcccgaggag gtggacgacg aggtgttcta cagcccccgc    960
agcctggtgt tccccgaggc cgagaaccgc aagtggacca tcatggccgt gatggtgagc   1020
ctgctgaccg actacagccc ccagctgcag aagcccaagt ctgaataag tga           1073

<210> SEQ ID NO 169
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 169
atgcttttca atctccgcat cctccttaac aacgccgcgt ttagaaacgg ccacaacttc      60
atggtccgga acttcagatg tggccagccg cttcaaaaca aggtccagct gaagggccgg    120
gatcttctga ccctgaagaa ctttactggc gaagagatca agtacatgct ctggctctcc    180
gcggacttga agttccgcat taagcagaag ggggaatacc ttccgctgct tcaaggaaag    240
agcctcggca tgatctttga aagcgctca accaggaccc gcctttctac tgaaaactggg    300 ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt ctagataag tgaa          1074

<210> SEQ ID NO 170
<211> LENGTH: 1073
<212> TYPE: DNA
<213> ORGANISM: Artificial sequence
<220> FEATURE:
<223> OTHER INFORMATION: Synthetic polynucleotide
```

```
<400> SEQUENCE: 170
atgctgttca acctgcgcat cctgctgaac aacgccgcct tccgcaacgg ccacaacttc      60
atggtgcgca acttccgctg cggccagccc ctgcagaaca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga gaagcgcagc acccgcaccc gcctgagcac cgagacaggc     300
ctggccctgc tgggcggcca ccctgcttc ctgaccaccc aggacatcca cctgggcgtg      360
aacgagagcc tgaccgacac cgcccgcgtg ctgagcagca tggccgacgc cgtgctggcc     420
cgcgtgtaca agcagagcga cctggacacc ctggccaagg aggccagcat ccccatcatc     480
aacggcctga cgacctgta ccaccccatc cagatcctgg ccgactacct gaccctgcag      540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
atcaccgaca cctggatcag catggggcag gaggaggaga agaagaagcg cctgcaggcc     840
ttccagggct accaggtgac catgaagacc gccaaggtgg ccgccagcga ctggaccttc     900
ctgcactgcc tgccccgcaa gcccgaggag gtggacgacg aggtgttcta cagccccgc     960
agcctggtgt tccccgaggc cgagaaccgc aagtggacca tcatggccgt gatggtgagc    1020
ctgctgaccg actacagccc ccagctgcag aagcccaagt tctgaataag tga          1073

<210> SEQ ID NO 171
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 171
atgcttttca acctgagaat cctcttgaac aatgctgctt ttcggaatgg ccacaacttt      60
atggttcgga acttccgttg cggccagcct ttacaaaaca aggtccagct gaagggccgg     120
gatttgctca cactaaagaa ctttactgga gaagagatca agtacatgct atggctgtcg     180
gccgacctga agttccgtat caagcagaag ggagaatacc ttccgctgct tcaaggaaag     240
agcctcggca tgatctttga gaagcgctca accaggaccc gcctttctac tgaaactggg     300
ttcgcgctgc tcggtggcca ccctgcttc ctgacgaccc aggacatcca cctcggagtg      360
aacgaatccc tcaccgatac cgcccgggtg ttatcgagca tggcagatgc cgtgctggcc     420
agggtgtaca acagtccga tctcgatacc ttggcaaagg aggcttccat tcccatcatc      480
aacggcctga cgacctgta ccacccaatc caaatcctgg ctgactacct gaccctgcaa      540
gagcactaca gcagcctgaa gggtctgacc ctgtcatgga ttggcgatgg aaacaatatt     600
ctgcactcca tcatgatgtc cgccgcgaag ttcggaatgc atctgcaagc cgccactcca     660
aaaggatacg aaccggatgc atccgtgacc aagttggcgg aacagtacgc gaaggagaac     720
ggaaccaagc tcctgctgac taacgacccg ctcgaggctg cgcatggggg taacgtgctg     780
attacggaca cctggatctc catggggcag gaggaagaga agaagaagag actgcaggca     840
ttccaggggt accaggtcac catgaaaacc gcaaaagtgg cagcttcgga ctggactttc     900
ctgcattgcc tgccgaggaa gccggaggaa gtcgacgacg aagtgttcta ctcgcctcgg     960
```

```
tccctggtgt tccccgaggc cgaaaaccgg aagtggacca tcatggccgt gatggtgtcc    1020
ttgctgactg actatagccc gcagctgcag aagcctaagt tctagataag tga           1073

<210> SEQ ID NO 172
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 172
atgcttttca atctccgcat cctccttaac aacgccgcgt ttagaaacgg ccacaacttc     60
atggtccgga acttcagatg tggccagccg cttcaaaaca aggtccagct gaagggccgg    120
gatcttctga ccctgaagaa ctttactggc gaagagatca agtacatgct ctggctctcc    180
gcggacttga agttccgcat taagcagaag ggggaatacc ttccgctgct tcaaggaaag    240
agcctcggca tgatctttga aagcgctca accaggaccc gcctttctac tgaaactggg     300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca acagtccga tctggacact ctggccaagg aggcgtcaat tcctattatc    480
aacggcctta gtgacctcta ccatccgatt cagatcctgg ccgattacct cacctgcaa    540 gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaagaagcg gctgcaggcg    840 ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctagataag tgaa         1074

<210> SEQ ID NO 173
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 173
atgctgttca acctgcgcat cctgctgaac aacgccgcct ccgcaacgg ccacaacttc     60 atggtgcgca acttccgctg cggccagccc ctgcagaaca aggtgcagct gaagggccgc    120
gacctgctga ccctgaagaa cttcaccggc gaggagatca agtacatgct gtggctgagc    180
gccgacctga agttccgcat caagcagaag ggcgagtacc tgcccctgct gcagggcaag    240
agcctgggca tgatcttcga aagcgcagc acccgcaccc gcctgagcac cgagacaggc    300
ctggccctgc tgggcggcca cccctgcttc ctgaccaccc aggacatcca cctgggcgtg    360
aacgagagcc tgaccgacac cgcccgcgtg ctgagcagca tggccgacgc cgtgctggcc    420
cgcgtgtaca gcagagcga cctggacacc ctggccaagg aggccagcat ccccatcatc    480
aacggcctga gcgacctgta ccaccccatc cagatcctgg ccgactacct gaccctgcag    540
```

```
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccg cccacggcgg caacgtgctg    780
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagccccgc     960 agcctggtgt tccccgaggc cgagaaccgc aagtggacca tcatggccgt gatggtgagc    1020
ctgctgaccg actacagccc ccagctgcag aagcccaagt tctgaataag tga           1073
```

<210> SEQ ID NO 174
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 174

```
atgcttttca acctgagaat cctcttgaac aatgctgctt ttcggaatgg ccacaacttt     60
atggttcgga acttccgttg cggccagcct ttacaaaaca aggtccagct gaagggccgg    120
gatttgctca cactaaagaa ctttactgga gaagagatca agtacatgct atggctgtcg    180
gccgacctga agttccgtat caagcagaag ggagaatacc ttccgctgct tcaaggaaag    240
agcctcggca tgatctttga agcgctcca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca acagtccga tctcgatacc ttggcaaagg aggcttccat tcccatcatc    480
aacgccctga cgacctgta ccacccaatc caaatcctgg ctgactacct gaccctgcaa    540
gagcactaca gcagcctgaa gggtctgacc ctgtcatgga ttggcgatgg aaacaatatt    600
ctgcactcca tcatgatgtc cgccgcgaag ttcggaatgc atctgcaagc cgccactcca    660
aaaggatacg aaccggatgc atccgtgacc aagttggcgg aacagtacgc gaaggagaac    720
ggaaccaagc tcctgctgac taacgacccg ctcgaggctg cgcatggggg taacgtgctg    780
attacggaca cctggatctc catggggcag gaggaagaga agaagaagag actgcaggca    840
ttccaggggt accaggtcac catgaaaacc gcaaaagtgg cagcttcgga ctggactttc    900
ctgcattgcc tgccgaggaa gccggaggaa gtcgacgacg aagtgttcta ctcgcctcgg    960
tccctggtgt tccccgaggc cgaaaaccgg aagtggacca tcatggccgt gatggtgtcc    1020
ttgctgactg actatagccc gcagctgcag aagcctaagt ctagataag tga            1073
```

<210> SEQ ID NO 175
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 175

```
atgctgttca acctgcgcat cctgctgaac aacgccgcct tccgcaacgg ccacaacttc     60
atggtgcgca acttccgctg cggccagccc ctgcagaaca aggtgcagct gaagggccgc    120
gacctgctga cccctgaagaa cttcaccggc gaggagatca agtacatgct gtggctgagc    180
```

```
gccgacctga agttccgcat caagcagaag ggcgagtacc tgcccctgct gcagggcaag      240
agcctgggca tgatcttcga gaagcgcagc acccgcaccc gcctgagcac cgagacaggc      300
ttcgccctgc tgggcggcca cccctgcttc ctgaccaccc aggacatcca cctgggcgtg      360
aacgagagcc tgaccgacac cgcccgcgtg ctgagcagca tggccgacgc cgtgctggcc      420
cgcgtgtaca gcagagcga cctggacacc ctggccaagg aggccagcat ccccatcatc      480
aacggcctga gcgacctgta ccaccccatc cagatcctgg ccgactacct gaccctgcag      540
gagcactaca gcagcctgaa gggcctgacc ctgagctgga tcggcgacgg caacaacatc      600
ctgcacagca tcatgatgag cgccgccaag ttcggcatgc acctgcaggc cgccaccccc      660
aagggctacg agcccgacgc cagcgtgacc aagctggccg agcagtacgc caaggagaac      720
ggcaccaagc tgctgctgac caacgacccc tggaggccg cccacggcgg caacgtgctg      780
atcaccgaca cctggatcag catgggccag gaggaggaga agaagaagcg cctgcaggcc      840
ttccagggct accaggtgac catgaagacc gccaaggtgg ccgccagcga ctggaccttc      900
ctgcactgcc tgccccgcaa gcccgaggag gtggacgacg aggtgttcta cagcccccgc      960
agcctggtgt tccccgaggc cgagaaccgc aagtggacca tcatggccgt gatggtgagc     1020
ctgctgaccg actacagccc ccagctgcag aagcccaagt tctga                     1065
```

<210> SEQ ID NO 176
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 176

```
atgctgttca acctgcgcat cctgctgaac aacgccgcct tccgcaacgg ccacaacttc       60
atggtgcgca acttccgctg cggccagccc ctgcagaaca aggtgcagct gaagggccgc      120
gacctgctga ccctgaagaa cttcaccggc gaggagatca agtacatgct gtggctgagc      180
gccgacctga agttccgcat caagcagaag ggcgagtacc tgcccctgct gcagggcaag      240
agcctgggca tgatcttcga gaagcgcagc acccgcaccc gcctgagcac cgagacaggc      300
ttcgccctgc tgggcggcca cccctgcttc ctgaccaccc aggacatcca cctgggcgtg      360
aacgagagcc tgaccgacac cgcccgcgtg ctgagcagca tggccgacgc cgtgctggcc      420
cgcgtgtaca gcagagcga cctggacacc ctggccaagg aggccagcat ccccatcatc      480
aacggcctga gcgacctgta ccaccccatc cagatcctgg ccgactacct gaccctgcag      540
gagcactaca gcagcctgaa gggcctgacc ctgagctgga tcggcgacgg caacaacatc      600
ctgcacagca tcatgatgag cgccgccaag ttcggcatgc acctgcaggc cgccaccccc      660
aagggctacg agcccgacgc cagcgtgacc aagctggccg agcagtacgc caaggagaac      720
ggcaccaagc tgctgctgac caacgacccc tggaggccg cccacggcgg caacgtgctg      780
atcaccgaca cctggatcag catgggccag gaggaggaga agaagaagcg cctgcaggcc      840
ttccagggct accaggtgac catgaagacc gccaaggtgg ccgccagcga ctggaccttc      900
ctgcactgcc tgccccgcaa gcccgaggag gtggacgacg aggtgttcta cagcccccgc      960
agcctggtgt tccccgaggc cgagaaccgc aagtggacca tcatggccgt gatggtgagc     1020
ctgctgaccg actacagccc ccagctgcag aagcccaagt tctga                     1065
```

<210> SEQ ID NO 177

```
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 177
atgctgttca acctgcgcat cctgctgaac aacgccgcct tccgcaacgg ccacaacttc      60
atggtgcgca acttccgctg cggccagccc ctgcagaaca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga gaagcgcagc acccgcaccc gcctgagcac cgagacaggc     300
ttcgccctgc tgggcggcca ccctgcttc ctgaccaccc aggacatcca cctgggcgtg     360
aacgagagcc tgaccgacac cgcccgcgtg ctgagcagca tggccgacgc cgtgctggcc     420
cgcgtgtaca gcagagcga cctggacacc ctggccaagg aggccagcat ccccatcatc     480
aacggcctga gcgacctgta ccaccccatc agatcctgg ccgactacct gaccctgcag     540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
atcaccgaca cctggatcag catgggccag gaggaggaga agaagaagcg cctgcaggcc     840
ttccagggct accaggtgac catgaagacc gccaaggtgg ccgccagcga ctggaccttc     900
ctgcactgcc tgccccgcaa gcccgaggag gtggacgacg aggtgttcta cagcccccgc     960
agcctggtgt tccccgaggc cgagaaccgc aagtggacca tcatggccgt gatggtgagc    1020
ctgctgaccg actacagccc ccagctgcag aagcccaagt tctga                    1065

<210> SEQ ID NO 178
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 178
atgctgttca acctgcgcat cctgctgaac aacgccgcct tccgcaacgg ccacaacttc      60
atggtgcgca acttccgctg cggccagccc ctgcagaaca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga gaagcgcagc acccgcaccc gcctgagcac cgagacaggc     300
ttcgccctgc tgggcggcca ccctgcttc ctgaccaccc aggacatcca cctgggcgtg     360
aacgagagcc tgaccgacac cgcccgcgtg ctgagcagca tggccgacgc cgtgctggcc     420
cgcgtgtaca gcagagcga cctggacacc ctggccaagg aggccagcat ccccatcatc     480
aacggcctga gcgacctgta ccaccccatc agatcctgg ccgactacct gaccctgcag     540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
```

| | |
|---|---|
| atcaccgaca cctggatcag catgggccag gaggaggaga agaagaagcg cctgcaggcc | 840 |
| ttccagggct accaggtgac catgaagacc gccaaggtgg ccgccagcga ctggaccttc | 900 |
| ctgcactgcc tgccccgcaa gcccgaggag gtggacgacg aggtgttcta cagccccgc | 960 |
| agcctggtgt tccccgaggc cgagaaccgc aagtggacca tcatggccgt gatggtgagc | 1020 |
| ctgctgaccg actacagccc ccagctgcag aagcccaagt tctgaataag tgaa | 1074 |

<210> SEQ ID NO 179
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 179

| | |
|---|---|
| atgggcgtct tcaacctgcg gatcctgctg aacaacgccg ccttccggaa cggccacaac | 60 |
| ttcatggtcc gcaacttcag atgcggccag cccctgcaga acaaggtgca gctgaagggc | 120 |
| cgggacctgc tgaccctgaa gaacttcacc ggcgaagaga tcaagtacat gctgtggctg | 180 |
| agcgccgacc tgaagttccg gatcaagcag aagggcgagt acctgcccct gctgcaaggc | 240 |
| aagagcctgg gcatgatctt cgagaagcgg agcacccgga cccggctgag caccgagaca | 300 |
| ggctttgccc tgctgggagg ccaccccctg tttctgacca cccaggacat ccacctgggc | 360 |
| gtgaacgaga gcctgaccga caccgccaga gtgctgagca gcatggccga cgccgtgctg | 420 |
| gcccgggtgt acaagcagag cgacctggac accctggcca agaggccag catccccatc | 480 |
| atcaacggcc tgagcgacct gtaccacccc atccagatcc tggccgacta cctgaccctg | 540 |
| caggaacact acagctccct gaagggcctg accctgagct ggatcggcga cggcaacaac | 600 |
| atcctgcaca gcatcatgat gagcgccgcc aagttcggca tgcatctgca ggccgccacc | 660 |
| cccaagggct acgagcctga tgccagcgtg accaagctgg ccgagcagta cgccaaagag | 720 |
| aacggcacca gctgctgct gaccaacgac ccctggaag ccgccacgg cggcaacgtg | 780 |
| ctgatcaccg acacctggat cagcatgggc caggaagagg aaaagaagaa gcggctgcag | 840 |
| gccttccagg gctaccaggt cacaatgaag accgccaagg tggccgccag cgactggacc | 900 |
| ttcctgcact gcctgccccg gaagcccgaa gaggtggacg acgaggtgtt ctacagcccc | 960 |
| cggtccctgg tgttccccga ggccgagaac cggaagtgga ccattatggc cgtgatggtg | 1020 |
| tccctgctga ccgactactc cccccagctg cagaagccca gttctagat aagtgaa | 1077 |

<210> SEQ ID NO 180
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 180

| | |
|---|---|
| atgggcgtct tcaacctgcg gatcctgctg aacaacgccg ccttccggaa cggccacaac | 60 |
| ttcatggtcc gcaacttcag atgcggccag cccctgcaga acagggtgca gctgaagggc | 120 |
| cgggacctgc tgaccctgaa gaacttcacc ggcgaagaga tcaggtacat gctgtggctg | 180 |
| agcgccgacc tgaagttccg gatcaagcag aagggcgagt acctgcccct gctgcaaggc | 240 |
| aagagcctgg gcatgatctt cgagaagcgg agcacccgga cccggctgag caccgagaca | 300 |
| ggctttgccc tgctgggagg ccaccccctg tttctgacca cccaggacat ccacctgggc | 360 |

```
gtgaacgaga gcctgaccga caccgccaga gtgctgagca gcatggccga cgccgtgctg      420
gcccgggtgt acaagcagag cgacctggac accctggcca agaggccag catccccatc       480 atcaacggcc tgagcgacct gtaccacccc atccagatcc tggccgacta cctgaccctg      540
caggaacact acagctccct gaagggcctg accctgagct ggatcggcga cggcaacaac      600
atcctgcaca gcatcatgat gagcgccgcc aagttcggca tgcatctgca ggccgccacc      660
cccaagggct acgagcctga tgccagcgtg accaagctgg ccgagcagta cgccaaagag      720
aacggcacca agctgctgct gaccaacgac cccctggaag ccgcccacgg cggcaacgtg      780
ctgatcaccg acacctggat cagcatgggc caggaagagg aaaagaagaa gcggctgcag      840
gccttccagg gctaccaggt cacaatgaag accgccaagg tggccgccag cgactggacc      900
ttcctgcact gcctgccccg gaagcccgaa gaggtggacg acgaggtgtt ctacagcccc      960
cggtccctgg tgttccccga ggccgagaac cggaagtgga ccattatggc cgtgatggtg     1020
tccctgctga ccgactactc cccccagctg cagaagccca gttctagat aagtgaa        1077
```

<210> SEQ ID NO 181
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 181

```
atgctggtct tcaacctgcg gatcctgctg aacaacgccg ccttccggaa cggccacaac        60
ttcatggtcc gcaacttcag atgcggccag cccctgcaga acagggtgca gctgaagggc      120
cgggacctgc tgaccctgaa gaacttcacc ggcgaagaga tcaggtacat gctgtggctg      180
agcgccgacc tgaagttccg gatcaagcag aagggcgagt acctgcccct gctgcaaggc      240
aagagcctgg gcatgatctt cgagaagcgg agcaccccga cccggctgag caccgagaca      300
ggctttgccc tgctgggagg ccacccctgc tttctgacca cccaggacat ccacctgggc      360
gtgaacgaga gcctgaccga caccgccaga gtgctgagca gcatggccga cgccgtgctg      420
gcccgggtgt acaagcagag cgacctggac accctggcca agaggccag catccccatc       480 atcaacggcc tgagcgacct gtaccacccc atccagatcc tggccgacta cctgaccctg      540
caggaacact acagctccct gaagggcctg accctgagct ggatcggcga cggcaacaac      600
atcctgcaca gcatcatgat gagcgccgcc aagttcggca tgcatctgca ggccgccacc      660
cccaagggct acgagcctga tgccagcgtg accaagctgg ccgagcagta cgccaaagag      720
aacggcacca agctgctgct gaccaacgac cccctggaag ccgcccacgg cggcaacgtg      780
ctgatcaccg acacctggat cagcatgggc caggaagagg aaaagaagaa gcggctgcag      840
gccttccagg gctaccaggt cacaatgaag accgccaagg tggccgccag cgactggacc      900
ttcctgcact gcctgccccg gaagcccgaa gaggtggacg acgaggtgtt ctacagcccc      960
cggtccctgg tgttccccga ggccgagaac cggaagtgga ccattatggc cgtgatggtg     1020
tccctgctga ccgactactc cccccagctg cagaagccca gttctagat aagtgaa         1077
```

<210> SEQ ID NO 182
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 182

| | |
|---|---|
| atgctgttca acctgaggat cctgctgaac aacgcagctt tcaggaacgg ccacaacttc | 60 |
| atggtgagga acttccggtg cggccagccc ctgcagaaca aggtgcagct gaagggcagg | 120 |
| gacctgctga ccctgaagaa cttcaccgga gaggagatca gtacatgct gtggctgagc | 180 |
| gcagacctga agttcaggat caagcagaag ggagagtacc tgcccctgct gcaggggaag | 240 |
| tccctgggca tgatcttcga agaggagagt accaggacca ggctgagcac cgaaaccggc | 300 |
| ttcgccctgc tgggaggaca ccctgcttc ctgaccaccc aggacatcca cctgggcgtg | 360 |
| aacgagagtc tgaccgacac cgccagggtg ctgtctagca tggccgacgc cgtgctggcc | 420 |
| agggtgtaca agcagtcaga cctggacacc ctggctaagg aggccagcat ccccatcatc | 480 |
| aacggcctga cgacctgta ccaccccatc cagatcctgg ctgactacct gaccctgcag | 540 |
| gagcactaca gctctctgaa gggcctgacc ctgagctgga tcggcgacgg gaacaacatc | 600 |
| ctgcacagca tcatgatgag cgccgccaag ttcggcatgc acctgcaggc cgctacccccc | 660 |
| aagggttacg agcccgacgc cagcgtgacc aagctggcag agcagtacgc caaggagaac | 720 |
| ggcaccaagc tgctgctgac caacgacccc ctggaggccg cccacggagg caacgtgctg | 780 |
| atcaccgaca cctggatcag catgggacag gaggaggaga agaagaagcg gctgcaggct | 840 |
| ttccagggtt accaggtgac catgaagacc gccaaggtgg ctgccagcga ctggaccttc | 900 |
| ctgcactgcc tgcccaggaa gcccgaggag gtggacgacg aggtgttcta ctctcccagg | 960 |
| agcctggtgt tccccgaggc cgagaacagg aagtggacca tcatggctgt gatggtgtcc | 1020 |
| ctgctgaccg actacagccc ccagctgcag aagcccaagt tctgaataag tgaa | 1074 |

<210> SEQ ID NO 183
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 183

| | |
|---|---|
| atgctgttca acctgaggat cctgctgaac aacgcagctt tcaggaacgg ccacaacttc | 60 |
| atggtgagga acttccggtg cggccagccc ctgcagaaca aggtgcagct gaagggcagg | 120 |
| gacctgctga ccctgaagaa cttcaccgga gaggagatca gtacatgct gtggctgagc | 180 |
| gcagacctga agttcaggat caagcagaag ggagagtacc tgcccctgct gcaggggaag | 240 |
| tccctgggca tgatcttcga agaggagagt accaggacca ggctgagcac cgaaaccggc | 300 |
| ttcgccctgc tgggaggaca ccctgcttc ctgacgaccc aggacatcca cctcggagtg | 360 |
| aacgaatccc tcaccgatac cgcccgggtg ttatcaagca tggcagatgc cgtgctggcc | 420 |
| agggtgtaca acagtccga tctggacact ctggctaagg aggccagcat ccccatcatc | 480 |
| aacggcctga cgacctgta ccaccccatc cagatcctgg ctgactacct gaccctgcag | 540 |
| gagcactaca gctctctgaa gggcctgacc ctgagctgga tcggcgacgg gaacaacatc | 600 |
| ctgcactcca tcatgatgtc cgccgcgaag ttcggaatgc atctgcaagc cgccacgcca | 660 |
| aaaggatacg aaccggatgc gcccgtgaca aagttggcgg aacagtacgc taaggagaac | 720 |
| ggaaccaagc tgctgctgac caacgacccc ctggaggccg cccacggagg caacgtgctg | 780 |
| atcaccgaca cctggatcag catgggacag gaggaggaga agaagaagcg gctgcaggct | 840 |
| ttccagggtt accaggtgac catgaagacc gccaaggtgg ctgccagcga ctggaccttc | 900 |

| ctgcactgcc tgcccaggaa gcccgaggag gtggacgacg aggtgttcta ctctcccagg | 960 |
| agcctggtgt tccccgaggc cgagaacagg aagtggacca tcatggctgt gatggtgtcc | 1020 |
| ctgctgaccg actacagccc ccagctgcag aagcccaagt tctgaataag tgaa | 1074 |

<210> SEQ ID NO 184
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 184

| atgctgttca acctgcgcat cctgctgaac aacgccgcct tccgcaacgg ccacaacttc | 60 |
| atggtgcgca acttccgctg cggccagccc ctgcagaaca aggtgcagct gaagggccgc | 120 |
| gacctgctga ccctgaagaa cttcaccggc gaggagatca agtacatgct gtggctgagc | 180 |
| gccgacctga agttccgcat caagcagaag ggcgagtacc tgcccctgct gcagggcaag | 240 |
| agcctgggca tgatcttcga gaagcgcagc acccgcaccc gctgagcac cgagacaggc | 300 |
| ttcgccctgc tgggcggcca cccctgcttc ctgaccaccc aggacatcca cctgggcgtg | 360 |
| aacgagagcc tgaccgacac cgcccgcgtg ctgagcagca tggccgacgc cgtgctggcc | 420 |
| cgcgtgtaca gcagagcga cctggacacc ctggccaagg aggccagcat ccccatcatc | 480 |
| aacggcctga gcgacctgta ccaccccatc cagatcctgg ccgactacct gaccctgcag | 540 |
| gagcactaca gcagcctgaa gggcctgacc ctgagctgga tcgcgacgg caacaacatc | 600 |
| ctgcacagca tcatgatgag cgccgccaag ttcggcatgc acctgcaggc cgccaccccc | 660 |
| aagggctacg agcccgacgc cagcgtgacc aagctggccg agcagtacgc caaggagaac | 720 |
| ggcaccaagc tgctgctgac caacgacccc tggaggccg cccacggcgg caacgtgctg | 780 |
| atcaccgaca cctggatcag catgggccag gaggaggaga agaagaagcg cctgcaggcc | 840 |
| ttccagggct accaggtgac catgaagacc gccaaggtgg ccgccagcga ctggaccttc | 900 |
| ctgcactgcc tgccccgcaa gcccgaggag gtggacgacg aggtgttcta cagccccgc | 960 |
| agcctggtgt tccccgaggc cgagaaccgc aagtggacca tcatggccgt gatggtgagc | 1020 |
| ctgctgaccg actacagccc ccagctgcag aagcccaagt tctgaataag tgaa | 1074 |

<210> SEQ ID NO 185
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 185

| atgctgttca acctgcgcat cctgctgaac aacgccgcct tccgcaacgg ccacaacttc | 60 |
| atggtgcgca acttccgctg cggccagccc ctgcagaaca aggtgcagct gaagggccgc | 120 |
| gacctgctga ccctgaagaa cttcaccggc gaggagatca agtacatgct gtggctgagc | 180 |
| gccgacctga agttccgcat caagcagaag ggcgagtacc tgcccctgct gcagggcaag | 240 |
| agcctgggca tgatcttcga gaagcgcagc acccgcaccc gctgagcac cgagacaggc | 300 |
| ttcgccctgc tgggcggcca cccctgcttc ctgaccaccc aggacatcca cctgggcgtg | 360 |
| aacgagagcc tgaccgacac cgcccgcgtg ctgagcagca tggccgacgc cgtgctggcc | 420 |
| cgcgtgtaca gcagagcga cctggacacc ctggccaagg aggccagcat ccccatcatc | 480 |
| aacggcctga gcgacctgta ccaccccatc cagatcctgg ccgactacct gaccctgcag | 540 |

```
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc tggaggccg cccacggcgg caacgtgctg    780
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagcccccgc    960
agcctggtgt tccccgaggc cgagaaccgc aagtggacca tcatggccgt gatggtgagc   1020
ctgctgaccg actacagccc ccagctgcag aagcccaagt tctgaataag tgaa         1074
```

<210> SEQ ID NO 186
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 186

```
atgcttttca acttgagaat cctgctgaac aacgccgcct tcgcaacgg tcacaatttt     60 atggtcagaa acttcagatg cggacagccc ctccaaaaca aggtccagct gaagggccgc    120
gatctcctca ccctgaagaa cttcacgggg gaggagatca agtacatgct gtggctctcc    180
gctgacctga agttcaggat caagcagaag ggagaatatc tgccgctgct gcaagggaag    240
tccctgggga tgattttcga gaagcggagc acccggactc ggctctccac tgaaactggt    300
ttcgcccttc tgggcggtca cccctgcttc ctgaccactc aagacattca cctcggagtg    360
aacgagtcct tgactgacac cgcccgggtg ctgtcgagca tggcagacgc cgtgctagcc    420
cgcgtgtaca gcagtcaga cctcgatacc ctggccaagg aggcttcgat cccgatcatc    480
aacgggttgt ccgacctgta ccacccgatt cagattctcg ccgactacct caccctgcaa    540
gagcattaca gctccctgaa ggggcttacc ctgtcctgga ttggcgacgg aaacaacatc    600
ctgcactcca ttatgatgtc ggcggccaag ttcggcatgc acctccaagc cgcgaccccct   660 aagggttacg aaccagacgc gtcagtgact aagctggccg aacagtacgc aaaggaaaat    720
ggcacgaagc tgctcctgac caacgatccg ttggaagccg cccatggcgg aaatgtgctc    780
atcaccgaca cctggatctc gatgggacag gaggaagaga agaagaagcg gctgcaggcg    840
ttccagggct accaggtcac catgaaaact gccaaggtgg ccgccagcga ctggaccttc    900
ctgcactgcc ttccgcgcaa gcctgaggag gtggacgatg aagtgttcta ctctccacgg    960
tccctggtgt tccccgaggc ggagaaccgc aaatggacca tcatggctgt gatggtcagc   1020
ctgctgaccg attacagccc tcagttgcaa aagccgaagt tttga                   1065
```

<210> SEQ ID NO 187
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 187

```
atgctgttca acctccgcat cctcctcaac aacgccgcat tcagaaacgg gcacaacttc     60
atggtcagaa acttccgctg cgggcaaccc ctacaaaaca aggtccagct caaggggcgg    120
```

| | |
|---|---|
| gacctcctga ccctgaagaa cttcaccggc gaagagatca agtacatgct gtggctctcc | 180 |
| gccgacctga agttccgcat caagcagaag ggagagtacc tcccgctgct gcaagggaag | 240 |
| tcgctgggga tgatcttcga gaagcggtca accagaaccc ggctgtcaac cgaaaccggg | 300 |
| ttcgcactgc tggggggaca cccgtgcttc ctgaccaccc aagacatcca cctgggagtg | 360 |
| aacgaatcgc tgaccgacac cgcccgcgtg ctgagctcaa tggcggacgc cgtgctggcc | 420 |
| cgcgtgtaca agcagtccga cctggacacc ctggccaagg aagcgtccat cccgatcatc | 480 |
| aacggactgt ccgacctgta ccacccgatc cagatcctgg cagactacct gaccctgcaa | 540 |
| gaacactaca gctccctgaa gggcctgacc ctgtcatgga tcggggacgg gaacaacatc | 600 |
| ctgcactcca taatgatgtc agccgccaag ttcggaatgc acctccaagc cgcaaccccg | 660 |
| aagggctacg aaccggacgc atcagtgacc aaactggccg agcagtacgc caaggaaaac | 720 |
| ggcaccaagc tcctgctgac caacgacccg ctggaggcca cacgggggg aacgtgctg | 780 |
| atcaccgaca cctggatctc catgggacag gaggaggaaa agaagaagcg gctgcaggcg | 840 |
| ttccagggt accaggtcac catgaaaacc gcgaaggtcg cggcatcaga ctggaccttc | 900 |
| ctgcactgcc tgccccggaa gccggaagag gtggacgacg aggtgttcta ctcgccgcgc | 960 |
| tcgctggtgt tccccgaggc ggagaacagg aagtggacca tcatggcggt gatggtcagc | 1020 |
| ctcctgaccg actactcgcc gcagctgcag aagccgaagt tctga | 1065 |

<210> SEQ ID NO 188
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 188

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct gaagggccgg | 120 |
| gatcttctga ccctgaagaa ctttactggc gaagagatca agtacatgct ctggctctcc | 180 |
| gcggacttga agttccgcat taagcagaag ggggaatacc ttccgctgct tcaaggaaag | 240 |
| agcctcggca tgatctttga gaagcgctca accaggaccc gccttttctac tgaaactggg | 300 |
| ttcgcgctgc tcggtggcca cccctgcttc ctgacgaccc aggacatcca cctcggagtg | 360 |
| aacgaatccc tcaccgatac cgcccgggtg ttatcgagca tggcagatgc cgtgctggcc | 420 |
| agggtgtaca acagtccga tctggacact ctggccaagg aggcgtcaat tcctattatc | 480 |
| aacggcctta gtgacctcta ccatccgatt cagatcctgg ccgattacct cacccctgcaa | 540 |
| gaacactaca gctccctgaa gggtctgaca ttgtcctgga tcgcgacgg caacaacatt | 600 |
| ctccattcca tcatgatgtc cgccgcaaaa ttcggcatgc atcttcaagc cgccacgccg | 660 |
| aagggttacg agcccgacgc ttccgtgact aagctcgccg agcagtacgc taaggagaac | 720 |
| ggaaccaagc ttctgctgac taacgaccca ctagaagcag cccacggggg caacgtgctt | 780 |
| attactgaca cctggatctc catgggccag gaagaagaga aaagaagcg gctgcaggcg | 840 |
| ttccagggat atcaggtcac catgaaaacc gccaaggtcg ctgcctccga ctggaccttc | 900 |
| ctgcactgcc tgcctcgcaa gcctgaagaa gtggacgacg aggtgttcta ctcgccacgg | 960 |
| agcctcgtgt tccccgaggc cgagaatagg aagtggacca tcatggccgt gatggtgtca | 1020 |
| ctgctcaccg actacagccc gcagcttcag aagcccaagt tctgaataag taga | 1074 |

<210> SEQ ID NO 189
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 189

| | | | | | |
|---|---|---|---|---|---|
| atgcttttca | acctgagaat | cctcttgaac | aatgctgctt | ttcggaatgg | ccacaacttt | 60 |
| atggttcgga | acttccgttg | cggccagcct | ttacaaaaca | aggtccagct | gaagggccgg | 120 |
| gatttgctca | cactaaagaa | ctttactgga | gaagagatca | agtacatgct | atggctgtcg | 180 |
| gccgacctga | agtccgtat | caagcagaag | ggagaatacc | ttccgctgct | tcaaggaaag | 240 |
| agcctcggca | tgatctttga | gaagcgctca | accaggaccc | gcctttctac | tgaaactggg | 300 |
| ttcgcgctgc | tcggtggcca | ccctgcttc | ctgacgaccc | aggacatcca | cctcggagtg | 360 |
| aacgaatccc | tcaccgatac | cgcccgggtg | ttatcgagca | tggcagatgc | cgtgctggcc | 420 |
| agggtgtaca | acagtccga | tctcgatacc | ttggcaaagg | aggcttccat | cccatcatc | 480 |
| aacggcctga | gcgacctgta | ccacccaatc | caaatcctgg | ctgactacct | gaccctgcaa | 540 |
| gagcactaca | gcagcctgaa | gggtctgacc | ctgtcatgga | ttggcgatgg | aaacaatatt | 600 |
| ctgcactcca | tcatgatgtc | cgccgcgaag | ttcggaatgc | atctgcaagc | cgccactcca | 660 |
| aaaggatacg | aaccggatgc | atccgtgacc | aagttggcgg | aacagtacgc | gaaggagaac | 720 |
| ggaaccaagc | tcctgctgac | taacgacccg | ctcgaggctg | cgcatggggg | taacgtgctg | 780 |
| attacggaca | cctggatctc | catggggcag | gaggaagaga | agaagaagag | actgcaggca | 840 |
| ttccaggggt | accaggtcac | catgaaaacc | gcaaaagtgg | cagcttcgga | ctggactttc | 900 |
| ctgcattgcc | tgccgaggaa | gccggaggaa | gtcgacgacg | aagtgttcta | ctcgcctcgg | 960 |
| tccctggtgt | tccccgaggc | cgaaaaccgg | aagtggacca | tcatggccgt | gatggtgtcc | 1020 |
| ttgctgactg | actatagccc | gcagctgcag | aagcctaagt | tctgaataag | taga | 1074 |

<210> SEQ ID NO 190
<211> LENGTH: 1074
<212> TYPE: DNA
<213> ORGANISM: Artificial sequence
<220> FEATURE:
<223> OTHER INFORMATION: Synthetic polynucleotide

<400> SEQUENCE: 190

| | | | | | |
|---|---|---|---|---|---|
| atgctgttca | acctgcgcat | cctgctgaac | aacgccgcct | tccgcaacgg | ccacaacttc | 60 |
| atggtgcgca | acttccgctg | cggccagccc | ctgcagaaca | aggtgcagct | gaagggccgc | 120 |
| gacctgctga | ccctgaagaa | cttcaccggc | gaggagatca | agtacatgct | gtggctgagc | 180 |
| gccgacctga | agtccgcat | caagcagaag | ggcgagtacc | tgccctgct | gcagggcaag | 240 |
| agcctgggca | tgatcttcga | gaagcgcagc | acccgcaccc | gcctgagcac | cgagacaggc | 300 |
| ctggccctgc | tgggcggcca | ccctgcttc | ctgaccaccc | aggacatcca | cctgggcgtg | 360 |
| aacgagagcc | tgaccgacac | cgcccgcgtg | ctgagcagca | tggccgacgc | cgtgctggcc | 420 |
| cgcgtgtaca | gcagagcga | cctggacacc | ctggccaagg | aggccagcat | cccatcatc | 480 |
| aacggcctga | gcgacctgta | ccacccatc | cagatcctgg | ccgactacct | gaccctgcag | 540 |
| gagcactaca | gcagcctgaa | gggcctgacc | ctgagctgga | tcggcgacgg | caacaacatc | 600 |
| ctgcacagca | tcatgatgag | cgccgccaag | ttcggcatgc | acctgcaggc | cgccaccccc | 660 |
| aagggctacg | agcccgacgc | cagcgtgacc | aagctggccg | agcagtacgc | caaggagaac | 720 |

| | |
|---|---|
| ggcaccaagc tgctgctgac caacgacccc ctggaggccg cccacggcgg caacgtgctg | 780 |
| atcaccgaca cctggatcag catgggccag gaggaggaga agaagaagcg cctgcaggcc | 840 |
| ttccagggct accaggtgac catgaagacc gccaaggtgg ccgccagcga ctggaccttc | 900 |
| ctgcactgcc tgccccgcaa gcccgaggag gtggacgacg aggtgttcta cagcccccgc | 960 |
| agcctggtgt tccccgaggc cgagaaccgc aagtggacca tcatggccgt gatggtgagc | 1020 |
| ctgctgaccg actacagccc ccagctgcag aagcccaagt ctgaataag taga | 1074 |

<210> SEQ ID NO 191
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 191

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct gaagggccgg | 120 |
| gatcttctga ccctgaagaa ctttactggc gaagagatca agtacatgct ctggctctcc | 180 |
| gcggacttga agttccgcat taagcagaag ggggaatacc ttccgctgct tcaaggaaag | 240 |
| agcctcggca tgatctttga gaagcgctca accaggaccc gcctttctac tgaaactggg | 300 |
| ttcgcgctgc tcggtggcca cccctgcttc ctgacgaccc aggacatcca cctcggagtg | 360 |
| aacgaatccc tcaccgatac cgcccgggtg ttatcgagca tggcagatgc cgtgctggcc | 420 |
| agggtgtaca acagtccga tctggacact ctggccaagg aggcgtcaat tcctattatc | 480 |
| aacggcctta gtgacctcta ccatccgatt cagatcctgg ccgattacct caccctgcaa | 540 |
| gaacactaca gctccctgaa gggtctgaca ttgtcctgga tcggcgacgg caacaacatt | 600 |
| ctccattcca tcatgatgtc cgccgcaaaa ttcggcatgc atcttcaagc cgccacgccg | 660 |
| aagggttacg agcccgacgc ttccgtgact aagctcgccg agcagtacgc taaggagaac | 720 |
| ggaaccaagc ttctgctgac taacgaccca ctagaagcag cccacggggg caacgtgctt | 780 |
| attactgaca cctggatctc catgggccag gaagaagaga aaaagaagcg gctgcaggcg | 840 |
| ttccagggat atcaggtcac catgaaaacc gccaaggtcg ctgcctccga ctggaccttc | 900 |
| ctgcactgcc tgcctcgcaa gcctgaagaa gtggacgacg aggtgttcta ctcgccacgg | 960 |
| agcctcgtgt tccccgaggc cgagaataga aagtggacca tcatggccgt gatggtgtca | 1020 |
| ctgctcaccg actacagccc gcagcttcag aagcccaagt ctag | 1065 |

<210> SEQ ID NO 192
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 192

| | |
|---|---|
| atgcttttca atctccgcat cctccttaac aacgccgcgt ttagaaacgg ccacaacttc | 60 |
| atggtccgga acttcagatg tggccagccg cttcaaaaca aggtccagct gaagggccgg | 120 |
| gatcttctga ccctgaagaa ctttactggc gaagagatca agtacatgct ctggctctcc | 180 |
| gcggacttga agttccgcat taagcagaag ggggaatacc ttccgctgct tcaaggaaag | 240 |
| agcctcggca tgatctttga gaagcgctca accaggaccc gcctttctac tgaaactggg | 300 |
| ttcgcgctgc tcggtggcca cccctgcttc ctgacgaccc aggacatcca cctcggagtg | 360 |

```
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                   1065
```

<210> SEQ ID NO 193
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 193

```
atgcttttca atctccgcat cctccttaac aacgccgcgt ttagaaacgg ccacaacttc     60
atggtccgga acttcagatg tggccagccg cttcaaaaca aggtccagct gaagggccgg    120
gatcttctga ccctgaagaa ctttactggc gaagagatca agtacatgct ctggctctcc    180
gcggacttga agttccgcat taagcagaag ggggaatacc ttccgctgct tcaaggaaag    240
agcctcggca tgatctttga aagcgctca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                   1065
```

<210> SEQ ID NO 194
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 194

```
atgcttttca atctccgcat cctccttaac aacgccgcgt ttagaaacgg ccacaacttc    60
atggtccgga acttcagatg tggccagccg cttcaaaaca aggtccagct gaagggccgg   120
gatcttctga ccctgaagaa ctttactggc gaagagatca agtacatgct ctggctctcc   180
gcggacttga agttccgcat taagcagaag ggggaatacc ttccgctgct tcaaggaaag   240
agcctcggca tgatctttga gaagcgctca accaggaccc gcctttctac tgaaactggg   300
ttcgcgctgc tcggtggcca cccctgcttc ctgacgaccc aggacatcca cctcggagtg   360
aacgaatccc tcaccgatac cgcccgggtg ttatcgagca tggcagatgc cgtgctggcc   420
agggtgtaca acagtccga tctggacact ctggccaagg aggcgtcaat tcctattatc   480
aacggcctta gtgacctcta ccatccgatt cagatcctgg ccgattacct caccctgcaa   540
gaacactaca gctccctgaa gggtctgaca ttgtcctgga tcggcgacgg caacaacatt   600
ctccattcca tcatgatgtc cgccgcaaaa ttcggcatgc atcttcaagc cgccacgccg   660
aagggttacg agcccgacgc ttccgtgact aagctcgccg agcagtacgc taaggagaac   720
ggaaccaagc ttctgctgac taacgaccca ctagaagcag cccacggggg caacgtgctt   780
attactgaca cctggatctc catgggccag gaagaagaga aaaagaagcg gctgcaggcg   840
ttccagggat atcaggtcac catgaaaacc gccaaggtcg ctgcctccga ctggaccttc   900
ctgcactgcc tgcctcgcaa gcctgaagaa gtggacgacg aggtgttcta ctcgccacgg   960
agcctcgtgt tccccgaggc cgagaataga aagtggacca tcatggccgt gatggtgtca  1020
ctgctcaccg actacagccc gcagcttcag aagcccaagt tctag                   1065
```

<210> SEQ ID NO 195
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 195

```
atgcttttca atctccgcat cctccttaac aacgccgcgt ttagaaacgg ccacaacttc    60
atggtccgga acttcagatg tggccagccg cttcaaaaca aggtccagct gaagggccgg   120
gatcttctga ccctgaagaa ctttactggc gaagagatca agtacatgct ctggctctcc   180
gcggacttga agttccgcat taagcagaag ggggaatacc ttccgctgct tcaaggaaag   240
agcctcggca tgatctttga gaagcgctca accaggaccc gcctttctac tgaaactggg   300
ttcgcgctgc tcggtggcca cccctgcttc ctgacgaccc aggacatcca cctcggagtg   360
aacgaatccc tcaccgatac cgcccgggtg ttatcgagca tggcagatgc cgtgctggcc   420
agggtgtaca acagtccga tctggacact ctggccaagg aggcgtcaat tcctattatc   480
aacggcctta gtgacctcta ccatccgatt cagatcctgg ccgattacct caccctgcaa   540
gaacactaca gctccctgaa gggtctgaca ttgtcctgga tcggcgacgg caacaacatt   600
ctccattcca tcatgatgtc cgccgcaaaa ttcggcatgc atcttcaagc cgccacgccg   660
aagggttacg agcccgacgc ttccgtgact aagctcgccg agcagtacgc taaggagaac   720
ggaaccaagc ttctgctgac taacgaccca ctagaagcag cccacggggg caacgtgctt   780
attactgaca cctggatctc catgggccag gaagaagaga aaaagaagcg gctgcaggcg   840
ttccagggat atcaggtcac catgaaaacc gccaaggtcg ctgcctccga ctggaccttc   900
ctgcactgcc tgcctcgcaa gcctgaagaa gtggacgacg aggtgttcta ctcgccacgg   960
```

```
agcctcgtgt tccccgaggc cgagaataga aagtggacca tcatggccgt gatggtgtca    1020
ctgctcaccg actacagccc gcagcttcag aagcccaagt tctag                   1065

<210> SEQ ID NO 196
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 196
atggtgttca acctccgcat cctcctcaac aacgccgcat tcagaaacgg gcacaacttc      60
atggtcagaa acttccgctg cgggcaaccc ctacaaaaca aggtccagct caaggggcgg     120
gacctcctga ccctgaagaa cttcaccggc aagagatca agtacatgct gtggctctcc      180
gccgacctga agttccgcat caagcagaag ggagagtacc tcccgctgct gcaagggaag     240
tcgctgggga tgatcttcga aagcggtca accagaaccc ggctgtcaac cgaaaccggg      300
ttcgcactgc tgggggaca cccgtgcttc ctgaccaccc aagacatcca cctgggagtg     360
aacgaatcgc tgaccgacac cgcccgcgtg ctgagctcaa tggcggacgc cgtgctggcc     420
cgcgtgtaca agcagtccga cctggacacc ctggccaagg aagcgtccat cccgatcatc     480
aacggactgt ccgacctgta ccacccgatc cagatcctgg cagactacct gaccctgcaa     540
gaacactaca gctccctgaa gggcctgacc ctgtcatgga tcggggacgg aacaacatc      600 ctgcactcca taatgatgtc agccgccaag ttcggaatgc acctccaagc cgcaaccccg     660
aagggctacg aaccggacgc atcagtgacc aaactggccg agcagtacgc caaggaaaac     720
ggcaccaagc tcctgctgac caacgacccg ctggaggccg cacacggggg gaacgtgctg     780
atcaccgaca cctggatctc catgggacag gaggaggaaa agaagaagcg gctgcaggcg     840
ttccaggggt accaggtcac catgaaaaac gcgaaggtcg cggcatcaga ctggaccttc     900
ctgcactgcc tgccccggaa gccggaagag gtggacgacg aggtgttcta ctcgccgcgc     960
tcgctggtgt tccccgaggc ggagaacagg aagtggacca tcatggcggt gatggtcagc   1020
ctcctgaccg actactcgcc gcagctgcag aagccgaagt tctga                   1065

<210> SEQ ID NO 197
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 197
atggtgttca acctccgcat cctcctcaac aacgccgcat tcagaaacgg gcacaacttc      60
atggtcagaa acttccgctg cgggcaaccc ctacaaaacc gggtccagct caaggggcgg    120
gacctcctga ccctgaagaa cttcaccggc aagagatca agtacatgct gtggctctcc      180
gccgacctga agttccgcat caagcagaag ggagagtacc tcccgctgct gcaagggaag    240
tcgctgggga tgatcttcga aagcggtca accagaaccc ggctgtcaac cgaaaccggg     300
ttcgcactgc tgggggaca cccgtgcttc ctgaccaccc aagacatcca cctgggagtg     360
aacgaatcgc tgaccgacac cgcccgcgtg ctgagctcaa tggcggacgc cgtgctggcc    420
cgcgtgtaca agcagtccga cctggacacc ctggccaagg aagcgtccat cccgatcatc    480
aacggactgt ccgacctgta ccacccgatc cagatcctgg cagactacct gaccctgcaa    540
```

| | |
|---|---|
| gaacactaca gctccctgaa gggcctgacc ctgtcatgga tcggggacgg gaacaacatc | 600 |
| ctgcactcca taatgatgtc agccgccaag ttcggaatgc acctccaagc cgcaaccccg | 660 |
| aagggctacg aaccggacgc atcagtgacc aaactggccg agcagtacgc caaggaaaac | 720 |
| ggcaccaagc tcctgctgac caacgacccg ctggaggccg cacacggggg gaacgtgctg | 780 |
| atcaccgaca cctggatctc catgggacag gaggaggaaa agaagaagcg gctgcaggcg | 840 |
| ttccaggggt accaggtcac catgaaaacc gcgaaggtcg cggcatcaga ctggaccttc | 900 |
| ctgcactgcc tgccccggaa gccggaagag gtggacgacg aggtgttcta ctcgccgcgc | 960 |
| tcgctggtgt tccccgaggc ggagaacagg aagtggacca tcatggcggt gatggtcagc | 1020 |
| ctcctgaccg actactcgcc gcagctgcag aagccgaagt tctga | 1065 |

<210> SEQ ID NO 198
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 198

| | |
|---|---|
| atggtgttca acctccgcat cctcctcaac aacgccgcat tcagaaacgg gcacaacttc | 60 |
| atggtcagaa acttccgctg cgggcaaccc ctacaaaacc gggtccagct caaggggcgg | 120 |
| gacctcctga ccctgaagaa cttcaccggc gaagagatcc ggtacatgct gtggctctcc | 180 |
| gccgacctga agttccgcat caagcagaag ggagagtacc tcccgctgct gcaagggaag | 240 |
| tcgctgggga tgatcttcga gaagcggtca accagaaccc ggctgtcaac cgaaaccggg | 300 |
| ttcgcactgc tgggggggaca cccgtgcttc ctgaccaccc aagacatcca cctgggagtg | 360 |
| aacgaatcgc tgaccgacac cgcccgcgtg ctgagctcaa tggcggacgc cgtgctggcc | 420 |
| cgcgtgtaca agcagtccga cctggacacc ctggccaagg aagcgtccat cccgatcatc | 480 |
| aacggactgt ccgacctgta ccacccgatc cagatcctgg cagactacct gaccctgcaa | 540 |
| gaacactaca gctccctgaa gggcctgacc ctgtcatgga tcggggacgg gaacaacatc | 600 |
| ctgcactcca taatgatgtc agccgccaag ttcggaatgc acctccaagc cgcaaccccg | 660 |
| aagggctacg aaccggacgc atcagtgacc aaactggccg agcagtacgc caaggaaaac | 720 |
| ggcaccaagc tcctgctgac caacgacccg ctggaggccg cacacggggg gaacgtgctg | 780 |
| atcaccgaca cctggatctc catgggacag gaggaggaaa agaagaagcg gctgcaggcg | 840 |
| ttccaggggt accaggtcac catgaaaacc gcgaaggtcg cggcatcaga ctggaccttc | 900 |
| ctgcactgcc tgccccggaa gccggaagag gtggacgacg aggtgttcta ctcgccgcgc | 960 |
| tcgctggtgt tccccgaggc ggagaacagg aagtggacca tcatggcggt gatggtcagc | 1020 |
| ctcctgaccg actactcgcc gcagctgcag aagccgaagt tctga | 1065 |

<210> SEQ ID NO 199
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 199

| | |
|---|---|
| atgctggtca acctccgcat cctcctcaac aacgccgcat tcagaaacgg gcacaacttc | 60 |
| atggtcagaa acttccgctg cgggcaaccc ctacaaaaca aggtccagct caaggggcgg | 120 |
| gacctcctga ccctgaagaa cttcaccggc gaagagatca agtacatgct gtggctctcc | 180 |

```
gccgacctga agttccgcat caagcagaag ggagagtacc tcccgctgct gcaagggaag    240
tcgctgggga tgatcttcga gaagcggtca accagaaccc ggctgtcaac cgaaaccggg    300
ttcgcactgc tggggggaca cccgtgcttc ctgaccaccc aagacatcca cctgggagtg    360
aacgaatcgc tgaccgacac cgcccgcgtg ctgagctcaa tggcggacgc cgtgctggcc    420
cgcgtgtaca agcagtccga cctggacacc ctggccaagg aagcgtccat cccgatcatc    480
aacggactgt ccgacctgta ccacccgatc cagatcctgg cagactacct gaccctgcaa    540
gaacactaca gctccctgaa gggcctgacc ctgtcatgga tcggggacgg gaacaacatc    600
ctgcactcca taatgatgtc agccgccaag ttcggaatgc acctccaagc cgcaaccccg    660
aagggctacg aaccggacgc atcagtgacc aaactggccg agcagtacgc caaggaaaac    720
ggcaccaagc tcctgctgac caacgacccg ctggaggccg cacacggggg gaacgtgctg    780
atcaccgaca cctggatctc catgggacag gaggaggaaa agaagaagcg gctgcaggcg    840
ttccaggggt accaggtcac catgaaaacc gcgaaggtcg cggcatcaga ctggaccttc    900
ctgcactgcc tgccccggaa gccggaagag gtggacgacg aggtgttcta ctcgccgcgc    960
tcgctggtgt tccccgaggc ggagaacagg aagtggacca tcatggcggt gatggtcagc   1020
ctcctgaccg actactcgcc gcagctgcag aagccgaagt tctga                  1065
```

<210> SEQ ID NO 200
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 200

```
atgctggtca acctccgcat cctcctcaac aacgccgcat tcagaaacgg gcacaacttc     60
atggtcagaa acttccgctg cgggcaaccc ctacaaaacc gggtccagct caaggggcgg    120
gacctcctga ccctgaagaa cttcaccggc gaagagatca agtacatgct gtggctctcc    180
gccgacctga agttccgcat caagcagaag ggagagtacc tcccgctgct gcaagggaag    240
tcgctgggga tgatcttcga gaagcggtca accagaaccc ggctgtcaac cgaaaccggg    300
ttcgcactgc tggggggaca cccgtgcttc ctgaccaccc aagacatcca cctgggagtg    360
aacgaatcgc tgaccgacac cgcccgcgtg ctgagctcaa tggcggacgc cgtgctggcc    420
cgcgtgtaca agcagtccga cctggacacc ctggccaagg aagcgtccat cccgatcatc    480
aacggactgt ccgacctgta ccacccgatc cagatcctgg cagactacct gaccctgcaa    540
gaacactaca gctccctgaa gggcctgacc ctgtcatgga tcggggacgg gaacaacatc    600
ctgcactcca taatgatgtc agccgccaag ttcggaatgc acctccaagc cgcaaccccg    660
aagggctacg aaccggacgc atcagtgacc aaactggccg agcagtacgc caaggaaaac    720
ggcaccaagc tcctgctgac caacgacccg ctggaggccg cacacggggg gaacgtgctg    780
atcaccgaca cctggatctc catgggacag gaggaggaaa agaagaagcg gctgcaggcg    840
ttccaggggt accaggtcac catgaaaacc gcgaaggtcg cggcatcaga ctggaccttc    900
ctgcactgcc tgccccggaa gccggaagag gtggacgacg aggtgttcta ctcgccgcgc    960
tcgctggtgt tccccgaggc ggagaacagg aagtggacca tcatggcggt gatggtcagc   1020
ctcctgaccg actactcgcc gcagctgcag aagccgaagt tctga                  1065
```

<210> SEQ ID NO 201

```
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 201
atgctggtca acctccgcat cctcctcaac aacgccgcat tcagaaacgg gcacaacttc      60
atggtcagaa acttccgctg cgggcaaccc ctacaaaacc gggtccagct caaggggcgg     120
gacctcctga ccctgaagaa cttcaccggc gaagagatcc ggtacatgct gtggctctcc     180
gccgacctga agttccgcat caagcagaag ggagagtacc tcccgctgct gcaagggaag     240
tcgctgggga tgatcttcga gaagcggtca accagaaccc ggctgtcaac cgaaaccggg     300
ttcgcactgc tggggggaca cccgtgcttc ctgaccaccc aagacatcca cctgggagtg     360
aacgaatcgc tgaccgacac cgcccgcgtg ctgagctcaa tggcggacgc cgtgctggcc     420
cgcgtgtaca agcagtccga cctggacacc ctggccaagg aagcgtccat cccgatcatc     480
aacggactgt ccgacctgta ccacccgatc agatcctgg cagactacct gaccctgcaa      540
gaacactaca gctccctgaa gggcctgacc ctgtcatgga tcggggacgg aacaacatc      600 ctgcactcca taatgatgtc agccgccaag ttcggaatgc acctccaagc cgcaaccccg     660
aagggctacg aaccggacgc atcagtgacc aaactggccg agcagtacgc caaggaaaac     720
ggcaccaagc tcctgctgac caacgacccg ctggaggccg cacacggggg gaacgtgctg     780
atcaccgaca cctggatctc catgggacag gaggaggaaa agaagaagcg gctgcaggcg     840
ttccaggggt accaggtcac catgaaaacc gcgaaggtcg cggcatcaga ctggaccttc     900
ctgcactgcc tgccccggaa gccggaagag gtggacgacg aggtgttcta ctcgccgcgc     960
tcgctggtgt tccccgaggc ggagaacagg aagtggacca tcatggcggt gatggtcagc    1020
ctcctgaccg actactcgcc gcagctgcag aagccgaagt tctga                    1065

<210> SEQ ID NO 202
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 202
atgctggtca acctgcgcat cctgctgaac aacgccgcct tccgcaacgg ccacaacttc      60
atggtgcgca acttccgctg cggccagccc ctgcagaaca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga gaagcgcagc acccgcaccc gcctgagcac cgagacaggc     300
ttcgccctgc tgggcggcca ccctgcttc ctgaccaccc aggacatcca cctgggcgtg      360
aacgagagcc tgaccgacac cgcccgcgtg ctgagcagca tggccgacgc cgtgctggcc     420
cgcgtgtaca agcagagcga cctggacacc ctggccaagg aggccagcat cccgatcatc     480
aacggcctga gcgacctgta ccaccccatc agatcctgg ccgactacct gaccctgcag      540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
```

```
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagccccgc     960 agcctggtgt tccccgaggc cgagaaccgc aagtggacca tcatggccgt gatggtgagc   1020
ctgctgaccg actacagccc ccagctgcag aagcccaagt ctga                    1065

<210> SEQ ID NO 203
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 203
atgctggtca acctgcgcat cctgctgaac aacgccgcct ccgcaacgg ccacaacttc      60 atggtgcgca acttccgctg cggccagccc ctgcagaacc gggtgcagct gaagggccgc   120
gacctgctga ccctgaagaa cttcaccggc gaggagatca agtacatgct gtggctgagc   180
gccgacctga agttccgcat caagcagaag ggcgagtacc tgcccctgct gcagggcaag   240
agcctgggca tgatcttcga gaagcgcagc acccgcaccc gcctgagcac cgagacaggc   300
ttcgccctgc tgggcggcca cccctgcttc ctgaccaccc aggacatcca cctgggcgtg   360
aacgagagcc tgaccgacac cgcccgcgtg ctgagcagca tggccgacgc cgtgctggcc   420
cgcgtgtaca gcagagcga cctggacacc ctggccaagg aggccagcat ccccatcatc   480
aacggcctga gcgacctgta ccaccccatc agatcctgg ccgactacct gaccctgcag    540
gagcactaca gcagcctgaa gggcctgacc ctgagctgga tcggcgacgg caacaacatc   600
ctgcacagca tcatgatgag cgccgccaag ttcggcatgc acctgcaggc cgccaccccc   660
aagggctacg agcccgacgc cagcgtgacc aagctggccg agcagtacgc caaggagaac   720
ggcaccaagc tgctgctgac caacgacccc ctggaggccc ccacggcgg caacgtgctg    780 atcaccgaca cctggatcag catgggccag gaggaggaga agaagaagcg cctgcaggcc   840
ttccagggct accaggtgac catgaagacc gccaaggtgg ccgccagcga ctggaccttc    900
ctgcactgcc tgccccgcaa gcccgaggag gtggacgacg aggtgttcta cagccccgc    960 agcctggtgt tccccgaggc cgagaaccgc aagtggacca tcatggccgt gatggtgagc  1020
ctgctgaccg actacagccc ccagctgcag aagcccaagt ctga                   1065

<210> SEQ ID NO 204
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 204
atgcttgtca atctccgcat cctccttaac aacgccgcgt ttagaaacgg ccacaacttc     60
atggtccgga acttcagatg tggccagccg cttcaaaaca aggtccagct gaagggccgg   120
gatcttctga ccctgaagaa ctttactggc gaagagatca agtacatgct ctggctctcc   180
gcggacttga agttccgcat taagcagaag ggggaatacc ttccgctgct tcaaggaaag   240
agcctcggca tgatctttga gaagcgctca accaggaccc gcctttctac tgaaactggg   300
ttcgcgctgc tcggtggcca cccctgcttc ctgacgaccc aggacatcca cctcggagtg   360
```

```
aacgaatccc tcaccgatac cgcccgggtg ttatcgagca tggcagatgc cgtgctggcc    420
agggtgtaca acagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaagaagcg gctgcaggcg    840 ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                    1065
```

<210> SEQ ID NO 205  
<211> LENGTH: 1065  
<212> TYPE: DNA  
<213> ORGANISM: Artificial sequence  
<220> FEATURE:  
<223> OTHER INFORMATION: Synthetic polynucleotide

<400> SEQUENCE: 205

```
atgcttgtca atctccgcat cctccttaac aacgccgcgt ttagaaacgg ccacaacttc     60
atggtccgga acttcagatg tggccagccg cttcaaaacc gggtccagct gaagggccgg    120
gatcttctga ccctgaagaa ctttactggc gaagagatca agtacatgct ctggctctcc    180
gcggacttga agttccgcat taagcagaag ggggaatacc ttccgctgct tcaaggaaag    240
agcctcggca tgatctttga gaagcgctca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca acagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaagaagcg gctgcaggcg    840 ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                    1065
```

<210> SEQ ID NO 206  
<211> LENGTH: 1068  
<212> TYPE: DNA  
<213> ORGANISM: Artificial sequence  
<220> FEATURE:  
<223> OTHER INFORMATION: Synthetic polynucleotide

<400> SEQUENCE: 206

```
atgggccttg tcaatctccg catcctcctt aacaacgccg cgtttagaaa cggccacaac      60
ttcatggtcc ggaacttcag atgtggccag ccgcttcaaa acaaggtcca gctgaagggc     120
cgggatcttc tgaccctgaa gaactttact ggcgaagaga tcaagtacat gctctggctc     180
tccgcggact tgaagttccg cattaagcag aaggggaat accttccgct gcttcaagga      240
aagagcctcg gcatgatctt tgagaagcgc tcaaccagga cccgcctttc tactgaaact     300
gggttcgcgc tgctcggtgg ccaccnctgc ttcctgacga cccaggacat ccacctcgga     360
gtgaacgaat ccctcaccga taccgccggg tgttatcga gcatggcaga tgccgtgctg      420
gccagggtgt acaaacagtc cgatctggac actctggcca aggaggcgtc aattcctatt     480
atcaacggcc ttagtgacct ctaccatccg attcagatcc tggccgatta cctcaccctg     540
caagaacact acagctccct gaagggtctg acattgtcct ggatcggcga cggcaacaac     600
attctccatt ccatcatgat gtccgccgca aaattcggca tgcatcttca agccgccacg     660
ccgaagggtt acgagcccga cgcttccgtg actaagctcg ccgagcagta cgctaaggag     720
aacggaacca agcttctgct gactaacgac ccactagaag cagcccacgg gggcaacgtg     780
cttattactg acacctggat ctccatgggc caggaagaag agaaaaagaa gcggctgcag     840
gcgttccagg gatatcaggt caccatgaaa accgccaagg tcgctgcctc cgactggacc     900
ttcctgcact gcctgcctcg caagcctgaa gaagtggacg acgaggtgtt ctactcgcca     960
cggagcctcg tgttccccga ggccgagaat agaaagtgga ccatcatggc cgtgatggtg    1020
tcactgctca ccgactacag cccgcagctt cagaagccca agttctag                 1068
```

<210> SEQ ID NO 207
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 207

```
atgggccttg tcaatctccg catcctcctt aacaacgccg cgtttagaaa cggccacaac      60
ttcatggtcc ggaacttcag atgtggccag ccgcttcaaa accgggtcca gctgaagggc     120
cgggatcttc tgaccctgaa gaactttact ggcgaagaga tcaagtacat gctctggctc     180
tccgcggact tgaagttccg cattaagcag aaggggaat accttccgct gcttcaagga      240
aagagcctcg gcatgatctt tgagaagcgc tcaaccagga cccgcctttc tactgaaact     300
gggttcgcgc tgctcggtgg ccaccnctgc ttcctgacga cccaggacat ccacctcgga     360
gtgaacgaat ccctcaccga taccgccggg tgttatcga gcatggcaga tgccgtgctg      420
gccagggtgt acaaacagtc cgatctggac actctggcca aggaggcgtc aattcctatt     480
atcaacggcc ttagtgacct ctaccatccg attcagatcc tggccgatta cctcaccctg     540
caagaacact acagctccct gaagggtctg acattgtcct ggatcggcga cggcaacaac     600
attctccatt ccatcatgat gtccgccgca aaattcggca tgcatcttca agccgccacg     660
ccgaagggtt acgagcccga cgcttccgtg actaagctcg ccgagcagta cgctaaggag     720
aacggaacca agcttctgct gactaacgac ccactagaag cagcccacgg gggcaacgtg     780
cttattactg acacctggat ctccatgggc caggaagaag agaaaaagaa gcggctgcag     840
gcgttccagg gatatcaggt caccatgaaa accgccaagg tcgctgcctc cgactggacc     900
```

| | | |
|---|---|---|
| ttcctgcact gcctgcctcg caagcctgaa gaagtggacg acgaggtgtt ctactcgcca | 960 | |
| cggagcctcg tgttcccga ggccgagaat agaaagtgga ccatcatggc cgtgatggtg | 1020 | |
| tcactgctca ccgactacag cccgcagctt cagaagccca agttctag | 1068 | |

```
<210> SEQ ID NO 208
<211> LENGTH: 1071
<212> TYPE: DNA
<213> ORGANISM: Artificial sequence
<220> FEATURE:
<223> OTHER INFORMATION: Synthetic polynucleotide

<400> SEQUENCE: 208
```

| | | |
|---|---|---|
| atgggcggac ttgtcaatct ccgcatcctc cttaacaacg ccgcgtttag aaacggccac | 60 | |
| aacttcatgg tccggaactt cagatgtggc cagccgcttc aaaacaaggt ccagctgaag | 120 | |
| ggccgggatc ttctgaccct gaagaacttt actggcgaag agatcaagta catgctctgg | 180 | |
| ctctccgcgg acttgaagtt ccgcattaag cagaagggg aataccttcc gctgcttcaa | 240 | |
| ggaaagagcc tcggcatgat ctttgagaag cgctcaacca ggacccgcct ttctactgaa | 300 | |
| actgggttcg cgctgctcgg tggccacccc tgcttcctga cgacccagga catccacctc | 360 | |
| ggagtgaacg aatccctcac cgataccgcc cgggtgttat cgagcatggc agatgccgtg | 420 | |
| ctggccaggg tgtacaaaca gtccgatctg acactctggc caaggaggc gtcaattcct | 480 | |
| attatcaacg gccttagtga cctctaccat ccgattcaga tcctggccga ttacctcacc | 540 | |
| ctgcaagaac actacagctc cctgaagggt ctgacattgt cctggatcgg cgacggcaac | 600 | |
| aacattctcc attccatcat gatgtccgcc gcaaaattcg gcatgcatct tcaagccgcc | 660 | |
| acgccgaagg gttacgagcc cgacgcttcc gtgactaagc tcgccgagca gtacgctaag | 720 | |
| gagaacggaa ccaagcttct gctgactaac gacccactag aagcagccca cggggcaac | 780 | |
| gtgcttatta ctgacacctg gatctccatg ggccaggaag aagagaaaaa gaagcggctg | 840 | |
| caggcgttcc agggatatca ggtcaccatg aaaaccgcca aggtcgctgc ctccgactgg | 900 | |
| accttcctgc actgcctgcc tcgcaagcct gaagaagtgg acgacgaggt gttctactcg | 960 | |
| ccacggagcc tcgtgttccc cgaggccgag aatagaaagt ggaccatcat ggccgtgatg | 1020 | |
| gtgtcactgc tcaccgacta cagcccgcag cttcagaagc ccaagttcta g | 1071 | |

```
<210> SEQ ID NO 209
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 209
```

| | | |
|---|---|---|
| atggccctttt caatctccg catcctcctt aacaacgccg cgtttagaaa cggccacaac | 60 | |
| ttcatggtcc ggaacttcag atgtggccag ccgcttcaag gcaaggtcca gctgaagggc | 120 | |
| cgggatcttc tgaccctgaa gaacttact ggcgaagaga tcaagtacat gctctggctc | 180 | |
| tccgcggact tgaagttccg cattaagcag aaggggaat accttccgct gcttcaagga | 240 | |
| aagagcctcg gcatgatctt tgagaagcgc tcaaccagga cccgcctttc tactgaaact | 300 | |
| gggttcgcgc tgctcggtgg ccacccctgc ttcctgacga cccaggacat ccacctcgga | 360 | |
| gtgaacgaat ccctcaccga taccgcccg gtgttatcga gcatggcaga tgccgtgctg | 420 | |
| gccagggtgt acaaacagtc cgatctgac actctggcca aggaggcgtc aattcctatt | 480 | |
| atcaacggcc ttagtgacct ctaccatccg attcagatcc tggccgatta cctcaccctg | 540 | |

```
caagaacact acagctccct gaagggtctg acattgtcct ggatcggcga cggcaacaac      600
attctccatt ccatcatgat gtccgccgca aaattcggca tgcatcttca agccgccacg      660
ccgaagggtt acgagcccga cgcttccgtg actaagctcg ccgagcagta cgctaaggag      720
aacggaacca agcttctgct gactaacgac ccactagaag cagcccacgg gggcaacgtg      780
cttattactg acacctggat ctccatgggc caggaagaag agaaaaagaa gcggctgcag      840
gcgttccagg gatatcaggt caccatgaaa accgccaagg tcgctgcctc cgactggacc      900
ttcctgcact gcctgcctcg caagcctgaa gaagtggacg acgaggtgtt ctactcgcca      960
cggagcctcg tgttccccga ggccgagaat agaaagtgga ccatcatggc cgtgatggtg     1020
tcactgctca ccgactacag cccgcagctt cagaagccca agttctagat aagtgaa        1077
```

<210> SEQ ID NO 210
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 210

```
atggcccttt tcaatctccg catcctcctt aacaacgccg cgtttagaaa cggccacaac       60
ttcatggtcc ggaacttcag atgtggccag ccgcttcaag gccgggtcca gctgaagggc      120
cgggatcttc tgaccctgaa gaactttact ggcgaagaga tcaagtacat gctctggctc      180
tccgcggact tgaagttccg cattaagcag aaggggaat  accttccgct gcttcaagga      240
aagagcctcg gcatgatctt tgagaagcgc tcaaccagga cccgccttc  tactgaaact      300 gggttcgcgc tgctcggtgg ccaccccctgc ttcctgacga cccaggacat ccacctcgga     360
gtgaacgaat ccctcaccga taccgcccgg tgttatcga  gcatggcaga tgccgtgctg      420
gccagggtgt acaaacagtc cgatctggac actctggcca aggaggcgtc aattcctatt      480
atcaacggcc ttagtgacct ctaccatccg attcagatcc tggccgatta cctcaccctg      540
caagaacact acagctccct gaagggtctg acattgtcct ggatcggcga cggcaacaac      600
attctccatt ccatcatgat gtccgccgca aaattcggca tgcatcttca agccgccacg      660
ccgaagggtt acgagcccga cgcttccgtg actaagctcg ccgagcagta cgctaaggag      720
aacggaacca agcttctgct gactaacgac ccactagaag cagcccacgg gggcaacgtg      780
cttattactg acacctggat ctccatgggc caggaagaag agaaaaagaa gcggctgcag      840
gcgttccagg gatatcaggt caccatgaaa accgccaagg tcgctgcctc cgactggacc      900
ttcctgcact gcctgcctcg caagcctgaa gaagtggacg acgaggtgtt ctactcgcca      960
cggagcctcg tgttccccga ggccgagaat agaaagtgga ccatcatggc cgtgatggtg     1020
tcactgctca ccgactacag cccgcagctt cagaagccca agttctagat aagtgaa        1077
```

<210> SEQ ID NO 211
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 211

```
atggcccttt tcaatctccg catcctcctt aacaacgccg cgtttagaaa cggccacaac       60
ttcatggtcc ggaacttcag atgtggccag ccgcttcaag gccgggtcca gctgaagggc      120
```

```
cgggatcttc tgaccctgaa gaactttact ggcgaagaga tcaggtacat gctctggctc      180
tccgcggact tgaagttccg cattaagcag aaggggaat accttccgct gcttcaagga       240
aagagcctcg gcatgatctt tgagaagcgc tcaaccagga cccgcctttc tactgaaact      300
gggttcgcgc tgctcggtgg ccaccctgc ttcctgacga cccaggacat ccacctcgga       360
gtgaacgaat ccctcaccga taccgcccgg gtgttatcga gcatggcaga tgccgtgctg      420
gccagggtgt acaaacagtc cgatctggac actctggcca aggaggcgtc aattcctatt      480
atcaacggcc ttagtgacct ctaccatccg attcagatcc tggccgatta cctcaccctg      540
caagaacact acagctccct gaagggtctg acattgtcct ggatcggcga cggcaacaac      600
attctccatt ccatcatgat gtccgccgca aaattcggca tgcatcttca agccgccacg      660
ccgaagggtt acgagcccga cgcttccgtg actaagctcg ccgagcagta cgctaaggag      720
aacggaacca agcttctgct gactaacgac ccactagaag cagcccacgg gggcaacgtg      780
cttattactg acacctggat ctccatgggc caggaagaag agaaaaagaa gcggctgcag      840
gcgttccagg gatatcaggt caccatgaaa accgccaagg tcgctgcctc cgactggacc      900
ttcctgcact gcctgcctcg caagcctgaa gaagtggacg acgaggtgtt ctactcgcca      960
cggagcctcg tgttccccga ggccgagaat agaaagtgga ccatcatggc cgtgatggtg     1020
tcactgctca ccgactacag cccgcagctt cagaagccca gttctagat aagtgaa        1077
```

<210> SEQ ID NO 212
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 212

```
atggcccttg tcaatctccg catcctcctt aacaacgccg cgtttagaaa cggccacaac       60
ttcatggtcc ggaacttcag atgtggccag ccgcttcaag gcagggtcca gctgaagggc      120
cgggatcttc tgaccctgaa gaactttact ggcgaagaga tcaagtacat gctctggctc      180
tccgcggact tgaagttccg cattaagcag aaggggaat accttccgct gcttcaagga       240
aagagcctcg gcatgatctt tgagaagcgc tcaaccagga cccgcctttc tactgaaact      300
gggttcgcgc tgctcggtgg ccaccctgc ttcctgacga cccaggacat ccacctcgga       360
gtgaacgaat ccctcaccga taccgcccgg gtgttatcga gcatggcaga tgccgtgctg      420
gccagggtgt acaaacagtc cgatctggac actctggcca aggaggcgtc aattcctatt      480
atcaacggcc ttagtgacct ctaccatccg attcagatcc tggccgatta cctcaccctg      540
caagaacact acagctccct gaagggtctg acattgtcct ggatcggcga cggcaacaac      600
attctccatt ccatcatgat gtccgccgca aaattcggca tgcatcttca agccgccacg      660
ccgaagggtt acgagcccga cgcttccgtg actaagctcg ccgagcagta cgctaaggag      720
aacggaacca agcttctgct gactaacgac ccactagaag cagcccacgg gggcaacgtg      780
cttattactg acacctggat ctccatgggc caggaagaag agaaaaagaa gcggctgcag      840
gcgttccagg gatatcaggt caccatgaaa accgccaagg tcgctgcctc cgactggacc      900
ttcctgcact gcctgcctcg caagcctgaa gaagtggacg acgaggtgtt ctactcgcca      960
cggagcctcg tgttccccga ggccgagaat agaaagtgga ccatcatggc cgtgatggtg     1020
tcactgctca ccgactacag cccgcagctt cagaagccca gttctaagt gaataga        1077
```

<210> SEQ ID NO 213
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 213

| | | | | | |
|---|---|---|---|---|---|
| atggcccttt | tcaatctccg | catcctcctt | aacaacgccg | cgtttagaaa | cggccacaac | 60 |
| ttcatggtcc | ggaacttcag | atgtggccag | ccgcttcaag | tcaaggtcca | gctgaagggc | 120 |
| cgggatcttc | tgaccctgaa | gaactttact | ggcgaagaga | tcaagtacat | gctctggctc | 180 |
| tccgcggact | tgaagttccg | cattaagcag | aaggggaat | accttccgct | gcttcaagga | 240 |
| aagagcctcg | gcatgatctt | tgagaagcgc | tcaaccagga | cccgcctttc | tactgaaact | 300 |
| gggttcgcgc | tgctcggtgg | ccaccccgtgc | ttcctgacga | cccaggacat | ccacctcgga | 360 |
| gtgaacgaat | ccctcaccga | taccgcccgg | gtgttatcga | gcatggcaga | tgccgtgctg | 420 |
| gccagggtgt | acaaacagtc | cgatctggac | actctggcca | aggaggcgtc | aattcctatt | 480 |
| atcaacggcc | ttagtgacct | ctaccatccg | attcagatcc | tggccgatta | cctcacccctg | 540 |
| caagaacact | acagctccct | gaagggtctg | acattgtcct | ggatcggcga | cggcaacaac | 600 |
| attctccatt | ccatcatgat | gtccgccgca | aaattcggca | tgcatcttca | agccgccacg | 660 |
| ccgaagggtt | acgagcccga | cgcttccgtg | actaagctcg | ccgagcagta | cgctaaggag | 720 |
| aacggaacca | agcttctgct | gactaacgac | ccactagaag | cagcccacgg | gggcaacgtg | 780 |
| cttattactg | acacctggat | ctccatgggc | caggaagaag | agaaaaagaa | gcggctgcag | 840 |
| gcgttccagg | gatatcaggt | caccatgaaa | accgccaagg | tcgctgcctc | cgactggacc | 900 |
| ttcctgcact | gcctgcctcg | caagcctgaa | gaagtggacg | acgaggtgtt | ctactcgcca | 960 |
| cggagcctcg | tgttccccga | ggccgagaat | agaaagtgga | ccatcatggc | cgtgatggtg | 1020 |
| tcactgctca | ccgactacag | cccgcagctt | cagaagccca | gttctagat | aagtgaa | 1077 |

<210> SEQ ID NO 214
<211> LENGTH: 1077
<212> TYPE: DNA
<213> ORGANISM: Artificial sequence
<220> FEATURE:
<223> OTHER INFORMATION: Synthetic polynucleotide

<400> SEQUENCE: 214

| | | | | | |
|---|---|---|---|---|---|
| atggcccttt | tcaatctccg | catcctcctt | aacaacgccg | cgtttagaaa | cggccacaac | 60 |
| ttcatggtcc | ggaacttcag | atgtggccag | ccgcttcaag | tcagggtcca | gctgaagggc | 120 |
| cgggatcttc | tgaccctgaa | gaactttact | ggcgaagaga | tcaagtacat | gctctggctc | 180 |
| tccgcggact | tgaagttccg | cattaagcag | aaggggaat | accttccgct | gcttcaagga | 240 |
| aagagcctcg | gcatgatctt | tgagaagcgc | tcaaccagga | cccgcctttc | tactgaaact | 300 |
| gggttcgcgc | tgctcggtgg | ccaccccgtgc | ttcctgacga | cccaggacat | ccacctcgga | 360 |
| gtgaacgaat | ccctcaccga | taccgcccgg | gtgttatcga | gcatggcaga | tgccgtgctg | 420 |
| gccagggtgt | acaaacagtc | cgatctggac | actctggcca | aggaggcgtc | aattcctatt | 480 |
| atcaacggcc | ttagtgacct | ctaccatccg | attcagatcc | tggccgatta | cctcacccctg | 540 |
| caagaacact | acagctccct | gaagggtctg | acattgtcct | ggatcggcga | cggcaacaac | 600 |
| attctccatt | ccatcatgat | gtccgccgca | aaattcggca | tgcatcttca | agccgccacg | 660 |
| ccgaagggtt | acgagcccga | cgcttccgtg | actaagctcg | ccgagcagta | cgctaaggag | 720 |

```
aacggaacca agcttctgct gactaacgac ccactagaag cagcccacgg gggcaacgtg    780
cttattactg acacctggat ctccatgggc caggaagaag agaaaaagaa gcggctgcag    840
gcgttccagg gatatcaggt caccatgaaa accgccaagg tcgctgcctc cgactggacc    900
ttcctgcact gcctgcctcg caagcctgaa gaagtggacg acgaggtgtt ctactcgcca    960
cggagcctcg tgttccccga ggccgagaat agaaagtgga ccatcatggc cgtgatggtg   1020
tcactgctca ccgactacag cccgcagctt cagaagccca agttctagat aagtgaa      1077
```

<210> SEQ ID NO 215
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 215

```
atgctgttca acctgcgcat cctgctgaac aacgccgcct tccgcaacgg ccacaacttc     60
atggtgcgca acttccgctg cggccagccc ctgcagaaca aggtgcagct gaagggccgc    120
gacctgctga ccctgaagaa cttcaccggc gaggagatca agtacatgct gtggctgagc    180
gccgacctga agttccgcat caagcagaag ggcgagtacc tgcccctgct gcagggcaag    240
agcctgggca tgatcttcga agcgcagc acccgcaccc gcctgagcac cgagacaggc      300
ttcgccctgc tgggcggcca cccctgcttc ctgaccaccc aggacatcca cctgggcgtg    360
aacgagagcc tgaccgacac cgcccgcgtg ctgagcagca tggccgacgc cgtgctggcc    420
cgcgtgtaca agcagagcga cctggacacc ctggccaagg aggccagcat ccccatcatc    480
aacggcctga gcgacctgta ccaccccatc cagatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccacccc     660 aagggctacg agcccgacgc cagcgtgacc aagctggccg agcagtacgc caaggagaac    720
ggcaccaagc tgctgctgac caacgacccc ctggaggccg cccacggcgg caacgtgctg    780
atcaccgaca cctggatcag catgggccag gaggaggaga gaagaagcg cctgcaggcc     840 ttccagggct accaggtgac catgaagacc gccaaggtgg ccgccagcga ctggaccttc    900
ctgcactgcc tgccccgcaa gcccgaggag gtggacgacg aggtgttcta cagccccgc    960 agcctggtgt tccccgaggc cgagaaccgc aagtggacca tcatggccgt gatggtgagc   1020
ctgctgaccg actacagccc ccagctgcag aagcccaagt tctga                   1065
```

<210> SEQ ID NO 216
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 216

```
atgggagtat tcaacctgcg catcctgctg aacaacgccg ccttccgcaa cggccacaac     60
ttcatggtgc gcaacttccg ctgcggccag cccctgcaga acaaggtgca gctgaagggc    120
cgcgacctgc tgaccctgaa gaacttcacc ggcgaggaga tcaagtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccccctgc ttcctgacca cccaggacat ccacctgggc    360
```

```
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca agctgctgct gaccaacgac ccctggagg ccgcccacgg cggcaacgtg    780
ctgatcaccg acacctggat cagcatgggc caggaggagg agaagaagaa cgcctgcag    840 gccttccagg gctaccaggt gaccatgaag accgccaagg tggccgccag cgactggacc    900
ttcctgcact gcctgccccg caagcccgag gaggtggacg acgaggtgtt ctacagcccc    960
cgcagcctgg tgttccccga ggccgagaac cgcaagtgga ccatcatggc cgtgatggtg    1020
agcctgctga ccgactacag ccccagctg cagaagccca agttctga    1068
```

<210> SEQ ID NO 217
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 217

```
atgggagtat tcaacctgcg catcctgctg aacaacgccg ccttccgcaa cggccacaac    60
ttcatggtgc gcaacttccg ctgcggccag ccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca agctgctgct gaccaacgac ccctggagg ccgcccacgg cggcaacgtg    780
ctgatcaccg acacctggat cagcatgggc caggaggagg agaagaagaa cgcctgcag    840 gccttccagg gctaccaggt gaccatgaag accgccaagg tggccgccag cgactggacc    900
ttcctgcact gcctgccccg caagcccgag gaggtggacg acgaggtgtt ctacagcccc    960
cgcagcctgg tgttccccga ggccgagaac cgcaagtgga ccatcatggc cgtgatggtg    1020
agcctgctga ccgactacag ccccagctg cagaagccca agttctga    1068
```

<210> SEQ ID NO 218
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 218

```
atgctggtat tcaacctgcg catcctgctg aacaacgccg ccttccgcaa cggccacaac      60
ttcatggtgc gcaacttccg ctgcggccag ccccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca gctgctgct gaccaacgac ccctggagg ccgcccacgg cggcaacgtg      780
ctgatcaccg acacctggat cagcatgggc caggaggagg agaagaagaa cgcctgcag    840
gccttccagg gctaccaggt gaccatgaag accgccaagg tggccgccag cgactggacc    900
ttcctgcact gcctgccccg caagcccgag gaggtggacg acgaggtgtt ctacagcccc    960
cgcagcctgg tgttccccga ggccgagaac cgcaagtgga ccatcatggc cgtgatggtg   1020
agcctgctga ccgactacag cccccagctg cagaagccca agttctga               1068
```

<210> SEQ ID NO 219
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 219

```
atgggagtat tcaacctgcg catcctgctg aacaacgccg ccttccgcaa cggccacaac      60
ttcatggtgc gcaacttccg ctgcggccag ccccctgcaga acaaggtgca gctgaagggc    120
cgcgacctgc tgaccctgaa gaacttcacc ggcgaggaga tcaagtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca gctgctgct gaccaacgac ccctggagg ccgcccacgg cggcaacgtg      780
ctgatcaccg acacctggat cagcatgggc caggaggagg agaagaagaa cgcctgcag    840
gccttccagg gctaccaggt gaccatgaag accgccaagg tggccgccag cgactggacc    900
ttcctgcact gcctgccccg caagcccgag gaggtggacg acgaggtgtt ctacagcccc    960
```

```
cgcagcctgg tgttccccga ggccgagaac cgcaagtgga ccatcatggc cgtgatggtg    1020
agcctgctga ccgactacag cccccagctg cagaagccca agttctga               1068

<210> SEQ ID NO 220
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 220
atgggagtat tcaacctgcg catcctgctg aacaacgccg ccttccgcaa cggccacaac      60
ttcatggtgc gcaacttccg ctgcggccag cccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca gctgctgct gaccaacgac cccctggagg ccgcccacgg cggcaacgtg    780
ctgatcaccg acacctggat cagcatgggc caggaggagg agaagaagaa cgcctgcag    840 gccttccagg gctaccaggt gaccatgaag accgccaagg tggccgccag cgactggacc    900
ttcctgcact gcctgccccg caagcccgag gaggtggacg acgaggtgtt ctacagcccc    960
cgcagcctgg tgttccccga ggccgagaac cgcaagtgga ccatcatggc cgtgatggtg    1020
agcctgctga ccgactacag cccccagctg cagaagccca agttctga                1068

<210> SEQ ID NO 221
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 221
atgctggtat tcaacctgcg catcctgctg aacaacgccg ccttccgcaa cggccacaac      60
ttcatggtgc gcaacttccg ctgcggccag cccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
```

-continued

| | |
|---|---|
| caggagcact acagcagcct gaagggcctg accctgagct ggatcggcga cggcaacaac | 600 |
| atcctgcaca gcatcatgat gagcgccgcc aagttcggca tgcacctgca ggccgccacc | 660 |
| cccaagggct acgagcccga cgccagcgtg accaagctgg ccgagcagta cgccaaggag | 720 |
| aacggcacca agctgctgct gaccaacgac ccctggagg ccgccacgg cggcaacgtg | 780 |
| ctgatcaccg acacctggat cagcatgggc caggaggagg agaagaagaa gcgcctgcag | 840 |
| gccttccagg gctaccaggt gaccatgaag accgccaagg tggccgccag cgactggacc | 900 |
| ttcctgcact gcctgccccg caagcccgag gaggtggacg acgaggtgtt ctacagcccc | 960 |
| cgcagcctgg tgttccccga ggccgagaac cgcaagtgga ccatcatggc cgtgatggtg | 1020 |
| agcctgctga ccgactacag cccccagctg cagaagccca gttctga | 1068 |

<210> SEQ ID NO 222
<211> LENGTH: 1073
<212> TYPE: DNA
<213> ORGANISM: Artificial sequence
<220> FEATURE:
<223> OTHER INFORMATION: Synthetic polynucleotide

<400> SEQUENCE: 222

| | |
|---|---|
| atgttgttca acttgaggat cttgttgaac aacgccgcct tcaggaacgg acacaacttc | 60 |
| atggtaagga acttcaggtg cggacagccc ttgcagaaca agtacagtt gaaaggaagg | 120 |
| gacttgttga cattgaaaaa cttcacagga gaagaaatca atacatgtt gtggttgtcg | 180 |
| gccgacttga aattcaggat caaacagaaa ggagaatact gcccttgtt gcagggaaaa | 240 |
| tcgttgggaa tgatcttcga aaaaggtcg acaaggacaa ggttgtcgac agaaacagga | 300 |
| ttcgccttgt tgggaggaca ccctgcttc ttgacaacac aggacatcca cttgggagta | 360 |
| aacgaatcgt tgacagacac agccaggta ttgtcgtcga tggccgacgc cgtattggcc | 420 |
| agggtataca acagtcgga cttggacaca ttggccaaag aagcctcgat ccccatcatc | 480 |
| aacgattgt cggacttgta ccaccccatc cagatcttgg ccgactactt gacattgcag | 540 |
| gaacactact cgtcgttgaa aggattgaca ttgtcgtgga tcggagacgg aaacaacatc | 600 |
| ttgcactcga tcatgatgtc ggccgccaaa ttcggaatgc acttgcaggc cgccacaccc | 660 |
| aaaggatacg aacccgacgc ctcggtaaca aaattggccg aacagtacgc caaagaaaac | 720 |
| ggaacaaaat tgttgttgac aaacgacccc ttggaagccg cccacggagg aaacgtattg | 780 |
| atcacagaca catggatctc gatgggacag gaagaagaaa aaaaaaaag gttgcaggcc | 840 |
| ttccagggat accaggtaac aatgaaaaca gccaaagtag ccgcctcgga ctggacattc | 900 |
| ttgcactgct gcccaggaa acccgaagaa gtagacgacg aagtattcta ctcgcccagg | 960 |
| tcgttggtat tccccgaagc cgaaaacagg aaatggacaa tcatggccgt aatggtatcg | 1020 |
| ttgttgacag actactcgcc ccagttgcag aaacccaaat tctgaatagt gaa | 1073 |

<210> SEQ ID NO 223
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 223

| | |
|---|---|
| atgctgttca acctgcgcat cctgctgaac aacgccgcct tccgcaacgg ccacaacttc | 60 |
| atggtgcgca acttccgctg cggccagccc ctgcagggca ggtgcagct gaagggccgc | 120 |
| gacctgctga ccctgaagaa cttcaccggc gaggagatca gtacatgct gtggctgagc | 180 |

```
gccgacctga agttccgcat caagcagaag ggcgagtacc tgcccctgct gcagggcaag    240
agcctgggca tgatcttcga gaagcgcagc acccgcaccc gcctgagcac cgagacaggc    300
ttcgccctgc tgggcggcca cccctgcttc ctgaccaccc aggacatcca cctgggcgtg    360
aacgagagcc tgaccgacac cgcccgcgtg ctgagcagca tggccgacgc cgtgctggcc    420
cgcgtgtaca agcagagcga cctggacacc ctggccaagg aggccagcat ccccatcatc    480
aacggcctga gcgacctgta ccaccccatc cagatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccg cccacggcgg caacgtgctg    780
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagcccccgc    960
agcctggtgt tccccgaggc cgagaaccgc aagtggacca tcatggccgt gatggtgagc   1020
ctgctgaccg actacagccc ccagctgcag aagcccaagt tctga                   1065
```

<210> SEQ ID NO 224
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 224

```
atgctgttca acctgcgcat cctgctgaac aacgccgcct tccgcaacgg ccacaacttc     60
atggtgcgca acttccgctg cggccagccc ctgcagggcc gggtgcagct gaagggccgc    120
gacctgctga ccctgaagaa cttcaccggc gaggagatca agtacatgct gtggctgagc    180
gccgacctga agttccgcat caagcagaag ggcgagtacc tgcccctgct gcagggcaag    240
agcctgggca tgatcttcga gaagcgcagc acccgcaccc gcctgagcac cgagacaggc    300
ttcgccctgc tgggcggcca cccctgcttc ctgaccaccc aggacatcca cctgggcgtg    360
aacgagagcc tgaccgacac cgcccgcgtg ctgagcagca tggccgacgc cgtgctggcc    420
cgcgtgtaca agcagagcga cctggacacc ctggccaagg aggccagcat ccccatcatc    480
aacggcctga gcgacctgta ccaccccatc cagatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccg cccacggcgg caacgtgctg    780
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagcccccgc    960
agcctggtgt tccccgaggc cgagaaccgc aagtggacca tcatggccgt gatggtgagc   1020
ctgctgaccg actacagccc ccagctgcag aagcccaagt tctga                   1065
```

<210> SEQ ID NO 225

```
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 225
atgctgttca acctgcgcat cctgctgaac aacgccgcct tccgcaacgg ccacaacttc      60
atggtgcgca acttccgctg cggccagccc ctgcagggcc gggtgcagct gaagggccgc     120
gacctgctga ccctgaagaa cttcaccggc gaggagatcc ggtacatgct gtggctgagc     180
gccgacctga agttccgcat caagcagaag ggcgagtacc tgcccctgct gcagggcaag     240
agcctgggca tgatcttcga agcgcagc acccgcaccc gcctgagcac cgagacaggc       300
ttcgccctgc tgggcggcca ccctgcttc ctgaccaccc aggacatcca cctgggcgtg      360
aacgagagcc tgaccgacac cgcccgcgtg ctgagcagca tggccgacgc cgtgctggcc     420
cgcgtgtaca gcagagcga cctggacacc ctggccaagg aggccagcat ccccatcatc      480
aacggcctga gcgacctgta ccaccccatc cagatcctgg ccgactacct gaccctgcag     540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
atcaccgaca cctggatcag catgggccag gaggaggaga agaagaagcg cctgcaggcc     840
ttccagggct accaggtgac catgaagacc gccaagtgg ccgccagcga ctggaccttc      900
ctgcactgcc tgccccgcaa gcccgaggag gtggacgacg aggtgttcta cagcccccgc     960
agcctggtgt ccccgaggc cgagaaccgc aagtggacca tcatggccgt gatggtgagc    1020
ctgctgaccg actacagccc ccagctgcag aagcccaagt tctga                    1065

<210> SEQ ID NO 226
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 226
atgctgttca acctgcgcat cctgctgaac aacgccgcct tccgcaacgg ccacaacttc      60
atggtgcgca acttccgctg cggccagccc ctgcagggca aggtgcagct gaagggccgc     120
gacctgctga ccctgaagaa cttcaccggc gaggagatca agtacatgct gtggctgagc     180
gccgacctga agttccgcat caagcagaag ggcgagtacc tgcccctgct gcagggcaag     240
agcctgggca tgatcttcga agcgcagc acccgcaccc gcctgagcac cgagacaggc       300
ttcgccctgc tgggcggcca ccctgcttc ctgaccaccc aggacatcca cctgggcgtg      360
aacgagagcc tgaccgacac cgcccgcgtg ctgagcagca tggccgacgc cgtgctggcc     420
cgcgtgtaca gcagagcga cctggacacc ctggccaagg aggccagcat ccccatcatc      480
aacggcctga gcgacctgta ccaccccatc cagatcctgg ccgactacct gaccctgcag     540
gagcactaca gcagcctgaa gggcctgacc ctgagctgga tcggcgacgg caacaacatc     600
ctgcacagca tcatgatgag cgccgccaag ttcggcatgc acctgcaggc cgccaccccc     660
aagggctacg agcccgacgc cagcgtgacc aagctggccg agcagtacgc caaggagaac     720
ggcaccaagc tgctgctgac caacgacccc ctggaggccg cccacggcgg caacgtgctg     780
```

```
atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagccccgc     960 agcctggtgt tccccgaggc cgagaaccgc aagtggacca tcatggccgt gatggtgagc   1020
ctgctgaccg actacagccc ccagctgcag aagcccaagt ctga                    1065

<210> SEQ ID NO 227
<211> LENGTH: 1065
<212> TYPE: DNA
<213> ORGANISM: Artificial sequence
<220> FEATURE:
<223> OTHER INFORMATION: Synthetic polynucleotide

<400> SEQUENCE: 227
atgctgttca acctgcgcat cctgctgaac aacgccgcct ccgcaacgg ccacaacttc      60 atggtgcgca acttccgctg cggccagccc ctgcagaaca aggtgcagct gaagggccgc    120
gacctgctga ccctgaagaa cttcaccggc gaggagatca agtacatgct gtggctgagc    180
gccgacctga agttccgcat caagcagaag ggcgagtacc tgccctgct gcagggcaag    240 agcctgggca tgatcttcga gaagcgcagc acccgcaccc gctgagcac cgagacaggc    300 ttcgccctgc tgggcggcca cccctgcttc ctgaccaccc aggacatcca cctgggcgtg    360
aacgagagcc tgaccgacac cgcccgcgtg ctgagcagca tggccgacgc cgtgctggcc    420
cgcgtgtaca gcagagcga cctggacacc ctggccaagg aggccagcat ccccatcatc    480
aacggcctga gcgacctgta ccaccccatc agatcctgg ccgactacct gaccctgcag    540
gagcactaca gcagcctgaa gggcctgacc ctgagctgga tcggcgacgg caacaacatc    600
ctgcacagca tcatgatgag cgccgccaag ttcggcatgc acctgcaggc cgccaccccc    660
aagggctacg agcccgacgc cagcgtgacc aagctggccg agcagtacgc caaggagaac    720
ggcaccaagc tgctgctgac caacgacccc ctggaggccc ccacggcgg caacgtgctg    780 atcaccgaca cctggatcag catgggccag gaggaggaga agaagaagcg cctgcaggcc    840
ttccagggct accaggtgac catgaagacc gccaaggtgg ccgccagcga ctggaccttc    900
ctgcactgcc tgccccgcaa gcccgaggag gtggacgacg aggtgttcta cagccccgc     960 agcctggtgt tccccgaggc cgagaaccgc aagtggacca tcatggccgt gatggtgagc   1020
ctgctgaccg actacagccc ccagctgcag aagcccaagt ctga                    1065

<210> SEQ ID NO 228
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 228
atgctggtat tcaacctgcg catcctgctg aacaacgccg ccttccgcaa cggccacaac     60
ttcatggtgc gcaacttccg ctgcggccag cccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccaccctgc ttcctgacca cccaggacat ccacctgggc    360
```

| | |
|---|---|
| gtgaacgaga gcctgaccga caccgcccgc gtgctgagca gcatggccga cgccgtgctg | 420 |
| gcccgcgtgt acaagcagag cgacctggac accctggcca aggaggccag catccccatc | 480 |
| atcaacggcc tgagcgacct gtaccacccc atccagatcc tggccgacta cctgaccctg | 540 |
| caggagcact acagcagcct gaagggcctg accctgagct ggatcggcga cggcaacaac | 600 |
| atcctgcaca gcatcatgat gagcgccgcc aagttcggca tgcacctgca ggccgccacc | 660 |
| cccaagggct acgagcccga cgccagcgtg accaagctgg ccgagcagta cgccaaggag | 720 |
| aacggcacca agctgctgct gaccaacgac cccctggagg ccgcccacgg cggcaacgtg | 780 |
| ctgatcaccg acacctggat cagcatgggc caggaggagg agaagaagaa gcgcctgcag | 840 |
| gccttccagg gctaccaggt gaccatgaag accgccaagg tggccgccag cgactggacc | 900 |
| ttcctgcact gcctgccccg caagcccgag gaggtggacg acgaggtgtt ctacagcccc | 960 |
| cgcagcctgg tgttccccga ggccgagaac cgcaagtgga ccatcatggc cgtgatggtg | 1020 |
| agcctgctga ccgactacag ccccccagctg cagaagccca agttctga | 1068 |

<210> SEQ ID NO 229
<211> LENGTH: 1068
<212> TYPE: DNA
<213> ORGANISM: Artificial sequence
<220> FEATURE:
<223> OTHER INFORMATION: Synthetic polynucleotide

<400> SEQUENCE: 229

| | |
|---|---|
| atgctggtat tcaacctgcg catcctgctg aacaacgccg ccttccgcaa cggccacaac | 60 |
| ttcatggtgc gcaacttccg ctgcggccag cccctgcaga accgggtgca gctgaagggc | 120 |
| cgcgacctgc tgaccctgaa gaacttcacc ggcgaggaga tccggtacat gctgtggctg | 180 |
| agcgccgacc tgaagttccg catcaagcag aagggcgagt acctgcccct gctgcagggc | 240 |
| aagagcctgg gcatgatctt cgagaagcgc agcacccgca cccgcctgag caccgagaca | 300 |
| ggcttcgccc tgctgggcgg ccaccccctgc ttcctgacca cccaggacat ccacctgggc | 360 |
| gtgaacgaga gcctgaccga caccgcccgc gtgctgagca gcatggccga cgccgtgctg | 420 |
| gcccgcgtgt acaagcagag cgacctggac accctggcca aggaggccag catccccatc | 480 |
| atcaacggcc tgagcgacct gtaccacccc atccagatcc tggccgacta cctgaccctg | 540 |
| caggagcact acagcagcct gaagggcctg accctgagct ggatcggcga cggcaacaac | 600 |
| atcctgcaca gcatcatgat gagcgccgcc aagttcggca tgcacctgca ggccgccacc | 660 |
| cccaagggct acgagcccga cgccagcgtg accaagctgg ccgagcagta cgccaaggag | 720 |
| aacggcacca agctgctgct gaccaacgac cccctggagg ccgcccacgg cggcaacgtg | 780 |
| ctgatcaccg acacctggat cagcatgggc caggaggagg agaagaagaa gcgcctgcag | 840 |
| gccttccagg gctaccaggt gaccatgaag accgccaagg tggccgccag cgactggacc | 900 |
| ttcctgcact gcctgccccg caagcccgag gaggtggacg acgaggtgtt ctacagcccc | 960 |
| cgcagcctgg tgttccccga ggccgagaac cgcaagtgga ccatcatggc cgtgatggtg | 1020 |
| agcctgctga ccgactacag ccccccagctg cagaagccca agttctga | 1068 |

<210> SEQ ID NO 230
<211> LENGTH: 21
<212> TYPE: RNA
<213> ORGANISM: Artificial sequence
<220> FEATURE:
<223> OTHER INFORMATION: Synthetic polynucleotide

```
<400> SEQUENCE: 230
aaccaaucga agaaaccaa a                                              21

<210> SEQ ID NO 231
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 231
cucuaaucac caggaguaaa a                                             21

<210> SEQ ID NO 232
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 232
gagagagauc uuaacaaaaa a                                             21

<210> SEQ ID NO 233
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 233
uguguaacaa caacaacaac a                                             21

<210> SEQ ID NO 234
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 234
ccgcaguagg aagagaaagc c                                             21

<210> SEQ ID NO 235
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 235
aaaaaaaaaa gaaaucauaa a                                             21

<210> SEQ ID NO 236
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 236
gagagaagaa agaagaagac g                                             21

<210> SEQ ID NO 237
```

```
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 237
caauuaaaaa uacuuaccaa a                                            21

<210> SEQ ID NO 238
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 238
gcaaacagag uaagcgaaac g                                            21

<210> SEQ ID NO 239
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 239
gcgaagaaga cgaacgcaaa g                                            21

<210> SEQ ID NO 240
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 240
uuaggacugu auugacuggc c                                            21

<210> SEQ ID NO 241
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 241
aucaucggaa uucggaaaaa g                                            21

<210> SEQ ID NO 242
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 242
aaaacaaaag uuaaagcaga c                                            21

<210> SEQ ID NO 243
<211> LENGTH: 21
<212> TYPE: RNA
<213> ORGANISM: Artificial sequence
<220> FEATURE:
<223> OTHER INFORMATION: Synthetic polynucleotide
```

```
<400> SEQUENCE: 243
uuuaucucaa auaagaaggc a                                              21

<210> SEQ ID NO 244
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 244 ggugggagg ugagauuucu u                                               21

<210> SEQ ID NO 245
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 245
ugauuaggaa acuacaaagc c                                              21

<210> SEQ ID NO 246
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 246 cauuuucaa uuucauaaaa c                                               21

<210> SEQ ID NO 247
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 247
uuacuuuuaa gcccaacaaa a                                              21

<210> SEQ ID NO 248
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 248
ggcgugugug uguuguug a                                                21

<210> SEQ ID NO 249
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 249
guggugaagg ggaagguuua g                                              21

<210> SEQ ID NO 250
```

```
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 250
uuguuuuuuu uugguuuggu u                                              21

<210> SEQ ID NO 251
<211> LENGTH: 1231
<212> TYPE: RNA
<213> ORGANISM: Artificial sequence
<220> FEATURE:
<223> OTHER INFORMATION: Synthetic polynucleotide

<400> SEQUENCE: 251
aggauuauua caucaaaaca aaaagccgcc accaugcugg uauucaaccu gcgcauccug      60
cugaacaacg ccgccuuccg caacggccac aacuucaugg ugcgcaacuu ccgcugcggc    120 cagcccugc agaaccgggu gcagcugaag ggccgcgacc ugcugacccu gaagaacuuc     180
accggcgagg agauccggua caugcugugg cugagcgccg accgaaguu ccgcaucaag     240 cagaagggcg aguaccugcc ccugcugcag ggcaagagcc ugggcaugau cuucgagaag    300
cgcagcaccc gcacccgccu gagcaccgag acaggcuucg cccugcuggg cggccacccc    360
ugcuuccuga ccacccagga cauccaccug ggcgugaacg agagccugac cgacaccgcc    420
cgcgugcuga gcagcauggc cgacgccgug cuggcccgcg uacaagca gagcgaccug      480 gacacccugg ccaaggaggc cagcauccc aucaucaacg ccugagcga ccuguaccac      540 cccauccaga uccuggccga cuaccugacc cugcaggagc acuacagcag ccugaagggc    600
cugacccuga gcuggaucgg cgacggcaac aacauccugc acagcaucau gaugagcgcc    660
gccaaguucg gcaugcaccu gcaggccgcc accccaagg gcuacgagcc cgacgccagc    720
gugaccaagc uggccgagca guacgccaag gagaacggca ccaagcugcu gcugaccaac    780 gaccccugg aggccgccca cggcggcaac gugcugauca ccgacaccug aucagcaug      840 ggccaggagg aggagaagaa gaagcgccug caggccuucc agggcuacca ggugaccaug    900
aagaccgcca ggggccgc cagcgacugg accuuccugc acugccugcc ccgcaagccc      960
gaggaggugg acgacgaggu guucuacagc ccccgcagcc uggugucc cgaggccgag     1020 aaccgcaagu ggaccaucau ggccgugaug gugagccugc ugaccgacua cagcccccag   1080
cugcagaagc ccaaguucug aggucucuag uaaugagcug gagccucggu agccgucu     1140 ccugcccgcu gggccuccca cgggcccuc cuccccuccu ugcaccggcc cuccuggcu     1200 uuugaauaaa gucugagugg gcagcaucua g                                  1231

<210> SEQ ID NO 252
<211> LENGTH: 1231
<212> TYPE: RNA
<213> ORGANISM: Artificial sequence
<220> FEATURE:
<223> OTHER INFORMATION: Synthetic polynucleotide

<400> SEQUENCE: 252
aggauuauua caucaaaaca aaaagccgcc accaugcugg uauucaaccu gcgcauccug     60
cugaacaacg ccgccuuccg caacggccac aacuucaugg ugcgcaacuu ccgcugcggc   120 cagcccugc agaaccgggu gcagcugaag ggccgcgacc ugcugacccu gaagaacuuc    180
accggcgagg agauccggua caugcugugg cugagcgccg accgaaguu ccgcaucaag    240
```

| | | | |
|---|---|---|---|
| cagaagggcg | aguaccugcc | ccugcugcag | ggcaagagcc uggcaugau cuucgagaag | 300 |
| cgcagcaccc | gcacccgccu | gagcaccgag | acaggcuucg cccugcuggg cggccacccc | 360 |
| ugcuuccuga | ccacccagga | cauccaccug | ggcgugaacg agagccugac cgacaccgcc | 420 |
| cgcgugcuga | gcagcauggc | cgacgccgug | cuggcccgcg uguacaagca gagcgaccug | 480 |
| gacacccugg | ccaaggaggc | cagcaucccc | aucaucaacg ccugagcga ccuguaccac | 540 |
| cccauccaga | uccuggccga | cuaccugacc | ugcaggagc acuacagcag ccugaagggc | 600 |
| cugacccuga | gcuggaucgg | cgacggcaac | aacauccugc acagcaucau gaugagcgcc | 660 |
| gccaaguucg | gcaugcaccu | gcaggccgcc | accccaaagg cuacgagcc cgacgccagc | 720 |
| gugaccaagc | uggccgagca | guacgccaag | gagaacggca ccaagcugcu gcugaccaac | 780 |
| gacccccugg | aggccgccca | cggcggcaac | gugcugauca ccgacaccug gaucagcaug | 840 |
| ggccaggagg | aggagaagaa | gaagcgccug | caggccuucc agggcuacca ggugaccaug | 900 |
| aagaccgcca | aggugccgc | cagcgacugg | accuuccugc acugccugcc ccgcaagccc | 960 |
| gaggaggugg | acgacgaggu | guucuacagc | ccccgcagcc uggugucccc cgaggccgag | 1020 |
| aaccgcaagu | ggaccaucau | ggccgugaug | gugagccug ugaccgacua cagccccag | 1080 |
| cugcagaagc | ccaaguucug | aggucucuag | uaaugagcug gagccucggu agccguuccu | 1140 |
| ccugcccgcu | gggccucca | acgggcccuc | cucccuccu ugcaccggcc cuuccugguc | 1200 |
| uuugaauaaa | gucugagugg | gcagcaucua | g | 1231 |

<210> SEQ ID NO 253
<211> LENGTH: 1228
<212> TYPE: RNA
<213> ORGANISM: Artificial sequence
<220> FEATURE:
<223> OTHER INFORMATION: Synthetic polynucleotide

<400> SEQUENCE: 253

| | | | |
|---|---|---|---|
| aggauuauua | caucaaaaca | aaaagccgcc | accaugcugu ucaaccugcg cauccugcug | 60 |
| aacaacgccg | ccuuccgcaa | cggccacaac | uucauggugc gcaacuuccg cugcggccag | 120 |
| ccccugcaga | acaaggugca | gcugaagggc | cgcgaccugc ugacccugaa gaacuucacc | 180 |
| ggcgaggaga | ucaaguacau | gcuguggcug | agcgccgacc ugaaguuccg caucaagcag | 240 |
| aagggcgagu | accugcccu | gcugcagggc | aagagccugg gcaugaucuu cgagaagcgc | 300 |
| agcacccgca | cccgccugag | caccgagaca | ggcuucgccc ugcugggcgg ccaccccugc | 360 |
| uuccugacca | cccaggacau | ccaccugggc | gugaacgaga gccugaccga caccgcccgc | 420 |
| gugcugagca | gcauggccga | cgccgugcug | gcccgcgugu acaagcagag cgaccuggac | 480 |
| acccuggcca | aggaggccag | caucccauc | aucaacggcc ugagcgaccu guaccacccc | 540 |
| auccagaucc | uggccgacua | ccugacccug | caggagcacu acagcagccu gaagggccug | 600 |
| acccugagcu | ggaucggcga | cggcaacaac | auccugcaca gcaucaugau gagcgccgcc | 660 |
| aaguucggca | ugcaccugca | ggccgccacc | cccaagggcu acgagcccga cgccagcgug | 720 |
| accaagcugg | ccgagcagua | cgccaaggag | aacggcacca agcugcugcu gaccaacgac | 780 |
| cccuggagg | ccgccacgg | cggcaacgug | cugaucaccg acaccuggau cagcaugggc | 840 |
| caggaggagg | agaagaagaa | gcgccugcag | gccuuccagg gcuaccaggu gaccaugaag | 900 |
| accgccaagg | uggccgccag | cgacuggacc | uuccugcacu gccugccccg caagcccgag | 960 |
| gagguggacg | acgagguguu | cuacagcccc | cgcagccugg uguccccga ggccgagaac | 1020 |

| cgcaagugga ccaucaugge cgugauggug ageeugeuga ccgacuacag ccccagcug | 1080 |
| cagaagccca aguucugagg ucucuaguaa ugagcuggag ccucgguage cguuccuccu | 1140 |
| gcccgcuggg ccucccaacg ggcccuccuc cccuccuugc accggcccuu ccuggucuuu | 1200 |
| gaauaaaguc ugaguggggca gcaucuag | 1228 |

<210> SEQ ID NO 254
<211> LENGTH: 1065
<212> TYPE: RNA
<213> ORGANISM: Artificial sequence
<220> FEATURE:
<223> OTHER INFORMATION: Synthetic polynucleotide

<400> SEQUENCE: 254

| augcuguuca accugcgcau ccugcugaac aacgccgccu uccgcaacgg ccacaacuuc | 60 |
| augqugcgca acuuccgcug cggccagccc cugcagaaca aggugcagcu gaagggccgc | 120 |
| gaccugcuga cccugaagaa cuucaccggc gaggagauca aguacaugcu guggcugagc | 180 |
| gccgaccuga aguccgcau caagcagaag ggcgaguacc ugcccugcu gcagggcaag | 240 |
| agccuggqca ugaucuucga gaagcgcagc acccgcaccc gccugagcac cgagacaggc | 300 |
| uucgcccugc uqqcqqccca ccccugcuuc cugaccaccc aggacaucca ccuqqqcqug | 360 |
| aacgagagcc ugaccgacac cgcccgcgug cugagcagca uggccgacgc cgugcuggcc | 420 |
| cgcquguaca agcagagcga ccuggacacc cuggccaagg aggccagcau ccccaucauc | 480 |
| aacggccuga gcgaccugua ccaccccauc cagauccugg ccgacuaccu gacccugcag | 540 |
| gagcacuaca gcagccugaa gggccugacc cugagcugga ucggcgacgg caacaacauc | 600 |
| cugcacagca ucaugaugag cgccgccaag uucggcaugc accugcaggc cgccacccce | 660 |
| aagggcuacg agcccgacgc cagcgugacc aagcuggccg agcaguacgc caaggagaac | 720 |
| ggcaccaagc ugcugcugac caacgacccc cuggaggccg cccacggcgg caacgugcug | 780 |
| aucaccgaca ccuggaucag caugggccag gaggaggaga agaaagcgc ccugcaggcc | 840 |
| uccagggcu accaggugac caugaagacc gccaaggugg ccgccagcga cuggaccuuc | 900 |
| cugcacugcc ugccccgcaa gcccgaggag guggacgacg aggguucua cagcccccgc | 960 |
| agccugguqu ccccgaggc cgagaaccgc aaguggacca ucauggccgu gauggugagc | 1020 |
| cugcugaccg acuacagccc ccagcugcag aagcccaagu ucuga | 1065 |

<210> SEQ ID NO 255
<211> LENGTH: 1068
<212> TYPE: RNA
<213> ORGANISM: Artificial sequence
<220> FEATURE:
<223> OTHER INFORMATION: Synthetic polynucleotide

<400> SEQUENCE: 255

| auqcugguau ucaaccugcg cauccugcug aacaacgccg ccuuccgcaa cggccacaac | 60 |
| uucauggugc gcaacuuccg cugcggccag ccccugcaga accggqugca gcugaagggc | 120 |
| cgcgaccugc ugacccugaa gaacuucacc ggcgaggaga uccgguacau gcuguggcug | 180 |
| agcgccgacc ugaaguuccg caucaagcag aagggcgagu accugccccu gcugcagggc | 240 |
| aagagccugg gcaugaucuu cgagaagcgc agcacccgca cccgccugag caccgagaca | 300 |
| ggcuucgccc ugcugggcgg ccaccccugc uucugacca ccaggacau ccaccuggqc | 360 |
| gugaacgaga gccugaccga caccgcccgc gugcugagca gcauggccga cgccgugcug | 420 |
| gcccgcgugu acaagcagag cgaccuggac acccuggcca aggaggccag cauccccauc | 480 |

```
aucaacggcc ugagcgaccu guaccacccc auccagauccc uggccgacua ccugacccug    540
caggagcacu acagcagccu gaagggccug acccugagcu ggaucggcga cggcaacaac    600
auccugcaca gcaucaugau gagcgccgcc aaguucggca ugcaccugca ggccgccacc    660
cccaagggcu acgagcccga cgccagcgug accaagcugg ccgagcagua cgccaaggag    720
aacggcacca agcugcugcu gaccaacgac ccccuggagg ccgcccacgg cggcaacgug    780
cugaucaccg acaccuggau cagcaugggc caggaggagg agaagaagaa cgccugcag     840 gccuuccagg cuaccaggu gaccaugaag accgccaagg uggccgccag cgacuggacc     900
uuccugcacu gccugccccg caagcccgag gagguggacg acgaggugu ucuacagcccc    960 cgcagccugg uguuccccga ggccgagaac cgcaagugga ccaucauggc cgugauggug   1020
agccugcuga ccgacuacag cccccagcug cagaagccca aguucuga                1068
```

<210> SEQ ID NO 256
<211> LENGTH: 1065
<212> TYPE: RNA
<213> ORGANISM: Artificial sequence
<220> FEATURE:
<223> OTHER INFORMATION: Synthetic polynucleotide

<400> SEQUENCE: 256

```
augcuguuca accugcgcau ccugcugaac aacgccgccu uccgcaacgg ccacaacuuc     60
auggugcgca cuuccgcug cggccagccc cugcagaaca aggugcagcu gaagggccgc    120
gaccugcuga cccugaagaa cuucaccggc gaggagauca aguacaugcu guggcugagc    180
gccgaccuga aguuccgcau caagcagaag ggcgaguacc ugccccugcu gcagggcaag    240
agccugggca ugaucuucga gaagcgcagc accgcgcaccc gccugagcac cgagacaggc    300
uucgcccugc ugggcggcca ccccugcuuc cugaccaccc aggacaucca ccugggcgug    360
aacgagagcc ugaccgacac cgccgcgug cugagcagca uggccgacgc cgugcuggcc    420
cgcguguaca agcagagcga ccuggacacc cuggccaagg aggccagcau ccccaucauc    480 aacgccuga gcgaccugua cccccccauc cagauccugg ccgacuaccu gacccugcag    540
gagcacuaca gcagccugaa gggccugacc cugagcugga ucggcgacgg caacaacauc    600
cugcacagca ucaugaugag cgccgccaag uucggcaugc accugcaggc cgccaccccc    660
aagggcuacg agcccgacgc cagcgugacc aagcuggccg agcaguacgc caaggagaac    720
ggcaccaagc ugcugcugac caacgacccc cuggaggccg cccacggcgg caacgugcug    780
aucaccgaca ccuggaucag cauggggccag gaggaggaga gaagaagcg ccugcaggcc    840 uuccagggcu accaggugac caugaagacc gccaaggugg ccgccagcga cuggaccuuc    900
cugcacugcc ugccccgcaa gcccgaggag guggacgacg agguuucua cagccccgc     960 agccuggugu uccccgaggc cgagaaccgc aaguggacca ucauggccgu gauggugagc   1020
cugcugaccg acuacagccc ccagcugcag aagcccaagu ucuga                   1065
```

<210> SEQ ID NO 257
<211> LENGTH: 1068
<212> TYPE: RNA
<213> ORGANISM: Artificial sequence
<220> FEATURE:
<223> OTHER INFORMATION: Synthetic polynucleotide

<400> SEQUENCE: 257

```
augcugguau ucaaccugcg cauccugcug aacaacgccg ccuuccgcaa cggccacaac    60
uucaugguga gcaacuuccg cugcggccag ccccugcaga accggguagca gcugaagggc   120
cgcgaccugc ugacccugaa gaacuucacc ggcgaggaga uccgguacau gcuguggcug   180
agcgccgacc ugaaguuccg caucaagcag aagggcgagu accugccccu gcugcagggc   240
aagagccugg gcaugaucuu cgagaagcgc agcacccgca cccgccugag caccgagaca   300
ggcuucgccc ugcugggcgg ccaccccugc uuccugacca cccaggacau ccaccugggc   360
gugaacgaga gccugaccga caccgcccgc gugcugagca gcauggccga cgccgugcug   420
gcccgcgugu acaagcagag cgaccuggac acccuggcca aggaggccag caucccccauc  480
aucaacggcc ugagcgaccu guaccacccc auccagaucc uggccgacua ccugacccug   540
caggagcacu acagcagccu gaagggccug acccugagcu ggaucggcga cggcaacaac   600
auccugcaca gcaucaugau gagcgccgcc aaguucggca ugcaccugca ggccgccacc   660
cccaagggcu acgagcccga cgccagcgug accaagcugg ccgagcagua cgccaaggag   720
aacggcacca agcugcugcu gaccaacgac ccccuggagg ccgcccacgg cggcaacgug   780
cugaucaccg acaccuggau cagcaugggc caggaggagg agaagaagaa cgccugcag   840
gccuuccagg gcuaccaggu gaccaugaag accgccaagg uggccgccag cgacuggacc   900
uuccugcacu gccugccccg caagcccgag gagguggacg acgagguguu cuacagcccc   960
cgcagccugg uguuccccga ggccgagaac cgcaaguugg accaucauggc cgugaugguu  1020
agccugcuga ccgacuacag cccccagcug cagaagccca aguucuga                 1068
```

<210> SEQ ID NO 258
<211> LENGTH: 1068
<212> TYPE: RNA
<213> ORGANISM: Artificial sequence
<220> FEATURE:
<223> OTHER INFORMATION: Synthetic polynucleotide

<400> SEQUENCE: 258

```
augcugguau ucaaccugcg cauccugcug aacaacgccg ccuuccgcaa cggccacaac    60
uucaugguga gcaacuuccg cugcggccag ccccugcaga accggguagca gcugaagggc   120
cgcgaccugc ugacccugaa gaacuucacc ggcgaggaga uccgguacau gcuguggcug   180
agcgccgacc ugaaguuccg caucaagcag aagggcgagu accugccccu gcugcagggc   240
aagagccugg gcaugaucuu cgagaagcgc agcacccgca cccgccugag caccgagaca   300
ggcuucgccc ugcugggcgg ccaccccugc uuccugacca cccaggacau ccaccugggc   360
gugaacgaga gccugaccga caccgcccgc gugcugagca gcauggccga cgccgugcug   420
gcccgcgugu acaagcagag cgaccuggac acccuggcca aggaggccag caucccccauc  480
aucaacggcc ugagcgaccu guaccacccc auccagaucc uggccgacua ccugacccug   540
caggagcacu acagcagccu gaagggccug acccugagcu ggaucggcga cggcaacaac   600
```

```
auccugcaca gcaucaugau gagcgccgcc aaguucggca ugcaccugca ggccgccacc    660
cccaagggcu acgagcccga cgccagcgug accaagcugg ccgagcagua cgccaaggag    720
aacggcacca agcugcugcu gaccaacgac ccccuggagg ccgcccacgg cggcaacgug    780
cugaucaccg acaccuggau cagcauggc caggaggag agaagaagaa gcgccugcag      840
gccuuccagg gcuaccaggu gaccaugaag accgccaagg uggccgccag cgacuggacc    900
uuccugcacu gccugcccg  caagcccgag gagguggacg acgaggguu cuacagcccc     960 cgcagccugg uguccccga ggccgagaac cgcaagugga ccaucauggc cgugauggug    1020
agccugcuga ccgacuacag cccccagcug cagaagccca aguucuga              1068
```

COMPOSITIONS AND METHODS FOR THE TREATMENT OF ORNITHINE TRANSCARBAMYLASE DEFICIENCY

CROSS-REFERENCES TO RELATED APPLICATIONS

This application claims priority to U.S. Provisional Application No. 62/984,764, filed Mar. 3, 2020, which is incorporated herein by reference in its entirety.

REFERENCE TO A SEQUENCE LISTING

The instant application contains a Sequence Listing which has been submitted electronically in ASCII format and is hereby incorporated by reference in its entirety. Said ASCII copy, created on Mar. 1, 2021 is named 049386-529001WO_SequenceListing_ST25.txt and is 379,650 bytes in size.

BACKGROUND

Field

The present disclosure relates to the use of mRNA as a therapeutic in the treatment of disease. More specifically, the present disclosure relates to lipid nanoparticle compositions and methods for treating the urea cycle disorder ornithine transcarbamylase (OTC) deficiency.

Background

The breakdown of amino acids by mammals results in the production of waste ammonia ($NH_3$). The buildup of ammonia in the body is a toxic hazard, and mammals have developed the urea cycle, a metabolic process for converting ammonia into urea ($(NH_2)_2CO$), which can then be safely secreted. The processes of the urea cycle mainly occur in the liver. Urea produced by the liver is then released into the bloodstream where it travels to the kidneys and is ultimately excreted in urine. When a mammal cannot adequately clear nitrogen from the body, a state of hyperammonemia can occur, which presents detrimental effects upon the body and can even result in brain damage or death.

Ornithine transcarbamylase (OTC) is one of six enzymes in the urea cycle that play a role in the breakdown of proteins and removal of ammonia from the body. This metabolic process primarily occurs in hepatocytes with OTC being found in the mitochondria. OTC is specifically responsible for converting carbamoyl phosphate and ornithine into citrulline. Native OTC mRNA encodes a mitochondrial signaling peptide (MSP) that is necessary to redirect the nascent pre-protein from the cytosol into the mitochondria. OTC protein exists as a precursor in the cytosol with the MSP redirecting the pre-peptide into the mitochondria, where it undergoes cleavage of the MSP and delivery of the functional protein into the mitochondrial matrix.

Deficiency of the OTC enzyme results in excessive accumulation of nitrogen, in the form of ammonia (hyperammonemia), in the blood. Excess ammonia, which is a neurotoxin, travels to the central nervous system through the blood, resulting in the symptoms and physical findings associated with OTC deficiency. These symptoms can include vomiting, refusal to eat, progressive lethargy, and coma. If left untreated a hyperammonemic episode may progress to coma and life-threatening complications.

The severity and age of onset of OTC deficiency vary from person to person, even within the same family. A severe form of the disorder affects some infants, typically males, shortly after birth (neonatal period). A milder form of the disorder affects some children later in infancy. Both males and females may develop symptoms of OTC deficiency during childhood. Presently, the treatment of OTC deficiency is aimed at preventing excessive ammonia from being formed or from removing excessive ammonia during a hyperammonemic episode through the use of ammonia scavengers. Long-term therapy for OTC deficiency combines dietary restrictions and the stimulation of alternative methods of converting and excreting nitrogen from the body (alternative pathways therapy).

Dietary restrictions in individuals with OTC deficiency are aimed at limiting the amount of protein intake to avoid the development of excess ammonia. However, enough protein must be taken in by an affected infant to ensure proper growth. Infants with OTC deficiency are placed on a low protein, high calorie diet supplemented by essential amino acids.

In addition to dietary restrictions, individuals with OTC deficiency are treated by medications that stimulate the removal of nitrogen from the body. These medications provide an alternative method to the urea cycle in converting and removing nitrogen waste. These medications are unpalatable to many patients and are often administered via a tube that is placed in the stomach through the abdominal wall (gastrostomy tube) or a narrow tube that reaches the stomach via the nose (nasogastric tube).

In cases where there is no improvement or in cases where hyperammonemic coma develops, the removal of wastes by filtering an affected individual's blood through a machine (hemodialysis) may be necessary. Hemodialysis is also used to treat infants, children, and adults who are first diagnosed with OTC deficiency during hyperammonemic coma.

In some cases, liver transplantation may be an appropriate treatment option, which has been shown as a potential cure to the hyperammonemia in OTC deficiency. However, this operation is risky and may result in post-operative complications. Also, after liver transplantation, patients will need to follow a medication regimen throughout their lives for immunosuppression therapy.

In contrast to the current available treatments, the use of nucleic acids as therapeutic agents is an emerging field of medicine that presents both great challenges and great potential in the treatment of disease. Among the possible treatment avenues using nucleic acids, delivery of a messenger RNA (mRNA) encoding a desired enzyme has the potential to provide the necessary enzymatic activity in a targeted cell of a subject. However, mRNA-based therapies face several obstacles including achieving an adequate in vivo half-life of the mRNA, achieving an adequate translation efficiency of the mRNA such that an effective amount of enzyme is produced, minimizing adverse reactions to the mRNA (e.g., immunogenicity), and effectively delivering the mRNA to a target cell type.

One method for delivering nucleic acids to target cells that has been successfully employed is the encapsulation of the nucleic acid in a lipid formulation such as a liposome or a lipid nanoparticle. While the use of lipid formulations has had some success, it has been found that several of the lipids used in these formulations show low in vivo degradability and low potency.

In light of the above challenges, novel approaches and therapies are still needed for the treatment of OTC enzyme deficiency, and strategies are needed that overcome the challenges and limitations associated with, for example, mRNA-based therapies. Poor stability, effective translocation of the OTC to the mitochondria, and efficient delivery to the target cells remain significant challenges.

SUMMARY

The present disclosure includes compositions and methods for the treatment of ornithine transcarbamylase (OTC) deficiency. The compositions of the present disclosure include a specially designed messenger RNA (mRNA) which shows enhanced in vivo stability and translation efficiency. In addition, the OTC protein translated from the specially designed mRNA shows enhanced uptake into hepatocytic mitochondria. The specially designed mRNA is further combined with a lipid formulation that includes a cationic lipid that offers a high potency (e.g., bioavailability) for delivery of the mRNA to hepatocytes as well as a high level of biodegradability, thus improving both the therapeutic effect of the composition and its safety profile.

In some embodiments, a composition is provided comprising an mRNA encoding an enzyme having ornithine transcarbamylase (OTC) activity; and a lipid formulation comprising an ionizable cationic lipid. In some embodiments, the ionizable cationic lipid is a compound of Formula (I) or any of its configurations described herein. In some embodiments, the ionizable cationic lipid is selected from

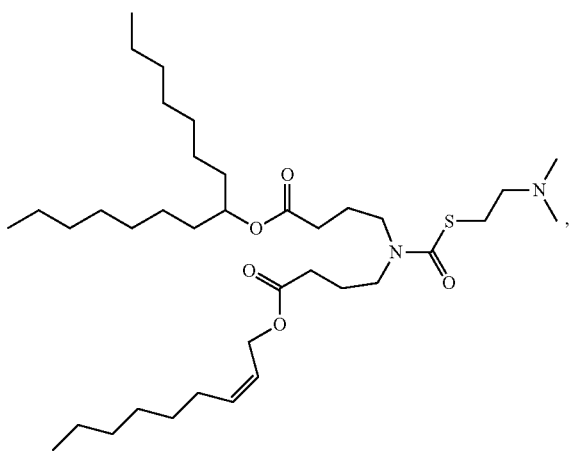

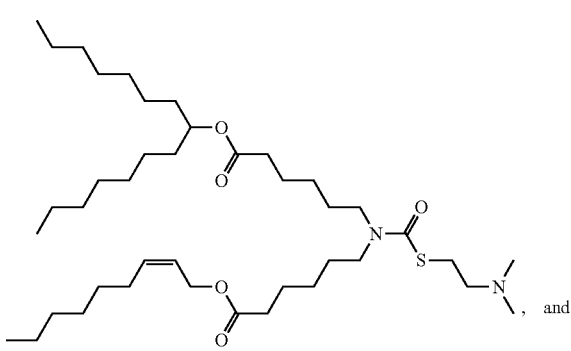

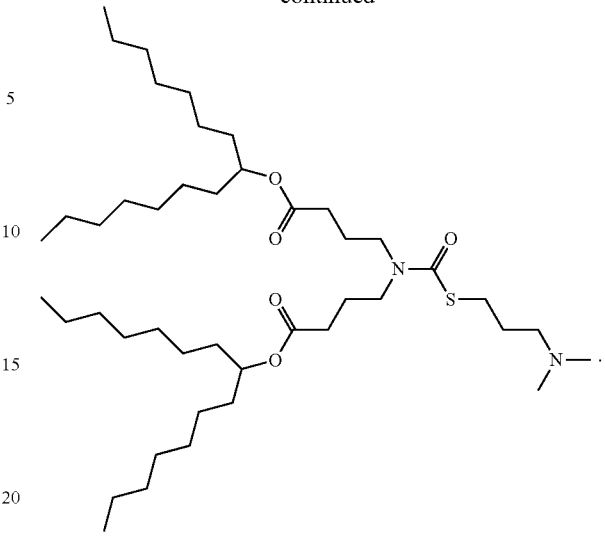

In some embodiments, the lipid formulation of the present disclosure further comprises a helper lipid (e.g., a neutral lipid or a noncationic lipid), a cholesterol, and/or a PEG-lipid.

In some embodiments, a method of treating OTC deficiency is provided comprising administering a composition described herein to a subject in need thereof.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

FIGS. 9A-9B show bar graphs depicting time course OTC expression levels in Spf/ash mice dosed with lipid-formulated human OTC (hOTC) mRNA at 10 mg/kg. Expression levels were measured by Multiple Reaction Monitoring (MRM) using heavy peptides specific for hOTC (FIG. 9A) or endogenous mouse OTC (FIG. 9B).

DETAILED DESCRIPTION

Figure 1A:
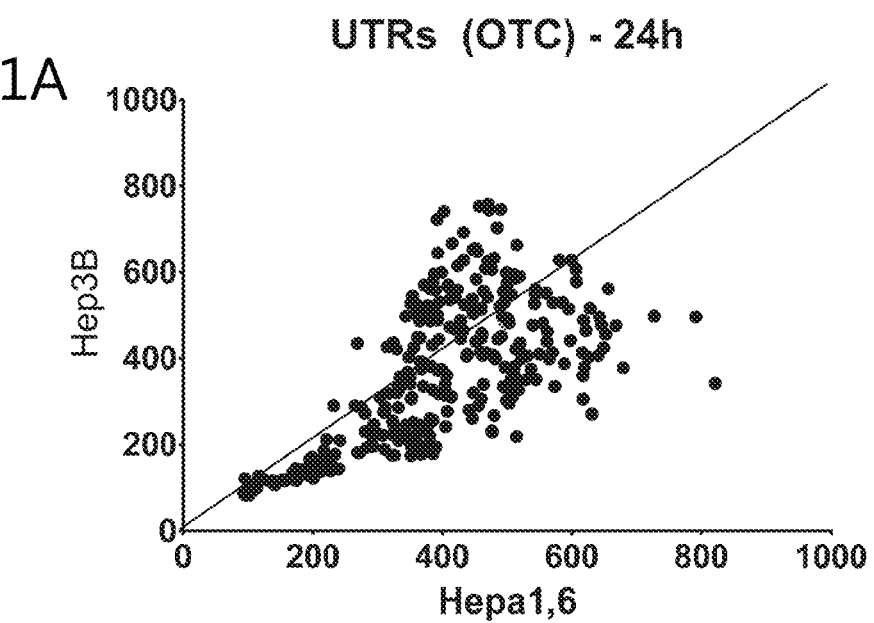
FIGS. 1A-1B show scatter plots illustrating ornithine transcarbamylase (OTC) protein expression in hepatocyte cell lines Hepa1,6 (mouse) and Hep3B (human) at 24 hours (FIG. 1A) and 48 hours (FIG. 1B) using In-Cell Western (ICW) assays.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details.

In some embodiments, a composition is provided comprising an mRNA encoding an enzyme having ornithine transcarbamylase (OTC) activity; and a lipid formulation comprising an ionizable cationic lipid selected from

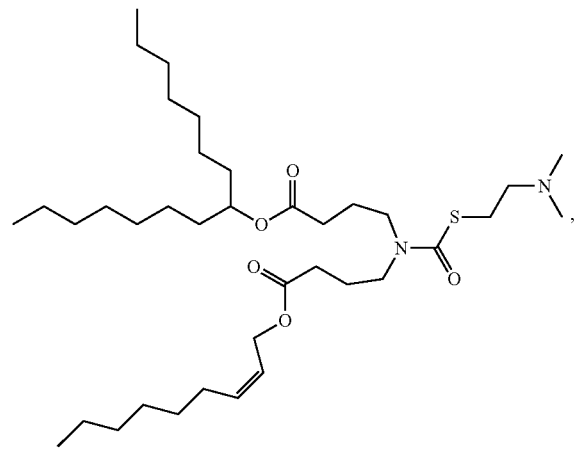 [SMILES: CCCCCC/C=C\COC(=O)CCCN(CCCC(=O)OC(CCCCCCC)CCCCCCC)C(=O)SCCN(C)C]

-continued

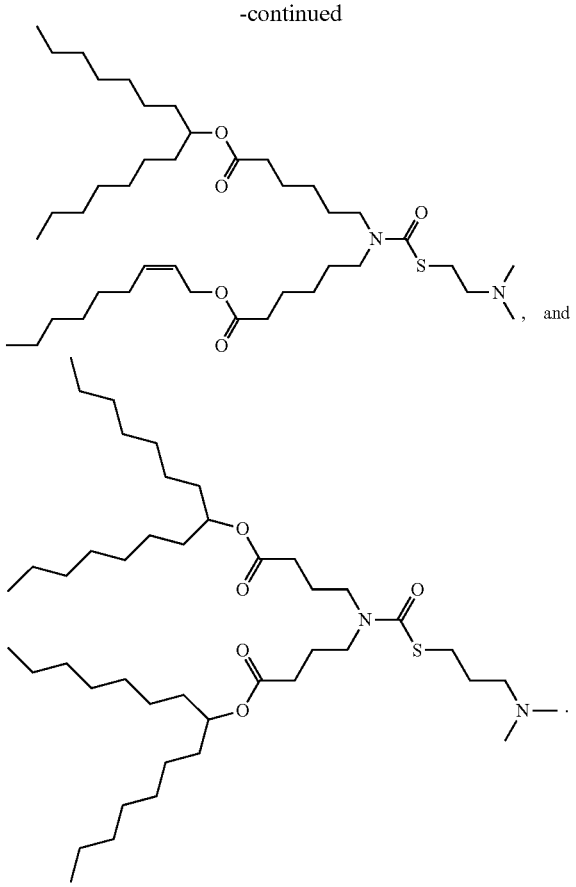

In some embodiments, the mRNA encodes an OTC enzyme having at least 95% identity to a sequence of SEQ ID NO: 3 or SEQ ID NO: 4. In some embodiments, the mRNA encodes an OTC enzyme consisting of a sequence of SEQ ID NO: 3. In some embodiments, the mRNA encodes an OTC enzyme consisting of a sequence of SEQ ID NO: 4. In some embodiments, the mRNA comprises a coding region having a sequence selected from the group consisting of SEQ ID NOs: 254-258. In some embodiments, the mRNA comprises a coding region having a sequence of SEQ ID NO: 254. In some embodiments, the mRNA comprises a coding region having a sequence of SEQ ID NO: 255. In some embodiments, the mRNA comprises a coding region having a sequence of SEQ ID NO: 256. In some embodiments, the mRNA comprises a coding region having a sequence of SEQ ID NO: 257. In some embodiments, the mRNA comprises a coding region having a sequence of SEQ ID NO: 258.

In some embodiments, the mRNA further comprises a 5' untranslated region (5' UTR) comprising a sequence of SEQ ID NO: 6.

In some embodiments, the mRNA further comprises a Kozak sequence having a sequence of SEQ ID NO: 23 or SEQ ID NO: 24.

In some embodiments, the mRNA further comprises a 3' untranslated region (3' UTR) comprising a sequence selected from SEQ ID NOs: 16-22.

In some embodiments, the mRNA further comprises a 3' poly-adenosine (poly-A) tail comprising about 60 to about 125 consecutive adenine nucleotides.

In some embodiments, the mRNA further comprises a 5' cap. In some embodiments, the 5' cap is m⁷GpppGm having the structure of Formula Cap (IV) disclosed herein, wherein $R^1$ and $R^2$ are each OH, $R^3$ is $OCH_3$, each L is a phosphate linked by phosphodiester bonds, mRNA is the mRNA encoding an enzyme having OTC activity linked at its 5' end, and n is 1.

In some embodiments, the 5' cap is m⁷GpppAmpG having the structure of Formula Cap (XI) disclosed herein, wherein $R^1$, $R^2$, and $R^4$ are each OH, n is 1, each L is a phosphate linked by phosphodiester bonds, and mRNA is the mRNA encoding an enzyme having OTC activity linked at its 5' end.

In some embodiments, the mRNA comprises a sequence selected from SEQ ID NOs: 1, 73, 119, and 251-253. In some embodiments, the mRNA comprises the sequence of SEQ ID NO: 1. In some embodiments, the mRNA comprises the sequence of SEQ ID NO: 73. In some embodiments, the mRNA comprises the sequence of SEQ ID NO: 119. In some embodiments, the mRNA comprises the sequence of SEQ ID NO: 251. In some embodiments, the sequence of SEQ ID NO: 252. In some embodiments, the mRNA comprises the sequence of SEQ ID NO: 253.

In embodiments, any one or more of the sequences described herein may be expressly excluded.

In some embodiments, about 1 to about 100% of the uridine nucleotides of the mRNA are 5-methoxy uridine or $N^1$-methyl pseudouridine. In some embodiments, 100% of the uridine nucleotides of the mRNA are 5-methoxy uridine. In some embodiments, 100% of the uridine nucleotides of the mRNA are $N^1$-methyl pseudouridine.

In some embodiments, the ionizable cationic lipid is

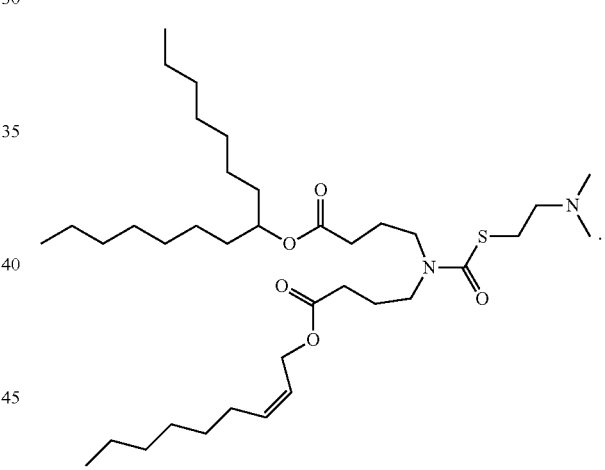

In some embodiments, the ionizable cationic lipid is

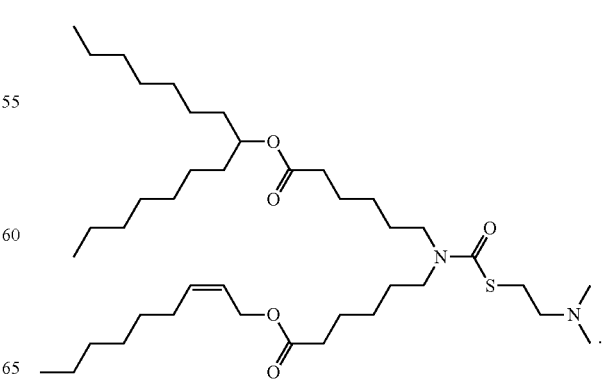

In some embodiments, the ionizable cationic lipid is

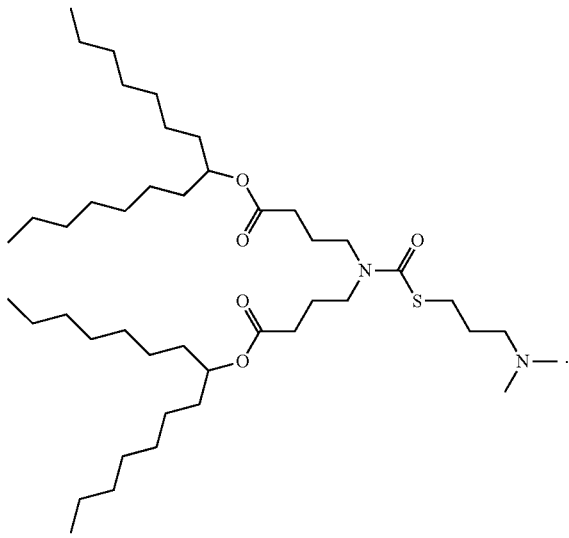 [SMILES: CCCCCCCC(CCCCCCC)OC(=O)CCCN(CCCC(=O)OC(CCCCCCC)CCCCCCC)C(=O)SCCCN(C)C]

In some embodiments, the lipid formulation comprises lipid nanoparticles. In some embodiments, the lipid nanoparticles have an average particle size of less than about 100 nm. In some embodiments, the lipid nanoparticles have an average particles size of about 55 nm to about 85 nm. In some embodiments, the lipid nanoparticles encapsulate at least about 50% of the mRNA. In some embodiments, the lipid nanoparticles encapsulate at least about 85% of the mRNA.

In some embodiments, the lipid formulation further comprises a helper lipid selected from dioleoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC). In some embodiments, the helper lipid is distearoylphosphatidylcholine (DSPC).

In some embodiments, the lipid formulation further comprises cholesterol.

In some embodiments, the lipid formulation further comprises a polyethylene glycol (PEG)-lipid conjugate. In some embodiments, the PEG-lipid conjugate is PEG-DMG. In some embodiments, the PEG-DMG is PEG2000-DMG.

In embodiments, any one or more of the recited lipids may be expressly excluded.

In some embodiments, the lipid portion of the lipid formulation comprises about 48 mol % to about 66 mol % of the ionizable cationic lipid, about 2 mol % to about 12 mol % DSPC, about 25 mol % to about 42 mol % cholesterol, and about 0.5 mol % to about 3 mol % PEG2000-DMG. In some embodiments, the lipid portion of the lipid formulation comprises about 55 mol % to about 61 mol % of the ionizable cationic lipid, about 5 mol % to about 9 mol % DSPC, about 29 mol % to about 38 mol % cholesterol, and about 1 mol % to about 2 mol % PEG2000-DMG. In some embodiments, the lipid portion of the lipid formulation comprises about 56 mol % to about 58 mol % of the ionizable cationic lipid, about 6 mol % to about 8 mol % DSPC, about 31 mol % to about 34 mol % cholesterol, and about 1.25 mol % to about 1.75 mol % PEG2000-DMG. The concentration may be any value or subrange within the recited ranges, including endpoints. The ratio may be any value or subrange within the recited ranges, including endpoints.

In some embodiments, the composition has a total lipid:mRNA weight ratio of about 50:1 to about 10:1. In some embodiments, the composition has a total lipid:mRNA weight ratio of about 40:1 to about 20:1. In some embodiments, the composition has a total lipid:mRNA weight ratio of about 35:1 to about 25:1. In some embodiments, the composition has a total lipid:mRNA weight ratio of about 28:1 to about 32:1. In some embodiments, the composition has a total lipid:mRNA weight ratio of about 29:1 to about 31:1.

In some embodiments, the composition comprises a HEPES buffer at a pH of about 7.4. In some embodiments, the HEPES buffer is at a concentration of about 7 mg/mL to about 15 mg/mL. In some embodiments, the composition further comprises about 2.0 mg/mL to about 4.0 mg/mL of NaCl. In some embodiments, the composition further comprises one or more cryoprotectants. In some embodiments, the one or more cryoprotectants are selected from sucrose, glycerol, or a combination of sucrose and glycerol. In some embodiments, the composition comprises a combination of sucrose at a concentration of about 70 mg/mL to about 110 mg/mL and glycerol at a concentration of about 50 mg/mL to about 70 mg/mL.

In some embodiments, a method of producing an ornithine transcarbamylase (OTC) enzyme in a cell is provided comprising contacting the cell with any of the compositions described herein. In some embodiments, the cell is a hepatocyte.

In some embodiments, a method of treating ornithine transcarbamylase (OTC) deficiency is provided comprising administering a therapeutically effective amount of any of the compositions described herein to a subject in need thereof. In some embodiments, the subject is an adult. In some embodiments, the subject is a child. In some embodiments, an enzyme having OTC activity is produced in hepatocytes of the subject. In some embodiments, the administering comprises intravenous administration. In some embodiments, the composition is administered to the subject at least once per month. In some embodiments, the composition is administered to the subject at least twice per month. In some embodiments, the composition is administered to the subject in a dose of from about 0.2 mg of the mRNA per kg of the subject to about 10 mg of the mRNA per kg of the subject. The amount may be any value or subrange within the recited ranges, including endpoints.

In some embodiments, a method of expressing an ornithine transcarbamylase (OTC) enzyme in a mammal is provided comprising administering any of the compositions of the present disclosure to the mammal.

In some embodiments, the present disclosure provides for the use of any of the compositions described herein in the treatment of ornithine transcarbamylase (OTC) deficiency.

Polynucleotides

The compositions and methods of the present disclosure include an mRNA that encodes an enzyme having ornithine transcarbamylase (OTC) activity. The mRNA can include several features that enhance its in vivo half-life and translation efficiency. In addition, the present disclosure provides for DNA scaffolds for producing an mRNA encoding an enzyme having OTC activity via transcription. The DNA scaffold can be any suitable form of DNA including a plasmid DNA. The polynucleotides contemplated by the present disclosure are further described in detail below.

In some embodiments, the OTC proteins encoded by the mRNA described herein are wildtype human OTC (hOTC). Preferably, the OTC proteins encoded by the mRNA described herein are produced from a heterologous mRNA construct comprising an open reading frame (ORF) also referred to herein as a "coding sequence" (CDS) encoding for an OTC protein. Preferably, the coding sequence is codon-optimized.

Preferably, a human OTC protein encoded by an mRNA described herein comprises a modified human OTC protein of SEQ ID NO: 4 shown in Table 1. SEQ ID NO: 4 has been modified from wild-type OTC of SEQ ID NO: 3 (Table 1) to remove one or more predicted ubiquitination sites resulting in a protein that is less susceptible to ubiquitination and degradation by ubiquitin ligases. The removal of predicted ubiquitination sites preferably comprises replacing N-terminus residues that have been found to support ubiquitination such as asparagine, arginine, leucine, lysine or phenylalanine with N-terminus residues that have been found to be stabilizing against ubiquitination such as alanine, glycine, methionine, serine, threonine, valine and proline. Stabilization of the modified OTC protein of SEQ ID NO: 4 in this manner is particularly advantageous for preserving the stability of the modified OTC protein during its transport from the cytosol to the mitochondria wherein it exerts its enzymatic activity.

Preferably, an OTC protein encoded by an mRNA described herein comprises a protein sequence that is at least about 70%, about 75%, about 80%, about 85%, about 90%, about 95% about 96%, about 97%, about 98%, about 99%, or about 100% identical to human wild type OTC protein of SEQ ID NO: 3 as shown in Table 1, while retaining the OTC protein activity of catalyzing the synthesis of citrulline (in the liver and small intestine) from carbamoyl phosphate and ornithine.

TABLE 1

Selected OTC Nucleotide and Peptide Sequences

| | |
|---|---|
| mRNA coding sequence for wild type human OTC (SEQ ID NO: 1) | AUGCUGUUUAAUCUGAGGAUCCUGUUAAACAAUGCAGCUUUUAGAAA<br>UGGUCACAACUUCAUGGUUCGAAAUUUUCGGUGUGGACAACCACUAC<br>AAAAUAAAGUGCAGCUGAAGGGCCGUGACCUUCUCACUCUAAAAAAC<br>UUUACCGGAGAAGAAAUUAAAUAUAUGCUAUGGCUAUCAGCAGAUCU<br>GAAAUUUAGGAUAAAACAGAAAGGAGAGUAUUUGCCUUUAUUGCAAG<br>GGAAGUCCUUAGGCAUGAUUUUUGAGAAAAGAAGUACUCGAACAAGA<br>UUGUCUACAGAAACAGGCUUUGCACUUCUGGGAGGACAUCCUUGUUU<br>UCUUACCACACAAGAUAUUCAUUUGGGUGUGAAUGAAAGUCUCACGG<br>ACACGGCCCGUGUAUUGUCUAGCAUGGCAGAUGCAGUAUUGGCUCGA<br>GUGUAUAAACAAUCAGAUUUGGACACCCUGGCUAAAGAAGCAUCCAU<br>CCCAAUUAUCAAUGGGCUGUCAGAUUUGUACCAUCCUAUCCAGAUCCU<br>GGCUGAUUACCUCACGCUCCAGGAACACUAUAGCUCUCUGAAAGGUCU<br>UACCCUCAGCUGGAUCGGGGAUGGGAACAAUAUCCUGCACUCCAUCAU<br>GAUGAGCGCAGCGAAAUUCGGAAUGCACCUUCAGGCAGCUACUCCAAA<br>GGGUUAUGAGCCGGAUGCUAGUGUAACCAAGUUGGCAGAGCAGUAUG<br>CCAAAGAGAAUGGUACCAAGCUGUUGCUGACAAAUGAUCCAUUGGAA<br>GCAGCGCAUGGAGGCAAUGUAUUAAUUACAGACACUUGGAUAAGCAU<br>GGGACAAGAAGAGGAGAAGAAAAAGCGGCUCCAGGCUUUCCAAGGUU<br>ACCAGGUUACAAUGAAGACUGCUAAAGUUGCUGCCUCUGACUGGACA<br>UUUUUACACUGCUUGCCCAGAAAGCCAGAAGAAGUGGAUGAUGAAGU<br>CUUUUAUUCUCCUCGAUCACUAGUGUUCCCAGAGGCAGAAAACAGAA<br>AGUUGGACAAUCAUGGCUGUCAUGGUGUCCCUGCUGACAGAUUACUCA<br>CCUCAGCUCCAGAAGCCUAAAUUUUGA |
| DNA coding sequence for wild type human OTC (SEQ ID NO: 2) | ATGCTGTTTAATCTGAGGATCCTGTTAAACAATGCAGCTTTTAGAAATGG<br>TCACAACTTCATGGTTCGAAATTTTCGGTGTGGACAACCACTACAAATA<br>AAGTGCAGCTGAAGGGCCGTGACCTTCTCACTCTAAAAAACTTTACCGG<br>AGAAGAAATTAAATATATGCTATGGCTATCAGCAGATCTGAAATTTAGG<br>ATAAAACAGAAAGGAGAGTATTTGCCTTTATTGCAAGGGAAGTCCTTAG<br>GCATGATTTTTGAGAAAAGAAGTACTCGAACAAGATTGTCTACAGAAAC<br>AGGCTTTGCACTTCTGGGAGGACATCCTTGTTTTCTTACCACACAAGATA<br>TTCATTTGGGTGTGAATGAAAGTCTCACGGACACGGCCCGTGTATTGTCT<br>AGCATGGCAGATGCAGTATTGGCTCGAGTGTATAAACAATCAGATTTGG<br>ACACCCTGGCTAAAGAAGCATCCATCCCAATTATCAATGGGCTGTCAGA<br>TTTGTACCATCCTATCCAGATCCTGGCTGATTACCTCACGCTCCAGGAAC<br>ACTATAGCTCTCTGAAAGGTCTTACCCTCAGCTGGATCGGGGATGGGAA<br>CAATATCCTGCACTCCATCATGATGAGCGCAGCGAAATTCGGAATGCAC<br>CTTCAGGCAGCTACTCCAAAGGGTTATGAGCCGGATGCTAGTGTAACCA<br>AGTTGGCAGAGCAGTATGCCAAAGAGAATGGTACCAAGCTGTTGCTGAC<br>AAATGATCCATTGGAAGCAGCGCATGGAGGCAATGTATTAATTACAGAC<br>ACTTGGATAAGCATGGGACAAGAAGAGGAGAAGAAAAAGCGGCTCCAG<br>GCTTTCCAAGGTTACCAGGTTACAATGAAGACTGCTAAAGTTGCTGCCTC<br>TGACTGGACATTTTTACACTGCTTGCCCAGAAAGCCAGAAGAAGTGGAT<br>GATGAAGTCTTTTATTCTCCTCGATCACTAGTGTTCCCAGAGGCAGAAAA<br>CAGAAAGTGGACAATCATGGCTGTCATGGTGTCCCTGCTGACAGATTAC<br>TCACCTCAGCTCCAGAAGCCTAAATTTTGA |
| Human wild type OTC amino acid sequence (The signal peptide for mitochondrial import is underlined*) (SEQ ID NO: 3) | MLFNLRILLNNAAFRNGHNFMVRNFRCGQPLQNKVQLKGRDLLTLKNFTG<br>EEIKYMLWLSADLKFRIKQKGEYLPLLQGKSLGMIFEKRSTRTRLSTETGFA<br>LLGGHPCFLTTQDIHLGVNESLTDTARVLSSMADAVLARVYKQSDLDTLAK<br>EASIPIFGLSDLYHPIQILADYLTLQEHYSSLKGLTLSWIGDGNNILHSIMMS<br>AAKFGMHLQAATPKGYEPDASVTKLAEQYAKENGTKLLLTNDPLEAAHGG<br>NVLITDTWISMGQEEEKKKRLQAFQGYQVTMKTAKVAASDWTFLHCLPRK<br>PEEVDDEVFYSPRSLVFPEAENRKWTIMAVMVSLLTDYSPQLQKPKF |

TABLE 1-continued

Selected OTC Nucleotide and Peptide Sequences

| Modified OTC amino acid sequence (The signal peptide for mitochondrial import is underlined*) (SEQ ID NO: 4) | MLVFNLRILLNNAAFRNGHNFMVRNFRCGQPLQNRVQLKGRDLLTLKNFTGE EIRYMLWLSADLKFRIKQKGEYLPLLQGKSLGMIFEKRSTRTRLSTETGFALLGGH PCFLTTQDIHLGVNESLTDTARVLSSMADAVLARVYKQSDLDTLAKEASIPIINGLS DLYHPIQILADYLTLQEHYSSLKGLTLSWIGDGNNILHSIMMSAAKFGMHLQAAT PKGYEPDASVTKLAEQYAKENGTKLLLTNDPLEAAHGGNVLITDTWISMGQEEEK KKRLQAFQGYQVTMKTAKVAASDWTFLHCLPRKPEEVDDEVFYSPRSLVFPEAEN RKWTIMAVMVSLLTDYSPQLQKPKF |

\* The OTC protein comprises a signal peptide which is translated and responsible for translocation to the mitochondria. This signal peptide is represented by the first 32 amino acids as underlined in SEQ ID NO: 3 and SEQ ID NO: 4 (corresponding nucleotide sequence is underlined in SEQ ID NO: 1 and SEQ ID NO: 2). The signal sequence of SEQ ID NO: 4 has also been modified as compared to SEQ ID NO: 3; specifically, an amino acid, valine is inserted at position 3 of SEQ ID NO: 4. This modification provides better mitochondrial localization of the modified OTC of SEQ ID NO: 4 as compared to wild type human OTC of SEQ ID NO: 3.

Preferably, the open reading frame (ORF) or coding sequence (CDS) of an mRNA sequence described herein encodes an amino acid sequence that is substantially identical to the modified OTC protein of SEQ ID NO: 4.

Preferably, the open reading frame (ORF) or coding sequence (CDS) of an mRNA sequence described herein encodes an amino acid sequence that is substantially identical to wild type human OTC protein of SEQ ID NO: 3. Preferably, an OTC protein encoded by an mRNA described herein comprises a protein sequence that is at least about 70%, about 75%, about 80%, about 85%, about 90%, about 95% about 96%, about 97%, about 98%, about 99%, or about 100% identical to a modified human OTC protein of SEQ ID NO: 3 shown in Table 1 while retaining the OTC protein activity of catalyzing the synthesis of citrulline (in the liver and small intestine) from carbamoyl phosphate and ornithine.

Preferably, the ORF or CDS of an mRNA described herein encodes an amino acid sequence that is substantially identical to modified human OTC protein of SEQ ID NO: 4.

Preferably, the ORF or CDS of an mRNA described herein encoding a human OTC protein comprises a codon optimized polynucleotide sequence at least about 70%, about 75%, about 80%, about 85%, about 90%, about 95%, about 96%, about 97%, about 98%, about 99%, or about 100% identical to the mRNA coding sequence of SEQ ID NO: 1 of Table 1.

Preferably an mRNA described herein further comprises a sequence immediately downstream (i.e., in the 3' direction from) of the CDS that creates a triple stop codon. The triple stop codon may be incorporated to enhance the efficiency of translation. In some embodiments, the translatable oligomer may comprise the sequence AUAAGUGAA (SEQ ID NO: 25) immediately downstream of an OTC CDS of an mRNA sequence described herein.

Codon Optimization

A polynucleotide sequence encoding a protein can be altered relative to the wild type for the same sequence to select the best combination of codons that code for the amino acids of the protein. For an mRNA, all or a portion of the mRNA, for example, the coding region or open reading frame (ORF), can be optimized with respect to the codons in that region. Codon optimized sequences can increase protein expression levels (Gustafsson et al., Codon bias and heterologous protein expression. 2004, Trends Biotechnol 22:346-53) of the encoded proteins while providing other advantages. Optimization of the codons in a sequence will depend on several characteristics of an mRNA construct including high codon adaptation index (CAI), the Low-U method, mRNA secondary structures, cis-regulatory sequences, GC content and many other similar variables. These variables have been shown to correlate with protein expression levels (Villalobos et al., Gene Designer: a synthetic biology tool for constructing artificial DNA segments. 2006, BMC Bioinformatics 7:285). The high CAI (codon adaptation index) method picks a most frequently used synonymous codon for an entire protein coding sequence. The most frequently used codon for each amino acid is deduced from 74,218 protein-coding genes from a human genome. The Low-U method targets only U-containing codons that can be replaced with a synonymous codon with fewer U moieties. If there are a few choices for the replacement, the more frequently used codon will be selected. The remaining codons in the sequence are not changed by the Low-U method. This method may be used in conjunction with the disclosed mRNAs to design coding sequences that are to be synthesized with, for example, 5-methoxyuridine or $N^1$-methyl pseudouridine. Methods of codon optimization in combination with the use of a modified nucleotide monomer are described in U.S. 2018/0327471, the contents of which are herein incorporated by reference.

In addition, the nucleotide sequence of any region of the mRNA or DNA template may be codon optimized. Codon optimization methods are known in the art and may be useful in efforts to achieve one or more of several goals. These goals include to match codon frequencies in target and host organisms to ensure proper folding, to bias GC nucleotide pair content to increase mRNA stability or reduce secondary structures, to minimize tandem repeat codons or base runs that may impair gene construction or expression, to customize transcriptional and translational control regions, to insert or remove protein trafficking sequences, to remove/add post translation modification sites in encoded protein (e.g. glycosylation sites), to add, remove or shuffle protein domains, to insert or delete restriction sites, to modify ribosome binding sites and mRNA degradation sites, to adjust translational rates to allow the various domains of the protein to fold properly, or to reduce or eliminate problematic secondary structures within the mRNA. Suitable codon optimization tools, algorithms and services are known in the art.

In some embodiments, the nucleotide sequence of any region of the mRNA or DNA templates described herein may be codon optimized. Preferably, the primary cDNA template may include reducing the occurrence or frequency of appearance of certain nucleotides in the template strand. For example, the occurrence of a nucleotide in a template may be reduced to a level below 25% of said nucleotides in the template. In further examples, the occurrence of a nucleotide in a template may be reduced to a level below 20% of said nucleotides in the template. In some examples, the occurrence of a nucleotide in a template may be reduced to a level below 16% of said nucleotides in the template. Preferably, the occurrence of a nucleotide in a template may be reduced to a level below 15%, and preferably may be reduced to a level below 12% of said nucleotides in the template.

In some embodiments, the nucleotide reduced is uridine. For example, the present disclosure provides nucleic acids with altered uracil content wherein at least one codon in the wild-type sequence has been replaced with an alternative codon to generate a uracil-altered sequence. Altered uracil sequences can have at least one of the following properties:
  (i) an increase or decrease in global uracil content (i.e., the percentage of uracil of the total nucleotide content in the nucleic acid of a section of the nucleic acid, e.g., the open reading frame);
  (ii) an increase or decrease in local uracil content (i.e., changes in uracil content are limited to specific subsequences);
  (iii) a change in uracil distribution without a change in the global uracil content;
  (iv) a change in uracil clustering (e.g., number of clusters, location of clusters, or distance between clusters); or
  (v) combinations thereof.

In some embodiments, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the nucleic acid sequences of the disclosure. The percentage uracil content can be determined by dividing the number of uracil in a sequence by the total number of nucleotides and multiplying by 100.

In some embodiments, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure. These subsequences can also be part of the wild-type sequences of the heterologous 5' and 3' UTR sequences of the present disclosure.

In some embodiments, codons in the nucleic acid sequence of the disclosure reduce or modify, for example, the number, size, location, or distribution of uracil clusters that could have deleterious effects on protein translation. Although lower uracil content is desirable in certain aspects, the uracil content, and in particular the local uracil content, of some subsequences of the wild-type sequence can be greater than the wild-type sequence and still maintain beneficial features (e.g., increased expression).

In some embodiments, the uracil-modified sequence induces a lower Toll-Like Receptor (TLR) response when compared to the wild-type sequence. Several TLRs recognize and respond to nucleic acids. Double-stranded (ds) RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial mRNA contains no nucleoside modifications, whereas mammalian mRNAs have modified nucleosides such as 5-methylcytidine ($m^5C$), $N^6$-methyladenosine ($m^6A$), inosine and many 2'-O-methylated nucleosides in addition to $N^7$-methylguanosine ($m^7G$).

In some embodiments, the uracil content of polynucleotides disclosed herein and preferably polynucleotides encoding the modified OTC protein of SEQ ID NO: 4 is less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the sequence in the reference sequence. In some embodiments, the uracil content of polynucleotides disclosed herein and preferably polynucleotides encoding the modified OTC protein of SEQ ID NO: 4, is between about 5% and about 25%. In some embodiments, the uracil content of polynucleotides disclosed herein and preferably polynucleotides encoding the modified OTC protein of SEQ ID NO: 4 is between about 15% and about 25%.

Natural and Modified Nucleotides

Preferably an mRNA described herein comprises one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of mRNA polynucleotides comprising chemically modified nucleotides have been shown to improve mRNA expression, expression rates, half-life and/or expressed protein concentrations. mRNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4,N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4,N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy) pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl) uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, $N^6$-threonylcarbamoyl-adenosine, $N^6$-methyl-$N^6$-threonylcarbamoyl-adenosine, 2-methylthio-$N^6$-threonylcarbamoyl-adenosine, $N^6,N^6$-dimethyladenosine, $N^6$-hydroxynorvalylcarbamoyladenosine, 2-methylthio-$N^6$-hydroxynorvalylcarbamoyl-adenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6,N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-alkylguanosines, $N^2$-alkylguanosines, thienoguanosines, 7-deazaguanosines, 8-oxoguanosines, 8-bromoguanosines, O6-alkylguanosines, xanthosines, inosines, and $N^1$-alkylinosines.

Examples of modified or chemically-modified nucleotides include $N^1$-methylguanosine, $N^2$-methylguanosine, thienoguanosine, 7-deazaguanosine, 8-oxoguanosine, 8-bromoguanosine, O6-methylguanosine, xanthosine, inosine, and $N^1$-methylinosine.

Examples of modified or chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine (also referred to herein as "N1MPU"), $N^1$-ethylpseudouridine, $N^1$-propylpseudouridine, NL cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5—C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include $N^6$-methyladenosine nucleotides.

Examples of modified and chemically-modified nucleotide monomers include nucleotide monomers with modified bases 5-(3-amino) propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include $N^1$-methylpseudouridine and 5-methoxyuridine.

Untranslated Region (UTR)

In molecular genetics, an untranslated region (UTR) refers to either of two sections, one on each side of a coding sequence on a strand of mRNA. If it is found on the 5' side, it is called the 5' UTR (or leader sequence), or if it is found on the 3' side, it is called the 3' UTR (or trailer sequence). As an mRNA is translated into a protein in vivo, several regions of the mRNA are usually not translated, including the 5' and 3' UTRs. In some embodiments, an mRNA described herein further comprises a 5' untranslated region (UTR) sequence. The 5' UTR is upstream from the coding sequence. Within the 5' UTR is a sequence that is recognized by the ribosome which allows the ribosome to bind and initiate translation. In contrast, the 3' UTR is typically found immediately following the translation stop codon of the coding region. The 3' UTR can play an important role in translation termination as well as post-transcriptional modification. Thus, as is understood in the art, the 5' and/or 3' UTR may affect an mRNA's stability or efficiency of translation. The 5' UTR may be derived from an mRNA molecule known in the art as relatively stable (e.g., histone, tubulin, globin, glyceraldehyde 1-phosphate dehydrogenase (GAPDH), actin, or citric acid cycle enzymes) to increase the stability of the translatable oligomer. In other embodiments, a 5' UTR sequence may include a partial sequence of a cytomegalovirus (CMV) immediate-early 1 (IE1) gene.

In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Examples of 5 UTRs and 3' UTRs are described in PCT/US2018/035419, the contents of which are herein incorporated by reference. Preferred 5' UTR sequences comprise SEQ ID NOs: 5-10, 125-127 and 230-250: as shown in Table 2.

TABLE 2

5'UTR sequences

| Name | Sequence | Seq ID No.: |
|---|---|---|
| EV | UCAACACAACAUAUACAAAACAAACGAAUCUCAAGCAAUCAAGCAUUC UACUUCUAUUGCAGCAAUUUAAAUCAUUUCUUUUAAAGCAAAAGCAA UUUUCUGAAAAUUUUCACCAUUUACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGGCGCUGCCUACGGAGGUGGCAGCCAUCUCCUUCUCGGC AUCAAGCUUACCAUGGUGCCCCAGGCCCUGCUCUUGGUCCCGCUGCUG GUGUUCCCCCUCUGCUUCGGCAAGUUCCCCAUCUACACCAUCCCCGAC AAGCUGGGGCCGUGGAGCCCCAUCGACAUCCACCACCUGUCCUGCCCC AACAACCUCGUGGUCGAGGACGAGGGCUGCACCAACCUGAGCGGGUU CUCCUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO: 8 |
| HUMAN ALBUMIN | AAUUAUUGGUUAAAGAAGUAUAUUAGUGCUAAUUUCCCUCCGUUUG UCCUAGCUUUUCUCUUCUGUCAACCCCACACGCCUUUGGCACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 125 |
| AT1G35720 | AACACUAAAAGUAGAAGAAAA | SEq ID NO: 126 |
| AT5G45900 | CUCAGAAAGAUAAGAUCAGCC | SEQ ID NO: 127 |
| AT5G61250 | AACCAAUCGAAAGAAACCAAA | SEQ ID NO: 230 |
| AT5G46430 | CUCUAAUCACCAGGAGUAAAA | SEQ ID NO: 231 |
| AT5G47110 | GAGAGAGAUCUUAACAAAAAA | SEQ ID NO: 232 |

TABLE 2-continued

5'UTR sequences

| Name | Sequence | Seq ID No.: |
|---|---|---|
| AT1G03110 | UGUGUAACAACAACAACAACA | SEQ ID NO: 233 |
| AT3G12380 | CCGCAGUAGGAAGAGAAAGCC | SEQ ID NO: 234 |
| AT5G45910 | AAAAAAAAAAGAAAUCAUAAA | SEQ ID NO: 235 |
| AT1G07260 | GAGAGAAGAAAGAAGAAGACG | SEQ ID NO: 236 |
| AT3G55500 | CAAUUAAAAAUACUUACCAAA | SEQ ID NO: 237 |
| AT3G46230 | GCAAACAGAGUAAGCGAAACG | SEQ ID NO: 238 |
| AT2G36170 | GCGAAGAAGACGAACGCAAAG | SEQ ID NO: 239 |
| AT1G10660 | UUAGGACUGUAUUGACUGGCC | SEQ ID NO: 240 |
| AT4G14340 | AUCAUCGGAAUUCGGAAAAAG | SEQ ID NO: 241 |
| AT1G49310 | AAAACAAAAGUUAAAGCAGAC | SEQ ID NO: 242 |
| AT4G14360 | UUUAUCUCAAAUAAGAAGGCA | SEQ ID NO: 243 |
| AT1G28520 | GGUGGGGAGGUGAGAUUUCUU | SEQ ID NO: 244 |
| AT1G20160 | UGAUUAGGAAACUACAAAGCC | SEQ ID NO: 245 |
| AT5G37370 | CAUUUUUCAAUUUCAUAAAAC | SEQ ID NO: 246 |
| AT4G11320 | UUACUUUUAAGCCCAACAAAA | SEQ ID NO: 247 |
| AT5G40850 | GGCGUGUGUGUGUGUUGUUGA | SEQ ID NO: 248 |
| AT1G06150 | GUGGUGAAGGGGAAGGUUUAG | SEQ ID NO: 249 |
| AT2G26080 | UUGUUUUUUUUUGGUUUGGUU | SEQ ID NO: 250 |

In some embodiments, the 5'UTR sequence comprises SEQ ID NO: 6 (AT1G58420).

In some embodiments, an mRNA described herein comprises a 3'UTR. In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and Xenopus beta globin, or fragments of any of the foregoing. In some embodiments, the 3' UTR is derived from Xenopus beta globin. Exemplary 3' UTR sequences include SEQ ID NOs: 16-22 as shown in Table 3.

TABLE 3

3'UTR sequences

| Name | Sequence | Seq ID No.: |
|---|---|---|
| XBG | CUAGUGACUGACUAGGAUCUGGUUACCACUAAACCAGCCUCAAG AACACCCGAAUGGAGUCUCUAAGCUACAUAAUACCAACUUACACU UACAAAAUGUUGUCCCCAAAAUGUAGCCAUUCGUAUCUGCUCC UAAUAAAAAGAAAGUUUCUUCACAU | SEQ ID NO: 16 |
| HUMAN HAPTOGLOBIN | UGCAAGGCUGGCCGGAAGCCCUUGCCUGAAAGCAAGAUUUCAGC CUGGAAGAGGGCAAAGUGGACGGGAGUGGACAGGAGUGGAUGC GAUAAGAUGUGGUUUGAAGCUGAUGGGUGCCAGCCCUGCAUUG CUGAGUCAAUCAAUAAAGAGCUUUCUUUUGACCCAU | SEQ ID NO: 17 |
| HUMAN APOLIPOPROTEIN E | ACGCCGAAGCCUGCAGCCAUGCGACCCCACGCCACCCCGUGCCUCC UGCCUCCGCGCAGCCUGCAGCGGGAGACCCUGUCCCCGCCCCAGC CGUCCUCCUGGGGUGGACCCUAGUUUAAUAAAGAUUCACCAAGU UUCACGCA | SEQ ID NO: 18 |
| HCV | UAGAGCGGCAAACCCUAGCUACACUCCAUAGCUAGUUUCUUUUU UUUUGUUUUUUUUUUUUUUUUUUUUUUUUUUUUUUU UUUUCCUUUCUUUUCCUUCUUUUUUUCCUCUUUUCUUGGUUGGC UCCAUCUUAGCCCUAGUCACGGCUAGCUGUGAAAGGUCCGUGAG CCGCAUGACUGCAGAGAGUGCCGUAACUGGUCUCUCUGCAGAUC AUGU | SEQ ID NO: 19 |

TABLE 3-continued

3'UTR sequences

| Name | Sequence | Seq ID No.: |
|---|---|---|
| MOUSE ALBUMIN | ACACAUCACAACCACAACCUUCUCAGGCUACCCUGAGAAAAAAAG ACAUGAAGACUCAGGACUCAUCUUUUCUGUUGGUGUAAAAUCA ACACCCUAAGGAACACAAAUUUCUUUAAACAUUUGACUUCUUGU CUCUGUGCUGCAAUUAAUAAAAAAUGGAAAGAAUCUAC | SEQ ID NO: 20 |
| HUMAN ALPHA GLOBIN | GCUGGAGCCUCGGUAGCCGUUCCUCCUGCCCGCUGGGCCUCCCA ACGGGCCCUCCUCCCCUCCUUGCACCGGCCCUUCCUGGUCUUUGA AUAAAGUCUGAGUGGGCAGCA | SEQ ID NO: 21 |
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Triple Stop Codon

In some embodiments, the translatable oligomer encoding OTC may comprise a sequence immediately downstream of a coding region (i.e., ORF) that creates a triple stop codon. A triple stop codon is a sequence of three consecutive stop codons. The triple stop codon can ensure total insulation of an expression cassette and may be incorporated to enhance the efficiency of translation. In some embodiments, the mRNA may comprise a triple combination of any of the sequences UAG, UGA, or UAA immediately downstream of a ORF described herein. The triple combination can be three of the same codons, three different codons, or any other permutation of the three stop codons.

Translation Enhancers and Kozak Sequences

For translation initiation, proper interactions between ribosomes and mRNAs must be established to determine the exact position of the translation initiation region. However, ribosomes also must dissociate from the translation initiation region to slide toward the downstream sequence during mRNA translation. Translation enhancers upstream from initiation sequences of mRNAs enhance the yields of protein biosynthesis. Several studies have investigated the effects of translation enhancers. In some embodiments, an mRNA described herein comprises a translation enhancer sequence. These translation enhancer sequences enhance the translation efficiency of an mRNA described herein and thereby provide increased production of the protein encoded by the mRNA. The translation enhancer region may be located in the 5' or 3' UTR of an mRNA sequence. Examples of translation enhancer regions include naturally-occurring enhancer regions from the TEV 5' UTR and the Xenopus beta-globin 3' UTR. Exemplary 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID Nos: 11-15 as shown in Table 4.

TABLE 4

5'UTR Enhancers

| Name | Sequence | Seq ID No.: |
|---|---|---|
| HSP70-P2 | GUCAGCUUUCAAACUCUUUGUUUCUUG UUUGUUGAUUGAGAAUA | SEQ ID NO: 11 |
| HSP70-M1 | CUCUCGCCUGAGAAAAAAAAUCCACGA ACCAAUUUCUCAGCAACCAGCAGCACG | SEQ ID NO: 12 |
| HSP72-M2 | ACCUGUGAGGGUUCGAAGGAAGUAGCA GUGUUUUUUGUUCCUAGAGGAAGAG | SEQ ID NO: 13 |
| HSP17.9 | ACACAGAAACAUUCGCAAAAACAAAAU CCCAGUAUCAAAAUUCUUCUCUUUUUU UCAUAUUUCGCAAAGAC | SEQ ID NO: 14 |
| HSP70-P1 | CAGAAAAAUUUGCUACAUUGUUUCACA AACUUCAAAUAUUAUUCAUUUAUUU | SEQ ID NO: 15 |

In some embodiments, an mRNA described herein comprises a Kozak sequence. As is understood in the art, a Kozak sequence is a short consensus sequence centered around the translational initiation site of eukaryotic mRNAs that allows for efficient initiation of translation of the mRNA. See, for example, Kozak, Marilyn (1988) Mol. and Cell Biol, 8:2737-2744; Kozak, Marilyn (1991) J. Biol. Chem, 266:19867-19870; Kozak, Marilyn (1990) Proc Natl. Acad. Sci. USA, 87:8301-8305; and Kozak, Marilyn (1989) J. Cell Biol, 108:229-241. It ensures that a protein is correctly translated from the genetic message, mediating ribosome assembly and translation initiation. The ribosomal translation machinery recognizes the AUG initiation codon in the context of the Kozak sequence. A Kozak sequence may be inserted upstream of the coding sequence for OTC, downstream of a 5' UTR or inserted upstream of the coding sequence for OTC and downstream of a 5' UTR. In some embodiments, an mRNA described herein comprises a Kozak sequence having the sequence GCCACC (SEQ ID NO: 23). Preferably an mRNA described herein comprises a partial Kozak sequence "p" having the sequence GCCA (SEQ ID NO: 24).

5' Cap

A Cap structure on the 5'-end of mRNAs, which is present in all eukaryotic organisms (and some viruses) is important for stabilizing mRNAs in vivo. Naturally occurring Cap structures comprise a ribo-guanosine residue that is methylated at position N7 of the guanine base. This 7-methyl-guanosine ($m^7G$) is linked via a 5'- to 5'-triphosphate chain at the 5'-end of the mRNA molecule. The presence of the $m^7$Gppp fragment on the 5'-end is essential for mRNA maturation as it protects the mRNAs from degradation by exonucleases, facilitates transport of mRNAs from the nucleus to the cytoplasm and plays a key role in assembly of the translation initiation complex (Cell 9:645-653, (1976); Nature 266:235, (1977); Federation of Experimental Biologists Society Letter 96:1-11, (1978); Cell 40:223-24, (1985); Prog. Nuc. Acid Res. 35:173-207, (1988); Ann. Rev. Biochem. 68:913-963, (1999); and J Biol. Chem. 274: 30337-3040, (1999)).

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43:482-492 (2015)).

Some examples of 5' cap structures and methods for preparing mRNAs comprising the same are given in WO2015/051169A2, WO/2015/061491, US 2018/0273576, and U.S. Pat. Nos. 8,093,367, 8,304,529, and 10,487,105. In some embodiments, the 5' cap is m$^7$GpppAmpG, which is known in the art. In some embodiments, the 5' cap is m$^7$GpppG or m$^7$GpppGm, which are known in the art. Structural formulas for embodiments of 5' cap structures are provided below.

In some embodiments, an mRNA described herein comprises a 5' cap having the structure of Formula (Cap I).

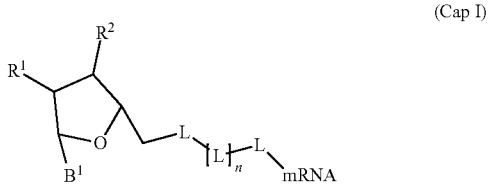

(Cap I)

wherein B$^1$ is a natural or modified nucleobase; R$^1$ and R$^2$ are each independently selected from a halogen, OH, and OCH$_3$; each L is independently selected from the group consisting of phosphate, phosphorothioate, and boranophosphate wherein each L is linked by diester bonds; n is 0 or 1, and mRNA represents an mRNA of the present disclosure linked at its 5' end. In some embodiments B$^1$ is G, m$^7$G, or A. In some embodiments n is 0. In some embodiments n is 1. In some embodiments, B$^1$ is A or m$^6$A and R$^1$ is OCH$_3$; wherein G is guanine, m$^7$G is 7-methylguanine, A is adenine, and m$^6$A is N$^6$-methyladenine.

In some embodiments, an mRNA described herein comprises a 5' cap having the structure of Formula (Cap II).

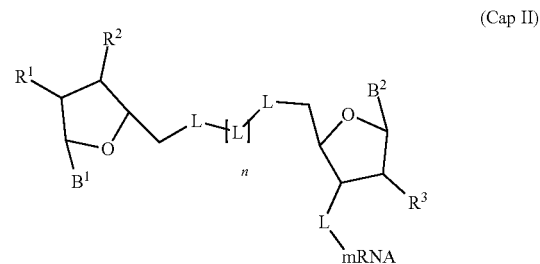

(Cap II)

wherein B$^1$ and B$^2$ are each independently a natural or modified nucleobase; R$^1$, R$^2$, and R$^3$ are each independently selected from a halogen, OH, and OCH$_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments B$^1$ is G, m$^7$G, or A. In some embodiments, n is 0. In some embodiments, n is 1. In some embodiments, B$^1$ is A or m$^6$A and R$^1$ is OCH$_3$; wherein G is guanine, m$^7$G is 7-methylguanine, A is adenine, and m$^6$A is N$^6$-methyladenine.

In some embodiments, an mRNA described herein comprises a 5' cap having the structure of Formula (Cap III).

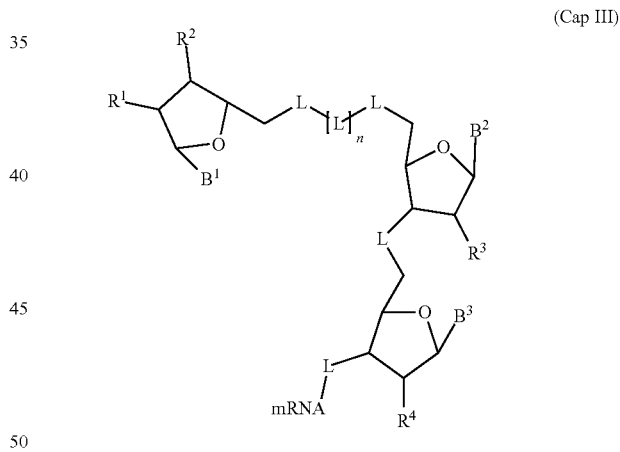

(Cap III)

wherein B$^1$, B$^2$, and B$^3$ are each independently a natural or modified nucleobase; R$^1$, R$^2$, R$^3$, and R$^4$ are each independently selected from a halogen, OH, and OCH$_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of R$^1$, R$^2$, R$^3$, and R$^4$ is OH. In some embodiments B$^1$ is G, m$^7$G, or A. In some embodiments, B$^1$ is A or m$^6$A and R$^1$ is OCH$_3$; wherein G is guanine, m$^7$G is 7-methylguanine, A is adenine, and m$^6$A is N$^6$-methyladenine. In some embodiments, n is 1.

In some embodiments, an mRNA described herein comprises a m$^7$GpppG 5' cap analog having the structure of Formula (Cap IV).

(Cap IV)

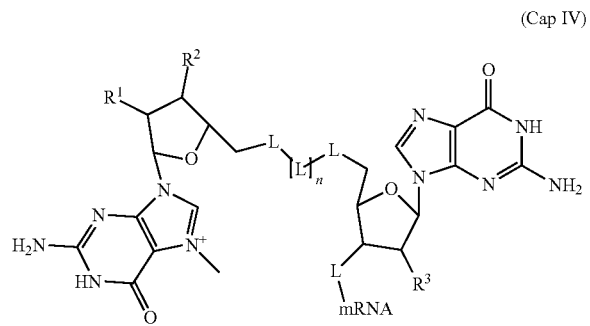

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, and $R^3$ is OH. In some embodiments, the 5' cap is $m^7$GpppG wherein $R^1$, $R^2$, and $R^3$ are each OH, n is 1, and each L is a phosphate. In some embodiments, n is 1. In some embodiments, the 5' cap is $m^7$GpppGm, wherein $R^1$ and $R^2$ are each OH, $R^3$ is $OCH_3$, each L is a phosphate, mRNA is the mRNA encoding an enzyme having OTC activity linked at its 5' end, and n is 1.

In some embodiments, an mRNA described herein comprises a $m^7$Gpppm$^7$G 5' cap analog having the structure of Formula (Cap V).

(Cap V)

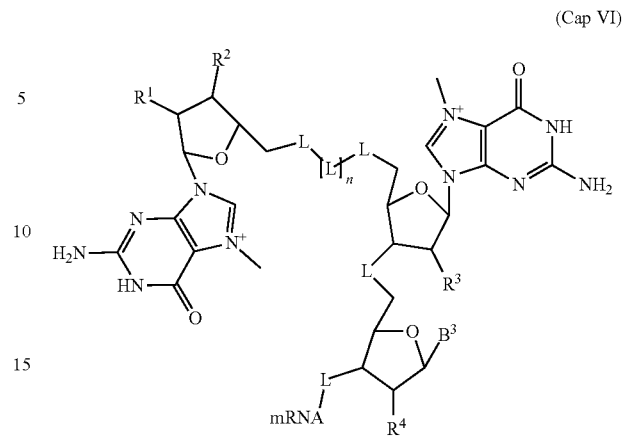

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, an mRNA described herein comprises a $m^7$Gpppm$^7$GpN, 5' cap analog, wherein N is a natural or modified nucleotide, the 5' cap analog having the structure of Formula (Cap VI).

(Cap VI)

wherein $B^3$ is a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 3. In some embodiments, at least one of $R^1$, $R^2$, $R^3$, and $R^4$ is OH. In some embodiments $B^1$ is G, $m^7$G, or A. In some embodiments, $B^1$ is A or $m^6$A and $R^1$ is $OCH_3$; wherein G is guanine, $m^7$G is 7-methylguanine, A is adenine, and $m^6$A is $N^6$-methyladenine. In some embodiments, n is 1.

In some embodiments, an mRNA described herein comprises a $m^7$Gpppm$^7$GpG 5' cap analog having the structure of Formula (Cap VII).

(Cap VII)

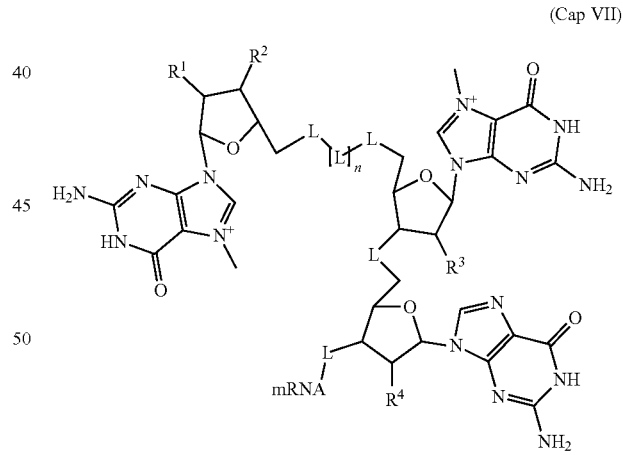

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, an mRNA described herein comprises a $m^7$Gpppm$^7$Gpm$^7$G 5' cap analog having the structure of Formula (Cap VIII).

(Cap VIII)

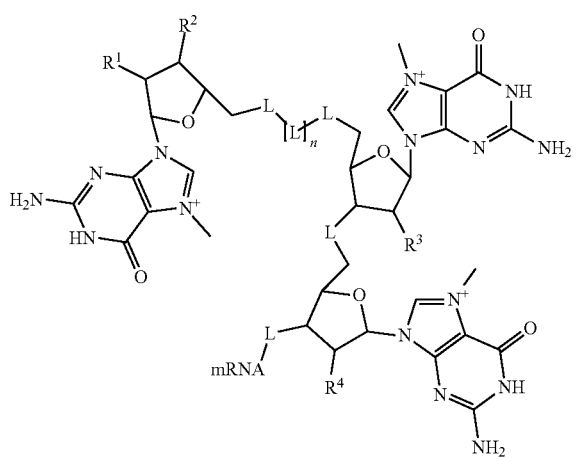

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, $R^3$, and $R^4$ is OH. In some embodiments, n is 1.

In some embodiments, an mRNA described herein comprises a $m^7$GpppA 5' cap analog having the structure of Formula (Cap IX).

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, an mRNA described herein comprises a $m^7$GpppApN 5' cap analog, wherein N is a natural or modified nucleotide, and the 5' cap has the structure of Formula (Cap X).

(Cap X)

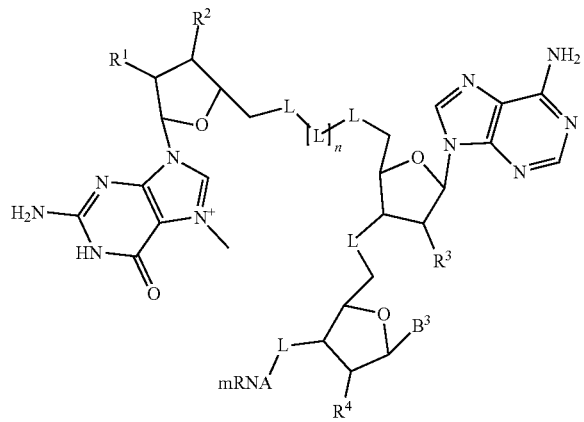

(Cap IX)

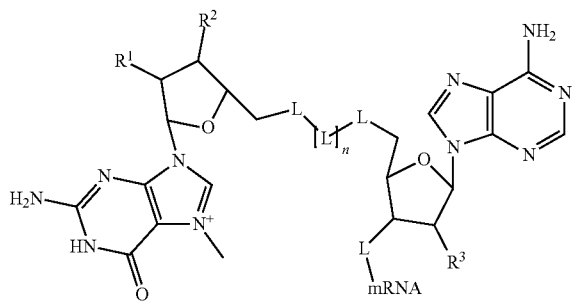

wherein $B^3$ is a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments $B^3$ is G, $m^7$G, A or $m^6$A; wherein G is guanine, $m^7$G is 7-methylguanine, A is adenine, and $m^6$A is $N^6$-methyladenine. In some embodiments, n is 1.

In some embodiments, an mRNA described herein comprises a m⁷GpppAmpG 5' cap analog having the structure of Formula (Cap XI).

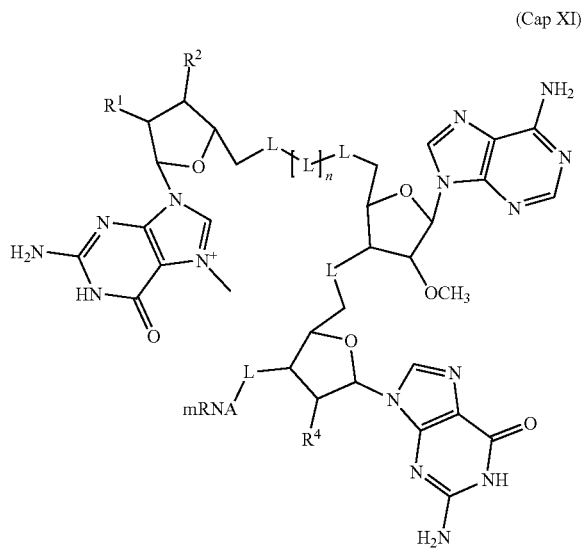

(Cap XI)

wherein, $R^1$, $R^2$, and $R^4$ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, the compound of Formula Cap XI is m⁷GpppAmpG, wherein $R^1$, $R^2$, and $R^4$ are each OH, n is 1, and each L is a phosphate linkage. In some embodiments, n is 1.

In some embodiments, an mRNA described herein comprises m⁷GpppApm⁷G 5' cap analog having the structure of Formula (Cap XII).

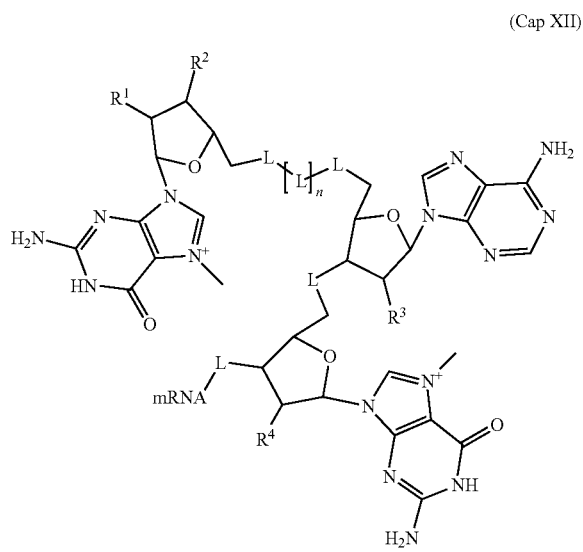

(Cap XII)

wherein, $R^1$, $R^2$, $R^3$, and $R^4$ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, an mRNA described herein comprises a m⁷GpppAmpm⁷G 5' cap analog having the structure of Formula (Cap XIII).

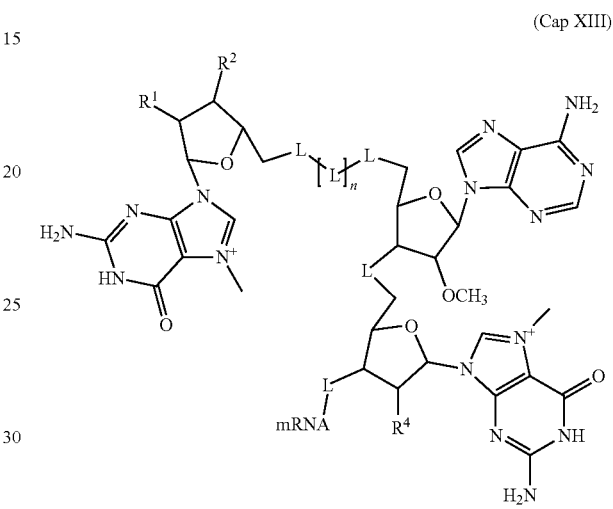

(Cap XIII)

wherein, $R^1$, $R^2$, and $R^4$ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, n is 1.

Poly-Adenine (Poly-A) Tail

Polyadenylation is the addition of a poly(A) tail, a chain of adenine nucleotides usually about 100-120 monomers in length, to an mRNA. In eukaryotes, polyadenylation is part of the process that produces mature mRNA for translation and begins as the transcription of a gene terminates. The 3'-most segment of a newly made pre-mRNA is first cleaved off by a set of proteins; these proteins then synthesize the poly(A) tail at the 3' end. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol.

Preferably, an mRNA described herein comprises a 3' tail region, which can serve to protect the mRNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; 112-121 sequential adenine nucleotides; 114-121 adenine sequential nucleotides; or 115 to 121 sequential adenine nucleotides. Preferably, a 3' poly(A) tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly(A) tails or the use of a ligase (e.g., via splint ligation using a T4 RNA ligase and/or T4 DNA ligase), wherein poly(A) may be ligated to the 3' end of a sense RNA. In some embodiments, a combination of any of the above methods is utilized.

Design and Synthesis of mRNA

The constructs for preferred mRNA sequences of the present disclosure are provided in Table 5.

TABLE 5

Exemplary mRNA Constructs

| mRNA Construct No. | Cap | 5'UTR | Kozak* | OTC Protein Encoded | 3'UTR | 3' Poly A Tail | mRNA Construct SEQ ID NO: |
|---|---|---|---|---|---|---|---|
| 563 | Cap1 | TEV | Yes | SEQ ID NO: 3 | XBG | Yes | 26 |
| 564 | Cap1 | TEV | Yes | SEQ ID NO: 3 | XBG | Yes | 27 |
| 565 | Cap1 | TEV | Yes | SEQ ID NO: 3 | XBG | Yes | 28 |
| 566 | Cap1 | TEV | Yes | SEQ ID NO: 3 | XBG | Yes | 29 |
| 567 | Cap1 | TEV | Yes | SEQ ID NO: 3 | XBG | Yes | 30 |
| 568 | Cap1 | TEV | Yes | SEQ ID NO: 3 | XBG | Yes | 31 |
| 569 | Cap1 | TEV | Yes | SEQ ID NO: 3 | XBG | Yes | 32 |
| 570 | Cap1 | TEV | Yes | SEQ ID NO: 3 | XBG | Yes | 33 |
| 571 | Cap1 | TEV | Yes | SEQ ID NO: 3 | XBG | Yes | 34 |
| 572 | Cap1 | TEV | Yes | SEQ ID NO: 3 | XBG | Yes | 35 |
| 573 | Cap1 | TEV | Yes | SEQ ID NO: 3 | XBG | Yes | 36 |
| 574 | Cap1 | TEV | Yes | SEQ ID NO: 3 | XBG | Yes | 37 |
| 575 | Cap1 | TEV | P | SEQ ID NO: 3 | XBG | Yes | 38 |
| 708 | Cap1 | TEV | P | SEQ ID NO: 3 | XBG | Yes | 39 |
| 709 | Cap1 | TEV | P | SEQ ID NO: 3 | XBG | Yes | 40 |
| 710 | Cap1 | TEV | P | SEQ ID NO: 3 | XBG | Yes | 41 |
| 711 | Cap1 | TEV | P | SEQ ID NO: 3 | XBG | Yes | 42 |
| 712 | Cap1 | TEV | Yes | SEQ ID NO: 3 | XBG | Yes | 43 |
| 713 | Cap1 | TEV | Yes | SEQ ID NO: 3 | XBG | Yes | 44 |
| 714 | Cap1 | TEV | Yes | SEQ ID NO: 3 | XBG | Yes | 45 |
| 715 | Cap1 | TEV | Yes | SEQ ID NO: 3 | XBG | Yes | 46 |
| 716 | Cap1 | TEV | Yes | SEQ ID NO: 3 | XBG | Yes | 47 |
| 717 | Cap1 | TEV | Yes | SEQ ID NO: 3 | XBG | Yes | 48 |
| 718 | Cap1 | TEV | Yes | SEQ ID NO: 3 | XBG | Yes | 49 |
| 719 | Cap1 | TEV | Yes | SEQ ID NO: 3 | XBG | Yes | 50 |
| 720 | Cap1 | TEV | Yes | SEQ ID NO: 3 | XBG | Yes | 51 |
| 721 | Cap1 | TEV | Yes | SEQ ID NO: 3 | XBG | Yes | 52 |
| 722 | Cap1 | TEV | Yes | SEQ ID NO: 3 | XBG | Yes | 53 |
| 723 | Cap1 | TEV | Yes | SEQ ID NO: 3 | XBG | Yes | 54 |
| 724 | Cap1 | TEV | Yes | SEQ ID NO: 3 | XBG | Yes | 55 |
| 725 | Cap1 | TEV | Yes | SEQ ID NO: 3 | XBG | Yes | 56 |
| 726 | Cap1 | TEV | Yes | SEQ ID NO: 3 | XBG | Yes | 57 |
| 727 | Cap1 | TEV | Yes | SEQ ID NO: 3 | XBG | Yes | 58 |
| 728 | Cap1 | TEV | Yes | SEQ ID NO: 3 | XBG | Yes | 59 |
| 729 | Cap1 | TEV | Yes | SEQ ID NO: 3 | XBG | Yes | 60 |
| 1787 | Cap1 | ARC5-2 | No | SEQ ID NO: 3 | Hu haptoglob | Yes | 61 |
| 1788 | Cap1 | AT1G58420 | P | SEQ ID NO: 3 | Hu ApoE | Yes | 62 |
| 1789 | Cap1 | ARC5-2 | No | SEQ ID NO: 3 | Hu haptoglob | Yes | 63 |
| 1790 | Cap1 | AT1G58420 | P | SEQ ID NO: 3 | Hu ApoE | Yes | 64 |
| 1791 | Cap1 | ARC5-2 | No | SEQ ID NO: 3 | Hu haptoglob | Yes | 65 |
| 1792 | Cap1 | HCV5' | P | SEQ ID NO: 3 | HCV3' | Yes | 66 |
| 1793 | Cap1 | AT1G58420 | P | SEQ ID NO: 3 | Hu a-glob | Yes | 67 |
| 1794 | Cap1 | AT1G58420 | P | SEQ ID NO: 3 | Hu a-glob | Yes | 68 |
| 1795 | Cap1 | AT1G58420 | P | SEQ ID NO: 3 | Hu a-glob | Yes | 69 |
| 1796 | Cap1 | Hu alb | No | SEQ ID NO: 3 | Ms Alb | Yes | 70 |
| 1797 | Cap1 | Hu alb | No | SEQ ID NO: 3 | Ms Alb | Yes | 71 |
| 1798 | Cap1 | Hu alb | No | SEQ ID NO: 3 | Ms Alb | Yes | 72 |
| 1799 | Cap1 | AT1G58420 | Yes | SEQ ID NO: 3 | Hu a-glob | Yes | 73 |
| 1800 | Cap1 | Hu alb | No | SEQ ID NO: 3 | Ms Alb | Yes | 74 |
| 1801 | Cap1 | AT1G58420 | P | SEQ ID NO: 3 | Hu ApoE | Yes | 75 |
| 1802 | Cap1 | ARC5-2 | No | SEQ ID NO: 3 | Hu haptoglob | Yes | 76 |
| 1803 | Cap1 | TEV | Yes | SEQ ID NO: 3 | XBG | Yes | 77 |
| 1804 | Cap1 | TEV | Yes | SEQ ID NO: 3 | XBG | Yes | 78 |
| 1805 | Cap1 | TEV | Yes | SEQ ID NO: 3 | XBG | Yes | 79 |
| 1806 | Cap1 | TEV | Yes | SEQ ID NO: 3 | XBG | Yes | 80 |
| 1808 | Cap1 | TEV | Yes | SEQ ID NO: 3 | XBG | Yes | 81 |
| 1809 | Cap1 | TEV | Yes | SEQ ID NO: 3 | XBG | Yes | 82 |
| 1816 | Cap1 | TEV | P | SEQ ID NO: 3 | XBG | Yes | 83 |
| 1822 | Cap1 | TEV | Yes | SEQ ID NO: 3 | XBG | Yes | 84 |
| 1823 | Cap1 | TEV | Yes | SEQ ID NO: 3 | XBG | Yes | 85 |
| 1840 | Cap1 | EMCV | No | SEQ ID NO: 3 | EMCV | Yes | 86 |
| 1841 | Cap1 | EMCV | No | SEQ ID NO: 3 | EMCV | Yes | 87 |

TABLE 5-continued

Exemplary mRNA Constructs

| mRNA Construct No. | Cap | 5'UTR | Kozak* | OTC Protein Encoded | 3'UTR | 3' Poly A Tail | mRNA Construct SEQ ID NO: |
|---|---|---|---|---|---|---|---|
| 1842 | Cap1 | EMCV | No | SEQ ID NO: 3 | EMCV | Yes | 88 |
| 1843 | Cap1 | HSP70-P2-TEV | Yes | SEQ ID NO: 3 | XBG | Yes | 89 |
| 1844 | Cap1 | HSP70-M1-TEV | Yes | SEQ ID NO: 3 | XBG | Yes | 90 |
| 1845 | Cap1 | HSP70-M2-TEV | Yes | SEQ ID NO: 3 | XBG | Yes | 91 |
| 1846 | Cap1 | HSP17.9-TEV | Yes | SEQ ID NO: 3 | XBG | Yes | 92 |
| 1847 | Cap1 | HSP70-P1-TEV | Yes | SEQ ID NO: 3 | XBG | Yes | 93 |
| 1882 | Cap1 | TEV | Yes | SEQ ID NO: 3 | XBG | Yes | 94 |
| 1883 | Cap1 | TEV | Yes | SEQ ID NO: 3 | XBG | Yes | 95 |
| 1884 | Cap1 | TEV | Yes | SEQ ID NO: 3 | XBG | Yes | 96 |
| 1885 | Cap1 | TEV | Yes | SEQ ID NO: 3 | XBG | Yes | 97 |
| 1886 | Cap1 | TEV | Yes | SEQ ID NO: 3 | XBG | Yes | 98 |
| 1887 | Cap1 | TEV | Yes | SEQ ID NO: 3 | XBG | Yes | 99 |
| 1888 | Cap1 | TEV | Yes | SEQ ID NO: 3 | XBG | Yes | 100 |
| 1889 | Cap1 | TEV | Yes | SEQ ID NO: 3 | XBG | Yes | 101 |
| 1890 | Cap1 | TEV | Yes | SEQ ID NO: 3 | XBG | Yes | 102 |
| 1891 | Cap1 | TEV | Yes | SEQ ID NO: 3 | XBG | Yes | 103 |
| 1898 | Cap1 | TEV | Yes | SEQ ID NO: 3 | XBG | Yes | 104 |
| 1899 | Cap1 | TEV | Yes | SEQ ID NO: 3 | XBG | Yes | 105 |
| 1900 | Cap1 | TEV | Yes | SEQ ID NO: 3 | XBG | Yes | 106 |
| 1903 | Cap1 | TEV | P | SEQ ID NO: 3 | XBG | Yes | 107 |
| 1904 | Cap1 | TEV | P | SEQ ID NO: 3 | XBG | Yes | 108 |
| 1905 | Cap1 | TEV | P | SEQ ID NO: 3 | XBG | Yes | 109 |
| 1906 | Cap1 | TEV | P | SEQ ID NO: 3 | XBG | Yes | 110 |
| 1907 | Cap1 | TEV | P | SEQ ID NO: 3 | XBG | Yes | 111 |
| 1908 | Cap1 | TEV | P | SEQ ID NO: 3 | XBG | Yes | 112 |
| 1915 | Cap1 | HSP70-P1-AT1G58420 | Yes | SEQ ID NO: 3 | Hu a-glob | Yes | 113 |
| 1916 | Cap1 | HSP70-P1-AT1G58420 | Yes | SEQ ID NO: 3 | Hu a-glob | Yes | 114 |
| 1917 | Cap1 | HSP70-P1-AT1G58420 | Yes | SEQ ID NO: 3 | Hu a-glob | Yes | 115 |
| 1918 | Cap1 | HSP70-P1-AT1G58420 | Yes | SEQ ID NO: 3 | Hu a-glob | Yes | 116 |
| 1919 | Cap1 | AT1G58420 | Yes | SEQ ID NO: 3 | Hu a-glob | Yes | 117 |
| 1920 | Cap1 | AT1G58420 | Yes | SEQ ID NO: 3 | Hu a-glob | Yes | 118 |
| 1921 | Cap1 | AT1G58420 | Yes | SEQ ID NO: 4** | Hu a-glob | Yes | 119 |
| 1925 | Cap1 | TEV | Yes | SEQ ID NO: 3 | XBG | Yes | 120 |
| 1926 | Cap1 | AT1G58420 | Yes | SEQ ID NO: 3 | Hu a-glob | Yes | 121 |
| 1927 | Cap1 | AT1G58420 | Yes | SEQ ID NO: 3 | Hu a-glob | Yes | 122 |
| 1928 | Cap1 | AT1G58420 | Yes | SEQ ID NO: 3 | Hu a-glob | Yes | 123 |
| 1929 | Cap1 | HSP70-P1-AT1G58420 | Yes | SEQ ID NO: 3 | Hu a-glob | Yes | 124 |
| 2016 | Cap1 | AT1G58420 | Yes | SEQ ID NO: 3 | Hu a-glob | Yes | 253 |
| 2260 | Cap1 | AT1G58420 | Yes | SEQ ID NO: 4** | Hu a-glob | Yes | 251 |
| 2262 | Cap1 | AT1G58420 | Yes | SEQ IS NO: 4** | Hu a-glob | Yes | 252 |

*Kozak sequence defined as GCCACC (SEQ ID NO: 23). Partial (P) Kozak defined as GCCA (SEQ ID NO: 24).
**Construct encodes modified human OTC protein of SEQ ID NO: 4.
*** The SEQ ID NOs associated with the constructs of the above table do not show the poly(A) tail as these can vary in length as further described herein.

Preferred mRNA sequences include all of the mRNA sequences listed in Table 5. In some embodiments, mRNA sequences of the present disclosure include all of the mRNA sequences listed in Table 5 in which 0% to 100%, preferably 1% to 100%, preferably 25% to 100%, preferably 50% to 100% and preferably 75% to 100% of the uracil nucleotides of the mRNA sequences are modified. Preferably, 1% to 100% of the uracil nucleotides are N¹-methylpseudouridine or 5-methoxyuridine. Preferably 100% of the uracil nucleotides are N¹-methylpseudouridine. Preferably 100% of the uracil nucleotides are 5-methoxyuridine.

In some embodiments, an mRNA sequence of the present disclosure comprises a 5' cap, a 5'UTR derived from a gene expressed by *Arabidopsis thaliana*, an optional translation enhancer sequence, an optional Kozak sequence or partial Kozak sequence, a codon optimized coding sequence (CDS/ORF) coding for an OTC protein, a 3' UTR and a poly(A) tail. In some embodiments, the codon optimized CDS encodes a protein of SEQ ID NO: 3 or SEQ ID NO: 4. In some embodiments, the 5' UTR that is derived from a gene expressed by *Arabidopsis thaliana* is selected from the 5' UTRs found in Table 2. In some embodiments, the 5' UTR that is derived from a gene expressed by *Arabidopsis thaliana* is selected from the group consisting of: SEQ ID NO: 6, SEQ ID NOs: 125-127 and SEQ ID NOs: 230-250. In some embodiments the 5' UTR sequence is AT1G58420 having at least 90% identity to the sequence of SEQ ID NO: 6. In some embodiments the 5' UTR sequence is AT1G58420 having the sequence of SEQ ID NO: 6. In some embodiments, the uracil content of the codon optimized sequence has been reduced with respect to the percentages of uracil content of SEQ ID NO: 1. In some embodiments, 0% to 100% of the uracil nucleotides of the mRNA sequences are modified. In some embodiments, 0% to 100% of the uracil nucleotides are $N^1$-methylpseudouridine or 5-methoxyuridine. In some embodiments 100% of the uracil nucleotides are $N^1$-methylpseudouridine. In some embodiments 100% of the uracil nucleotides are 5-methoxyuridine.

Preferred mRNA constructs comprise codon optimized coding sequences and a 5' UTR from a gene expressed by *Arabidopsis thaliana* and are selected from: SEQ ID NOs: 62, 67, 68, 69, 73, 113-119, and 121-127.

A preferred mRNA construct of the disclosure comprises mRNA construct 1921 (SEQ ID NO: 119) having an optimized ORF encoding the modified human OTC protein of SEQ ID NO: 4 and comprising a 3' Poly A tail of 121 nucleotides. Another preferred mRNA construct comprises construct 2260 (SEQ ID NO: 251) encoding the modified human OTC protein of SEQ ID NO: 4 and comprising a 3' Poly(A) tail of 100 nucleotides. Another preferred mRNA construct comprises construct 2262 (SEQ ID NO: 252) encoding the modified human OTC protein of SEQ ID NO: 4 and comprising a 3' Poly(A) tail of 100 nucleotides.

A preferred mRNA sequence of the disclosure includes the mRNA construct 1799 (SEQ ID NO:73) having a codon optimized ORF encoding wild type human OTC of SEQ ID NO: 3 and having a 3' Poly(A) tail of 121 nucleotides. Another preferred mRNA construct of the disclosure includes the mRNA construct 2016 (SEQ ID NO: 253) having a codon optimized ORF encoding wild type human OTC of SEQ ID NO: 3 and comprising a 3' Poly(A) tail of 100 nucleotides.

In some embodiments 100% of the uridine nucleotides of mRNA constructs 1799, 2016, 1921, 2260 and 2262, are $N^1$-methylpseudouridine. In some embodiments 100% of the uracil nucleotides of mRNA constructs 1799, 2016, 1921, 2260 and 2262, are 5-methoxyuridine.

The mRNA for use in accordance with this disclosure can exhibit increased translation efficiency. As used herein, translation efficiency refers to a measure of the production of a protein or polypeptide by translation of an mRNA in accordance with the disclosure. In some embodiments, an mRNA of the disclosure can exhibit at least 2-fold, 3-fold, 5-fold, or 10-fold increased translation efficiency in vivo as compared to mRNA encoding SEQ ID NO: 3 or SEQ ID NO: 4 that is not codon optimized in accordance with the disclosure and/or that does not comprise the preferred UTRs of the disclosure. In some embodiments an mRNA of the disclosure can provide at least a 2-fold, 3-fold, 5-fold, or 10-fold increased polypeptide or protein level in vivo as compared to mRNA encoding SEQ ID NO: 3 or SEQ ID NO: 4 that is not codon optimized and/or does not comprise the preferred UTRs of the disclosure. In some embodiments, an mRNA of the disclosure can provide increased levels of a polypeptide or protein in vivo as compared to mRNA encoding SEQ ID NO: 3 or SEQ ID NO: 4 that is not codon optimized in accordance with the disclosure and/or that does not comprise the preferred UTRs of the disclosure. For example, the level of a polypeptide or protein can be increased by about 10%, or about 20%, or about 30%, or about 40%, or about 50%, or more.

In some embodiments the mRNA of the disclosure can provide increased functional half-life in the cytoplasm of mammalian cells over mRNA encoding SEQ ID NO: 3 or SEQ ID NO: 4 that is not codon optimized in accordance with the disclosure and/or that does not comprise the preferred UTRs of the disclosure. The inventive translatable molecules can have increased half-life of activity as compared to mRNA encoding SEQ ID NO: 3 or SEQ ID NO: 4 that is not codon optimized in accordance with the disclosure and/or that does not comprise the preferred UTRs of the disclosure.

In some embodiments, the mRNA of the disclosure can reduce cellular innate immune response as compared to mRNA encoding SEQ ID NO: 3 or SEQ ID NO: 4 that is not codon optimized in accordance with the disclosure and/or that does not comprise the preferred UTRs of the disclosure.

In some embodiments, the mRNA of the disclosure can reduce the dose levels required for efficacious therapy as compared to mRNA encoding SEQ ID NO: 3 or SEQ ID NO: 4 that is not codon optimized in accordance with the disclosure and/or that does not comprise the preferred UTRs of the disclosure.

The mRNA agents of the present disclosure may be obtained by any suitable means. Methods for the manufacture of mRNA are known in the art and would be readily apparent to a person of ordinary skill. An mRNA for use in accordance with the present disclosure may be prepared according to any available technique including, but not limited to chemical synthesis, in vitro transcription (IVT) or enzymatic or chemical cleavage of a longer precursor, etc.

In some embodiments, mRNA is produced from a primary complementary DNA (cDNA) construct. The cDNA constructs can be produced on an RNA template by the action of a reverse transcriptase (e.g., RNA-dependent DNA-polymerase). The process of design and synthesis of the primary cDNA constructs described herein generally includes the steps of gene construction, mRNA production (either with or without modifications) and purification. In the IVT method, a target polynucleotide sequence encoding an OTC protein is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a human OTC protein (e.g. SEQ ID NO: 3 or SEQ ID NO: 4) is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

The cDNA templates may be transcribed to produce an mRNA sequence described herein using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed mRNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or capping at initiation of in vitro transcription, by for example, including a capping agent as part of the IVT reaction. (Nuc. Acids Symp. (2009) 53:129). A poly(A) tailing reaction may be performed by methods known in the art, such as, but not limited to, 2' O-methyltransferase and by methods as described herein. If the primary construct generated from cDNA does not include a poly-T, it may be beneficial to perform the poly(A)-tailing reaction before the primary construct is cleaned.

Codon optimized cDNA constructs encoding an ornithine transcarbamylase (OTC) protein are particularly suitable for generating mRNA sequences described herein. For example, such cDNA constructs may be used as the basis to transcribe, in vitro, a polyribonucleotide encoding an ornithine transcarbamylase (OTC) protein. Table 6 provides a listing of exemplary cDNA ORF templates used for in vitro transcription of the mRNA sequences listed in Table 5.

TABLE 6

Exemplary cDNA Templates

| DNA Construct No***: | SEQ ID NO: | Protein encoded by cDNA template SEQ ID NO: |
| --- | --- | --- |
| p563 | 128 | SEQ ID NO: 3* |
| p564 | 129 | SEQ ID NO: 3* |
| p565 | 130 | SEQ ID NO: 3* |
| p566 | 131 | SEQ ID NO: 3* |
| p567 | 132 | SEQ ID NO: 3* |
| p568 | 133 | SEQ ID NO: 3* |
| p569 | 134 | SEQ ID NO: 3* |
| p570 | 135 | SEQ ID NO: 3* |
| p571 | 136 | SEQ ID NO: 3* |
| p572 | 137 | SEQ ID NO: 3* |
| p573 | 138 | SEQ ID NO: 3* |
| p574 | 139 | SEQ ID NO: 3* |
| p575 | 140 | SEQ ID NO: 3* |
| p708 | 141 | SEQ ID NO: 3* |
| p709 | 142 | SEQ ID NO: 3* |
| p710 | 143 | SEQ ID NO: 3* |
| p711 | 144 | SEQ ID NO: 3* |
| p712 | 145 | SEQ ID NO: 3* |
| p713 | 146 | SEQ ID NO: 3* |
| p714 | 147 | SEQ ID NO: 3* |
| p715 | 148 | SEQ ID NO: 3* |
| p716 | 149 | SEQ ID NO: 3* |
| p717 | 150 | SEQ ID NO: 3* |
| p718 | 151 | SEQ ID NO: 3* |
| p719 | 152 | SEQ ID NO: 3* |
| p720 | 153 | SEQ ID NO: 3* |
| p721 | 154 | SEQ ID NO: 3* |
| p722 | 155 | SEQ ID NO: 3* |
| p723 | 156 | SEQ ID NO: 3* |
| p724 | 157 | SEQ ID NO: 3* |
| p725 | 158 | SEQ ID NO: 3* |
| p726 | 159 | SEQ ID NO: 3* |
| p727 | 160 | SEQ ID NO: 3* |
| p728 | 161 | SEQ ID NO: 3* |
| p729 | 162 | SEQ ID NO: 3* |
| p1787 | 163 | SEQ ID NO: 3* |
| p1788 | 164 | SEQ ID NO: 3* |
| p1789 | 165 | SEQ ID NO: 3* |

TABLE 6-continued

Exemplary cDNA Templates

| DNA Construct No***: | SEQ ID NO: | Protein encoded by cDNA template SEQ ID NO: |
| --- | --- | --- |
| p1790 | 166 | SEQ ID NO: 3* |
| p1791 | 167 | SEQ ID NO: 3* |
| p1792 | 168 | SEQ ID NO: 3* |
| p1793 | 169 | SEQ ID NO: 3* |
| p1794 | 170 | SEQ ID NO: 3* |
| p1795 | 171 | SEQ ID NO: 3* |
| p1796 | 172 | SEQ ID NO: 3* |
| p1797 | 173 | SEQ ID NO: 3* |
| p1798 | 174 | SEQ ID NO: 3* |
| p1799 | 175 | SEQ ID NO: 3* |
| p1800 | 176 | SEQ ID NO: 3* |
| p1801 | 177 | SEQ ID NO: 3* |
| p1802 | 178 | SEQ ID NO: 3* |
| p1803 | 179 | SEQ ID NO: 3* |
| p1804 | 180 | SEQ ID NO: 3* |
| p1805 | 181 | SEQ ID NO: 3* |
| p1806 | 182 | SEQ ID NO: 3* |
| p1808 | 183 | SEQ ID NO: 3* |
| p1809 | 184 | SEQ ID NO: 3* |
| p1816 | 185 | SEQ ID NO: 3* |
| p1822 | 186 | SEQ ID NO: 3* |
| p1823 | 187 | SEQ ID NO: 3* |
| p1840 | 188 | SEQ ID NO: 3* |
| p1841 | 189 | SEQ ID NO: 3* |
| p1842 | 190 | SEQ ID NO: 3* |
| p1843 | 191 | SEQ ID NO: 3* |
| p1844 | 192 | SEQ ID NO: 3* |
| p1845 | 193 | SEQ ID NO: 3* |
| p1846 | 194 | SEQ ID NO: 3* |
| p1847 | 195 | SEQ ID NO: 3* |
| p1882 | 196 | SEQ ID NO: 3* |
| p1883 | 197 | SEQ ID NO: 3* |
| p1884 | 198 | SEQ ID NO: 3* |
| p1885 | 199 | SEQ ID NO: 3* |
| p1886 | 200 | SEQ ID NO: 3* |
| p1887 | 201 | SEQ ID NO: 3* |
| p1888 | 202 | SEQ ID NO: 3* |
| p1889 | 203 | SEQ ID NO: 3* |
| p1890 | 204 | SEQ ID NO: 3* |
| p1891 | 205 | SEQ ID NO: 3* |
| p1898 | 206 | SEQ ID NO: 3* |
| p1899 | 207 | SEQ ID NO: 3* |
| p1900 | 208 | SEQ ID NO: 3* |
| p1903 | 209 | SEQ ID NO: 3* |
| p1904 | 210 | SEQ ID NO: 3* |
| p1905 | 211 | SEQ ID NO: 3* |
| p1906 | 212 | SEQ ID NO: 3* |
| p1907 | 213 | SEQ ID NO: 3* |
| p1908 | 214 | SEQ ID NO: 3* |
| p1915 | 215 | SEQ ID NO: 3* |
| p1916 | 216 | SEQ ID NO: 3* |
| p1917 | 217 | SEQ ID NO: 3* |
| p1918 | 218 | SEQ ID NO: 3* |
| p1919 | 219 | SEQ ID NO: 3* |
| p1920 | 220 | SEQ ID NO: 3* |
| p1921 | 221 | SEQ ID NO: 4** |
| p1925 | 222 | SEQ ID NO: 3* |
| p1926 | 223 | SEQ ID NO: 3* |
| p1927 | 224 | SEQ ID NO: 3* |
| p1928 | 225 | SEQ ID NO: 3* |
| p1929 | 226 | SEQ ID NO: 3* |
| p2016 | 227 | SEQ ID NO: 3* |
| p2260 | 228 | SEQ ID NO: 4** |
| p2262 | 229 | SEQ ID NO: 4** |

*SEQ ID NO: 3 is the amino acid sequence for wild type human OTC.
**SEQ ID NO: 4 is the amino acid sequence for modified human OTC.
***The entire plasmid sequence is not included.

Preferred cDNA template sequences include the DNA sequence of SEQ ID NO: 175 (p1779) having an optimized coding sequence encoding wild type human OTC of SEQ ID NO: 3. Preferred cDNA template sequences also include cDNA sequence of SEQ ID NO: 221 (p1921), having an optimized coding sequence encoding a modified OTC protein of SEQ ID NO: 4.

The present disclosure also provides expression vectors comprising a nucleotide sequence encoding an ornithine transcarbamylase (OTC) protein that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides polynucleotides (e.g. DNA, RNA, cDNA, mRNA, etc.) encoding a human OTC protein that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

The present disclosure also provides a host cell transfected with an mRNA or DNA described herein which encodes an ornithine transcarbamylase (OTC) polypeptide described herein. In some embodiments, the human OTC polypeptide has the sequence of SEQ ID NO: 4. The host cell may be any prokaryotic or eukaryotic cell. For example, an ornithine transcarbamylase (OTC) polypeptide may be expressed in bacterial cells such as *E. coli*, insect cells (e.g., using a baculovirus expression system), yeast, or mammalian cells. Other suitable host cells are known to those skilled in the art.

The present disclosure also provides a host cell comprising a vector comprising a polynucleotide which encodes an mRNA sequence of any one of SEQ ID NOs: 26-229.

The present disclosure also provides methods of producing a human wild type OTC protein of SEQ ID NO: 3 or a modified human OTC protein SEQ ID NO: 4. In some embodiments, the OTC protein is SEQ ID NO: 4 and is encoded by mRNA of SEQ ID NO 119. For example, a host cell transfected with an expression vector encoding an OTC protein can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed OTC proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the (OTC polypeptide).

Lipid-Based Formulations

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 June; 12 (6): 825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), release at the cytoplasm (for RNA), and so on. Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still under ongoing development.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16:307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and would be within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicle (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several non-concentric lipid bilayers.

Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843). In their use as drug delivery vehicles, because a liposome has an aqueous solution core surrounded 1 by a hydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid will be contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed hereinbelow.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell is formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (Imparted by the cationic lipid) result in rapid plasma clearance, hemolytic and other toxicities, as well as immune system activation.

Lipid-mRNA Formulations

An mRNA as disclosed herein or a pharmaceutically acceptable salt thereof can be incorporated into a lipid formulation (i.e., a lipid-based delivery vehicle).

In the context of the present disclosure, a lipid-based delivery vehicle typically serves to transport a desired mRNA to a target cell or tissue. The lipid-based delivery vehicle can be any suitable lipid-based delivery vehicle known in the art. In some embodiments, the lipid-based delivery vehicle is a liposome, a cationic liposome, or a lipid nanoparticle containing an mRNA of the present disclosure. In some embodiments, the lipid-based delivery vehicle comprises a nanoparticle or a bilayer of lipid molecules and an mRNA of the present disclosure. In some embodiments, the lipid bilayer preferably further comprises a neutral lipid or a polymer. In some embodiments, the lipid formulation preferably comprises a liquid medium. In some embodiments, the formulation preferably further encapsulates a nucleic acid. In some embodiments, the lipid formulation preferably further comprises a nucleic acid and a neutral lipid or a polymer. In some embodiments, the lipid formulation preferably encapsulates the nucleic acid.

The description provides lipid formulations comprising one or more therapeutic mRNA molecules encapsulated within the lipid formulation. In some embodiments, the lipid formulation comprises liposomes. In some embodiments, the lipid formulation comprises cationic liposomes. In some embodiments, the lipid formulation comprises lipid nanoparticles.

In some embodiments, the mRNA is fully encapsulated within the lipid portion of the lipid formulation such that the mRNA in the lipid formulation is resistant in aqueous solution to nuclease degradation. In other embodiments, the lipid formulations described herein are substantially non-toxic to mammals such as humans.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 38:1, or from about 10:1 to about 40:1, or from about 15:1 to about 35:1, or from about 20:1 to about 40:1; or from about 25:1 to about 35:1; or from about 27:1 to about 32:1; or from about 28:1 to about 32:1; or from about 29:1 to about 31:1. In some preferred embodiments, the total lipid:RNA ratio (mass/mass ratio) is from about 25:1 to about 35:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, are resistant in aqueous solution to degradation with a nuclease.

In preferred embodiments, the lipid formulations comprise an mRNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol.

In the nucleic acid-lipid formulations, the mRNA may be fully encapsulated within the lipid portion of the formulation, thereby protecting the nucleic acid from nuclease degradation. In preferred embodiments, a lipid formulation comprising an mRNA is fully encapsulated within the lipid portion of the lipid formulation, thereby protecting the nucleic acid from nuclease degradation. In certain instances, the mRNA in the lipid formulation is not substantially degraded after exposure of the particle to a nuclease at 37° C. for at least 20, 30, 45, or 60 minutes. In certain other instances, the mRNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the formulation. One of the benefits of the formulations of the present disclosure is that the nucleic acid-lipid compositions are substantially non-toxic to mammals such as humans.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present disclosure provides a nucleic acid-lipid composition comprising a plurality of nucleic acid-liposomes, nucleic acid-cationic liposomes, or nucleic acid-lipid nanoparticles. In some embodiments, the nucleic acid-lipid composition comprises a plurality of mRNA-liposomes. In some embodiments, the nucleic acid-lipid composition comprises a plurality of mRNA-cationic liposomes. In some embodiments, the nucleic acid-lipid composition comprises a plurality of mRNA-lipid nanoparticles.

In some embodiments, the lipid formulations comprise mRNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the mRNA encapsulated therein. The amount may be any value or subvalue within the recited ranges, including endpoints.

Depending on the intended use of the lipid formulation, the proportions of the components can be varied, and the delivery efficiency of a particular formulation can be measured using assays known in the art.

According to some embodiments, the expressible polynucleotides and heterologous mRNA constructs described herein are lipid formulated. The lipid formulation is preferably selected from, but not limited to, liposomes, cationic liposomes, and lipid nanoparticles. In one preferred embodiment, a lipid formulation is a cationic liposome or a lipid nanoparticle (LNP) comprising:

(a) an mRNA of the present disclosure,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In one some embodiments, the cationic lipid is an ionizable cationic lipid. In one embodiment, the lipid nanoparticle formulation consists of (i) at least one cationic lipid; (ii) a helper lipid; (iii) a sterol (e.g., cholesterol); and (iv) a PEG-lipid, in a molar ratio of about 40-70% ionizable cationic lipid: about 2-15% helper lipid: about 20-45% sterol; about 0.5-5% PEG-lipid. Exemplary cationic lipids (including ionizable cationic lipids), helper lipids (e.g., neutral lipids), sterols, and ligand-containing lipids (e.g., PEG-lipids) are described hereinbelow.

Cationic Lipids

The lipid formulation preferably includes a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-[1-(2,3-dioleoyloxy) propyl]-N,N,N-trimethylammonium methyl sulfate) can form complexes or lipoplexes with negatively charged nucleic acids by electrostatic interaction, providing high in vitro transfection efficiency.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy) propyl)-N,N,N-trimethylammonium chloride and 1,2-Dioleyloxy-3-trimethylaminopropane chloride salt), N-(1-(2,3-dioleyloxy) propyl)-N,N,N-trimethylammonium chloride (DOTMA), N,N-dimethyl-2,3-dioleyloxy) propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino) propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino) ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta [d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl) (2-hydroxydodecyl)amino)ethyl) piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3β-(N—(N',N'-dimethylaminoethane)-carbamoyl) cholesterol (DC-Chol), N-(1-(2,3-dioleyloxy) propyl)-N-2-(sperminecarboxamido) ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107 (5), 1864-69, 2010, the contents of which are herein incorporated by reference.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I:

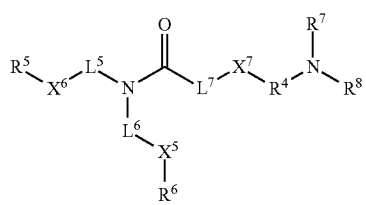

(I)

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, $X^7$ is S.

In some embodiments, $X^5$ is —C(O)O—, whereby —C(O)O—$R^6$ is formed and $X^6$ is —C(O)O— whereby —C(O)O—$R^5$ is formed.

In some embodiments, $R^7$ and $R^8$ are each independently selected from the group consisting of methyl, ethyl and isopropyl.

In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond. In some embodiments, $R^5$ and $R^6$ are each alkyl. In some embodiments, $R^5$ is a branched alkyl. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —CH(($CH_2)_p CH_3)_2$ or —CH(($CH_2)_p CH_3$)(($CH_2)_{p-1}CH_3$), wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is a $C_1$-$C_3$ alkyl. In some embodiments, $R^5$ consists of —CH(($CH_2)_p CH_3$)(($CH_2)_{p-1}CH_3$), wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments, $X^7$ is S, $X^5$ is —C(O)O—, whereby —C(O)O—$R^6$ is formed, $X^6$ is —C(O)O— whereby —C(O)O—$R^5$ is formed, $L^5$ and $L^6$ are each independently a linear $C_3$-$C_7$ alkyl, $L^7$ is absent, $R^5$ is —CH(($CH_2)_p CH_3)_2$, and $R^6$ is $C_7$-$C_{12}$ alkenyl. In some further embodiments, p is 6 and $R^6$ is $C_9$ alkenyl.

In some embodiments, the lipid formulation comprises an ionizable cationic lipid selected from the group consisting of

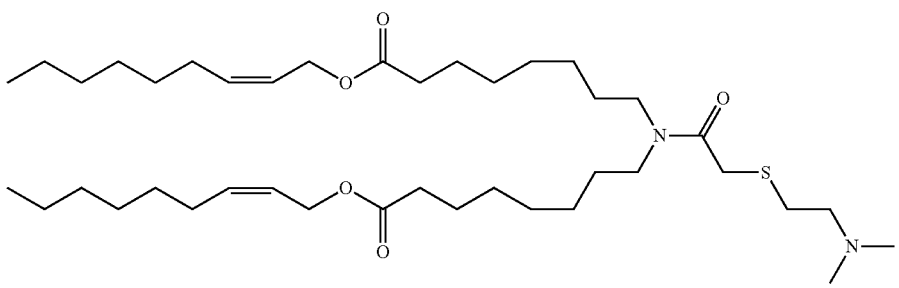

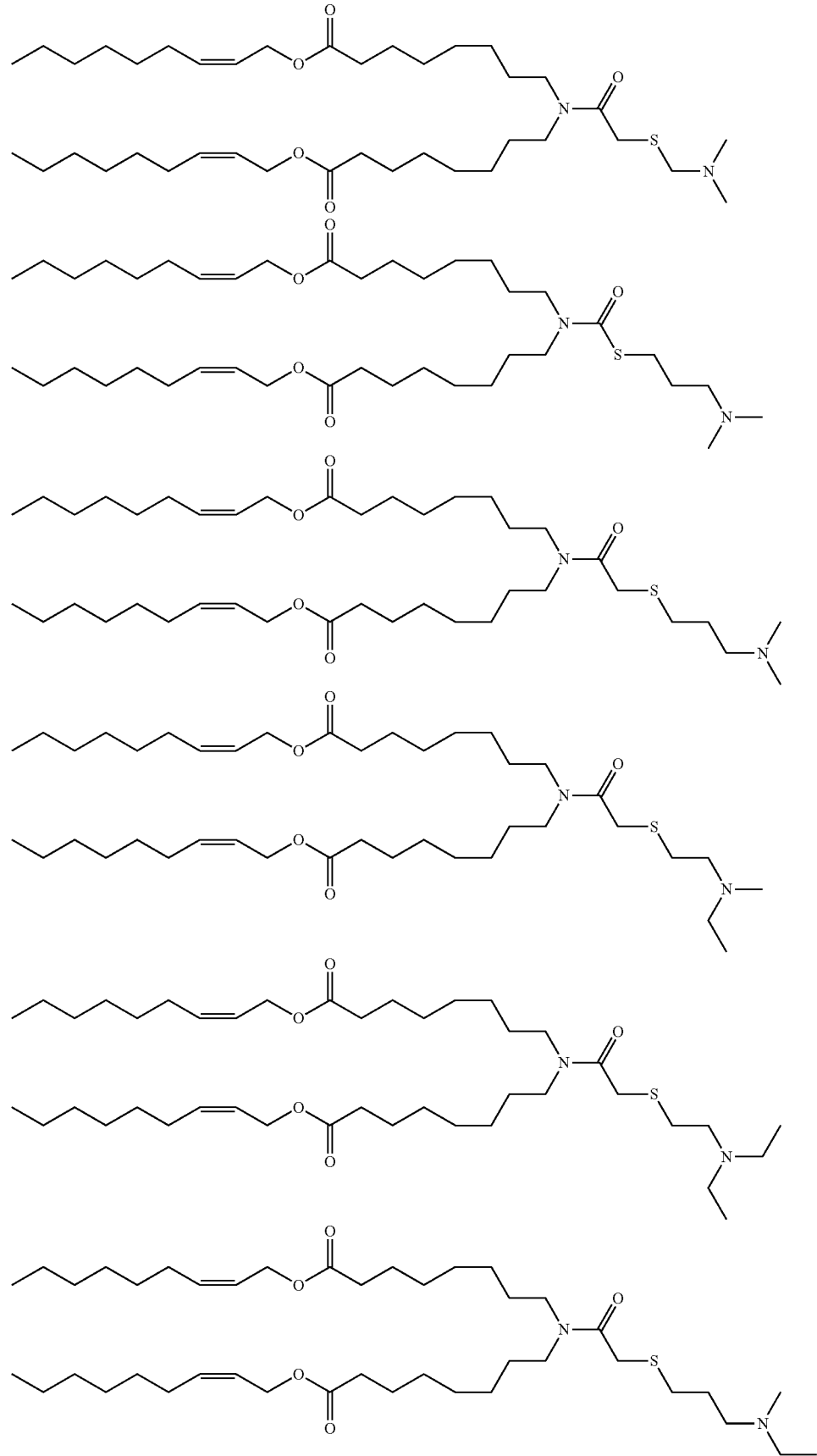

-continued
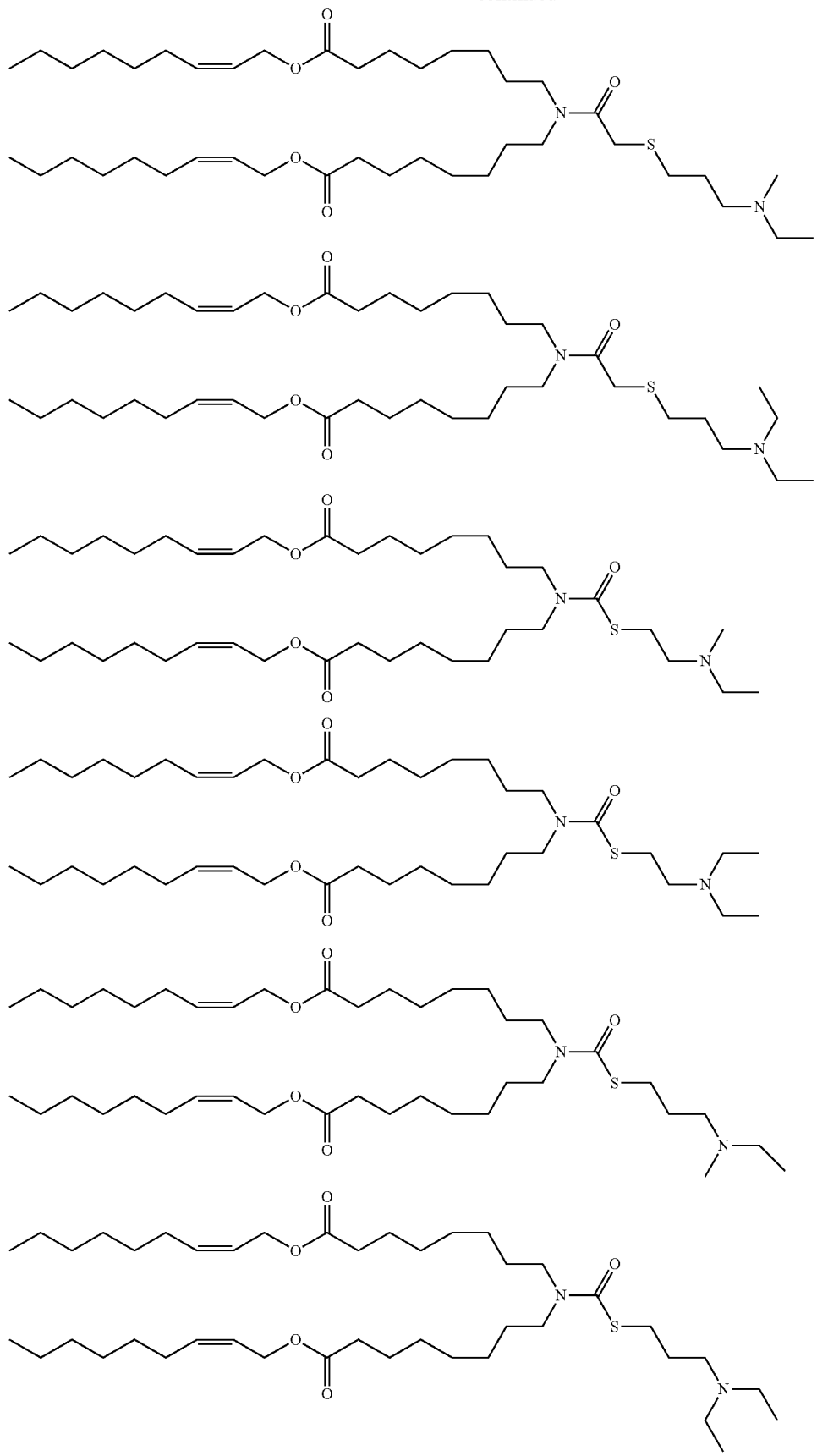

-continued
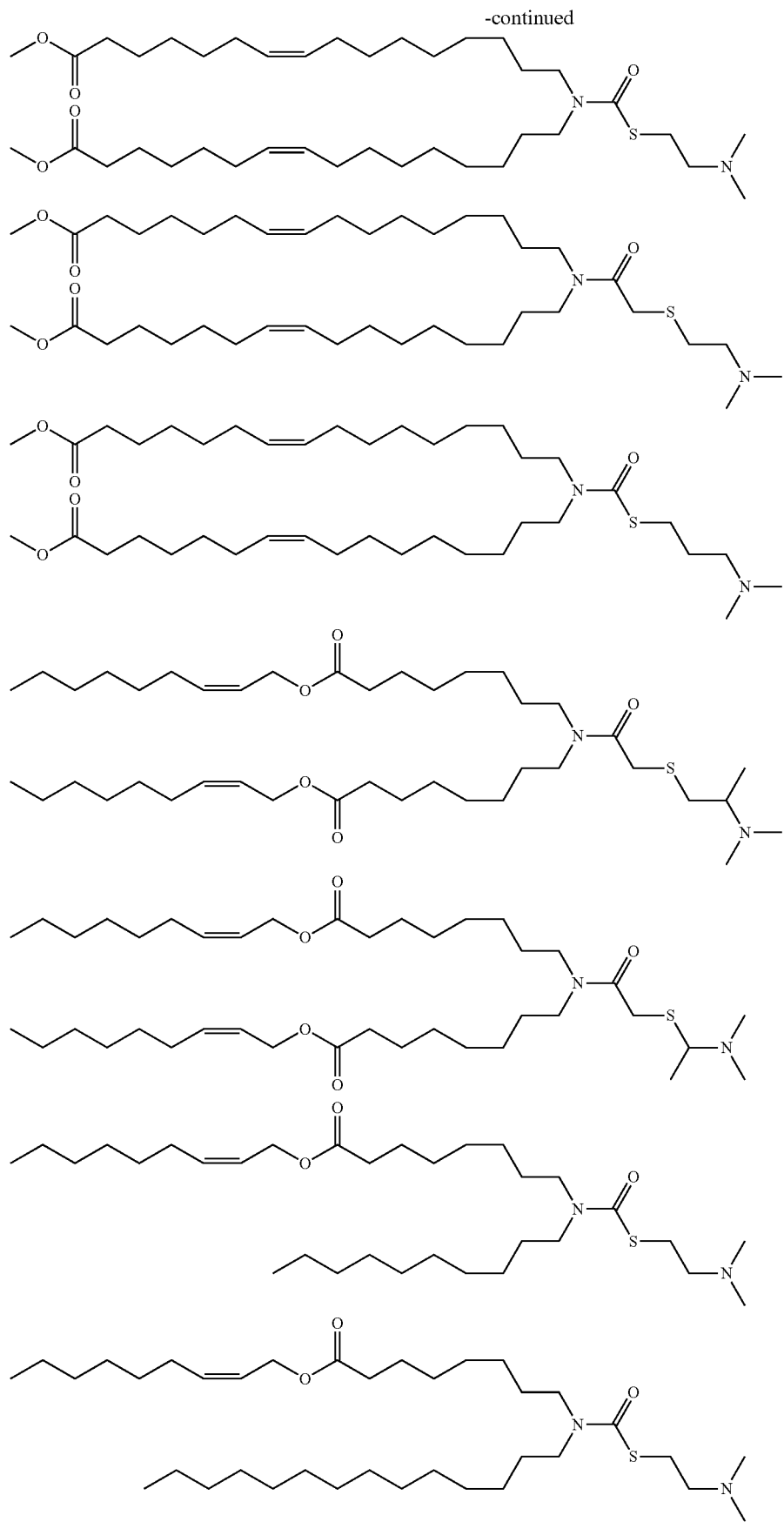

-continued
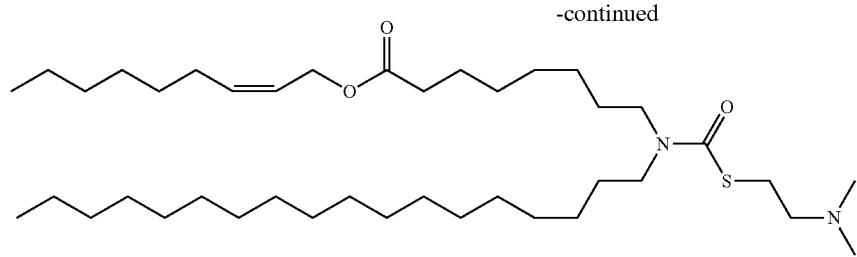
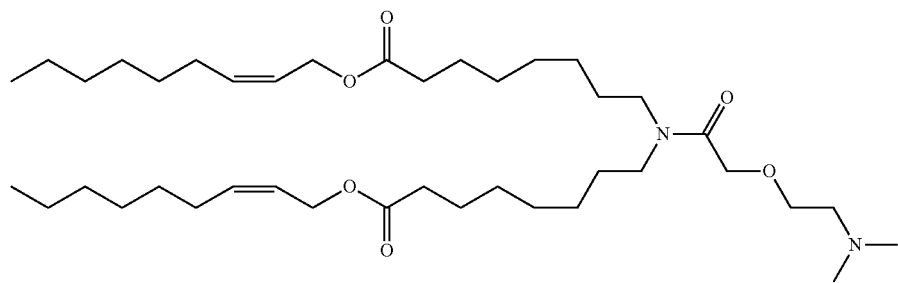
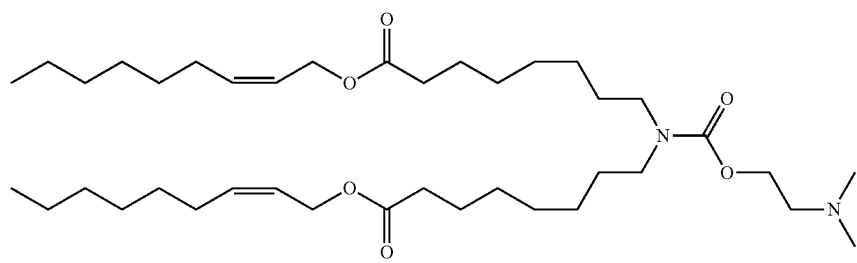
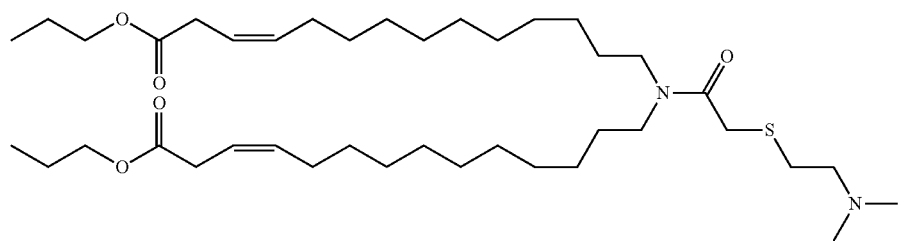
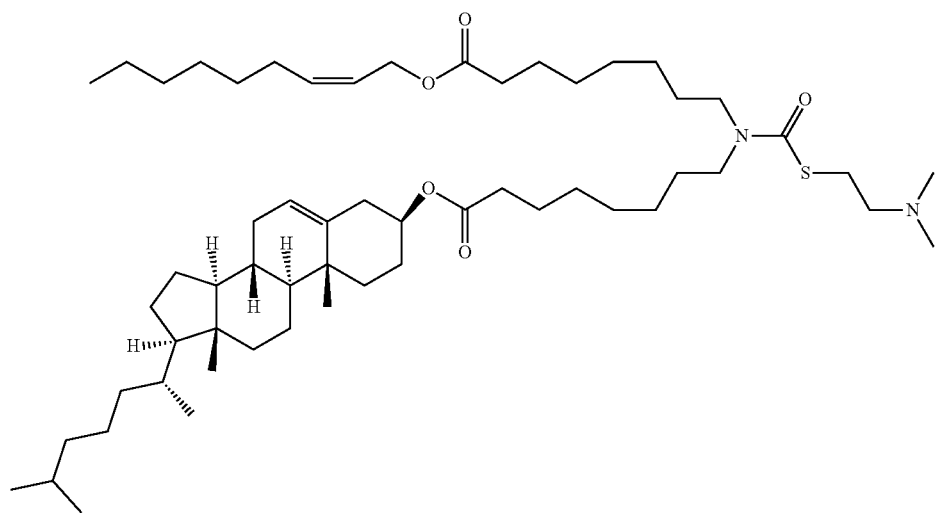

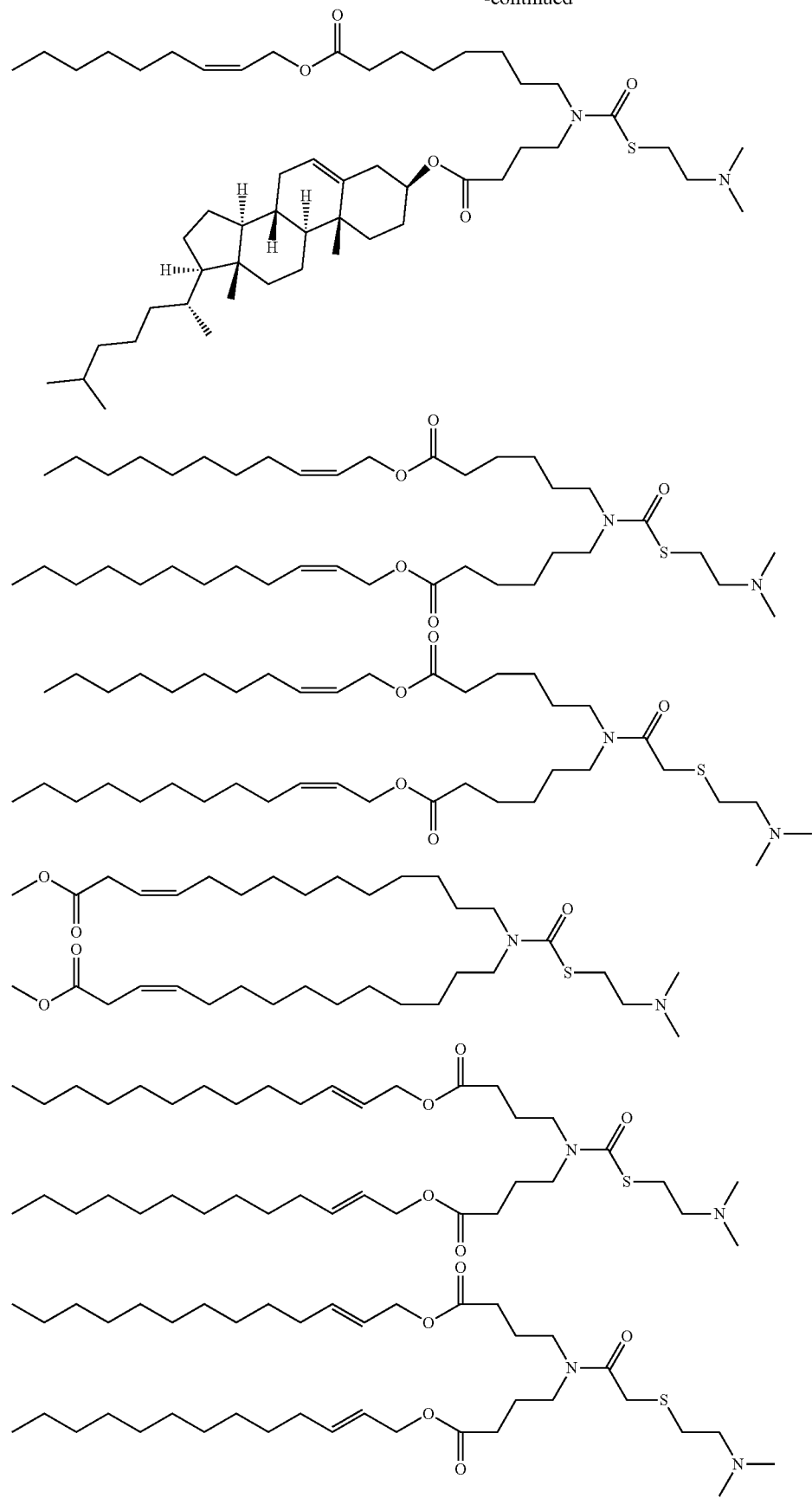

-continued
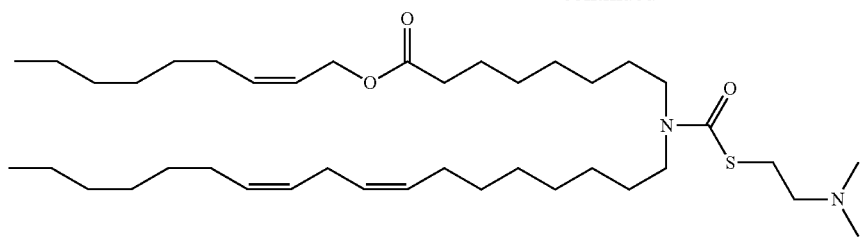
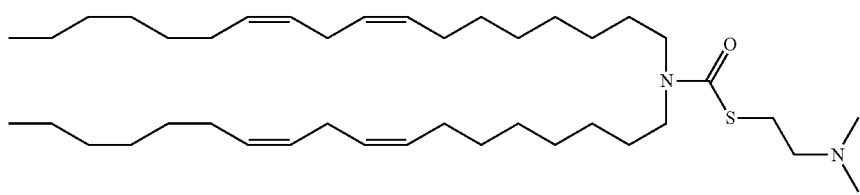
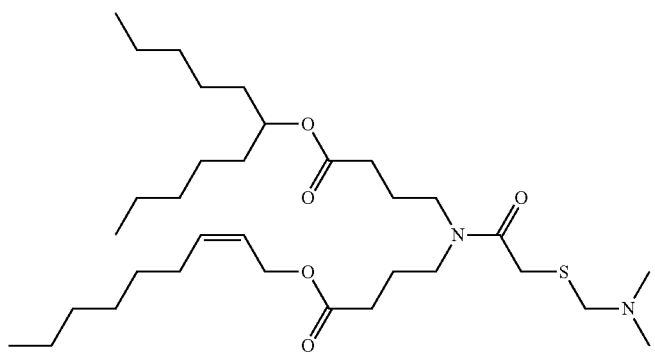
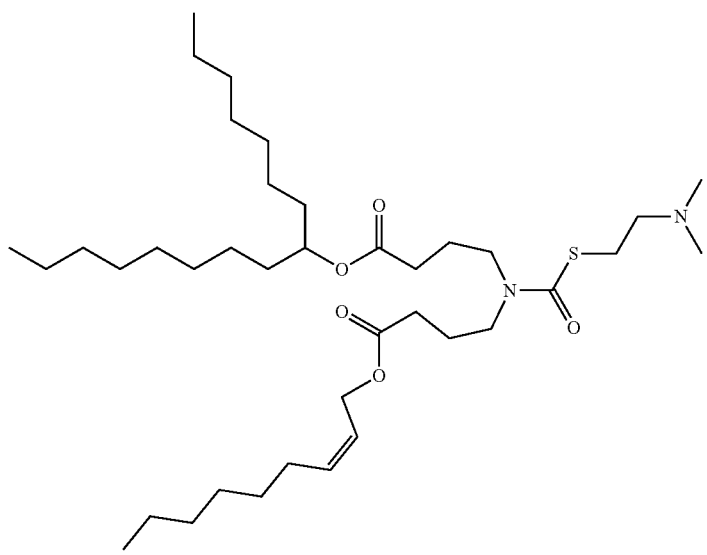

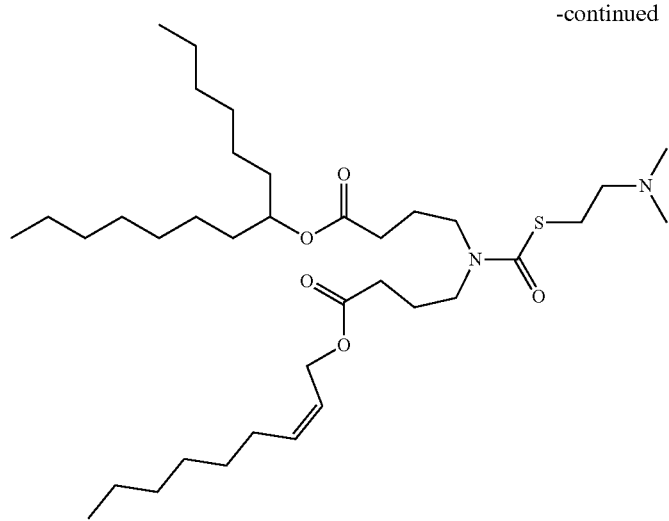
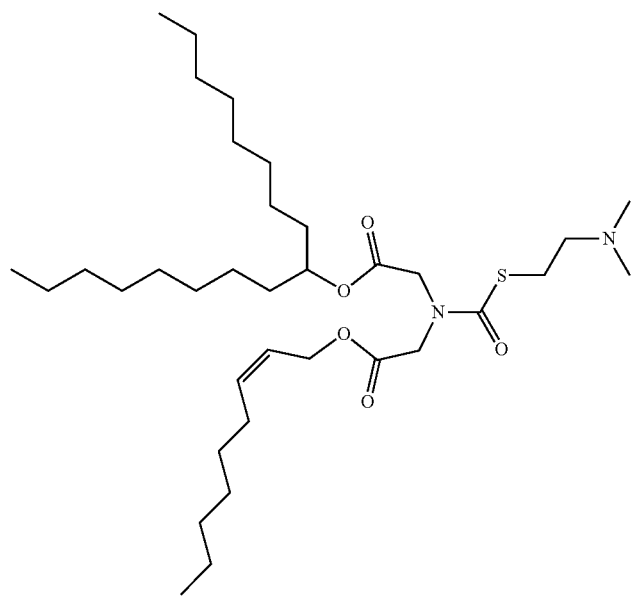
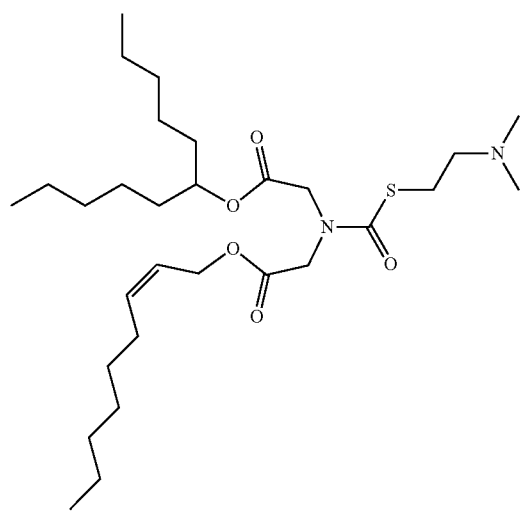
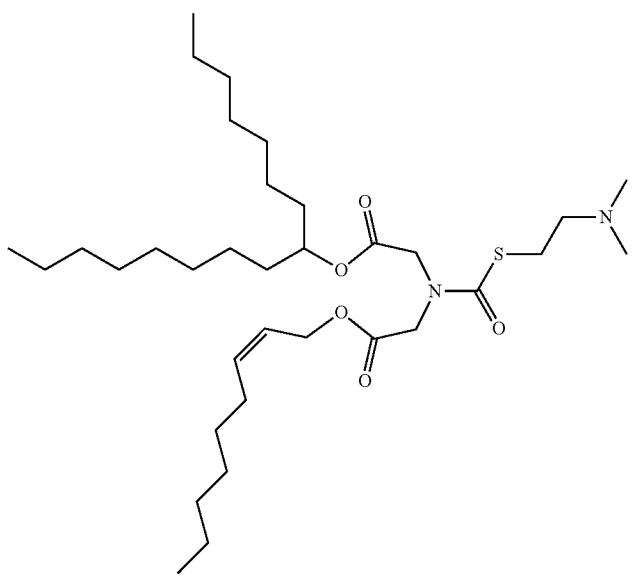

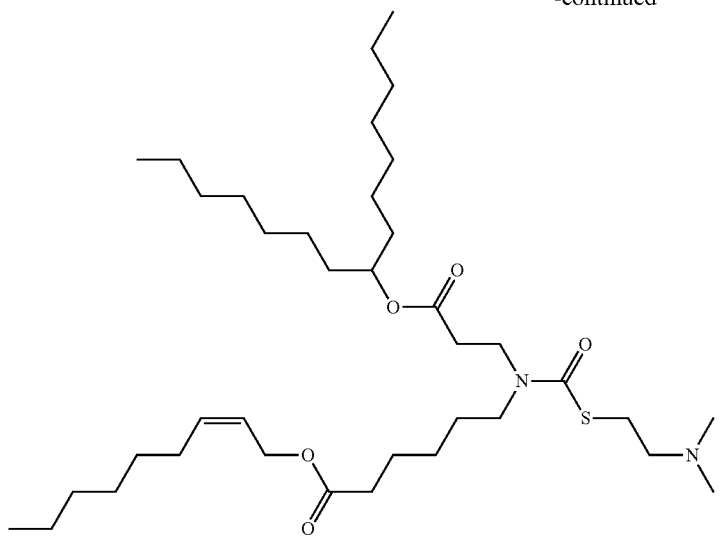
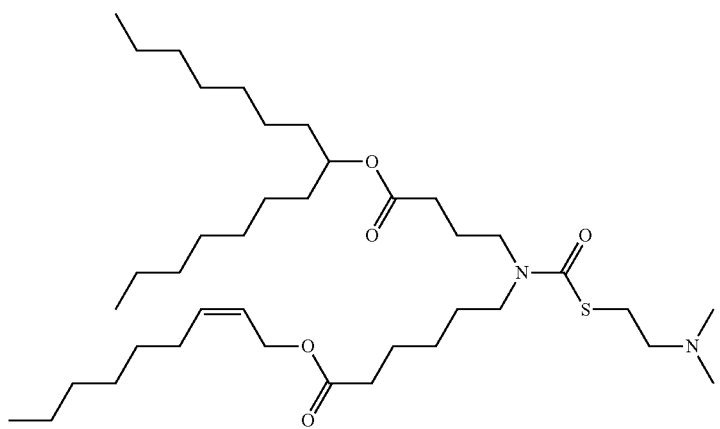
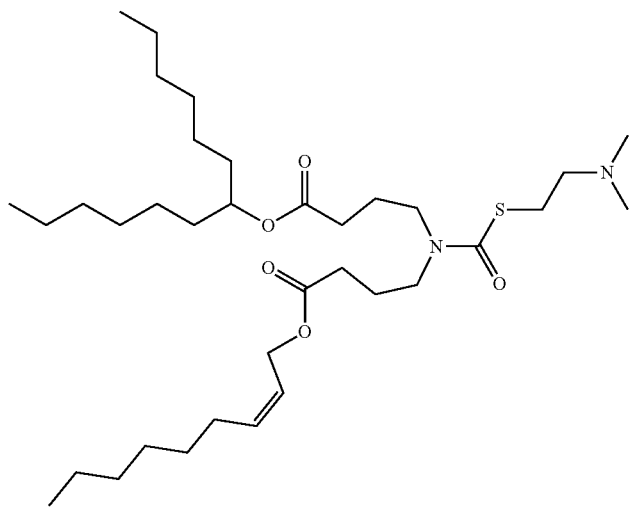

-continued
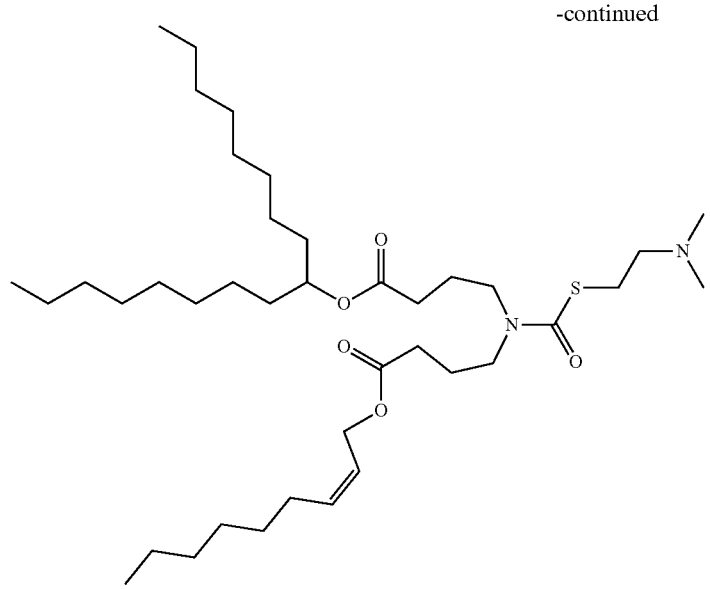
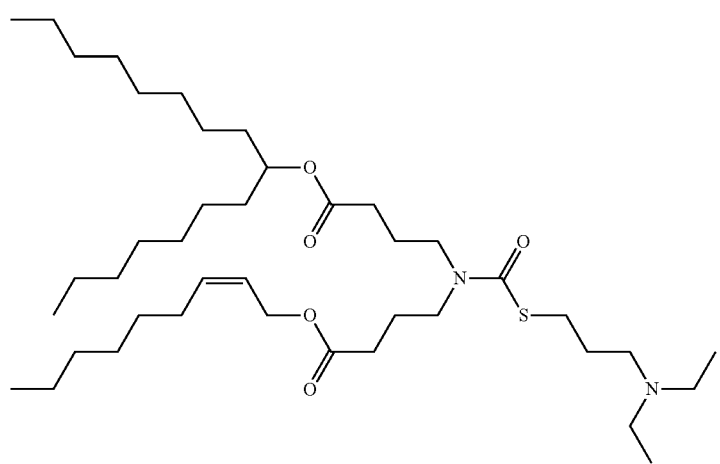
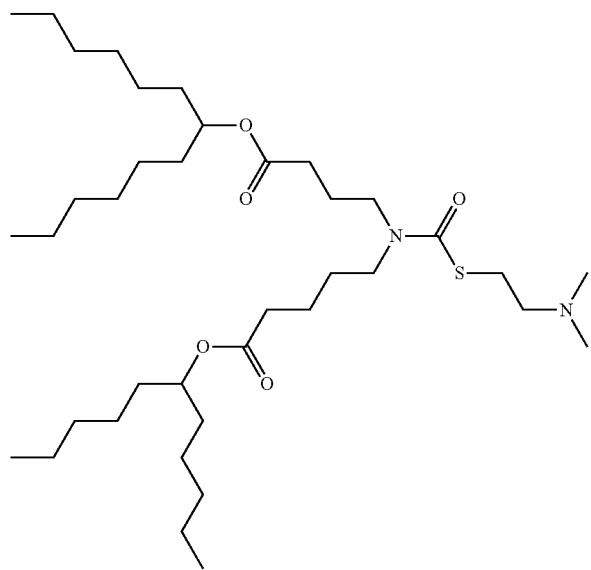

-continued
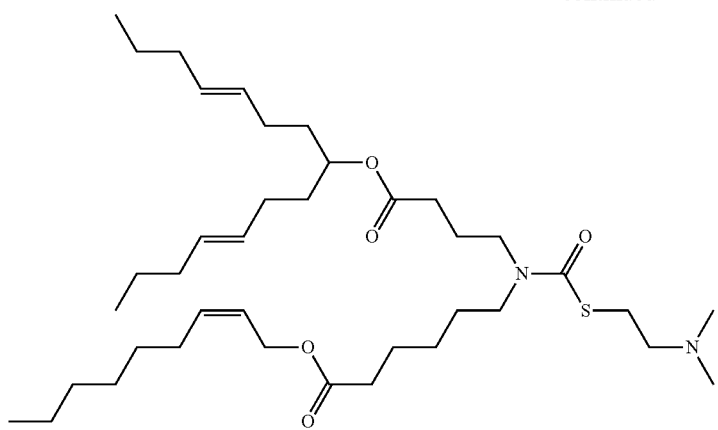
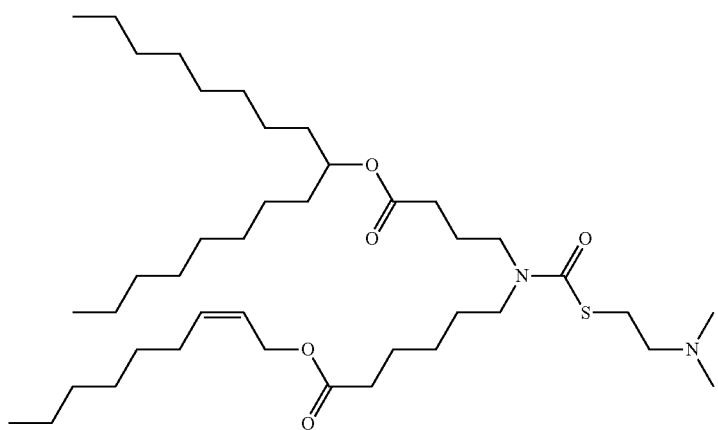
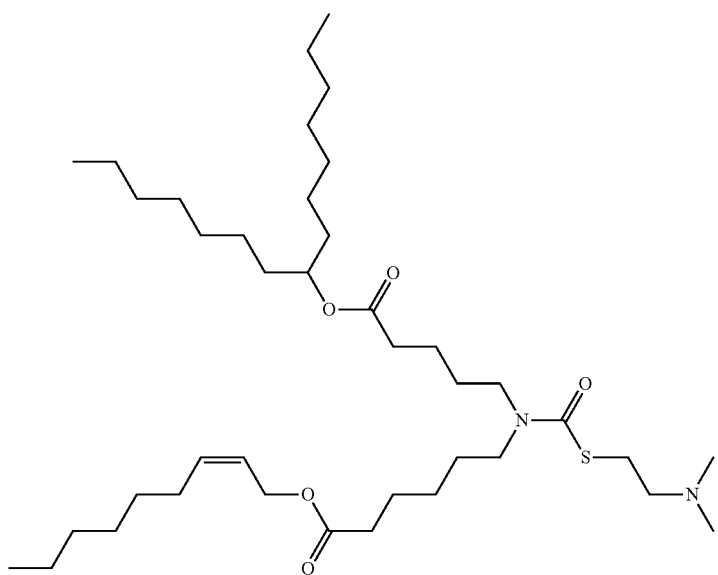

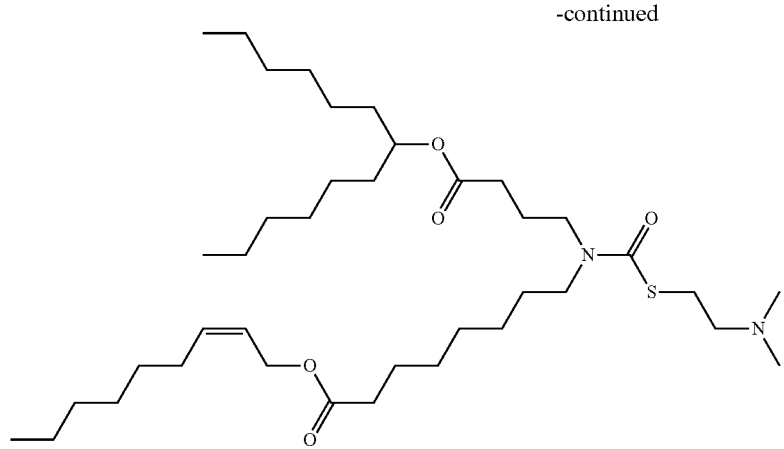
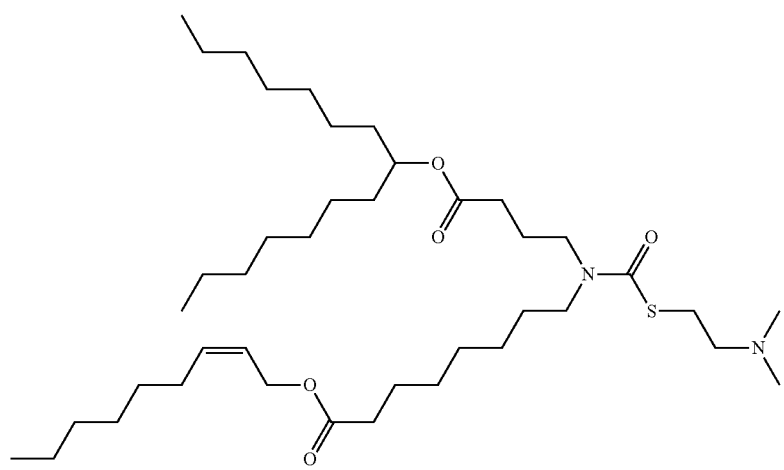
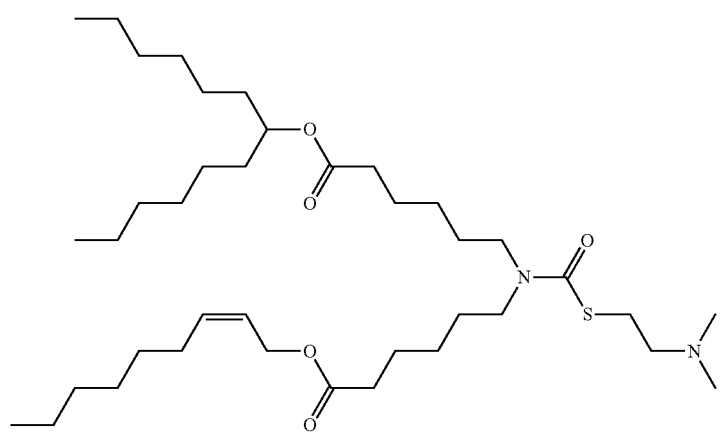

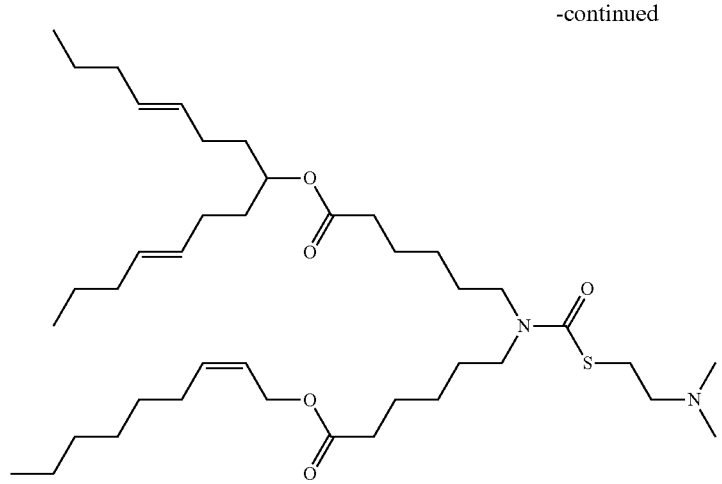
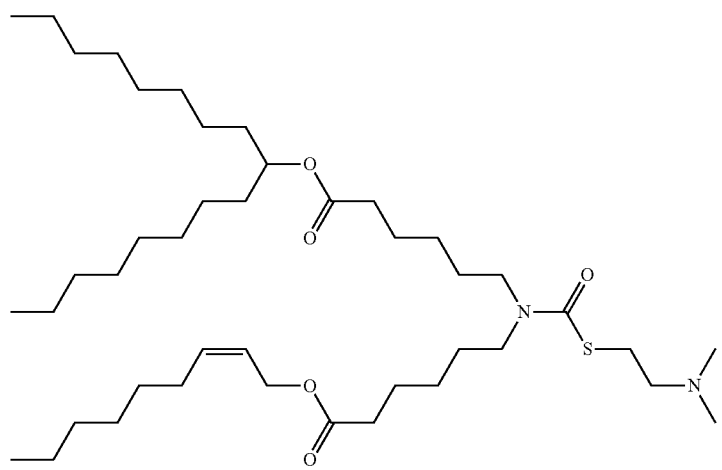
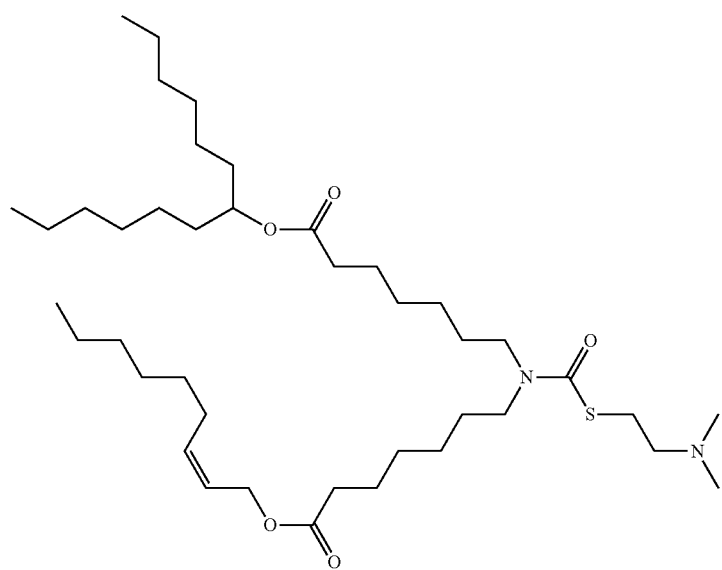

-continued
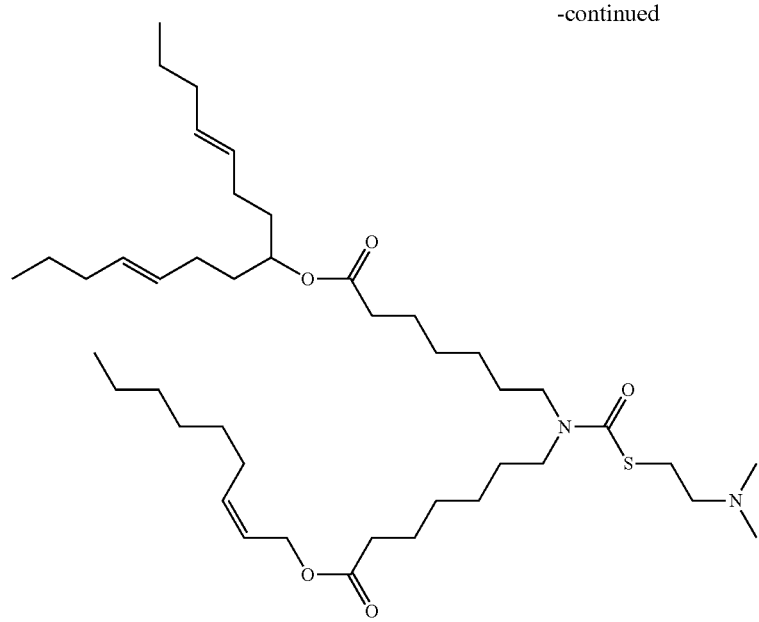
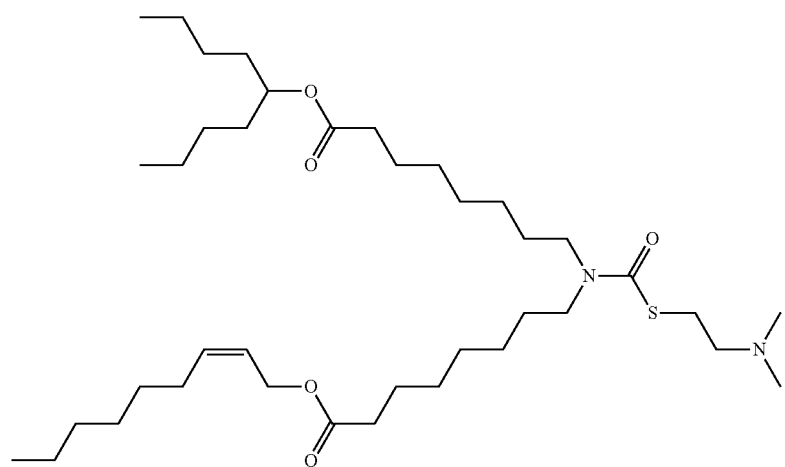
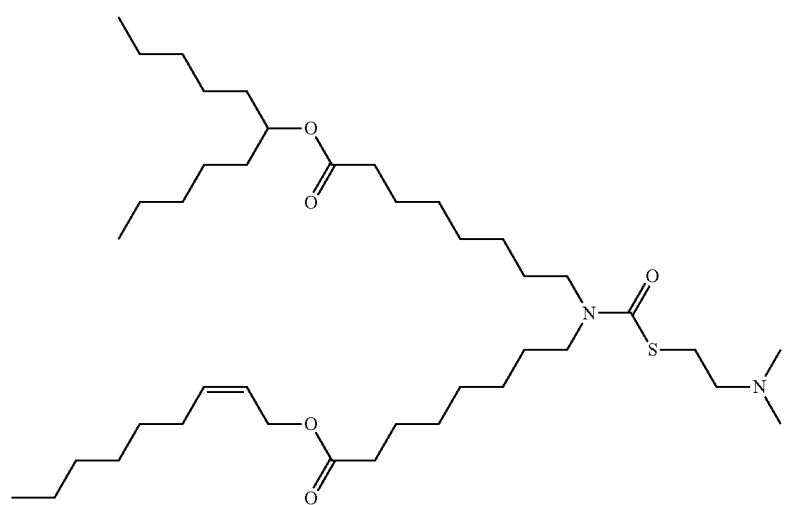

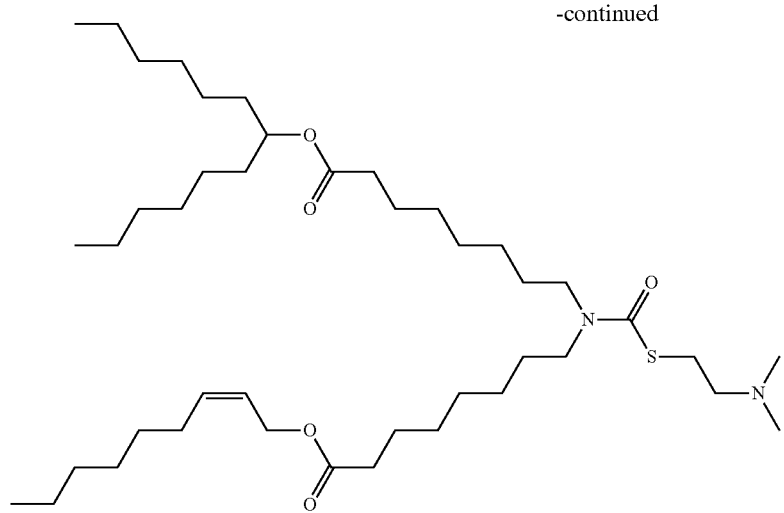
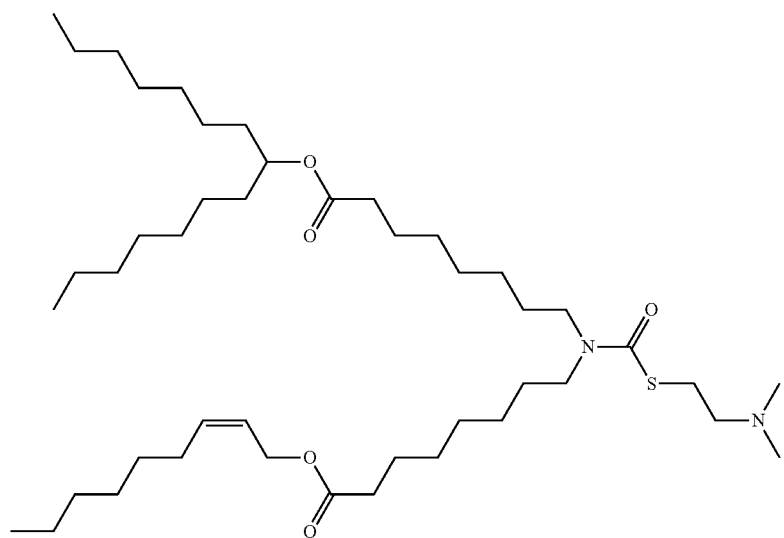
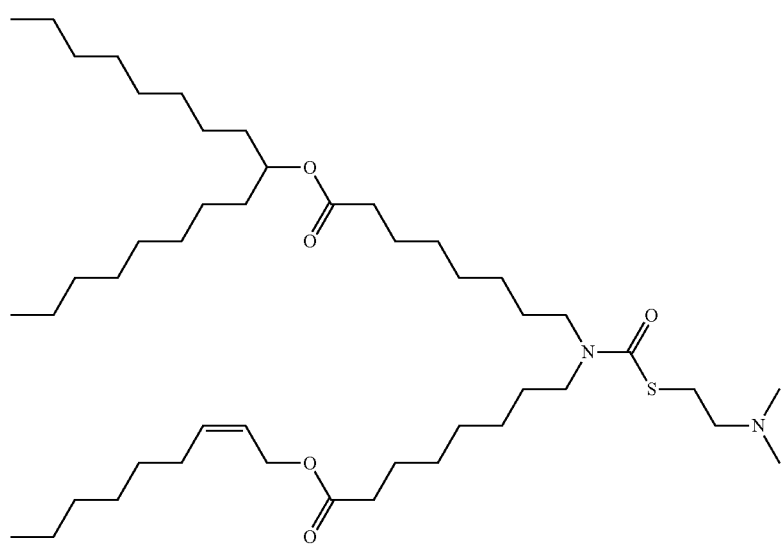

79
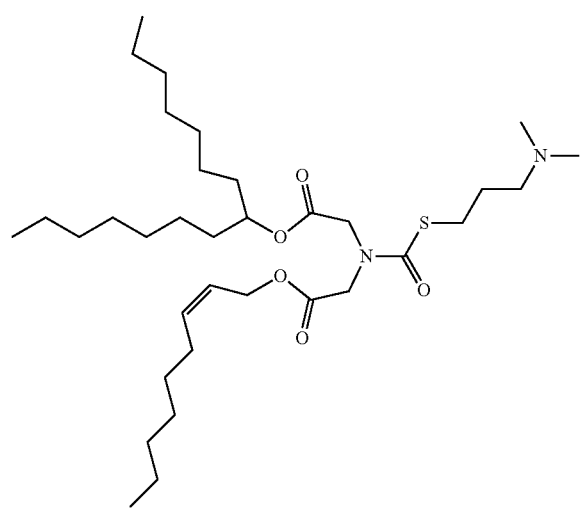
80
-continued
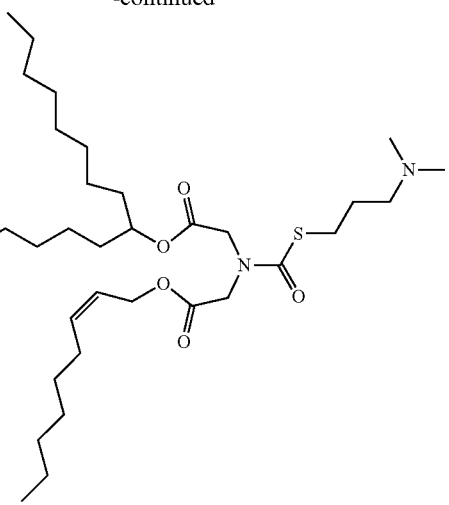
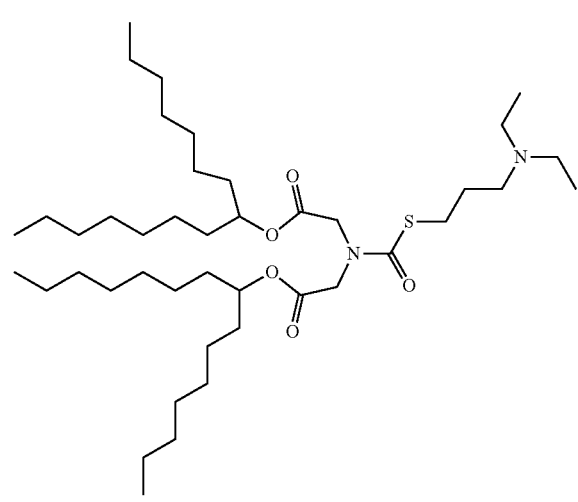
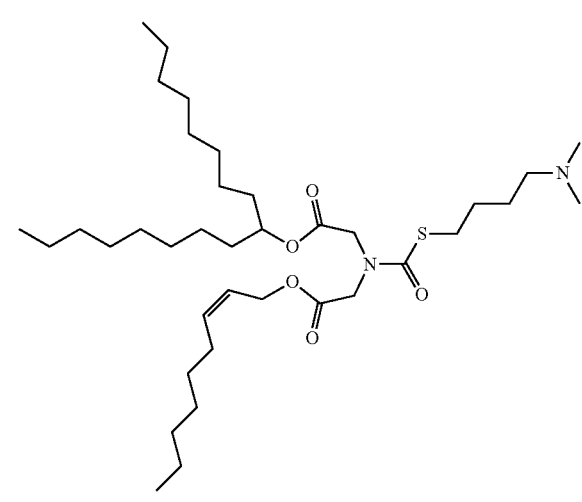

81
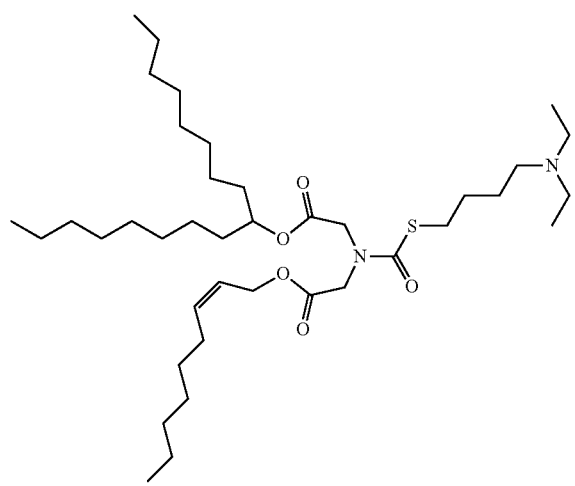
82
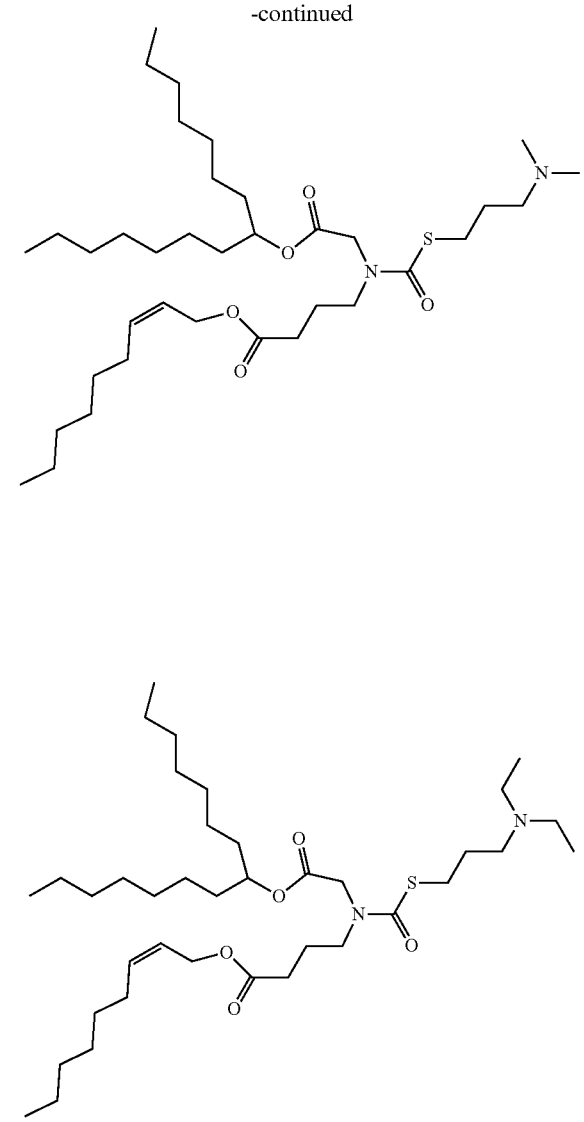
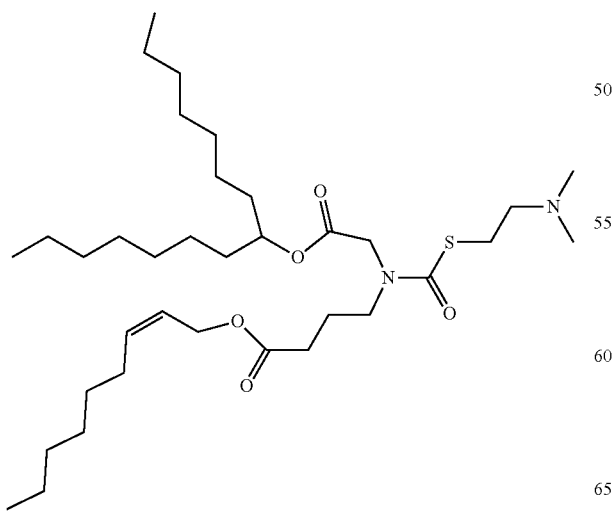

83
-continued
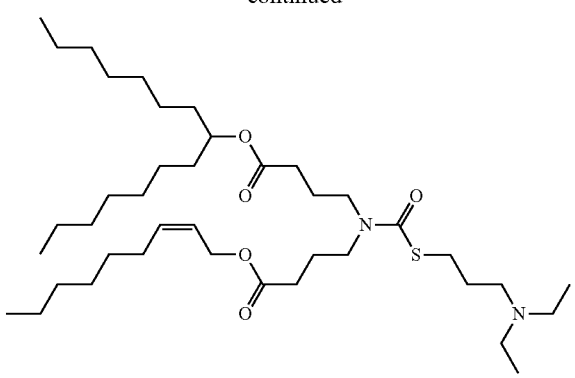
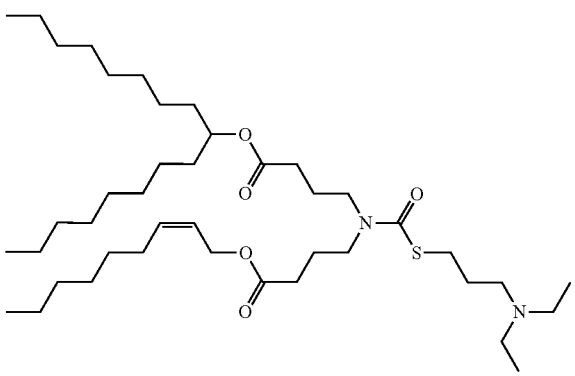
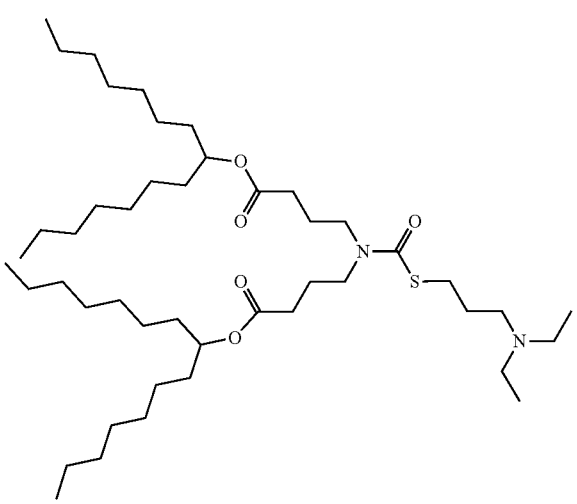
84
-continued
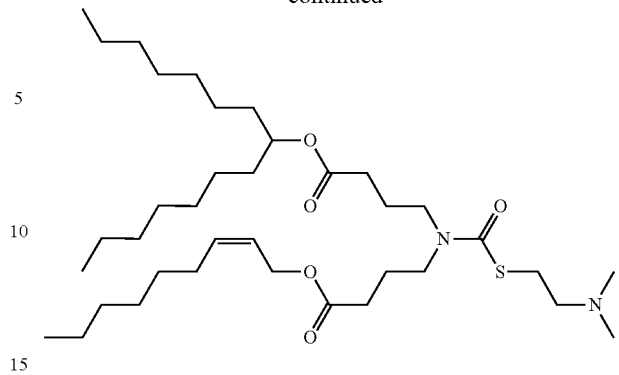
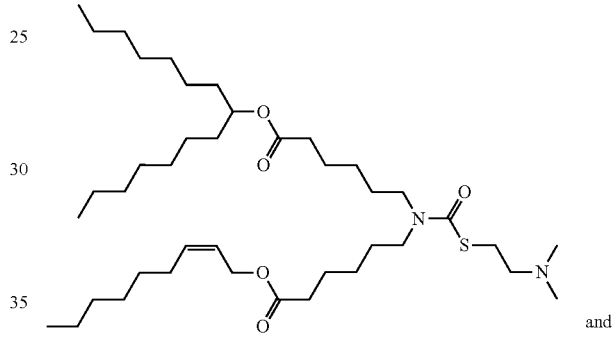
and
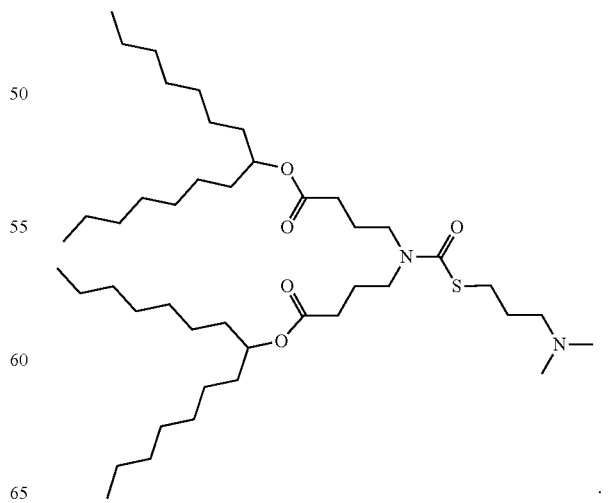

In some embodiments, the lipid formulation can comprise an ionizable cationic lipid selected from the group consisting of LIPID #1 to LIPID #8:
| LIPID # | STRUCTURE |
|---|---|
| 1 | 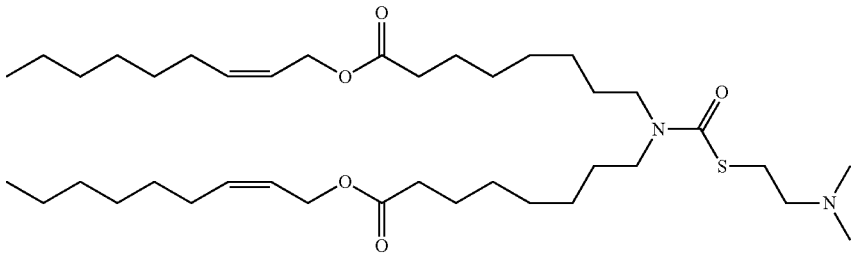 [SMILES: CCCCCC/C=C\COC(=O)CCCCCCCN(CCCCCCCC(=O)OC/C=C\CCCCCC)C(=O)SCCN(C)C] |
| 2 | 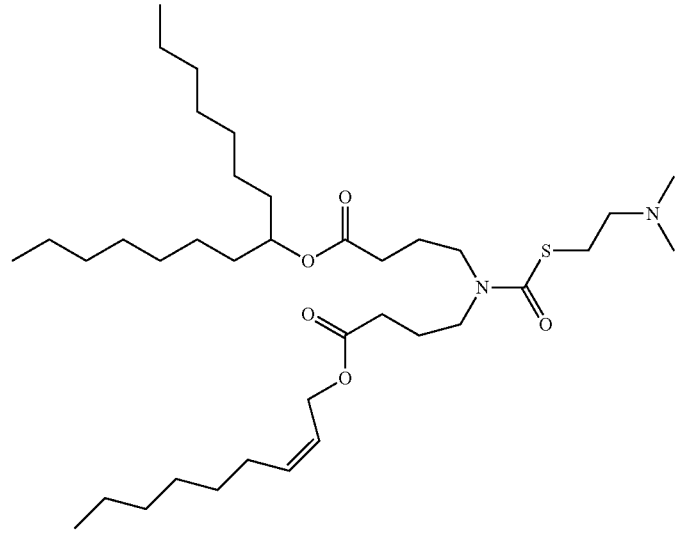 [SMILES: CCCCCC/C=C\COC(=O)CCCN(CCCC(=O)OC(CCCCCCC)CCCCCCC)C(=O)SCCN(C)C] |
| 3 | 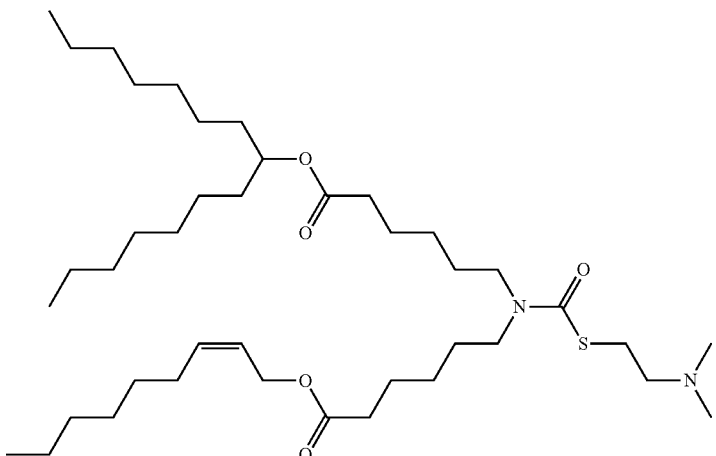 |

| LIPID # | STRUCTURE |
|---|---|
| 4 | 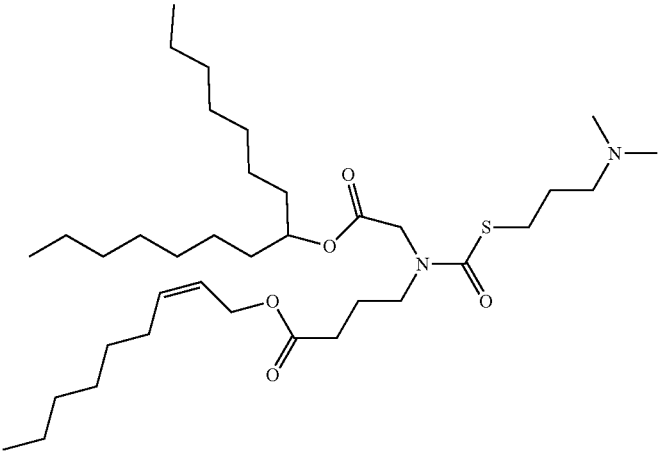 [SMILES: CCCCCC/C=C\COC(=O)CCCN(CC(=O)OC(CCCCCCC)CCCCCCC)C(=O)SCCCN(C)C] |
| 5 | 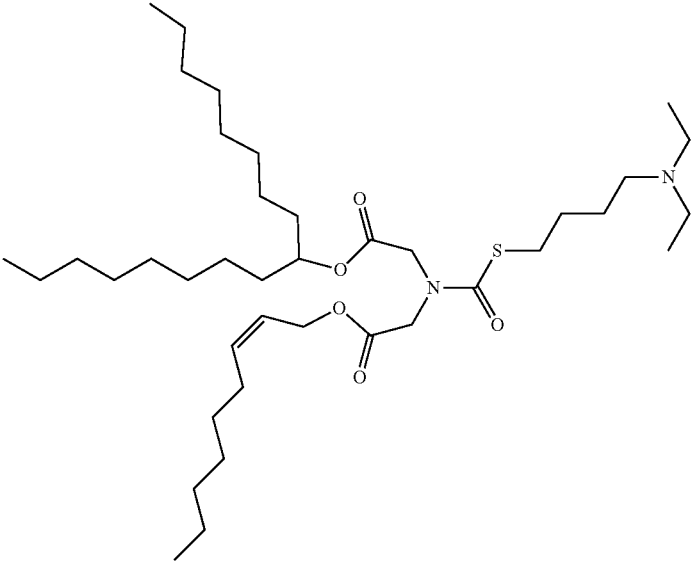 [SMILES: CCCCCC/C=C\COC(=O)CN(CC(=O)OC(CCCCCCCC)CCCCCCCC)C(=O)SCCCCN(CC)CC] |
| 6 | 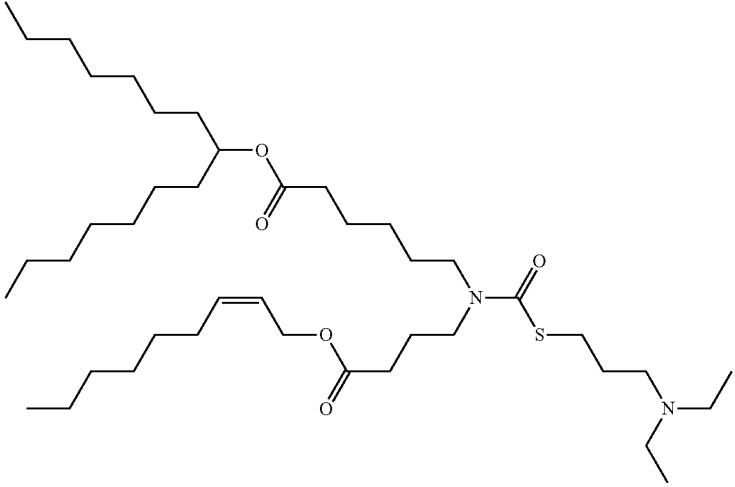 [SMILES: CCCCCC/C=C\COC(=O)CCCN(CCCCCC(=O)OC(CCCCCCC)CCCCCCC)C(=O)SCCCN(CC)CC] |

| LIPID # | STRUCTURE |
|---|---|
| 7 | 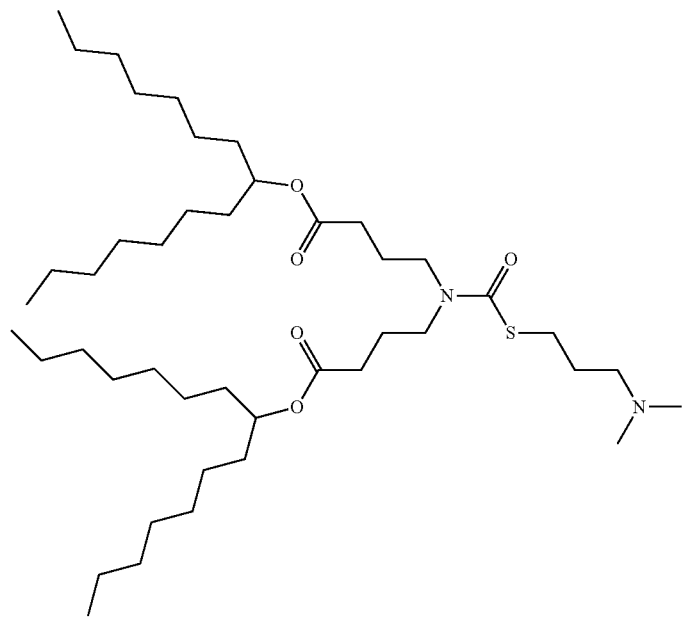 [SMILES: CCCCCCCC(CCCCCCC)OC(=O)CCCN(CCCC(=O)OC(CCCCCCC)CCCCCCC)C(=O)SCCCN(C)C] |
| 8 | 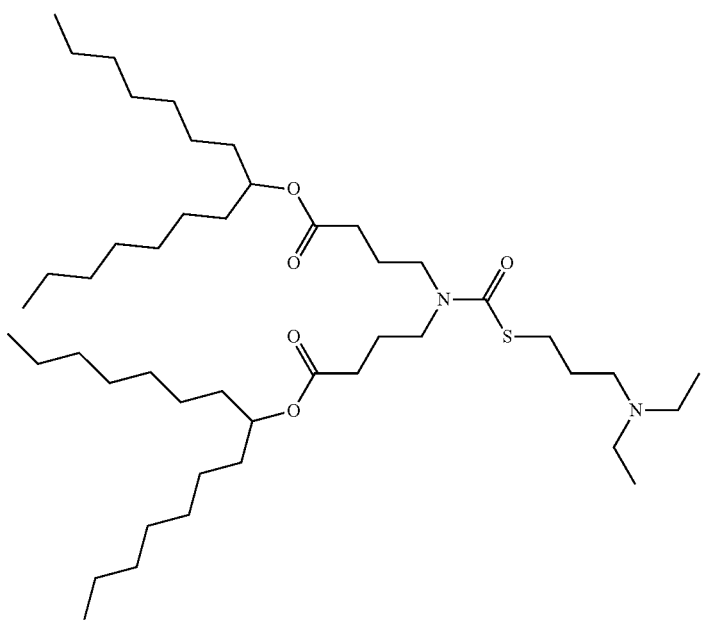 [SMILES: CCCCCCCC(CCCCCCC)OC(=O)CCCN(CCCC(=O)OC(CCCCCCC)CCCCCCC)C(=O)SCCCN(CC)CC] |

In some embodiments, the lipid formulation comprises an ionizable cationic lipid having a structure selected from

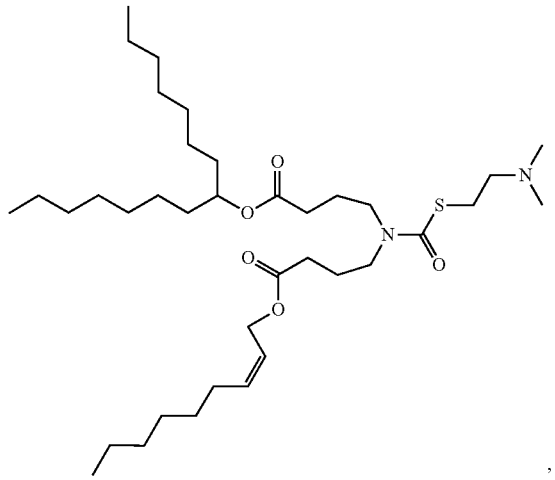

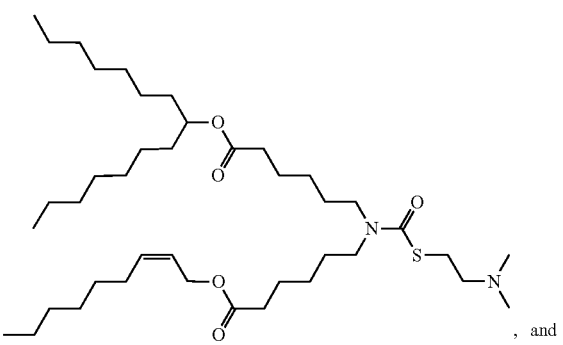

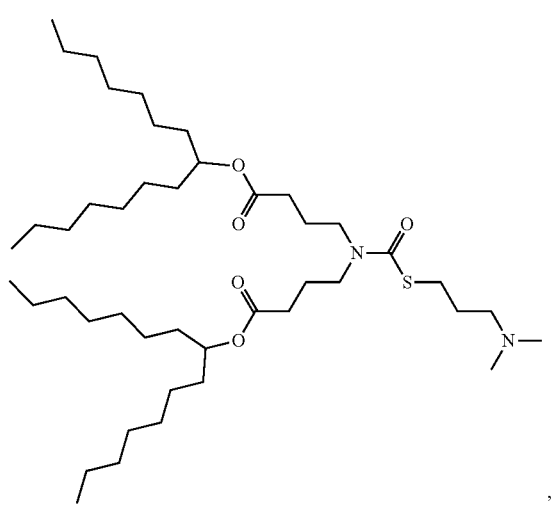

or a pharmaceutically acceptable salt thereof.

In some preferred embodiments, the lipid formulation comprises an ionizable cationic lipid having the structure

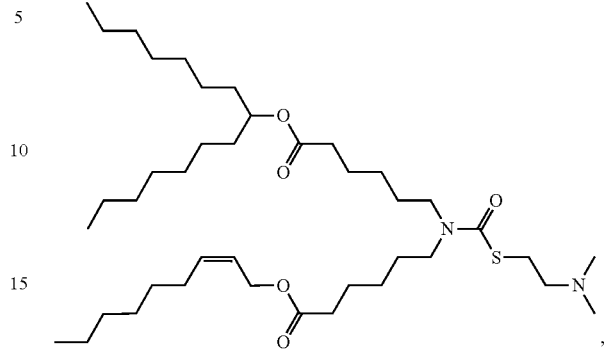

or a pharmaceutically acceptable salt thereof.

In embodiments, any one or more lipids recited herein may be expressly excluded.

Helper Lipids and Sterols

The mRNA-lipid formulations of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15 (9): 882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9 (1): 105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethylphosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. One study concluded that as a helper lipid, cholesterol increases the spacing of the charges of the lipid layer interfacing with the nucleic acid making the charge distribution match that of the nucleic acid more closely. (J. R. Soc. Interface. 2012 Mar. 7; 9 (68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the helper lipid present in the lipid formulation comprises or consists of a mixture of one or more phospholipids and cholesterol or a derivative thereof. In other embodiments, the neutral lipid present in the lipid formulation comprises or consists of one or more phospholipids, e.g., a cholesterol-free lipid formulation. In yet other embodiments, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The cholesterol or cholesterol derivative in the lipid formulation may comprise up to about 40 mol %, about 45 mol %, about 50 mol %, about 55 mol %, or about 60 mol % of the total lipid present in the lipid formulation. In some embodiments, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid formulation.

In some embodiments, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The percentage of helper lipid present in the lipid formulation is a target amount, and the actual amount of helper lipid present in the formulation may vary, for example, by ±5 mol %.

A lipid formulation containing a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some embodiments, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid formulations described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In a preferred embodiment, the lipid conjugate is a PEG-lipid. The inclusion of polyethylene glycol (PEG) in a lipid formulation as a coating or surface ligand, a technique referred to as PEGylation, helps to protects nanoparticles from the immune system and their escape from RES uptake (Nanomedicine (Lond). 2011 June; 6 (4): 715-28). PEGylation has been widely used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). It has been shown that increased PEGylation leads to a significant increase in the circulation half-life of lipid formulations (Annu. Rev. Biomed. Eng. 2011 Aug. 15; 13( ) 507-30; J. Control Release. 2010 Aug. 3; 145(3): 178-81).

Suitable examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$).

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In preferred embodiments, the PEG moiety has an average molecular weight of about 2,000 daltons or about 750 daltons. The average molecular weight may be any value or subvalue within the recited ranges, including endpoints.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH$_2$CH$_2$C(O)—), succinamidyl (—NHC(O)CH$_2$CH$_2$C(O)NH—), ether, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

In some embodiments, the PEG-DAA conjugate is a PEG-didecyloxypropyl (C$_{10}$) conjugate, a PEG-dilauryloxypropyl (C$_{12}$) conjugate, a PEG-dimyristyloxypropyl (C$_{14}$) conjugate, a PEG-dipalmityloxypropyl (C$_{16}$) conjugate, or a PEG-distearyloxypropyl (C$_{18}$) conjugate. In these embodiments, the PEG preferably has an average molecular weight of about 750 or about 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

Mechanism of Action for Cellular Uptake of Lipid Formulations

Lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28 (3): 146-157, 2018). Specifically, in the case of an ornithine transcarbamylase mRNA-lipid formulation described herein, the mRNA-lipid formulation enters hepatocytes in the liver through Apo-E receptor mediated endocytosis. Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately undergoes the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For mRNA payloads, the cell's own internal translation processes will then translate the mRNA into the encoded protein. The encoded protein can further undergo postranslation processing, including transportation to a targeted organelle or location within the cell. In the case of an OTC protein, the OTC protein is transported to the mitochondria.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual assymetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) A simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

OTC mRNA Lipid Formulations

The present disclosure provides for lipid formulations comprising an mRNA encoding an enzyme having ornithine transcarbamylase (OTC) activity (OTC mRNA). Following transfection of one or more target cells by the OTC mRNA lipid formulations of the present disclosure, expression of the OTC enzyme encoded by such mRNA will be stimulated and the capability of such target cells to express the OTC enzyme is enhanced. The OTC mRNA can be any suitable mRNA for expressing an OTC enzyme in vivo. In some embodiments, the OTC mRNA encodes a modified OTC enzyme engineered to have increased in vivo stability against cellular degradation and/or increased mitochondrial uptake, including the OTC enzyme of SEQ ID NO: 4.

In a first OTC mRNA-lipid formulation, an OTC mRNA-lipid formulation comprises a compound of Formula (I) and an mRNA encoding an enzyme having OTC activity. In some embodiments the mRNA encodes an OTC enzyme consisting of a sequence having 95% identity to SEQ ID NO: 3. In some embodiments, the mRNA encodes an OTC enzyme consisting of SEQ ID NO: 3. In some embodiments the mRNA encodes an OTC enzyme consisting of a sequence having 95% identity to SEQ ID NO: 4. In some embodiments, the mRNA encodes an OTC enzyme consisting of SEQ ID NO: 4. The compound of Formula I can be selected based on desirable properties including its lipophilicity, potency, selectivity for a specific target cell, in vivo biodegradability, toxicity and immunogenicity profile, and the pKa of the ionizable/protonatable group on the compound of Formula (I).

In some embodiments of the first OTC mRNA-lipid formulation, $X^7$ is S. In some embodiments, $X^5$ is —C(O)O—, whereby —C(O)O—$R^6$ is formed and $X^6$ is —C(O)O— whereby —C(O)O—$R^5$ is formed. In some embodiments, $R^7$ and $R^8$ are each independently selected from the group consisting of methyl, ethyl and isopropyl. In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl. In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond. In some embodiments, $R^5$ and $R^6$ are each alkyl. In some embodiments, $R^5$ is a branched alkane. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —CH$((CH_2)_pCH_3)_2$ or —CH$((CH_2)_pCH_3)((CH_2)_{p-1}CH_3)$, wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is a $C_1$-$C_3$ alkyl. In some embodiments, $R^5$ consists of —CH$((CH_2)_pCH_3)((CH_2)_{p-1}CH_3)$, wherein p is 7 or 8. In some embodiments, $R^4$ is ethylene or propylene. In some embodiments, $R^4$ is n-propylene or isobutylene. In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments of the first OTC mRNA-lipid formulation, $X^7$ is S, $X^5$ is —C(O)O—, whereby —C(O)O—$R^6$ is formed and $X^6$ is —C(O)O—, whereby —C(O)O—$R^5$ is formed, $L^5$ and $L^6$ are each independently a linear $C_3$-$C_7$ alkyl $L^7$ is absent, $R^5$ is —CH$((CH_2)_pCH_3)_2$, and $R^6$ is $C_7$-$C_{12}$ alkenyl. In some further embodiments, p is 6 and $R^6$ is $C_9$ alkenyl.

Any mRNA encoding an enzyme having OTC activity is suitable for inclusion in the first OTC mRNA-lipid formulation of the present disclosure. In some embodiments, a suitable mRNA is a wild-type human OTC mRNA of sequence SEQ ID NO: 3. Preferably, the OTC mRNA has low immunogenicity, high in vivo stability, and high translation efficiency. In some embodiments, the OTC mRNA is expressible in human hepatocytes. In some embodiments, the OTC mRNA has a coding region that is codon-optimized. In some embodiments, the OTC mRNA comprises modified uridine nucleotides. In some embodiments, the modified uridine nucleotides are $N^1$-methylpseudouridine or 5-methoxyuridine. In some embodiments, the modified uridine nucleotides are 5-methoxyuridine. In some embodiments, the OTC mRNA can be any of the OTC mRNA constructs described herein.

In some embodiments of the first OTC mRNA-lipid formulation, the mRNA comprises an open reading frame (ORF or coding region) selected from SEQ ID NOs: 254-258. In some embodiments, the mRNA comprises an ORF having a sequence of SEQ ID NO: 254. In some embodiments, the mRNA comprises an ORF having a sequence of SEQ ID NO: 255. In some embodiments, the mRNA comprises an ORF having a sequence of SEQ ID NO: 256. In some embodiments, the mRNA comprises an ORF having a sequence of SEQ ID NO: 257. In some embodiments, the mRNA comprises an ORF having a sequence of SEQ ID NO: 258. In some embodiments, the mRNA comprises a sequence having about 85% identity to a sequence selected from SEQ ID NOs: 73, 119, and 251-253. In some embodiments, the mRNA comprises a sequence having about 90% identity to a sequence selected from SEQ ID NOs: 73, 119, and 251-253. In some embodiments, the mRNA comprises a sequence having about 95% identity to a sequence selected from SEQ ID NOs: 73, 119, and 251-253. In some embodiments, the mRNA comprises a sequence having about 96% identity to a sequence selected from SEQ ID NOs: 73, 119, and 251-253. In some embodiments, the mRNA comprises a sequence having about 97% identity to a sequence selected from SEQ ID NOs: 73, 119, and 251-253. In some embodiments, the mRNA comprises a sequence having about 98% identity to a sequence selected from SEQ ID NOs: 73, 119, and 251-253. In some embodiments, the mRNA comprises a sequence having about 99% identity to a sequence selected from SEQ ID NOs: 73, 119, and 251-253. In some embodiments, the mRNA comprises a sequence having about 99.5% identity to a sequence selected from SEQ ID NOs: 73, 119, and 251-253. In some embodiments, the mRNA comprises a sequence selected from SEQ ID NOS: 73, 119, and 251-253. In some embodiments, the mRNA comprises a sequence selected from SEQ ID NO: 1.

In any of the embodiments of the first OTC mRNA-lipid formulation, the OTC mRNA-lipid formulation comprises lipid nanoparticles. In some embodiments, the lipid nanoparticles completely encapsulate the OTC mRNA.

In some embodiments, the lipid nanoparticles have an average particle size of less than about 100 nm. In some embodiments, the lipid nanoparticles have an average particles size of about 55 to about 85 nm. In some embodiments, the lipid nanoparticles encapsulate at least about 50% of the mRNA. In some embodiments, the lipid nanoparticles encapsulate at least about 85% of the mRNA. In some embodiments, the lipid nanoparticles have greater than about 90% encapsulation efficiency. In some embodiments, the lipid nanoparticles have greater than about 95% encapsulation efficiency.

In a second OTC mRNA-lipid formulation, an OTC mRNA-lipid formulation comprises a compound selected from:

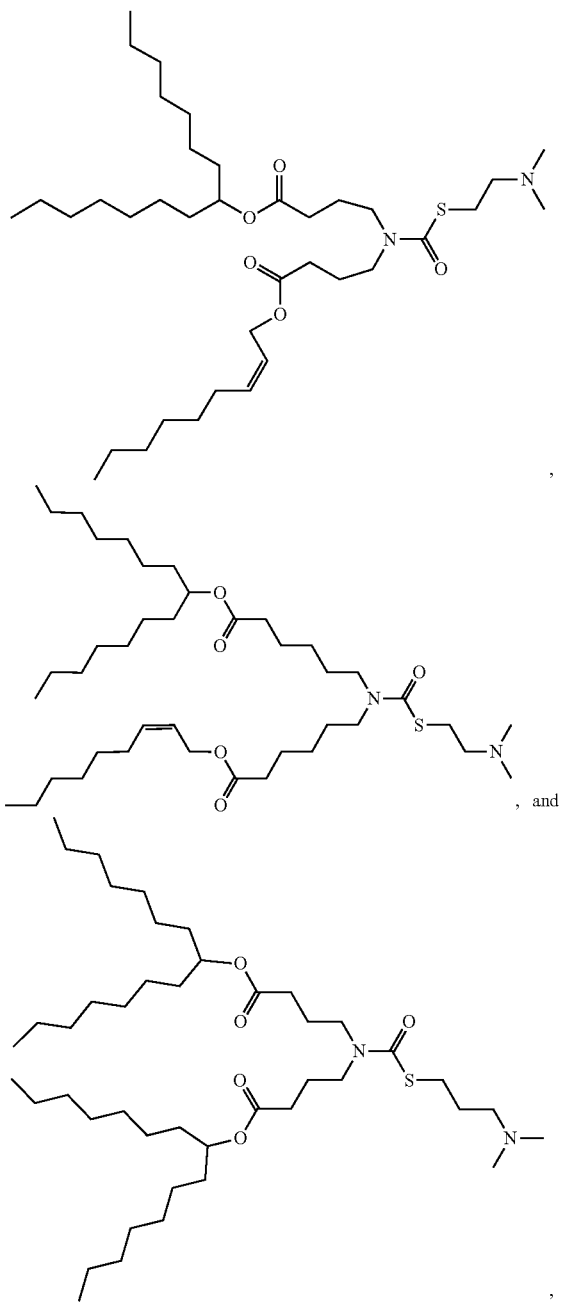

, and or a pharmaceutically acceptable salt thereof and an mRNA encoding an enzyme having OTC activity.

Any mRNA encoding an enzyme having OTC activity is suitable for inclusion in the second OTC mRNA-lipid formulation of the present disclosure. In some embodiments, a suitable mRNA is a wild-type human OTC mRNA of SEQ ID NO: 3. In some embodiments the mRNA encodes an OTC enzyme consisting of a sequence having 95% identity to SEQ ID NO: 3. In some embodiments, the mRNA encodes an OTC enzyme consisting of SEQ ID NO: 3. In some embodiments the mRNA encodes an OTC enzyme consisting of a sequence having 95% identity to SEQ ID NO: 4. In some embodiments, the mRNA encodes an OTC enzyme consisting of SEQ ID NO: 4. Preferably, the OTC mRNA has low immunogenicity, high in vivo stability, and high translation efficiency. In some embodiments, the OTC mRNA is expressible in human hepatocytes. In some embodiments, the OTC mRNA has a coding region that is codon-optimized. In some embodiments, the OTC mRNA comprises modified uridine nucleotides. In some embodiments, the modified uridine nucleotides are $N^1$-methylpseudouridine or 5-methoxyuridine. In some embodiments, the modified uridine nucleotides are 5-methoxyuridine. In some embodiments, the OTC mRNA can be any of the OTC mRNA constructs described herein.

In some embodiments of the second OTC mRNA-lipid formulation, the mRNA comprises an open reading frame (ORF or coding region) selected from SEQ ID Nos: 254-258. In some embodiments, the mRNA comprises an ORF having a sequence of SEQ ID NO: 254. In some embodiments, the mRNA comprises an ORF having a sequence of SEQ ID NO: 255. In some embodiments, the mRNA comprises an ORF having a sequence of SEQ ID NO: 256. In some embodiments, the mRNA comprises an ORF having a sequence of SEQ ID NO: 257. In some embodiments, the mRNA comprises an ORF having a sequence of SEQ ID NO: 258. In some embodiments, the mRNA comprises a sequence having about 85% identity to a sequence selected from SEQ ID NOS: 73, 119, and 251-253. In some embodiments, the mRNA comprises a sequence having about 90% identity to a sequence selected from SEQ ID NOs: 73, 119, and 251-253. In some embodiments, the mRNA comprises a sequence having about 95% identity to a sequence selected from SEQ ID NOs: 73, 119, and 251-253. In some embodiments, the mRNA comprises a sequence having about 96% identity to a sequence selected from SEQ ID NOs: 73, 119, and 251-253. In some embodiments, the mRNA comprises a sequence having about 97% identity to a sequence selected from SEQ ID NOs: 73, 119, and 251-253. In some embodiments, the mRNA comprises a sequence having about 98% identity to a sequence selected from SEQ ID NOs: 73, 119, and 251-253. In some embodiments, the mRNA comprises a sequence having about 99% identity to a sequence selected from SEQ ID NOs: 73, 119, and 251-253. In some embodiments, the mRNA comprises a sequence having about 99.5% identity to a sequence selected from SEQ ID NOs: 73, 119, and 251-253. In some embodiments, the mRNA comprises a sequence selected from SEQ ID NOS: 73, 119, and 251-253. In some embodiments, the mRNA comprises a sequence selected from SEQ ID NO: 1.

In any of the embodiments of the second OTC mRNA-lipid formulation, the OTC mRNA-lipid formulation comprises lipid nanoparticles. In some embodiments, the lipid nanoparticles completely encapsulate the OTC mRNA.

In some embodiments, the lipid nanoparticles have an average particle size of less than about 100 nm. In some embodiments, the lipid nanoparticles have an average particles size of about 55 nm to about 85 nm. In some embodiments, the lipid nanoparticles encapsulate at least about 50% of the mRNA. In some embodiments, the lipid nanoparticles encapsulate at least about 85% of the mRNA. In some embodiments, the lipid nanoparticles have greater than about 90% encapsulation efficiency.

In some embodiments, either the first or second OTC mRNA-lipid formulation further comprises a helper lipid. In some embodiments, the helper lipid is selected from the group consisting of neutral and anionic lipids. In some embodiments, the helper lipid is selected from the group consisting of dipalmitoyl phosphatidylcholine (DPPC), phosphatidylcholine (PC), dioleoylphosphatidyl ethanolamine (DOPE), dimyristoylphosphatidyl choline (DMPC), distearoylphosphatidyl choline, and dimyristoylphosphatidyl glycerol (DMPG). In some embodiments, the noncationic lipid is distearoylphosphatidylcholine (DSPC).

In some embodiments, either the first or second OTC mRNA-lipid formulation further comprises cholesterol.

In some embodiments, either the first or second OTC mRNA-lipid formulation further comprises a polyethylene glycol (PEG)-lipid conjugate. In some embodiments, the PEG-lipid conjugate is PEG-DMG. In some embodiments, the PEG-DMG is PEG2000-DMG.

In some embodiments, the lipid portion (meaning the total amount of lipids in the formulation) of either the first or second OTC mRNA-lipid formulation comprises about 48 mol % to about 66 mol % of the cationic lipid, about 2 mol % to about 12 mol % DSPC, about 25 to about 42 mol % cholesterol, and about 0.5 mol % to about 3 mol % PEG2000-DMG.

In some embodiments, the lipid portion of either the first or second OTC mRNA-lipid formulation comprises about 55 mol % to about 61 mol % of the cationic lipid, about 5 mol % to about 9 mol % DSPC, about 29 mol % to about 38 mol % cholesterol, and about 1 mol % to about 2 mol % PEG2000-DMG.

In some embodiments, the lipid portion of either the first or second OTC mRNA-lipid formulation comprises about 56 mol % to about 60 mol % of the cationic lipid, about 6 mol % to about 8 mol % DSPC, about 31 mol % to about 34 mol % cholesterol, and about 1.25 mol % to about 1.75 mol % PEG2000-DMG.

In some embodiments, either the first or second OTC mRNA-lipid formulation has a total lipid:mRNA weight ratio of about 50:1 to about 10:1. In some embodiments, either the first or second OTC mRNA-lipid formulation has a total lipid:mRNA weight ratio of about 40:1 to about 20:1. In some embodiments, either the first or second OTC mRNA-lipid formulation has a total lipid:mRNA weight ratio of about 35:1 to about 25:1. In some embodiments, either the first or second OTC mRNA-lipid formulation has a total lipid:mRNA weight ratio of about 28:1 to about 32:1. In some embodiments, either the first or second OTC mRNA-lipid formulation has a total lipid:mRNA weight ratio of about 29:1 to about 31:1.

Pharmaceutical Compositions and Methods of Treatment

To facilitate expression of mRNA in vivo, the nucleic acid lipid formulation delivery vehicles described herein can be combined with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. Preferably, the nucleic acid lipid formulation is an OTC mRNA lipid nanoparticle formulation as described herein. In some embodiments, the pharmaceutical composition further comprises pharmaceutically acceptable excipients. Pharmaceutical compositions disclosed herein preferably facilitate expression of OTC mRNA in vivo.

The lipid formulations and pharmaceutical compositions of the present disclosure may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

In some embodiments, the pharmaceutical compositions described are administered systemically. Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the pharmaceutical composition is administered intravenously. In some embodiments, the administration results in delivery of the mRNA to a hepatocyte (i.e., liver cell). In some embodiments, the administration shows a selectivity towards hepatocytes over other types of liver cells (e.g., stellate cells, etc.).

Pharmaceutical compositions may be administered to any desired tissue. In some embodiments, the OTC mRNA delivered is expressed in a tissue different from the tissue in which the lipid formulation or pharmaceutical composition was administered. In preferred embodiments, OTC mRNA is delivered and expressed in the liver.

The pharmaceutical compositions disclosed herein can be formulated using one or more excipients to: (1) increase stability; (2) increase cell transfection; (3) permit a sustained or delayed release (e.g., from a depot formulation of the polynucleotide, primary construct, or mRNA); (4) alter the biodistribution (e.g., target the polynucleotide, primary construct, or mRNA to specific tissues or cell types); (5) increase the translation of encoded protein in vivo; and/or (6) alter the release profile of encoded protein in vivo.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or mRNA (e.g., for transplantation into a subject), hyaluronidase, nanoparticle mimics and combinations thereof.

Accordingly, the pharmaceutical compositions described herein can include one or more excipients, each in an amount that together increases the stability of the nucleic acid in the lipid formulation, increases cell transfection by the nucleic acid, increases the expression of the encoded protein, and/or alters the release profile of encoded proteins. Further, the mRNA of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

A dosage form of the composition of this disclosure can be solid, which can be reconstituted in a liquid prior to administration. The solid can be administered as a powder. The solid can be in the form of a capsule, tablet, or gel. In some embodiments, the pharmaceutical composition comprises a nucleic acid lipid formulation that has been lyophilized.

In a preferred embodiment, the dosage form of the pharmaceutical compositions described herein can be a liquid suspension of OTC mRNA lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In some embodiments, the suspension is frozen during storage and thawed prior to administration. In some embodiments, the suspension is frozen at a temperature below about 70° C. In some embodiments, the suspension is diluted with sterile water during intravenous administration. In some embodiments, intravenous administration comprises diluting the suspension with about 2 volumes to about 6 volumes of sterile water. In some embodiments, the suspension comprises about 0.1 mg to about 3.0 mg OTC mRNA/mL, about 15 mg/mL to about 25 mg/mL of an ionizable cationic lipid, about 0.5 mg/mL to about 2.5 mg/mL of a PEG-lipid, about 1.8 mg/mL to about 3.5 mg/mL of a helper lipid, about 4.5 mg/mL to about 7.5 mg/mL of a cholesterol, about 7 mg/mL to about 15 mg/mL of a buffer, about 2.0 mg/mL to about 4.0 mg/mL of NaCl, about 70 mg/mL to about 110 mg/mL of sucrose, and about 50 mg/mL to about 70 mg/mL of glycerol. In some embodiments, a lyophilized OTC-mRNA lipid nanoparticle formulation can be resuspended in a buffer as described herein.

The pharmaceutical compositions of this disclosure may further contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the mRNA-lipid formulation may be administered in a time release formulation, for example in a composition which includes a slow release polymer. The active agent can be prepared with carriers that will protect against rapid release, for example a controlled release vehicle such as a polymer, microencapsulated delivery system, or a bioadhesive gel. Prolonged delivery of the mRNA, in various compositions of the disclosure can be brought about by including in the composition agents that delay absorption, for example, aluminum monostearate hydrogels and gelatin.

Following administration of the composition to the subject, the protein product encoded by the mRNA (e.g., a functional OTC protein or enzyme) is detectable in the target tissues for at least about one to seven days or longer. The amount of protein product necessary to achieve a therapeutic effect will vary depending on the severity of ornithine transcarbamylase deficiency or other disorder being treated and the condition of the patient. For example, the protein product may be detectable in the target tissues at a concentration (e.g., a therapeutic concentration) of at least about 0.025-1.5 g/ml (e.g., at least about 0.050 µg/ml, at least about 0.075 µg/ml, at least about 0.1 µg/ml, at least about 0.2 µg/ml, at least about 0.3 µg/ml, at least about 0.4 µg/ml, at least about 0.5 µg/ml, at least about 0.6 µg/ml, at least about 0.7 µg/ml, at least about 0.8 µg/ml, at least about 0.9 µg/ml, at least about 1.0 µg/ml, at least about 1.1 µg/ml, at least about 1.2 µg/ml, at least about 1.3 µg/ml, at least about 1.4 µg/ml, or at least about 1.5 µg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

In some embodiments, the compositions of the disclosure are administered to a subject such that a OTC mRNA concentration of at least about 0.05 mg/kg, at least about 0.1 mg/kg, at least about 0.5 mg/kg, at least about 1.0 mg/kg, at least about 2.0 mg/kg, at least about 3.0 mg/kg, at least about 4.0 mg/kg, at least about 5.0 mg/kg of body weight is administered in a single dose or as part of single treatment cycle. In some embodiments, the compositions of the disclosure are administered to a subject such that a total amount of at least about 0.1 mg, at least about 0.5 mg, at least about 1.0 mg, at least about 2.0 mg, at least about 3.0 mg, at least about 4.0 mg, at least about 5.0 mg, at least about 6.0 mg, at least about 7.0 mg, at least about 8.0 mg, at least about 9.0 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, or at least about 125 mg OTC mRNA is administered in one or more doses up to a maximum dose of about 300 mg, about 350 mg, about 400 mg, about 450 mg, or about 500 mg OTC mRNA.

The compositions and polynucleotides of the present disclosure may be used to treat a subject who is suffering from or susceptible to ornithine transcarbamylase (OTC) deficiency. OTC is a homotrimeric mitochondrial enzyme which is expressed almost exclusively in the liver and which encodes a precursor OTC protein that is cleaved in two steps upon incorporation into the mitochondrial matrix. (Horwich A L., et al. Cell 1986; 44:451-459). OTC deficiency is a genetic disorder which results in a mutated and biologically inactive form of the enzyme ornithine transcarbamylase. OTC deficiency often becomes evident in the first few days of life, typically after protein ingestion. In the classic severe form of OTC deficiency, within the first days of life patients present with lethargy, convulsions, coma and severe hyperammonemia, which quickly leads to a deteriorating and fatal outcome absent appropriate medical intervention. (Morrish S., et al., Genetics for Pediatricians; Remedica, Cold Spring Harbor Laboratory (2005)). If improperly treated or if left untreated, complications from OTC deficiency may include developmental delay and mental retardation. OTC deficient subjects may also present with progressive liver damage, skin lesions, and brittle hair. In some affected individuals, signs and symptoms of OTC deficiency may be less severe, and may not appear until later in life.

The OTC gene, which is located on the short arm of the X chromosome within band Xp21.1, spans more than 85 kb and is comprised of 10 exons encoding a protein of 1062 amino acids. (Lindgren V., et al. Science 1984; 226: 6987700; Horwich, A L., et al. Science 224:1068-1074, 1984; Horwich, A L. et al., Cell 44:451-459, 1986; Hata, A., et al., J. Biochem. 100:717-725, 1986, which are incorporated herein by reference). The OTC enzyme catalyzes the conversion or ornithine and carbamoyl phosphate to citrulline. Since OTC is on the X chromosome, females are primarily carriers while males with nonconservative mutations rarely survive past 72 hours of birth.

In some embodiments, a pharmaceutical composition of the present disclosure is administered to a subject once per month. In some embodiments, a pharmaceutical composition of the present disclosure is administered to a subject twice per month. In some embodiments, a pharmaceutical composition of the present disclosure is administered to a subject three times per month. In some embodiments, a pharmaceutical composition of the present disclosure is administered to a subject four times per month.

In healthy subjects, OTC is expressed almost exclusively in hepatocellular mitochondria. Although not expressed in the brain of healthy subjects, OTC deficiency can lead to neurological disorders. For example, one of the usual symptoms of OTC deficiency, which is heterogeneous in its presentation, is hyperammonaemic coma (Gordon, N., Eur J Paediatr Neural 2003; 7:115-121.).

OTC deficiency is heterogeneous, with over 200 unique mutations reported and large deletions that account for approximately 10-15% of all mutations, while the remainder generally comprises missense point mutations with smaller numbers of nonsense, splice-site and small deletion mutations. (Morrish A., et al.) The phenotypic manifestations of OTC deficiency is also highly heterogeneous, which can range from acute neonatal hyperammonemic coma to asymptomatic hemizygous adults. (Gordon N. Eur J. Paediatr. Neurol. 2003; 7:115-121). Those mutations that result in severe and life threatening neonatal disease are clustered in important structural and functional domains in the interior of the protein at sites of enzyme activity or at the interchain surface, while mutations associated with late-onset disease are located on the protein surface (Morrish A., et al.) Patients with milder or partial forms of OTC deficiency may have onset of disease later in life, which may present as recurrent vomiting, neurobehavioral changes or seizures associated with hyperammonemia.

Alternatively, the compositions of the present disclosure may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present disclosure can be inhaled (for nasal, tracheal, or bronchial delivery); compositions of the present disclosure can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present disclosure complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

According to the present disclosure, a therapeutically effective dose of the provided composition, when administered regularly, results in an increased OTC protein expression or activity level in a subject as compared to a baseline OTC protein expression or activity level before treatment. Typically, the OTC protein expression or activity level is measured in a biological sample obtained from the subject such as blood, plasma or serum, urine, or solid tissue extracts. The baseline level can be measured immediately before treatment. In some embodiments, administering a pharmaceutical composition described herein results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment for at least about 24 hours, at least about 48 hours, at least about 72 hours, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

In some embodiments, a therapeutically effective dose of the provided composition, when administered regularly, results in an increased citrulline production in a subject as compared to a baseline citrulline production before treatment. Typically, the citrulline level before or after the treatment may be measured in a biological sample obtained from the subject such as, blood, plasma or serum, urine, or solid tissue extracts. In some embodiments, treatment according to the present disclosure results in an increase of the citrulline level in a biological sample (e.g., plasma, serum, or urine) by at least about 10%, 20%, 30%, 40%, 50%, 60%, 70%, 80%, 90%, 1-fold, 1.5-fold, 2-fold, 2.5-fold, or 3-fold as compared to the baseline citrulline level, respectively.

According to the present disclosure, a therapeutically effective dose of the provided composition, when administered regularly, results in reduction of at least one symptom or feature of the OTC deficiency, including in intensity, severity, or frequency or the symptom has delayed onset. In some embodiments, a therapeutically effective dose of the provided composition, when administered regularly, results in a reduced orotic acid level in a subject as compared to a baseline orotic acid level before treatment. In some embodiments, a therapeutically effective dose of the provided composition, when administered regularly, results in a reduced ammonia level in a subject as compared to a baseline ammonia level before treatment. In some embodiments, a therapeutically effective dose of the provided composition, when administered regularly, results in a reduced glutamine level in a subject as compared to a baseline glutamine level before treatment.

Typically, the orotic acid, ammonia or glutamine level before or after the treatment may be measured in a biological sample obtained from the subject such as, blood, plasma, serum, urine, or solid tissue extracts. The baseline orotic acid, ammonia or glutamine level can be measured immediately before treatment. In some embodiments, treatment according to the present disclosure results in a reduction of the orotic acid, ammonia, or glutamine level in a biological sample (e.g., blood, serum, or urine) obtained from the subject by at least about 10%, 20%, 30%, 40%, 50%, 60%, 70%, 80%, 90%, or 95% as compared to the baseline orotic acid, ammonia, or glutamine level, respectively. In some embodiments, a therapeutically effective dose of the provided composition, when administered regularly, results in a reduced plasma ammonia level to less than about 500 µmol/L, 400 µmol/L, 300 µmol/L, 200 µmol/L, 150 µmol/L, or 100 µmol/L. In some embodiments, a therapeutically effective dose of the provided composition, when administered regularly, results in a reduced plasma glutamine level to less than about 800 µmol/L, 700 µmol/L, or 600 µmol/L. In some embodiments, a therapeutically effective dose of the provided composition, when administered regularly, results in a reduced urinary orotic acid level to less than about 20 µmol/mmol creatinine, 15 µmol/mmol creatinine, or 10 µmol/mmol creatinine.

In some embodiments, administering the provided composition results in an increased OTC protein level in the liver of a subject as compared to a baseline level before treatment. Typically, the baseline level is measured immediately before treatment. In some embodiments, administering the provided composition results in an increased OTC protein level in the liver by at least about 10%, 20%, 30%, 40%, 50%, 60%, 70%, 80%, 90%, or 95% as compared to a baseline level before treatment. In some embodiments, administering the provided composition results in an increased OTC protein level in the liver as compared to a OTC protein level in the liver of subjects who are not treated.

In some embodiments, administering the provided composition results in an increased level of OTC protein in a liver cell (e.g., a hepatocyte) of a subject as compared to a baseline level before treatment. Typically, the baseline level is measured immediately before treatment. In some embodiments, administering the provided composition results in an increased OTC protein level in the liver cell by at least about 10%, 20%, 30%, 40%, 50%, 60%, 70%, 80%, 90%, or 95% as compared to a baseline level before treatment. In some embodiments, administering the provided composition results in an increased OTC protein level in a liver cell as compared to the OTC protein level a liver cell of subjects who are not treated.

In some embodiments, administering the provided composition results in an increased OTC protein level in plasma or serum of a subject as compared to a baseline level before treatment. Typically, the baseline level is measured immediately before treatment. In some embodiments, administering the provided composition results in an increased OTC protein level in plasma or serum by at least about 10%, 20%, 30%, 40%, 50%, 60%, 70%, 80%, 90%, or 95% as compared to a baseline level before treatment. In some embodiments, administering the provided composition results in an increased OTC protein level in plasma or serum as compared to an OTC protein level in plasma or serum of subjects who are not treated.

In some embodiments, administering the provided composition results in increased OTC enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased OTC enzyme activity by at least about 10%, 20%, 30%, 40%, 50%, 60%, 70%, 80%, 90%, or 95% as compared to a baseline level immediately before treatment. In some embodiments, administering the provided composition results in an increased OTC enzyme activity as compared to OTC enzyme activity in subjects who are not treated.

In some embodiments, provided herein are methods of administering a therapeutic intervention to a subject suspected of having an ornithine transcarbamylase (OTC) enzyme deficiency including measuring in the subject a level of OTC enzyme activity indicator and administering to the subject a therapeutic intervention when an OTC enzyme indicator signals deficient OTC enzyme activity. In some embodiments, the subject is a human. In some embodiments, the subject is an adult. In some embodiments, the subject is a human neonate. In some embodiments, the therapeutic intervention includes administering a composition according to any of the various embodiments described herein. In some embodiments, measuring a level of an OTC enzyme activity indicator is selected from measuring OTC enzyme levels in a liver biopsy, measuring nitrogen levels in a blood sample from the subject, measuring citrulline levels in a liver biopsy, and measuring orotic acid in a urinary sample from the subject. In some embodiments, measuring a level of an OTC enzyme activity indicator includes measuring OTC enzyme levels in a liver biopsy. In some embodiments, measuring a level of an OTC enzyme activity indicator includes measuring nitrogen levels in a blood sample from the subject, measuring citrulline levels in a liver biopsy. In some embodiments, measuring a level of an OTC enzyme activity indicator includes measuring orotic acid in a urinary sample from the subject.

In some embodiments, provided herein are methods of treating OTC deficiency in a subject identified as suffering from OTC deficiency. In some embodiments, methods provided herein include administering to the subject any composition provided herein. In some embodiments, an OTC enzyme including a sequence of SEQ ID NO:3 is expressed in the subject. In some embodiments, an OTC enzyme including a sequence of SEQ ID NO:4 is expressed in the subject.

Combinations

The OTC mRNA, formulations thereof, or encoded OTC proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, mRNA disclosed herein and preferably an mRNA sequence comprising SEQ ID NO: 251 encoding a modified OTC protein of SEQ ID NO: 4 may be used in combination with a pharmaceutical agent for the treatment of OTC deficiency. The pharmaceutical agent includes, but is not limited to one or more of: sodium phenylbutyrate, glycerol phenylbutyrate (marketed e.g., as Ravicti®), sodium phenylacetate, sodium benzoate, arginine, citrulline, Multiple vitamins, calcium supplements or combined with a low protein/high caloric diet regimen. In general, it is expected that agents utilized in combination with the presently disclosed OTC mRNA and formulations thereof be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The phrases "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically engineered animal, or a clone.

The terms "approximately" or "about," as applied to one or more values of interest, refers to a value that is similar to a stated reference value. In certain embodiments, the term "approximately" or "about" refers to a range of values that fall within +/−10% of the recited value unless otherwise stated or otherwise evident from the context (except where such number would exceed 100% of a possible value).

The terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkoxy" represents a chemical substituent of formula-OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkoxyalkyl" represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl," as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylalkyl," as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkoxycarbonylalkenyl," as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3)amino, as defined herein (e.g., unsubstituted amino (i.e., —$NH_2$) or a substituted amino (i.e., —N($R^{N1}$)$_2$, where $R^{N1}$ is as defined for amino); (4) —C(O)O— or —OC(O)-aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ to aryl, (d) hydrogen, (e) $C_{1-6}$ alkyl-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)$NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ to aryl, and (d) $C_{1-6}$ alkyl-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alkyl-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alkyl-$C_{6-10}$ aryl; (18) —C(O)$R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alkyl-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alkyl-$C_{6-10}$ aryl, (f2) amino-$C_{1-20}$, alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2)amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alkyl-$C_{6-10}$ aryl, (f2) amino-$C_{1-20}$ alkyl, (g2) polyethylene glycol of $(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2)amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkyl group of a $C_1$-alkaryl can be further substituted with an oxo group to afford the respective aryloyl substituent.

The term "lower alkyl" means a group having one to six carbons in the chain which chain may be straight or branched. Non-limiting examples of suitable alkyl groups include methyl, ethyl, n-propyl, isopropyl, n-butyl, t-butyl, n-pentyl, and hexyl.

The term "alkylsulfinyl," as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2$$R^{N2}$, SO$R^{N2}$, an N-protecting group, alkyl, alkenyl, alkynyl, alkoxy, aryl, alkaryl, cycloalkyl, alkylcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkylheterocyclyl (e.g., alkylheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the disclosure can be an unsubstituted amino (i.e., —NH$_2$) or a substituted amino (i.e., —N(R')$_2$). In a preferred embodiment, amino is —NH$_2$ or —NH$R^{N1}$, wherein $R^{N1}$ is, independently, OH, NO$_2$, NH$_2$, N$R^{N2}$$_2$, SO$_2$O$R^{N2}$, SO$_2$$R^{N2}$, SO$R^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, C$_{1-20}$ alkyl (e.g., C$_{1-6}$ alkyl), or C$_{1-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkylaryl, alkylheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) C$_{1-6}$ alkoxy; (2) C$_{1-6}$ alkylsulfinyl; (3)amino, as defined herein (e.g., unsubstituted amino (i.e., —NH$_2$) or a substituted amino (i.e., —N($R^{N1}$)$_2$, where $R^{N1}$ is as defined for amino); (4) C$_{6-10}$ aryl-C$_{1-6}$ alkoxy; (5) azido; (6) halo; (7) (C$_{2-9}$ heterocyclyl)oxy; (8) hydroxy; (9) nitro; (10) oxo (e.g., carboxyaldehyde or acyl); (11) C$_{1-7}$ spirocyclyl; (12) thioalkoxy; (13) thiol; (14) —CO$_2$$R^{A'}$, where $R^{A'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alkyl-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (15) —C(O)NR$^{B'}$R$^{C'}$, where each of R$^{B'}$ and R$^{C'}$ is, independently, selected from the group consisting of (a) hydrogen, (b) C$_{1-6}$ alkyl, (c) C$_{6-10}$ aryl, and (d) C$_{1-6}$ alkyl-C$_{6-10}$ aryl; (16) —SO$_2$RD', where RD' is selected from the group consisting of (a) C$_{1-6}$ alkyl, (b) C$_{6-10}$ aryl, (c) C$_{1-6}$ alkyl-C$_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) C$_{1-6}$ alkyl, (c) C$_{6-10}$ aryl and (d) C$_{1-6}$ alkyl-C$_{6-10}$ aryl; (18) —C(O)R$^{G'}$, where R$^{G'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alkyl-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (19) —NR$^{H'}$C(O)R', wherein R$^{H'}$ is selected from the group consisting of (a1) hydrogen and (b1) C$_{1-6}$ alkyl, and R' is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alkyl-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H C$_{1-20}$ or alkyl, and 1 (h2)amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (20) —NR$^{J'}$C(O)OR$^{K'}$, wherein R$^{J'}$ is selected from the group consisting of (a1) hydrogen and (b1) C$_{1-6}$ alkyl, and R$^{K'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alkyl-C$_{6-10}$ aryl, (f2) amino-C$_{1-20}$ alkyl, (92) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2)amino-polyethylene glycol of —NR$^{N1}$(CH)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; and amidine. In some embodiments, each of these groups can be further substituted as described herein.

The term "aminoalkoxy," as used herein, represents an alkoxy group, as defined herein, substituted by an amino group, as defined herein. The alkyl and amino each can be further substituted with 1, 2, 3, or 4 substituent groups as described herein for the respective group (e.g., CO$_2$R$^{A'}$, where R$^{A'}$ is selected from the group consisting of (a) $C_{1-6}$ alkyl, (b) $C_{6-10}$ aryl, (c) hydrogen, and (d) $C_{1-6}$ alkyl-$C_{6-10}$ aryl, e.g., carboxy).

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group (e.g., CO$_2$R$^{A'}$, where R$^{A'}$ is selected from the group consisting of (a) $C_{1-6}$ alkyl, (b) $C_{6-10}$ aryl, (c) hydrogen, and (d) $C_{1-6}$ alkyl-$C_{6-10}$ aryl, e.g., carboxy, and/or an N-protecting group).

The term "aminoalkenyl," as used herein, represents an alkenyl group, as defined herein, substituted by an amino group, as defined herein. The alkenyl and amino each can be further substituted with 1, 2, 3, or 4 substituent groups as described herein for the respective group (e.g., CO$_2$R$^{A'}$, where R$^{A'}$ is selected from the group consisting of (a) $C_{1-6}$ alkyl, (b) $C_{6-10}$ aryl, (c) hydrogen, and (d) $C_{1-6}$ alkyl-$C_{6-10}$ aryl, e.g., carboxy, and/or an N-protecting group).

The term "anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The terms "include," "have," or the like is used in the description or the claims, such term is intended to be inclusive in a manner similar to the term "comprise" as "comprise" is interpreted when employed as a transitional word in a claim.

The term "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The term "boranyl," as used herein, represents —B(R$^{B1}$)$_3$, where each R$^{B1}$ is, independently, selected from the group consisting of H and optionally substituted alkyl. In some embodiments, the boranyl group can be substituted with 1, 2, 3, or 4 substituents as defined herein for alkyl.

The term "biocompatible" means compatible with living cells, tissues, organs or systems posing little to no risk of injury, toxicity or rejection by the immune system.

The term "biodegradable" means capable of being broken down into innocuous products by the action of living things.

The phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present disclosure may be considered biologically active if even a portion of the polynucleotide is biologically active or mimics an activity considered biologically relevant.

The term "boranophosphate" has the ordinary meaning as understood in the art and can include protonated, deprotonated, and tautomeric forms thereof. For example, a boranophosphate within the context of a compound can have the structure

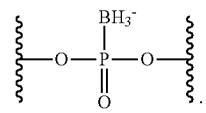

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl," as used herein, represents —C(O)—N(R$^{N1}$)$_2$, where the meaning of each R$^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl," as used herein, refers to a carbamate group having the structure —NR$^{N1}$C(=O)OR or —OC(=O)N(R$^{N1}$)$_2$, where the meaning of each R$^{N1}$ is found in the definition of "amino" provided herein, and R is alkyl, cycloalkyl, alkylcycloalkyl, aryl, alkylaryl, heterocyclyl (e.g., heteroaryl), or alkylheterocyclyl (e.g., alkylheteroaryl), as defined herein.

The term "carbonyl," as used herein, represents a C(O) group, which can also be represented as C=O.

The term "carboxyaldehyde" represents an acyl group having the structure-C(O)H.

The term "carboxy," as used herein, means —$CO_2H$.

The term "cationic lipid" means amphiphilic lipids and salts thereof having a positive, hydrophilic head group; one, two, three, or more hydrophobic fatty acid or fatty alkyl chains; and a connector between these two domains. An ionizable or protonatable cationic lipid is typically protonated (i.e., positively charged) at a pH below its $pK_a$ and is substantially neutral at a pH above the $pK_a$. Preferred ionizable cationic lipids are those having a $pK_a$ that is less than physiological pH, which is typically about 7.4. The cationic lipids of the disclosure may also be termed titratable cationic lipids. The cationic lipids can be an "amino lipid" having a protonatable tertiary amine (e.g., pH-titratable) head group. Some amino exemplary amino lipid can include $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, γ-DLen-C2K-DMA, DLin-M-C2-DMA (also known as MC2), DLin-M-C3-DMA (also known as MC3) and (DLin-MP-DMA) (also known as 1-B1 1).

The term "comprising" is intended to be open and permits but does not require the inclusion of additional elements or steps. When the term "comprising" is used herein, the term "consisting of" is thus also encompassed and disclosed.

The term "composition" means a product comprising the specified ingredients in the specified amounts, as well as any product that results, directly or indirectly, from combination of the specified ingredients in the specified amounts.

The term "commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

The phrase "compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif., 1972; T. L. Glichrist, "Heterocyclic Chemistry," 2nd Ed. John Wiley and Sons, New York, 1992; J. March, "Advanced Organic Chemistry: reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

The term "complementary nucleotide bases" means a pair of nucleotide bases that form hydrogen bonds with each other. Adenine (A) pairs with thymine (T) in DNA or with uracil (U) in RNA, and guanine (G) pairs with cytosine (C). Complementary segments or strands of nucleic acid hybridize (i.e. join by hydrogen bonding) with each other. By "complementary" is meant that a nucleic acid can form hydrogen bond(s) with another nucleic acid sequence either by traditional Watson-Crick or by other non-traditional modes of binding.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this disclosure can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{12}$ alkoxy (e.g., $C_{1-6}$ alkoxy, such as perfluoroalkoxy); (4) $C_{1-6}$ alkylsulfinyl; (5) $C_{6-10}$ aryl; (6)amino; (7) $C_{1-6}$ alkyl-$C_{6-10}$ aryl; (8) azido; (9) $C_{3-8}$ cycloalkyl; (10) $C_{1-6}$ alkyl-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alkyl-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alkyl-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alkyl-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alkyl-$C_{1-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alkyl-$C_{1-12}$ heterocyclyl (e.g., $C_{1-6}$ alkyl-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkyl group of a $C_1$-alkaryl or a $C_1$-alkylheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl).

The term "dialkyloxypropyl" or "DAA" includes a compound having 2 alkyl chains, R and R, both of which have independently between 2 and 30 carbons. The alkyl groups can be saturated or have varying degrees of unsaturation.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the disclosure, having an optical purity or enantiomeric excess (as determined by methods standard in the art) of at least 80% (i.e., at least 90% of one enantiomer and at most 10% of the other enantiomer), preferably at least 90% and more preferably at least 98%.

An "enzyme having ornithine transcarbamylase activity", an "enzyme having OTC activity" or "an OTC enzyme" means a protein or an enzyme that catalyzes a reaction between carbamoyl phosphate and ornithine to form citrulline and phosphate. OTC plays an essential role in the urea cycle which has the purpose of capturing toxic ammonia and transforming it into a less toxic urea nitrogen source for excretion.

The term "fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

The terms "halo" and "Halogen", as used herein, represents a halogen selected from bromine, chlorine, iodine, or fluorine.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —CHICH$_3$. In some embodiments, the haloalkyl group can be further substituted with 1, 2, 3, or 4 substituent groups as described herein for alkyl groups.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "hydroxyalkenyl," as used herein, represents an alkenyl group, as defined herein, substituted by one to three hydroxy groups, with the proviso that no more than one hydroxy group may be attached to a single carbon atom of the alkyl group, and is exemplified by dihydroxypropenyl, hydroxyisopentenyl, and the like. In some embodiments, the hydroxyalkenyl group can be substituted with 1, 2, 3, or 4 substituent groups (e.g., O-protecting groups) as defined herein for an alkyl.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like. In some embodiments, the hydroxyalkyl group can be substituted with 1, 2, 3, or 4 substituent groups (e.g., O-protecting groups) as defined herein for an alkyl.

The term "hydrate" means a solvate wherein the solvent molecule is $H_2O$.

The term "isomer," as used herein, means any tautomer, stereoisomer, enantiomer, or diastereomer of any compound of the disclosure. It is recognized that the compounds of the disclosure can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "nucleic acid" means deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

The term "oxo" as used herein, represents =O.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

The term "sulfonyl," as used herein, represents an —S(O)$_2$— group.

The term "compound," is meant to include all stereoisomers, geometric isomers, tautomers, and isotopes of the structures depicted.

The term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

The term "cyclic" refers to the presence of a continuous loop. Cyclic molecules need not be circular, only joined to form an unbroken chain of subunits. Cyclic molecules such as the mRNA of the present disclosure may be single units or multimers or comprise one or more components of a complex or higher order structure.

The term "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

The term "delivery" refers to the act or manner of delivering a compound, substance, entity, moiety, cargo or payload.

The term "delivery agent" or "delivery vehicle" refers to any substance which facilitates, at least in part, the in vivo delivery of a polynucleotide to targeted cells.

The term "digest" means to break apart into smaller pieces or components. When referring to polypeptides or proteins, digestion results in the production of peptides.

The phrase "encoded protein cleavage signal" refers to the nucleotide sequence which encodes a protein cleavage signal.

The term "engineered" when they are designed to have a feature or property, whether structural or chemical, that varies from a starting point, wild type or native molecule.

The term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

The term "feature" refers to a characteristic, a property, or a distinctive element.

The term "fragment," as used herein, refers to a portion. For example, fragments of proteins may comprise polypeptides obtained by digesting full-length protein isolated from cultured cells.

The term "functional" biological molecule is a biological molecule in a form in which it exhibits a property and/or activity by which it is characterized.

The term "homology" refers to the overall relatedness between polymeric molecules, e.g. between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

The term "hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna. CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12 (1), 387 (1984)), BLASTP, BLASTN, and FASTA Altschul, S. F. et al., *J. Molec. Biol.,* 215, 403 (1990)).

The term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

The term "lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

The term "lipid delivery vehicle" means a lipid formulation that can be used to deliver a therapeutic nucleic acid (e.g., mRNA) to a target site of interest (e.g., cell, tissue, organ, and the like). The lipid delivery vehicle can be a nucleic acid-lipid particle, which can be formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

The term "lipid encapsulated" means a nucleic acid such as an mRNA that is completely encapsulated, partial encapsulated, or both in a lipid formulation. In a preferred embodiment, the nucleic acid (e.g., mRNA) is fully encapsulated in the lipid particle.

The term "lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "amphipathic lipid" or "amphiphilic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

The term "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form multimers (e.g., through linkage of two or more polynucleotides) or conjugates, as well as to administer a payload, as described herein. Examples of chemical groups that can be incorporated into the linker include, but are not limited to, alkyl, alkenyl, alkynyl, amido, amino, ether, thioether, ester, alkyl, heteroalkyl, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

The term "mammal" means a human or other mammal or means a human being.

The term "messenger RNA" (mRNA) refers to any polynucleotide which encodes a protein or polypeptide of interest and which is capable of being translated to produce the encoded protein or polypeptide of interest in vitro, in vivo, in situ or ex vivo.

The term "modified" refers to a changed state or structure of a molecule of the disclosure or of an otherwise standard reference molecule. Molecules may be modified in many ways including chemically, structurally, and functionally. In one embodiment, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they may differ from the chemical structure of the A, C, G, U ribonucleotides.

The term "naturally occurring" means existing in nature without artificial aid.

The term "nonhuman vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

The term "nucleotide" is meant to include nucleotides that have natural bases (standard) or modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

The term "off target" refers to any unintended effect on any one or more target, gene, or cellular transcript.

The term "codon-optimized" means a natural (or purposefully designed variant of a natural) coding sequence which has been redesigned by choosing different codons without altering the encoded protein amino acid sequence increasing the protein expression levels (Gustafsson et al, Codon bias and heterologous protein expression. 2004, Trends Biotechnol 22:346-53). Variables such as high codon adaptation index (CAI), LowU method, mRNA secondary structures, cis-regulatory sequences, GC content and many other similar variables have been shown to somewhat correlate with protein expression levels (Villalobos et al., Gene Designer: a synthetic biology tool for constructing artificial DNA segments. 2006, BMC Bioinformatics 7:285). High CAI (codon adaptation index) method picks a most frequently used synonymous codon for an entire protein coding sequence. The most frequently used codon for each amino acid is deduced from 74218 protein-coding genes from a human genome. The LowU method targets only U-containing codons that can be replaced with a synonymous codon with fewer U moieties. If there are a few choices for the replacement, the more frequently used codon will be selected. The remaining codons in the sequence are not changed by the LowU method. This method may be used in conjunction with the disclosed mRNAs to design coding sequences that are to be synthesized with 5-methoxy uridine.

The term "open reading frame" or "ORF" to a nucleic acid sequence (DNA or RNA) refers to the portion of a sequence that is capable of encoding a polypeptide of interest. ORFs generally begin with the start codon ATG, and end with a nonsense or termination codon or signal.

The phrase "operably linked" refers to a functional connection between two or more molecules, constructs, transcripts, entities, moieties or the like.

The term "patient" refers to a subject who may seek or be in need of treatment, requires treatment, is receiving treatment, will receive treatment, or a subject who is under care by a trained professional for a particular disease or condition.

The phrase "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

The term "peptide" is less than or equal to 50 amino acids long, e.g., about 5, 10, 15, 20, 25, 30, 35, 40, 45, or 50 amino acids long.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The phrase "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

The term "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

The term "pharmaceutically acceptable solvate," as used herein, means a compound of the disclosure wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "phosphate" is used in its ordinary sense as understood by those skilled in the art and includes its protonated forms, for example

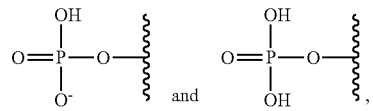 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

The term "phosphorothioate" refers to a compound of the general formula

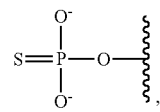

its protonated forms, for example,

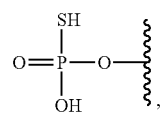

and its tautomers such as

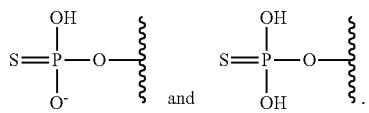 [SMILES: *OP([O-])(O)=S ; *OP(O)(O)=S]

The term "physicochemical" means of or relating to a physical and/or chemical property.

The term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term "protein cleavage site" refers to a site where controlled cleavage of the amino acid chain can be accomplished by chemical, enzymatic or photochemical means.

The phrase "protein cleavage signal" refers to at least one amino acid that flags or marks a polypeptide for cleavage.

The term "proteins of interest" or "desired proteins" include those provided herein and fragments, mutants, variants, and alterations thereof.

The terms "purify," "purified," "purification" means to make substantially pure or clear from unwanted components, material defilement, admixture or imperfection.

The term "RNA" means a molecule comprising at least one ribonucleotide residue. By "ribonucleotide" is meant a nucleotide with a hydroxyl group at the 2' position of a β-D-ribo-furanose moiety. The terms includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA.

The term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

The phrases "signal sequences" or "signal peptide" refer to a sequence which can direct the transport or localization of a protein.

The terms "significant" or "significantly" are used synonymously with the term "substantially."

The phrase "single unit dose" is a dose of any therapeutic administered in one dose/at one time/single route/single point of contact, i.e., single administration event.

The term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

The term "solvate" means a physical association of a compound of this disclosure with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "split dose" is the division of single unit dose or total daily dose into two or more doses.

The term "stable" refers to a compound that is sufficiently robust to survive isolation to a useful degree of purity from a reaction mixture, and preferably capable of formulation into an efficacious therapeutic agent.

The terms "stabilize", "stabilized," "stabilized region" means to make or become stable.

The term "substituted" means substitution with specified groups other than hydrogen, or with one or more groups, moieties, or radicals which can be the same or different, with each, for example, being independently selected.

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "Substantially equal" relates to time differences between doses, the term means plus/minus 2%.

The phrase "substantially simultaneously" relates to plurality of doses, the term means within 2 seconds.

The phrase "suffering from" relates to an individual who is "suffering from" a disease, disorder, and/or condition has been diagnosed with or displays one or more symptoms of a disease, disorder, and/or condition.

The phrase "susceptible to" relates to an individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The term "synthetic" means produced, prepared, and/or manufactured by the hand of man. Synthesis of polynucleotides or polypeptides or other molecules of the present disclosure may be chemical or enzymatic.

The term "targeted cells" refers to any one or more cells of interest. The cells may be found in vitro, in vivo, in situ or in the tissue or organ of an organism. The organism may be an animal, preferably a mammal, more preferably a human and most preferably a patient.

The term "therapeutic agent" refers to any agent that, when administered to a subject, has a therapeutic, diagnostic, and/or prophylactic effect and/or elicits a desired biological and/or pharmacological effect.

The term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

The term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

The term "total daily dose" is an amount given or prescribed in 24 hr period. It may be administered as a single unit dose.

The term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

The term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

The term "half-life" is the time required for a quantity such as nucleic acid or protein concentration or activity to fall to half of its value as measured at the beginning of a time period.

The term "in vitro" refers to events that occur in an artificial environment, e.g., in a test tube or reaction vessel, in cell culture, in a Petri dish, etc., rather than within an organism (e.g., animal, plant, or microbe).

The term "in vivo" refers to events that occur within an organism (e.g., animal, plant, or microbe or cell or tissue thereof).

The term "monomer" refers to a single unit, e.g., a single nucleic acid, which may be joined with another molecule of the same or different type to form an oligomer. In some embodiments, a monomer may be an unlocked nucleic acid, i.e., a UNA monomer.

The term "neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" means an amphipathic lipid, a neutral lipid or anionic lipid as described herein.

The term "oligomer" may be used interchangeably with "polynucleotide" and refers to a molecule comprising at least two monomers and includes oligonucleotides such as DNAs and RNAs. In the case of oligomers containing RNA monomers and/or unlocked nucleic acid (UNA) monomers, the oligomers of the present disclosure may contain sequences in addition to the coding sequence (CDS). These additional sequences may be untranslated sequences, i.e., sequences which are not converted to protein by a host cell. These untranslated sequences can include a 5' cap, a 5' untranslated region (5' UTR), a 3' untranslated region (3' UTR), and a tail region, e.g., a poly A tail region. As described in further detail herein, any of these untranslated sequences may contain one or more UNA monomers—these UNA monomers are not capable of being translated by a host cell's machinery. In the context of the present disclosure, a "mRNA sequence", a "mRNA sequence", "translatable polynucleotide", or "translatable compound" refers to a sequence that comprises a region, e.g., the coding region of an RNA (e.g., the coding sequence of human CFTR or a codon-optimized version thereof), that is capable of being converted to a protein or a fragment thereof, e.g., the human CFTR protein or a fragment thereof.

The terms "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

The term "translatable" may be used interchangeably with the term "expressible" and refers to the ability of polynucleotide, or a portion thereof, to be converted to a polypeptide by a host cell. As is understood in the art, translation is the process in which ribosomes in a cell's cytoplasm create polypeptides. In translation, messenger RNA (mRNA) is decoded by tRNAs in a ribosome complex to produce a specific amino acid chain, or polypeptide. Furthermore, the term "translatable" when used in this specification in reference to an oligomer, means that at least a portion of the oligomer, e.g., the coding region of an oligomer sequence (also known as the coding sequence or CDS), is capable of being converted to a protein or a fragment thereof.

The term "translation efficiency" refers to a measure of the production of a protein or polypeptide by translation of an mRNA sequence in vitro or in vivo. This disclosure provides a range of mRNA sequence molecules wherein the mRNA sequence can be expressible to provide a polypeptide or protein.

The term "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

EXAMPLES

Additional embodiments of the present disclosure are illustrated in further detail in the following examples, which are not in any way intended to limit the scope of the claims.

Example 1: In Vitro Transcription Protocol

Material and Methods

Constructs of mRNAs described herein were synthesized in vitro using T7RNA polymerase-mediated, DNA-dependent RNA transcription. In the transcription reaction, modified and unmodified uridine triphosphates (UTP) were used depending on the desired polynucleotide configuration. Modified UTPs used included 5-methoxy UTP (5MeOU), $N^1$-methyl pseudo UTP, N1-methoxy methyl pseudo UTP (N1-MOM), 5-hydroxy methyl UTP, 5-carboxy UTP, and a mixture of modified UTPs, using a linearized template for each UTR combination. The mRNA was purified using column chromatography, the DNA and double stranded RNA contamination of all mRNAs was removed using an enzymatic reaction, and the mRNA was concentrated, and buffer exchanged.

Preparation of Lipid Encapsulated mRNA

Lipid encapsulated mRNA particles were prepared by mixing lipids (ionizable cationic lipid: DSPC: Cholesterol: PEG-DMG) in ethanol with OTC mRNA dissolved in citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 40-60 mM NaCl and 7-12% sucrose, pH 7.3. The formulation was concentrated followed by 0.2 µm filtration using PES filters. The mRNA concentration in the formulation was then measured by Ribogreen fluorimetric assay following which the concentration was adjusted to a final desired concentration by diluting with HEPES buffer containing 40-60 mM NaCl, 7-12% sucrose, pH 7.3 containing glycerol. The final formulation was then filtered through a 0.2 µm filter and filled into glass vials, stoppered, capped and placed at -70±5° C. The frozen formulations were characterized for their mRNA content by HPLC or Ribogreen assay and percent encapsulation by Ribogreen assay, mRNA integrity by fragment analyzer, lipid content by high performance liquid chromatography (HPLC), particle size by dynamic light scattering on a Malvern Zetasizer Nano ZS, pH and osmolality.

In-Cell Western (ICW)

96-well collagen plates were used to seed the cells at the appropriate density in Dulbecco's Modified Eagle Media (DMEM)/Fetal Bovine Serum (FBS) culture media. At the optimal confluence, cells were transfected with the targeted mRNAs diluted in the transfection reagent mix (Messenger-Max and Opti-MEM). Cells were placed in a $CO_2$ incubator and allowed to grow. At the desired timepoint, media was removed, and cells were fixed in 4% fresh paraformaldehyde (PFA) for 20 min. After that, fixative was removed, and cells were permeabilized several times in Tris buffered saline with TWEEN (TBST) for 5 minutes each time. When permeabilization washes were complete, cells were incubated with a blocking buffer (ODYSSEY® Blocking Buffer (PBS) (Li-Cor, Lincoln, NE)) for 45 min. Primary antibody was then added and incubated for 1 hour at room temperature.

Cells were then washed several times in TBST and incubated for 1 hour with a secondary antibody diluted in blocking buffer and containing a CellTag 700 stain. Cells were washed several times in TBST followed by a last wash in Tris-buffered saline (TBS). The plate was imaged using the Licor detection system, and data was normalized to the total number of cells labeled by the CellTag 700.

Example 2: UTRs Screening in Hepa1,6 and Hep3B—Correlation at 24 h and 48 h

Figure 1B:
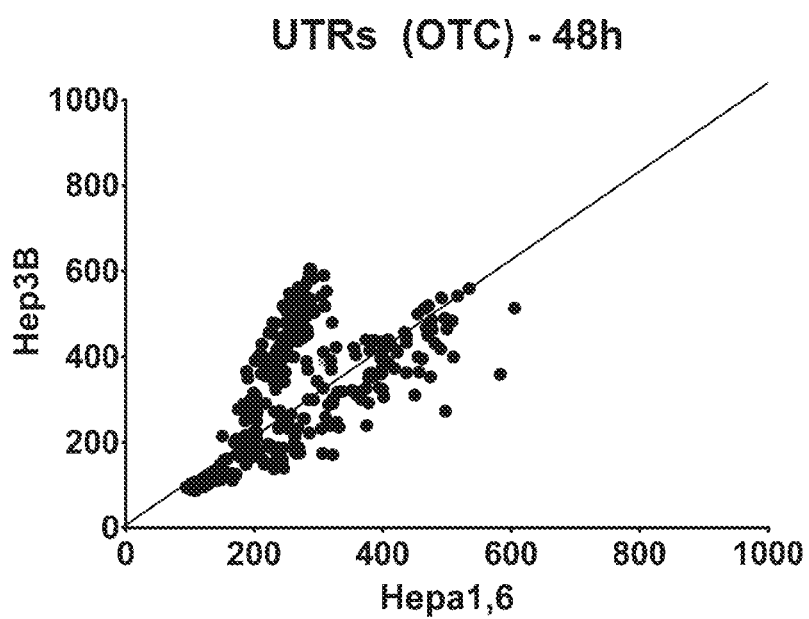

A UTR library was screened in vitro using mRNA construct #571 comprising the sequence of SEQ ID NO: 34 as the CDS (coding sequence). Hepa1,6 and Hep3B cells were transfected with the different mRNAs using commercially available transfection reagents and protein expression was measured, as described above (In-Cell Western assays, Example 1). OTC protein expression levels were measured by near-infrared fluorescent imaging systems. Commercially available antibodies for OTC were used for detection. Untransfected cells and reference sequences were used as internal controls. FIG. 1A is a scatter plot of OTC protein expression levels found in Hepa1,6 and Hep3B cells at 24 hours. FIG. 1B is a scatter plot of OTC protein expression levels found in Hepa1,6 and Hep3B cells at 48 hours. The aim of the screen was to determine a UTR-specific impact on OTC expression levels in a human (Hep3B) and a mouse (Hepa1,6) liver cell line to determine which UTRs would work best in both models and, in particular, to assess translatability from mouse-to-human. Top expressing UTRs were used in further profiling studies.

Figure 2:
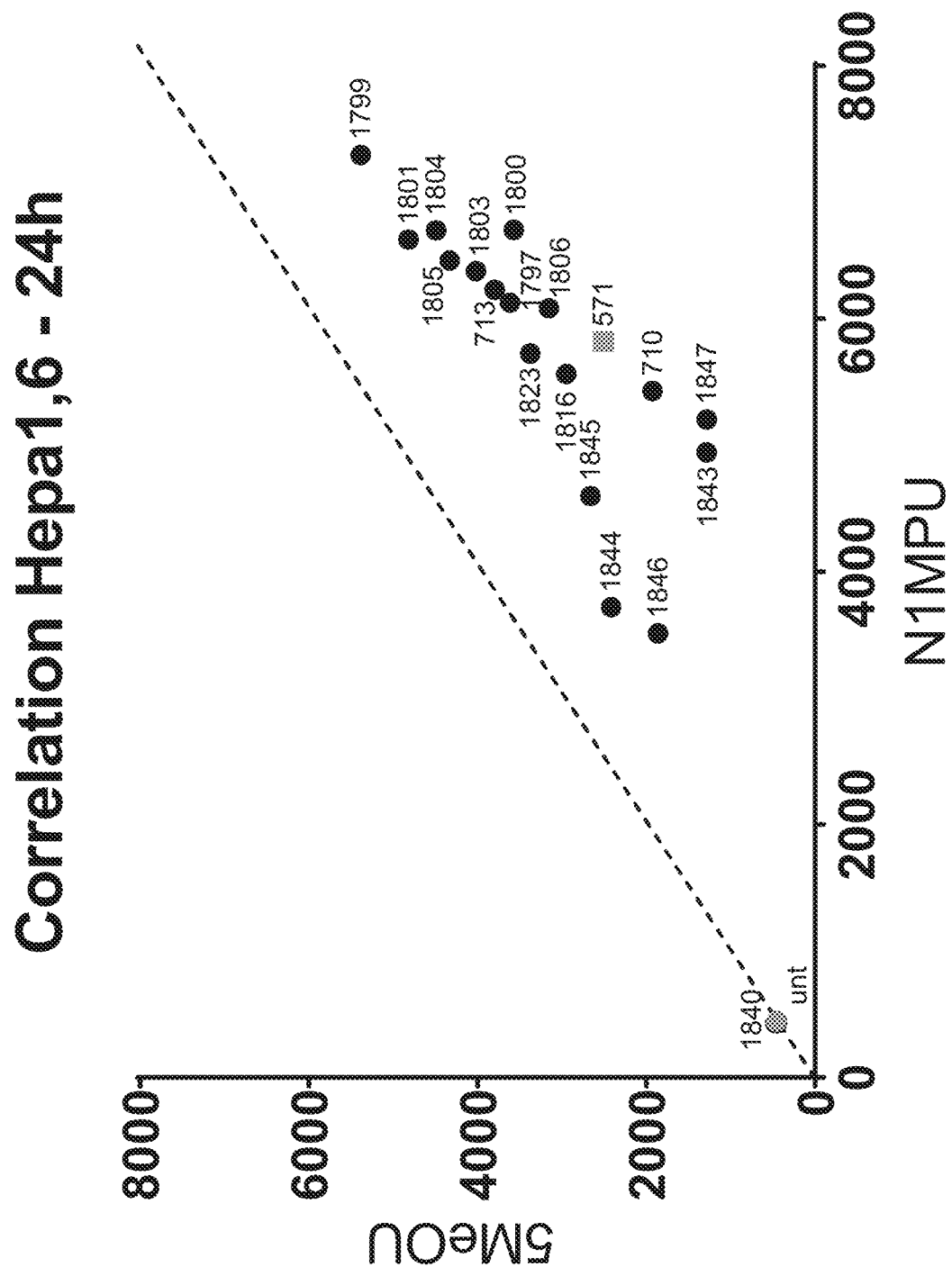
FIG. 2 shows a scatter plot that illustrates the correlation of protein stability with compounds screened in Hepa1,6 cells at 24 hours in a first round of screening.
Figure 3:
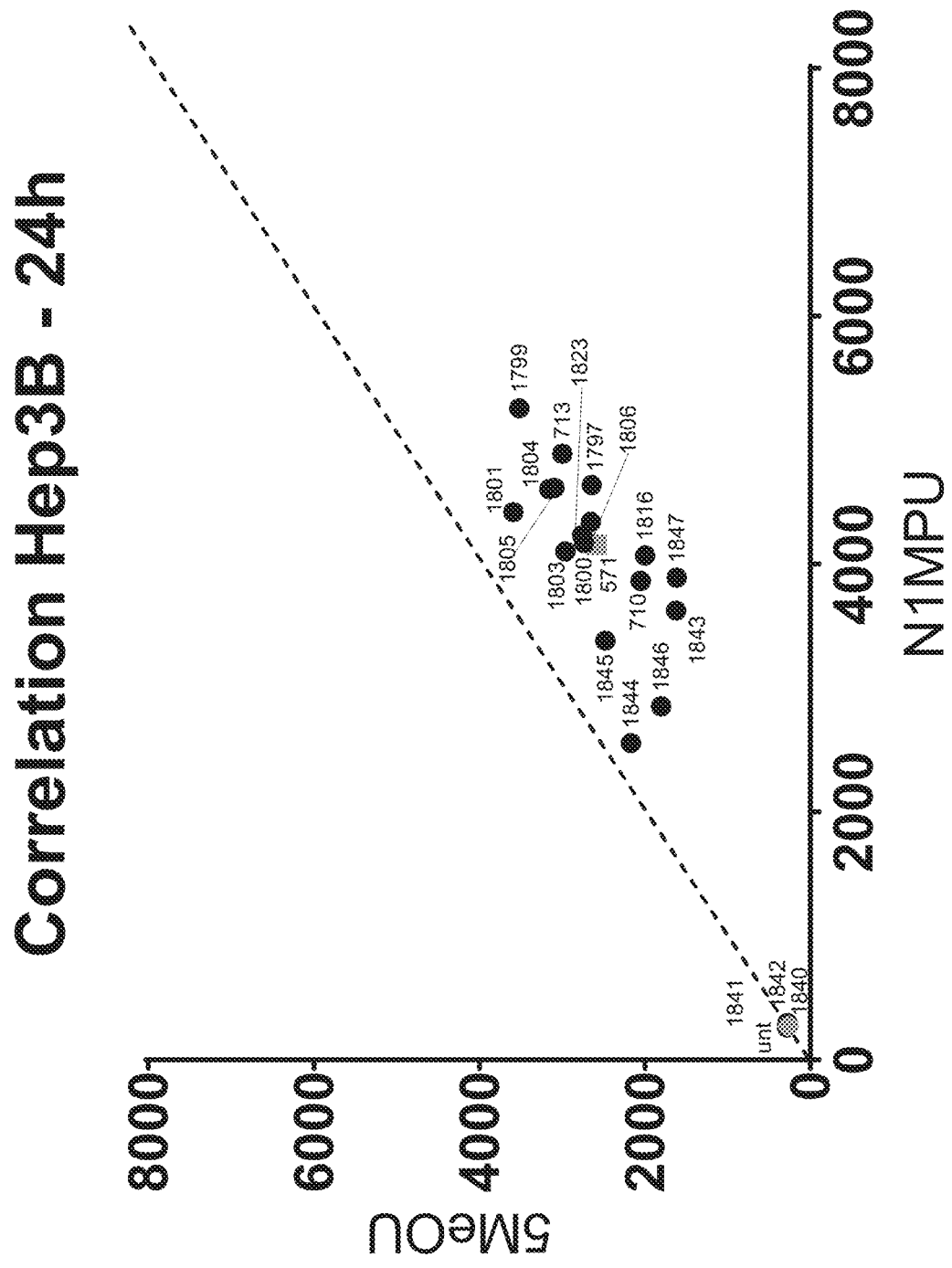
FIG. 3 shows a scatter plot that illustrates the correlation of protein stability with compounds screened in Hep3B cells at 24 hours in a first round of screening.

Example 3: Round 1 of Protein Stability mRNA Compound Screening in Hepa1,6 and Hep3B at 24 h—Correlation In vitro screening of certain mRNA constructs of Table 5 that were designed based on a protein-stability approach was performed. mRNA constructs with two different types of chemistries for the uridine residues were tested: $N^1$-methyl pseudouridine (N1MPU) and 5-methoxyuridine (5MeOU). In these experiments, 100% of the uridines in each mRNA were either N1MPU only or 5MeOU only (not a combination of 5MeOU or N1MPU). Hepa1,6 and Hep3B cells were transfected with the different mRNAs using commercially available transfection reagents and protein expression was measured, as described above (In-Cell Western (ICW) assays, Example 1). OTC protein expression levels were measured by near-infrared fluorescent imaging systems. Commercially available antibodies for OTC were used for detection. Untransfected cells and reference sequences were used as internal controls. FIG. 2 is a scatter plot showing the correlation of OTC protein expression levels in Hepa1,6 cells at 24 hours as a function of mRNAs tested and including N1MPU and 5MeOU chemistries. FIG. 3 is a scatter plot showing the correlation of OTC protein expression levels in Hep3B cells at 24 hours as a function of mRNAs tested and including N1MPU and 5MeOU chemistries. Shown in the figures is the degree of variability in expression levels for mRNAs with two different chemistries tested in a mouse and a human liver cell line. It can be seen that, in this experiment, most of the mRNA compounds express better when an N1MPU chemistry is used.

Figure 4:
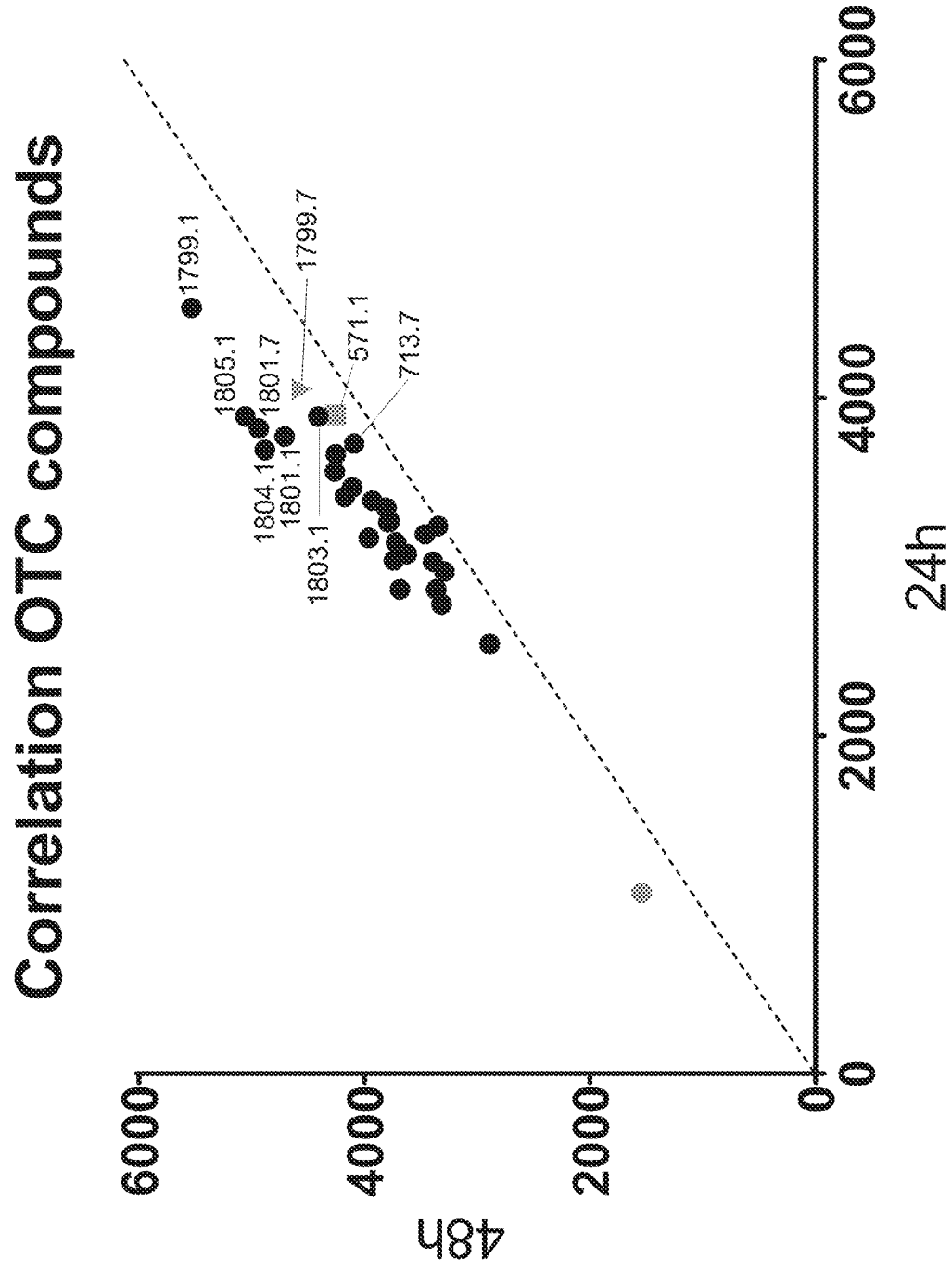
FIG. 4 shows a scatter plot illustrating the correlation of protein stability of compounds screened in human primary hepatocytes at 24 hours and 48 hours in a second round of screening (newly designed compounds based on the first round).
Figure 5:
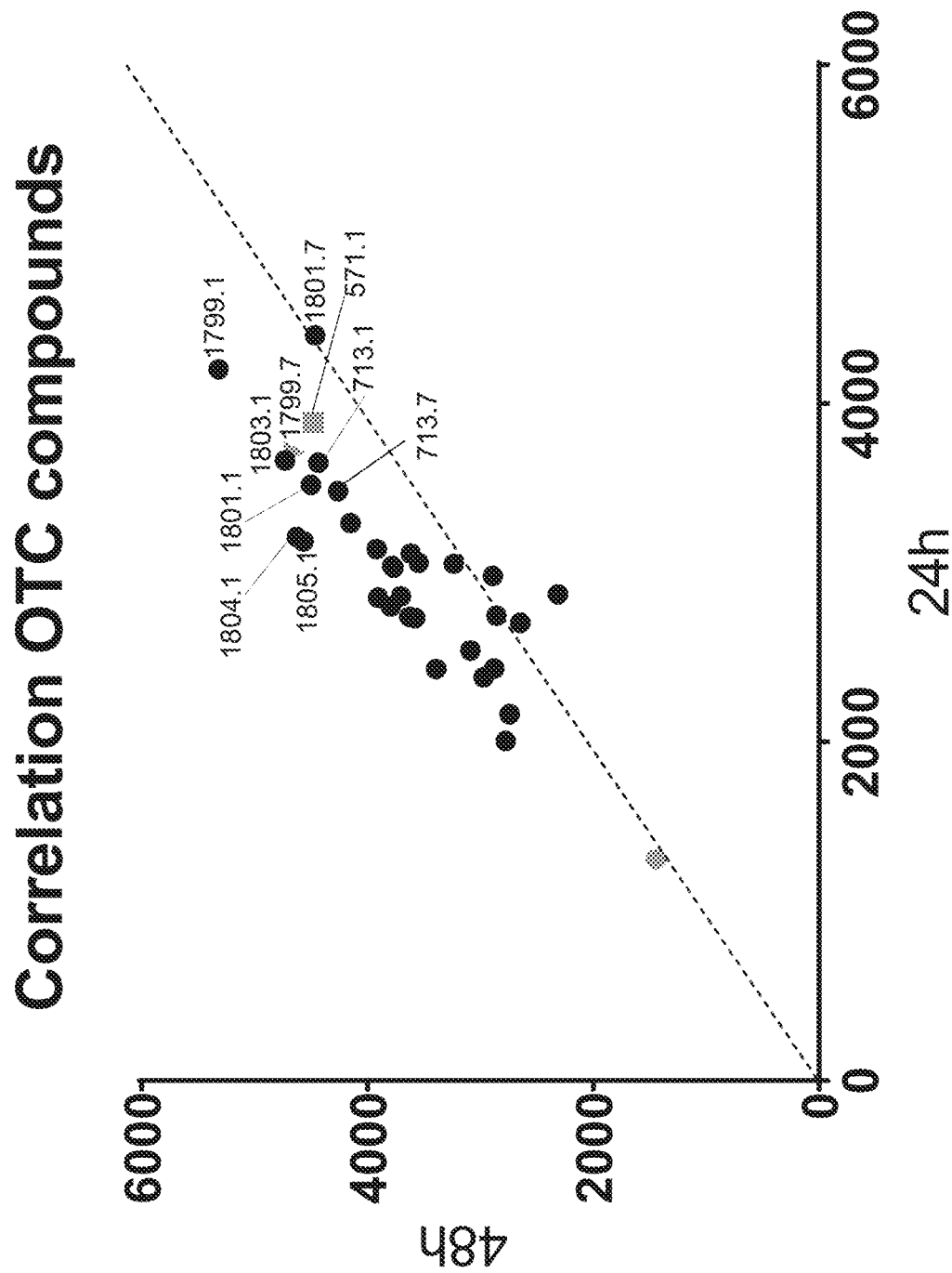
FIG. 5 shows a scatter plot illustrating the correlation of protein stability of compounds screened in human primary hepatocytes at 24 hours and 48 hours in a second round of screening (newly designed compounds based on the first round).

Example 4: Round 2 of Protein Stability mRNA Compound Screening in Human Primary Hepatocytes at 24 h and 48 h—Correlation In vitro screening of certain mRNA constructs of Table 5 that were designed based on a protein stability approach was performed. mRNAs with two different chemistries were tested: 100% of the uridines being N1MPU, which constructs are indicated by the designation of the mRNA construct followed by "0.1" and 100% of the uridines being 5MeOU, which constructs are indicated by the designation of the mRNA construct followed by "0.7". Human primary hepatocytes were transfected with the different mRNAs using commercially available transfection reagents and protein expression was measured, as described above (In-Cell Western (ICW), Example 1). OTC protein expression levels were measured by near-infrared fluorescent imaging systems. Commercially available antibodies for OTC were used for detection. Untransfected cells and reference sequences were used as internal controls (FIG. 4 and FIG. 5). The results indicate that, in contrast to the experiments conducted in cancer cell lines (Hepa1,6; Hep3B; Example 3), mRNAs with both chemistries expressed similarly in human primary hepatocytes.

Figure 6:
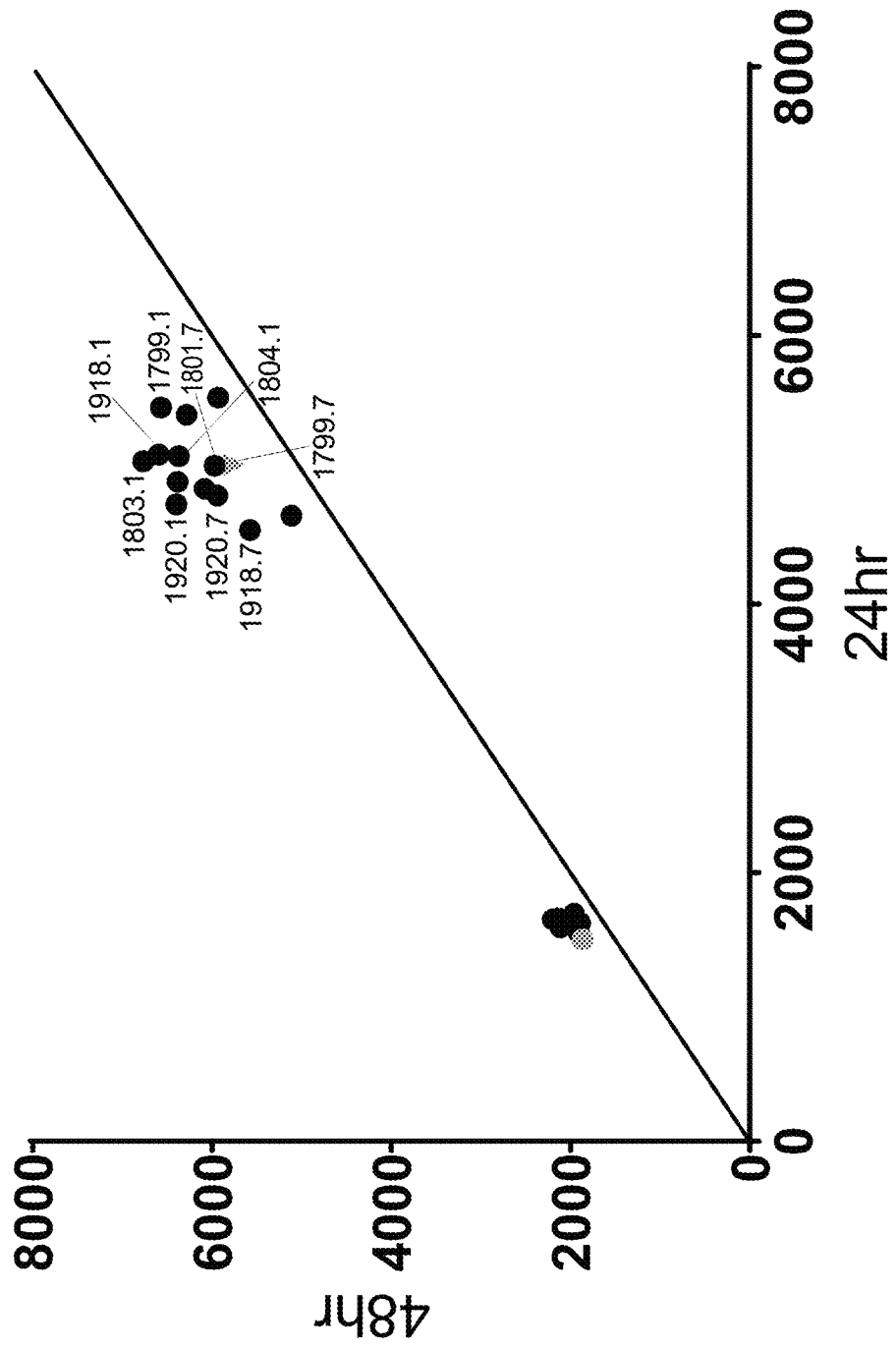
FIG. 6 shows a scatter plot illustrating the correlation of protein stability of compounds screened in human primary hepatocytes at 24 hours and 48 hours in a third round of screening (newly designed compounds based on rounds 1 and 2).
Figure 7:
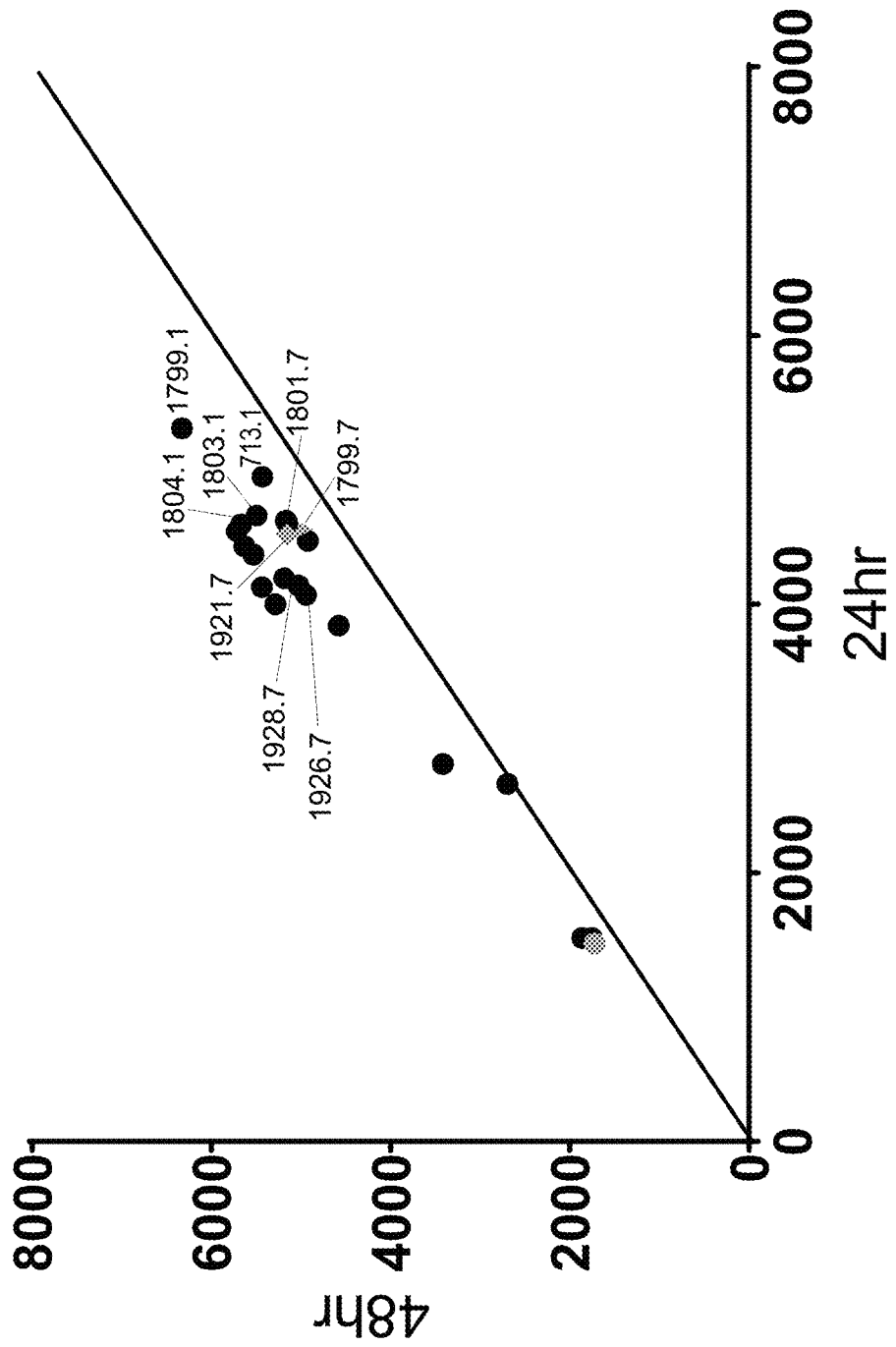
FIG. 7 shows a scatter plot illustrating the correlation of protein stability of compounds screened in human primary hepatocytes at 24 hours and 48 hours in a third round of screening (newly designed compounds based on rounds 1 and 2).

Example 5: Round 3 of Protein Stability Compound Screening in Human Primary Hepatocytes at 24 h and 48 h—Correlation An in vitro screen of novel compounds designed based on a protein stability approach was performed. mRNAs with two different chemistries were tested, with N1MPU indicated by the name of mRNA constructs followed by "0.1" and 5MeOU indicated by the name of mRNA constructs followed by "0.7". Human primary hepatocytes were transfected with the different mRNAs using commercially available transfection reagents and protein expression was measured, as described above (In-Cell Western (ICW) assays, Example 1). OTC protein expression levels were measured by near-infrared fluorescent imaging systems. Commercially available antibodies for OTC protein were used for detection. Untransfected cells and reference sequences were used as internal controls (FIG. 6 and FIG. 7). The results indicate that, in contrast to the experiments conducted in cancer cell lines (Hepa1,6; Hep3B; Example 3), mRNAs with both chemistries expressed similarly in human primary hepatocytes.

Example 6: OTC Protein-Expression Levels in Human Primary Cells Transfected with OTC mRNA Constructs 1799.7 (5MeOU Chemistry) Encoding the OTC Protein of SEQ ID NO: 3 and 1921.7 (5MeOU Chemistry) Encoding the Modified OTC Protein of SEQ ID NO: 4

Figure 8:
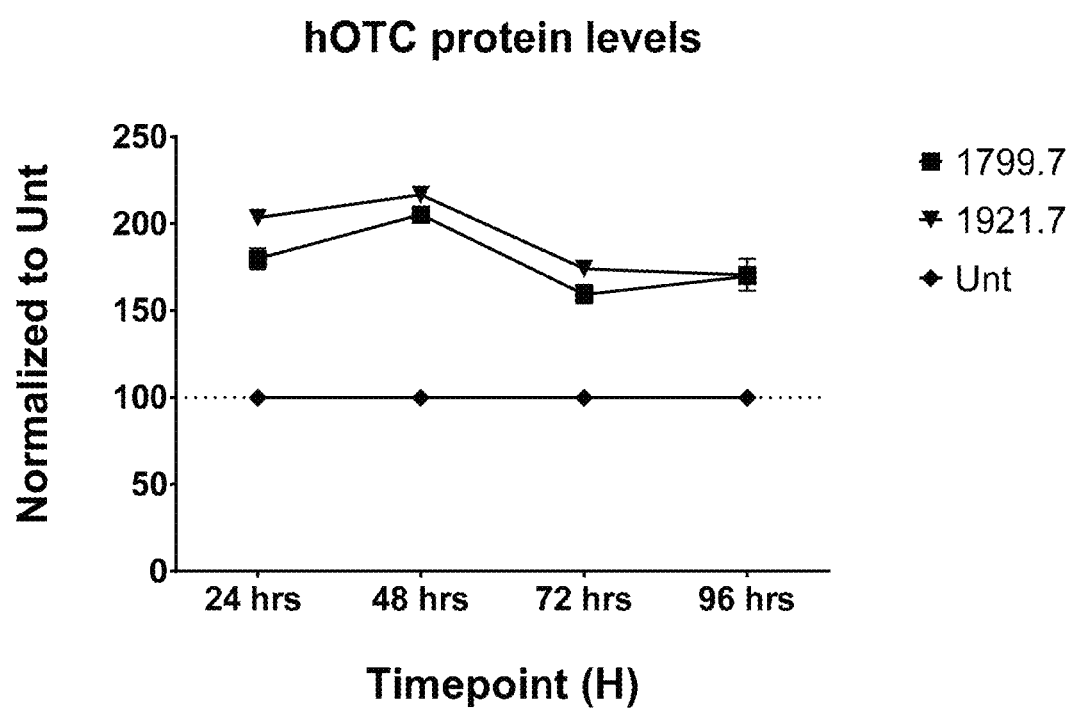
FIG. 8 is a plot illustrating OTC protein expression levels in human primary hepatocytes transfected with selected OTC mRNAs. Construct 1799.7 is an mRNA having the sequence of SEQ ID NO: 175 in which 100% of the uridines in SEQ ID NO: 175 are 5-methoxyuridine (5MeOU).

Human primary hepatocytes were transfected with the different mRNAs using commercially available transfection reagents and protein expression was measured, as described above (In-Cell Western (ICW) assays, Example 1). OTC protein expression levels were measured by near-infrared fluorescent imaging systems during a time course study of up to 96 hours. Commercially available OTC antibodies were used for detection. Untransfected cells were used as internal control. The resultant plot shows OTC protein levels normalized to untransfected controls (FIG. 8). The purpose of this study was to evaluate the half-life of the unmodified versus the modified protein sequence (encoded by constructs 1799.7 and 1921.7, respectively) under in vitro conditions in transfected human primary hepatocytes. The results indicate that 1921.7 demonstrated more stable expression than 1799.7.

Example 7: OTC Expression Levels Measured by Multiple Reaction Monitoring (MRM) Mass Spectrometry in Spf/Ash Mice Dosed at 10 mg/kg Spf/ash mice received an IV injection with either PBS or lipid-formulated (as described in Example 1) hOTC-mRNA at a 10 mg/kg dose level. WT mice were used as internal controls to determine endogenous levels. A time course (6 hours, 24 hours and 48 hours) was performed, and expression levels were measured by MRM using human- and mouse-specific epitopes for OTC. Human- and mouse-specific heavy peptides were designed to measure total levels of OTC from both species. Graphs represent the amount of protein (ng/mg tissue) detected by MRM specific for human OTC (FIG. 9A) or mouse OTC (FIG. 9B). This data set shows that quantitative levels of human OTC (hOTC) were observed in treated mice that derived from translation of the delivered mRNAs. A high level of quantifiable hOTC protein was seen up to 48 hours.

Figure 10:
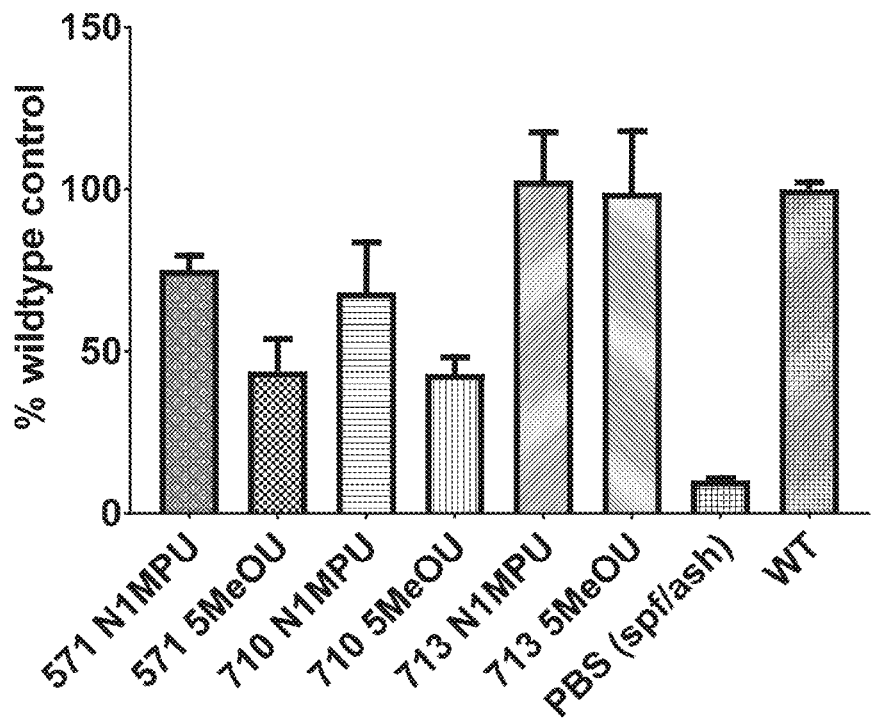
FIG. 10 is a bar graph depicting OTC expression levels in Spf/ash mice dosed at 3 mg/kg with OTC-mRNAs using two different uridine chemistries wherein 100% of the uridines are $N^1$-methylpseudouridine (N1MPU) and 100% of the uridines are 5-methoxyuridine (5MeOU).

Example 8: OTC Expression Levels Measured by Western Blot in Mice Dosed at 3 mg/kg Spf/ash mice received an IV injection with either phosphate buffered saline (PBS) or lipid-formulated OTC-mRNAs at a 3 mg/kg dose using two different uridine nucleotide chemistries (N1MPU and 5MeOU). WT mice were used as internal controls to determine endogenous levels. Animals were sacrificed 24 hours post-dose. OTC expression levels were measured by Western Blot (WB) using an OTC specific antibody. In the results provided in FIG. 10, the bars represent the percentage of expression relative to WT levels (100%). The data shows that WT levels of total OTC were achieved for several codon-optimized sequences in a mouse background.

Figure 11:
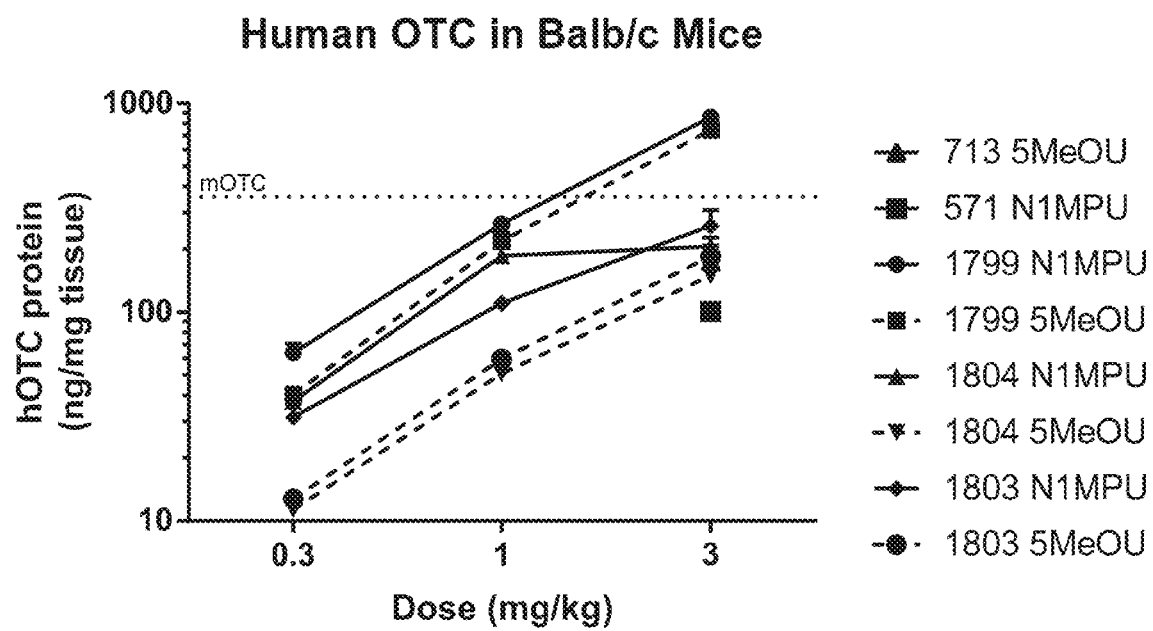
FIG. 11 is a graph depicting OTC expression levels in Balb/c mice dosed with OTC mRNAs at three different doses and using two different uridine chemistries (N1MPU and 5MeOU).

Example 9: OTC Expression Levels Measured by MRM in a Dose Range-Finding Study Balb/c mice received an IV injection with either PBS or lipid-formulated OTC-mRNAs at three different doses (0.3 mg/kg, 1 mg/kg and 3 mg/kg) and using two different uridine chemistries (N1MPU and 5MeOU). Animals were sacrificed 24 hours post-dose and expression levels were measured by MRM using human and mouse specific epitopes for OTC. MRM was used to quantitatively determine human-specific and mouse-specific OTC protein levels (FIG. 11). The graph in FIG. 11 shows expression of human OTC in Balb/c mice (ng per mg of liver tissue). The horizontal dotted line represents relative mouse OTC levels in Balb/c mice (FIG. 11). Expression levels of human OTC (hOTC) protein for mRNA construct 713 using 5MeOU and mRNA construct 571 using N1MPU are shown in FIG. 11. The data generated in this figure shows that WT levels of human OTC were achieved with the codon-optimized sequences disclosed herein in a dose-dependent manner in a mouse background.

Figure 12:
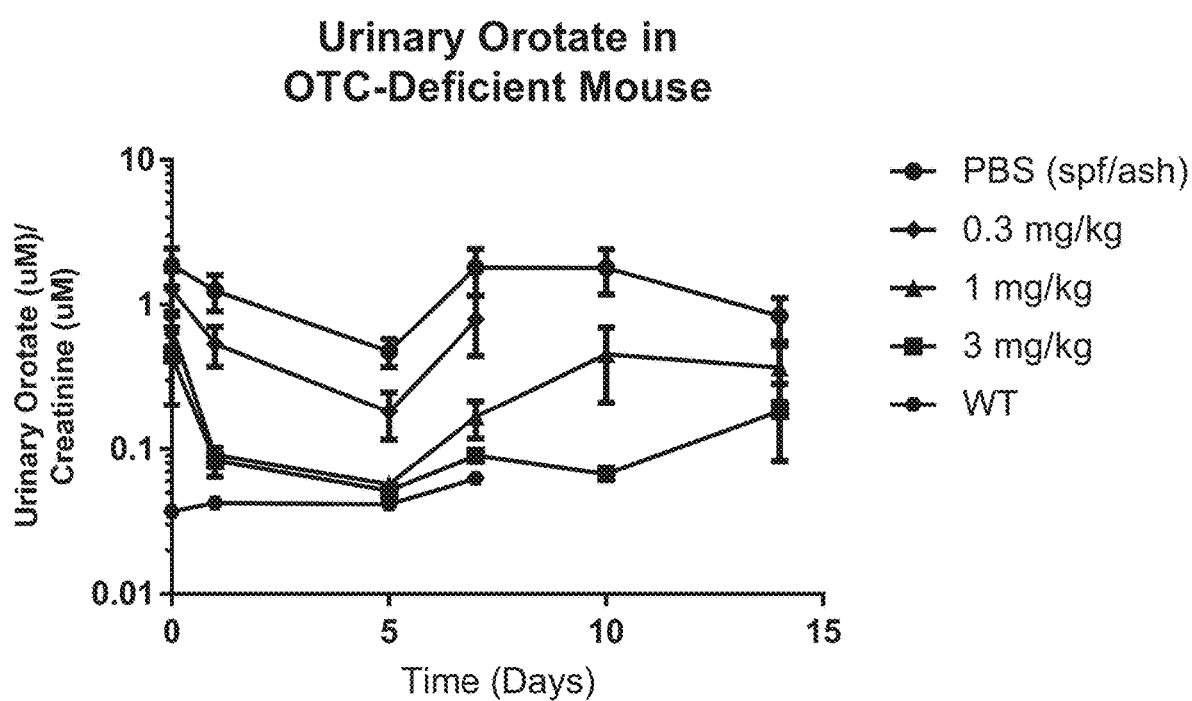
FIG. 12 is a graph depicting urinary orotate levels measured in Spf/ash mice dosed with OTC mRNA 1799.7 at three different doses: 0.3 mg/kg, 1 mg/kg and 3 mg/kg. Construct 1799.7 is an mRNA having the sequence of SEQ ID NO: 175 wherein 100% of the uridines in SEQ ID NO: 175 are 5MeOU.

Example 10: Urinary Orotate Levels Measured in PBS- and mRNA-Treated Spf/Ash Mice Spf/ash mice received an IV injection with either PBS or lipid-formulated OTC-mRNA construct 1799.7 (5MeOU chemistry) at three different doses: 0.3 mg/kg, 1 mg/kg and 3 mg/kg. Urinary orotate levels were determined in untreated wild-type (WT) and both untreated and treated Spf/ash mice. A urinary orotate time course was performed in Spf/ash and WT mice, and urinary orotate levels were measured at each timepoint. The results can be seen in FIG. 12. Urinary orotate was normalized to creatinine, which is represented in the graph on the y-axis throughout the time course and served as a proof-of-concept of functional restoration of OTC activity post-injection. At 3 mg/kg, a sustainable reduction of urinary orotate levels was observed for up to 14 days, with reduced urinary orotate levels in treated Spf/ash mice comparable to urinary orotate levels in WT mice.

Figure 13:
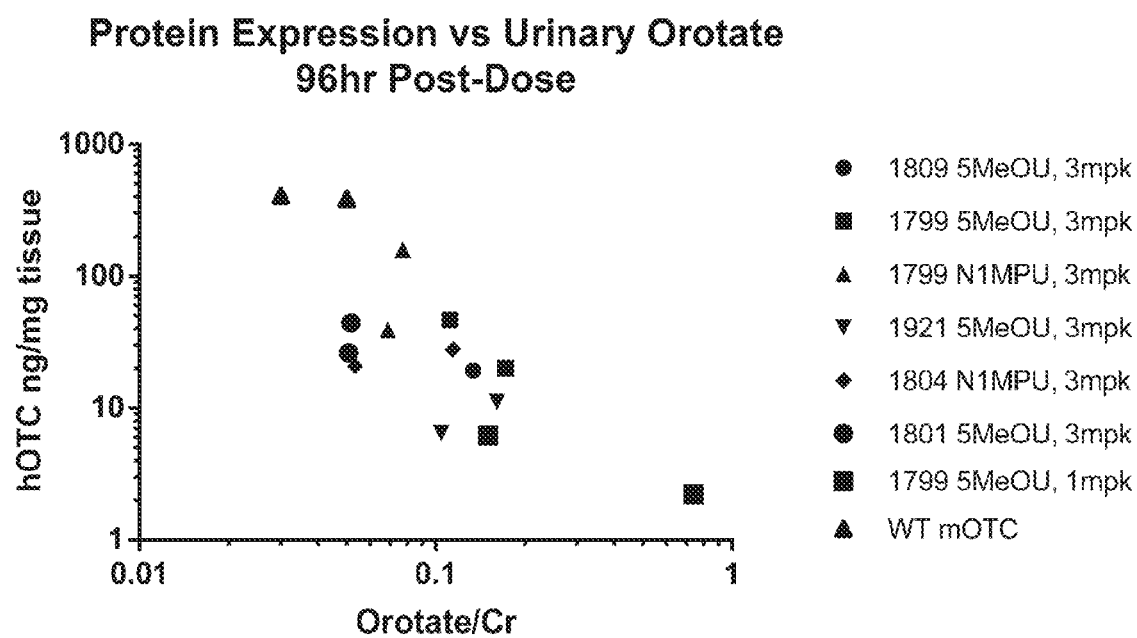
FIG. 13 is a scatter plot comparing human OTC expression levels and urinary orotate at 96 hours in Spf/ash mice dosed with OTC mRNAs at 1 mg/kg and 3 mg/kg using two different uridine chemistries (N1MPU and 5MeOU).

Example 11: Pharmacokinetic/Pharmacodynamic (PK/PD) Analysis Comparing Human OTC Expression Levels and Urinary Orotate at 96 Hours Post Dose Spf/ash mice received an IV injection with either PBS or certain lipid-formulated OTC-mRNAs from Table 5 at 1 mg/kg and 3 mg/kg using two different uridine chemistries (N1MPU and 5MeOU). WT mice were used as internal controls. Human-specific OTC levels were measured by MRM, and urinary orotate was determined in each sample and normalized to creatinine. The resultant PK/PD profile is plotted in FIG. 13 and the PK/PD analysis shows the correlation between protein expression levels and reduction of urinary orotate in a compound-specific manner. Construct 1799.7 (5MeOU chemistry) showed a high PK/PD correlation.

Figure 14:
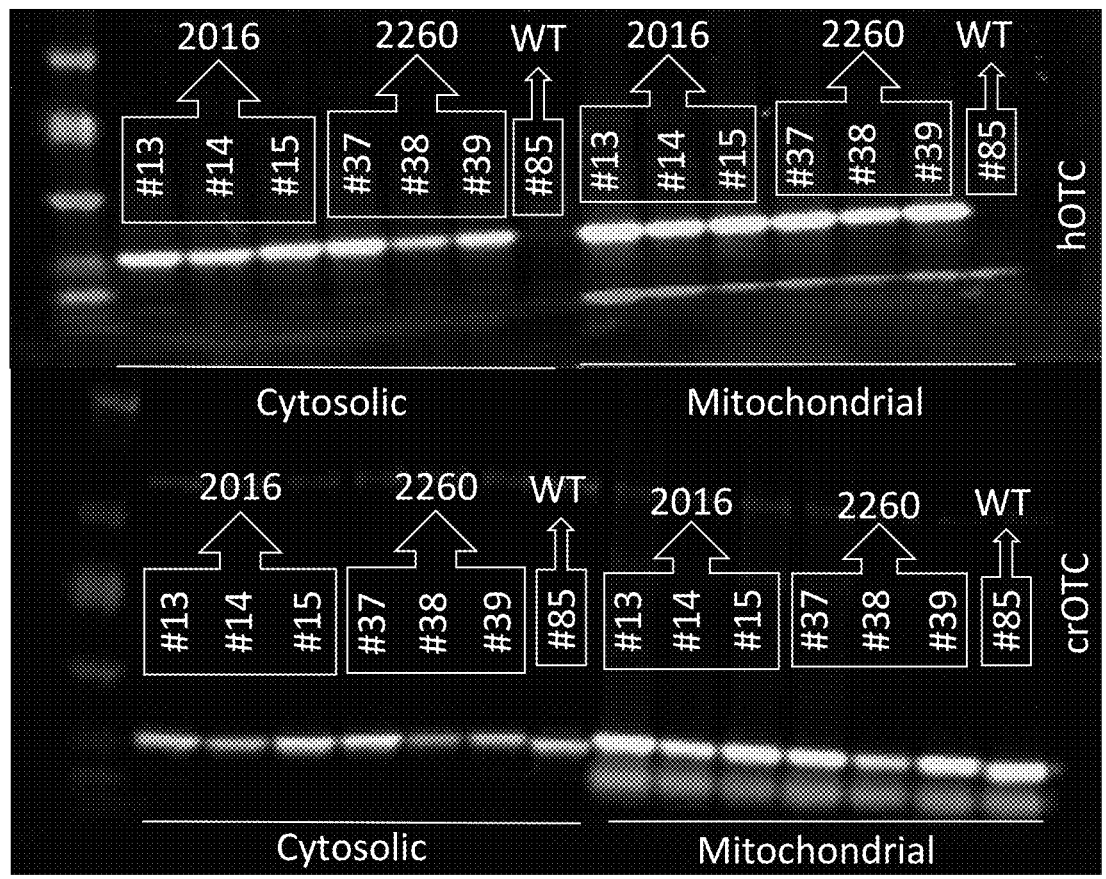
FIG. 14 is a western blot illustrating the protein expression levels of OTC mRNAs in Spf/ash mice dosed at 1 mg/kg and 3 mg/kg with selected OTC mRNAs.

Example 12: Fractioning of Spf/Ash Mice In Vivo Samples Treated with Selected mRNAs Spf/ash mice received an IV injection with either PBS or lipid-formulated (as described in Example 1) OTC-mRNAs at 1 mg/kg and 3 mg/kg. WT mice were used as internal controls. Livers were harvested from the mice and sample fractionation was performed on the liver samples, separating the cytosolic and mitochondrial fractions. OTC levels were measured by Western Blot (WB) using human specific (hOTC) and crossreactive (crOTC) antibodies (FIG. 14). Cyclooxygenase IV (CoxIV) was used as a mitochondrial control. OTC protein expression levels were measured by near-infrared fluorescent imaging systems and normalized to total protein. The WB results indicate differences in OTC expression levels within mitochondrial and cytosolic fractions when the 2016 and 2260 mRNA constructs were delivered in the Spf/ash mice. These results indicate that both compounds can efficiently target the mitochondria.

Example 13: Plot of the Mitochondrial Vs Cytosolic Fractions of Spf/Ash Mouse Samples Treated with mRNA Constructs 2016 and 2260

Figure 15:
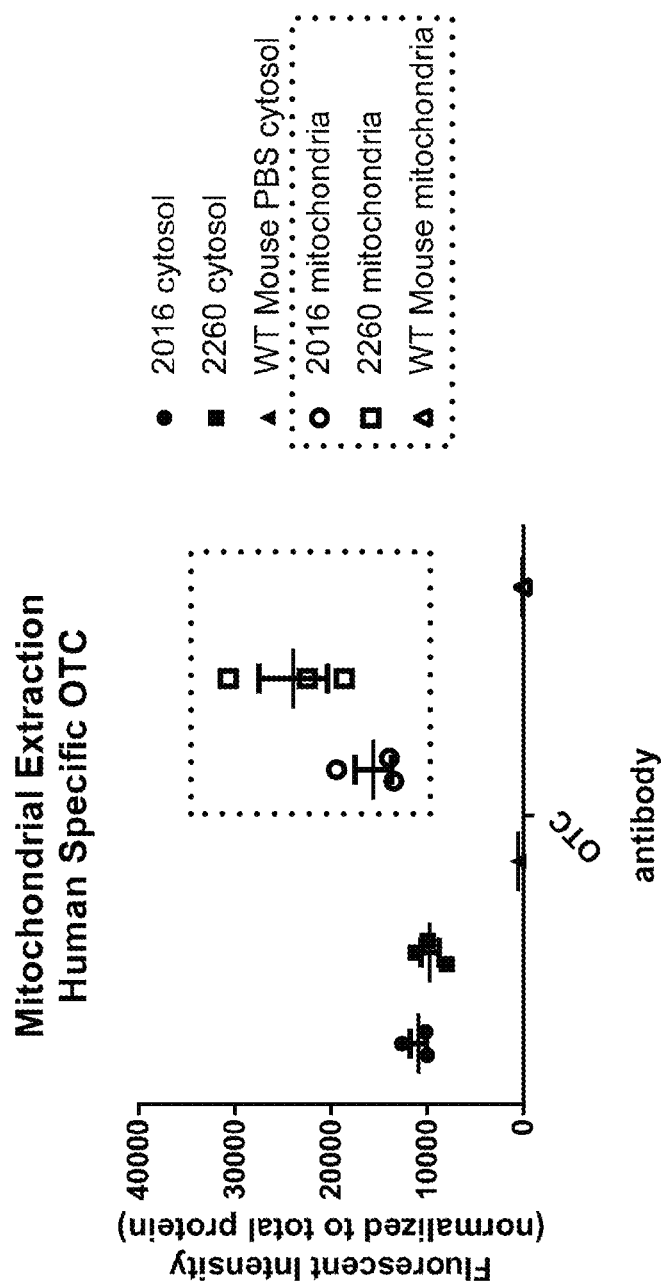
FIG. 15 shows results of a western blot illustrating the protein expression levels in mitochondrial vs. cytosolic fractions of Spf/ash mice treated with selected OTC mRNAs.

Spf/ash mice received an IV injection with either PBS or lipid-formulated OTC-mRNAs at 3 mg/kg. WT mice were used as internal controls. Sample fractionation was performed on liver samples harvested from the mice, separating the cytosolic and mitochondrial fractions. OTC levels were measured by Western Blot using a human specific antibody. OTC protein expression levels were measured by near-infrared fluorescent imaging systems and both fractions, normalized to total protein, were plotted (FIG. 15). The plot of protein expression levels shown in FIG. 14 (Example 12) indicates that even though both compounds, 2016 and 2260, deliver similar protein levels in the cytosol, 2260 delivers more human OTC than 2016 in the mitochondria. The 2260 compound includes a modified mitochondrial signaling peptide sequence provided herein.

Example 14: Urinary Orotate Levels in Spf/Ash Mice Treated with mRNA Construct 2260

Figure 16:
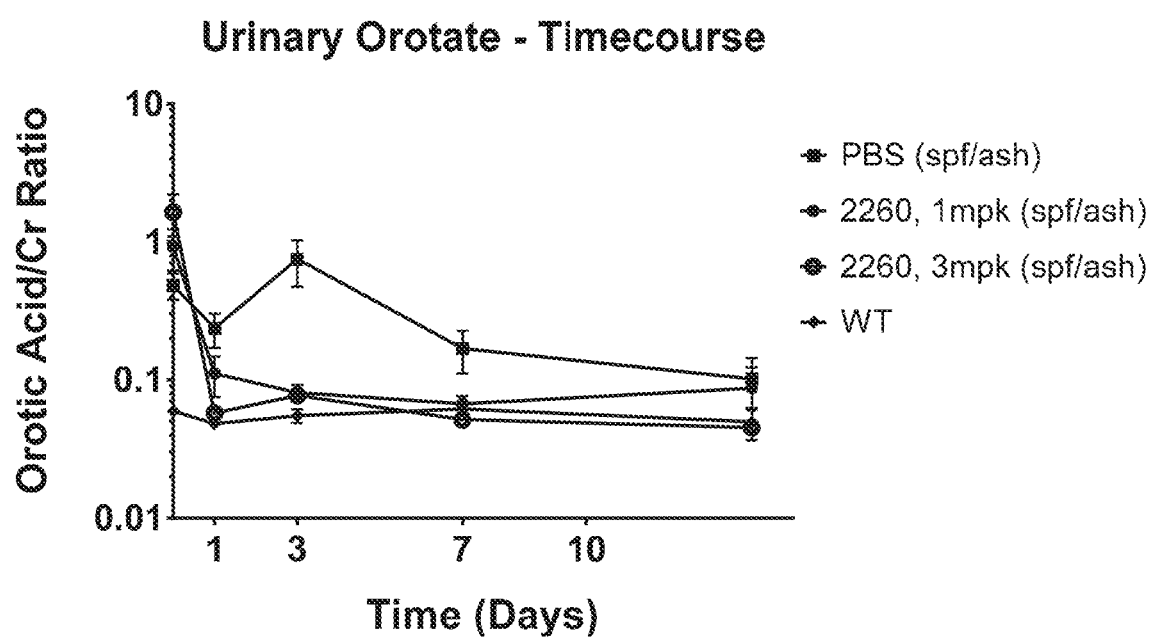
FIG. 16 is a plot illustrating the time course of expression of urinary orotate levels in Spf/ash mice treated with selected OTC mRNA.

Spf/ash mice received an IV injection with either PBS or lipid-formulated (as described in Example 1) OTC-mRNA at 1 mg/kg and 3 mg/kg. WT mice were included as an internal control. Urinary orotate levels were measured at 0, 1, 3, 7 and 14 days, and levels were normalized to creatinine (FIG. 16). The functional read-out of this assay shows that urinary orotate levels were reduced for up to 14 days with compound 2260 in a dose-dependent manner.

Example 15: Survival of Spf/Ash Mice on a High Protein Diet During Treatment with OTC-mRNA Construct 1799.7 (5MeOU Chemistry)

Figure 17:
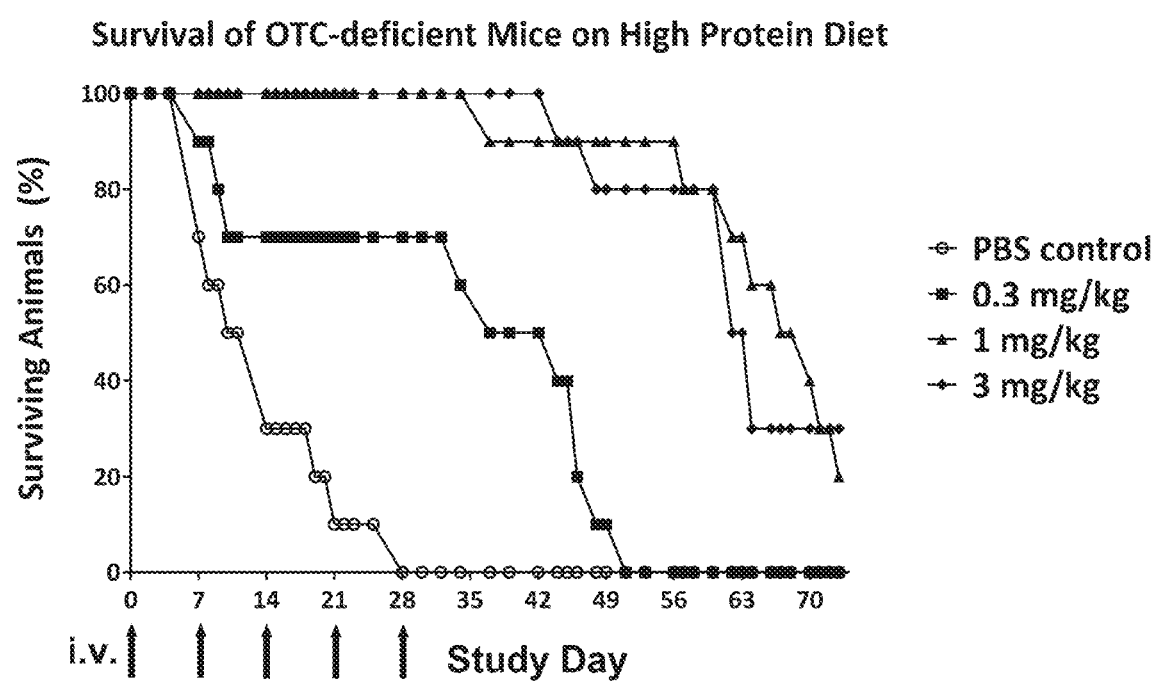
FIG. 17 is a plot illustrating the survival of OTC-deficient mice (Spf/ash) on a high protein diet during treatment with three different doses of OTC mRNA 1799.7.

Spf/ash mice received an IV injection with either PBS or lipid-formulated OTC-mRNA (1799.7) at three doses: 0.3 mg/kg, 1 mg/kg and 3 mg/kg. Mice were fed a high protein diet from day 0 to the end of the study. Treated animals were injected intravenously on days 0, 7, 14, 21 and 28 (indicated by the arrows in the chart in FIG. 17). Survival rates were determined every week. The plot in FIG. 17 summarizes the entire study timeline and the survival rates observed for the different groups. The results show that animals treated with human OTC mRNAs described herein displayed greater survival during a hyperammonemic crisis, suggesting a protective role of OTC mRNAs described herein in detoxifying the animals from toxic ammonia. The survival rate was dose-dependent, and animals treated with a 3 mg/kg dose had a higher survival rate than animals treated at 1 mg/kg or 0.3 mg/kg.

Figure 18:
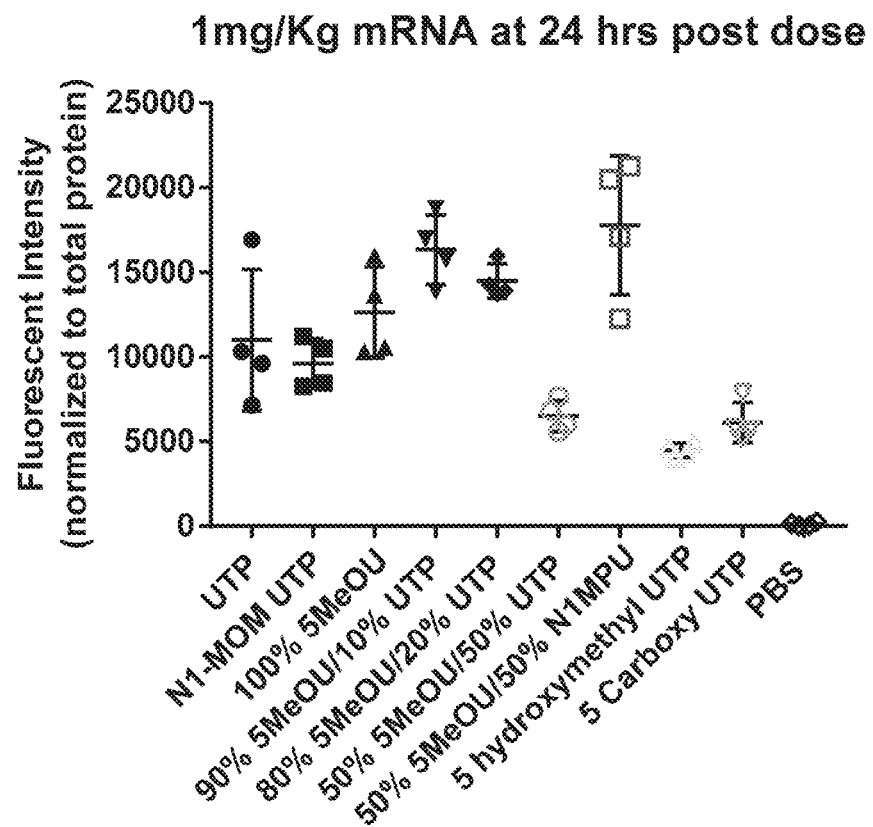
FIG. 18 is a plot illustrating hOTC expression levels in male Balb/c mice dosed with OTC mRNAs (Construct 2262) having different modifications.

Example 16: Comparison of hOTC Expression Levels from mRNAs with Different Modifications Doses of lipid-formulated OTC-mRNA construct 2262 were injected intravenously into 8 to 10 week-old female Balb/c mice at a dose of 1 mg/kg. Different chemistries were used in this study as indicated in the bottom (x) axis of the chart provided in FIG. 18. Mouse livers were harvested at 24 hours post IV-administration, and western blotting was performed using a hOTC specific antibody. Levels were normalized to total protein (FIG. 18). Each construct was formulated as a lipid nanoparticle comprising an ionizable cationic lipid as described in Example 1. This dataset shows the impact of different uridine chemistries on the expression levels of the codon-optimized mRNAs described herein.

Example 17: Lipid Formulation Development Studies

Lipid formulations were prepared as in Example 1 to evaluate ionizable cationic lipids in the lipid formulations for their physicochemical properties: particle size (desired to be 55 to 85 nm), polydispersity index (should not be more than 0.2) and percent encapsulated mRNA (not less than 85%). The physicochemical properties of the formulations are summarized in Table 7 below:

TABLE 7

Analytical Data Summary of Lipid Formulations

| Lipid | Batch ID | Particle Size (nm) | Polydispersity Index | % Encapsulated mRNA |
|---|---|---|---|---|
| Lipid # 1 | YB17_00506 | 80.5 | 0.06 | 95.2 |
| Lipid # 2 | YB17_00507 | 67.8 | 0.09 | 95.5 |
| Lipid # 3 | YB17_00508 | 72.7 | 0.08 | 95.5 |
| Lipid # 7 | YB17_00510 | 76.6 | 0.09 | 95.4 |

Assessment of formulation physicochemical properties (particle size, polydispersity index and percent encapsulated mRNA) in combination with in vivo potency (as measured by protein expression) led to the selection of three lipids (Lipid #2, Lipid #3, and Lipid #7) for further evaluation with OTC mRNA.

Parallel formulation development studies were performed that focused on determining optimal molar percentages of the ionizable cationic lipid, DSPC, Cholesterol and PEG2000-DMG in the formulation, utilizing Lipid #7 as the tool lipid, based on a Design of Experiments (DOE) approach. The study evaluated Lipid #7 and DSPC ratios with a fixed PEG2000-DMG ratio at 1.5%. The PEG2000-DMG ratio was fixed to 1.5% to maximize mRNA encapsulation and in vivo potency. The DOE study focused on the assessment of formulation physicochemical properties: particle size (55 to 85 nm), polydispersity index (not more than 0.2) and percent encapsulated mRNA (not less than 85%).

The measured physicochemical properties of the lipid formulations from the DOE study are outlined in Table 8 below:

TABLE 8

Analytical Data Summary of Lipid Formulations for DOE Study

| DOE Run # | Batch ID | Lipid Molar Ratios (%) [Lipid #7:DSPC:CHOL:PEG2000-DMG], CHOL level | 1F/T Data at 0.06 mg/mL | | |
|---|---|---|---|---|---|
| | | | Particle Size (nm) | PDI | % encapsulated mRNA |
| 1 | YB18_00783 | [42:13:43.5:1.5], high | 66.9 | 0.19 | 96.5 |
| 2 | YB18_00784 | [50:10:38.5:1.5], medium | 68.8 | 0.18 | 95.0 |
| 3 | YB18_00786 | [42:7:49.5:1.5], high | 67.1 | 0.24 | 93.5 |
| 4 | YB18_00787 | [50:13:35.5:1.5], medium | 70.0 | 0.18 | 95.3 |
| 5 | YB18_00788 | [58:13:27.5:1.5], low | 74.9 | 0.13 | 93.2 |
| 6 | YB18_00789 | [42:10:46.5:1.5], high | 71.9 | 0.21 | 95.8 |

TABLE 8-continued

Analytical Data Summary of Lipid Formulations for DOE Study

| DOE Run # | Batch ID | Lipid Molar Ratios (%) [Lipid #7:DSPC:CHOL:PEG2000-DMG], CHOL level | 1F/T Data at 0.06 mg/mL | | |
|---|---|---|---|---|---|
| | | | Particle Size (nm) | PDI | % encapsulated mRNA |
| 7 | YB18_00790 | [50:7:41.5:1.5], medium | 72.2 | 0.16 | 95.4 |
| 8 | YB18_00791 | [58:10:30.5:1.5], low | 83.7 | 0.14 | 92.2 |

Based on the data above, the molar percentage of Lipid #7 played an important role in the physicochemical properties of the formulation. Most notably, formulations containing 42% of Lipid #7 had the highest PDI (with two out of three formulations outside of the acceptable range), while formulations containing 58% of Lipid #7 had the lowest PDI. Conversely, formulations containing 58% of Lipid #7 had the greatest particle size, but were still within the acceptable range. The percent encapsulated mRNA for all formulations were within the acceptable range, with formulations containing 42% or 50% of Lipid #7 having slightly higher % encapsulated mRNA.

Figure 19:
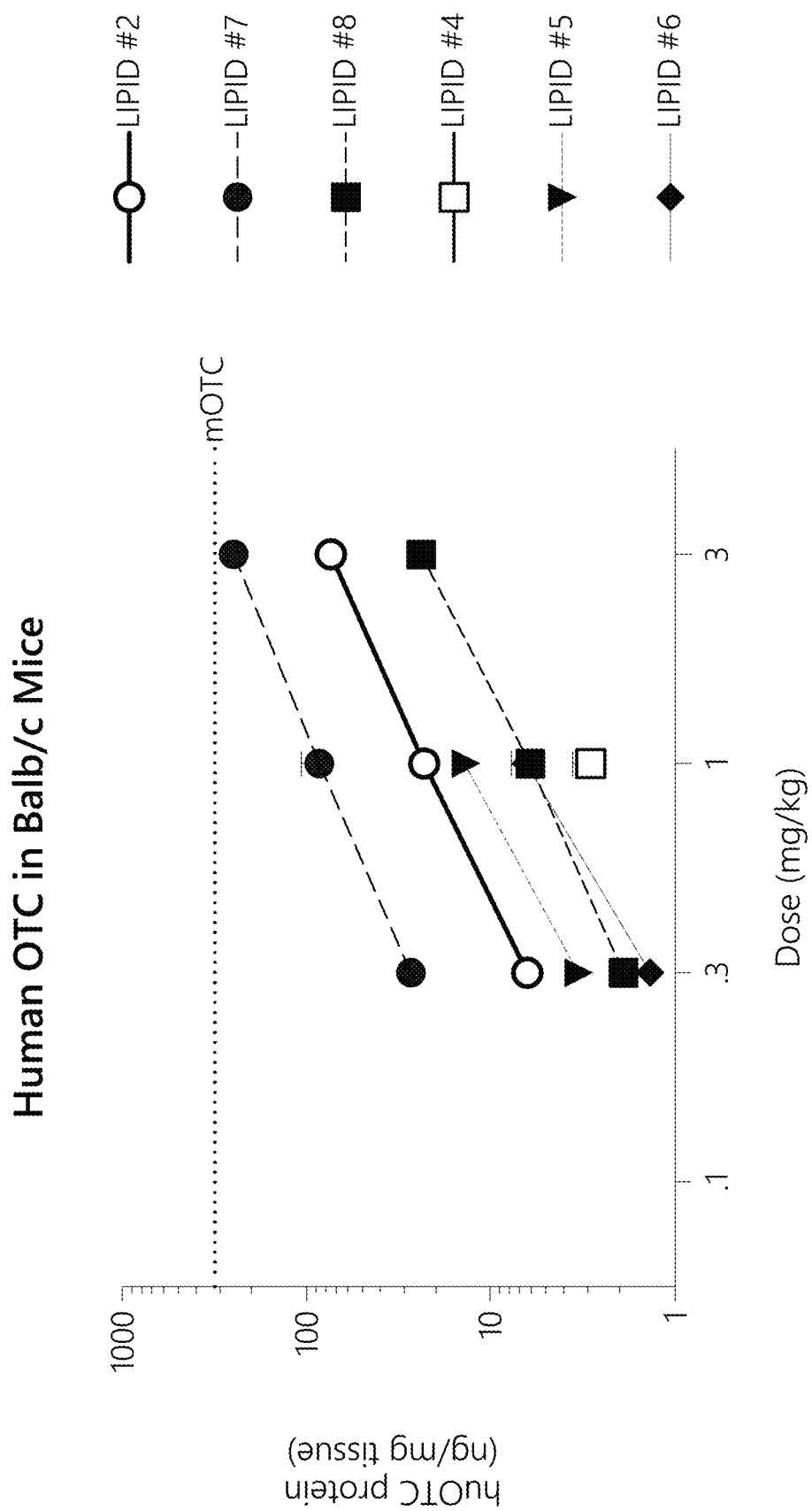
FIG. 19 is a graph that shows the levels of human OTC protein expression in wild-type mice for several different OTC mRNA lipid formulations at doses of 0.3 mg/kg, 1.0 mg/kg, and 3.0 mg/kg. The dotted line labeled as mOTC represents the baseline level of expression for mouse OTC in wildtype mice.

Example 18: Comparison of the Effect of Ionizable Cationic Lipids on OTC Expression in Balb/c Mice Lipid formulations were prepared as in Example 1, using the 571 mRNA construct for each of Lipid #2, Lipid #7, Lipid #8, Lipid #4, Lipid #5, and Lipid #6 to test the dose-dependent effect of these lipids on the expression of hOTC in Balb/c mice. Formulations of each of these lipids were administered intravenously to the mice at doses of 0.3 mg/kg, 1.0 mg/kg, and 3.0 mg/kg. The expression levels are shown relative to wild-type mouse OTC (mOTC) expression levels in FIG. 19. As can be seen in this figure, each of the formulations showed dose-dependent expression, with increasing concentrations of hOTC seen as doses increased. The formulations comprising Lipid #2 and Lipid #7 showed the greatest levels of hOTC expression, with Lipid #7 showing about 3 to 4-fold greater expression than Lipid #2.

Figure 20:
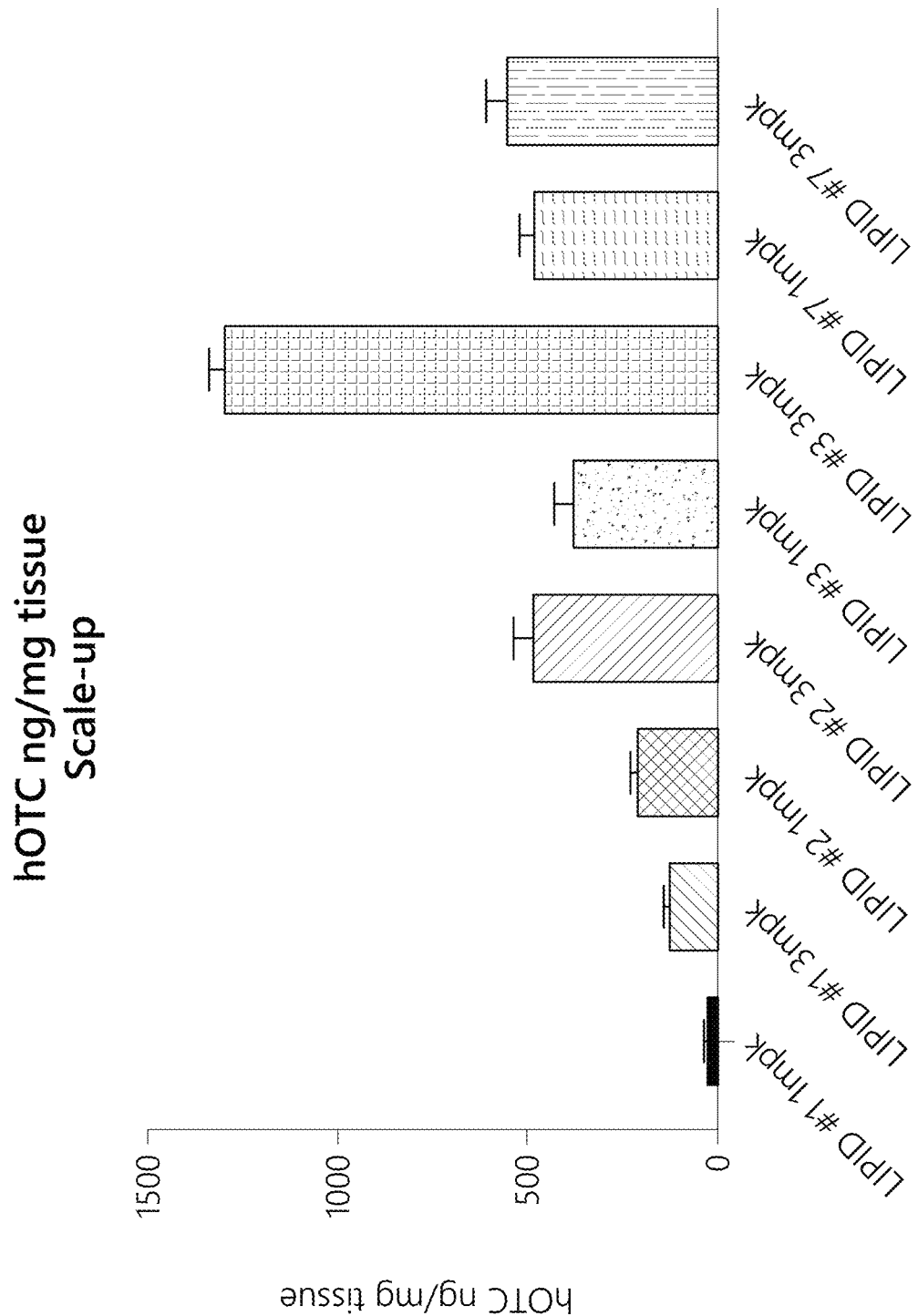
FIG. 20 is a graph that shows human OTC (hOTC) expression in tissue samples of wild-type mice for four different OTC mRNA lipid formulations at doses of 1.0 mg/kg and 3.0 mg/kg.

Example 19: Further Comparisons of the Effect of Ionizable Cationic Lipids on OTC Expression Further lipid formulations were prepared as in Example 1, using the 571 mRNA construct for each of Lipid #1, Lipid #2, Lipid #3, and Lipid #7 to test the dose-dependent effect of these lipids on the expression of hOTC in Balb/c mice. Formulations of each of these lipids were administered intravenously to the mice at doses of 1.0 mg/kg and 3.0 mg/kg. The expressions levels are shown in FIG. 20. As can be seen, there was a dose-related increase in hOTC expression. Lipid #3 showed an exceptional dose-response as the dose increased, while Lipid #7 appeared to have only a small dose response.

Example 20: Survival Rate of Spf/Ash Mice for Lipid Formulations Using Different Ionizable Cationic Lipids The pharmacology of the OTC mRNA lipid formulations was investigated in studies that elucidated their efficacy and potential mechanism of action in a series of studies in the hemizygous male Spf/ash mouse model. These mice possess a genetic mutation on the X-chromosome (hypomorphic model) that causes abnormal splicing of the endogenous OTC mRNA, resulting in less than 10% of residual OTC enzymatic activity in the liver. The hypomorphic Spf/ash mouse shares similar biochemical features with OTCD patients, including elevated concentrations of urinary orotic acid (orotate), blood glutamine, and decreased concentrations of blood citrulline and arginine. The hemizygous male Spf/ash mice used in the pharmacology studies were derived by crossing B6EiC3Sn a/A-Otcspfash/J Het mice x B6EiC3SnF1/J mice as homozygous mice are not viable. The heterozygous male B6EiC3SnF1/J mice were used as wildtype (WT) controls.

Spf/ash mice do not typically display severe hyperammonemia and reduced ureagenesis. Acute disruption of their urea acid cycle was induced by a bolus administration of ammonium chloride ($NH_4Cl$), resulting in hyperammonemia and reduced ureagenesis. In addition, their urea cycle was also stressed by maintaining these mice on a high protein diet (HPD).

Figure 21:
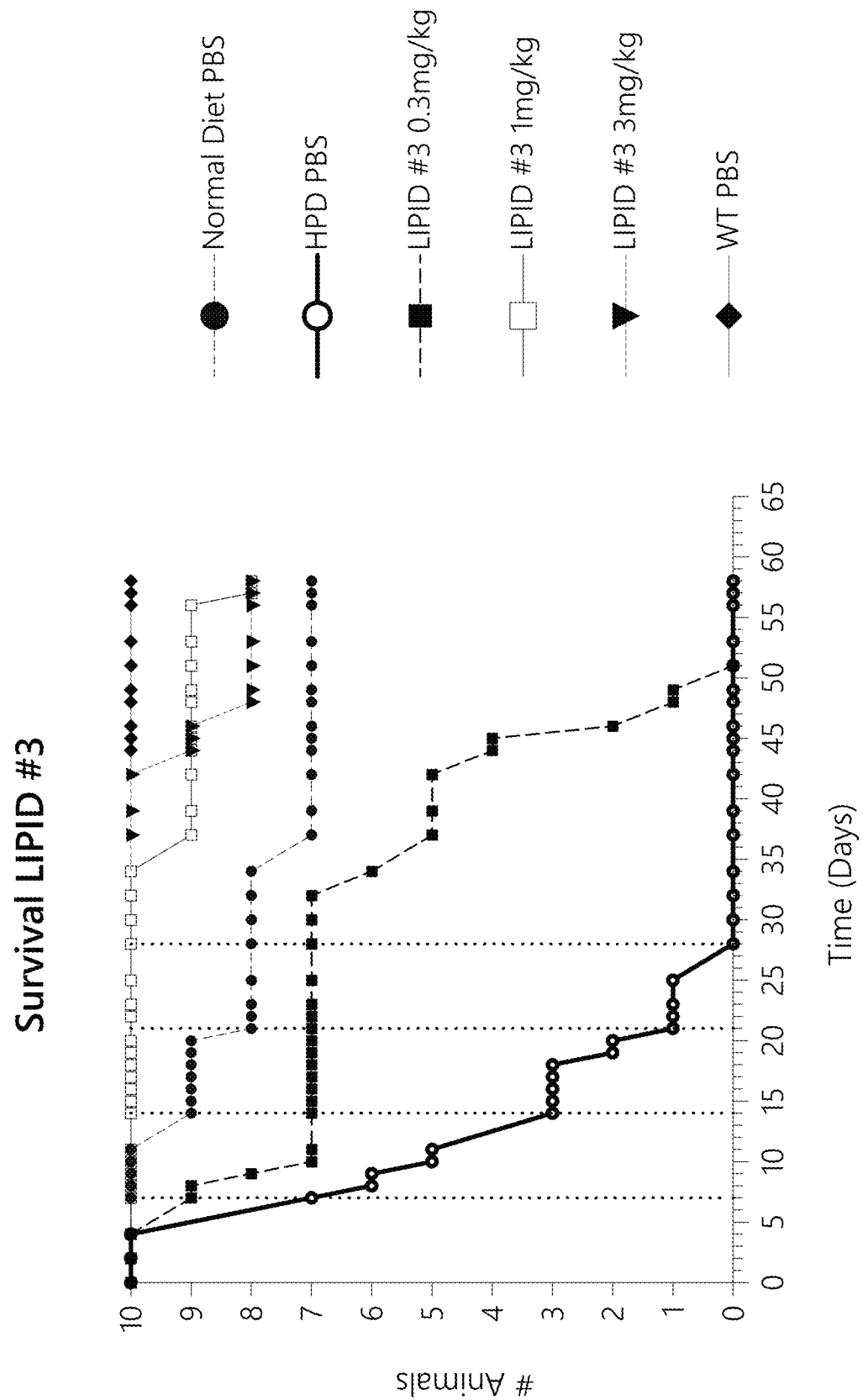
FIG. 21 is a graph that shows the survival of Spf/ash (OTC hypomorph) mice, after inducing hyperammonemia and being fed on a high protein diet (HPD), for a lipid formulation comprising Lipid #3 as described herein.
Figure 22:
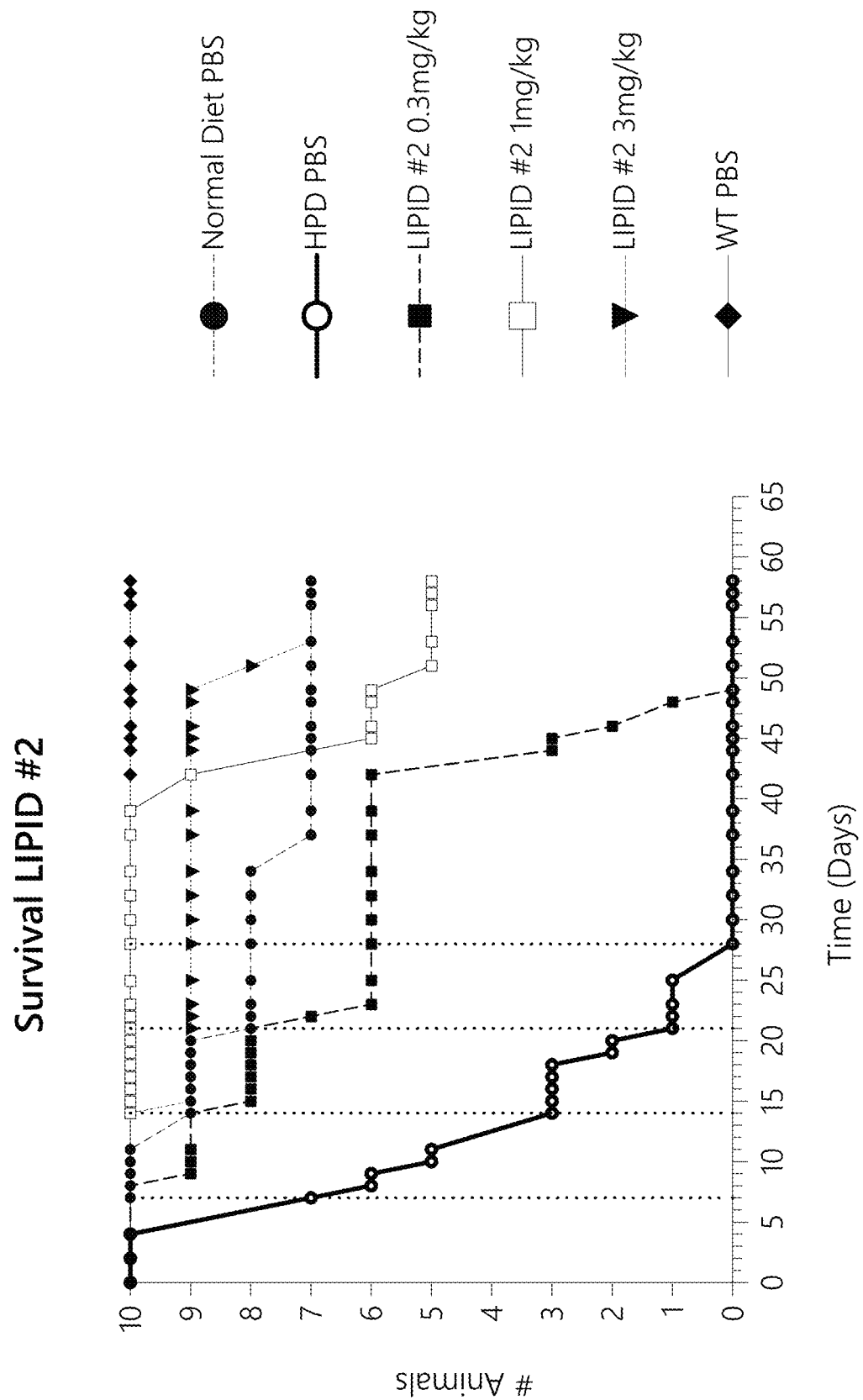
FIG. 22 is a graph that shows the survival of Spf/ash (OTC hypomorph) mice, after inducing hyperammonemia and being fed on a high protein diet (HPD), for a lipid formulation comprising Lipid #2 as described herein.
Figure 23:
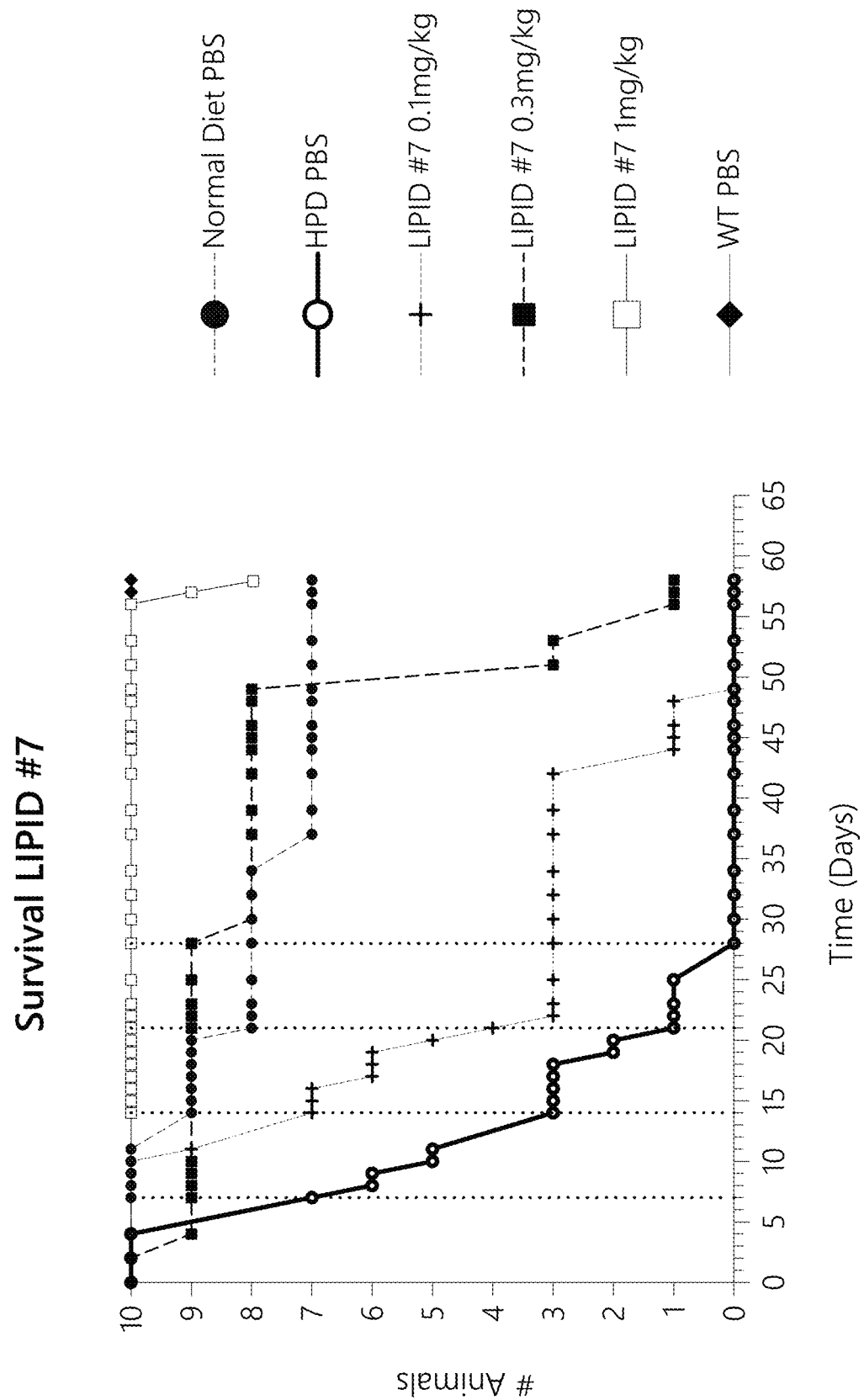
FIG. 23 is a graph that shows the survival of Spf/ash (OTC hypomorph) mice, after inducing hyperammonemia and being fed on a high protein diet (HPD), for a lipid formulation comprising Lipid #7 as described herein.

To study the effect of different ionizable cationic lipids on survival rate, Spf/ash mice received an IV injection with either PBS or one of three different lipid-formulated OTC-mRNA (1799.7) compositions. The three different compositions were prepared as in Example 1 above, and had either Lipid #3, Lipid #2, or Lipid #7. The formulations were administered at three doses: 0.3 mg/kg, 1 mg/kg and 3 mg/kg for the Lipid #2 and Lipid #3 formulations and 0.1 mg/kg, 0.3 mg/kg, and 1.0 mg/kg for the Lipid #7 formulation. Mice were on a high protein diet from day 0 to the end of the study. Treated animals were injected by intravenously on days 0, 7, 14, 21 and 28 (indicated by the dashed lines in the charts in FIGS. 21-23). Survival rates were determined daily. The plots in FIGS. 21-23 summarize the entire study timeline and the survival rates observed for the different groups. The results show that animals treated with human OTC mRNAs described herein displayed greater survival during a hyperammonemic crisis, suggesting a protective role of OTC mRNAs described herein in detoxifying the animals from toxic ammonia. The survival rate was dose-dependent.

Upon exposure to a high protein diet, mortality was observed as early as Day 4 (Lipid #7, 0.3 mg/kg). A high protein diet and treatment with PBS resulted in a steep mortality rate of Spf/ash mice beginning on Day 7, with 100% mortality by Day 28. Low dose treatments significantly extended the survival rate by at least two weeks, with 100% mortality observed on Day 49 for Lipid #2, Day 51 for Lipid #3, and Day 49 for Lipid #7, respectively. Mid and high dose treatments resulted in 90-100% survival rates throughout the dose administration period, with Lipid #7 at 1 mg/kg achieving a 100% survival rate. Dose-related improvement of survival rates was also seen from Day 28 through Day 70, the "washout period." At the high dose levels, Spf/ash mice were protected from hyperammonemia-induced death for at least two weeks after the last dose. At the mid and high dose levels, 100% mortality was not seen for a monitoring period out to six weeks after the last dose. At both the 0.3 mg/kg and 1.0 mg/kg levels, Lipid #7 was the most efficacious in prolonging survival, followed by Lipid #3, then Lipid #2. For the 3.0 mg/kg level, Lipid #3 was more efficacious than Lipid #2.

Example 21: Lipid Formulations Tolerability Study

To test the tolerability of OTC mRNA lipid formulations, lipid formulations as prepared in Example 1 using mRNA construct 1799.7 and either Lipid #2, Lipid #3, or Lipid #7 were tested in CD-1 mice at high dosages. All animals received an intravenous bolus treatment at a dosing volume of 10 mL/kg, once a week on Day 0, Day 7, Day 14, Day 21, and Day 28 of the study. Animals were observed daily for morbidity and mortality and body weights were determined twice weekly. Blood was collected from all animals for the measurement of ALT, AST and serum cytokines at 6 hours after the first and last dose. Animals were terminated 72 hours after the final dose (Day 31) for gross observation, measurement of whole body and organ weights (liver and spleen), tissue collection for histopathology (liver, kidney, spleen, heart and lung) and blood collection for analysis of cytokines, hematology and clinical chemistry.

Figure 24:
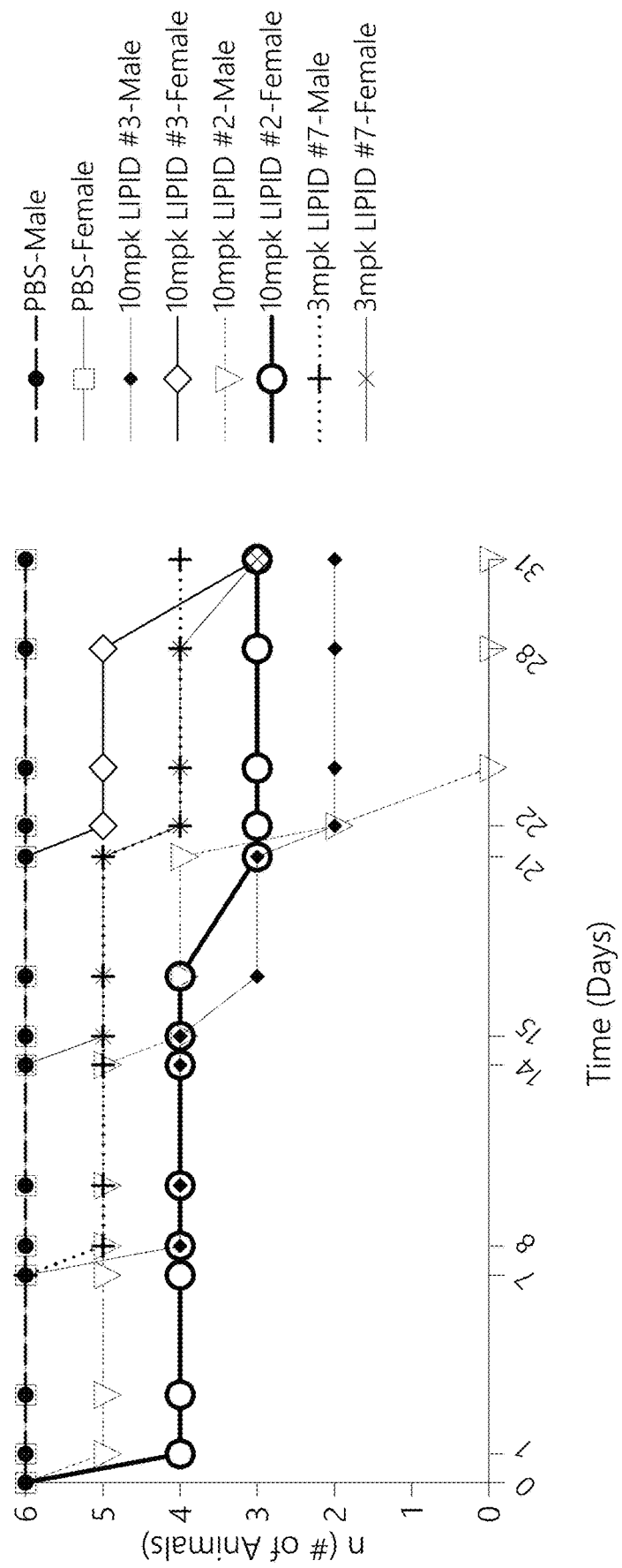
FIG. 24 is a graph that shows the survival rate of wild-type mice in a lipid tolerability study using OTC mRNA formulations having different ionizable cationic lipids described herein.

The survival rate results from this study are depicted in FIG. 24, which shows the dose-dependent effect of OTC mRNA lipid formulation treatment on survival rate after multiple dose administrations. A 100% survival rate was observed at the 3 mg/kg dose level for both Lipid #3 and Lipid #2 and at 1 mg/kg for Lipid #7 (in both genders). Males appeared to be more sensitive than females for Lipid #3 and Lipid #2, with 100% mortality observed in the Lipid #2 10 mg/kg male group. Furthermore, mortality was observed at the 10 mg/kg dose level for Lipid #3 and Lipid #2, and at the 3 mg/kg dose level for Lipid #7. At 10 mg/kg, Lipid #3 was better tolerated than Lipid #2. Data resulting from this study suggested a ranking of Lipid #3>Lipid #2>Lipid #7 for tolerability.

A full assessment of the in vivo tolerability study (including body weight, ALT/AST, and cytokine analysis) was also performed. A dose-dependent trend in body weight effects was observed that corresponded to survival. However, there did not appear to be a biologically meaningful effect on overall body weight gains throughout the study. Hematology parameters were evaluated 72 hours after the final dose. No meaningful effects were observed for RBC, Hg, HCT, MCV, MCH, lymphocytes, monocytes, white blood cells. While minor changes were observed, due to variability among animals and lack of dose dependency, they could not be attributed to the administration of the OTC mRNA lipid formulations. A trend for increases in eosinophils and basophils and an increase in basophils for Lipid #3 at 10 mg/kg was observed.

Serum cytokines were evaluated both at 6 hours after the first and final dose and 72 hours after the final dose. Significant dose-dependent increases (for some cytokines >100-fold) were observed 6 hours after the first and final dose for TNF-α, IL1-β, IFNγ, MCP-1, IL-6, and IFNα for all lipid-formulated OTC mRNA-treated animals that returned to baseline 72 hours after the final dose, with the exception of TNF-α and IFNγ for Lipid #7 at 3 mg/kg. While there were other changes observed at the 72-hour post dose time point, due to variability within the dose group and a lack of dose dependency, they were not attributed to the administration of the OTC mRNA formulation.

Example 22: In Vivo Tissue Lipid Clearance Studies

Figure 25:
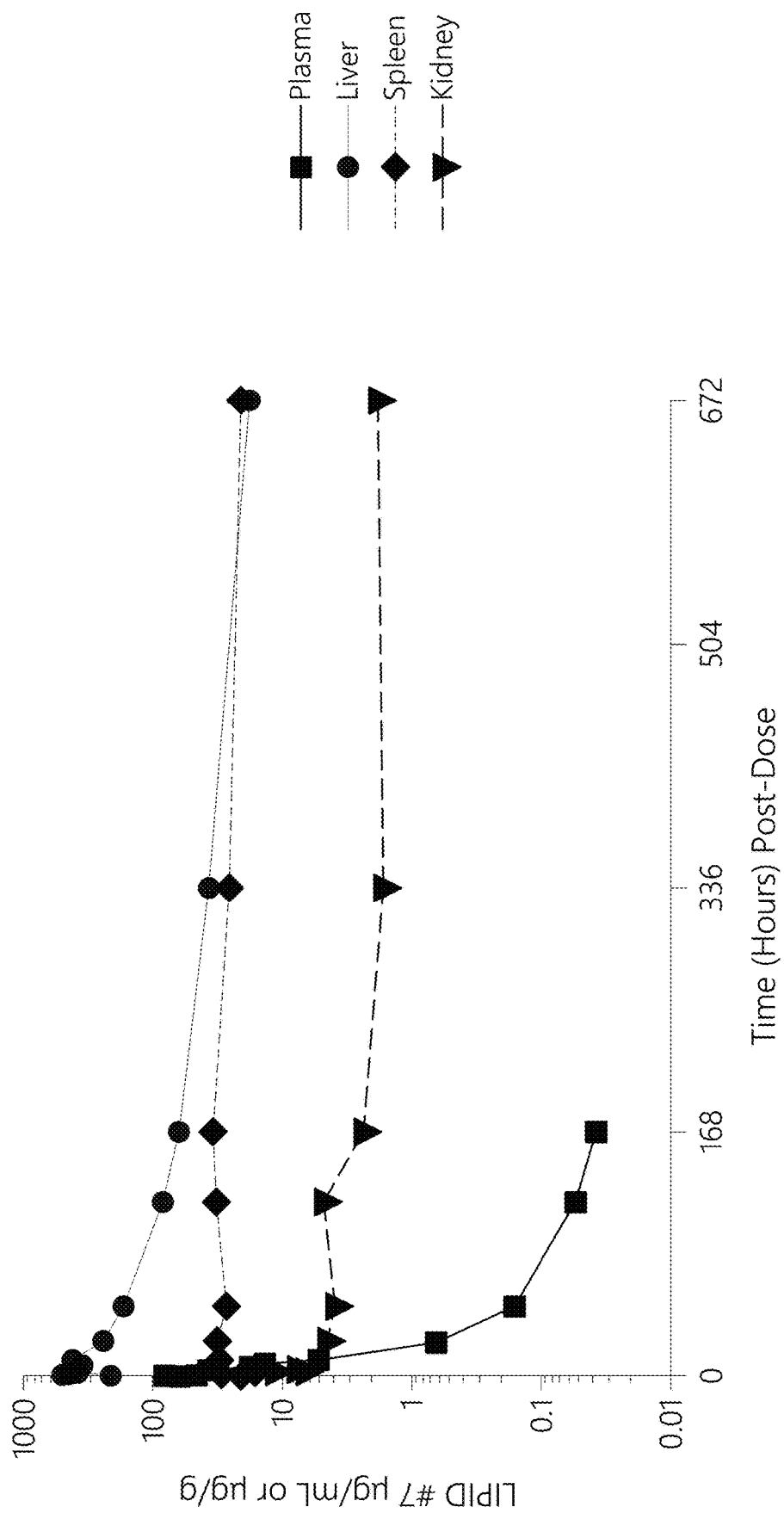
FIG. 25 is a graph that shows lipid clearance over time for tissue samples from mice dosed with an OTC mRNA lipid formulation comprising Lipid #7 described herein.
Figure 26:
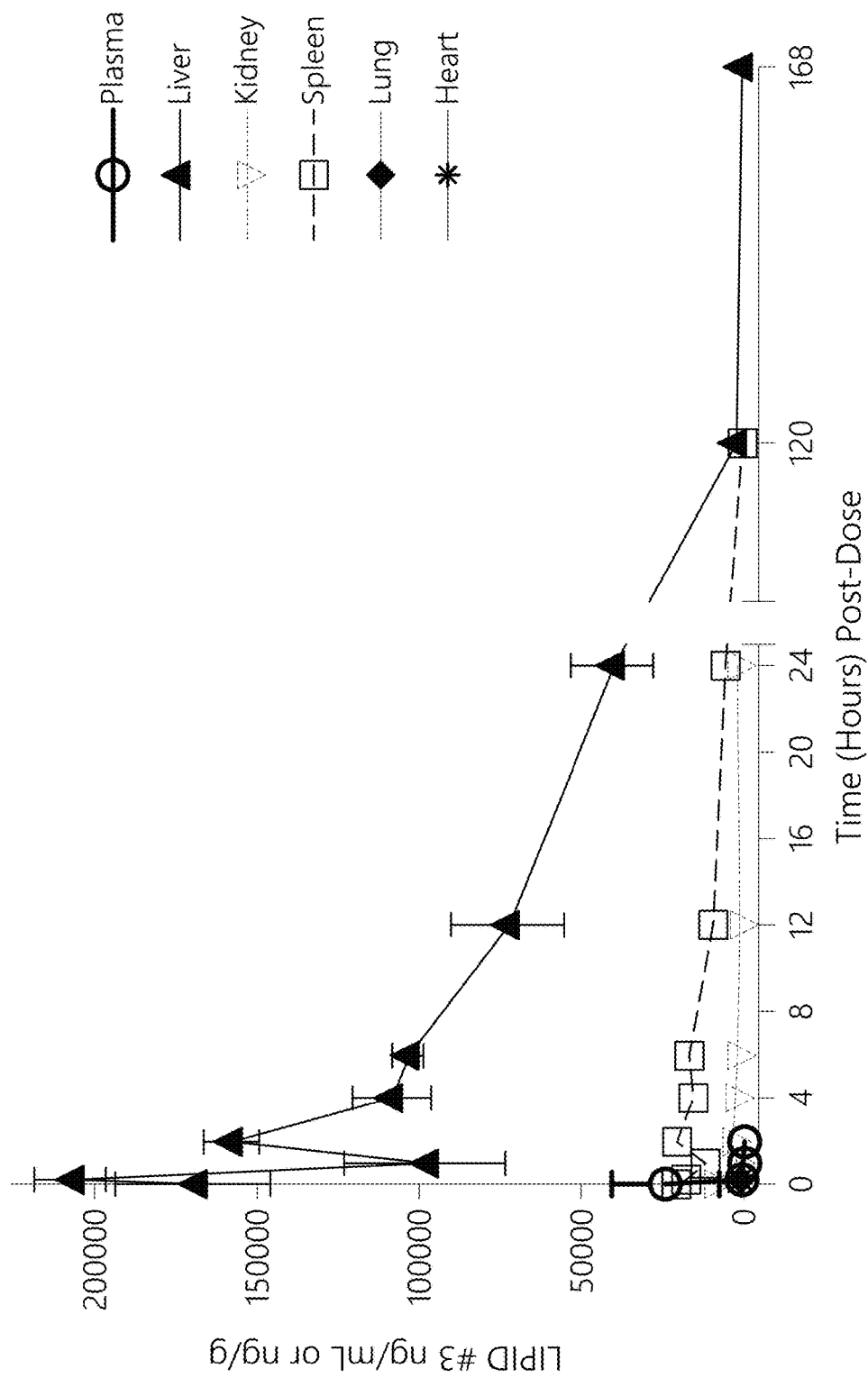
FIG. 26 is a graph that shows lipid clearance over time for tissue samples from mice dosed with an OTC mRNA lipid formulation comprising Lipid #3 described herein.

Additional studies were conducted to evaluate the in vivo tissue clearance profile of Lipid #7 and Lipid #3 in Balb/c mice. The clearance profiles in mouse tissue and plasma can be found in FIG. 25 (for Lipid #7) and FIG. 26 (for Lipid #3). All animals received a single intravenous bolus treatment of 1 mg/kg of the Lipid #7 formulation at a dosing volume of 10 mL/kg. Plasma, liver, kidney, and spleen were collected from mice (n=3 mice per timepoint) at 0, 2, 15, 30 minutes; 1, 2, 4, 6, 8, 12, 24, 48 hours; and 5, 7, 21, 28 days post-dose. All samples were analyzed for Lipid #7 concentrations.

The highest level of Lipid #7 was observed in the liver, with a ranking of liver>spleen>plasma>kidney. In the plasma, Lipid #7 was no longer detected by 14 days post-dose. By 28 days post-dose (the last time point evaluated), Lipid #7 was detected at a concentration of 18,433 pg/mL in the spleen, 17,233 pg/mL in the liver and 2,340 pg/mL in the kidney. The half-life for Lipid #7 was determined to be 57 hours for plasma, 84 hours for liver, and 234 hours for kidney. Tissue half-life of Lipid #7 could not be determined for the spleen.

All animals received a single intravenous bolus treatment of 1 mg/kg of the Lipid #3 formulation at a dosing volume of 10 mL/kg. Plasma was collected from mice (n=3 per timepoint) at 0.25, 1, 2, 4, 6, 12, 24, 120, and 168 hours post-dose. Liver, kidney, and spleen were collected from mice (n=3 per timepoint) at 0.033, 0.25, 1, 2, 4, 6, 12, 24, 120, and 168 hours; 1, 2, 3, 4-weeks post-dose. Heart, brain and lungs were collected from mice (n=3 per timepoint) at 0.25 hours; 1, 2-weeks post-dose. Only samples from 0.25 hrs to 1-week post-dose were analyzed for Lipid #3 tissue concentrations.

The highest level of Lipid #3 was observed in the liver, with a ranking of liver>plasma>spleen>kidney>lung>heart>brain. In the plasma, Lipid #3 was no longer detected by 4 hours post-dose. Lipid #3 was not detected in brain tissue at either time point post-dose. Lipid #3 $T_{max}$ occurred at 0.033 to 1 hour post-dose in kidney, 0.033 to 1-hour post-dose in liver, and 1 to 2 hours post-dose in spleen. Because only two time points were assessed for heart and lung, the $T_{max}$ of Lipid #3 could not be determined. Lipid #3 concentrations persisted through 168 hours post-dose in liver and 120 hours post-dose in all other tissues, but were measured close to the lower limit of quantitation (LLOQ) of the assay. The half-life for Lipid #3 was determined to be 0.45 hours for plasma, 22 hours for liver, 19 hours for kidney, and 24 hours for spleen, indicating rapid tissue clearance. Tissue half-life of Lipid #3 could not be determined for the lung and heart.

Further Considerations

The foregoing description is provided to enable a person skilled in the art to practice the various configurations described herein. There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A composition comprising:
   a. an mRNA encoding an enzyme comprising a sequence having at least 95% identity to a sequence of SEQ ID NO: 3 or SEQ ID NO: 4 and having ornithine transcarbamylase (OTC) activity; and
   b. a lipid formulation comprising an ionizable cationic lipid selected from

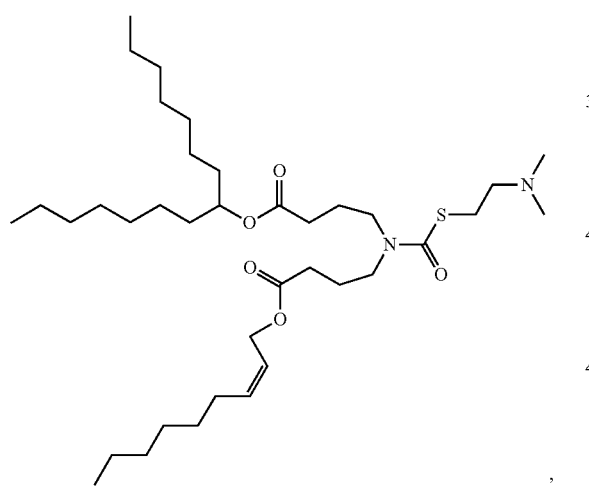

,

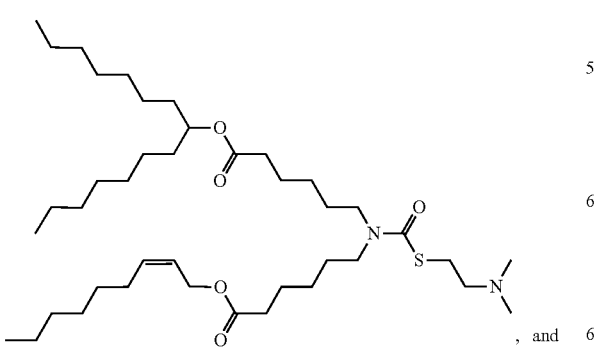

, and

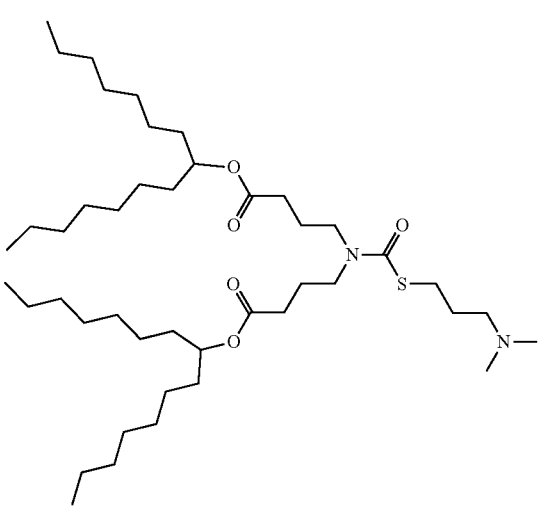

.

2. The composition of claim 1, wherein the mRNA encodes an OTC enzyme consisting of a sequence of SEQ ID NO: 3 or SEQ ID NO: 4.

3. The composition of claim 1, wherein the mRNA comprises a coding region having a sequence selected from SEQ ID NOs: 254-258.

4. The composition of claim 1, wherein the mRNA further comprises a 5' untranslated region (5' UTR) comprising a sequence of SEQ ID NO: 6 and a 3' untranslated region (3' UTR) comprising a sequence selected from SEQ ID NOs: 16-22.

5. The composition of claim 4, wherein the mRNA comprises a Kozak sequence having a sequence of SEQ ID NO: 23 or SEQ ID NO: 24.

6. The composition of claim 4, wherein the mRNA further comprises a 3' poly-adenosine (poly-A) tail comprising about 60 to about 125 consecutive adenine nucleotides.

7. The composition of claim 3, wherein the mRNA further comprises a 5' cap.

8. The composition of claim 7, wherein the 5' cap is m⁷GpppAmpG having a structure of Formula Cap XI:

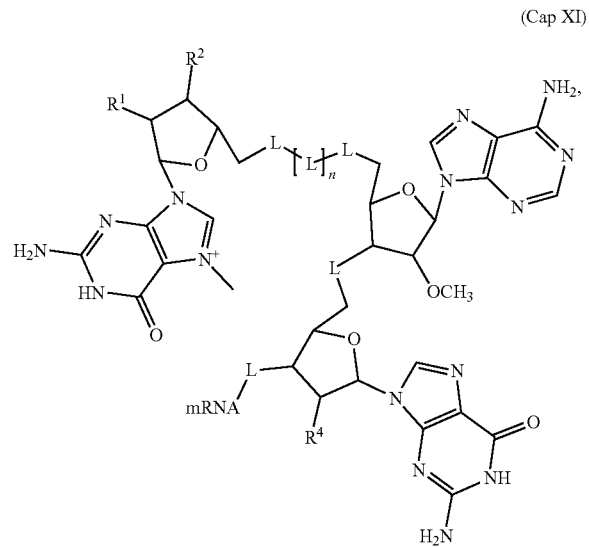

(Cap XI)

wherein $R^1$, $R^2$, and $R^4$ are each OH; n is 1; each L is a phosphate linked by diester bonds; and mRNA of Cap XI is the mRNA encoding the enzyme having OTC activity linked at its 5' end.

9. The composition of claim 1, wherein the mRNA comprises a sequence selected from SEQ ID NOs: 1, 73, 119, and 251-253.

10. The composition of claim 1, wherein about 1% to about 100% of the uridine nucleotides of the mRNA are 5-methoxyuridine or $N^1$-methylpseudouridine.

11. The composition of claim 10, wherein 100% of the uridine nucleotides of the mRNA are 5-methoxyuridine or $N^1$-methylpseudouridine.

12. The composition of claim 1, wherein the ionizable cationic lipid is

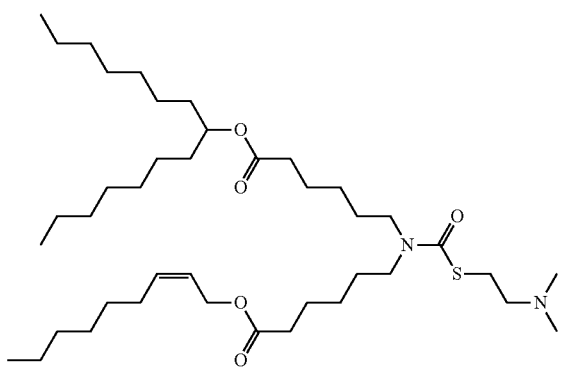

13. The composition of claim 1, wherein the lipid formulation comprises lipid nanoparticles.

14. The composition of claim 13, wherein the lipid nanoparticles have an average particle size of less than about 100 nm.

15. The composition of claim 14, wherein the lipid nanoparticles have an average particle size of about 55 nm to about 85 nm.

16. The composition of claim 13, wherein the lipid nanoparticles encapsulate at least about 50% of the mRNA.

17. The composition of claim 1, wherein the lipid formulation further comprises a helper lipid selected from dioleoylphosphatidyl ethanolamine (DOPE), dimyristoylphosphatidyl choline (DMPC), distearoylphosphatidylcholine (DSPC), dimyristoylphosphatidyl glycerol (DMPG), dipalmitoyl phosphatidylcholine (DPPC), and phosphatidylcholine (PC).

18. The composition of claim 17, wherein the helper lipid is distearoylphosphatidylcholine (DSPC).

19. The composition of claim 1, wherein the lipid formulation further comprises cholesterol.

20. The composition of claim 1, wherein the lipid formulation further comprises a polyethylene glycol (PEG)-lipid conjugate.

21. The composition of claim 20, wherein the PEG-lipid conjugate is PEG-DMG.

22. The composition of claim 1, wherein the lipid formulation comprises about 48 mol % to about 66 mol % of the ionizable cationic lipid, about 2 mol % to about 12 mol % DSPC, about 25 mol % to about 42 mol % cholesterol, and about 0.5 mol % to about 3 mol % PEG2000-DMG.

23. The composition of claim 22, wherein the lipid formulation comprises about 50 mol % to about 61 mol % of the ionizable cationic lipid, about 5 mol % to about 9 mol % DSPC, about 29 mol % to about 38 mol % cholesterol, and about 1 mol % to about 2 mol % PEG2000-DMG.

24. The composition of claim 22, wherein the lipid formulation comprises about 56 mol % to about 58 mol % of the ionizable cationic lipid, about 6 mol % to about 8 mol % DSPC, about 31 mol % to about 34 mol % cholesterol, and about 1.25 mol % to about 1.75 mol % PEG2000-DMG.

25. The composition of claim 1, wherein the composition has a total lipid:mRNA weight ratio of about 50:1 to about 10:1.

26. The composition of claim 25, wherein the composition has a total lipid:mRNA weight ratio of about 35:1 to about 25:1.

27. The composition of claim 1, wherein the composition comprises a HEPES buffer at a pH of about 7.4.

28. The composition of claim 27, wherein the HEPES buffer is at a concentration of about 7 mg/mL to about 15 mg/mL.

29. The composition of claim 27, wherein the composition further comprises about 2.0 mg/mL to about 4.0 mg/mL of NaCl.

30. The composition of claim 27, wherein the composition further comprises one or more cryoprotectants.

31. The composition of claim 30, wherein the one or more cryoprotectants are selected from sucrose, glycerol, or a combination of sucrose and glycerol.

32. The composition of claim 31, wherein the composition comprises a combination of sucrose at a concentration of about 70 mg/mL to about 110 mg/mL and glycerol at a concentration of about 50 mg/mL to about 70 mg/mL.

33. A method of treating ornithine transcarbamylase (OTC) deficiency comprising administering a therapeutically effective amount of the composition of claim 1 to a subject in need thereof, wherein an enzyme having OTC activity is produced in hepatocytes of the subject.

34. The method of claim 33, wherein the administering comprises intravenous administration.

35. The method of claim 33, wherein the composition is administered to the subject at least once per month or at least twice per month.

36. The method of claim 33, wherein the composition is administered to the subject in a dose of from about 0.2 mg of the mRNA per kg of the subject to about 10 mg of the mRNA per kg of the subject.

37. A method of treating OTC deficiency in a subject identified as suffering from OTC deficiency comprising administering to the subject a composition of claim 1, wherein an OTC enzyme comprising a sequence of SEQ ID NO: 3 or SEQ ID NO: 4 is expressed in the subject.

* * * * *